US012644131B2

(12) United States Patent
Gradinaru et al.

(10) Patent No.: US 12,644,131 B2
(45) Date of Patent: Jun. 2, 2026

(54) VIRUS COMPOSITIONS WITH ENHANCED SPECIFICITY IN THE BRAIN

(71) Applicant: California Institute of Technology, Pasadena, CA (US)

(72) Inventors: Viviana Gradinaru, Pasadena, CA (US); Sripriya Ravindra Kumar, Chennai (IN); Benjamin Deverman, Boston, MA (US)

(73) Assignee: California Institute of Technology, Pasadena, CA (US)

( * ) Notice: Subject to any disclaimer, the term of this patent is extended or adjusted under 35 U.S.C. 154(b) by 1048 days.

(21) Appl. No.: 17/602,505

(22) PCT Filed: Apr. 10, 2020

(86) PCT No.: PCT/US2020/027708
§ 371 (c)(1),
(2) Date: Oct. 8, 2021

(87) PCT Pub. No.: WO2020/210655
PCT Pub. Date: Oct. 15, 2020

(65) Prior Publication Data
US 2022/0220502 A1 Jul. 14, 2022

Related U.S. Application Data

(60) Provisional application No. 62/832,826, filed on Apr. 11, 2019.

(51) Int. Cl.
*C12N 15/80* (2006.01)
*C07K 14/005* (2006.01)
*C12N 7/00* (2006.01)
*C12N 15/86* (2006.01)

(52) U.S. Cl.
CPC ........... *C12N 15/86* (2013.01); *C07K 14/005* (2013.01); *C12N 7/00* (2013.01); *C12N 2750/14122* (2013.01); *C12N 2750/14143* (2013.01); *C12N 2750/14151* (2013.01); *C12N 2750/14171* (2013.01)

(58) Field of Classification Search
CPC .................. C07K 14/005; C12N 15/86; C12N 2750/14122; C12N 2750/14143; C12N 2750/14151; C12N 2750/14145; A61K 48/00; A61K 31/7105; A61K 38/465; A61K 47/64; A61P 25/00
USPC ...................................................... 435/320.1
See application file for complete search history.

(56) References Cited

U.S. PATENT DOCUMENTS 6,566,118 B1 5/2003 Atkinson et al.
2015/0079038 A1 3/2015 Deverman et al.
2018/0230186 A1 8/2018 Deverman et al.

FOREIGN PATENT DOCUMENTS

JP 2019-506141 A 3/2019
JP 2019-509032 A 4/2019
WO 1998/09657 A2 3/1998
WO 2017/100671 A1 6/2017
WO 2019/046069 A1 3/2019

OTHER PUBLICATIONS

Devos et al., Proteins: Structure, Function and Genetics, 2000, vol. 41: pp. 98-107.*
Whisstock et al., Quarterly Reviews of Biophysics , 2003, vol. 36 (3): pp. 307-340.*
Witkowski et al., Biochemistry, 1999, 38:, pp. 11643-11650.*
Kisselev L., Structure, 2002, vol. 10: pp. 8-9.*
Extended European Search Report issued in European Application No. 20787580.8, Mach 10, 2023, 12 pages.
Korbelin, 2016, A brain microvasculature endothelial cell specific viral vector with the potential to treat neurovascular and neurological diseases, EMBO Molecular Medicine (Online), 8(6):609-625.
Challis, 2019, Systemic AAV vectors for widespread and targeted gene delivery in rodents, Nat Protoc 14(2):379-414.
Chan, 2017, Engineered AAV's for efficient noninvasive gene delivery to the central and peripheral nervous systems, Nat. Neurosci 20:1172-1179.
Clark, 1999, Highly purified recombinant adeno-associated virus vectors are biologically active and free of detectable helper and wild-type viruses, Hum Gene Ther., 10(6):1031-9.
De, 2006, High levels of persistent expression of alpha1-antitrypsin mediated by the nonhuman primate serotype rh. 10 adeno-associated virus despite preexisting immunity to common human adeno-associated viruses, Mol. Ther. 13(1):67-76.
Deverman, 2016, Credependent selection yields AAV variants for widespread gene transfer to the adult brain, Nat. Biotechnol. 34:204-209.
Gao, 2004, Clades of Adeno-Associated Viruses are Widely Disseminated in Human Tissues, J Virol 78:6381-6388.
International Search Report and Written Opinion issued in International Application No. PCT/US2020/27708, date of mailing: Jul. 29, 2020, 9 pages.
Mori, 2004, Two novel adeno-associated viruses from cynomolgus monkey: pseudotyping characterization of capsid protein, Virology 330(2):375-383.

(Continued)

*Primary Examiner* — Tekchand Saidha
*Assistant Examiner* — Mohammad Y Meah
(74) *Attorney, Agent, or Firm* — Brown Rudnick LLP; Adam M. Schoen

(57) ABSTRACT

Provided are compositions and kits comprising recombinant adeno-associated viruses (rAAVs) with tropisms showing increased specificity and efficiency of viral transduction in targeted cell-types, for e.g., the brain and the liver. Therapeutic and biomedical research applications of the rAAVs are also described, including without limitation methods of discovering rAAVs using a multiplexed Cre recombination-based AAV targeted evolution (M-CREATE) method, and methods of treating various diseases and conditions by rAAV-mediated transgene therapy.

12 Claims, 215 Drawing Sheets

Specification includes a Sequence Listing.

(56) References Cited

OTHER PUBLICATIONS

Schnepp, 2002, Highly purified recombinant adeno-associated virus vectors. Preparation and quantification, Methods Mol. Med., 69:427-43.

Srivastava, 1983, Nucleotide sequence and organization of the adeno-associates virus 2 genome, J Virol 45(2):555-564.

* cited by examiner

*AAV9: 60-mer*     *Trimer*     *Monomer*

*3-fold axis*     *588-589 insertion site*
*5-fold axis*     *in 3-fold axis*

R1 *pre-in vivo* selection

Relative abundance of variants

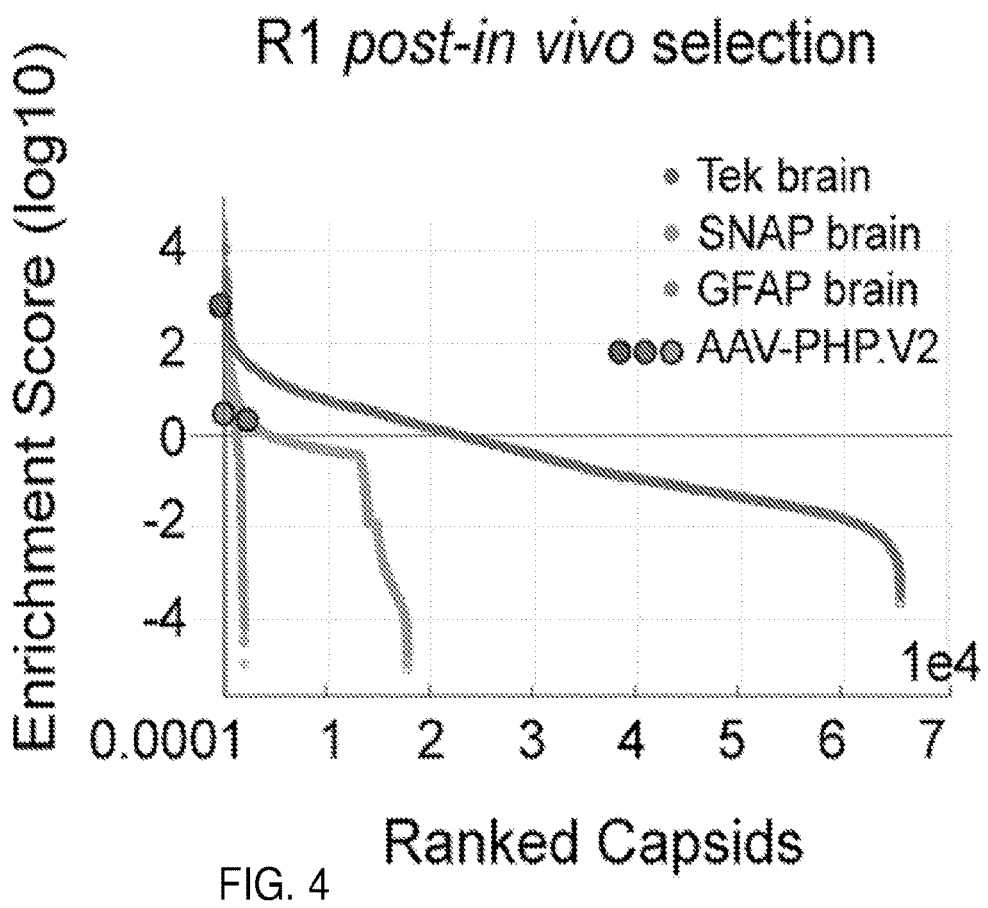
FIG. 4
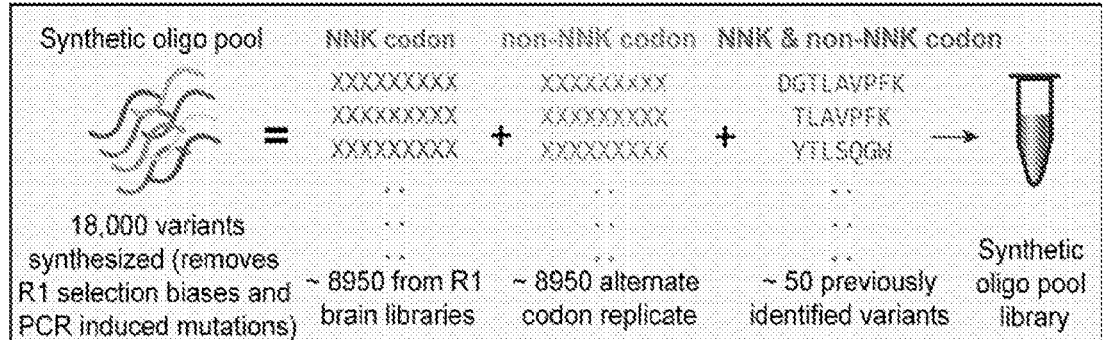
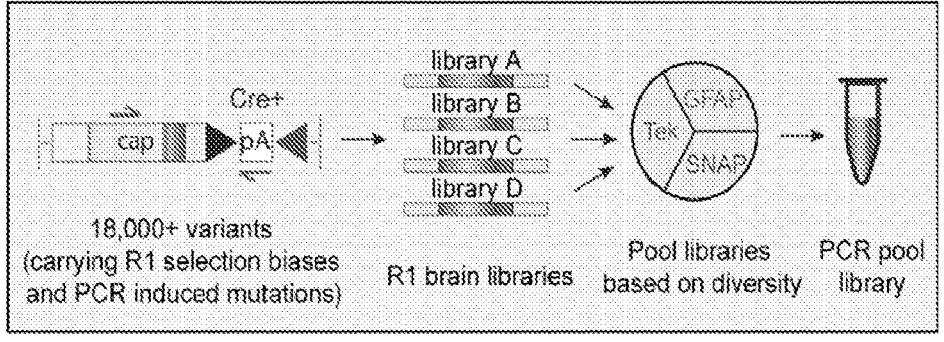
FIG. 5

Codon 1: enrichment score (log10)

```
                          588         589
                           ▼           ▼

AAV9:          AQ-------AQ
PHP.B:         AQTLAVPFKAQ
PHP.eB:        DGTLAVPFKAQ

PHP.V1:        AQTALKPFLAQ
PHP.V2:        AQTTLKPFLAQ
PHP.B4:        AQTLQIPFKAQ
PHP.B5:        AQTLQLPFKAQ
PHP.B6:        AQTLQQPFKAQ
PHP.B7:        AQSIERPFKAQ
PHP.B8:        AQTMQKPFIAQ
PHP.C1:        AQRYQGDSVAQ
```

FIG. 13

*Neurons*

*Astrocytes*

*Oligodendrocyte lineage cells*

*Vgat brain library*

*AAV-PHP.N (1x10¹¹vg/adult C57BL/6J)*

```
                        588          589
                         ▼            ▼

AAV9:    AQ-------AQ

PHP.V1:    AQTALKPFLAQ
       PHP.V2:    AQTTLKPFLAQ
        PHP.N:    AQTLAVPFSNP
       PHP.eB:    DGTLAVPFKAQ
        PHP.B:    AQTLAVPFKAQ
       PHP.B2:    AQSVSKPFLAQ
       PHP.B3:    AQFTLTTPKAQ
       PHP.B4:    AQTLQIPFKAQ
       PHP.B5:    AQTLQLPFKAQ
       PHP.B6:    AQTLQQPFKAQ
       PHP.B7:    AQSIERPFKAQ
       PHP.B8:    AQTMQKPFIAQ

PHP.C1:    AQRYQGDSVAQ
       PHP.C2:    AQWSTNAGYAQ
       PHP.C3:    AQERVGFAQAQ
```

| Enrich_ rank (within libraries) | SEQ ID NO: | Sequence (for 11 mer AA) | SEQ ID NO: | 11 mer Amino Acid | SEQ ID NO: | 7 mer Amino acid | Brain- mean- enrichme nt score (log10) | Brain- mean- standardiz ed-read count |
|---|---|---|---|---|---|---|---|---|
| SyS1 | 1074 | GCCCAAACGTTGCAGATTCCTTTAAGGCACAG | 5663 | AQTLQIPFKAQ | 10252 | TLQIPFK | 2.730563 | 26.96166 |
| TS1 | 1075 | GCCCAAACCGCCCTCAAACCCTTCCTCGCACAG | 5664 | AQTALKPFLAQ | 10253 | TALKPFL | 2.536397 | 6.252175 |
| TS2 | 1076 | GCCCAAACCACCCTCAAACCCTTCCTCGCACAG | 5665 | AQTTLKPFLAQ | 10254 | TTLKPFL | 2.513839 | 10.4831 |
| SyS2 | 1077 | GCCCAAAGCATCGAAAGACCCTTCAAAGCACAG | 5666 | AQSIERPFKAQ | 10255 | SIERPFK | 2.357132 | 30.18586 |
| GS4 | 1078 | GCCCAAACCCAAAACAGACCCTTCCTCGCACAG | 5667 | AQTQNRPFLAQ | 10256 | TQNRPFL | 2.22812 | 8.911382 |
| TS3 | 1079 | GCCCAAACCATGCAAAAACCCTTCATCGCACAG | 5668 | AQTMQKPFIAQ | 10257 | TMQKPFI | 2.165359 | 12.68417 |
| GS5 | 1080 | GCCCAAACTAGTACGCGGCCGTTTTGGCACAG | 5669 | AQTSTRPFLAQ | 10258 | TSTRPFL | 2.14357 | 7.139476 |
| SyS5 | 1081 | GCCCAAGGCACCTTCGTCCCCCACCGCACAG | 5670 | AQGTFVPPTAQ | 10259 | GTFVPPT | 2.110151 | 7.82868 |
| SyS6 | 1082 | GCCCAATGGTCGACTAATGCGGGTTATGCACAG | 5671 | AQWSTNAGYAQ | 10260 | WSTNAGY | 1.979177 | 10.16316 |
| SyS9 | 1083 | GCCCAAACCCTGAAAGACCCTTCACCGCACAG | 5672 | AQTLERPFTAQ | 10261 | TLERPFT | 1.892846 | 9.19788 |
| SP1 | 1084 | GCCCAAACTGCTGCTAAGCCGTTTCTGGCACAG | 5673 | AQTAAKPFLAQ | 10262 | TAAKPFL | 1.863541 | 0.239884 |
| GS8 | 1085 | GCCCAAATTAGGATTGGTTATTCGCAGGCACAG | 5674 | AQIRIGYSQAQ | 10263 | IRIGYSQ | 1.835644 | 2.556906 |
| SyS10 | 1086 | GCCCAAGAGAGCGTGTGGGTTTGCTCAGGCACAG | 5675 | AQERVGFAQAQ | 10264 | ERVGFAQ | 1.73803 | 5.438205 |
| SyS12 | 1087 | GCCCAAGCCGACCTCCTCAACTACAGAGCACAG | 5676 | AQADLLNYRAQ | 10265 | ADLLNYR | 1.599571 | 1.410457 |
| SyS13 | 1088 | GCCCAACTCGTCGCCGGCTTCAGCCAAGCACAG | 5677 | AQLVAGFSQAQ | 10266 | LVAGFSQ | 1.591793 | 6.106031 |
| SyP5 | 1089 | GCCCAATCGTCTCTGAAGCCTTTTCTGGCACAG | 5678 | AQSSLKPFLAQ | 10267 | SSLKPFL | 1.574365 | -0.00792 |
| TS8 | 1090 | GCCCAAACGCATTCTAGGCCGTTTATTGCACAG | 5679 | AQTHSRPFIAQ | 10268 | THSRPFI | 1.566468 | 1.399717 |
| GP3 | 1091 | GCCCAACCTTTCCTGGTTATTCTGCGGCACAG | 5680 | AQPFPGYSAAQ | 10269 | PFPGYSA | 1.555967 | 0.122481 |
| SyP6 | 1092 | GCCCAAATTATTGTTGGGTATAGTCAGGCACAG | 5681 | AQIIVGYSQAQ | 10270 | IIVGYSQ | 1.515858 | -0.03845 |
| SS12 | 1093 | GCCCAAAGGTATCAGGGTGATTCTGTTGCACAG | 5682 | AQRYQGDSVAQ | 10271 | RYQGDSV | 1.486197 | 2.200634 |
| GS13 | 1094 | GCCCAAAGGTATGCTGGGGATTCTATTGCACAG | 5683 | AQRYAGDSIAQ | 10272 | RYAGDSI | 1.456352 | 2.513518 |
| SyS15 | 1095 | GCCCAAAAGACGATTGGGGAGCATTGGGCACAG | 5684 | AQKTIGEHWAQ | 10273 | KTIGEHW | 1.44094 | 1.156576 |
| SyS16 | 1096 | GCCCAATGGATGACGCATGGTTCTGCGGGCACAG | 5685 | AQWMTHGSAAQ | 10274 | WMTHGSA | 1.432726 | 5.12209 |
| GS16 | 1097 | GCCCAAGCTGCTTCGAGGCCGTTTCTTGCACAG | 5686 | AQAASRPFLAQ | 10275 | AASRPFL | 1.3791 | 1.903527 |

FIG. 33

| Label | ID | DNA sequence | ID | Peptide (AQ) | ID | Peptide | Value 1 | Value 2 |
|---|---|---|---|---|---|---|---|---|
| TP5 | 1098 | GCCCAAACTACTTCTAGGCCGTTTCTTGCACAG | 5687 | AQTTSRPFLAQ | 10276 | TTSRPFL | 1.353519 | -0.09501 |
| SyS17 | 1099 | GCCCAAGCTCGTGTGGGGTTTGGCTCAGGCACAG | 5688 | AQARVGLAQAQ | 10277 | ARVGLAQ | 1.345499 | 1.982916 |
| GP5 | 1100 | GCCCAAGGGACTAGTCCGAATCTTGCGGCACAG | 5689 | AQGTSPNLAAQ | 10278 | GTSPNLA | 1.306429 | 0.315395 |
| SyS19 | 1101 | GCCCAAGTGCGTACGGGGTATAGTTCTGCACAG | 5690 | AQVRTGYSSAQ | 10279 | VRTGYSS | 1.302979 | 4.055383 |
| SyS20 | 1102 | GCCCAAATTCGGGTGGGGGTATAGTTCTGCACAG | 5691 | AQIRVGYSSAQ | 10280 | IRVGYSS | 1.286795 | 1.856458 |
| TP6 | 1103 | GCCCAAACTACTTTGCGTCCGTTATTGCACAG | 5692 | AQTTLRPFIAQ | 10281 | TTLRPFI | 1.284391 | -0.12323 |
| SyP9 | 1104 | GCCCAAGGTATTACGTCTCTGTTTAAGGCACAG | 5693 | AQGITSLFKAQ | 10282 | GITSLFK | 1.251837 | 0.032947 |
| SyS21 | 1105 | GCCCAAACCACCCAAACCCCCTTCAGAGCACAG | 5694 | AQTTQTPFRAQ | 10283 | TTQTPFR | 1.192121 | 2.176002 |
| TP8 | 1106 | GCCCAAACTGTGTCGAGGCCGTTTTTGGCACAG | 5695 | AQTVSRPFLAQ | 10284 | TVSRPFL | 1.171604 | -0.12785 |
| SyP11 | 1107 | GCCCAATATGGGACGAATCCGTTTCGTGCACAG | 5696 | AQYGTNPFRAQ | 10285 | YGTNPFR | 1.13664 | -0.03961 |
| SyS25 | 1108 | GCCCAACCCACCACCATGGTCGACAGCAGCGCACAG | 5697 | AQPTMVDSSAQ | 10286 | PTMVDSS | 1.099202 | 0.266059 |
| GP9 | 1109 | GCCCAAAATAAGGCTAGTTCTCAGAATGCACAG | 5698 | AQNKASSQNAQ | 10287 | NKASSQN | 1.084711 | 0.150465 |
| GP10 | 1110 | GCCCAAACTTTTCGTAGTTGTTGAATGATGCACAG | 5699 | AQTFRSSNDAQ | 10288 | TFRSSND | 1.032118 | 0.297543 |
| GP11 | 1111 | GCCCAACTGCCGGATCGTTATCCTAATGCACAG | 5700 | AQLPDRYPNAQ | 10289 | LPDRYPN | 1.019382 | 0.311223 |
| GP12 | 1112 | GCCCAACAGAATGTTACGGAAGGGTGTTGCACAG | 5701 | AQQNVTKGVAQ | 10290 | QNVTKGV | 1.000865 | 0.069558 |
| SyS26 | 1113 | GCCCAAGCTCAGTCTCCGATTCTTCGGGCACAG | 5702 | AQAQSPILRAQ | 10291 | AQSPILR | 0.979922 | 0.194304 |
| SyS27 | 1114 | GCCCAAGTGGCTACTGGTTATTCTTCGGCACAG | 5703 | AQVATGYSSAQ | 10292 | VATGYSS | 0.978116 | 1.060347 |
| GP13 | 1115 | GCCCAATTGAATTCGAATCGGCCTAATGCACAG | 5704 | AQLNSNRPNAQ | 10293 | LNSNRPN | 0.9672 | 0.275423 |
| GP14 | 1116 | GCCCAAACGATTCGTAATAATACGATTGCACAG | 5705 | AQTIRNNTIAQ | 10294 | TIRNNTI | 0.959641 | 0.134651 |
| SyP21 | 1117 | GCCCAAGATCTTAGTCGTATTTTTAAGGCACAG | 5706 | AQDLSRIFKAQ | 10295 | DLSRIFK | 0.950386 | 0.011306 |
| SyS28 | 1118 | GCCCAACTCAGCAACAGCGCCAGCAAGCACAG | 5707 | AQLSNSASQAQ | 10296 | LSNSASQ | 0.941212 | 0.142825 |
| SyS29 | 1119 | GCCCAACTCGAAAAACATGGTCATGAGCGCACAG | 5708 | AQLENMVMSAQ | 10297 | LENMVMS | 0.937552 | 0.152227 |
| SyS30 | 1120 | GCCCAATTGACTCAGCAGACGGATGTTGCACAG | 5709 | AQLTQQTDVAQ | 10298 | LTQQTDV | 0.936974 | 0.055201 |
| SyS31 | 1121 | GCCCAAGCGGCCTCGCCCACGCCACCGCACAG | 5710 | AQAGLAHATAQ | 10299 | AGLAHAT | 0.936046 | 0.0038 |
| SyS32 | 1122 | GCCCAAAATGCTCATACTGCGCTGGATGCACAG | 5711 | AQNAHTALDAQ | 10300 | NAHTALD | 0.933184 | 0.121259 |
| TP14 | 1123 | GCCCAATGGCCGATTCTTCGGGCTGATGCACAG | 5712 | AQWPILRADAQ | 10301 | WPILRAD | 0.931545 | -0.12619 |
| GP15 | 1124 | GCCCAAGCGCTGGCTGGTCTGTCTCTGGCACAG | 5713 | AQALAGLSLAQ | 10302 | ALAGLSL | 0.930454 | 0.12621 |
| GS21 | 1125 | GCCCAACGTATTGATATGCCTTTTAAGGCACAG | 5714 | AQRIDMPFKAQ | 10303 | RIDMPFK | 0.920205 | 0.015073 |
| GP16 | 1126 | GCCCAAACGATGTCGTTGAGTAGTAGTGCACAG | 5715 | AQTMSLSSSAQ | 10304 | TMSLSSS | 0.919718 | 0.304165 |
| GS23 | 1127 | GCCCAACAAAACGTGCCAAAAACCTGCGCACAG | 5716 | AQQNVAKNLAQ | 10305 | QNVAKNL | 0.916602 | 0.813873 |
| GS33 | 1128 | GCCCAATTCGACAACCCCAACAACGTCGCACAG | 5717 | AQFDNPNNVAQ | 10306 | FDNPNNV | 0.915503 | 0.086072 |
| GS24 | 1129 | GCCCAAGTCCTCATGAGAGAAAGCCTCGCACAG | 5718 | AQVLMRESLAQ | 10307 | VLMRESL | 0.914386 | 0.141782 |

FIG. 33 (Continued)

| | | | | | | | | |
|---|---|---|---|---|---|---|---|---|
| SyS34 | 1130 | GCCCAACACCACGACACCGGCAGCGCCGCACAG | 5719 | AQHHDTGSAAQ | 10308 | HHDTGSA | 0.912951 | -0.01452 |
| GP17 | 1131 | GCCCAAGATGCGCCGAATAGTGTGGATGCACAG | 5720 | AQDAPNSVDAQ | 10309 | DAPNSVD | 0.901999 | 0.074694 |
| GP18 | 1132 | GCCCAAACTGGGAGTAGGGATGCTAAGGCACAG | 5721 | AQTASRDAKAQ | 10310 | TASRDAK | 0.889552 | 0.305208 |
| TS16 | 1133 | GCCCAAACTAATTATACGAAGCAGATTGCACAG | 5722 | AQTNYTKQIAQ | 10311 | TNYTKQI | 0.889024 | 1.292832 |
| GP20 | 1134 | GCCCAACCTCATAATGCTTCTGTGTTGGCACAG | 5723 | AQPHNASVLAQ | 10312 | PHNASVL | 0.864707 | 0.119015 |
| TS17 | 1135 | GCCCAAACCAACAACACCAGAAACATCGCACAG | 5724 | AQTNNTRNIAQ | 10313 | TNNTRNI | 0.862873 | 3.066317 |
| GP21 | 1136 | GCCCAAATGGTTCCTAATCATTCTGGTGCACAG | 5725 | AQMVPNHSGAQ | 10314 | MVPNHSG | 0.859604 | 0.10671 |
| SyS36 | 1137 | GCCCAACCGGTGCCGCAGTCTGAGCATGCACAG | 5726 | AQPVPQSEHAQ | 10315 | PVPQSEH | 0.852761 | 0.005712 |
| SyS37 | 1138 | GCCCAACTCTACCACGGCGGCAGCACCGCACAG | 5727 | AQLYHGGSTAQ | 10316 | LYHGGST | 0.851158 | 1.723386 |
| GP22 | 1139 | GCCCAAATGATTCATACTAGGGAGACGGCACAG | 5728 | AQMIHTRETAQ | 10317 | MIHTRET | 0.850116 | 0.21081 |
| TS18 | 1140 | GCCCAAACTAATAATACGAAGCCTCTTGCACAG | 5729 | AQTNNTKPLAQ | 10318 | TNNTKPL | 0.849557 | 1.523 |
| TS20 | 1141 | GCCCAACTCAACACCACCAGAAACACCGCACAG | 5730 | AQLNTTRNTAQ | 10319 | LNTTRNT | 0.839304 | 2.098399 |
| GP24 | 1142 | GCCCAAGCTTTGCATAATTCTCAGAATGCACAG | 5731 | AQALHNSQNAQ | 10320 | ALHNSQN | 0.827469 | 0.061402 |
| TS21 | 1143 | GCCCAAGTGAATAGTACGAGGAATGTTGCACAG | 5732 | AQVNSTRNVAQ | 10321 | VNSTRNV | 0.826565 | 1.260315 |
| GP25 | 1144 | GCCCAAGGTGTTGGGGTTGTTACGAAGGCACAG | 5733 | AQGVGVVTKAQ | 10322 | GVGVVTK | 0.820556 | 0.292663 |
| GP26 | 1145 | GCCCAAGTTTGTCGAAGCAGTTGGCTGCACAG | 5734 | AQVLSKQLAAQ | 10323 | VLSKQLA | 0.816495 | 0.216922 |
| SyS38 | 1146 | GCCCAATCTAAGTCTCTGCAGCCGTTGGTCACAG | 5735 | AQSKSLQPLAQ | 10324 | SKSLQPL | 0.815502 | -0.01826 |
| TS22 | 1147 | GCCCAATCGAATTCTACGCGGTGGTTGGTCACAG | 5736 | AQSNSTRLVAQ | 10325 | SNSTRLV | 0.815119 | 1.172623 |
| TS23 | 1148 | GCCCAACTCAACCAAACAAATCGCACAG | 5737 | AQLNQTKQIAQ | 10326 | LNQTKQI | 0.811665 | 0.576331 |
| TS24 | 1149 | GCCCAAAACAACAGCGTCAGACAACTCGCACAG | 5738 | AQNNSVRQLAQ | 10327 | NNSVRQL | 0.806765 | 2.286879 |
| SyS40 | 1150 | GCCCAAATGTCGGGGTATTGCATACTGCACAG | 5739 | AQMSGYSHTAQ | 10328 | MSGYSHT | 0.804194 | -0.01048 |
| GS26 | 1151 | GCCCAAGTCAAAGTCCCATCATCACCGCACAG | 5740 | AQVKVPIITAQ | 10329 | VKVPIIT | 0.799412 | -0.10413 |
| TS25 | 1152 | GCCCAAGGGAATAATACTCGGGCGGTGGCACAG | 5741 | AQGNNTRAVAQ | 10330 | GNNTRAV | 0.797634 | 1.315071 |
| TS26 | 1153 | GCCCAACAGAATCAGATTAAGAATATTGCACAG | 5742 | AQQNQIKNIAQ | 10331 | QNQIKNI | 0.797303 | 0.74103 |
| TS27 | 1154 | GCCCAAACCAACAACATGACCAAACCCTCGCACAG | 5743 | AQTNMTKPLAQ | 10332 | TNMTKPL | 0.791064 | 0.75073 |
| TS28 | 1155 | GCCCAAAACAACAGCACCAGACTCAGCGCACAG | 5744 | AQNNSTRLSAQ | 10333 | NNSTRLS | 0.790429 | 1.381045 |
| SyS41 | 1156 | GCCCAAAGCATGCTCACCAGCATCGTCGCACAG | 5745 | AQSMLTSIVAQ | 10334 | SMLTSIV | 0.790252 | 0.060228 |
| SyS42 | 1157 | GCCCAACTCAACGCCACCGCCAGCAGAGCACAG | 5746 | AQLNATASRAQ | 10335 | LNATASR | 0.785269 | 1.621315 |
| SyS43 | 1158 | GCCCAAAATACTGGGGTGCAGGTTAGGGCACAG | 5747 | AQNTGVQVRAQ | 10336 | NTGVQVR | 0.785026 | -0.11955 |
| TS29 | 1159 | GCCCAAACCAACACCGTCAGACCCATCGCACAG | 5748 | AQTNTVRPIAQ | 10337 | TNTVRPI | 0.780569 | 1.015192 |
| SyP24 | 1160 | GCCCAACAGTCTACGCGGGGGCTACTGCACAG | 5749 | AQQSTPGATAQ | 10338 | QSTPGAT | 0.779842 | -0.03057 |
| SP19 | 1161 | GCCCAAGGTCATTCTGAGAATTCTCGTGTGCACAG | 5750 | AQGHSENSRAQ | 10339 | GHSENSR | 0.778724 | -0.03149 |

FIG. 33 (Continued)

| | | | | | | | | |
|---|---|---|---|---|---|---|---|---|
| SyS44 | 1162 | GCCCAACTCCCACCCAAACCCTCAGAGCACAG | 5751 | AQLPTQTLRAQ | 10340 | LPTQTLR | 0.773756 | 0.51102 |
| GS27 | 1163 | GCCCAAAAGAATGCTCCGATGCCTGATGCACAG | 5752 | AQKNAPMPDAQ | 10341 | KNAPMPD | 0.772397 | 0.130152 |
| TS31 | 1164 | GCCCAAGAAGCAACAGCACCAAACCACCGCACAG | 5753 | AQSNSTKPTAQ | 10342 | SNSTKPT | 0.768053 | 2.108136 |
| SyS45 | 1165 | GCCCAACCTATTATTACTATGCCTGCTGCACAG | 5754 | AQPIITMPAAQ | 10343 | PIITMPA | 0.767318 | -0.10299 |
| GS28 | 1166 | GCCCAACCCTCAAAGGCATCGGCAGGCACAG | 5755 | AQPLKGIGSAQ | 10344 | PLKGIGS | 0.767253 | -0.07052 |
| GS29 | 1167 | GCCCAAGTCCTCAGCGTCAACCACCTCGCACAG | 5756 | AQVLSVNHLAQ | 10345 | VLSVNHL | 0.765014 | 0.050802 |
| SyS46 | 1168 | GCCCAAAGTGTGGCTGCTGTGCATATGGCACAG | 5757 | AQSVAAVHMAQ | 10346 | SVAAVHM | 0.764013 | 0.277236 |
| TS32 | 1169 | GCCCAAAGCAACAGCATCAGACTCGTCGCACAG | 5758 | AQSNSIRLVAQ | 10347 | SNSIRLV | 0.763114 | 1.058208 |
| TS33 | 1170 | GCCCAACATAATGATACTCGTCCTCTTGCACAG | 5759 | AQHNDTRPLAQ | 10348 | HNDTRPL | 0.759962 | -0.04126 |
| GS31 | 1171 | GCCCAACCTCCGGTGAGGTCTACGGCTGCACAG | 5760 | AQPPVRSTAAQ | 10349 | PPVRSTA | 0.755777 | -0.09946 |
| TS34 | 1172 | GCCCAAATGAACACCGTCAGAAACCTCGCACAG | 5761 | AQMNTVRNLAQ | 10350 | MNTVRNL | 0.754463 | 1.394996 |
| GS32 | 1173 | GCCCAATTGACGGATGGTCATCGGATTGCACAG | 5762 | AQLTDGHRIAQ | 10351 | LTDGHRI | 0.754429 | 0.32562 |
| TS35 | 1174 | GCCCAAACGAATGCGGTGAAGCTGACTGCACAG | 5763 | AQTNAVKLTAQ | 10352 | TNAVKLT | 0.752766 | 1.157992 |
| SyS48 | 1175 | GCCCAACGTGTGGATGCGGTTTGAGTGCACAG | 5764 | AQRVDAVLSAQ | 10353 | RVDAVLS | 0.750458 | 0.650222 |
| TS36 | 1176 | GCCCAAACCAACGCCGTCAAAAGCACCGCACAG | 5765 | AQTNAVKSTAQ | 10354 | TNAVKST | 0.749271 | 1.812411 |
| SyS49 | 1177 | GCCCAAATGCTCAACACCACCACCGCCAGAGCACAG | 5766 | AQMLNTTARAQ | 10355 | MLNTTAR | 0.747921 | 2.456673 |
| TS37 | 1178 | GCCCAAGGCAACAACAGTCTGGGGGTAGTGCGTTGGCACAG | 5767 | AQGNNTRPTAQ | 10356 | GNNTRPT | 0.747523 | 1.945144 |
| GP29 | 1179 | GCCCAACAGTCTGGGGGTAGTGCGTTGGCACAG | 5768 | AQQSGGSALAQ | 10357 | QSGGSAL | 0.744332 | 0.320051 |
| SyS50 | 1180 | GCCCAAGTGATTGCTTTGTCTACTATGGCACAG | 5769 | AQVIALSTMAQ | 10358 | VIALSTM | 0.743901 | -0.08342 |
| TS38 | 1181 | GCCCAACTGAATACGATTCGGAATGTGGCACAG | 5770 | AQLNTIRNVAQ | 10359 | LNTIRNV | 0.743811 | 0.509953 |
| TS39 | 1182 | GCCCAAAGCAACGCCACCAGAAGCGTCGCACAG | 5771 | AQSNATRSVAQ | 10360 | SNATRSV | 0.740235 | 2.030618 |
| TS40 | 1183 | GCCCAAGGCAACGGCACCAAATTCATCGCACAG | 5772 | AQGNGTKFIAQ | 10361 | GNGTKFI | 0.736944 | 0.870325 |
| TS41 | 1184 | GCCCAAAGCAACAACACCATCAGACCCGTCGCACAG | 5773 | AQSNTIRPVAQ | 10362 | SNTIRPV | 0.736197 | 0.921801 |
| TS42 | 1185 | GCCCAAAGCAACAGCACCAGAGCCATCGCACAG | 5774 | AQSNSTRAIAQ | 10363 | SNSTRAI | 0.734716 | 1.769995 |
| SyS51 | 1186 | GCCCAATTTCATTTGACTGATGATAGGGGTGCACAG | 5775 | AQFHLTDRGAQ | 10364 | FHLTDRG | 0.733831 | -0.11858 |
| GS33 | 1187 | GCCCAACCGATTAGGTCGGATACTGTTGGCACAG | 5776 | AQPIRSDTVAQ | 10365 | PIRSDTV | 0.731286 | -0.03233 |
| GS34 | 1188 | GCCCAAGCCAACCAAATCCACACAACCGCACAG | 5777 | AQANQIHNTAQ | 10366 | ANQIHNT | 0.730071 | 1.693251 |
| TS44 | 1189 | GCCCAATCGAATACGGTTCGGAATACTGCACAG | 5778 | AQSNTVRNTAQ | 10367 | SNTVRNT | 0.727807 | 1.688407 |
| SyS52 | 1190 | GCCCAAACCAGCCTCGGCTACAGCAGGCACAG | 5779 | AQTSLGYSSAQ | 10368 | TSLGYSS | 0.727167 | 0.736367 |
| SyS53 | 1191 | GCCCAAATCAGCGGCGTCCAAACCAGAGCACAG | 5780 | AQISGVQTRAQ | 10369 | ISGVQTR | 0.724309 | -0.03855 |
| TS45 | 1192 | GCCCAATGAATGCTGTTAGGCAGACTGCACAG | 5781 | AQSNAVRQTAQ | 10370 | SNAVRQT | 0.72361 | 1.522098 |
| SyS54 | 1193 | GCCCAATCTCTTTCTGAGCTTAGGATTGCACAG | 5782 | AQSLSELRIAQ | 10371 | SLSELRI | 0.723061 | -0.02338 |

FIG. 33 (Continued)

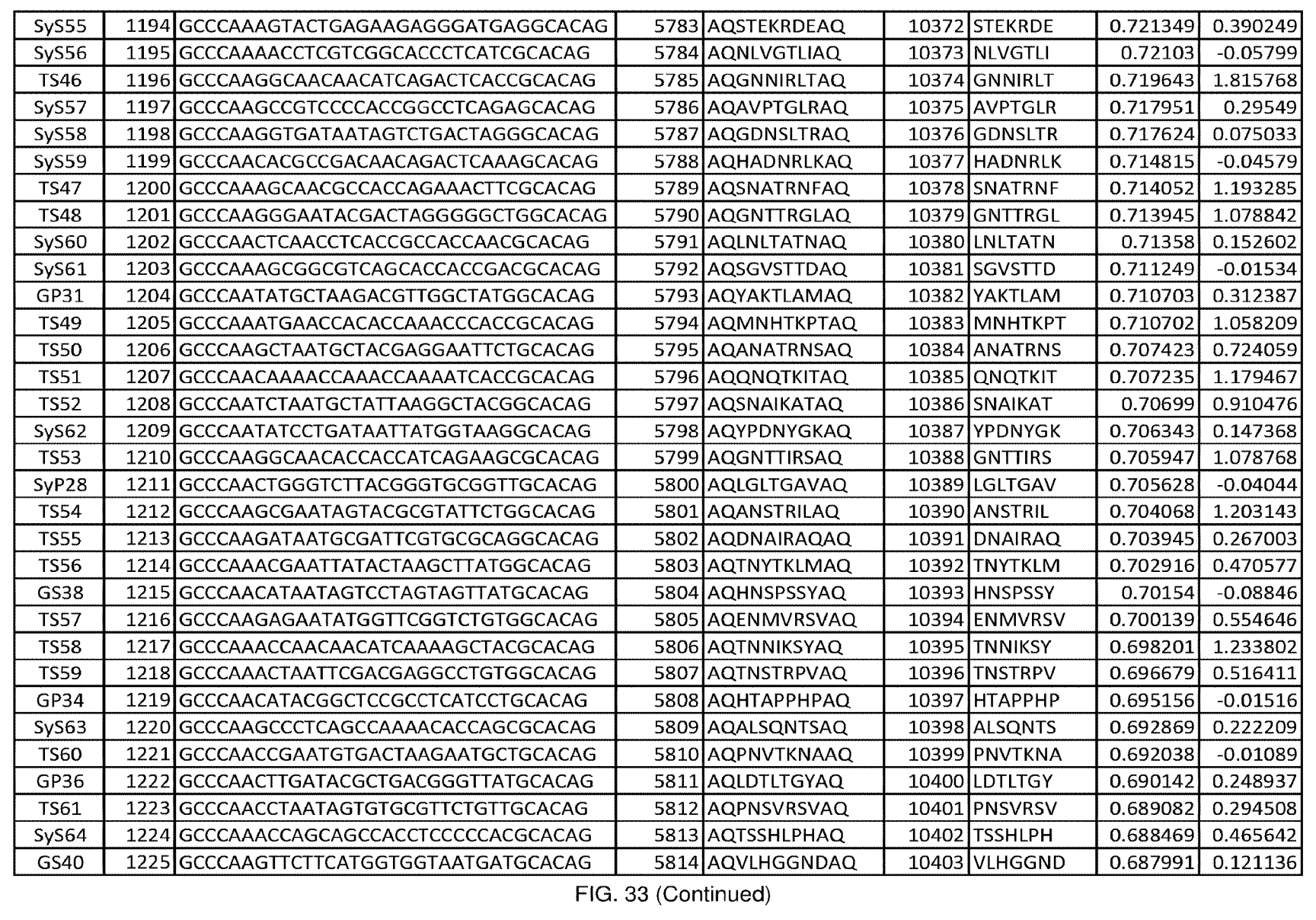

| | | | | | | | | |
|---|---|---|---|---|---|---|---|---|
| SyS55 | 1194 | GCCCAAAGTACTGAGAAGAGAGGGATGAGGCACAG | 5783 | AQSTEKRDEAQ | 10372 | STEKRDE | 0.721349 | 0.390249 |
| SyS56 | 1195 | GCCCAAAACCTCGTCGGCACCCTCATCGCACAG | 5784 | AQNLVGTLIAQ | 10373 | NLVGTLI | 0.72103 | -0.05799 |
| TS46 | 1196 | GCCCAAGGCAACAACATCAGACTCACCGCACAG | 5785 | AQGNNIRLTAQ | 10374 | GNNIRLT | 0.719643 | 1.815768 |
| SyS57 | 1197 | GCCCAAGCCGTCCCACCGGCCTCAGAGCACAG | 5786 | AQAVPTGLRAQ | 10375 | AVPTGLR | 0.717951 | 0.29549 |
| SyS58 | 1198 | GCCCAAGGTGATAATAGTCTGACTAGGGCACAG | 5787 | AQGDNSLTRAQ | 10376 | GDNSLTR | 0.717624 | 0.075033 |
| SyS59 | 1199 | GCCCAACACGCGACAACAGACTCAAAGCACAG | 5788 | AQHADNRLKAQ | 10377 | HADNRLK | 0.714815 | -0.04579 |
| TS47 | 1200 | GCCCAAAGCAACGCCACCAGAAACTTCGCACAG | 5789 | AQSNATRNFAQ | 10378 | SNATRNF | 0.714052 | 1.193285 |
| TS48 | 1201 | GCCCAAGGGAATACGACTAGGGGGCTGGCACAG | 5790 | AQGNTTRGLAQ | 10379 | GNTTRGL | 0.713945 | 1.078842 |
| SyS60 | 1202 | GCCCAACTCAACCTCACCGCCACCAACGCACAG | 5791 | AQLNLTATNAQ | 10380 | LNLTATN | 0.71358 | 0.152602 |
| SyS61 | 1203 | GCCCAAAGCGGCGGTCAGCACCACCGACGCACAG | 5792 | AQSGVSTTDAQ | 10381 | SGVSTTD | 0.711249 | -0.01534 |
| GP31 | 1204 | GCCCAATATGCTAAGACGTTGGCTATGGCACAG | 5793 | AQYAKTLAMAQ | 10382 | YAKTLAM | 0.710703 | 0.312387 |
| TS49 | 1205 | GCCCAAATGAACCACACCAAACCACCGCACAG | 5794 | AQMNHTKPTAQ | 10383 | MNHTKPT | 0.710702 | 1.058209 |
| TS50 | 1206 | GCCCAAGCTAATGCTACGAGGAATTCTGCACAG | 5795 | AQANATRNSAQ | 10384 | ANATRNS | 0.707423 | 0.724059 |
| TS51 | 1207 | GCCCAACAAAACCAAACCAAAATCACCGCACAG | 5796 | AQQNQTKITAQ | 10385 | QNQTKIT | 0.707235 | 1.179467 |
| TS52 | 1208 | GCCCAATCTAATGCTATTAAGGCTACGGCACAG | 5797 | AQSNAIKATAQ | 10386 | SNAIKAT | 0.70699 | 0.910476 |
| SyS62 | 1209 | GCCCAATATCCTGATAATTATGGTAAGGCACAG | 5798 | AQYPDNYGKAQ | 10387 | YPDNYGK | 0.706343 | 0.147368 |
| TS53 | 1210 | GCCCAAGGCAACACCACCATCAGAAGCGCACAG | 5799 | AQGNTTIRSAQ | 10388 | GNTTIRS | 0.705947 | 1.078768 |
| SyP28 | 1211 | GCCCAACTGGGTCTTACGGGTGCGGTTGCACAG | 5800 | AQLGLTGAVAQ | 10389 | LGLTGAV | 0.705628 | -0.04044 |
| TS54 | 1212 | GCCCAAGCGAATAGTACGCGTATTCTGGCACAG | 5801 | AQANSTRILAQ | 10390 | ANSTRIL | 0.704068 | 1.203143 |
| TS55 | 1213 | GCCCAAGATAATGCGATTCGTGCGCAGGCACAG | 5802 | AQDNAIRAQAQ | 10391 | DNAIRAQ | 0.703945 | 0.267003 |
| TS56 | 1214 | GCCCAAACGAATTATACTAAGCTTATGGCACAG | 5803 | AQTNYTKLMAQ | 10392 | TNYTKLM | 0.702916 | 0.470577 |
| GS38 | 1215 | GCCCAACAACATAGTCCTAGTAGTTATGCACAG | 5804 | AQHNSPSSYAQ | 10393 | HNSPSSY | 0.70154 | -0.08846 |
| TS57 | 1216 | GCCCAAGAGAATATGGTTCGGTGTCGTGGCACAG | 5805 | AQENMVRSVAQ | 10394 | ENMVRSV | 0.700139 | 0.554646 |
| TS58 | 1217 | GCCCAAACCAACAACATCAAAAGCTACGCACAG | 5806 | AQTNNIKSYAQ | 10395 | TNNIKSY | 0.698201 | 1.233802 |
| TS59 | 1218 | GCCCAACCAACTAATTCGACGAGGCCTGTGGCACAG | 5807 | AQTNSTRPVAQ | 10396 | TNSTRPV | 0.696679 | 0.516411 |
| GP34 | 1219 | GCCCAACATACGGCTCCGCCTCATCCTGCACAG | 5808 | AQHTAPPHPAQ | 10397 | HTAPPHP | 0.695156 | -0.01516 |
| SyS63 | 1220 | GCCCAAGCCCTCAGCCAAAACACCAGCGCACAG | 5809 | AQALSQNTSAQ | 10398 | ALSQNTS | 0.692869 | 0.222209 |
| TS60 | 1221 | GCCCAACCGAATGTGACTAAGAATGCTGCACAG | 5810 | AQPNVTKNAAQ | 10399 | PNVTKNA | 0.692038 | -0.01089 |
| GP36 | 1222 | GCCCAACTTGATACGCTGACGGGTTATGCACAG | 5811 | AQLDTLTGYAQ | 10400 | LDTLTGY | 0.690142 | 0.248937 |
| TS61 | 1223 | GCCCAACCTAATAGTAGTGCGTTCTGTTGCACAG | 5812 | AQPNSVRSVAQ | 10401 | PNSVRSV | 0.689082 | 0.294508 |
| SyS64 | 1224 | GCCCAAACCAGCAGCCACCTCCCCACGCACAG | 5813 | AQTSSHLPHAQ | 10402 | TSSHLPH | 0.688469 | 0.465642 |
| GS40 | 1225 | GCCCAAGTTCTTCATGGTGGTAATGATGCACAG | 5814 | AQVLHGGNDAQ | 10403 | VLHGGND | 0.687991 | 0.121136 |

FIG. 33 (Continued)

| | | | | | | | | |
|---|---|---|---|---|---|---|---|---|
| TS62 | 1226 | GCCCAAAGCAACTACGTCAAAAGCGCCGCACAG | 5815 | AQSNYVKSAAQ | 10404 | SNYVKSA | 0.687276 | 0.620002 |
| TS63 | 1227 | GCCCAAGACAACAACAGCACCAGATGGGCACAG | 5816 | AQDNNSTRWAQ | 10405 | DNNSTRW | 0.687057 | 0.34274 |
| GP37 | 1228 | GCCCAAACTGTGTGATGAAGGGTTTACTGCACAG | 5817 | AQTVMKGFTAQ | 10406 | TVMKGFT | 0.687036 | 0.307342 |
| SyS65 | 1229 | GCCCAAAGCCACACCCTCAGCACCCTCGCACAG | 5818 | AQSHTLSTLAQ | 10407 | SHTLSTL | 0.686592 | 0.104749 |
| SyS66 | 1230 | GCCCAACCTGGTCCTCAGCAGGCGAAGGCACAG | 5819 | AQPGPQQAKAQ | 10408 | PGPQQAK | 0.685365 | 0.364455 |
| GS41 | 1231 | GCCCAAACTTTTGGGACGTCTAAGTTGGCACAG | 5820 | AQTFGTSKLAQ | 10409 | TFGTSKL | 0.684153 | 0.041123 |
| SyS67 | 1232 | GCCCAAAGCAAGCGCCGTCACCAACAGAGCACAG | 5821 | AQSNAVTNRAQ | 10410 | SNAVTNR | 0.683838 | 2.350107 |
| GP38 | 1233 | GCCCAATTGTCTATGTCGACGGTGCCTGCACAG | 5822 | AQLSMSTVPAQ | 10411 | LSMSTVP | 0.682136 | 0.463832 |
| GS42 | 1234 | GCCCAAAGGCGTTATGATGGTAGGGAGGCACAG | 5823 | AQRRYDGREAQ | 10412 | RRYDGRE | 0.681722 | -0.04926 |
| TS64 | 1235 | GCCCAAACCAACAGCACCAAAAACATCGCACAG | 5824 | AQTNSTKNIAQ | 10413 | TNSTKNI | 0.678439 | 2.312433 |
| GS43 | 1236 | GCCCAAATTAATGCTCAGTGGTCTGCGGCACAG | 5825 | AQINAQWSAAQ | 10414 | INAQWSA | 0.672085 | 0.020513 |
| SyS68 | 1237 | GCCCAAGCCAAACCAGCAACGACCCCGCACAG | 5826 | AQAQTSNDPAQ | 10415 | AQTSNDP | 0.669325 | 0.289379 |
| TS65 | 1238 | GCCCAAACGAATGAGACTAGGAGGATGGTGGCACAG | 5827 | AQTNETRMVAQ | 10416 | TNETRMV | 0.669307 | 0.50614 |
| TS66 | 1239 | GCCCAAGCCAACGCCACCAGAGGCGTCGCACAG | 5828 | AQANATRGVAQ | 10417 | ANATRGV | 0.667153 | 0.206293 |
| SyS69 | 1240 | GCCCAAGCGGATGTGAATGCTTCGGGGTGCACAG | 5829 | AQADVNASGAQ | 10418 | ADVNASG | 0.666574 | -0.04779 |
| GP39 | 1241 | GCCCAACTTAGTGAGCGGAATTATGTGGCACAG | 5830 | AQLSERNYVAQ | 10419 | LSERNYV | 0.665675 | 0.088761 |
| GP40 | 1242 | GCCCAAAGTGGTGAGCTTGCGCGGGCGGCACAG | 5831 | AQSGELARAAQ | 10420 | SGELARA | 0.663381 | 0.117091 |
| TS67 | 1243 | GCCCAAGGGAATACTGCTAAGAATATTGCACAG | 5832 | AQGNTAKNIAQ | 10421 | GNTAKNI | 0.662988 | 0.420415 |
| TS68 | 1244 | GCCCAAGACAACGCCGTCAGACCCCTCGCACAG | 5833 | AQDNAVRPLAQ | 10422 | DNAVRPL | 0.662435 | 0.259838 |
| SyS70 | 1245 | GCCCAAATGATGCTCAGCGGCCTCAACGCACAG | 5834 | AQMMLSGLNAQ | 10423 | MMLSGLN | 0.660837 | 0.004421 |
| TS70 | 1246 | GCCCAACCCAACACCATCAGAAACGTCGCACAG | 5835 | AQPNTIRNVAQ | 10424 | PNTIRNV | 0.660528 | 0.629407 |
| TS71 | 1247 | GCCCAAGAGAATTTGACGCGTGGGGTGGCACAG | 5836 | AQENLTRGVAQ | 10425 | ENLTRGV | 0.659884 | 0.188249 |
| GP41 | 1248 | GCCCAATTTAGTGCTCGGAGTACGGGGGCACAG | 5837 | AQFSARSTGAQ | 10426 | FSARSTG | 0.659095 | 0.105157 |
| TS72 | 1249 | GCCCAAGAAAACGCCACCAGAACCTACGCACAG | 5838 | AQENATRTYAQ | 10427 | ENATRTY | 0.657305 | 1.105462 |
| TS73 | 1250 | GCCCAAGGCAACAGCACCAGAATGAACGCACAG | 5839 | AQGNSTRMNAQ | 10428 | GNSTRMN | 0.656999 | 0.923491 |
| TS74 | 1251 | GCCCAAGGGAATTCTACTAAGTCTCCTGCACAG | 5840 | AQGNSTKSPAQ | 10429 | GNSTKSP | 0.656908 | 0.716749 |
| GS44 | 1252 | GCCCAAATGCAAACCACCCTCCACCTCGCACAG | 5841 | AQMQTTLHLAQ | 10430 | MQTTLHL | 0.656525 | -0.09797 |
| SyS71 | 1253 | GCCCAAAACCCACCCTCATCACCCTCGCACAG | 5842 | AQNPTLITLAQ | 10431 | NPTLITL | 0.655924 | 0.146275 |
| SyS72 | 1254 | GCCCAACTTATTTCTGGTCATGCGCAGGCACAG | 5843 | AQLISGHAQAQ | 10432 | LISGHAQ | 0.655121 | 0.171881 |
| SyS73 | 1255 | GCCCAATTCAACCAAGTCAGAAGCCTCGCACAG | 5844 | AQFNQVRSLAQ | 10433 | FNQVRSL | 0.65493 | 0.025869 |
| GS45 | 1256 | GCCCAAATGAACATCCTCAGAGAGAGTCGCACAG | 5845 | AQMNILREVAQ | 10434 | MNILREV | 0.654097 | -0.09985 |
| GP42 | 1257 | GCCCAAAGTGCTATGATGCGTGGTGTTGCACAG | 5846 | AQSAMMRGVAQ | 10435 | SAMMRGV | 0.653566 | -0.06697 |

FIG. 33 (Continued)

| | | | | | | | | |
|---|---|---|---|---|---|---|---|---|
| SyS74 | 1258 | GCCCAACCCATGCTCAGCAGCCCAGCGCACAG | 5847 | AQPMLSSPSAQ | 10436 | PMLSSPS | 0.652269 | -0.07485 |
| TS75 | 1259 | GCCCAACAGAATAATACGCTTAGGTCGGCACAG | 5848 | AQQNNTLRSAQ | 10437 | QNNTLRS | 0.651653 | 0.733737 |
| GS46 | 1260 | GCCCAAAGGCATTCGGATCCGGTGGAGGCACAG | 5849 | AQRHSDPVEAQ | 10438 | RHSDPVE | 0.65144 | -0.07331 |
| GS47 | 1261 | GCCCAAGTGAATACGACGTTTCTACGCACAG | 5850 | AQVNTTFSTAQ | 10439 | VNTTFST | 0.65142 | -0.00755 |
| TS76 | 1262 | GCCCAAATCAACAGCACCAGAGGCATCGCACAG | 5851 | AQINSTRGIAQ | 10440 | INSTRGI | 0.650374 | 0.746658 |
| TS77 | 1263 | GCCCAACCAACGCCGTCAGAGACCTCGCACAG | 5852 | AQTNAVRDLAQ | 10441 | TNAVRDL | 0.649865 | 0.608962 |
| TS78 | 1264 | GCCCAATCTAATAGTACTAGGCTGTCGGCACAG | 5853 | AQSNSTRLSAQ | 10442 | SNSTRLS | 0.649567 | 1.213202 |
| SyS75 | 1265 | GCCCAAACGTCTATTGCTGGGTCGTTTGCACAG | 5854 | AQTSIAGSFAQ | 10443 | TSIAGSF | 0.647793 | 0.065679 |
| SS27 | 1266 | GCCCAACTCGGCAGCACCTACCCCAGAGCACAG | 5855 | AQLGSTYPRAQ | 10444 | LGSTYPR | 0.644533 | -0.23408 |
| SyS76 | 1267 | GCCCAAGCCAACGTCACCACCCAAAGAGCACAG | 5856 | AQANVTTQRAQ | 10445 | ANVTTQR | 0.643299 | 0.597905 |
| TS79 | 1268 | GCCCAAAGCAACAGCGTCAGACTCAGCGCACAG | 5857 | AQSNSVRLSAQ | 10446 | SNSVRLS | 0.641635 | 0.657122 |
| GS48 | 1269 | GCCCAAGCTACGAATGAGCGTGATCGGGCACAG | 5858 | AQATNEPDRAQ | 10447 | ATNEPDR | 0.641008 | -0.06388 |
| GS49 | 1270 | GCCCAAAGAATGAACCCGAACAAAGCGCACAG | 5859 | AQRMNPEQSAQ | 10448 | RMNPEQS | 0.640866 | 0.123792 |
| GS50 | 1271 | GCCCAATCGGTTAGTGGTTCGGCTAATGCACAG | 5860 | AQSVSGSANAQ | 10449 | SVSGSAN | 0.640362 | -0.07276 |
| GS51 | 1272 | GCCCAACCGAGTAATAGTACTACGCCGTGCACAG | 5861 | AQPSNSTTRAQ | 10450 | PSNSTTR | 0.639664 | 0.069013 |
| GP43 | 1273 | GCCCAACTTTTCATGGTACGCATGAGGCACAG | 5862 | AQLFHGTHEAQ | 10451 | LFHGTHE | 0.639176 | 0.186361 |
| SyS77 | 1274 | GCCCAACCCCAACTCGGCAGCACCAAAGCACAG | 5863 | AQPQLGSTKAQ | 10452 | PQLGSTK | 0.638022 | 0.187838 |
| SyS78 | 1275 | GCCCAACCATCAGCGCAACAGACTCGCACAG | 5864 | AQPISANRLAQ | 10453 | PISANRL | 0.637814 | -0.06902 |
| SyS79 | 1276 | GCCCAAAATTCGGGTAATCTTTCTATGGCACAG | 5865 | AQNSGNLSMAQ | 10454 | NSGNLSM | 0.637206 | 0.248456 |
| SyS80 | 1277 | GCCCAAAAGGTTGAGGCTATTGGGATGGCACAG | 5866 | AQKVEAIGMAQ | 10455 | KVEAIGM | 0.63585 | 0.196256 |
| SyS81 | 1278 | GCCCAAAAGACTTTGCTTAATAGTGTTGCACAG | 5867 | AQKTLLNSVAQ | 10456 | KTLLNSV | 0.635567 | -0.07329 |
| GS52 | 1279 | GCCCAAAATGCTATGGATCTTAAGGTGGCACAG | 5868 | AQNAMDLKVAQ | 10457 | NAMDLKV | 0.633592 | -0.04013 |
| SyS82 | 1280 | GCCCAAATGATGGGTAATGGGTCTTCGGCACAG | 5869 | AQMMGNGSSAQ | 10458 | MMGNGSS | 0.632846 | -0.04467 |
| TS80 | 1281 | GCCCAAAGCAACAGCACCAAAGCCCTCGCACAG | 5870 | AQSNSTKALAQ | 10459 | SNSTKAL | 0.630646 | 1.07834 |
| TS81 | 1282 | GCCCAATCTAATAGTACGGCGGGTACGGCACAG | 5871 | AQSNSTRGTAQ | 10460 | SNSTRGT | 0.630359 | 1.275033 |
| GS53 | 1283 | GCCCAAAGCCTCAGCAGCCTCCACGTCGCACAG | 5872 | AQSLSSLHVAQ | 10461 | SLSSLHV | 0.629137 | -0.08892 |
| SyS83 | 1284 | GCCCAAACCCTCAGCGGCGCCCTCACCGCACAG | 5873 | AQTLSGALTAQ | 10462 | TLSGALT | 0.628275 | 0.306806 |
| TS82 | 1285 | GCCCAACCGAATACGGTGAGGAATAATGCACAG | 5874 | AQPNTVRNNAQ | 10463 | PNTVRNN | 0.627943 | 1.035691 |
| TS83 | 1286 | GCCCAAAATAATAATGTGAAGATGACTGCACAG | 5875 | AQNNNVKMTAQ | 10464 | NNNVKMT | 0.627302 | 0.23573 |
| GP46 | 1287 | GCCCAAAGTGTTGCTAAGCCTTTTATGGCACAG | 5876 | AQSVAKPFMAQ | 10465 | SVAKPFM | 0.627075 | 0.17477 |
| SyP29 | 1288 | GCCCAAACGCAGACGACTCGGCTTTCGGCACAG | 5877 | AQTQTTRLSAQ | 10466 | TQTTRLS | 0.625657 | -0.04236 |
| TS84 | 1289 | GCCCAAAATAATGCGACTCGGGGTGGGGGCACAG | 5878 | AQNNATRGGAQ | 10467 | NNATRGG | 0.622765 | 0.76061 |

FIG. 33 (Continued)

| | | | | | | | | |
|---|---|---|---|---|---|---|---|---|
| TS85 | 1290 | GCCCAAACCAACACCACCGCCAGAATCGCACAG | 5879 | AQTNTTARIAQ | 10468 | TNTTARI | 0.621665 | 0.649749 |
| TS86 | 1291 | GCCCAAGAGAATAGTATTCGGACTATTGCACAG | 5880 | AQENSIRTIAQ | 10469 | ENSIRTI | 0.619021 | 0.750947 |
| GS55 | 1292 | GCCCAAATTAGGGAGACTTCTGGGAAGGCACAG | 5881 | AQIRETSGKAQ | 10470 | IRETSGK | 0.618732 | -0.00781 |
| SyS84 | 1293 | GCCCAAAGCATCTACTACCACCGAAGCACAG | 5882 | AQSIYYHTEAQ | 10471 | SIYYHTE | 0.618441 | -0.07907 |
| SyS85 | 1294 | GCCCAAGTCCTCGACAACAGCGGCCAAGCACAG | 5883 | AQVLDNSGQAQ | 10472 | VLDNSGQ | 0.618183 | -0.1396 |
| GS56 | 1295 | GCCCAAAGCCACAACATGACCATCAGAGCACAG | 5884 | AQSHNMTIRAQ | 10473 | SHNMTIR | 0.614114 | 0.473069 |
| SyS86 | 1296 | GCCCAAACCATCCCAGCGCCGGCAAAGCACAG | 5885 | AQTIPSAGKAQ | 10474 | TIPSAGK | 0.612816 | 0.150798 |
| SyP30 | 1297 | GCCCCACCTAGGCATACTTTGAGTCAGGCACAG | 5886 | APPRHTLSQAQ | 10475 | PRHTLSQ | 0.60799 | -0.00929 |
| SyS87 | 1298 | GCCCAATCGCTTAATGTGCGAGGATGTGGCACAG | 5887 | AQSLNVQDVAQ | 10476 | SLNVQDV | 0.607203 | 0.057645 |
| GP48 | 1299 | GCCCAATATCAGTCTCTGGCTAATCCGGCACAG | 5888 | AQYQSLANPAQ | 10477 | YQSLANP | 0.607005 | 0.036857 |
| GS58 | 1300 | GCCCAAATTCTGAATATGTCTACGGATGCACAG | 5889 | AQILNMSTDAQ | 10478 | ILNMSTD | 0.606834 | -0.1435 |
| SyS88 | 1301 | GCCCAAGTCCTCCACCTCGGCCACAGCGCACAG | 5890 | AQVLHLGHSAQ | 10479 | VLHLGHS | 0.605932 | 0.104512 |
| SyS89 | 1302 | GCCCAAGGTGTTACTCAGACTCCGCGTGCACAG | 5891 | AQGVTQTPRAQ | 10480 | GVTQTPR | 0.6059 | 0.243764 |
| TS88 | 1303 | GCCCAAACCAACGACACCAGAGAATCGCACAG | 5892 | AQTNDTRRIAQ | 10481 | TNDTRRI | 0.604587 | 1.419603 |
| SyS90 | 1304 | GCCCAACAAACCGACCACCAGCAGAGCACAG | 5893 | AQQTDHTSRAQ | 10482 | QTDHTSR | 0.604031 | 0.279435 |
| TS90 | 1305 | GCCCAAAAGAATGAGAATTAAGAATGTGGCACAG | 5894 | AQKNEIKNVAQ | 10483 | KNEIKNV | 0.603838 | 0.384157 |
| GP49 | 1306 | GCCCAATGGACTGGTAATGAGAGGCTTGCACAG | 5895 | AQWTGNERLAQ | 10484 | WTGNERL | 0.603412 | -0.0735 |
| SyS91 | 1307 | GCCCAAGGTAAGAGTGATGTCTATGCGGGCACAG | 5896 | AQGKSDAMRAQ | 10485 | GKSDAMR | 0.603322 | 0.227787 |
| TS91 | 1308 | GCCCAAGGGAATGCGACTCGTACTTATGCACAG | 5897 | AQGNATRTYAQ | 10486 | GNATRTY | 0.602016 | 0.746216 |
| SyS92 | 1309 | GCCCAAGCCAGCAACCTCGGCCTCCCCGCACAG | 5898 | AQASNLGLPAQ | 10487 | ASNLGLP | 0.600647 | 0.212421 |
| SyS93 | 1310 | GCCCAAAGCAGCCTCAGCGGCAGCCCCGCACAG | 5899 | AQSSLSGSPAQ | 10488 | SSLSGSP | 0.599424 | 0.229985 |
| SyS94 | 1311 | GCCCAAGCCGCGTCAACCAAGGCGTCGCACAG | 5900 | AQAAVNQGVAQ | 10489 | AAVNQGV | 0.599283 | 0.365845 |
| GS60 | 1312 | GCCCAAGACCAAAACCAACCCAGAGAAGCACAG | 5901 | AQDQNQPREAQ | 10490 | DQNQPRE | 0.59872 | -0.04719 |
| GS61 | 1313 | GCCCAACTCACCCAAGACAAACAAGCCGCACAG | 5902 | AQLTQDKQAAQ | 10491 | LTQDKQA | 0.59843 | 0.025835 |
| SyS95 | 1314 | GCCCAATTCGGCAGCAACGAACAACGCACACAG | 5903 | AQFGSNEHNAQ | 10492 | FGSNEHN | 0.59773 | 0.246632 |
| GS62 | 1315 | GCCCAACTGAATCAGCCGAATGTGCGGGCACAG | 5904 | AQLNQPNVRAQ | 10493 | LNQPNVR | 0.59703 | -0.00684 |
| TS92 | 1316 | GCCCAAATGAATACTACACGCGTAATCTGGCACAG | 5905 | AQMNTTRNLAQ | 10494 | MNTTRNL | 0.596819 | 0.171297 |
| TS93 | 1317 | GCCCAAACTAATTCTACTAGGACGAGTGCACAG | 5906 | AQTNSTRTSAQ | 10495 | TNSTRTS | 0.596817 | 0.587886 |
| SyS96 | 1318 | GCCCAATTGAGCTTTCGCATGTGCCTGCACAG | 5907 | AQFELSHVPAQ | 10496 | FELSHVP | 0.595373 | 0.012267 |
| SyS97 | 1319 | GCCCAAGAAGGCCTCGGCAACGCCGCGCACAG | 5908 | AQEGLGNAAAQ | 10497 | EGLGNAA | 0.59339 | -0.02116 |
| SyS98 | 1320 | GCCCAACTCACCGTCACCCTCAACCACGCACAG | 5909 | AQLTVTLNHAQ | 10498 | LTVTLNH | 0.593104 | 0.120283 |
| SyS99 | 1321 | GCCCAATTTGGGAATGCGGATTCAGTCTGCACAG | 5910 | AQFGNAIQSAQ | 10499 | FGNAIQS | 0.593063 | 0.321334 |

FIG. 33 (Continued)

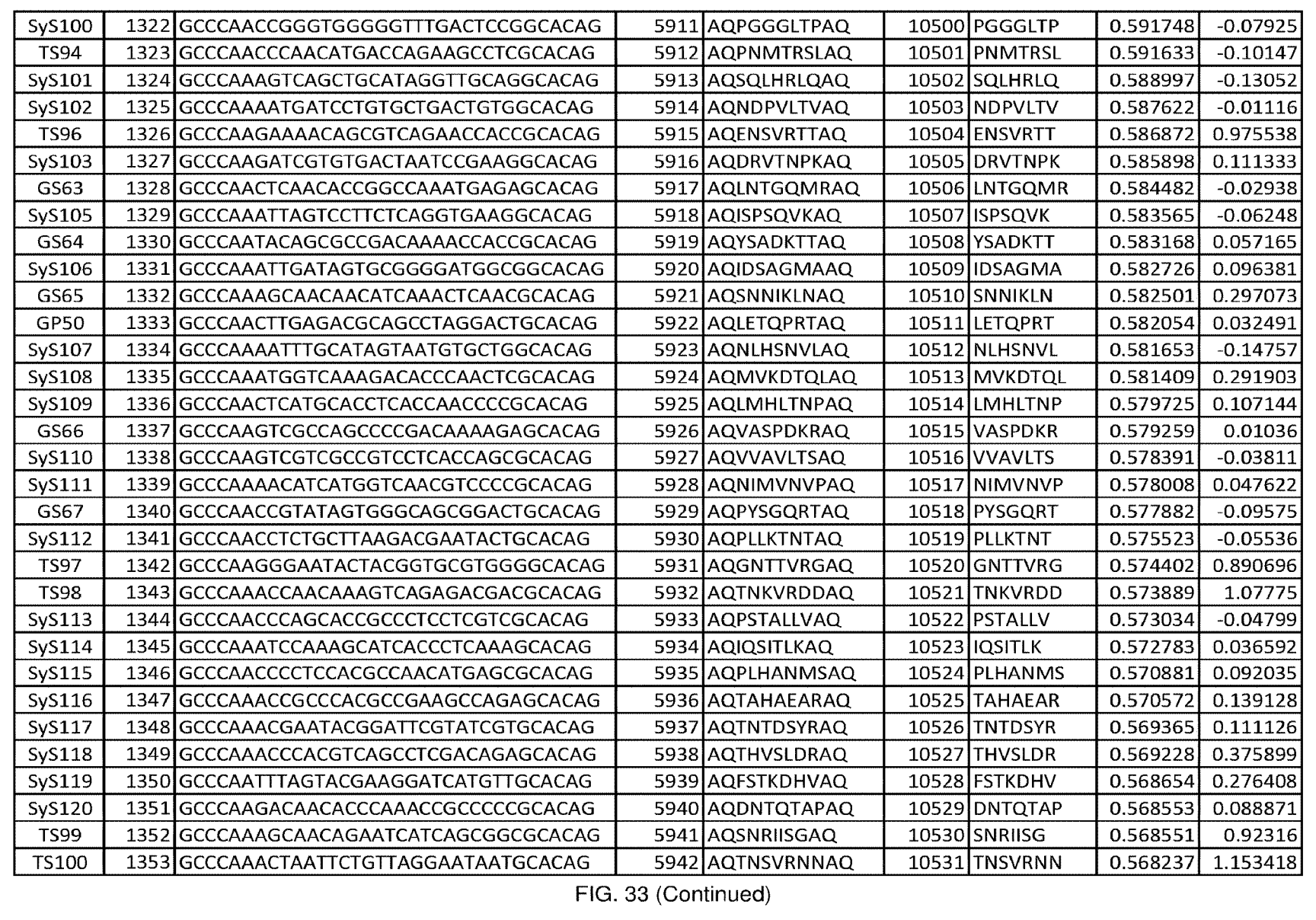

| | | | | | | | | |
|---|---|---|---|---|---|---|---|---|
| SyS100 | 1322 | GCCCAACCGGGTGGGGTTTGACTCCGGCACAG | 5911 | AQPGGGLTPAQ | 10500 | PGGGLTP | 0.591748 | -0.07925 |
| TS94 | 1323 | GCCCAACCCAACATGACCAGAAGCCTGCACAG | 5912 | AQPNMTRSLAQ | 10501 | PNMTRSL | 0.591633 | -0.10147 |
| SyS101 | 1324 | GCCCAAAGTCAGCTGCATAGGTTGCAGGCACAG | 5913 | AQSQLHRLQAQ | 10502 | SQLHRLQ | 0.588997 | -0.13052 |
| SyS102 | 1325 | GCCCAAAATGATCCTGTGCTGACTGTGGCACAG | 5914 | AQNDPVLTVAQ | 10503 | NDPVLTV | 0.587622 | -0.01116 |
| TS96 | 1326 | GCCCAAGAGAAACAGCGTCAGAACCACCGCACAG | 5915 | AQENSVRTTAQ | 10504 | ENSVRTT | 0.586872 | 0.975538 |
| SyS103 | 1327 | GCCCAAGATCGTGTGACTAATCCGAAGGCACAG | 5916 | AQDRVTNPKAQ | 10505 | DRVTNPK | 0.585898 | 0.111333 |
| GS63 | 1328 | GCCCAACTCAACACCGGCCAAATGAGAGGCACAG | 5917 | AQLNTGQMRAQ | 10506 | LNTGQMR | 0.584482 | -0.02938 |
| SyS105 | 1329 | GCCCAAATTAGTCCTTCTCAGGTGAAGGCACAG | 5918 | AQISPSQVKAQ | 10507 | ISPSQVK | 0.583565 | -0.06248 |
| GS64 | 1330 | GCCCAATACAGCGCCGACAAAACCACCGCACAG | 5919 | AQYSADKTTAQ | 10508 | YSADKTT | 0.583168 | 0.057165 |
| SyS106 | 1331 | GCCCAAATTGATAGTGCGGGGATGGCGGCACAG | 5920 | AQIDSAGMAAQ | 10509 | IDSAGMA | 0.582726 | 0.096381 |
| GS65 | 1332 | GCCCAAAGCAACAACATCAAACTCAACGCACAG | 5921 | AQSNNIKLNAQ | 10510 | SNNIKLN | 0.582501 | 0.297073 |
| GP50 | 1333 | GCCCAACTTGAGACGCAGCCTAGGACTGCACAG | 5922 | AQLETQPRTAQ | 10511 | LETQPRT | 0.582054 | 0.032491 |
| SyS107 | 1334 | GCCCAAAATTTGCATAGTAATGTGCTGGCACAG | 5923 | AQNLHSNVLAQ | 10512 | NLHSNVL | 0.581653 | -0.14757 |
| SyS108 | 1335 | GCCCAAATGGTCAAAGACACCCAACTCGCACAG | 5924 | AQMVKDTQLAQ | 10513 | MVKDTQL | 0.581409 | 0.291903 |
| SyS109 | 1336 | GCCCAACTCATGCACCTCACCAACCCCGCACAG | 5925 | AQLMHLTNPAQ | 10514 | LMHLTNP | 0.579725 | 0.107144 |
| GS66 | 1337 | GCCCAAGTCGCCAGCCCGACAAAAGAGCACAG | 5926 | AQVASPDKRAQ | 10515 | VASPDKR | 0.579259 | 0.01036 |
| SyS110 | 1338 | GCCCAAGTCGTCGCCGTCCTCACCAGCGCACAG | 5927 | AQVVAVLTSAQ | 10516 | VVAVLTS | 0.578391 | -0.03811 |
| SyS111 | 1339 | GCCCAAAAACATCATGGTCAACGTCCCGCACAG | 5928 | AQNIMVNVPAQ | 10517 | NIMVNVP | 0.578008 | 0.047622 |
| GS67 | 1340 | GCCCAACCGTATAGTGGGCAGCGGACTGCACAG | 5929 | AQPYSGQRTAQ | 10518 | PYSGQRT | 0.577882 | -0.09575 |
| SyS112 | 1341 | GCCCAACCTCTGCTTAAGACGAATACTGCACAG | 5930 | AQPLLKTNTAQ | 10519 | PLLKTNT | 0.575523 | -0.05536 |
| TS97 | 1342 | GCCCAAGGGAATACTACGGTGCGTGGGGCACAG | 5931 | AQGNTTVRGAQ | 10520 | GNTTVRG | 0.574402 | 0.890696 |
| TS98 | 1343 | GCCCAAAACCAACAAAGTCAGAGACGACGCACAG | 5932 | AQTNKVRDDAQ | 10521 | TNKVRDD | 0.573889 | 1.07775 |
| SyS113 | 1344 | GCCCAACCCAGCACCGCCCTCCTCGTCGCACAG | 5933 | AQPSTALLVAQ | 10522 | PSTALLV | 0.573034 | -0.04799 |
| SyS114 | 1345 | GCCCAAATCCAAAGCATCACCCTCAAAGCACAG | 5934 | AQIQSITLKAQ | 10523 | IQSITLK | 0.572783 | 0.036592 |
| SyS115 | 1346 | GCCCAACCCTCCAGCCCAACATGAGCGCACAG | 5935 | AQPLHANMSAQ | 10524 | PLHANMS | 0.570881 | 0.092035 |
| SyS116 | 1347 | GCCCAAACGCCCAGCGCGAAGCCAGAGCACAG | 5936 | AQTAHAEARAQ | 10525 | TAHAEAR | 0.570572 | 0.139128 |
| SyS117 | 1348 | GCCCAAACGAATACGGATTCGTATCGTGCACAG | 5937 | AQTNTDSYRAQ | 10526 | TNTDSYR | 0.569365 | 0.111126 |
| SyS118 | 1349 | GCCCAAACCCACGTCAGCCTCGACAGAGCACAG | 5938 | AQTHVSLDRAQ | 10527 | THVSLDR | 0.569228 | 0.375899 |
| SyS119 | 1350 | GCCCAATTTAGTACGAAGGATCATGTTGCACAG | 5939 | AQFSTKDHVAQ | 10528 | FSTKDHV | 0.568654 | 0.276408 |
| SyS120 | 1351 | GCCCAAGACAACACCAACCGCCCCGCCGCACAG | 5940 | AQDNTQTAPAQ | 10529 | DNTQTAP | 0.568553 | 0.088871 |
| TS99 | 1352 | GCCCAAAGCAACAGAATCATCAGCGGCGCACAG | 5941 | AQSNRIISGAQ | 10530 | SNRIISG | 0.568551 | 0.92316 |
| TS100 | 1353 | GCCCAAAACTAATTCTGTTAGGAATAATGCACAG | 5942 | AQTNSVRNNAQ | 10531 | TNSVRNN | 0.568237 | 1.153418 |

FIG. 33 (Continued)

| | | | | | | | | |
|---|---|---|---|---|---|---|---|---|
| TS101 | 1354 | GCCCAAAGCAACGAAGTCAGAAACATGGCACAG | 5943 | AQSNEVRNMAQ | 10532 | SNEVRNM | 0.567847 | 0.744396 |
| SyS121 | 1355 | GCCCAAGAACTCTACAAACCCAGCAGAGCACAG | 5944 | AQELYKPSRAQ | 10533 | ELYKPSR | 0.567258 | -0.07221 |
| GS69 | 1356 | GCCCAATGGATTACGGGGGTGCGAGTGCACAG | 5945 | AQWITGGASAQ | 10534 | WITGGAS | 0.567159 | 0.345096 |
| TS102 | 1357 | GCCCAAAACAACACAGCGTCAGACCCACCGCACAG | 5946 | AQNNSVRPTAQ | 10535 | NNSVRPT | 0.566945 | 0.624336 |
| GS70 | 1358 | GCCCAACACACGCCGTCCTCAGAACCGCACAG | 5947 | AQHTAVLRTAQ | 10536 | HTAVLRT | 0.565911 | -0.03197 |
| SyS122 | 1359 | GCCCAAAATACTTTGTCTCTTGTCTCCTGCACAG | 5948 | AQNTLSLAPAQ | 10537 | NTLSLAP | 0.564955 | 0.155579 |
| SyS123 | 1360 | GCCCAACCCAACGCCAGCGTCAACAGCGCACAG | 5949 | AQPNASVNSAQ | 10538 | PNASVNS | 0.564885 | 0.097515 |
| GS71 | 1361 | GCCCAAGTTACTGGTGGGAATACTTATGCACAG | 5950 | AQVTGGNTYAQ | 10539 | VTGGNTY | 0.564099 | -0.05591 |
| SyS124 | 1362 | GCCCAAGTCAACGAAAACCTCATCGAAGCACAG | 5951 | AQVNENLIEAQ | 10540 | VNENLIE | 0.563902 | -0.13408 |
| SyS125 | 1363 | GCCCAAGTTTGACGACTCATTCGAATGCACAG | 5952 | AQVLTTHSNAQ | 10541 | VLTTHSN | 0.563552 | -0.14541 |
| GS72 | 1364 | GCCCAACACACCCAACTCCCCTCACGCACAG | 5953 | AQHTQLPLTAQ | 10542 | HTQLPLT | 0.562802 | -0.07685 |
| SyS126 | 1365 | GCCCAACGGCAGTCTCTTGAGGCGTTGGCACAG | 5954 | AQRQSLEALAQ | 10543 | RQSLEAL | 0.562715 | -0.07009 |
| SyS127 | 1366 | GCCCAACCCGACGTCACCGAAGGCAGAGCACAG | 5955 | AQPDVTEGRAQ | 10544 | PDVTEGR | 0.560929 | -0.0307 |
| SyS128 | 1367 | GCCCAACCGACTAATATATGCTTGATGCACAG | 5956 | AQPTNIMLDAQ | 10545 | PTNIMLD | 0.560313 | -0.07894 |
| SyS129 | 1368 | GCCCAACCAACCAACATGAGCGCCATGAATCGCACAG | 5957 | AQPNMSAMIAQ | 10546 | PNMSAMI | 0.559451 | 0.270198 |
| SyS130 | 1369 | GCCCAAATTATGAATGGTCAGGCTCTGGCACAG | 5958 | AQIMNGQALAQ | 10547 | IMNGQAL | 0.558677 | 0.015194 |
| TS103 | 1370 | GCCCAAAATAATAATTGACGCGTTTTGCACAG | 5959 | AQNNNSTRFAQ | 10548 | NNNSTRF | 0.558656 | 0.432697 |
| TS104 | 1371 | GCCCAAGCCAACGTCACCAGAAGCACCGCACAG | 5960 | AQANVTRSTAQ | 10549 | ANVTRST | 0.558653 | 0.70621 |
| SyS131 | 1372 | GCCCAACAGAATCTTGGTCTTAATGTGGCACAG | 5961 | AQQNLGLNVAQ | 10550 | QNLGLNV | 0.558202 | -0.12084 |
| SyS132 | 1373 | GCCCAACAAGCCAAATGAGCAGCGCCGGCACAG | 5962 | AQQAQMSSAAQ | 10551 | QAQMSSA | 0.557238 | 0.147605 |
| SyS133 | 1374 | GCCCAACTCACCATGGCCACCAACGTCGCACAG | 5963 | AQLTMATNVAQ | 10552 | LTMATNV | 0.556779 | 0.286866 |
| SyS134 | 1375 | GCCCAAGATCGTGATTCTGTGCAGAATGCACAG | 5964 | AQDRDSVQNAQ | 10553 | DRDSVQN | 0.55654 | -0.05483 |
| GS73 | 1376 | GCCCAAGTCAACCCCACCAACAACCTCGCACAG | 5965 | AQVNPTNNLAQ | 10554 | VNPTNNL | 0.555076 | -0.00968 |
| GP51 | 1377 | GCCCAACCGTCTTTACGACTATGAGTGCACAG | 5966 | AQPSFTTMSAQ | 10555 | PSFTTMS | 0.554811 | 0.065283 |
| GS74 | 1378 | GCCCAAAGGGAGAGCGCCTATTCCTAAGGCACAG | 5967 | AQRETPIPKAQ | 10556 | RETPIPK | 0.553803 | -0.0639 |
| SyS135 | 1379 | GCCCAAAGCCTCAACTTCACCACCGCCGCACAG | 5968 | AQSLNFTTAAQ | 10557 | SLNFTTA | 0.553055 | 0.475212 |
| SyS136 | 1380 | GCCCAAGGTATGAGTGGGGTTGCTCAGGCACAG | 5969 | AQGMSGVAQAQ | 10558 | GMSGVAQ | 0.552736 | -0.0578 |
| GP52 | 1381 | GCCCAAAAGGTTGATGCGGCTCAGAGTGCACAG | 5970 | AQKVDAAQSAQ | 10559 | KVDAAQS | 0.552569 | 0.100209 |
| GS75 | 1382 | GCCCAACATATTACGACTAATGTGTCTGCACAG | 5971 | AQHITTNVSAQ | 10560 | HITTNVS | 0.552479 | 0.112469 |
| SyP32 | 1383 | GCCCAAGAGCGGGAGTCGGCTCGTCTTGCACAG | 5972 | AQERESARLAQ | 10561 | ERESARL | 0.551876 | -0.04251 |
| TS106 | 1384 | GCCCAAGATAATAGGACTCAGAGGACGGGCACAG | 5973 | AQDNRTQRTAQ | 10562 | DNRTQRT | 0.551636 | 0.853173 |
| SyS137 | 1385 | GCCCAATCTGCGCTAATGTGACTATTGCACAG | 5974 | AQSAPNVTIAQ | 10563 | SAPNVTI | 0.551278 | 0.041441 |

FIG. 33 (Continued)

| | | | | | | | | |
|---|---|---|---|---|---|---|---|---|
| TS107 | 1386 | GCCCAAGAGAAAACGGCACCAGAAACACCGCACAG | 5975 | AQENGTRNTAQ | 10564 | ENGTRNT | 0.55012 | 0.5646 |
| SyS138 | 1387 | GCCCAAGGCACCGCCGTCTTCACCGCCGCACAG | 5976 | AQGTAVFTAAQ | 10565 | GTAVFTA | 0.549912 | 0.15966 |
| SyS139 | 1388 | GCCCAAGCCAACAACATGAGCCAAACCGCACAG | 5977 | AQANNMSQTAQ | 10566 | ANNMSQT | 0.549519 | 0.239635 |
| TS108 | 1389 | GCCCAAGGTAATCATCACTTATAATCTGGCACAG | 5978 | AQGNHTYNLAQ | 10567 | GNHTYNL | 0.549264 | -0.25467 |
| GP53 | 1390 | GCCCAACTGAGTCCTTCGAATTCTAATGCACAG | 5979 | AQLSPSNSNAQ | 10568 | LSPSNSN | 0.549019 | -0.07079 |
| SyS140 | 1391 | GCCCAAATGGGCGCCGACCAGAACCGCACAG | 5980 | AQMGADHRTAQ | 10569 | MGADHRT | 0.548749 | 0.159265 |
| TS109 | 1392 | GCCCAAAGTAATTCGACGCGTGGTTCTGCACAG | 5981 | AQSNSTRGSAQ | 10570 | SNSTRGS | 0.548705 | 0.187139 |
| SyS141 | 1393 | GCCCAAAATACTTCTGGTGTGCCTAAGGCACAG | 5982 | AQNTSGVPKAQ | 10571 | NTSGVPK | 0.548579 | -0.08828 |
| GS78 | 1394 | GCCCAAATCAACACCGCCGTCGTCAGCGCACAG | 5983 | AQINTAVVSAQ | 10572 | INTAVVS | 0.54846 | -0.10485 |
| SyS142 | 1395 | GCCCAAATGGGGGTTCAGGTTATGTGGCACAG | 5984 | AQMGVQAYVAQ | 10573 | MGVQAYV | 0.54845 | -0.12925 |
| TS110 | 1396 | GCCCAAGGGAATTTGTTAAGCCGAATGCACAG | 5985 | AQGNFVKPNAQ | 10574 | GNFVKPN | 0.547942 | 0.278497 |
| TS111 | 1397 | GCCCAAGTGAATTCGGTGAGGATGATTGCACAG | 5986 | AQVNSVRMIAQ | 10575 | VNSVRMI | 0.547171 | 0.096718 |
| GS79 | 1398 | GCCCAACACGACAGCGCCAACAGCAGAGCACAG | 5987 | AQHDSANSRAQ | 10576 | HDSANSR | 0.54671 | -0.08012 |
| SyS143 | 1399 | GCCCAACTCGGCGTCAGAGACGACAGCGCACAG | 5988 | AQLGVRDDSAQ | 10577 | LGVRDDS | 0.545708 | -0.07131 |
| TS113 | 1400 | GCCCAAAGCAACGCCGTCAGAGCCAACGCACAG | 5989 | AQSNAVRANAQ | 10578 | SNAVRAN | 0.545674 | 0.453866 |
| SyS144 | 1401 | GCCCAACCCGTCCTCGCCGCCACCATGGCACAG | 5990 | AQPVLAATMAQ | 10579 | PVLAATM | 0.545458 | -0.13314 |
| GP54 | 1402 | GCCCAAAATAAAGCCTGTGTCTGGTAATGCACAG | 5991 | AQNKPVSGNAQ | 10580 | NKPVSGN | 0.544076 | 0.079545 |
| SyS145 | 1403 | GCCCAAGTCGGCCTCGCCAGCCACCGCACAG | 5992 | AQVGLASHTAQ | 10581 | VGLASHT | 0.541637 | -0.04601 |
| SyS146 | 1404 | GCCCAAGGCAGCAACACCAACATGAAAGCACAG | 5993 | AQGSNTNMKAQ | 10582 | GSNTNMK | 0.540634 | 0.026539 |
| GS81 | 1405 | GCCCAAGTTGCTACTACTGTGCATAATGCACAG | 5994 | AQVATTVHNAQ | 10583 | VATTVHN | 0.540191 | -0.11662 |
| GS82 | 1406 | GCCCAAAACACCCTCGACACGAGAGTCGCACAG | 5995 | AQNTLDSRVAQ | 10584 | NTLDSRV | 0.539923 | -0.05177 |
| SyS147 | 1407 | GCCCAAAGGGAGGCTAATTGCAGGCGGCACAG | 5996 | AQREANLQAAQ | 10585 | REANLQA | 0.539717 | 0.293254 |
| SyS148 | 1408 | GCCCAAGTCGACGCCCTCAGCCACCATGGCACAG | 5997 | AQVDALSHMAQ | 10586 | VDALSHM | 0.539694 | 0.216373 |
| GS83 | 1409 | GCCCAACTTCGTCTTGCTGGTCTTGCTGCACAG | 5998 | AQLRLAGLAAQ | 10587 | LRLAGLA | 0.539525 | -0.09739 |
| GP55 | 1410 | GCCCAAATTACGGTGACTAATTATTCGGCACAG | 5999 | AQITVTNYSAQ | 10588 | ITVTNYS | 0.539447 | 0.273677 |
| SyS149 | 1411 | GCCCAATGGGACAGCGGCAGCGGCGAAGCACAG | 6000 | AQWDSGSGEAQ | 10589 | WDSGSGE | 0.539198 | -0.07979 |
| SyS150 | 1412 | GCCCAATTCGCCAGCGAAACCGTCGCCGCACAG | 6001 | AQFASETVAAQ | 10590 | FASETVA | 0.537906 | -0.02698 |
| SyS151 | 1413 | GCCCAACAGAATGTTACGGGGACGAGGGCACAG | 6002 | AQQNVTGTRAQ | 10591 | QNVTGTR | 0.537867 | 0.272466 |
| SyS152 | 1414 | GCCCAACTTAATGGGTTGAATGTGTCTGCACAG | 6003 | AQLNGLNVSAQ | 10592 | LNGLNVS | 0.537505 | -0.02999 |
| GS84 | 1415 | GCCCAAAATATGCTTAAGCAGAGTGAGGCACAG | 6004 | AQNMLKQSEAQ | 10593 | NMLKQSE | 0.537354 | -0.06179 |
| SyS153 | 1416 | GCCCAATTTAATGAGGTTCCGAAGGCGGCACAG | 6005 | AQFNEVPKAAQ | 10594 | FNEVPKA | 0.537144 | -0.03003 |
| SyS154 | 1417 | GCCCAACTCGGCGACATCACCGGCTTCGCACAG | 6006 | AQLGDITGFAQ | 10595 | LGDITGF | 0.537047 | -0.10198 |

FIG. 33 (Continued)

| | | | | | | | | |
|---|---|---|---|---|---|---|---|---|
| SyS155 | 1418 | GCCCAAATTTCGGCTTCTCATTCTCGTGCACAG | 6007 | AQISASHSRAQ | 10596 | ISASHSR | 0.536983 | -0.06923 |
| SyS156 | 1419 | GCCCAAAGTCAGAGACGCAGATTGCTCTTGCACAG | 6008 | AQSQTQIALAQ | 10597 | SQTQIAL | 0.53684 | -0.07569 |
| SyS157 | 1420 | GCCCAAAATATGGCTACTCAGATGAAGGCACAG | 6009 | AQNMATQMKAQ | 10598 | NMATQMK | 0.536747 | -0.11797 |
| SyS158 | 1421 | GCCCAAGTCAACCACAACATCAGACTCGCACAG | 6010 | AQVNHNIRLAQ | 10599 | VNHNIRL | 0.53652 | -0.01096 |
| SyS159 | 1422 | GCCCAAAACGCCCTCCAAGTCCCGTCGCACAG | 6011 | AQNALQVPVAQ | 10600 | NALQVPV | 0.536474 | 0.059794 |
| SyS160 | 1423 | GCCCAAAATTCGACGGGTATTGATACGGCACAG | 6012 | AQNSTGIDTAQ | 10601 | NSTGIDT | 0.53526 | -0.06524 |
| SyS161 | 1424 | GCCCAAGTTGTTGCTGGGCATCTTAATGCACAG | 6013 | AQVVAGHLNAQ | 10602 | VVAGHLN | 0.534827 | -0.11989 |
| SyS162 | 1425 | GCCCAACGGAATGATGCGATTCTGAATGCACAG | 6014 | AQRNDAILNAQ | 10603 | RNDAILN | 0.53456 | 0.251531 |
| GS85 | 1426 | GCCCAAAATCGGGTTGATTCGCGGGCTGCACAG | 6015 | AQNRVDSRAAQ | 10604 | NRVDSRA | 0.53408 | 0.01415 |
| GS86 | 1427 | GCCCAATCGACGCATTCTACTTATGTGGCACAG | 6016 | AQSTHSTYVAQ | 10605 | STHSTYV | 0.533753 | -0.09066 |
| SyS164 | 1428 | GCCCAAAGTGGGCATGGGACTCTGCGGGCACAG | 6017 | AQSGHGTLRAQ | 10606 | SGHGTLR | 0.532267 | -0.1652 |
| SyS165 | 1429 | GCCCAACCCAACAGCACCACCCTCAGCGCACAG | 6018 | AQPNSTTLSAQ | 10607 | PNSTTLS | 0.531723 | -0.01811 |
| GS87 | 1430 | GCCCAAGACACCAAACCCACACCGCACACAG | 6019 | AQDTKPTNTAQ | 10608 | DTKPTNT | 0.531589 | 0.18326 |
| SyS166 | 1431 | GCCCAAAACAGAGACACCATCAACAACGCACAG | 6020 | AQNRDTINNAQ | 10609 | NRDTINN | 0.531212 | 0.532142 |
| GS88 | 1432 | GCCCAACCCAGAACCCTCAGCGACGGCGCACAG | 6021 | AQPRTLSDGAQ | 10610 | PRTLSDG | 0.530962 | 0.113902 |
| GS89 | 1433 | GCCCAAACCAAAGACGTCACCACCAGCGCACAG | 6022 | AQTKDVTTSAQ | 10611 | TKDVTTS | 0.53023 | -0.05088 |
| SS31 | 1434 | GCCCAACTGGGTAATCCTACGCCTTCTGCACAG | 6023 | AQLGNPTPSAQ | 10612 | LGNPTPS | 0.529624 | -0.27772 |
| GP56 | 1435 | GCCCAATATCAGGCGATGTATAGGGATGCACAG | 6024 | AQYQAMYRDAQ | 10613 | YQAMYRD | 0.528592 | 0.013767 |
| GS90 | 1436 | GCCCAAAGCGGCGGTCCAAGAATTCGACGCACAG | 6025 | AQSGVQEFDAQ | 10614 | SGVQEFD | 0.528493 | -0.16214 |
| SyS167 | 1437 | GCCCAATCTAATCATCTGTCGACGGTTGCACAG | 6026 | AQSNHLSTVAQ | 10615 | SNHLSTV | 0.528046 | 0.269982 |
| SyS168 | 1438 | GCCCAACACGACGAAAGAGCCAACATGGCACAG | 6027 | AQHDERANMAQ | 10616 | HDERANM | 0.526932 | 0.005367 |
| TS114 | 1439 | GCCCAAACGAATAGTACTCGGTCGCCTGCACAG | 6028 | AQTNSTRSPAQ | 10617 | TNSTRSP | 0.526707 | 0.094198 |
| SP27 | 1440 | GCCCAACCGACGGATAAGTCTTATCCGGCACAG | 6029 | AQPTDKSYPAQ | 10618 | PTDKSYP | 0.525687 | -0.03596 |
| SyS170 | 1441 | GCCCAAATGACCGAACAAAGAACCGCCGCACAG | 6030 | AQMTEQRTAAQ | 10619 | MTEQRTA | 0.524729 | 0.151606 |
| GS92 | 1442 | GCCCAAACCAACGCCACCCAGCAAAGCACAG | 6031 | AQTNATHSKAQ | 10620 | TNATHSK | 0.523113 | 0.600566 |
| GP58 | 1443 | GCCCAAAATCGGGGTACTTTTAGTGCGGCACAG | 6032 | AQNRGTFSAAQ | 10621 | NRGTFSA | 0.522986 | -0.0735 |
| TS115 | 1444 | GCCCAAAACACCACCAAATTCAACACCGCACAG | 6033 | AQNTKFNTAQ | 10622 | NTTKFNT | 0.522899 | 0.168453 |
| SyS171 | 1445 | GCCCAAGGGATTCCGCCTTTGACTAAGGCACAG | 6034 | AQGIPPLTKAQ | 10623 | GIPPLTK | 0.522659 | 0.148866 |
| SyS172 | 1446 | GCCCAAACCGCCAACAGCACCCAAAGAGCACAG | 6035 | AQTANSTQRAQ | 10624 | TANSTQR | 0.522626 | 0.365056 |
| SyS173 | 1447 | GCCCAAACTCAGGGTCCGGGTCCGAAGGCACAG | 6036 | AQTQGPGPKAQ | 10625 | TQGPGPK | 0.522239 | 0.297383 |
| TS116 | 1448 | GCCCAAATGAATACTACGCGGAATTATGCACAG | 6037 | AQMNTTRNYAQ | 10626 | MNTTRNY | 0.522193 | 0.354477 |
| GS94 | 1449 | GCCCAACTCAGAGAGAAGGCACCTTCATGGCACAG | 6038 | AQLREGTFMAQ | 10627 | LREGTFM | 0.521554 | -0.02029 |

FIG. 33 (Continued)

| | | | | | | | | |
|---|---|---|---|---|---|---|---|---|
| SyS174 | 1450 | GCCCAAAACATCAGCAGCACGACAGAGCACAG | 6039 | AQNISSTDRAQ | 10628 | NISSTDR | 0.521154 | 0.307406 |
| SyP33 | 1451 | GCCCAATCGGTTAGTCGGCCGTTTCAGGCACAG | 6040 | AQSVSRPFQAQ | 10629 | SVSRPFQ | 0.520365 | -0.03773 |
| GS96 | 1452 | GCCCAACCTATGTCTGCTAATGGGAAGGCACAG | 6041 | AQPMSANGKAQ | 10630 | PMSANGK | 0.518792 | -0.0464 |
| SyS175 | 1453 | GCCCAAGAAGTCAGAGGCAACACCTTCGCACAG | 6042 | AQEVRGNTFAQ | 10631 | EVRGNTF | 0.518514 | 0.312168 |
| GS97 | 1454 | GCCCAATCGCGAGAAGGGTCTGTCTGTGGCACAG | 6043 | AQSQKGLSVAQ | 10632 | SQKGLSV | 0.518477 | -0.04267 |
| SyS176 | 1455 | GCCCAAATTGCTGAGAATCGAGTGCTGCACAG | 6044 | AQIAENLSAAQ | 10633 | IAENLSA | 0.517935 | -0.10864 |
| SyS177 | 1456 | GCCCAATTCAGCAACACATGAACCTCAAAGCACAG | 6045 | AQFSNMNLKAQ | 10634 | FSNMNLK | 0.517734 | -0.05191 |
| GP59 | 1457 | GCCCAACCTCGTGAGCGGGACTTATACTGCACAG | 6046 | AQPRERTYTAQ | 10635 | PRERTYT | 0.516835 | 0.003871 |
| GS99 | 1458 | GCCCAATGGTCGCATAATCCGGATTCTGCACAG | 6047 | AQWSHNPDSAQ | 10636 | WSHNPDS | 0.516248 | -0.11545 |
| GP60 | 1459 | GCCCAAGGTCTTCAGACTCTGATTACGGCACAG | 6048 | AQGLQTLITAQ | 10637 | GLQTLIT | 0.516123 | 0.282215 |
| TS117 | 1460 | GCCCAAAGCAACAGAACCAAAGACATCGCACAG | 6049 | AQSNRTKDIAQ | 10638 | SNRTKDI | 0.515515 | 0.733669 |
| SyS179 | 1461 | GCCCAAGTGACTGAGACGATTCTTAAGGCACAG | 6050 | AQVTETILKAQ | 10639 | VTETILK | 0.515459 | -0.16223 |
| GS100 | 1462 | GCCCAATATGTTACGCGTAGTGGTCTGGCACAG | 6051 | AQYVTRSGLAQ | 10640 | YVTRSGL | 0.515319 | -0.09386 |
| SS32 | 1463 | GCCCAAATGAACGCCAACATCCTCGTCGCACAG | 6052 | AQMNANILVAQ | 10641 | MNANILV | 0.514679 | -0.31431 |
| GP61 | 1464 | GCCCAAACTACGAATCGGGTGGGTACGGCACAG | 6053 | AQTTNRVGTAQ | 10642 | TTNRVGT | 0.51427 | -0.05638 |
| GS101 | 1465 | GCCCAAGTCCTCAAAAGCCACCTCCAAGCACAG | 6054 | AQVLKSHLQAQ | 10643 | VLKSHLQ | 0.51406 | -0.01612 |
| SyS180 | 1466 | GCCCAAAGCGACGGCCTCAGAACCCAAGCACAG | 6055 | AQSDGLRTQAQ | 10644 | SDGLRTQ | 0.514048 | -0.0323 |
| TS118 | 1467 | GCCCAACTCAACAGCGTCAAACCCAAGCACAG | 6056 | AQLNSVKPNAQ | 10645 | LNSVKPN | 0.513525 | -0.03938 |
| SS33 | 1468 | GCCCAAAGCCAAGCCATCGCCCCCAAAGCACAG | 6057 | AQSQAIAPKAQ | 10646 | SQAIAPK | 0.51343 | -0.30374 |
| TS119 | 1469 | GCCCAATCTAATAATGTTCGTGCTCCGGCACAG | 6058 | AQSNNVRAPAQ | 10647 | SNNVRAP | 0.513257 | 0.427193 |
| SyS182 | 1470 | GCCCAAATCAGCCACCTCAGCGAAAGCGCACAG | 6059 | AQISHLSESAQ | 10648 | ISHLSES | 0.511503 | 0.085806 |
| SyS183 | 1471 | GCCCAACTCCTCCCCGGCATGAGATTCGCACAG | 6060 | AQLLPGMRFAQ | 10649 | LLPGMRF | 0.5114 | -0.16587 |
| GS102 | 1472 | GCCCAACTTCTTGCGTCGGCTACGAAGGCACAG | 6061 | AQILASATKAQ | 10650 | LLASATK | 0.510718 | 0.025387 |
| SS34 | 1473 | GCCCAAAACCACAACAGGCATGGTCAGCGCACAG | 6062 | AQNHNGMVSAQ | 10651 | NHNGMVS | 0.510709 | -0.38341 |
| GS103 | 1474 | GCCCAACAGCGGCGAACTCAACAACGCACAG | 6063 | AQHSGELNNAQ | 10652 | HSGELNN | 0.510488 | -0.05547 |
| GS104 | 1475 | GCCCAACTTTCTGCGGCCTAAGGATACTGCACAG | 6064 | AQLSAPKDTAQ | 10653 | LSAPKDT | 0.509967 | -0.10921 |
| SyS184 | 1476 | GCCCAAATTGGGACTCATGTGGGGACGGCACAG | 6065 | AQIGTHVGTAQ | 10654 | IGTHVGT | 0.509748 | -0.17337 |
| SyS185 | 1477 | GCCCAAGCCGTCGCCCTCGCCAGCGCCGCACAG | 6066 | AQAVALASAAQ | 10655 | AVALASA | 0.509614 | -0.02018 |
| SyS186 | 1478 | GCCCAAATTACTCTTCAGTCTAATGCTGCACAG | 6067 | AQITLQSNAAQ | 10656 | ITLQSNA | 0.509556 | 0.125675 |
| SyS187 | 1479 | GCCCAAGTCGACCACAGCCTCACCAGCGCACAG | 6068 | AQVDHSLTSAQ | 10657 | VDHSLTS | 0.509193 | -0.04316 |
| SyS188 | 1480 | GCCCAAGGCAACGAAGCCACCAGCCTCGCACAG | 6069 | AQGNEATSLAQ | 10658 | GNEATSL | 0.508729 | -0.04706 |
| SyS189 | 1481 | GCCCAACCCGTCAGCAGCACCACCCTCGCACAG | 6070 | AQPVSSTTLAQ | 10659 | PVSSTTL | 0.507682 | 0.051712 |

FIG. 33 (Continued)

| | | | | | | | | |
|---|---|---|---|---|---|---|---|---|
| SyS190 | 1482 | GCCCAACCCTACCAAACCAGCAGGCGGCCGCACAG | 6071 | AQPYQTSSAAQ | 10660 | PYQTSSA | 0.507351 | -0.04626 |
| GS105 | 1483 | GCCCAAACCAGCGTCGTCAGCGCCTTCGCACAG | 6072 | AQTSVVSAFAQ | 10661 | TSVVSAF | 0.507058 | -0.11758 |
| SyS191 | 1484 | GCCCAAAACGGGCGTCCCGACAACAACGCACAG | 6073 | AQNGVPDNNAQ | 10662 | NGVPDNN | 0.50693 | 0.070537 |
| SyS192 | 1485 | GCCCAAAGCACCCAAACCATCGGCTTCGCACAG | 6074 | AQSTQTIGFAQ | 10663 | STQTIGF | 0.505905 | 0.112417 |
| GP62 | 1486 | GCCCAAATTCGGAGTTCTGATCTTGCGGCACAG | 6075 | AQIRSSDLAAQ | 10664 | IRSSDLA | 0.505273 | 0.288145 |
| GS106 | 1487 | GCCCAAAAACACCAAAGCGCCAAATACGCACAG | 6076 | AQNTQSAKYAQ | 10665 | NTQSAKY | 0.504002 | -0.02585 |
| GS107 | 1488 | GCCCAAAGTCTTGAGTCGTCTAGGCAGGCACAG | 6077 | AQSLESSRQAQ | 10666 | SLESSRQ | 0.503575 | -0.02602 |
| GS108 | 1489 | GCCCAACTCAACCTCGCCAGCGGCAGAGCACAG | 6078 | AQLNLASGRAQ | 10667 | LNLASGR | 0.503463 | 0.027635 |
| GS110 | 1490 | GCCCAAATGCAGGAGCGGTCGGGAGTATGCACAG | 6079 | AQMQERREYAQ | 10668 | MQERREY | 0.503055 | -0.00468 |
| GS111 | 1491 | GCCCAATGGCTCCTCAAAGACGGCTACGCACAG | 6080 | AQWLLKDGYAQ | 10669 | WLLKDGY | 0.502893 | -0.11186 |
| GS112 | 1492 | GCCCAAGGCAGATACCAAACCACCAGCGCACAG | 6081 | AQGRYQTTSAQ | 10670 | GRYQTTS | 0.502776 | 0.049992 |
| TS120 | 1493 | GCCCAAAATACGACGAAGTTTCGTTTGCACAG | 6082 | AQNTTKFPFAQ | 10671 | NTTKFPF | 0.502408 | -0.33072 |
| SyS193 | 1494 | GCCCAAATGAGCAACGGCATCAGCAGAGCACAG | 6083 | AQMSNGISRAQ | 10672 | MSNGISR | 0.501897 | 0.448521 |
| GP65 | 1495 | GCCCAACCGATTCGGGATCCGGAGAAGGCACAG | 6084 | AQPIRDPEKAQ | 10673 | PIRDPEK | 0.501479 | -0.07322 |
| SyS194 | 1496 | GCCCAAGTACGCTGAGTCCGCATGTTGCACAG | 6085 | AQSTLSPHVAQ | 10674 | STLSPHV | 0.501315 | 0.165485 |
| GS113 | 1497 | GCCCAATTCATGCCCATCAGCAGCGCCGCACAG | 6086 | AQFMPISSAAQ | 10675 | FMPISSA | 0.50124 | -0.12446 |
| SS35 | 1498 | GCCCAAAGAAGGCGACACCCAAAGCAGCGCACAG | 6087 | AQRSDTQSSAQ | 10676 | RSDTQSS | 0.500462 | -0.28596 |
| GS114 | 1499 | GCCCAAGATAATCATGTTATGGCTCGTGCACAG | 6088 | AQDNHVMARAQ | 10677 | DNHVMAR | 0.499435 | 0.39719 |
| GS115 | 1500 | GCCCAAAATCTGTCTTCTTAAGAGTTGGGCACAG | 6089 | AQNLSSKSWAQ | 10678 | NLSSKSW | 0.499211 | -0.15138 |
| SyS195 | 1501 | GCCCAATCTACGATTCTGAAGGATACTGCACAG | 6090 | AQSTILKDTAQ | 10679 | STILKDT | 0.499066 | -0.11454 |
| GS116 | 1502 | GCCCAACCTACTCATCAGTCTAAGCCGCACAG | 6091 | AQPTHQSKPAQ | 10680 | PTHQSKP | 0.498305 | -0.04153 |
| SyS196 | 1503 | GCCCAAACGGAGGTGACTCAGAATAAGGCACAG | 6092 | AQTEVTQNKAQ | 10681 | TEVTQNK | 0.498059 | -0.01173 |
| SyS197 | 1504 | GCCCAACACCTGACACGAACGGCAGCGCACAG | 6093 | AQHLDSNGSAQ | 10682 | HLDSNGS | 0.496498 | -0.10873 |
| GP66 | 1505 | GCCCAAAATACTGATTCTCGTGTGTGGGGCACAG | 6094 | AQNTDSRVGAQ | 10683 | NTDSRVG | 0.496267 | 0.009692 |
| SyS198 | 1506 | GCCCAAAGCATGGGCCTCAAAGAAAAAGCACAG | 6095 | AQSMGLKEKAQ | 10684 | SMGLKEK | 0.495749 | -0.04266 |
| SyS199 | 1507 | GCCCAATTGAGTACGTCGTATACTCGGGCACAG | 6096 | AQLSTSYTRAQ | 10685 | LSTSYTR | 0.495598 | 0.048715 |
| SyS200 | 1508 | GCCCAATCTCGGGATGAGTAATAATCATGCACAG | 6097 | AQSGMSNNHAQ | 10686 | SGMSNNH | 0.494806 | -0.1025 |
| GS117 | 1509 | GCCCAAACCAACTACGACCTCAGAGCCGCACAG | 6098 | AQTNYDLRAAQ | 10687 | TNYDLRA | 0.494623 | -0.03099 |
| SyS201 | 1510 | GCCCAAACCCCCAAAGCCAAGAAATGGCACAG | 6099 | AQTPQSQEMAQ | 10688 | TPQSQEM | 0.494147 | 0.127468 |
| SyS202 | 1511 | GCCCAAAATAGTAATATGGTTACGCCTGCACAG | 6100 | AQNSNMVTPAQ | 10689 | NSNMVTP | 0.493868 | -0.16466 |
| SyS203 | 1512 | GCCCAATCGGCTGTTCCGAATGTTAAGGCACAG | 6101 | AQSAVPNVKAQ | 10690 | SAVPNVK | 0.493528 | 0.157825 |
| SyS204 | 1513 | GCCCAAGTCCTCGTCGCCGGCAGCAGAGCACAG | 6102 | AQVLVAGSRAQ | 10691 | VLVAGSR | 0.492961 | 0.099713 |

FIG. 33 (Continued)

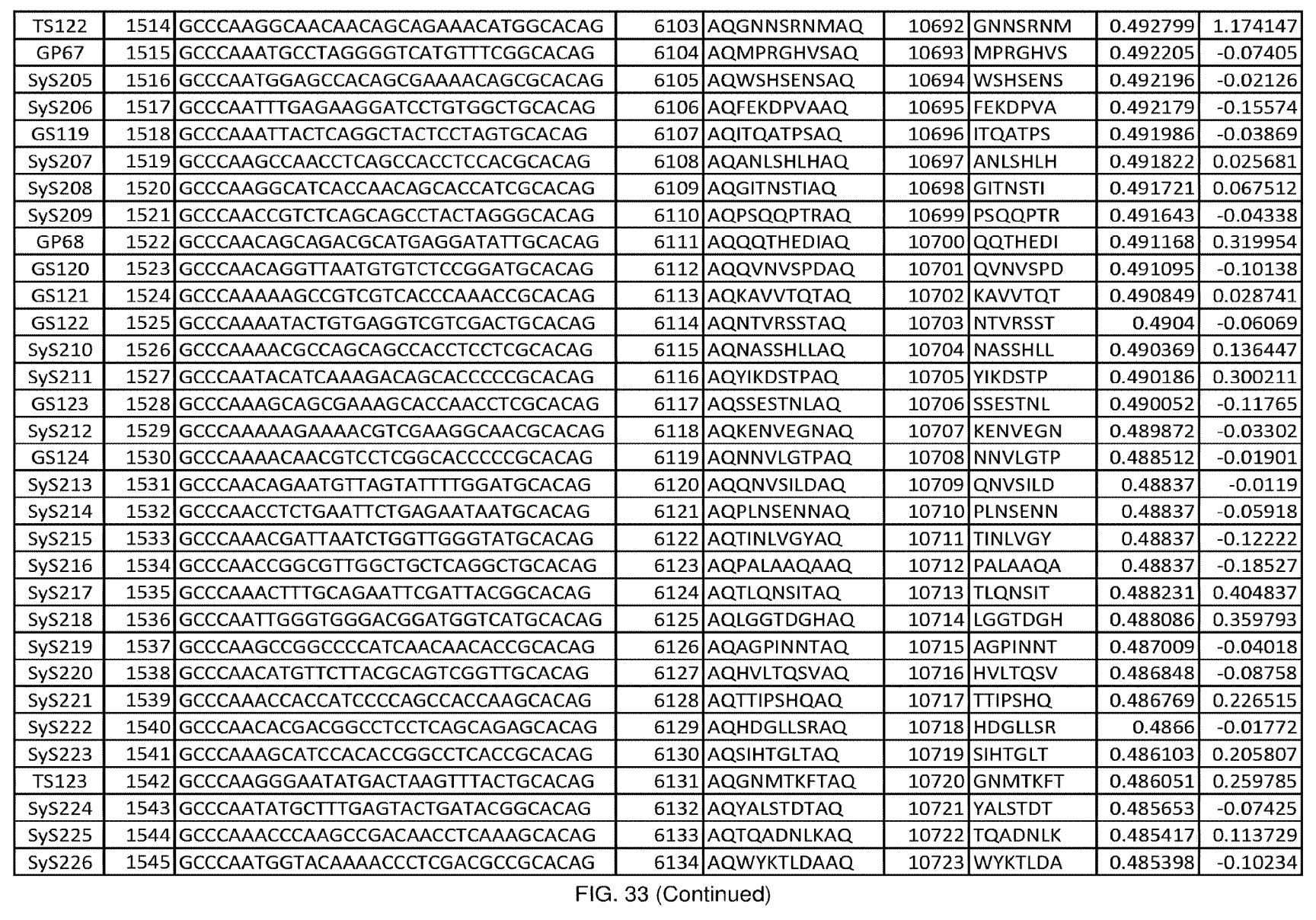

| | | | | | | | | |
|---|---|---|---|---|---|---|---|---|
| TS122 | 1514 | GCCCAAGGCAACAACAGCAGAAACATGGCACAG | 6103 | AQGNNSRNMAQ | 10692 | GNNSRNM | 0.492799 | 1.174147 |
| GP67 | 1515 | GCCCAAATGCCTAGGGGTCATGTTTCGGCACAG | 6104 | AQMPRGHVSAQ | 10693 | MPRGHVS | 0.492205 | -0.07405 |
| SyS205 | 1516 | GCCCAATGGAGCCACAGCGAAAACAGCGCACAG | 6105 | AQWSHSENSAQ | 10694 | WSHSENS | 0.492196 | -0.02126 |
| SyS206 | 1517 | GCCCAATTTGAGAAGGATCCTGTGGCTGCACAG | 6106 | AQFEKDPVAAQ | 10695 | FEKDPVA | 0.492179 | -0.15574 |
| GS119 | 1518 | GCCCAAATTACTCAGGCTACTCCTAGTGCACAG | 6107 | AQITQATPSAQ | 10696 | ITQATPS | 0.491986 | -0.03869 |
| SyS207 | 1519 | GCCCAAGCCAACCTCAGCCACCTCCACGCACAG | 6108 | AQANLSHLHAQ | 10697 | ANLSHLH | 0.491822 | 0.025681 |
| SyS208 | 1520 | GCCCAAGGCATCACCAACAGCACCATCGCACAG | 6109 | AQGITNSTIAQ | 10698 | GITNSTI | 0.491721 | 0.067512 |
| SyS209 | 1521 | GCCCAACCGTCTCAGCAGCCTACTAGGGCACAG | 6110 | AQPSQQPTRAQ | 10699 | PSQQPTR | 0.491643 | -0.04338 |
| GP68 | 1522 | GCCCAACAGCAGACGCATGAGGATATTGCACAG | 6111 | AQQQTHEDIAQ | 10700 | QQTHEDI | 0.491168 | 0.319954 |
| GS120 | 1523 | GCCCAACAGGTTAATGTGTCTCCGGATGCACAG | 6112 | AQQVNVSPDAQ | 10701 | QVNVSPD | 0.491095 | -0.10138 |
| GS121 | 1524 | GCCCAAAAAGCCGTCGTCACCCAAACGCACAG | 6113 | AQKAVVTQTAQ | 10702 | KAVVTQT | 0.490849 | 0.028741 |
| GS122 | 1525 | GCCCAAAATACTGTGAGGTCGTGACTGCACAG | 6114 | AQNTVRSSTAQ | 10703 | NTVRSST | 0.4904 | -0.06069 |
| SyS210 | 1526 | GCCCAAAACGCCAGCAGCCACCTCCTCGCACAG | 6115 | AQNASSHLLAQ | 10704 | NASSHLL | 0.490369 | 0.136447 |
| SyS211 | 1527 | GCCCAATACATCAAAGACAGCACCCCGCACAG | 6116 | AQYIKDSTPAQ | 10705 | YIKDSTP | 0.490186 | 0.300211 |
| GS123 | 1528 | GCCCAAGCAGCGAAAGCACCAACCTCGCACAG | 6117 | AQSSESTNLAQ | 10706 | SSESTNL | 0.490052 | -0.11765 |
| SyS212 | 1529 | GCCCAAAAAGAAAACGTCGAAGGCAACGCACAG | 6118 | AQKENVEGNAQ | 10707 | KENVEGN | 0.489872 | -0.03302 |
| GS124 | 1530 | GCCCAAAACAACGTCCTCGGCACCCCGCACAG | 6119 | AQNNVLGTPAQ | 10708 | NNVLGTP | 0.488512 | -0.01901 |
| SyS213 | 1531 | GCCCAACAGAATGTTAGTATTTGGATGCACAG | 6120 | AQQNVSILDAQ | 10709 | QNVSILD | 0.48837 | -0.0119 |
| SyS214 | 1532 | GCCCAACCTCTGAATTCTGAGAATAATGCACAG | 6121 | AQPLNSENNAQ | 10710 | PLNSENN | 0.48837 | -0.05918 |
| SyS215 | 1533 | GCCCAAACGATTAATCTGGTTGGGTATGCACAG | 6122 | AQTINLVGYAQ | 10711 | TINLVGY | 0.48837 | -0.12222 |
| SyS216 | 1534 | GCCCAACCGGCGTTGGCTGCTCAGGCTGCACAG | 6123 | AQPALAAQAAQ | 10712 | PALAAQA | 0.48837 | -0.18527 |
| SyS217 | 1535 | GCCCAAACTTTGCAGAATTCGATTACGGCACAG | 6124 | AQTLQNSITAQ | 10713 | TLQNSIT | 0.488231 | 0.404837 |
| SyS218 | 1536 | GCCCAATTGGGTGGGACGGATGGTCATGCACAG | 6125 | AQLGGTDGHAQ | 10714 | LGGTDGH | 0.488086 | 0.359793 |
| SyS219 | 1537 | GCCCAAGCGGCCCCATCAACAACACCGCACAG | 6126 | AQAGPINNTAQ | 10715 | AGPINNT | 0.487009 | -0.04018 |
| SyS220 | 1538 | GCCCAACATGTTCTTACGCAGTCGGTTGCACAG | 6127 | AQHVLTQSVAQ | 10716 | HVLTQSV | 0.486848 | -0.08758 |
| SyS221 | 1539 | GCCCAAACCACCATCCCCAGCCACCAAGCACAG | 6128 | AQTTIPSHQAQ | 10717 | TTIPSHQ | 0.486769 | 0.226515 |
| SyS222 | 1540 | GCCCAACACGACGGCCTCCTCAGCAGAGCACAG | 6129 | AQHDGLLSRAQ | 10718 | HDGLLSR | 0.4866 | -0.01772 |
| SyS223 | 1541 | GCCCAAAGCATCCACACCGGCCTCACCGCACAG | 6130 | AQSIHTGLTAQ | 10719 | SIHTGLT | 0.486103 | 0.205807 |
| TS123 | 1542 | GCCCAAGGAATATGACTAAGTTTACTGCACAG | 6131 | AQGNMTKFTAQ | 10720 | GNMTKFT | 0.486051 | 0.259785 |
| SyS224 | 1543 | GCCCAATATGCTTTGAGTACTGATACGGCACAG | 6132 | AQYALSTDTAQ | 10721 | YALSTDT | 0.485653 | -0.07425 |
| SyS225 | 1544 | GCCCAAACCCAAGCCGACAACCTCAAAGCACAG | 6133 | AQTQADNLKAQ | 10722 | TQADNLK | 0.485417 | 0.113729 |
| SyS226 | 1545 | GCCCAATGGTACAAAACCCTCGACGCGCACAG | 6134 | AQWYKTLDAAQ | 10723 | WYKTLDA | 0.485398 | -0.10234 |

FIG. 33 (Continued)

| | | | | | | | | |
|---|---|---|---|---|---|---|---|---|
| GS126 | 1546 | GCCCAACCCCAATACGCCAAAATCAGCGCACAG | 6135 | AQPQYAKISAQ | 10724 | PQYAKIS | 0.485373 | -0.12737 |
| SyS227 | 1547 | GCCCAACTCGCCACCGACAACAAAAGCGCACAG | 6136 | AQLATDNKSAQ | 10725 | LATDNKS | 0.485187 | 0.216017 |
| SyS228 | 1548 | GCCCAACTCAGCGTCGTCATCACCAGCGCACAG | 6137 | AQLSVVITSAQ | 10726 | LSVVITS | 0.484761 | -0.14162 |
| SyS229 | 1549 | GCCCAAAATGTGCCGACTTCGCCGCGGGCACAG | 6138 | AQNVPTSPRAQ | 10727 | NVPTSPR | 0.484481 | -0.00571 |
| SyS230 | 1550 | GCCCAAGCCAGACCCGACCTCAAACTCGCACAG | 6139 | AQARPDLKLAQ | 10728 | ARPDLKL | 0.484242 | 0.080867 |
| SyS231 | 1551 | GCCCAAAGCGCCCTGCCAACACCCTGCACAG | 6140 | AQSALANTLAQ | 10729 | SALANTL | 0.483363 | 0.057201 |
| SyS232 | 1552 | GCCCAACTCATGGACTTCAGCAACCCGCACAG | 6141 | AQLMDFSNPAQ | 10730 | LMDFSNP | 0.483298 | 0.044546 |
| SyS233 | 1553 | GCCCAACCTCGGACGGAGTTGATTAGTGCACAG | 6142 | AQPRTELISAQ | 10731 | PRTELIS | 0.483008 | 0.271785 |
| SyS234 | 1554 | GCCCAAACCAGCGACATCAAAAGCAAAGCACAG | 6143 | AQTSDIKSKAQ | 10732 | TSDIKSK | 0.482661 | 0.009004 |
| GS127 | 1555 | GCCCAAGCAACGCCACCATGAGATTCGCACAG | 6144 | AQSNATMRFAQ | 10733 | SNATMRF | 0.482544 | 0.332692 |
| SyS235 | 1556 | GCCCAAGTCCAAAGCCCCGCCCTCCAAGCACAG | 6145 | AQVQSPALQAQ | 10734 | VQSPALQ | 0.482506 | -0.10268 |
| SS37 | 1557 | GCCCAAACCGCCAACACCAGCAGCAGAGCACAG | 6146 | AQTANTTSRAQ | 10735 | TANTTSR | 0.481309 | -0.14344 |
| GS128 | 1558 | GCCCAACAACACATGACCAGCCAAATCGCACAG | 6147 | AQQHMTSQIAQ | 10736 | QHMTSQI | 0.481226 | 0.067575 |
| GS129 | 1559 | GCCCAAGTAATATGTCGTTGAGTAGTGCACAG | 6148 | AQSNMSLSSAQ | 10737 | SNMSLSS | 0.481136 | -0.01785 |
| SyS237 | 1560 | GCCCAAATTACGGGGATTCCGACGTCGGCACAG | 6149 | AQITGIPTSAQ | 10738 | ITGIPTS | 0.480328 | 0.061154 |
| GS130 | 1561 | GCCCAATTTACTAATAATGTGAGGGATGCACAG | 6150 | AQFTNNVRDAQ | 10739 | FTNNVRD | 0.480193 | 0.04554 |
| SyS238 | 1562 | GCCCAAAACAGCAACGCCGGCGGCAAAGCACAG | 6151 | AQNSNAGGKAQ | 10740 | NSNAGGK | 0.479053 | 0.658688 |
| SyS239 | 1563 | GCCCAATACAACACCGACATCACCAAAGCACAG | 6152 | AQYNTDITKAQ | 10741 | YNTDITK | 0.478109 | 0.317854 |
| SyS240 | 1564 | GCCCAATTTTCGAATCCGGATAAGATGGCACAG | 6153 | AQFSNPDKMAQ | 10742 | FSNPDKM | 0.477665 | -0.02779 |
| SyS241 | 1565 | GCCCAACTCATGACCACCAGCACCATCGCACAG | 6154 | AQLMTTSTIAQ | 10743 | LMTTSTI | 0.476766 | 0.149339 |
| TS124 | 1566 | GCCCAAACGAATAGTACTCTTAGGCAGGCACAG | 6155 | AQTNSTLRQAQ | 10744 | TNSTLRQ | 0.476574 | 0.068959 |
| TS125 | 1567 | GCCCAATCGAATTATACTAAGATTATTGCACAG | 6156 | AQSNYTKIIAQ | 10745 | SNYTKII | 0.475873 | 0.12486 |
| GS132 | 1568 | GCCCAATCTGCTGGGCTTATTCTTCGGCACAG | 6157 | AQSAGLISSAQ | 10746 | SAGLISS | 0.475737 | -0.10204 |
| SyS242 | 1569 | GCCCAAAAGCAGGGTCCGATGCTGTCTGCACAG | 6158 | AQKQGPMLSAQ | 10747 | KQGPMLS | 0.475731 | -0.02565 |
| SyS243 | 1570 | GCCCAAGTGAGGACTCCGGGTGTGTGCAGGCACAG | 6159 | AQVRTPGVQAQ | 10748 | VRTPGVQ | 0.475278 | 0.173488 |
| SyS244 | 1571 | GCCCAAACTCCTGATCATCGGGAGCGGGGCACAG | 6160 | AQTPDHRERAQ | 10749 | TPDHRER | 0.473388 | -0.13798 |
| SyS245 | 1572 | GCCCAAATGAATGCTACTGTTCCTTCTGCACAG | 6161 | AQMNATVPSAQ | 10750 | MNATVPS | 0.472837 | 0.213593 |
| SyS246 | 1573 | GCCCAACTCCACAGCATGTCGCCCCGCACAG | 6162 | AQLHSMLAPAQ | 10751 | LHSMLAP | 0.472535 | 0.03056 |
| SyS247 | 1574 | GCCCAAGACATGCACCACCGCACCGGCACAG | 6163 | AQDMHHSQPAQ | 10752 | DMHHSQP | 0.472429 | 0.422194 |
| GS133 | 1575 | GCCCAAAAACCCTCCCACCACCTACGCGCACAG | 6164 | AQKPLPTTYAQ | 10753 | KPLPTTY | 0.472296 | -0.09564 |
| GS134 | 1576 | GCCCAAGCCATGCAAGTCACCCTCAGCGCACAG | 6165 | AQAMQVTLSAQ | 10754 | AMQVTLS | 0.471652 | -0.13615 |
| GS135 | 1577 | GCCCAAGCCCACCCAGCGCCAGAGCACAG | 6166 | AQSPTHDARAQ | 10755 | SPTHDAR | 0.471243 | -0.00229 |

FIG. 33 (Continued)

| | | | | | | | |
|---|---|---|---|---|---|---|---|
| SyS248 | 1578 | GCCCAAGGCGCTTTCTGTTAAGGAGCTTGCACAG | AQALSVKELAQ | 10756 | ALSVKEL | 0.470954 | -0.13187 |
| GP70 | 1579 | GCCCAACCGTCTCGTGTGCCGACTCAGGCACAG | AQPSRVPTQAQ | 10757 | PSRVPTQ | 0.470688 | -0.07252 |
| SyS250 | 1580 | GCCCAAGGCAGCCTCGGCCTGGCAAAGCACAG | AQGSLGLGKAQ | 10758 | GSLGLGK | 0.470335 | 0.013558 |
| SyS251 | 1581 | GCCCAACACATAGTTCGTATTCGTCGAAGGCACAG | AQHSSYSSKAQ | 10759 | HSSYSSK | 0.469692 | -0.15617 |
| GS136 | 1582 | GCCCAACCGAATCCTAGTAATCCTTCTGCACAG | AQPNPSNPSAQ | 10760 | PNPSNPS | 0.469689 | -0.12006 |
| GP71 | 1583 | GCCCAAACTAAGAATGGTGTTGCGCAGGCACAG | AQTKNGVAQAQ | 10761 | TKNGVAQ | 0.469615 | 0.072268 |
| GP72 | 1584 | GCCCAAGGTAGTACGAGTAGTGCTTATGCACAG | AQGSTSSAYAQ | 10762 | GSTSSAY | 0.469559 | 0.258704 |
| SyS253 | 1585 | GCCCAAAGAAGCACCCACGAAAACACCGCACAG | AQRSTHENTAQ | 10763 | RSTHENT | 0.467377 | 0.19944 |
| SyS254 | 1586 | GCCCAATCTGGTCATGATCGTGATGCTGCACAG | AQSGHDRDAAQ | 10764 | SGHDRDA | 0.466417 | 0.040229 |
| SyS255 | 1587 | GCCCAAAATACTACTCAGTCTTATACTAGTGCACAG | AQNTQSYTSAQ | 10765 | NTQSYTS | 0.466373 | -0.08867 |
| SyS256 | 1588 | GCCCAAGATCGTGTTCCGCATTTGCGGGCACAG | AQDRVPHLRAQ | 10766 | DRVPHLR | 0.466296 | -0.16397 |
| SyS257 | 1589 | GCCCAAAATAATCCGCCTCATATGCGGGCACAG | AQNNPPHMRAQ | 10767 | NNPPHMR | 0.465834 | -0.1254 |
| SyS258 | 1590 | GCCCAAAGAAGCCTCCAAAGCCAATTCGCACAG | AQRSLQSQFAQ | 10768 | RSLQSQF | 0.465601 | -0.06774 |
| SyS259 | 1591 | GCCCAAATTCGTGATGATCGGTCTTTGGCACAG | AQIRDDRSLAQ | 10769 | IRDDRSL | 0.465259 | 0.094784 |
| GS137 | 1592 | GCCCAAATGTTGTCTGCTCCGCTGCCGGCACAG | AQMLSAPLPAQ | 10770 | MLSAPLP | 0.465145 | -0.10658 |
| SyS260 | 1593 | GCCCAAACTTCGAGTATTTGACTACGGCACAG | AQTSSILTTAQ | 10771 | TSSILTT | 0.465093 | 0.037804 |
| SyS261 | 1594 | GCCCAACGTGAGCAGATGAATCTTGTGGCACAG | AQREQMNLVAQ | 10772 | REQMNLV | 0.464872 | -0.01918 |
| SyS262 | 1595 | GCCCAAAAGACGCAGAGTTGAGTAATGCACAG | AQKTQSLSNAQ | 10773 | KTQSLSN | 0.464418 | 0.284303 |
| SyS263 | 1596 | GCCCAATTGAAGACTGCTGAGTATACTGCACAG | AQLKTAEYTAQ | 10774 | LKTAEYT | 0.464287 | 0.205827 |
| SyS264 | 1597 | GCCCAATCGAGTGAGAAGCCGTTTCGGGCACAG | AQSSEKPFRAQ | 10775 | SSEKPFR | 0.464115 | 0.348084 |
| SyS265 | 1598 | GCCCAACCACCAGCGGCGCGTCTTCGGCGCACAG | AQPTSGVFGAQ | 10776 | PTSGVFG | 0.464095 | -0.13314 |
| SyS266 | 1599 | GCCCAAGGCCCAGCCCAGCATCGTCACCATGGCACAG | AQGPSIVTMAQ | 10777 | GPSIVTM | 0.464061 | 0.018407 |
| SyS267 | 1600 | GCCCAAACGAGTGATAAGAGTTCGCTTGCACAG | AQTSDKSSLAQ | 10778 | TSDKSSL | 0.463586 | 0.196158 |
| SyS268 | 1601 | GCCCAAAATACTATTACTATGGCTAAGGCACAG | AQNTITMAKAQ | 10779 | NTITMAK | 0.46346 | 0.027199 |
| GS139 | 1602 | GCCCAACGAATCAGCCTGTTCCGAGTGCACAG | AQRNQPVPSAQ | 10780 | RNQPVPS | 0.463054 | -0.12521 |
| SyS269 | 1603 | GCCCAAAGCGTCCACCTCAACCTCCAAGCACAG | AQSVHLNLQAQ | 10781 | SVHLNLQ | 0.463008 | -0.15411 |
| SyS270 | 1604 | GCCCAATATAATCTGACGATGGTTAGTGCACAG | AQYNLTMVSAQ | 10782 | YNLTMVS | 0.462794 | -0.10646 |
| GS140 | 1605 | GCCCAAAACCGCGACAGCAGCCACCCAGAGCACAG | AQTADSHPRAQ | 10783 | TADSHPR | 0.462708 | -0.06423 |
| SyS271 | 1606 | GCCCAATTGCTTGGTGAGAAGGTGATGGCACAG | AQLLGEKVMAQ | 10784 | LLGEKVM | 0.462387 | 0.138902 |
| SyS272 | 1607 | GCCCAATGGGATCTGACTGCTCCGCAGGCACAG | AQWDLTAPQAQ | 10785 | WDLTAPQ | 0.462376 | -0.1489 |
| SyS273 | 1608 | GCCCAAGTGCTTGCTGATCGTCTTCCGGCACAG | AQVLADRLPAQ | 10786 | VLADRLP | 0.461956 | -0.00299 |
| SyS274 | 1609 | GCCCAATCTCGTGCGCTGCCGAATTCGGCACAG | AQSRALPNSAQ | 10787 | SRALPNS | 0.461886 | -0.05729 |

FIG. 33 (Continued)

| SyS276 | 1610 | GCCCAAAGCAGCCTCAACATGCCCAGAGCACAG | 6199 | AQSSLNMPRAQ | 10788 | SSLNMPR | 0.461752 | 0.063904 |
|---|---|---|---|---|---|---|---|---|
| GS141 | 1611 | GCCCAACAGAGAAGGTTTCGATTTGGCTGCACAG | 6200 | AQQKVSILAAQ | 10789 | QKVSILA | 0.461267 | -0.03269 |
| GS142 | 1612 | GCCCAAAGAGAGGCGACAACAGCAGACTCGCACAG | 6201 | AQRGDNSRLAQ | 10790 | RGDNSRL | 0.461258 | -0.08034 |
| SyS277 | 1613 | GCCCAAAGAATCGACCTCGGCAGCCAAGCACAG | 6202 | AQRIDLGSQAQ | 10791 | RIDLGSQ | 0.461247 | 0.339499 |
| SyS278 | 1614 | GCCCAAGCGTCGCTGGGTCTTCGGGCTGCACAG | 6203 | AQASLGLRAAQ | 10792 | ASLGLRA | 0.461166 | -0.04662 |
| GS143 | 1615 | GCCCAATCGATGCAGAATGGTCTTCGGGCACAG | 6204 | AQSMQNGLRAQ | 10793 | SMQNGLR | 0.460831 | -0.12628 |
| SyS279 | 1616 | GCCCAAACGTTGGCTGTGTGGGGATTGCGGCACAG | 6205 | AQTLAVGIAAQ | 10794 | TLAVGIA | 0.46068 | 0.081823 |
| SyS280 | 1617 | GCCCAAGGGCAGACTGTGACGGGGGCGGCACAG | 6206 | AQGQTVTGAAQ | 10795 | GQTVTGA | 0.460554 | 0.339252 |
| SyS281 | 1618 | GCCCAACATGCTTTGAGTCCTTCTCCGGCACAG | 6207 | AQHALSPSPAQ | 10796 | HALSPSP | 0.459785 | 0.442724 |
| GS144 | 1619 | GCCCAAGTCAGCAGCGTCTTCACCGAAGCACAG | 6208 | AQVSSVFTEAQ | 10797 | VSSVFTE | 0.459264 | -0.12544 |
| GS145 | 1620 | GCCCAATACGGGCGCCGGCGCGTCAAAGCACAG | 6209 | AQYGAGAVKAQ | 10798 | YGAGAVK | 0.459168 | -0.15792 |
| GS146 | 1621 | GCCCAAAAAGAAACCCTCCCCAACGCGCACAG | 6210 | AQKETLPNAAQ | 10799 | KETLPNA | 0.458924 | 0.031664 |
| GS147 | 1622 | GCCCAAATCCCAGCCAAACCCCCTCGCACAG | 6211 | AQIPSQTPLAQ | 10800 | IPSQTPL | 0.458515 | 0.02063 |
| SyS282 | 1623 | GCCCAAAGGCCATCAGCACCTTCGTCGCACAG | 6212 | AQSAISTFVAQ | 10801 | SAISTFV | 0.458157 | 0.041708 |
| SyS283 | 1624 | GCCCAAGTCAACAGCACCAGCAGCACCGCACAG | 6213 | AQVNSTSSTAQ | 10802 | VNSTSST | 0.458101 | 0.362297 |
| GS148 | 1625 | GCCCAACCTACGCGTGATTATAAGGAGGCACAG | 6214 | AQPTRDYKEAQ | 10803 | PTRDYKE | 0.457355 | -0.10546 |
| GS149 | 1626 | GCCCAAAACAACCCGCCAGCACCCAAGCACAG | 6215 | AQNNPASTQAQ | 10804 | NNPASTQ | 0.457315 | -0.17195 |
| SyS284 | 1627 | GCCCAAGTGACGCAGAACGTCTGTTAATGCACAG | 6216 | AQVTQTSVNAQ | 10805 | VTQTSVN | 0.456877 | 0.386968 |
| SyS285 | 1628 | GCCCAATGGGCCGGCACCACCAGCCACGCACAG | 6217 | AQWAGTTSHAQ | 10806 | WAGTTSH | 0.45637 | 0.26665 |
| SyS286 | 1629 | GCCCAAGTCACCGCGGCTTCAGCGCCGCACAG | 6218 | AQVTAGFSAAQ | 10807 | VTAGFSA | 0.455591 | 0.020831 |
| SyS287 | 1630 | GCCCAATTGCATTCTCCTTCTATGCAGGCACAG | 6219 | AQLHSPSMQAQ | 10808 | LHSPSMQ | 0.454973 | -0.08509 |
| GS151 | 1631 | GCCCAATTTCCTACGCAGCCTTCGATGGCACAG | 6220 | AQFPTQPSMAQ | 10809 | FPTQPSM | 0.454886 | -0.05716 |
| SyS288 | 1632 | GCCCAAGCCAAAGCGTCAACGACGGCGCACAG | 6221 | AQAQSVNDGAQ | 10810 | AQSVNDG | 0.454548 | -0.14283 |
| SyS289 | 1633 | GCCCAAGTCGCCAGCACCACCTACACCGCACAG | 6222 | AQVASTTYTAQ | 10811 | VASTTYT | 0.454439 | 0.100393 |
| SyS290 | 1634 | GCCCAACTGGGGGGGTTGAATTCGGTGGCACAG | 6223 | AQLGGLNSVAQ | 10812 | LGGLNSV | 0.454111 | 0.166066 |
| SyS291 | 1635 | GCCCAAGCCGGCGCCCCAGCCTCAGCGCACAG | 6224 | AQAGAPSLSAQ | 10813 | AGAPSLS | 0.452883 | -0.02402 |
| TS126 | 1636 | GCCCAAAGTAATAGGAAGATTGATGATGCACAG | 6225 | AQSNRKIDDAQ | 10814 | SNRKIDD | 0.452682 | 0.231949 |
| GP73 | 1637 | GCCCAATCTCCTAATAATAGGGCTGTGGCACAG | 6226 | AQSPNNRAVAQ | 10815 | SPNNRAV | 0.452479 | 0.244087 |
| SyS293 | 1638 | GCCCAAGTTTGAGGGAGGATCAGTCGGCACAG | 6227 | AQVLREDQSAQ | 10816 | VLREDQS | 0.452095 | -0.02524 |
| SyS294 | 1639 | GCCCAACTTCTTGCGACTGGGCTTAAGGCACAG | 6228 | AQLLATGLKAQ | 10817 | LLATGLK | 0.452095 | -0.17193 |
| GS152 | 1640 | GCCCAAGTCCACCTCAGAAGCCAAATCGCACAG | 6229 | AQVHLRSQIAQ | 10818 | VHLRSQI | 0.451987 | -0.18149 |
| GS153 | 1641 | GCCCAAAGTGCGAATTTGAAGGCACAG | 6230 | AQSANSNLKAQ | 10819 | SANSNLK | 0.451973 | 0.020578 |

FIG. 33 (Continued)

| | | | | | | | | |
|---|---|---|---|---|---|---|---|---|
| SyS295 | 1642 | GCCCAAAGCAAAGCGGCGGCGAAGGCAACGCACAG | 6231 | AQSKAGEGNAQ | 10820 | SKAGEGN | 0.451948 | 0.034237 |
| SyS296 | 1643 | GCCCAAGTCAGCAACCCCGCCATGAAAGCACAG | 6232 | AQVSNPAMKAQ | 10821 | VSNPAMK | 0.451812 | 0.252408 |
| GS154 | 1644 | GCCCAAATCAACGGCAACAACCAAAGAGCACAG | 6233 | AQINGNNQRAQ | 10822 | INGNNQR | 0.451801 | 0.154055 |
| SP30 | 1645 | GCCCAATATAAGTCGACGACTCTTTCTGCACAG | 6234 | AQYKSTTLSAQ | 10823 | YKSTTLS | 0.451779 | -0.05333 |
| SyS297 | 1646 | GCCCAAAAAGAGAGGCCTCGTCGCAGCAGAGCACAG | 6235 | AQKEGLVSRAQ | 10824 | KEGLVSR | 0.451637 | 0.196029 |
| GS155 | 1647 | GCCCAACACCTCAAAGTCATGACCATCGCACAG | 6236 | AQHLKVMTIAQ | 10825 | HLKVMTI | 0.451183 | -0.16304 |
| SyS298 | 1648 | GCCCAAAGAACCAACGACCACAGCAGCGCACAG | 6237 | AQRTNDHSSAQ | 10826 | RTNDHSS | 0.45114 | 0.269153 |
| SyS299 | 1649 | GCCCAACTGCCTTCTCAGTCTGCTAAGGCACAG | 6238 | AQIPSQSAKAQ | 10827 | LPSQSAK | 0.450976 | -0.15061 |
| GS156 | 1650 | GCCCAAATTACGCTGAGGCATTTGCAGGCACAG | 6239 | AQITLRHLQAQ | 10828 | ITLRHLQ | 0.45092 | -0.16814 |
| SyS300 | 1651 | GCCCAACAAAATGATCGCCAACATCCCCGCACAG | 6240 | AQQMIANIPAQ | 10829 | QMIANIP | 0.450647 | 0.113255 |
| SyS301 | 1652 | GCCCAAAGTTCTTCGACTGATCAGCATGCACAG | 6241 | AQSSSTDQHAQ | 10830 | SSSTDQH | 0.450468 | -0.09886 |
| SyS302 | 1653 | GCCCAAAGAAGCACCGACTTCACCCCGCACAG | 6242 | AQRSTDFTPAQ | 10831 | RSTDFTP | 0.450431 | -0.13428 |
| SyS303 | 1654 | GCCCAACAGCATGCGTCTATTTCTGCTGCACAG | 6243 | AQQHASISAAQ | 10832 | QHASISA | 0.450427 | 0.019295 |
| GS157 | 1655 | GCCCAAAAACATCAGCAGCATGCAAATGGCACAG | 6244 | AQNISSMQMAQ | 10833 | NISSMQM | 0.450075 | -0.06541 |
| GS158 | 1656 | GCCCAATCGGGGAATGTTGTGGGGCGGGGCACAG | 6245 | AQSGNVVGRAQ | 10834 | SGNVVGR | 0.449772 | -0.03169 |
| SyS304 | 1657 | GCCCAAAGCAAAGGCGACACCAGCGCCGCACAG | 6246 | AQSKGDTSAAQ | 10835 | SKGDTSA | 0.449763 | 0.203441 |
| SyS306 | 1658 | GCCCAACTGCTGAATACGGGGACTAAGGCACAG | 6247 | AQILNTGTKAQ | 10836 | LLNTGTK | 0.448254 | 0.095948 |
| GS159 | 1659 | GCCCAAGGTACTGGGGTAGTATGAATGCACAG | 6248 | AQGTGASMNAQ | 10837 | GTGASMN | 0.448204 | -0.05716 |
| SyS307 | 1660 | GCCCAACGTCTTGATGCGAATTCTACGGCACAG | 6249 | AQRLDANSTAQ | 10838 | RLDANST | 0.448191 | 0.242147 |
| GS161 | 1661 | GCCCAACTCCCGGAAAGACCCAACAGCGCACAG | 6250 | AQLPERPNSAQ | 10839 | LPERPNS | 0.448013 | -0.01858 |
| SyS308 | 1662 | GCCCAAGCCAGAGAAAATCCTCAACCACGCACAG | 6251 | AQAREILNHAQ | 10840 | AREILNH | 0.447539 | -0.01147 |
| GS162 | 1663 | GCCCAAAACTTCAAAACCACCAACAGCGCACAG | 6252 | AQNFKTTNSAQ | 10841 | NFKTTNS | 0.447528 | 0.230441 |
| GS163 | 1664 | GCCCAAGGCAGAACCGTCCAAGACAGAGACAG | 6253 | AQGRTVQDRAQ | 10842 | GRTVQDR | 0.447505 | 0.075102 |
| GS164 | 1665 | GCCCAAGGTATGAATCAGACGAGACTGCACAG | 6254 | AQGMNQTTTAQ | 10843 | GMNQTTT | 0.446073 | -0.05268 |
| SyS309 | 1666 | GCCCAAGTCGGCAAAGAGACGGGCGTCTGCACAG | 6255 | AQVGKDGVLAQ | 10844 | VGKDGVL | 0.445922 | 0.442273 |
| GS165 | 1667 | GCCCAAGTCACCAGAGACGGGCCAAAGCACAG | 6256 | AQVTRDGAKAQ | 10845 | VTRDGAK | 0.444855 | 0.06699 |
| GS166 | 1668 | GCCCAAGGTACTGCTACGTATGGTAAGGCACAG | 6257 | AQGTATYGKAQ | 10846 | GTATYGK | 0.444487 | -0.00843 |
| SyS310 | 1669 | GCCCAAATGTTGGGTGCTGAGGGGTATGCACAG | 6258 | AQMLGAEGYAQ | 10847 | MLGAEGY | 0.444372 | -0.08881 |
| SyS311 | 1670 | GCCCAAGTCACCCAACAAAACCACCACGCACAG | 6259 | AQVTQQNHHAQ | 10848 | VTQQNHH | 0.444284 | 0.142962 |
| SyS312 | 1671 | GCCCAAACCGTCAACGCCGACCAACTCGCACAG | 6260 | AQTVNADQLAQ | 10849 | TVNADQL | 0.444272 | 0.091137 |
| GS167 | 1672 | GCCCAACAGATGCAGAATAGTCCTATTGCACAG | 6261 | AQQMQNSPIAQ | 10850 | QMQNSPI | 0.443818 | -0.13896 |
| SyS313 | 1673 | GCCCAAGGGACGCTGGCGAGTTCGAAGGCACAG | 6262 | AQGTLASSKAQ | 10851 | GTLASSK | 0.443282 | 0.256025 |

FIG. 33 (Continued)

| | | | | | | | | |
|---|---|---|---|---|---|---|---|---|
| GS169 | 1674 | GCCCAATCTAATGTGACGATTGCGCATGCACAG | 6263 | AQSNVTIAHAQ | 10852 | SNVTIAH | 0.442526 | -0.12177 |
| GS170 | 1675 | GCCCAAGCGAATAATTCTCGTTCGTTTGCACAG | 6264 | AQANNSRPFAQ | 10853 | ANNSRPF | 0.442454 | 0.419078 |
| SyS314 | 1676 | GCCCAAATTGCGACGGCGGGTGGTCCTGCACAG | 6265 | AQIATAGGPAQ | 10854 | IATAGGP | 0.441873 | 0.058602 |
| SyS315 | 1677 | GCCCAAGCCTTCAGCGGCCCCAGCAGAGCACAG | 6266 | AQAFSGPSRAQ | 10855 | AFSGPSR | 0.441659 | 0.035379 |
| SyS316 | 1678 | GCCCAACTCACCAACCTCGTCAGCAGAGCACAG | 6267 | AQLTNLVSRAQ | 10856 | LTNLVSR | 0.441549 | 0.067167 |
| SyS317 | 1679 | GCCCAAGCGGCCAACACCTCGCCCTCGCACAG | 6268 | AQAGQHLALAQ | 10857 | AGQHLAL | 0.441104 | -0.01578 |
| SyS318 | 1680 | GCCCAAAGTGTTGTGGCGTCTGCGAATGCACAG | 6269 | AQSVVASANAQ | 10858 | SVVASAN | 0.441056 | 0.010976 |
| SyS319 | 1681 | GCCCAAGAGACTGTTTCGACTAGTCTTGCACAG | 6270 | AQETVSTSLAQ | 10859 | ETVSTSL | 0.441048 | -0.09691 |
| SyS320 | 1682 | GCCCAAATCCTCGCGCCCTCACCGGCGCACAG | 6271 | AQILAALTGAQ | 10860 | ILAALTG | 0.440956 | -0.10525 |
| SyS321 | 1683 | GCCCAAACGACGGATAAGGCTGCGCTTGCACAG | 6272 | AQTTDKAALAQ | 10861 | TTDKAAL | 0.440639 | 0.0093 |
| SyS322 | 1684 | GCCCAATACCTGACAAACCGGCGCCGCACAG | 6273 | AQYLDKPGAAQ | 10862 | YLDKPGA | 0.43977 | 0.043522 |
| SyS323 | 1685 | GCCCAACCCAACCTCAGCAACCTCATGGCACAG | 6274 | AQPNLSNLMAQ | 10863 | PNLSNLM | 0.439343 | 0.188183 |
| SyS324 | 1686 | GCCCAAATTAATGCGCCTACGGCTAGTGCACAG | 6275 | AQINAPTASAQ | 10864 | INAPTAS | 0.439282 | 0.11633 |
| SyS325 | 1687 | GCCCAACATGGTGGTACGAGTCTGGCTGCACAG | 6276 | AQHGGTSLAAQ | 10865 | HGGTSLA | 0.439114 | 0.231778 |
| SyS326 | 1688 | GCCCAAAATATTCAGTTGTCTCTTGCTGCACAG | 6277 | AQNIQLSLAAQ | 10866 | NIQLSLA | 0.438906 | -0.04774 |
| SyS327 | 1689 | GCCCAAACTCTTCATATGTCTAGTAAGGCACAG | 6278 | AQTLHMSSKAQ | 10867 | TLHMSSK | 0.438887 | -0.06151 |
| GS171 | 1690 | GCCCAAGCCATCATCAACCCCACAGCGCACAG | 6279 | AQAIINPHSAQ | 10868 | AIINPHS | 0.438571 | -0.07991 |
| SyS328 | 1691 | GCCCAAAATACTCTGATTAATGTTAGTGCACAG | 6280 | AQNTLINVSAQ | 10869 | NTLINVS | 0.438518 | -0.09555 |
| SyS329 | 1692 | GCCCAAAACAGCGTCGTCCTCGCCATGGCACAG | 6281 | AQNSVVLAMAQ | 10870 | NSVVLAM | 0.438471 | -0.12176 |
| SyS330 | 1693 | GCCCAAAATATGGCTTCTTTGTCGGCGGCACAG | 6282 | AQNMASLSAAQ | 10871 | NMASLSA | 0.438292 | 0.417265 |
| GS172 | 1694 | GCCCAAGCAGCAGCACCACCTCGCGCACAG | 6283 | AQSSTHLLAAQ | 10872 | SSTHLLA | 0.438222 | -0.05576 |
| SyS331 | 1695 | GCCCAAGACAACAGCAAAGCGACAAAGCACAG | 6284 | AQDNSQSDKAQ | 10873 | DNSQSDK | 0.437981 | -0.03541 |
| GS173 | 1696 | GCCCAAGGCATCACCACCAACGCCCAGCGCACAG | 6285 | AQGITTNAHAQ | 10874 | GITTNAH | 0.437698 | 0.041733 |
| SyS332 | 1697 | GCCCAATCTAGTACTATTAATGGGTATGCACAG | 6286 | AQSSTINGYAQ | 10875 | SSTINGY | 0.437133 | -0.0969 |
| SyS333 | 1698 | GCCCAAAATCATACGCGGATGAATGAGGCACAG | 6287 | AQNHTRMNEAQ | 10876 | NHTRMNE | 0.436984 | 0.166362 |
| GS174 | 1699 | GCCCAAGGCAACCAACAAAAAACCTCGCACAG | 6288 | AQGNQQKNLAQ | 10877 | GNQQKNL | 0.436441 | -0.03233 |
| GS175 | 1700 | GCCCAAGGTACGAGTGATCGGCAGCAGGCACAG | 6289 | AQGTSDRQQAQ | 10878 | GTSDRQQ | 0.436147 | 0.02699 |
| GS176 | 1701 | GCCCAAAGCGACAGCGAATACAAACCCGCACAG | 6290 | AQSDSEYKPAQ | 10879 | SDSEYKP | 0.435589 | -0.08679 |
| SyS334 | 1702 | GCCCAAACGGCTGCGCATGTTAGTTATGCACAG | 6291 | AQTAAHVSYAQ | 10880 | TAAHVSY | 0.435197 | -0.16291 |
| SyS335 | 1703 | GCCCAAATGGCCACCACCACGCCGCGCACAG | 6292 | AQMATTHAAAQ | 10881 | MATTHAA | 0.434993 | 0.274299 |
| TS128 | 1704 | GCCCAAAACAGCGTCAGACAAAGCCTCGCACAG | 6293 | AQNSVRQSLAQ | 10882 | NSVRQSL | 0.434805 | -0.16564 |
| SyS336 | 1705 | GCCCAATCGGGTAGTGGTGTTAGTAGTGCACAG | 6294 | AQSGSGVSSAQ | 10883 | SGSGVSS | 0.434548 | 0.291222 |

FIG. 33 (Continued)

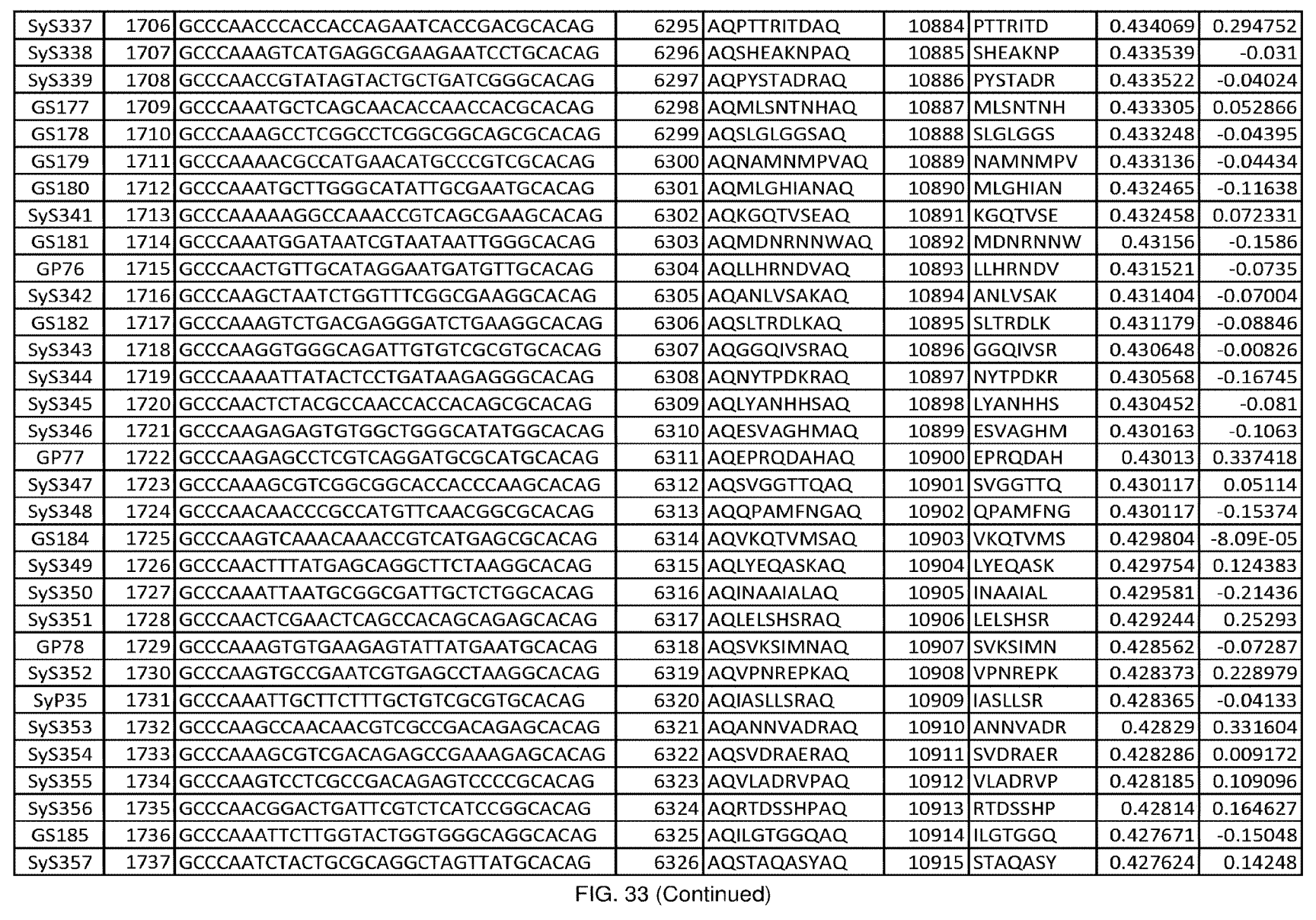

| | | | | | | | | |
|---|---|---|---|---|---|---|---|---|
| SyS337 | 1706 | GCCCAACCACCACCAGAATCACCGACGCACAG | 6295 | AQPTTRITDAQ | 10884 | PTTRITD | 0.434069 | 0.294752 |
| SyS338 | 1707 | GCCCAAAGTCATGAGGCGAAGAATCCTGCACAG | 6296 | AQSHEAKNPAQ | 10885 | SHEAKNP | 0.433539 | -0.031 |
| SyS339 | 1708 | GCCCAACCGTATAGTACTGCTGATCGGGCACAG | 6297 | AQPYSTADRAQ | 10886 | PYSTADR | 0.433522 | -0.04024 |
| GS177 | 1709 | GCCCAAATGCTCAGCAACCAACCACGCACAG | 6298 | AQMLSNTNHAQ | 10887 | MLSNTNH | 0.433305 | 0.052866 |
| GS178 | 1710 | GCCCAAAGCTCGGCCTCGGCGGCAGCGCACAG | 6299 | AQSLGLGGSAQ | 10888 | SLGLGGS | 0.433248 | -0.04395 |
| GS179 | 1711 | GCCCAAAACGCCATGAACATGCCCGTCGCACAG | 6300 | AQNAMNMPVAQ | 10889 | NAMNMPV | 0.433136 | -0.04434 |
| GS180 | 1712 | GCCCAAATGCTTGGGCATATTGCGAATGCACAG | 6301 | AQMLGHIANAQ | 10890 | MLGHIAN | 0.432465 | -0.11638 |
| SyS341 | 1713 | GCCCAAAAAGGCCAAACCGTCAGCGAAGCACAG | 6302 | AQKGQTVSEAQ | 10891 | KGQTVSE | 0.432458 | 0.072331 |
| GS181 | 1714 | GCCCAAATGGATAATCGTAATAATTGGGCACAG | 6303 | AQMDNRNNWAQ | 10892 | MDNRNNW | 0.43156 | -0.1586 |
| GP76 | 1715 | GCCCAACTGTTGCATAGGAATGATGTTGCACAG | 6304 | AQLLHRNDVAQ | 10893 | LLHRNDV | 0.431521 | -0.0735 |
| SyS342 | 1716 | GCCCAAGCTAATCTGGTTTCGGCGAAGGCACAG | 6305 | AQANLVSAKAQ | 10894 | ANLVSAK | 0.431404 | -0.07004 |
| GS182 | 1717 | GCCCAAAGTCTGACGAGGGATCTGAAGGCACAG | 6306 | AQSLTRDLKAQ | 10895 | SLTRDLK | 0.431179 | -0.08846 |
| SyS343 | 1718 | GCCCAAGGTGGGCAGATTGTGTCGCGTGCACAG | 6307 | AQGGQIVSRAQ | 10896 | GGQIVSR | 0.430648 | -0.00826 |
| SyS344 | 1719 | GCCCAAAATTATATCCTGATAAGAGGGCACAG | 6308 | AQNYTPDKRAQ | 10897 | NYTPDKR | 0.430568 | -0.16745 |
| SyS345 | 1720 | GCCCAACTCTACGCCAACCACCAGCGCACAG | 6309 | AQLYANHHSAQ | 10898 | LYANHHS | 0.430452 | -0.081 |
| SyS346 | 1721 | GCCCAAGAGAGTGTGGCTGGGCATATGGCACAG | 6310 | AQESVAGHMAQ | 10899 | ESVAGHM | 0.430163 | -0.1063 |
| GP77 | 1722 | GCCCAAGAGCCTCGTCAGGATGCGCATGCACAG | 6311 | AQEPRQDAHAQ | 10900 | EPRQDAH | 0.43013 | 0.337418 |
| SyS347 | 1723 | GCCCAAAGCGTCGGCGGCGCACCCAAGCACAG | 6312 | AQSVGGTTQAQ | 10901 | SVGGTTQ | 0.430117 | 0.05114 |
| SyS348 | 1724 | GCCCAACAACCCGCCATGTTCAACGGCGCACAG | 6313 | AQQPAMFNGAQ | 10902 | QPAMFNG | 0.430117 | -0.15374 |
| GS184 | 1725 | GCCCAAGTCAAACAAACCGTCATGAGCGCACAG | 6314 | AQVKQTVMSAQ | 10903 | VKQTVMS | 0.429804 | -8.09E-05 |
| SyS349 | 1726 | GCCCAACTTTATGAGCAGGCTTCTAAGGCACAG | 6315 | AQLYEQASKAQ | 10904 | LYEQASK | 0.429754 | 0.124383 |
| SyS350 | 1727 | GCCCAAATTAATGCGGCGATTGCTCTGGCACAG | 6316 | AQINAAIALAQ | 10905 | INAAIAL | 0.429581 | -0.21436 |
| SyS351 | 1728 | GCCCAACTCGAACTCAGCCACAGCAGAGCACAG | 6317 | AQLELSHSRAQ | 10906 | LELSHSR | 0.429244 | 0.25293 |
| GP78 | 1729 | GCCCAAAGTGTGAAAGAGTATTATGAATGCACAG | 6318 | AQSVKSIMNAQ | 10907 | SVKSIMN | 0.428562 | -0.07287 |
| SyS352 | 1730 | GCCCAAGTGCCGAATCGTGAGCCTAAGGCACAG | 6319 | AQVPNREPKAQ | 10908 | VPNREPK | 0.428373 | 0.228979 |
| SyP35 | 1731 | GCCCAAATTGCTTCTTCTTTGCGTGTCGCACAG | 6320 | AQIASLLSRAQ | 10909 | IASLLSR | 0.428365 | -0.04133 |
| SyS353 | 1732 | GCCCAAGCCAACAACGTCGCCGACAGAGCACAG | 6321 | AQANNVADRAQ | 10910 | ANNVADR | 0.42829 | 0.331604 |
| SyS354 | 1733 | GCCCAAAGCGTCGACAGAGCGAAAGAGCACAG | 6322 | AQSVDRAERAQ | 10911 | SVDRAER | 0.428286 | 0.009172 |
| SyS355 | 1734 | GCCCAAGTCCTCGCCGACAGAGTCCCGCACAG | 6323 | AQVLADRVPAQ | 10912 | VLADRVP | 0.428185 | 0.109096 |
| SyS356 | 1735 | GCCCAACGGACTGATTCGTCATCCGGCACAG | 6324 | AQRTDSSHPAQ | 10913 | RTDSSHP | 0.42814 | 0.164627 |
| GS185 | 1736 | GCCCAAATTCTTGGTACTGGTGGGCAGGCACAG | 6325 | AQILGTGGQAQ | 10914 | ILGTGGQ | 0.427671 | -0.15048 |
| SyS357 | 1737 | GCCCAATCTACTGCGCAGGCTAGTTATGCACAG | 6326 | AQSTAQASYAQ | 10915 | STAQASY | 0.427624 | 0.14248 |

FIG. 33 (Continued)

| | | | | | | | | |
|---|---|---|---|---|---|---|---|---|
| SyS358 | 1738 | GCCCAAGTCGGCCCCATCAACACCGTCGCACAG | 6327 | AQVGPINTVAQ | 10916 | VGPINTV | 0.427596 | 0.270593 |
| SyS359 | 1739 | GCCCAACAAACCAACACACCGTCAGAGCACAG | 6328 | AQQTNNTVRAQ | 10917 | QTNNTVR | 0.427534 | 0.514292 |
| TS129 | 1740 | GCCCAACAAGGCAACGCCGTCAGAAGCACCGCACAG | 6329 | AQGNAVRSTAQ | 10918 | GNAVRST | 0.427529 | 1.114857 |
| SyS360 | 1741 | GCCCAACAGAATTGACTAAGGGTCAGGCACAG | 6330 | AQQNLTKGQAQ | 10919 | QNLTKGQ | 0.427304 | 0.307102 |
| GS186 | 1742 | GCCCAAAAACAACTCAGCAAAGACTACGCACAG | 6331 | AQKQLSKDYAQ | 10920 | KQLSKDY | 0.427204 | 0.142161 |
| SyS361 | 1743 | GCCCAAATGGTTCAGAATGGTCTGATTGCACAG | 6332 | AQMVQNGLIAQ | 10921 | MVQNGLI | 0.426778 | 0.092359 |
| SyS362 | 1744 | GCCCAAATCGTCGAACACATGCCCCTCGCACAG | 6333 | AQIVEHMPLAQ | 10922 | IVEHMPL | 0.426165 | -0.1101 |
| GS187 | 1745 | GCCCAATACGACACCACCAGCATCTTCGCACAG | 6334 | AQYDTTSIFAQ | 10923 | YDTTSIF | 0.425436 | -0.10346 |
| GS188 | 1746 | GCCCAAAATAGTATTTCGTCTTCGGCTGCACAG | 6335 | AQNSISSSAAQ | 10924 | NSISSSA | 0.425239 | 0.069039 |
| SyS364 | 1747 | GCCCAAGGCGGCAACAACAGCCTCCACGCACAG | 6336 | AQGGNNSLHAQ | 10925 | GGNNSLH | 0.425087 | 0.214382 |
| SyS365 | 1748 | GCCCAAATTTCTGGTGCGTCTCTTATGGCACAG | 6337 | AQISGASLMAQ | 10926 | ISGASLM | 0.424892 | -0.11822 |
| GP79 | 1749 | GCCCAAGCTACTCTTTCGAGGAATGTTGCACAG | 6338 | AQATLSRNVAQ | 10927 | ATLSRNV | 0.424839 | -0.0735 |
| SyS366 | 1750 | GCCCAACTGGCTAATAATGTTCCGCTTGCACAG | 6339 | AQLANNVPLAQ | 10928 | LANNVPL | 0.424655 | -0.08052 |
| SyS367 | 1751 | GCCCAATGGAGCGACCCCAGCGACCTCGCACAG | 6340 | AQWSDPSDLAQ | 10929 | WSDPSDL | 0.424504 | -0.17072 |
| SyS368 | 1752 | GCCCAAGCAGCCTCACCGACCAACCGCACAG | 6341 | AQSSLTDQPAQ | 10930 | SSLTDQP | 0.424278 | 0.005071 |
| SyS369 | 1753 | GCCCAATACGTCCCCGACCACCACCAGAGCACAG | 6342 | AQYVPDHTRAQ | 10931 | VVPDHTR | 0.424216 | 0.056561 |
| SyS370 | 1754 | GCCCAAAATAATACGGAGGGGTAAGGCGGCACAG | 6343 | AQNNTEGKAAQ | 10932 | NNTEGKA | 0.423868 | 0.141109 |
| TS130 | 1755 | GCCCAAGGTAATAGTGTTTAGGTTGATTGCACAG | 6344 | AQGNSVRLIAQ | 10933 | GNSVRLI | 0.423672 | -0.10341 |
| SyS371 | 1756 | GCCCAAATTGCGCAGTCGAATACTCTTGCACAG | 6345 | AQIAQSNTLAQ | 10934 | IAQSNTL | 0.423532 | 0.211326 |
| GS189 | 1757 | GCCCAACACGACAACGCCACCAAATACGCACAG | 6346 | AQHDNATKYAQ | 10935 | HDNATKY | 0.423515 | 0.078962 |
| SyS372 | 1758 | GCCCAAACTAAGGCTAATGAGATGCAGGCACAG | 6347 | AQTKANEMQAQ | 10936 | TKANEMQ | 0.423482 | 0.265014 |
| GS190 | 1759 | GCCCAATATTTGGGTACGGTTGTTGCGGCACAG | 6348 | AQYLGTVVAAQ | 10937 | YLGTVVA | 0.423467 | -0.07819 |
| SyS373 | 1760 | GCCCAACCTTCGATTGAGCTTAAGCCTGCACAG | 6349 | AQPSIELKPAQ | 10938 | PSIELKP | 0.423417 | -0.09703 |
| SyS374 | 1761 | GCCCAAGCTGCGGGGAATGTTCTTATGGCACAG | 6350 | AQAAGNVLMAQ | 10939 | AAGNVLM | 0.423413 | 0.035242 |
| SyS375 | 1762 | GCCCAAACGTCTGTGGCTAATTTGCGTGCACAG | 6351 | AQTSVANLRAQ | 10940 | TSVANLR | 0.422924 | 0.030491 |
| GS191 | 1763 | GCCCAATTTTCGCGTGAGCCGAAGCCTGCACAG | 6352 | AQFSREPKPAQ | 10941 | FSREPKP | 0.422561 | -0.02217 |
| SyS376 | 1764 | GCCCAAACCCCAGAGAAAACTGGGGCGCACAG | 6353 | AQTPRENWGAQ | 10942 | TPRENWG | 0.422534 | -0.00948 |
| SyS377 | 1765 | GCCCAATCGCAGAATGTTGGTACTAAGGCACAG | 6354 | AQSQNVGTKAQ | 10943 | SQNVGTK | 0.422488 | -0.06393 |
| GS192 | 1766 | GCCCAATATCTGGATAAGGGGAGGACTGCACAG | 6355 | AQYLDKGRTAQ | 10944 | YLDKGRT | 0.422461 | -0.04855 |
| GP80 | 1767 | GCCCAAACGAGTACGACGCCTTTTCTTGCACAG | 6356 | AQTSTTPFLAQ | 10945 | TSTTPFL | 0.422363 | -0.0737 |
| SyS378 | 1768 | GCCCAACGGCAGGATAATCTGGAGCTGGCACAG | 6357 | AQRQDNLELAQ | 10946 | RQDNLEL | 0.422343 | -0.03114 |
| SyS379 | 1769 | GCCCAAATCAGCGACACAGCAGAGTCCACGCACAG | 6358 | AQISDSRVHAQ | 10947 | ISDSRVH | 0.421868 | 0.204338 |

FIG. 33 (Continued)

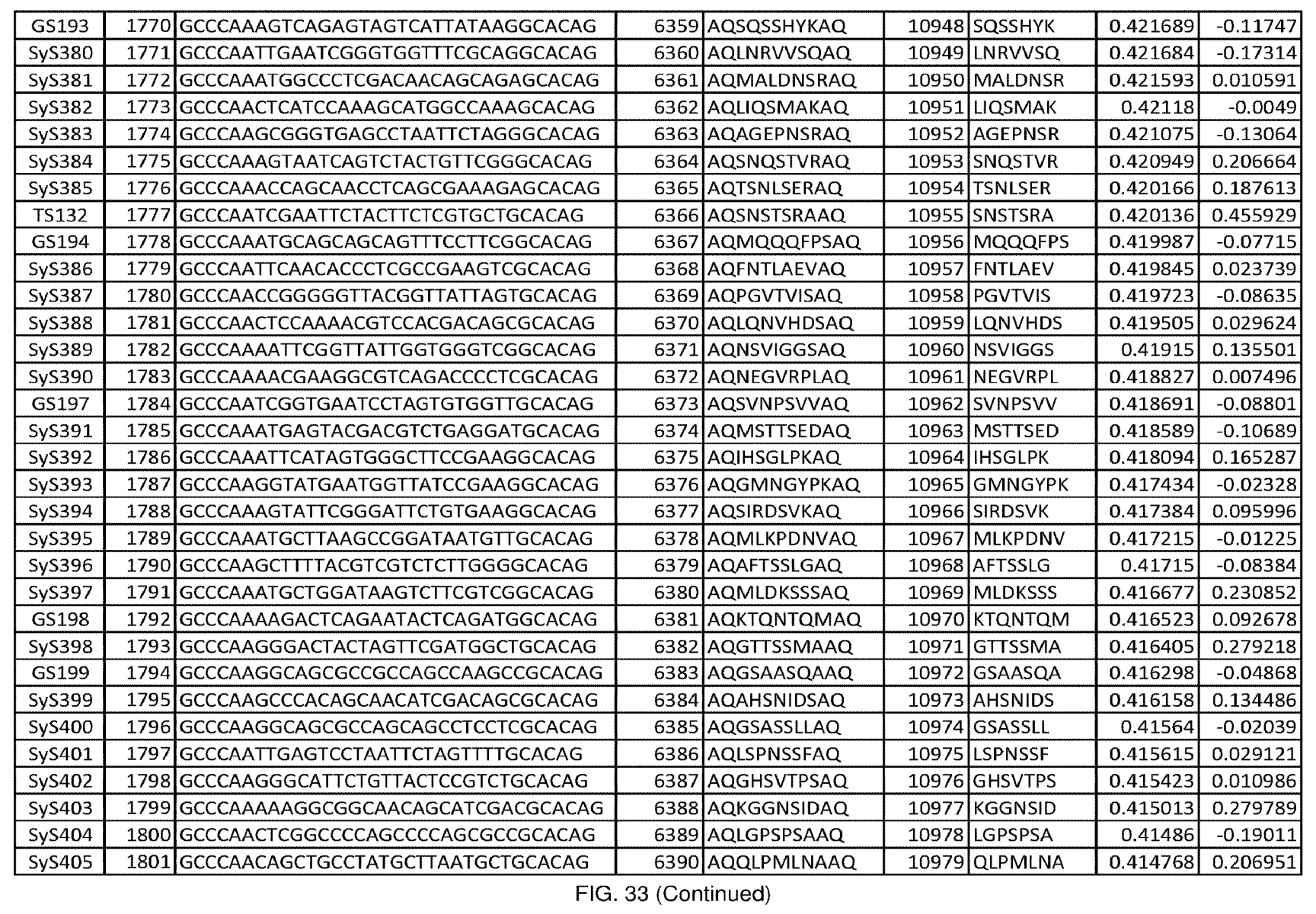

| | | | | | | | | |
|---|---|---|---|---|---|---|---|---|
| GS193 | 1770 | GCCCAAAGTCAGAGTAGTCATTATAAGGCACAG | 6359 | AQSQSSHYKAQ | 10948 | SQSSHYK | 0.421689 | -0.11747 |
| SyS380 | 1771 | GCCCAATTGAATCGGGTGGTTTCGCAGGCACAG | 6360 | AQINRVVSQAQ | 10949 | LNRVVSQ | 0.421684 | -0.17314 |
| SyS381 | 1772 | GCCCAAATGGCCCTCGACAACAGCAGAGCACAG | 6361 | AQMALDNSRAQ | 10950 | MALDNSR | 0.421593 | 0.010591 |
| SyS382 | 1773 | GCCCAACTCATCCAAAGCATGGCCAAAGCACAG | 6362 | AQLIQSMAKAQ | 10951 | LIQSMAK | 0.42118 | -0.0049 |
| SyS383 | 1774 | GCCCAAGCGGGTGAGCCTAATTCTAGGGCACAG | 6363 | AQAGEPNSRAQ | 10952 | AGEPNSR | 0.421075 | -0.13064 |
| SyS384 | 1775 | GCCCAAAGTAATCAGTCTACTGTTCGGGCACAG | 6364 | AQSNQSTVRAQ | 10953 | SNQSTVR | 0.420949 | 0.206664 |
| SyS385 | 1776 | GCCCAAACCAGCAACCTCAGCGAAAGAGCACAG | 6365 | AQTSNLSERAQ | 10954 | TSNLSER | 0.420166 | 0.187613 |
| TS132 | 1777 | GCCCAATCGAATTCTACTTCTCGTGCTGCACAG | 6366 | AQSNSTSRAAQ | 10955 | SNSTSRA | 0.420136 | 0.455929 |
| GS194 | 1778 | GCCCAAATGCAGCAGCAGTTCCTTCGGGCACAG | 6367 | AQMQQQFPSAQ | 10956 | MQQQFPS | 0.419987 | -0.07715 |
| SyS386 | 1779 | GCCCAATTCAACACCCTGCGCGAAGTCGCACAG | 6368 | AQFNTLAEVAQ | 10957 | FNTLAEV | 0.419845 | 0.023739 |
| SyS387 | 1780 | GCCCAACCGGGGGTTACGGTTATTAGTGCACAG | 6369 | AQPGVTVISAQ | 10958 | PGVTVIS | 0.419723 | -0.08635 |
| SyS388 | 1781 | GCCCAACTCCAAAACGTCCACGACAGCGCACAG | 6370 | AQLQNVHDSAQ | 10959 | LQNVHDS | 0.419505 | 0.029624 |
| SyS389 | 1782 | GCCCAAAATTCGGTTATTGGTGGGTCGGCACAG | 6371 | AQNSVIGGSAQ | 10960 | NSVIGGS | 0.41915 | 0.135501 |
| SyS390 | 1783 | GCCCAAAACGAAGGCGTCAGACCCCTCGCACAG | 6372 | AQNEGVRPLAQ | 10961 | NEGVRPL | 0.418827 | 0.007496 |
| GS197 | 1784 | GCCCAATCGGTGAATCCTAGTGTGGTTGCACAG | 6373 | AQSVNPSVVAQ | 10962 | SVNPSVV | 0.418691 | -0.08801 |
| SyS391 | 1785 | GCCCAAATGAGTACGACGTCTGAGGATGCACAG | 6374 | AQMSTTSEDAQ | 10963 | MSTTSED | 0.418589 | -0.10689 |
| SyS392 | 1786 | GCCCAAATTCATAGTGGGCTTCGAAGGCACAG | 6375 | AQIHSGLPKAQ | 10964 | IHSGLPK | 0.418094 | 0.165287 |
| SyS393 | 1787 | GCCCAAGGTATGAATGGTTATCCGAAGGCACAG | 6376 | AQGMNGYPKAQ | 10965 | GMNGYPK | 0.417434 | -0.02328 |
| SyS394 | 1788 | GCCCAAAGTATTCGGGATTCTGTGAAGGCACAG | 6377 | AQSIRDSVKAQ | 10966 | SIRDSVK | 0.417384 | 0.095996 |
| SyS395 | 1789 | GCCCAAAATGCTTAAGCGGGATAAATGTTGCACAG | 6378 | AQMLKPDNVAQ | 10967 | MLKPDNV | 0.417215 | -0.01225 |
| SyS396 | 1790 | GCCCAAGCTTTTACGTCGTCTTCTTGGGGCACAG | 6379 | AQAFTSSLGAQ | 10968 | AFTSSLG | 0.41715 | -0.08384 |
| SyS397 | 1791 | GCCCAAATGCTGGATAAGTCTTCGTCGGCACAG | 6380 | AQMLDKSSSAQ | 10969 | MLDKSSS | 0.416677 | 0.230852 |
| GS198 | 1792 | GCCCAAAAGACTCAGAATACTCAGATGGCACAG | 6381 | AQKTQNTQMAQ | 10970 | KTQNTQM | 0.416523 | 0.092678 |
| SyS398 | 1793 | GCCCAAGGGACTACTAGTTCGATGGCTGCACAG | 6382 | AQGTTSSMAAQ | 10971 | GTTSSMA | 0.416405 | 0.279218 |
| GS199 | 1794 | GCCCAAGGCAGCGGCGCCAAGCCGCACAG | 6383 | AQGSAASQAAQ | 10972 | GSAASQA | 0.416298 | -0.04868 |
| SyS399 | 1795 | GCCCAAGCCCACAGCAACATCGACAGCGCACAG | 6384 | AQAHSNIDSAQ | 10973 | AHSNIDS | 0.416158 | 0.134486 |
| SyS400 | 1796 | GCCCAAGGCAGCGCCAGCAGCCTCCTCGCACAG | 6385 | AQGSASSLLAQ | 10974 | GSASSLL | 0.41564 | -0.02039 |
| SyS401 | 1797 | GCCCAATTGAGTCCTAATTCTAGTTTTGCACAG | 6386 | AQLSPNSSFAQ | 10975 | LSPNSSF | 0.415615 | 0.029121 |
| SyS402 | 1798 | GCCCAAGGGCATTCTGTTACTCCGTCTGCACAG | 6387 | AQGHSVTPSAQ | 10976 | GHSVTPS | 0.415423 | 0.010986 |
| SyS403 | 1799 | GCCCAAAAAGGCGGCAACAGCATCGACGCACAG | 6388 | AQKGGNSIDAQ | 10977 | KGGNSID | 0.415013 | 0.279789 |
| SyS404 | 1800 | GCCCAACTCGGCCCCAGCCCCAGCGCCGCACAG | 6389 | AQLGPSPSAAQ | 10978 | LGPSPSA | 0.41486 | -0.19011 |
| SyS405 | 1801 | GCCCAACAGCTGCCTATGCTTAATGCTGCACAG | 6390 | AQQLPMLNAAQ | 10979 | QLPMLNA | 0.414768 | 0.206951 |

FIG. 33 (Continued)

| | | | | | | | | |
|---|---|---|---|---|---|---|---|---|
| SyS407 | 1802 | GCCCAAGCTACGAATATTCTTACTGCGGCACAG | 6391 | AQATNILTAAQ | 10980 | ATNILTA | 0.413225 | -0.04554 |
| GS201 | 1803 | GCCCAACTCATGCAAAACGGCCAAAAAGCACAG | 6392 | AQLMQNGQKAQ | 10981 | LMQNGQK | 0.413036 | 0.001705 |
| SyS408 | 1804 | GCCCAACATAATAAATGGGCAGGCTTTGGCACAG | 6393 | AQHNNGQALAQ | 10982 | HNNGQAL | 0.412853 | -0.18614 |
| SyS409 | 1805 | GCCCAATCTATTACTCAGACTCTTTCTGCACAG | 6394 | AQSITQTLSAQ | 10983 | SITQTLS | 0.412719 | 0.059774 |
| TS135 | 1806 | GCCCAAGGGAATAGGATTAGTAATACGGCACAG | 6395 | AQGNRISNTAQ | 10984 | GNRISNT | 0.412694 | 0.198634 |
| SyS410 | 1807 | GCCCAAGGTCCTCAGAATGATCCGCCGGCACAG | 6396 | AQGPQNDPPAQ | 10985 | GPQNDPP | 0.41264 | -0.03615 |
| GS202 | 1808 | GCCCAAATCAACGGCATGGGCCCCAACGCACAG | 6397 | AQINGMGPNAQ | 10986 | INGMGPN | 0.412563 | 0.028973 |
| SyS411 | 1809 | GCCCAAACTGGGAATGCGCATCCTAATGCACAG | 6398 | AQTGNAHPNAQ | 10987 | TGNAHPN | 0.412504 | -0.09192 |
| SyS412 | 1810 | GCCCAAGCTGTGAATCTGAATAATGCACAG | 6399 | AQYAVNLNNAQ | 10988 | YAVNLNN | 0.412504 | -0.15859 |
| GS203 | 1811 | GCCCAAGCGTTGATTTCTAATAGTACGGCACAG | 6400 | AQALISNSTAQ | 10989 | ALISNST | 0.412484 | -0.03295 |
| SyS413 | 1812 | GCCCAATCTCATGTTTCTACTACTATGGCACAG | 6401 | AQSHVSTTMAQ | 10990 | SHVSTTM | 0.412469 | 0.018515 |
| SyS414 | 1813 | GCCCAACTGGATGATTTGTGAGGCCGGCACAG | 6402 | AQLDDFVRPAQ | 10991 | LDDFVRP | 0.41244 | -0.19203 |
| GS204 | 1814 | GCCCAAAATAATACTGCGCGGGTCTGTTGCACAG | 6403 | AQNNTARSVAQ | 10992 | NNTARSV | 0.412149 | -0.09946 |
| SyS415 | 1815 | GCCCAAAACAAATACCCCCAACCAGCGCACAG | 6404 | AQNKYPQPSAQ | 10993 | NKYPQPS | 0.412005 | -0.11816 |
| SyS416 | 1816 | GCCCAATATGCGTCGGAGTTGTTTGTTGCACAG | 6405 | AQYASELFVAQ | 10994 | YASELFV | 0.411713 | -0.19254 |
| GS205 | 1817 | GCCCAATTCTACACCGCCAACGCCAGCGCACAG | 6406 | AQFYTANASAQ | 10995 | FYTANAS | 0.411179 | -0.07392 |
| GP83 | 1818 | GCCCAATTTACGAAGTGAATGCGGACTGCACAG | 6407 | AQFTKSNATAQ | 10996 | FTKSNAT | 0.411133 | -0.07308 |
| SyS417 | 1819 | GCCCAACTCGCCGTCAGCCAAATGAGAGCACAG | 6408 | AQLAVSQMRAQ | 10997 | LAVSQMR | 0.411001 | -0.03857 |
| SyS418 | 1820 | GCCCAAAGGAATGGTCAGCTGATTGTGGCACAG | 6409 | AQRNGQLIVAQ | 10998 | RNGQLIV | 0.410978 | 0.234351 |
| SyS419 | 1821 | GCCCAAGACACCGCCAACACGGCCAGAGCACAG | 6410 | AQDTANTARAQ | 10999 | DTANTAR | 0.410859 | 0.147093 |
| GS207 | 1822 | GCCCAAAAACCCACCGAAGTCCAACACGCACAG | 6411 | AQKPTEVQHAQ | 11000 | KPTEVQH | 0.410623 | -0.02471 |
| SyS420 | 1823 | GCCCAACTTACTAATGCGGGCGACTTATGCACAG | 6412 | AQLTNAATYAQ | 11001 | LTNAATY | 0.410298 | 0.266975 |
| SyS421 | 1824 | GCCCAAATCAGCAACGTCCAAGCCAACGCACAG | 6413 | AQISNVQANAQ | 11002 | ISNVQAN | 0.410249 | 0.422795 |
| SyS422 | 1825 | GCCCAAGAGAGTCGTAATAATGGGTTTGCACAG | 6414 | AQESRNNGFAQ | 11003 | ESRNNGF | 0.410147 | -0.09761 |
| SyS423 | 1826 | GCCCAAAGCACCGGCCCCACCATGCACGCACAG | 6415 | AQSTGPTMHAQ | 11004 | STGPTMH | 0.409836 | 0.093513 |
| SyS424 | 1827 | GCCCAAACGCCTGGTGAGTCGCATAAAGGCACAG | 6416 | AQTPGESHKAQ | 11005 | TPGESHK | 0.409786 | -0.15011 |
| GS208 | 1828 | GCCCAAAGCGTCAGCATCGCCAGCAGCGCACAG | 6417 | AQSVSIASSAQ | 11006 | SVSIASS | 0.409517 | -0.03488 |
| SyS425 | 1829 | GCCCAAAATGGTGTTACGCAGTCTAAGGCACAG | 6418 | AQNGVTQSKAQ | 11007 | NGVTQSK | 0.409482 | -0.08464 |
| GS209 | 1830 | GCCCAAGCTAAGAATACGTATGCTTCTGCACAG | 6419 | AQAKNTYASAQ | 11008 | AKNTYAS | 0.409391 | -0.06675 |
| SyS426 | 1831 | GCCCAAGGTACTTCGGATGGTCATAGGGCACAG | 6420 | AQGTSDGHRAQ | 11009 | GTSDGHR | 0.408706 | -0.00891 |
| SP33 | 1832 | GCCCAATGGTCTCAGAATAAGGGGTATGCACAG | 6421 | AQWSQNKGYAQ | 11010 | WSQNKGY | 0.408567 | -0.04954 |
| SyS427 | 1833 | GCCCAAGGTCAGTTGGCGCGGGTCTGTTGCACAG | 6422 | AQGQLARSVAQ | 11011 | GQLARSV | 0.408524 | -0.00072 |

FIG. 33 (Continued)

| | | | | | | | | |
|---|---|---|---|---|---|---|---|---|
| GS210 | 1834 | GCCCAAATCGGCGGCGGCGGCCCAAAAAGCACAG | 6423 | AQIGGGAQKAQ | 11012 | IGGGAQK | 0.408472 | 0.032961 |
| GS211 | 1835 | GCCCAAGCGCGGCAACGCCAGCCACACGCACAG | 6424 | AQAGNASHTAQ | 11013 | AGNASHT | 0.408162 | -0.12162 |
| SyS428 | 1836 | GCCCAATTCAACCAAGTCGGCAAAATGGCACAG | 6425 | AQFNQVGKMAQ | 11014 | FNQVGKM | 0.407791 | 0.16513 |
| SyS429 | 1837 | GCCCAAACGAGGGATACTCTGTATAAGGCACAG | 6426 | AQTRDTLYKAQ | 11015 | TRDTLYK | 0.407466 | -0.16866 |
| SyS430 | 1838 | GCCCAAAACGGCAGCCCCAGCTACAACGCACAG | 6427 | AQNGSPSYNAQ | 11016 | NGSPSYN | 0.407246 | -0.15253 |
| SyS431 | 1839 | GCCCAATTGGCTGAGGCGCATGCTCGTGCACAG | 6428 | AQLAEAHARAQ | 11017 | LAEAHAR | 0.407096 | -0.17435 |
| SyS432 | 1840 | GCCCAACCTATGTCTAATTCGGAGCGTGCACAG | 6429 | AQPMSNSERAQ | 11018 | PMSNSER | 0.407062 | 0.211218 |
| SyS434 | 1841 | GCCCAACACGTCACCAGCCTCAACGACGCACAG | 6430 | AQHVTSLNDAQ | 11019 | HVTSLND | 0.406789 | 0.247538 |
| GS212 | 1842 | GCCCAAGGGGCTCCGCATGTTTCGAGGGCACAG | 6431 | AQGAPHVSRAQ | 11020 | GAPHVSR | 0.406617 | -0.07068 |
| SyS435 | 1843 | GCCCAAAATACTAATGGGAATAGTGCGGCACAG | 6432 | AQNTNGNSAAQ | 11021 | NTNGNSA | 0.405996 | 0.106612 |
| SyS436 | 1844 | GCCCAAAACGAACTCACCGGCATGCTCGCACAG | 6433 | AQNELTGMLAQ | 11022 | NELTGML | 0.405204 | -0.12222 |
| SyS437 | 1845 | GCCCAAAGTTCTCTTTTGCCTGCTGCTGCACAG | 6434 | AQSSLLPAAAQ | 11023 | SSLLPAA | 0.404837 | -0.11667 |
| SyS438 | 1846 | GCCCAACCGGTTGGTCAGTCGTTGACTGCACAG | 6435 | AQPVGQSLTAQ | 11024 | PVGQSLT | 0.404833 | -0.00463 |
| SyS439 | 1847 | GCCCAATTGACTGCTGCGAAGGGTCTTGCACAG | 6436 | AQLTAAKGLAQ | 11025 | LTAAKGL | 0.404775 | -0.07979 |
| GP85 | 1848 | GCCCAACTGATTGGGCGGCTGACTTCTGCACAG | 6437 | AQLIGRLTSAQ | 11026 | LIGRLTS | 0.404569 | -0.07322 |
| GP86 | 1849 | GCCCAAGCTAAGCATAATGATAATATTGCACAG | 6438 | AQAKHNDNIAQ | 11027 | AKHNDNI | 0.404338 | 0.076246 |
| SyS440 | 1850 | GCCCAATTGCGTAGTGGTGATGAGATGGCACAG | 6439 | AQLRSGDEMAQ | 11028 | LRSGDEM | 0.404093 | -0.0112 |
| SyS441 | 1851 | GCCCAACCCAAAACAGCACCACCGCCGCACAG | 6440 | AQPQNSTTAAQ | 11029 | PQNSTTA | 0.404089 | -0.04125 |
| GS213 | 1852 | GCCCAACTGGCTACTGGGCCTCTTTTGCACAG | 6441 | AQLATGPLFAQ | 11030 | LATGPLF | 0.403608 | -0.16394 |
| SyS442 | 1853 | GCCCAAGCGTCTGCTGTGAGTCAGAAGGCACAG | 6442 | AQASAVSQKAQ | 11031 | ASAVSQK | 0.403527 | 0.110544 |
| SyS443 | 1854 | GCCCAAGCGCCTGTTAGTTCTGCGTTGGCACAG | 6443 | AQAPVSSALAQ | 11032 | APVSSAL | 0.40338 | -0.15617 |
| SyS444 | 1855 | GCCCAAACGATGCCGAGTCTGGATAGTGCACAG | 6444 | AQTMPSLDSAQ | 11033 | TMPSLDS | 0.403287 | -0.20951 |
| GS215 | 1856 | GCCCAACATATGAATTTTCCGAATCCGGCACAG | 6445 | AQHMNFPNPAQ | 11034 | HMNFPNP | 0.403183 | -0.14779 |
| SP34 | 1857 | GCCCAAGCGTCTGCGAGGATGGATGCGGGCACAG | 6446 | AQASARMDAAQ | 11035 | ASARMDA | 0.402718 | -0.05379 |
| SyS445 | 1858 | GCCCAAACCGTCATCGTCGGCGGCAGAGCACAG | 6447 | AQTVIVGGRAQ | 11036 | TVIVGGR | 0.402646 | -0.15534 |
| GS216 | 1859 | GCCCAAAGTAGTCAGAGTCAGACTGTTGCACAG | 6448 | AQSSQSQTVAQ | 11037 | SSQSQTV | 0.40259 | -0.00826 |
| SyS446 | 1860 | GCCCAAATCAACACCACCAGCCAAAAAGCACAG | 6449 | AQINTTSQKAQ | 11038 | INTTSQK | 0.402505 | 0.195122 |
| SyS447 | 1861 | GCCCAAGCTGGGGCGCGGTGTTACGGAGGCACAG | 6450 | AQAGARVTEAQ | 11039 | AGARVTE | 0.402225 | 0.012345 |
| GS217 | 1862 | GCCCAACCCGCCCCCCACAGCGGCAGCGCACAG | 6451 | AQPAPHSGSAQ | 11040 | PAPHSGS | 0.402189 | -0.18099 |
| SyS448 | 1863 | GCCCAACTCAACGTCATGTACAACCCCGCACAG | 6452 | AQLNVMYNPAQ | 11041 | LNVMYNP | 0.402132 | -0.11495 |
| GS218 | 1864 | GCCCAAGGGCATGCTCAGACTCTTTATGCACAG | 6453 | AQGHAQTLYAQ | 11042 | GHAQTLY | 0.402085 | -0.07242 |
| GS219 | 1865 | GCCCAAACTCCTAATCTGTCTACTCATGCACAG | 6454 | AQTPNLSTHAQ | 11043 | TPNLSTH | 0.401391 | -0.11638 |

FIG. 33 (Continued)

| | | | | | | | | |
|---|---|---|---|---|---|---|---|---|
| SyS449 | 1866 | GCCCAAAGCGGCCGAAAGAACCAAGTCGCACAG | 6455 | AQSAERTNVAQ | 11044 | SAERTNV | 0.40125 | 0.211168 |
| TS136 | 1867 | GCCCAAAACAACCTCAGACCCGTCTACGCACAG | 6456 | AQNNLRPVYAQ | 11045 | NNLRPVY | 0.401221 | -0.16565 |
| SyS450 | 1868 | GCCCAAAATCAGCAGTCTGCTTATACGGCACAG | 6457 | AQNQQSAYTAQ | 11046 | NQQSAYT | 0.400966 | 0.20764 |
| SyS451 | 1869 | GCCCAAGTCGTCGACGGCAAAACCCAAGCACAG | 6458 | AQVVDGKTQAQ | 11047 | VVDGKTQ | 0.400944 | 0.002558 |
| SyS452 | 1870 | GCCCAACCCCTCCCCAACAACTCGACGCACAG | 6459 | AQPLPQQLDAQ | 11048 | PLPQQLD | 0.40087 | -0.04961 |
| SyS453 | 1871 | GCCCAAGTCGCGAAATCGTCCAACTCGCACAG | 6460 | AQVAEIVQLAQ | 11049 | VAEIVQL | 0.400846 | -0.19011 |
| SS41 | 1872 | GCCCAAGACAGAAACACCACCGTCAGAGCACAG | 6461 | AQDRNTTVRAQ | 11050 | DRNTTVR | 0.40065 | -0.05681 |
| SyS454 | 1873 | GCCCAAAATATGATGAAGACGGGGATGGCACAG | 6462 | AQNMMKTGMAQ | 11051 | NMMKTGM | 0.400506 | 0.125092 |
| SyS455 | 1874 | GCCCAAGTCCAATTCAACACCAGCAAAGCACAG | 6463 | AQVQFNTSKAQ | 11052 | VQFNTSK | 0.400373 | 0.028343 |
| SyS456 | 1875 | GCCCAACCTGGGAATGCTAGTATTCGTGCACAG | 6464 | AQPGNASIRAQ | 11053 | PGNASIR | 0.400324 | -0.16951 |
| SyS457 | 1876 | GCCCAACTCGGCGGCATCCTCAGCGCCGCACAG | 6465 | AQLGGILSAAQ | 11054 | LGGILSA | 0.400238 | -0.08048 |
| SyS458 | 1877 | GCCCAACAGACGGATCATTCGCATCTTGCACAG | 6466 | AQQTDHSHLAQ | 11055 | QTDHSHL | 0.400082 | -0.00343 |
| SyS459 | 1878 | GCCCAAAACGCTGCATGCTGAGTTTAGTGCACAG | 6467 | AQTLHAEFSAQ | 11056 | TLHAEFS | 0.399977 | -0.08783 |
| GP87 | 1879 | GCCCAACTGTCGGATCGTCTGAATGCGGCACAG | 6468 | AQLSDRLNAAQ | 11057 | LSDRLNA | 0.399921 | 0.343918 |
| GS222 | 1880 | GCCCAACTGAATGAGCGTATTGGTGGGGCACAG | 6469 | AQLNERIGGAQ | 11058 | LNERIGG | 0.399725 | 0.141871 |
| SyS460 | 1881 | GCCCAAACTTTGAATTCGACGGCGTCGGCACAG | 6470 | AQTLNSTASAQ | 11059 | TLNSTAS | 0.399702 | -0.02669 |
| GS223 | 1882 | GCCCAATCTGGGCGGGTTGTTGCGCAGGCACAG | 6471 | AQSGRVVAQAQ | 11060 | SGRVVAQ | 0.399629 | -0.09114 |
| TS137 | 1883 | GCCCAAAATAATCGTACGACTAATAATGCACAG | 6472 | AQNNRTTNNAQ | 11061 | NNRTTNN | 0.399086 | 0.311194 |
| SS42 | 1884 | GCCCAAAACGTCCCCAGCAGCACCTACGCACAG | 6473 | AQNVPSSTYAQ | 11062 | NVPSSTY | 0.39867 | -0.28456 |
| SyS461 | 1885 | GCCCAAGTCCCCAGCACCGCCCTCAAAGCACAG | 6474 | AQVPSTALKAQ | 11063 | VPSTALK | 0.3985 | 0.103803 |
| SyS462 | 1886 | GCCCAACCTCCTAATACTCAGAGTCTGGCACAG | 6475 | AQPPNTQSLAQ | 11064 | PPNTQSL | 0.398398 | -0.08905 |
| TS138 | 1887 | GCCCAAACGAATACGACGCGGGCGATGGCACAG | 6476 | AQTNTTRAMAQ | 11065 | TNTTRAM | 0.397943 | 0.551742 |
| TS139 | 1888 | GCCCAAAGCAACAGAACCGTCAGAGAAGCACAG | 6477 | AQSNRTVREAQ | 11066 | SNRTVRE | 0.397876 | 0.454359 |
| SyS463 | 1889 | GCCCAAGCTTCGACTCAGATTATGAGGGCACAG | 6478 | AQASTQIMRAQ | 11067 | ASTQIMR | 0.397639 | -0.12339 |
| SyS464 | 1890 | GCCCAAACGGTGATTAGTTCTAGTCGTGTGCACAG | 6479 | AQTVISSSRAQ | 11068 | TVISSSR | 0.397266 | -0.01675 |
| GS226 | 1891 | GCCCAAGTCTACAGCCCCAAGGCACCGCACAG | 6480 | AQVYSPQGTAQ | 11069 | VYSPQGT | 0.397151 | 0.052156 |
| SyS465 | 1892 | GCCCAAGGCAGCGCCCCACCCAAAGCATGGCACAG | 6481 | AQGSPTQSMAQ | 11070 | GSPTQSM | 0.396853 | 0.092045 |
| SyS466 | 1893 | GCCCAAGCGGTGTCGTGCGGAGGCTCGTGCACAG | 6482 | AQAVSSEARAQ | 11071 | AVSSEAR | 0.396674 | -0.15767 |
| SyS467 | 1894 | GCCCAAGGTTCGGTTGCGACTCTTACTGCACAG | 6483 | AQGSVATLTAQ | 11072 | GSVATLT | 0.396673 | 0.012454 |
| SyS468 | 1895 | GCCCAAAGCGCCAAACACCGGCACCGGCGCACAG | 6484 | AQSANTGTGAQ | 11073 | SANTGTG | 0.396431 | -0.10276 |
| SyS469 | 1896 | GCCCAAATTGTTCAGGGGACTAGTATGGCACAG | 6485 | AQIVQGTSMAQ | 11074 | IVQGTSM | 0.39631 | 0.142036 |
| GS227 | 1897 | GCCCAAACTCCTTCGCTTGGTGTTCTTGCACAG | 6486 | AQTPSLGVLAQ | 11075 | TPSLGVL | 0.395938 | -0.05178 |

FIG. 33 (Continued)

| | | | | | | | | |
|---|---|---|---|---|---|---|---|---|
| SyS470 | 1898 | GCCCAACCCAACACATGATGGGCAGCAGCGCACAG | 6487 | AQPNMMGSSAQ | 11076 | PNMMGSS | 0.395744 | -0.10497 |
| GS228 | 1899 | GCCCAACTCACCCAAAGCCCGCCCCGCGCACAG | 6488 | AQLTQSPAPAQ | 11077 | LTQSPAP | 0.395705 | -0.03746 |
| GS229 | 1900 | GCCCAAAAGGCAGCAACAGCACCCTCGCACAG | 6489 | AQKGSNSTLAQ | 11078 | KGSNSTL | 0.395617 | 0.158094 |
| SyS471 | 1901 | GCCCAACCCATGGCGCGCGCCCCAGAGCACAG | 6490 | AQPMAAAPRAQ | 11079 | PMAAAPR | 0.394928 | -0.11822 |
| GS230 | 1902 | GCCCAAGTTACGACGGGTCCGAGTCGTGCACAG | 6491 | AQVTTGPSRAQ | 11080 | VTTGPSR | 0.39486 | -0.05507 |
| GS231 | 1903 | GCCCAAGTCGTCAGCCCCCTCAGCTACGCACAG | 6492 | AQVVSPLSYAQ | 11081 | VVSPLSY | 0.394822 | -0.12073 |
| SyS472 | 1904 | GCCCAAGTGACGGGGTTCTGTGCAGAAGGCACAG | 6493 | AQVTGSVQKAQ | 11082 | VTGSVQK | 0.394696 | -0.04095 |
| GS232 | 1905 | GCCCAAGGCGGGCACCACCGTCCAAACCGCACAG | 6494 | AQGGTTVQTAQ | 11083 | GGTTVQT | 0.39469 | -0.06883 |
| SyS473 | 1906 | GCCCAAAACAGCGCCCAAATCAACATGGCACAG | 6495 | AQNSAQINMAQ | 11084 | NSAQINM | 0.394642 | 0.174839 |
| GS234 | 1907 | GCCCAACCCGGCACCCAAAAACCCACCGCACAG | 6496 | AQPGTQKPTAQ | 11085 | PGTQKPT | 0.394239 | -0.04567 |
| GP88 | 1908 | GCCCAAGGGAAGGCTAGTCATTATCCTGCACAG | 6497 | AQGKASHYPAQ | 11086 | GKASHYP | 0.394204 | -0.07412 |
| GP89 | 1909 | GCCCAATATAATAGTGTTCCGTCGGCGGCACAG | 6498 | AQYNSVPSAAQ | 11087 | YNSVPSA | 0.393949 | 0.00863 |
| SyS474 | 1910 | GCCCAAGTTTATGAGCGGGTTTCTCATGCACAG | 6499 | AQVYERVSHAQ | 11088 | VYERVSH | 0.393656 | 0.020329 |
| SyS475 | 1911 | GCCCAAGATGTGAATAATAGGTCTATGGCACAG | 6500 | AQDVNNRSMAQ | 11089 | DVNNRSM | 0.393538 | -0.20588 |
| GS235 | 1912 | GCCCAACCTCATGCGGTTTCTATGCTTGCACAG | 6501 | AQPHAVSMLAQ | 11090 | PHAVSML | 0.392826 | -0.1747 |
| GP90 | 1913 | GCCCAAGGGATGCCTGCTCCTCTTGGTGCACAG | 6502 | AQGMPAPLGAQ | 11091 | GMPAPLG | 0.392659 | -0.07169 |
| SyS476 | 1914 | GCCCAACAGCTTCAGATTAATCGGCTGCACAG | 6503 | AQQLQINPAAQ | 11092 | QLQINPA | 0.392185 | -0.12586 |
| SyS477 | 1915 | GCCCAAACTATGGATCTGTCGCCGCGGCACAG | 6504 | AQTMDLSPPAQ | 11093 | TMDLSPP | 0.392185 | -0.12586 |
| SyS478 | 1916 | GCCCAAACCACCGACCTCCACGCCAAAGCACAG | 6505 | AQTTDLHAKAQ | 11094 | TTDLHAK | 0.392056 | -0.00463 |
| GS236 | 1917 | GCCCAACACCACCACCAAACCACCGCACAG | 6506 | AQHHTTQTTAQ | 11095 | HHTTQTT | 0.39199 | -0.07609 |
| SyS479 | 1918 | GCCCAACCGAGTTCTAATTCTACTAATGCACAG | 6507 | AQPSSNSTNAQ | 11096 | PSSNSTN | 0.391964 | -0.12824 |
| SyS480 | 1919 | GCCCAAACCAGATACAACGTGCGACCCCGCACAG | 6508 | AQTRYNVDPAQ | 11097 | TRYNVDP | 0.391808 | 0.095996 |
| SyS481 | 1920 | GCCCAAAGCGTCGTCAGCCTCAGCCCCGCACAG | 6509 | AQSVVSLSPAQ | 11098 | SVVSLSP | 0.391603 | 0.006038 |
| SyS482 | 1921 | GCCCAAGAAAAAGTCGACCAACTCAGAGCACAG | 6510 | AQEKVDQLRAQ | 11099 | EKVDQLR | 0.391412 | -0.13677 |
| SyS483 | 1922 | GCCCAAAGCGACAGCAGACGACAAACCCTCGCACAG | 6511 | AQSDSRQTLAQ | 11100 | SDSRQTL | 0.391412 | -0.13677 |
| SyS484 | 1923 | GCCCAAACTTATCCTGCTACGAGTGATGCACAG | 6512 | AQTYPATSDAQ | 11101 | TYPATSD | 0.391335 | 0.284964 |
| GS237 | 1924 | GCCCAAAGCATGAACGTCGGCAGCGCCGCACAG | 6513 | AQSMNVGSAAQ | 11102 | SMNVGSA | 0.391048 | -0.05003 |
| GS238 | 1925 | GCCCAACTTGAGTCTAGTAATGCTATTGCACAG | 6514 | AQLESSNAIAQ | 11103 | LESSNAI | 0.3905 | -0.13061 |
| GP91 | 1926 | GCCCAATCTCCGACGAATCATCATGCTGCACAG | 6515 | AQSPTNHAPAQ | 11104 | SPTNHAP | 0.389815 | 0.121844 |
| SyS486 | 1927 | GCCCAAGCGCATGAGGGGATGGTTAAGGCACAG | 6516 | AQAHEGMVKAQ | 11105 | AHEGMVK | 0.389656 | 0.111097 |
| SyS487 | 1928 | GCCCAAGTTGATACTTTGTTGTCGAAGGCACAG | 6517 | AQVDTLLSKAQ | 11106 | VDTLLSK | 0.389333 | -0.13837 |
| GS240 | 1929 | GCCCAAACCGCGGGCCAACTCACCTGGGCACAG | 6518 | AQTAGQLTWAQ | 11107 | TAGQLTW | 0.38913 | -0.16432 |

FIG. 33 (Continued)

| | | | | | | | |
|---|---|---|---|---|---|---|---|
| SyS488 | 1930 | GCCCAAATGGGCATGGACGGCCAAATCGCACAG | 6519 | AQMGMDGQIAQ | 11108 | MGMDGQI | 0.38907 | -0.16766 |
| SyS489 | 1931 | GCCCAAGAGAGCTGGGAGAATGGTCGTGTGCACAG | 6520 | AQELENGRRAQ | 11109 | ELENGRR | 0.38896 | -0.14888 |
| GS241 | 1932 | GCCCAACTCGACCTCAGCGTCAGCAGAGCACAG | 6521 | AQLDLSVSRAQ | 11110 | LDLSVSR | 0.388881 | -0.12807 |
| SyS490 | 1933 | GCCCAATCTCAGCATCCGAATATGACGGCACAG | 6522 | AQSQHPNMTAQ | 11111 | SQHPNMT | 0.388765 | 0.328765 |
| SyS491 | 1934 | GCCCAATATCATGAGGTGTCGGAGCATGCACAG | 6523 | AQYHEVSEHAQ | 11112 | YHEVSEH | 0.388683 | -0.07979 |
| GS242 | 1935 | GCCCAAATGCGGTCGCCGCCTCCTACGGCACAG | 6524 | AQMRSPPPTAQ | 11113 | MRSPPPT | 0.388551 | -0.14906 |
| GS243 | 1936 | GCCCAAGGTAGTGGTAGTTCGACGATTGCACAG | 6525 | AQGSGSSTIAQ | 11114 | GSGSSTI | 0.388493 | -0.05911 |
| SyS492 | 1937 | GCCCAAGGTGGTGATGCTGGGAGGTGGGCACAG | 6526 | AQGGDAGRWAQ | 11115 | GGDAGRW | 0.388134 | -0.0507 |
| SyS493 | 1938 | GCCCAAAAGGCTGAGGCGATGGTTATTGCACAG | 6527 | AQKAEAMVIAQ | 11116 | KAEAMVI | 0.387828 | -0.0246 |
| SyS494 | 1939 | GCCCAAGCCAACAAAGACCTCGGCGTCGCACAG | 6528 | AQANKDLGVAQ | 11117 | ANKDLGV | 0.387437 | 0.102738 |
| GS244 | 1940 | GCCCAAACGTCGTCGGAGAATAGGACTGCACAG | 6529 | AQTSSENRTAQ | 11118 | TSSENRT | 0.387311 | -0.10606 |
| SyS495 | 1941 | GCCCAAGGCCCGACAGAAACCGCCGCCGCACAG | 6530 | AQGPDRTAAAQ | 11119 | GPDRTAA | 0.387298 | -0.02676 |
| SyS496 | 1942 | GCCCAAGGCAGCACCGTCGTCCACCTCGCACAG | 6531 | AQGSTVVHLAQ | 11120 | GSTVVHL | 0.386932 | 0.060317 |
| SyS497 | 1943 | GCCCAAACTGCGGTGGTGGTGCCTCAGGCACAG | 6532 | AQTAVVVPQAQ | 11121 | TAVVVPQ | 0.386787 | 0.055989 |
| SyS498 | 1944 | GCCCAAGCGGTTAATATTGCTAATGCGGCACAG | 6533 | AQAVNIANAAQ | 11122 | AVNIANA | 0.386669 | -0.05398 |
| SyS499 | 1945 | GCCCAATTGCTGTCTCAGAGTGGGGTGGCACAG | 6534 | AQLLSQSGVAQ | 11123 | LLSQSGV | 0.386652 | -0.15808 |
| SyS500 | 1946 | GCCCAACACACCGGCGAAGGCAAACTCGCACAG | 6535 | AQHTGEGKLAQ | 11124 | HTGEGKL | 0.386636 | 0.213701 |
| SyS501 | 1947 | GCCCAAAGCAACGGCAACAACATCAGAGCACAG | 6536 | AQSNGNNIRAQ | 11125 | SNGNNIR | 0.386253 | 0.22344 |
| GS245 | 1948 | GCCCAAGAAGTCACCCTCATGCACAAAGCACAG | 6537 | AQEVTLMHKAQ | 11126 | EVTLMHK | 0.386174 | -0.15766 |
| GP92 | 1949 | GCCCAACTTACTACTACGGGGAGTAATGCACAG | 6538 | AQLTTTGSNAQ | 11127 | LTTTGSN | 0.385682 | 0.152692 |
| GS247 | 1950 | GCCCAAGACATCAGCGGCAAAATCGCGGCACAG | 6539 | AQDISGKIAAQ | 11128 | DISGKIA | 0.385274 | -0.05387 |
| GS249 | 1951 | GCCCAAATTTCGCCGAATGTTTATAGTGCACAG | 6540 | AQISPNVYSAQ | 11129 | ISPNVYS | 0.384876 | 0.050202 |
| GS250 | 1952 | GCCCAATATAATAAGCTTGTTGATGGTGCACAG | 6541 | AQYNKLVDGAQ | 11130 | YNKLVDG | 0.38484 | -0.16146 |
| GS251 | 1953 | GCCCAATTTCATACGCATCCTACGAGTGCACAG | 6542 | AQFHTHPTSAQ | 11131 | FHTHPTS | 0.384812 | -0.07443 |
| GP93 | 1954 | GCCCAACCTACTCTGGAGGCTACGAGTGCACAG | 6543 | AQPTLEATSAQ | 11132 | PTLEATS | 0.384801 | 0.117964 |
| SyS503 | 1955 | GCCCAAGAACTCGGCAGAAACGGCCCCGCACAG | 6544 | AQELGRNGPAQ | 11133 | ELGRNGP | 0.38437 | 0.084485 |
| SyS504 | 1956 | GCCCAAGTCGACAAAGTCGAAAGACTCGCACAG | 6545 | AQVDKVERLAQ | 11134 | VDKVERL | 0.384245 | -0.07403 |
| SyS505 | 1957 | GCCCAAACCACCACCATGACCCCAGAGCACAG | 6546 | AQTTTMTPRAQ | 11135 | TTTMTPR | 0.384195 | 0.082987 |
| SyS506 | 1958 | GCCCAACTCCAACAAATCCCCACCCCGCACAG | 6547 | AQLQQIPTPAQ | 11136 | LQQIPTP | 0.384174 | -0.14405 |
| SyS507 | 1959 | GCCCAAACGACAGACAGCAACAGCCTCCAAGCACAG | 6548 | AQTDSNSLQAQ | 11137 | TDSNSLQ | 0.384026 | -0.11495 |
| GS252 | 1960 | GCCCAAGACGACAGAGAGCGTCAGATTCGCACAG | 6549 | AQDDRSVRFAQ | 11138 | DDRSVRF | 0.384013 | -0.08841 |
| GS253 | 1961 | GCCCAACTTGCTACTCAGAATGCTTCGGCACAG | 6550 | AQLATQNASAQ | 11139 | LATQNAS | 0.383747 | -0.11907 |

FIG. 33 (Continued)

| | | | | | | | | |
|---|---|---|---|---|---|---|---|---|
| GS254 | 1962 | GCCCAAGTCGGCACCCACATCCACAGCGCACAG | 6551 | AQVGTHIHSAQ | 11140 | VGTHIHS | 0.383741 | -0.07376 |
| SyS508 | 1963 | GCCCAAGGCGAAAGAAGCAGCAGCGTCAAAGCACAG | 6552 | AQSERSSVKAQ | 11141 | SERSSVK | 0.38368 | -0.04815 |
| GS255 | 1964 | GCCCAAGGCTACGCCCACAGCATGATCGCACAG | 6553 | AQGYAHSMIAQ | 11142 | GYAHSMI | 0.383633 | -0.16718 |
| GS256 | 1965 | GCCCAACCGTTGAGTGGGGGTGTTCGTGCACAG | 6554 | AQPLSGGVRAQ | 11143 | PLSGGVR | 0.383535 | -0.18245 |
| GS257 | 1966 | GCCCAACTCACCTACGTCGCCAGCAGCGCACAG | 6555 | AQLTYVASSAQ | 11144 | LTYVASS | 0.383535 | -0.18245 |
| GS258 | 1967 | GCCCAAGTCGACAAAACCCTCAGCAGAGCACAG | 6556 | AQVDKTLSRAQ | 11145 | VDKTLSR | 0.383399 | 0.00026 |
| SyS509 | 1968 | GCCCAACCAACCTCGTCGGCGTCCCGCACAG | 6557 | AQPNLVGVPAQ | 11146 | PNLVGVP | 0.383392 | -0.17259 |
| SS45 | 1969 | GCCCAAACCAAAATCGACACCGTCAGAGCACAG | 6558 | AQTKIDTVRAQ | 11147 | TKIDTVR | 0.383311 | -0.33355 |
| SyS510 | 1970 | GCCCAAAGCGGCGGCACCCAAGCCAGAGCACAG | 6559 | AQSGGTQARAQ | 11148 | SGGTQAR | 0.383037 | 0.132131 |
| SyS511 | 1971 | GCCCAACATAGTACGCCGCTGGTGTCGGCACAG | 6560 | AQHSTPLVSAQ | 11149 | HSTPLVS | 0.382943 | 0.058414 |
| SyS512 | 1972 | GCCCAACATTCGGGGACGAATCTTCGTGCACAG | 6561 | AQHSGTNLRAQ | 11150 | HSGTNLR | 0.382943 | -0.13556 |
| SyS513 | 1973 | GCCCAAGGCGCAGCCTAGGCTGGTGACTGCACAG | 6562 | AQAQPRLVTAQ | 11151 | AQPRLVT | 0.382943 | -0.13556 |
| SyS514 | 1974 | GCCCAACCTCTTGGTGCGCATGGTTCGGCACAG | 6563 | AQPLGAHGSAQ | 11152 | PLGAHGS | 0.382943 | -0.16466 |
| SyS515 | 1975 | GCCCAAATCAGCGACGCCAGCGTCCTCGCACAG | 6564 | AQISDASVLAQ | 11153 | ISDASVL | 0.382943 | -0.16466 |
| SyS516 | 1976 | GCCCAAATGAGCGTCGGCGTCAAAACCGCACAG | 6565 | AQMSVGVKTAQ | 11154 | MSVGVKT | 0.382941 | 0.297777 |
| GS259 | 1977 | GCCCAAAACATCGCCGAAGGCCTCAGCGCACAG | 6566 | AQNIAEGLSAQ | 11155 | NIAEGLS | 0.382807 | -0.14958 |
| SyS517 | 1978 | GCCCAATCGTCGAATTCTGATGGGATTGCACAG | 6567 | AQSSNSDGIAQ | 11156 | SSNSDGI | 0.382517 | -0.12782 |
| SyS518 | 1979 | GCCCAAGTCGGCCAAACCACCAACAGCGCACAG | 6568 | AQVGQTTNSAQ | 11157 | VGQTTNS | 0.382475 | 0.202682 |
| SyS519 | 1980 | GCCCAAGAGTCGAAGCGGCCCTTTTCTTGCACAG | 6569 | AQESKRPFLAQ | 11158 | ESKRPFL | 0.382336 | -0.02035 |
| SyP37 | 1981 | GCCCAAAGTCAGGAGAATAGTCGTACTGCACAG | 6570 | AQSQENSRTAQ | 11159 | SQENSRT | 0.382175 | -0.03831 |
| SyS520 | 1982 | GCCCAAAATACTGGGACTGATCATCCGGCACAG | 6571 | AQNTGTDHPAQ | 11160 | NTGTDHP | 0.382096 | 0.093385 |
| TS140 | 1983 | GCCCAAGGGAATTGGGTTAAGGATATTGCACAG | 6572 | AQGNWVKDIAQ | 11161 | GNWVKDI | 0.382083 | 0.231014 |
| SyS521 | 1984 | GCCCAAAGACTCACCGAAACCGTCACGCACAG | 6573 | AQRLTETVTAQ | 11162 | RLTETVT | 0.381934 | -0.02213 |
| SyS522 | 1985 | GCCCAAGGCGAAATCGGGCGTCCTCTACGCACAG | 6574 | AQGEIGVLYAQ | 11163 | GEIGVLY | 0.381809 | -0.12707 |
| SyS523 | 1986 | GCCCAACTGGCTCCGGAGCCGCTTAAGGCACAG | 6575 | AQLAPEPLKAQ | 11164 | LAPEPLK | 0.38143 | -0.18527 |
| SyS524 | 1987 | GCCCAAAACAAACTCCCCGCCCTGGCACAG | 6576 | AQNKLPPALAQ | 11165 | NKLPPAL | 0.381262 | 0.008029 |
| SyS525 | 1988 | GCCCAAAATATTGGGACTCGGGATGCGGCACAG | 6577 | AQNIGTRDAAQ | 11166 | NIGTRDA | 0.38124 | -0.20466 |
| GS262 | 1989 | GCCCAAACCGTCAGAGAACTCCAACCGCACAG | 6578 | AQTVRELQPAQ | 11167 | TVRELQP | 0.380962 | -0.03275 |
| SyS526 | 1990 | GCCCAAGAGAATCATGGTACGACTAGTGCACAG | 6579 | AQENHGTTSAQ | 11168 | ENHGTTS | 0.380821 | 0.0704 |
| GS263 | 1991 | GCCCAACAACACGACAGAAACTACGTCGCACAG | 6580 | AQHTDRNYVAQ | 11169 | HTDRNYV | 0.380666 | -0.06073 |
| SyS528 | 1992 | GCCCAAACTGTTGGTCCGACGTCTCATGCACAG | 6581 | AQTVGPTSHAQ | 11170 | TVGPTSH | 0.380499 | 0.283908 |
| SyS529 | 1993 | GCCCAAGGCCTCGTCAAAGACCACCCCGCACAG | 6582 | AQGLVKDHPAQ | 11171 | GLVKDHP | 0.380297 | 0.060613 |

FIG. 33 (Continued)

| | | | | | | | | |
|---|---|---|---|---|---|---|---|---|
| SyS530 | 1994 | GCCCAAATCAACGCCCTCACCAACGGGCACAG | 6583 | AQINALTNGAQ | 11172 | INALTNG | 0.380078 | 0.298241 |
| SyS531 | 1995 | GCCCAACCCTCGACAGCAACAGAGACGCACAG | 6584 | AQPLDSNRDAQ | 11173 | PLDSNRD | 0.380007 | -0.00615 |
| GP94 | 1996 | GCCCAACTTAAGGTGACGAAGAGATTGATGCACAG | 6585 | AQLKVTKIDAQ | 11174 | LKVTKID | 0.379542 | -0.07197 |
| GS264 | 1997 | GCCCAACATAATAGTAATCCTGGGTTGGCACAG | 6586 | AQHNSNPGLAQ | 11175 | HNSNPGL | 0.379381 | -0.02297 |
| GS265 | 1998 | GCCCAAACCACCGTCATCTCAAAACCGCACAG | 6587 | AQTTVILKTAQ | 11176 | TTVILKT | 0.379349 | -0.13952 |
| GS266 | 1999 | GCCCAACTTGGTAAGGGTATGACTGCGGCACAG | 6588 | AQLGKGMTAAQ | 11177 | LGKGMTA | 0.379294 | 0.02198 |
| SyS532 | 2000 | GCCCAATTCAGCATCAGCGACCTCAAAGCACAG | 6589 | AQFSISDLKAQ | 11178 | FSISDLK | 0.379031 | -0.02524 |
| SyS533 | 2001 | GCCCAAAGTACGGATACTCATCTTCCTGCACAG | 6590 | AQSTDTHLPAQ | 11179 | STDTHLP | 0.378372 | -0.01675 |
| TS141 | 2002 | GCCCAATTGAATGCTGTTAAGAATGTTGCACAG | 6591 | AQLNAVKNVAQ | 11180 | LNAVKNV | 0.378181 | 0.632673 |
| GP95 | 2003 | GCCCAACGTTCGACTCCGAATACGATTGCACAG | 6592 | AQRSTPNTIAQ | 11181 | RSTPNTI | 0.377505 | 0.34596 |
| GP96 | 2004 | GCCCAATTGAGTATTAAGTTGCAGAATGCACAG | 6593 | AQLSIKLQNAQ | 11182 | LSIKLQN | 0.377502 | -0.02247 |
| SyS534 | 2005 | GCCCAAAGTCTTGCGATTACTAGTAGTGCACAG | 6594 | AQSLAITSSAQ | 11183 | SLAITSS | 0.37731 | -0.04258 |
| GS270 | 2006 | GCCCAACGGCAGGATATTACTATTGCTGCACAG | 6595 | AQRQDITIAAQ | 11184 | RQDITIA | 0.377132 | -0.06485 |
| GS271 | 2007 | GCCCAAGGTAATGCTACGCCTCGGTCTGCACAG | 6596 | AQGNATPRSAQ | 11185 | GNATPRS | 0.377091 | 0.192946 |
| SyS536 | 2008 | GCCCAAAGCCTCGTCGGCACCACCAGCGCACAG | 6597 | AQSLVGTTSAQ | 11186 | SLVGTTS | 0.376972 | 0.04223 |
| GS272 | 2009 | GCCCAATGGCAGACTCAGGATAAGGAGGCACAG | 6598 | AQWQTQDKEAQ | 11187 | WQTQDKE | 0.376959 | -0.16753 |
| SyS537 | 2010 | GCCCAAACGCCTAATGTGCCGTCTCCGGCACAG | 6599 | AQTPNVPSPAQ | 11188 | TPNVPSP | 0.376726 | -0.06646 |
| SyS539 | 2011 | GCCCAAATTAATACTATTAGTCCGAAGGCACAG | 6600 | AQINTISPKAQ | 11189 | INTISPK | 0.376382 | -0.16102 |
| SyS541 | 2012 | GCCCAACCCCTCGGCACCAGCAACACCGCACAG | 6601 | AQPLGTSNTAQ | 11190 | PLGTSNT | 0.376355 | 0.102187 |
| SyS542 | 2013 | GCCCAAAGCCAAGTCAACGGCGGCAAAGCACAG | 6602 | AQSQVNGGKAQ | 11191 | SQVNGGK | 0.37633 | 0.282579 |
| SyS543 | 2014 | GCCCAACCGATTAATGATAAGGTGATGGCACAG | 6603 | AQPINDKVMAQ | 11192 | PINDKVM | 0.376049 | 0.017194 |
| GS545 | 2015 | GCCCAAAACGTCAGCAGCATCCTCGCACAG | 6604 | AQNVSSSILAQ | 11193 | NVSSSIL | 0.375885 | 0.134279 |
| GS273 | 2016 | GCCCAACAGGCGAATTGGACTGCGTCTGCACAG | 6605 | AQQANWTASAQ | 11194 | QANWTAS | 0.375563 | -0.10129 |
| SyS546 | 2017 | GCCCAAAGACCCGAAAAACCACACAGCAGCGCACAG | 6606 | AQRPENHSSAQ | 11195 | RPENHSS | 0.375415 | 0.065176 |
| GS274 | 2018 | GCCCAAACTAGGAATTTGGATGTTCATGCACAG | 6607 | AQTRNLDVHAQ | 11196 | TRNLDVH | 0.374612 | -0.17829 |
| SyS547 | 2019 | GCCCAAATTAATAGTTCGTTTTCTAAGGCACAG | 6608 | AQINSSFSKAQ | 11197 | INSSFSK | 0.374256 | -0.0095 |
| SyS548 | 2020 | GCCCAATCTATTCAGGGGTCTCAGCGGGCACAG | 6609 | AQSIQGSQRAQ | 11198 | SIQGSQR | 0.374054 | 0.007566 |
| SyS549 | 2021 | GCCCAAGTTGTGGCGGTTGGTCAGTTTGCACAG | 6610 | AQVVAVGQFAQ | 11199 | VVAVGQF | 0.373702 | -0.13556 |
| TS143 | 2022 | GCCCAAGTCAACAAAGTCAGAGACGTCGCACAG | 6611 | AQVNKVRDVAQ | 11200 | VNKVRDV | 0.373538 | -0.18383 |
| SyS550 | 2023 | GCCCAAAAGCCTAATGCTCAGATTCAGGCACAG | 6612 | AQKPNAQIQAQ | 11201 | KPNAQIQ | 0.373406 | -0.06161 |
| SyS551 | 2024 | GCCCAAATGTCTATTGGTACGGGGTTCGGCACAG | 6613 | AQMSIGTGSAQ | 11202 | MSIGTGS | 0.373384 | 0.053851 |
| GS276 | 2025 | GCCCAAGGGCTGCAGGCGACGTATTCTGCACAG | 6614 | AQGLQATYSAQ | 11203 | GLQATYS | 0.373212 | -0.09754 |

FIG. 33 (Continued)

| | | | | | | | | |
|---|---|---|---|---|---|---|---|---|
| SyS552 | 2026 | GCCCAACAAACCCTCAGGCGCCAGCAGGCACAG | 6615 | AQQTLSASSAQ | 11204 | QTLSASS | 0.373145 | -0.04342 |
| GS277 | 2027 | GCCCAAGAGACCCCCCAACAAATTCCCGCACAG | 6616 | AQDPPNKFPAQ | 11205 | DPPNKFP | 0.373042 | 0.030997 |
| SyS554 | 2028 | GCCCAAAGAATCAGCACCCTCGGCCTCGCACAG | 6617 | AQRISTLGLAQ | 11206 | RISTLGL | 0.373026 | -0.22891 |
| SyS555 | 2029 | GCCCAAAATTCGGATCGTTCGGTTAGTGCACAG | 6618 | AQNSDRSVSAQ | 11207 | NSDRSVS | 0.372705 | -0.18284 |
| GP97 | 2030 | GCCCAATATAATCTGCGTCTTGGGGGGCACAG | 6619 | AQYNLRLGGAQ | 11208 | YNLRLGG | 0.37241 | -0.00505 |
| SyS556 | 2031 | GCCCAAGTTCAGGATCGGGCGATGACTGCACAG | 6620 | AQVQDRAMTAQ | 11209 | VQDRAMT | 0.37233 | 0.095998 |
| SyS557 | 2032 | GCCCAAAGCAGCAGCACCCTCCCAGAGCACAG | 6621 | AQSSSTLPRAQ | 11210 | SSSTLPR | 0.37218 | 0.075239 |
| SyS558 | 2033 | GCCCAAGGCGGCGGTCCAAACCGACAGCGCACAG | 6622 | AQGGVQTDSAQ | 11211 | GGVQTDS | 0.371805 | -0.08222 |
| SS48 | 2034 | GCCCAATTGTGTCTAATAATACTCGGGCACAG | 6623 | AQLLSNNTRAQ | 11212 | LLSNNTR | 0.371753 | -0.20449 |
| SyS559 | 2035 | GCCCAATATCATGCTGCTCAGGCTGTTGCACAG | 6624 | AQYHAAQAVAQ | 11213 | YHAAQAV | 0.371353 | 0.02988 |
| GP98 | 2036 | GCCCAAATGAGTGGTGGTGGGTAGTTCGGCACAG | 6625 | AQMSGVGSSAQ | 11214 | MSGVGSS | 0.371229 | 0.337397 |
| SyS560 | 2037 | GCCCAACTCACCGGCCAAGTCCTCGTCGCACAG | 6626 | AQLTGQVLVAQ | 11215 | LTGQVLV | 0.370851 | -0.08343 |
| SyS561 | 2038 | GCCCAAGCGGTTAATAGGCTGCCTATTGCACAG | 6627 | AQAVNRLPIAQ | 11216 | AVNRLPI | 0.370811 | -0.12454 |
| SyS562 | 2039 | GCCCAAAGTTCTCAGATGCCGTTGCGGGCACAG | 6628 | AQSSQMPLRAQ | 11217 | SSQMPLR | 0.370795 | -0.05174 |
| GS279 | 2040 | GCCCAAGCAGCAACATCGCCGACAGCGCACAG | 6629 | AQSSNIADSAQ | 11218 | SSNIADS | 0.370754 | -0.10675 |
| SyS563 | 2041 | GCCCAAGTTGTTACGCCGCAGATTAGTGCACAG | 6630 | AQVVTPQISAQ | 11219 | VVTPQIS | 0.37058 | -0.15746 |
| GS280 | 2042 | GCCCAAGATTCTAAGAAGATGAGTTGGGCACAG | 6631 | AQDSKKMSWAQ | 11220 | DSKKMSW | 0.370419 | -0.09553 |
| SyS564 | 2043 | GCCCAAGAGACGTATAAGACTACTCTGGCACAG | 6632 | AQETYKTTLAQ | 11221 | ETYKTTL | 0.370166 | -0.03857 |
| SyS565 | 2044 | GCCCAACTTACTATGGGTAATTCTCTGGCACAG | 6633 | AQLTMGNSLAQ | 11222 | LTMGNSL | 0.36988 | 0.014405 |
| SyS566 | 2045 | GCCCAATTTAAGGTTAGTATTCAGCAGGCACAG | 6634 | AQFKVSIQQAQ | 11223 | FKVSIQQ | 0.369779 | -0.20345 |
| SyS567 | 2046 | GCCCAAGATGGTCATGCTCATCTTCCGGCACAG | 6635 | AQDGHAHLPAQ | 11224 | DGHAHLP | 0.369646 | -0.11191 |
| SyS568 | 2047 | GCCCAAACCGCCGTCAGCCTCAGCAACGCACAG | 6636 | AQTAVSLSNAQ | 11225 | TAVSLSN | 0.369523 | -0.01275 |
| SyS569 | 2048 | GCCCAAAGCCAAAACCAAATGCAAACCGCACAG | 6637 | AQSQNQMQTAQ | 11226 | SQNQMQT | 0.369507 | -0.13071 |
| SyS570 | 2049 | GCCCAACAGAGTGTGACTACGCAGCATGCACAG | 6638 | AQQSVTTQHAQ | 11227 | QSVTTQH | 0.369126 | 0.146422 |
| SyS571 | 2050 | GCCCAACTCAGCACCGCCCTCACCGTCGCACAG | 6639 | AQLSTALTVAQ | 11228 | LSTALTV | 0.369039 | -0.00037 |
| SyS572 | 2051 | GCCCAACTCGCCAACGCCGTCACCAAAGCACAG | 6640 | AQLANAVTKAQ | 11229 | LANAVTK | 0.368954 | 0.183009 |
| GS281 | 2052 | GCCCAAACCGGCCACGTCCACGAAAACGCACAG | 6641 | AQTGHVHENAQ | 11230 | TGHVHEN | 0.368935 | -0.08669 |
| SyS573 | 2053 | GCCCAATCGATTTCGGATACGGCTTCTGCACAG | 6642 | AQSISDTASAQ | 11231 | SISDTAS | 0.368929 | -0.0313 |
| GS282 | 2054 | GCCCAACCCGTCGTCCAAAGCGTCGGGCACAG | 6643 | AQPVVQSVGAQ | 11232 | PVVQSVG | 0.368793 | -0.15766 |
| GS283 | 2055 | GCCCAACAACACCTCAGCACCGTCAACGCACAG | 6644 | AQQHLSTVNAQ | 11233 | QHLSTVN | 0.368559 | -0.15574 |
| SyS575 | 2056 | GCCCAACTGAGTCATAATACGACGCATGCACAG | 6645 | AQLSHNTTHAQ | 11234 | LSHNTTH | 0.368528 | 0.093848 |
| SyS576 | 2057 | GCCCAACCTTCGAATTTTCTGAATTCTGCACAG | 6646 | AQPSNFSNSAQ | 11235 | PSNFSNS | 0.368509 | 0.141011 |

FIG. 33 (Continued)

| | | | | | | | |
|---|---|---|---|---|---|---|---|
| SyS577 | 2058 | GCCCAATTTGATAAGTCTGTTCCTAGTGCACAG | 6647 | AQFDKSVPSAQ | 11236 | FDKSVPS | 0.368326 | -0.04816 |
| GS284 | 2059 | GCCCAAACCCAAGCCACCGAAAAAGACGCACAG | 6648 | AQTQATEKDAQ | 11237 | TQATEKD | 0.368256 | -0.09754 |
| SyS578 | 2060 | GCCCAATTGAGTGCGAAGGCTAGTCAGGCACAG | 6649 | AQLSAKASQAQ | 11238 | LSAKASQ | 0.368184 | 0.299581 |
| SyS579 | 2061 | GCCCAATCGGTTCAGCTGCGGTGTCGGCACAG | 6650 | AQSVQPAVSAQ | 11239 | SVQPAVS | 0.367991 | 0.197439 |
| SyS580 | 2062 | GCCCAAAGTTTGATGCATGGGACGGCTGCACAG | 6651 | AQSLMHGTPAQ | 11240 | SLMHGTP | 0.367985 | 0.049386 |
| GS285 | 2063 | GCCCAACCCACCATCAGAACCAACACCGCACAG | 6652 | AQPTIRTNTAQ | 11241 | PTIRTNT | 0.367694 | -0.04787 |
| SyS581 | 2064 | GCCCAAAATGATTCGCTTAAGGTTAATGCACAG | 6653 | AQNDSLKVNAQ | 11242 | NDSLKVN | 0.367645 | -0.2268 |
| SyS582 | 2065 | GCCCAAAGCACCCAACCCGTCAACAGAGCACAG | 6654 | AQSTQPVNRAQ | 11243 | STQPVNR | 0.367609 | -0.15981 |
| GS286 | 2066 | GCCCAATCTTCGGATAAGCATAATCCTGCACAG | 6655 | AQSSDKHNPAQ | 11244 | SSDKHNP | 0.367604 | 0.108588 |
| SyS583 | 2067 | GCCCAATTCCTCGAAAACGCCAAAATCGCACAG | 6656 | AQFLENAKIAQ | 11245 | FLENAKI | 0.367535 | 0.026006 |
| SyS584 | 2068 | GCCCAAGTGTCTACTGGTACTCTTAAGGCACAG | 6657 | AQVSTGTLKAQ | 11246 | VSTGTLK | 0.367523 | -0.07858 |
| GS287 | 2069 | GCCCAACGTGATGCGTCGTCTTTGAGTACTGCACAG | 6658 | AQRDASLSTAQ | 11247 | RDASLST | 0.36722 | -0.14238 |
| SyS585 | 2070 | GCCCAAAAGGGTACTGAGATTAAGCTTGCACAG | 6659 | AQKGTEIKLAQ | 11248 | KGTEIKL | 0.367015 | -0.01863 |
| SyS586 | 2071 | GCCCAAATTATGAATCAGCTGGGTGATGCACAG | 6660 | AQIMNQLGDAQ | 11249 | IMNQLGD | 0.36699 | -0.08828 |
| SyS587 | 2072 | GCCCAACCTAGTAATAATACTCAGATTGCACAG | 6661 | AQPSNNTQIAQ | 11250 | PSNNTQI | 0.366851 | -0.10646 |
| SyS588 | 2073 | GCCCAAACTTCGAGTAGTATTACGACTGCACAG | 6662 | AQTSSSITTAQ | 11251 | TSSSITT | 0.366832 | 0.041648 |
| SyS589 | 2074 | GCCCAAAGGGATCTGAATGCGCATAATGCACAG | 6663 | AQRDLNAHNAQ | 11252 | RDLNAHN | 0.366746 | 0.001434 |
| SyS590 | 2075 | GCCCAAACCGGCTTCGCCAGAAGCGAAGCACAG | 6664 | AQTGFARSEAQ | 11253 | TGFARSE | 0.366503 | -0.14283 |
| GS288 | 2076 | GCCCAACTCGAACAACTCGCCCCCAAAGCACAG | 6665 | AQLEQLAPKAQ | 11254 | LEQLAPK | 0.36606 | -0.18054 |
| SyS591 | 2077 | GCCCAAGCCGCCATGCAAAGCGAAAGAGCACAG | 6666 | AQAAMQSERAQ | 11255 | AAMQSER | 0.365747 | 0.085313 |
| SyS290 | 2078 | GCCCAACAGCTTAATTATGAGGCGCATGCACAG | 6667 | AQQLNYEAHAQ | 11256 | QLNYEAH | 0.36537 | -0.15497 |
| SyS592 | 2079 | GCCCAAGCCAACCCGGCAGCCTCCTCGCACAG | 6668 | AQANPGSLLAQ | 11257 | ANPGSLL | 0.365151 | 0.332343 |
| GS291 | 2080 | GCCCAACTTAGGCATATTGAGACGCCTGCACAG | 6669 | AQLRHIETPAQ | 11258 | LRHIETP | 0.365122 | -0.10472 |
| SS49 | 2081 | GCCCAACTTCCTCAGAATTCGGCGAAGGCACAG | 6670 | AQLPQNSAKAQ | 11259 | LPQNSAK | 0.36494 | -0.2215 |
| SyS593 | 2082 | GCCCAAGCCGGCAGCCCCATCAGCAGAGCACAG | 6671 | AQAGSPISRAQ | 11260 | AGSPISR | 0.364661 | 0.254221 |
| SyS594 | 2083 | GCCCAAAGAGCCACCAACGTCGAAGTCGCACAG | 6672 | AQRATNVEVAQ | 11261 | RATNVEV | 0.364602 | 0.350302 |
| SyS595 | 2084 | GCCCAACCCAACCCAACCAACAGAGGCGCACAG | 6673 | AQPQPNNRGAQ | 11262 | PQPNNRG | 0.364568 | 0.149339 |
| SyS596 | 2085 | GCCCAATCTCCTTCGACGCCTCATCTTGCACAG | 6674 | AQSPSTPHLAQ | 11263 | SPSTPHL | 0.364561 | -0.038 |
| SyS597 | 2086 | GCCCAACTTTCGAATACTTTGACTAATGCACAG | 6675 | AQLSNTLTNAQ | 11264 | LSNTLTN | 0.364377 | -0.02217 |
| GS292 | 2087 | GCCCAATCGAATAGGGAGGGTTTGATGGCACAG | 6676 | AQSNREGLMAQ | 11265 | SNREGLM | 0.364262 | -0.06434 |
| SyS598 | 2088 | GCCCAAGTGCGCCCACAGCCCCCCAGCGCACAG | 6677 | AQVAHSPPSAQ | 11266 | VAHSPPS | 0.364259 | 0.059626 |
| GS293 | 2089 | GCCCAAAGCGTCAAAAACATGCTCACCGCACAG | 6678 | AQSVKNMLTAQ | 11267 | SVKNMLT | 0.364054 | -0.01456 |

FIG. 33 (Continued)

| | | | | | | | | |
|---|---|---|---|---|---|---|---|---|
| GS294 | 2090 | GCCCAAGGGCTTTCGACTGGTCTTGCTGCACAG | 6679 | AQGLSTGLAAQ | 11268 | GLSTGLA | 0.36383 | -0.09664 |
| GS295 | 2091 | GCCCAAGCCATGAGCAGACCGAACTCGCACAG | 6680 | AQAMSRPELAQ | 11269 | AMSRPEL | 0.363746 | -0.09205 |
| SyS599 | 2092 | GCCCAAGCCATGGACCTCAAACTCCAAGCACAG | 6681 | AQAMDLKLQAQ | 11270 | AMDLKLQ | 0.363654 | -0.13677 |
| SyS600 | 2093 | GCCCAAGCCGTCGCCGGCCCCACCAAAGCACAG | 6682 | AQAVAGPTKAQ | 11271 | AVAGPTK | 0.363564 | 0.026302 |
| SyS601 | 2094 | GCCCAACCTACTCTTGGGTCGCGTACTGCACAG | 6683 | AQPTLGSRTAQ | 11272 | PTLGSRT | 0.363533 | 0.006254 |
| SyS602 | 2095 | GCCCAAAGTGAGAATCCTATTGATCCGGCACAG | 6684 | AQSENPIDPAQ | 11273 | SENPIDP | 0.363529 | -0.19011 |
| SyS603 | 2096 | GCCCAAACCAACAACAGCCCGGCACCGCACAG | 6685 | AQTNNSPGTAQ | 11274 | TNNSPGT | 0.36339 | 0.163927 |
| SyS604 | 2097 | GCCCAACACACCAGCCCACCAGCCTCGCACAG | 6686 | AQHTSPTSLAQ | 11275 | HTSPTSL | 0.363168 | 0.036859 |
| GS297 | 2098 | GCCCAAAACAACGCGGCATCAGCATGGCACAG | 6687 | AQNNAGISMAQ | 11276 | NNAGISM | 0.362679 | -0.08459 |
| GS298 | 2099 | GCCCAACTCGTCTACAGCAACAACACCGCACAG | 6688 | AQLVYSNNTAQ | 11277 | LVYSNNT | 0.362616 | -0.14524 |
| SyS605 | 2100 | GCCCAACGGCGAGTCAGTCTACGACTGCACAG | 6689 | AQPASQSTTAQ | 11278 | PASQSTT | 0.362362 | 0.055989 |
| SyS606 | 2101 | GCCCAAGTTCAGGTTGGGCATCCTCTTGCACAG | 6690 | AQVQVGHPLAQ | 11279 | VQVGHPL | 0.362247 | -0.16466 |
| SyS607 | 2102 | GCCCAAGACGCCAGTCACACCGGCACCGCACAG | 6691 | AQDASYTGTAQ | 11280 | DASYTGT | 0.361961 | -0.19133 |
| SyS608 | 2103 | GCCCAAGGGATTACTACTGAGGCGGGGCACAG | 6692 | AQGITTEARAQ | 11281 | GITTEAR | 0.361378 | -0.11715 |
| SyS609 | 2104 | GCCCAATCTATGCCTCAGCATGCTATTGCACAG | 6693 | AQSMPQHAIAQ | 11282 | SMPQHAI | 0.361137 | -0.01957 |
| SyS610 | 2105 | GCCCAACTCCAAAGCGCCCTCCAAAACGCACAG | 6694 | AQLQSALQNAQ | 11283 | LQSALQN | 0.361126 | -0.20951 |
| SyS611 | 2106 | GCCCAAAAAGCAGCGACAGCACCAGCGCACAG | 6695 | AQKSSDSTSAQ | 11284 | KSSDSTS | 0.360758 | 0.203964 |
| GS300 | 2107 | GCCCAAAAAAGCCCGGCGCCTCGCACAG | 6696 | AQKSPAGALAQ | 11285 | KSPAGAL | 0.360597 | -0.10382 |
| SyS613 | 2108 | GCCCAAACCGAAATGAGCCTCACCAGCGCACAG | 6697 | AQTEMSLTSAQ | 11286 | TEMSLTS | 0.360316 | -0.1489 |
| SyS614 | 2109 | GCCCAATTGAATAGTGAGACTTTCTGCACAG | 6698 | AQLNSETFPAQ | 11287 | LNSETFP | 0.360064 | -0.18405 |
| SyS615 | 2110 | GCCCAAGCGCCCTCAGCCAACAATACGCACAG | 6699 | AQSALSQQYAQ | 11288 | SALSQQY | 0.359961 | -0.08871 |
| GP99 | 2111 | GCCCAACGTTCGGTGGCTAATGTGCCGGCACAG | 6700 | AQRSVANVPAQ | 11289 | RSVANVP | 0.359888 | 0.151036 |
| SyS616 | 2112 | GCCCAAAGCAGCGGCGGCGCCACCCTCCAAGCACAG | 6701 | AQSSGATLQAQ | 11290 | SSGATLQ | 0.359857 | 0.069108 |
| SyS617 | 2113 | GCCCAACTCAACGGCGGCGGGCGCCAGCGCACAG | 6702 | AQLNGGAASAQ | 11291 | LNGGAAS | 0.359832 | -0.13192 |
| SyS619 | 2114 | GCCCAAAGCCACCAACACCACCCCACCGCACAG | 6703 | AQSHQTTPTAQ | 11292 | SHQTTPT | 0.359233 | -0.10135 |
| GS301 | 2115 | GCCCAATATGAGAATAGTAGTTTGGCACAG | 6704 | AQYENSSSLAQ | 11293 | YENSSSL | 0.359035 | -0.14003 |
| SyS620 | 2116 | GCCCAAATTCAGACTTCTGCTCATACTGCACAG | 6705 | AQIQTSAHTAQ | 11294 | IQTSAHT | 0.358854 | 0.06834 |
| SyS621 | 2117 | GCCCAAAGAGAAATCCAAAAAATGAGCGCACAG | 6706 | AQREIQKMSAQ | 11295 | REIQKMS | 0.358714 | -0.09495 |
| SyS622 | 2118 | GCCCAAAGCGCCGGCATGATCAGCCACGCACAG | 6707 | AQSAGMISHAQ | 11296 | SAGMISH | 0.358383 | 0.117139 |
| SyS623 | 2119 | GCCCAAATGAGAAGCACCGACAGCGAAGCACAG | 6708 | AQMRSTDSEAQ | 11297 | MRSTDSE | 0.358219 | 0.15208 |
| SyS624 | 2120 | GCCCAAAGCCACCCCCAAGGCGACAGCGCACAG | 6709 | AQSHPQGDSAQ | 11298 | SHPQGDS | 0.358104 | -0.12208 |
| SyS625 | 2121 | GCCCAACTCATCGACACCAAAATCAGCGCACAG | 6710 | AQLIDTKISAQ | 11299 | LIDTKIS | 0.358044 | 0.03053 |

FIG. 33 (Continued)

| | | | | | | | | |
|---|---|---|---|---|---|---|---|---|
| SyS626 | 2122 | GCCCAAACCCACCTCAAAGACCTCCTGCACAG | 6711 | AQTHLKDLLAQ | 11300 | THLKDLL | 0.357945 | 0.035942 |
| GS302 | 2123 | GCCCAAGGTACTTCGAGTGTGCTGATTGCACAG | 6712 | AQGTSSVLIAQ | 11301 | GTSSVLI | 0.357908 | 0.009233 |
| SyS627 | 2124 | GCCCAACCTTTGGTTACGAATGAGCCTGCACAG | 6713 | AQPLVTNEPAQ | 11302 | PLVTNEP | 0.357827 | -0.06917 |
| GS303 | 2125 | GCCCAAAGAGACCTCAGCCACAACAGCGCACAG | 6714 | AQRDLSHNSAQ | 11303 | RDLSHNS | 0.357777 | -0.14151 |
| SyS628 | 2126 | GCCCAATATGATAATGAGCATAGGCGGCACAG | 6715 | AQYDNEHRPAQ | 11304 | YDNEHRP | 0.3577 | 0.184576 |
| SyP39 | 2127 | GCCCAAGTTGGGAGTCATACTATGACGGCACAG | 6716 | AQVGSHTMTAQ | 11305 | VGSHTMT | 0.357557 | -0.04335 |
| SyS629 | 2128 | GCCCAAGGGCATACGAGTGTGTCTTGGCACAG | 6717 | AQGHTSVSLAQ | 11306 | GHTSVSL | 0.357531 | -0.06038 |
| SyS630 | 2129 | GCCCAACTCGACCTCAAAAACCAAAGAGCACAG | 6718 | AQLDLKNQRAQ | 11307 | LDLKNQR | 0.357396 | 0.14998 |
| SyS631 | 2130 | GCCCAACCGTCGCCAAAATCACCAGCGCACAG | 6719 | AQPVAKITSAQ | 11308 | PVAKITS | 0.357222 | -0.08463 |
| GS305 | 2131 | GCCCAACTTGAGAATGGGAAGCCTAAGGCACAG | 6720 | AQLENGKPKAQ | 11309 | LENGKPK | 0.356969 | -0.1617 |
| GS306 | 2132 | GCCCAAGACCTCGCCAGAGCCACCCTCGCACAG | 6721 | AQDLARATLAQ | 11310 | DLARATL | 0.356925 | -0.11281 |
| GS307 | 2133 | GCCCAAAAGGTTCGTGATGATAAGCCTGCACAG | 6722 | AQKVRDDKPAQ | 11311 | KVRDDKP | 0.356843 | 0.02987 |
| SS50 | 2134 | GCCCAACACAACGTCGCCATCACCCCGCACAG | 6723 | AQHNVAITPAQ | 11312 | HNVAITP | 0.356745 | -0.25276 |
| GS308 | 2135 | GCCCAAACTTCAACGCCACCTACGCCGCACAG | 6724 | AQTFNATYAAQ | 11313 | TFNATYA | 0.35665 | -0.07129 |
| SyS632 | 2136 | GCCCAAGGCAGCCAAGGCACCATCAGAGCACAG | 6725 | AQGSQGTIRAQ | 11314 | GSQGTIR | 0.356647 | 0.346418 |
| GS309 | 2137 | GCCCAAAGCCTCGGCCACGACGGCCAGAGCACAG | 6726 | AQSLGHDARAQ | 11315 | SLGHDAR | 0.356616 | -0.07956 |
| SyS633 | 2138 | GCCCAACGTAGTGGGCCGGATTCTTCTGCACAG | 6727 | AQRSGPDSSAQ | 11316 | RSGPDSS | 0.356605 | 0.13964 |
| SyS634 | 2139 | GCCCAAGCTATGAATCTTCAGAATTTGGCACAG | 6728 | AQAMNLQNLAQ | 11317 | AMNLQNL | 0.355956 | -0.06641 |
| SyP40 | 2140 | GCCCAACTTCGGGCTGGTCCGGGTGTGGCACAG | 6729 | AQLRAGPGVAQ | 11318 | LRAGPGV | 0.355879 | -0.04263 |
| SyS636 | 2141 | GCCCAAACCGTCATGAGCAGCAGCAGCGCACAG | 6730 | AQTVMSSSSAQ | 11319 | TVMSSSS | 0.355682 | 0.155451 |
| GS313 | 2142 | GCCCAACACATACTTCTCCTGTGGGTTATGCACAG | 6731 | AQHTSPVGYAQ | 11320 | HTSPVGY | 0.355451 | -0.07506 |
| SyP41 | 2143 | GCCCAATGGACTTCTCAGGCTACGGCGGCACAG | 6732 | AQWTSQATAAQ | 11321 | WTSQATA | 0.355301 | -0.03985 |
| SyS637 | 2144 | GCCCAAACGATGAATTCTGTTCCTCGTGCACAG | 6733 | AQTMNSVPRAQ | 11322 | TMNSVPR | 0.355114 | -0.10975 |
| GS315 | 2145 | GCCCAAGTCAACGGCGGCATGGTCAACGCACAG | 6734 | AQVNGGMVNAQ | 11323 | VNGGMVN | 0.3551 | -0.17381 |
| GS316 | 2146 | GCCCAAACTAATGCTAGGATGAATACTGCACAG | 6735 | AQTNARMNTAQ | 11324 | TNARMNT | 0.354728 | -0.01679 |
| SyS638 | 2147 | GCCCAAATCAGCGGCAACATGCACAGCGCACAG | 6736 | AQISGNMHSAQ | 11325 | ISGNMHS | 0.354683 | 0.134397 |
| GS317 | 2148 | GCCCAAAGCGTCGGCGGCGCCAGCTTCGCACAG | 6737 | AQSVGGASFAQ | 11326 | SVGGASF | 0.354664 | -0.04069 |
| GS318 | 2149 | GCCCAAACCAGCGAAAGCCCTACAAAGCACAG | 6738 | AQTSESPYKAQ | 11327 | TSESPYK | 0.354593 | -0.18278 |
| SyS639 | 2150 | GCCCAAGGTCATTTTGGTACTATGTCGGCACAG | 6739 | AQGHFGTMSAQ | 11328 | GHFGTMS | 0.354408 | -0.06031 |
| SyS640 | 2151 | GCCCAACTTACGACTAGTGGTCTGAAGGCACAG | 6740 | AQLTTSGLKAQ | 11329 | LTTSGLK | 0.354396 | 0.01345 |
| GS319 | 2152 | GCCCAAAGGATTAATTCGTCTACGTATGCACAG | 6741 | AQRINSSTYAQ | 11330 | RINSSTY | 0.354303 | -0.18727 |
| GP100 | 2153 | GCCCAACTGACTGGTAGTTCGTTGACTGCACAG | 6742 | AQLTGSSLTAQ | 11331 | LTGSSLT | 0.354102 | -0.07405 |

FIG. 33 (Continued)

| | | | | | | | | |
|---|---|---|---|---|---|---|---|---|
| SyS641 | 2154 | GCCCAACCGATTCGGGTACTATTTATGCACAG | 6743 | AQPIRGTIYAQ | 11332 | PIRGTIY | 0.354066 | -0.08153 |
| GS320 | 2155 | GCCCAAACCACCAGCAACACACCCAGCACAG | 6744 | AQTTSNNTHAQ | 11333 | TTSNNTH | 0.354066 | 0.118932 |
| SyS642 | 2156 | GCCCAACAGGTGACTACTAATTTGGATGCACAG | 6745 | AQQVTTNLDAQ | 11334 | QVTTNLD | 0.353947 | -0.09555 |
| SyS643 | 2157 | GCCCAAGCTTTGGATTCTAGTGAGCCGGCACAG | 6746 | AQALDSSEPAQ | 11335 | ALDSSEP | 0.353947 | -0.1889 |
| SyS644 | 2158 | GCCCAATACCCCAAAAACGTCGCCTGGGCACAG | 6747 | AQYPKNVAWAQ | 11336 | YPKNVAW | 0.353947 | -0.20588 |
| SyS645 | 2159 | GCCCAATCTACTACTGGGCGGAATCTGGCACAG | 6748 | AQSTTGRNLAQ | 11337 | STTGRNL | 0.353947 | -0.21436 |
| SyS646 | 2160 | GCCCAAACGAAGCTTATGCAGTCTAATGCACAG | 6749 | AQTKLMQSNAQ | 11338 | TKLMQSN | 0.353941 | 0.01478 |
| SyS647 | 2161 | GCCCAAAACAGCTACGGCGACGCCGCCGCACAG | 6750 | AQNSYGDAAAQ | 11339 | NSYGDAA | 0.3539 | -0.07546 |
| SyS648 | 2162 | GCCCAAGAGCATACGGGTGCGCCTGTCGCACAG | 6751 | AQEHTGAPAAQ | 11340 | EHTGAPA | 0.353742 | -0.18861 |
| SyS649 | 2163 | GCCCAACTGCGGACTGAGACGGCGAATGCACAG | 6752 | AQLRTETANAQ | 11341 | LRTETAN | 0.353402 | -0.03968 |
| SyS650 | 2164 | GCCCAAGTCCTGACGTCAACACCCTCGCACAG | 6753 | AQVLDVNTLAQ | 11342 | VLDVNTL | 0.353275 | -0.15041 |
| SyS651 | 2165 | GCCCAAGACAGAGAGGCAACGACAAACTCGCACAG | 6754 | AQDRGNDKLAQ | 11343 | DRGNDKL | 0.353216 | 0.297443 |
| GS321 | 2166 | GCCCAAAGCTTCACCAACAGCACCCAGCACAG | 6755 | AQSFTNSTHAQ | 11344 | SFTNSTH | 0.352987 | 0.109223 |
| SyS652 | 2167 | GCCCAACTGCGCCCACAGCAGCCTCAGCGCACAG | 6756 | AQLAHSSLSAQ | 11345 | LAHSSLS | 0.352724 | -0.00659 |
| GS323 | 2168 | GCCCAAAGACTCGTCGACCCCATCCCCGCACAG | 6757 | AQRLVDPIPAQ | 11346 | RLVDPIP | 0.352703 | -0.09391 |
| SyS653 | 2169 | GCCCAATGGGGCGACAAAGAAACCTTCGCACAG | 6758 | AQWGDKETFAQ | 11347 | WGDKETF | 0.352651 | -0.15617 |
| SyS654 | 2170 | GCCCAAAGAGAGACGACAACCTCAGCACCGCACAG | 6759 | AQRDDNLSTAQ | 11348 | RDDNLST | 0.352538 | -0.05395 |
| SyS655 | 2171 | GCCCAATCTAAGCAGTTGATTGATACTGCACAG | 6760 | AQSKQLIDTAQ | 11349 | SKQLIDT | 0.352442 | -0.22803 |
| GS325 | 2172 | GCCCAATTTCAGAATCAGACTGTTGGTGCACAG | 6761 | AQFQNQTVGAQ | 11350 | FQNQTVG | 0.352245 | -0.04999 |
| SyS656 | 2173 | GCCCAAGTCTTCAGCAGCGACAGCCTCGCACAG | 6762 | AQVFSSDSLAQ | 11351 | VFSSDSL | 0.352214 | 0.031487 |
| SyS657 | 2174 | GCCCAATATGCGCAGCAGTTGCCTGTGGCACAG | 6763 | AQYAQQLPVAQ | 11352 | YAQQLPV | 0.352069 | -0.06517 |
| SyS658 | 2175 | GCCCAAATTGTGACTGGTACGCAGGCACAG | 6764 | AQIVTGTTQAQ | 11353 | IVTGTTQ | 0.351501 | -0.17505 |
| SyS659 | 2176 | GCCCAAAGCAAGATCACCGAAAGCAACGCACAG | 6765 | AQSKITESNAQ | 11354 | SKITESN | 0.351451 | 0.084909 |
| SyS660 | 2177 | GCCCAAATTGCTGGGCAGGTGGGGGCACAG | 6766 | AQIAGQVGAAQ | 11355 | IAGQVGA | 0.351384 | 0.33939 |
| SyS661 | 2178 | GCCCAAGGTTATAGTCAGACGCCTCATGCACAG | 6767 | AQGYSQTPHAQ | 11356 | GYSQTPH | 0.351298 | 0.03403 |
| GS326 | 2179 | GCCCAAGGTTTGGCGTTGCGTCCTGATGCACAG | 6768 | AQGLALRPDAQ | 11357 | GLALRPD | 0.35125 | -0.09087 |
| SyS662 | 2180 | GCCCAAAAACGCCGTCAGCAACAACACCGCACAG | 6769 | AQNAVSNNTAQ | 11358 | NAVSNNT | 0.351208 | 0.221429 |
| SyS663 | 2181 | GCCCAAAACCAAAGCACCCTCCCCACGCACAG | 6770 | AQNQSTLPTAQ | 11359 | NQSTLPT | 0.351121 | 0.2934 |
| GS328 | 2182 | GCCCAAACCAGCATCCCCGACAAACCCGCACAG | 6771 | AQTSIPDKPAQ | 11360 | TSIPDKP | 0.351033 | -0.02153 |
| SyS664 | 2183 | GCCCAAGGCAGCACCGCCAGCCTCGCACAG | 6772 | AQGSSTASLAQ | 11361 | GSSTASL | 0.350993 | 0.260874 |
| GS329 | 2184 | GCCCAAAGAATCATCGGCACCGCCACCGCACAG | 6773 | AQRIIGTATAQ | 11362 | RIIGTAT | 0.350979 | -0.11461 |
| GP101 | 2185 | GCCCAAAGTTTGAATGGGGGTCGGACGGCACAG | 6774 | AQSLNGGRTAQ | 11363 | SLNGGRT | 0.35082 | 0.208517 |

FIG. 33 (Continued)

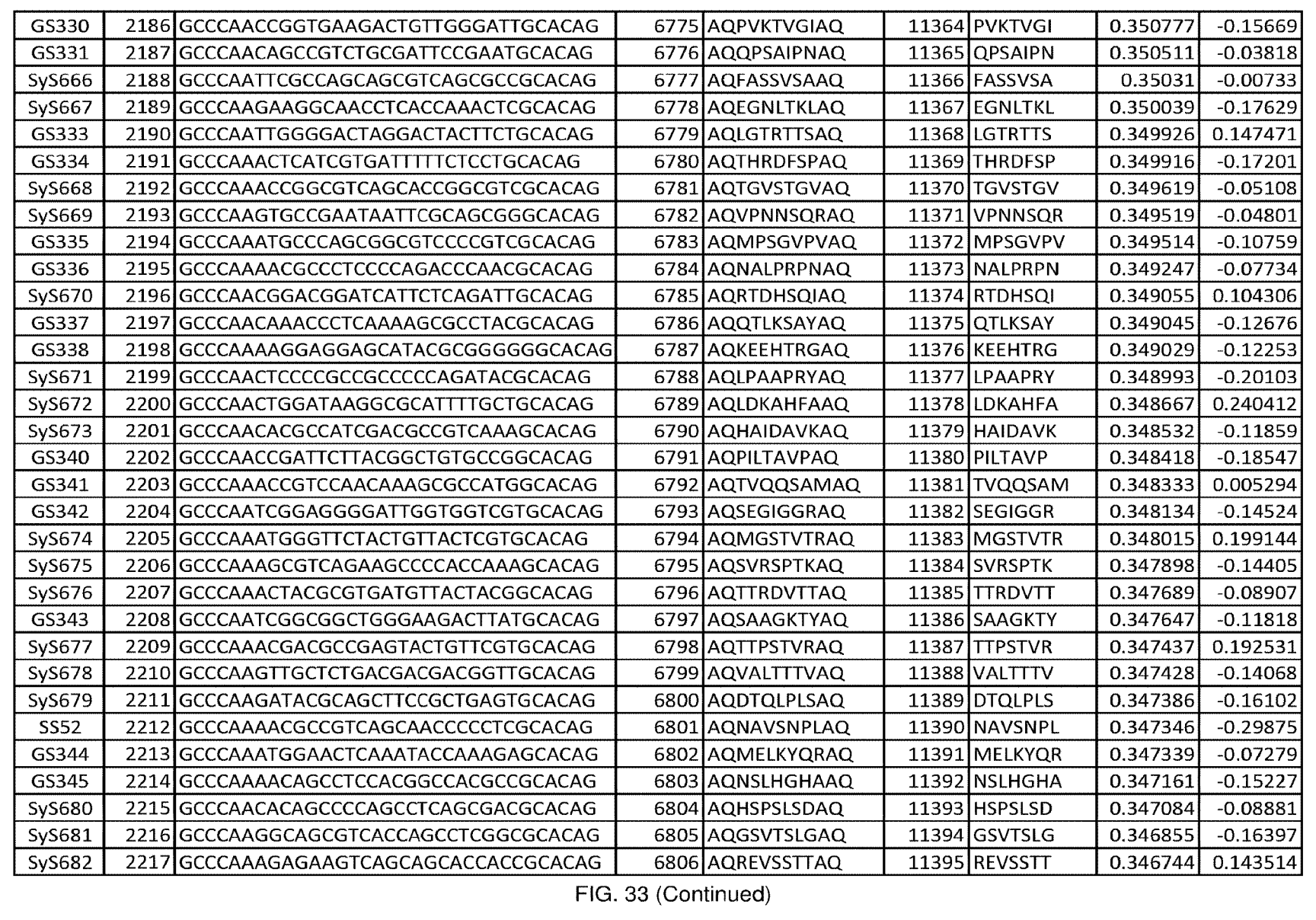

| | | | | | | | | |
|---|---|---|---|---|---|---|---|---|
| GS330 | 2186 | GCCCAACCGGTGAAGACTGTTGGGATTGCACAG | 6775 | AQPVKTVGIAQ | 11364 | PVKTVGI | 0.350777 | -0.15669 |
| GS331 | 2187 | GCCCAACAGCCGTCTGCGATTCCGAATGCACAG | 6776 | AQQPSAIPNAQ | 11365 | QPSAIPN | 0.350511 | -0.03818 |
| SyS666 | 2188 | GCCCAATTCGCCAGCAGCGTCAGCGCCGCACAG | 6777 | AQFASSVSAAQ | 11366 | FASSVSA | 0.35031 | -0.00733 |
| SyS667 | 2189 | GCCCAAGAAGGCAACCTCACCAAACTCGCACAG | 6778 | AQEGNLTKLAQ | 11367 | EGNLTKL | 0.350039 | -0.17629 |
| GS333 | 2190 | GCCCAATTGGGGACTAGGACTACTTCTGCACAG | 6779 | AQLGTRTTSAQ | 11368 | LGTRTTS | 0.349926 | 0.147471 |
| GS334 | 2191 | GCCCAAACTCATCGTGATTTTTCTCCTGCACAG | 6780 | AQTHRDFSPAQ | 11369 | THRDFSP | 0.349916 | -0.17201 |
| SyS668 | 2192 | GCCCAAACCGGCGTCAGCACCGGCGTCGCACAG | 6781 | AQTGVSTGVAQ | 11370 | TGVSTGV | 0.349619 | -0.05108 |
| SyS669 | 2193 | GCCCAAGTGCCGAATAATTCGCAGCGGGCACAG | 6782 | AQVPNNSQRAQ | 11371 | VPNNSQR | 0.349519 | -0.04801 |
| GS335 | 2194 | GCCCAAATGCCAGCGGCGGTCCCGTCGCACAG | 6783 | AQMPSGVPVAQ | 11372 | MPSGVPV | 0.349514 | -0.10759 |
| GS336 | 2195 | GCCCAAAACGCCCTCCCCAGACCCAACGCACAG | 6784 | AQNALPRPNAQ | 11373 | NALPRPN | 0.349247 | -0.07734 |
| SyS670 | 2196 | GCCCAACGGACGGATCATTCTCAGATTGCACAG | 6785 | AQRTDHSQIAQ | 11374 | RTDHSQI | 0.349055 | 0.104306 |
| GS337 | 2197 | GCCCAACAAACCCTCAAAAGGCCTACGCACAG | 6786 | AQQTLKSAYAQ | 11375 | QTLKSAY | 0.349045 | -0.12676 |
| GS338 | 2198 | GCCCAAAAGGAGGAGCATACGCGGGGGGCACAG | 6787 | AQKEEHTRGAQ | 11376 | KEEHTRG | 0.349029 | -0.12253 |
| SyS671 | 2199 | GCCCAACTCCCCGCCGCCCCAGATACGCACAG | 6788 | AQLPAAPRYAQ | 11377 | LPAAPRY | 0.348993 | -0.20103 |
| SyS672 | 2200 | GCCCAACTGGATAAGGCGCATTTTGCTGCACAG | 6789 | AQLDKAHFAAQ | 11378 | LDKAHFA | 0.348667 | 0.240412 |
| SyS673 | 2201 | GCCCAACACGCCATCGACGCCGTCAAAGCACAG | 6790 | AQHAIDAVKAQ | 11379 | HAIDAVK | 0.348532 | -0.11859 |
| GS340 | 2202 | GCCCAACCGATTCTTACGGCTGTGCCGGCACAG | 6791 | AQPILTAVPAQ | 11380 | PILTAVP | 0.348418 | -0.18547 |
| GS341 | 2203 | GCCCAAACGTCCAACAAAGCGCCATGGCACAG | 6792 | AQTVQQSAMAQ | 11381 | TVQQSAM | 0.348333 | 0.005294 |
| GS342 | 2204 | GCCCAATCGGAGGGGATTGGTGGTCGTGCACAG | 6793 | AQSEGIGGRAQ | 11382 | SEGIGGR | 0.348134 | -0.14524 |
| SyS674 | 2205 | GCCCAAATGGGTTCTACTGTTACTCGTGCACAG | 6794 | AQMGSTVTRAQ | 11383 | MGSTVTR | 0.348015 | 0.199144 |
| SyS675 | 2206 | GCCCAAAGCGTCAGAAGCCCACCAAAGCACAG | 6795 | AQSVRSPTKAQ | 11384 | SVRSPTK | 0.347898 | -0.14405 |
| SyS676 | 2207 | GCCCAAACTACGCGTGATGTTACTACGGCACAG | 6796 | AQTTRDVTTAQ | 11385 | TTRDVTT | 0.347689 | -0.08907 |
| GS343 | 2208 | GCCCAATCGGCGGCTGGGAAGACTTATGCACAG | 6797 | AQSAAGKTYAQ | 11386 | SAAGKTY | 0.347647 | -0.11818 |
| SyS677 | 2209 | GCCCAAACGACGCCGAGTACTGTTCGTGCACAG | 6798 | AQTTPSTVRAQ | 11387 | TTPSTVR | 0.347437 | 0.192531 |
| SyS678 | 2210 | GCCCAAGTTGCTCTGACGACGACGGTTGCACAG | 6799 | AQVALTTTVAQ | 11388 | VALTTTV | 0.347428 | -0.14068 |
| SyS679 | 2211 | GCCCAAGATACGCAGCTTCCGCTGAGTGCACAG | 6800 | AQDTQLPLSAQ | 11389 | DTQLPLS | 0.347386 | -0.16102 |
| SS52 | 2212 | GCCCAAAACGCCGTCAGCAACCCCTCGCACAG | 6801 | AQNAVSNPLAQ | 11390 | NAVSNPL | 0.347346 | -0.29875 |
| GS344 | 2213 | GCCCAAATGGAACTCAAATACCAAAGAGCACAG | 6802 | AQMELKYQRAQ | 11391 | MELKYQR | 0.347339 | -0.07279 |
| GS345 | 2214 | GCCCAAAACAGCCTCCACGGCCACGCGCACAG | 6803 | AQNSLHGHAAQ | 11392 | NSLHGHA | 0.347161 | -0.15227 |
| SyS680 | 2215 | GCCCAACACAGCCCCAGCCTCAGCGACGCACAG | 6804 | AQHSPSLSDAQ | 11393 | HSPSLSD | 0.347084 | -0.08881 |
| SyS681 | 2216 | GCCCAAGGCAGCGTCACCAGCCTCGGGCGCACAG | 6805 | AQGSVTSLGAQ | 11394 | GSVTSLG | 0.346855 | -0.16397 |
| SyS682 | 2217 | GCCCAAAGAGAAGAGTCAGCAGCACCACCGCACAG | 6806 | AQREVSSTTAQ | 11395 | REVSSTT | 0.346744 | 0.143514 |

FIG. 33 (Continued)

| | | | | | | | | |
|---|---|---|---|---|---|---|---|---|
| GS346 | 2218 | GCCCAAGGTAAGGCGACGCTTGATACTGCACAG | 6807 | AQGKATLDTAQ | 11396 | GKATLDT | 0.346704 | -0.12044 |
| GS347 | 2219 | GCCCAACTTAATCCTCCTTTGAATAAATGCACAG | 6808 | AQINPPLNNAQ | 11397 | LNPPLNN | 0.346683 | -0.15676 |
| SyS683 | 2220 | GCCCAAACTTCTGGGCATTCGCCGTCGGCACAG | 6809 | AQTSGHSPSAQ | 11398 | TSGHSPS | 0.346676 | 0.010364 |
| SyS684 | 2221 | GCCCAAGACGTCACCGCCACCGCCCCCGCACAG | 6810 | AQDVTATAPAQ | 11399 | DVTATAP | 0.346433 | -0.18648 |
| GS349 | 2222 | GCCCAACACCAAAAACACCGGCAGCGTCGCACAG | 6811 | AQHQNTGSVAQ | 11400 | HQNTGSV | 0.346357 | -0.01619 |
| SyS686 | 2223 | GCCCAAGATCTTACGCATACTTTGATGCACAG | 6812 | AQDLTHTFDAQ | 11401 | DLTHTFD | 0.34605 | -0.19496 |
| GS350 | 2224 | GCCCAATACCTCCCAACAAAGAAAGAGCACAG | 6813 | AQYLPNKERAQ | 11402 | YLPNKER | 0.345987 | -0.05272 |
| SyS687 | 2225 | GCCCAAGTGGATGGTACGTATACGGTGGCACAG | 6814 | AQVDGTYTVAQ | 11403 | VDGTYTV | 0.345915 | -0.0622 |
| SyS688 | 2226 | GCCCAATACCTCACCAGCGGCGGGCTACGCACAG | 6815 | AQYLTSGGYAQ | 11404 | YLTSGGY | 0.345752 | -0.13798 |
| SyS689 | 2227 | GCCCAAGCCAGCCTCGTCGTCGCGCGCACAG | 6816 | AQASLVVVAAQ | 11405 | ASLVVVA | 0.3457 | -0.17072 |
| SyS690 | 2228 | GCCCAATTTGATGCTAATTGAAGATTGCACAG | 6817 | AQFDANSKIAQ | 11406 | FDANSKI | 0.345431 | -0.14647 |
| SyS691 | 2229 | GCCCAATACCTCACCGAAAGCCCCGGCGCACAG | 6818 | AQYLTESPGAQ | 11407 | YLTESPG | 0.345425 | -0.15781 |
| GS351 | 2230 | GCCCAAAGAAACGCCAGCCTCGACCCGCACAG | 6819 | AQRNASLDPAQ | 11408 | RNASLDP | 0.345339 | -0.0446 |
| GP103 | 2231 | GCCCAAGCGGGGAGTCCTGCGTGCGGGTGCACAG | 6820 | AQAGSPRAGAQ | 11409 | AGSPRAG | 0.345002 | -0.07336 |
| SyS692 | 2232 | GCCCAAAGAGTCGAAAAACTCACCCCGCACAG | 6821 | AQRVEKLTPAQ | 11410 | RVEKLTP | 0.344773 | -0.07567 |
| SyS693 | 2233 | GCCCAAAGAACCACCGGCGACAACACCGCACAG | 6822 | AQRTTGDNTAQ | 11411 | RTTGDNT | 0.344747 | 0.190402 |
| SyS694 | 2234 | GCCCAACCCGCCGCCACCAGCGGCTTCGCACAG | 6823 | AQPAATSGFAQ | 11412 | PAATSGF | 0.344706 | -0.16344 |
| SyS695 | 2235 | GCCCAAATTCTTACGATTCATACGCATGCACAG | 6824 | AQILTIHTHAQ | 11413 | ILTIHTH | 0.344626 | -0.22042 |
| GS354 | 2236 | GCCCAAATCAACATCAGCAGCGTCGCACAG | 6825 | AQINISSHVAQ | 11414 | INISSHV | 0.34453 | -0.03881 |
| GS355 | 2237 | GCCCAACCCAGCGGCGCAGCGCCAGAAGCGCACAG | 6826 | AQPSGSARSAQ | 11415 | PSGSARS | 0.344116 | -0.15192 |
| SyS696 | 2238 | GCCCAAAGTACGATGCCGACTAGGCTGGCACAG | 6827 | AQSTMPTRLAQ | 11416 | STMPTRL | 0.344089 | -0.10729 |
| SyS697 | 2239 | GCCCAACTCTACGCCGGCGTGGGGCGTCGCACAG | 6828 | AQLYASAGVAQ | 11417 | LYASAGV | 0.34374 | -0.13192 |
| GP104 | 2240 | GCCCAATTGGTTCAGACGGGCTGCTGGCACAG | 6829 | AQLVQTGLLAQ | 11418 | LVQTGLL | 0.343691 | -0.07266 |
| GS357 | 2241 | GCCCAAGTCAGCCTCAACAGAACCGAAGCACAG | 6830 | AQVSLNRTEAQ | 11419 | VSLNRTE | 0.343359 | -0.01647 |
| SyP42 | 2242 | GCCCAAGGTGGGAGGAGGAGTTCTTTGGCACAG | 6831 | AQGGRESSLAQ | 11420 | GGRESSL | 0.343358 | -0.04339 |
| GS358 | 2243 | GCCCAAGTGGAGAGAGGATGCCGAGGATGGCACAG | 6832 | AQVERMPRMAQ | 11421 | VERMPRM | 0.343043 | -0.03534 |
| SyS699 | 2244 | GCCCAACCCAAATCGGCATCCCGACGCACAG | 6833 | AQPQIGIPDAQ | 11422 | PQIGIPD | 0.342946 | -0.05619 |
| GS359 | 2245 | GCCCAAGCTACGGTGAAGTCGAGTACTGCACAG | 6834 | AQATVKSSTAQ | 11423 | ATVKSST | 0.342874 | 0.027178 |
| SyS700 | 2246 | GCCCAAGGCGGCAACGTCCAAGCCATCGCACAG | 6835 | AQGGNVQAIAQ | 11424 | GGNVQAI | 0.342847 | -0.0119 |
| SyS701 | 2247 | GCCCAAACTATTGTTAATGTTACTAGTGCACAG | 6836 | AQTIVNVTSAQ | 11425 | TIVNVTS | 0.342809 | -0.19739 |
| SyS702 | 2248 | GCCCAAGGGCGACCCCGCCCAAAGCAGCGCACAG | 6837 | AQGDPAQSSAQ | 11426 | GDPAQSS | 0.342651 | -0.10889 |
| SyS703 | 2249 | GCCCAAACTAAGAATACTGATTTTCAGGCACAG | 6838 | AQTKNTDFQAQ | 11427 | TKNTDFQ | 0.34251 | -0.02105 |

FIG. 33 (Continued)

| | | | | | | | | |
|---|---|---|---|---|---|---|---|---|
| GS361 | 2250 | GCCCAAAGACACACCGACGCCGTCATCGCACAG | 6839 | AQRHTDAVIAQ | 11428 | RHTDAVI | 0.342481 | -0.12298 |
| SyS704 | 2251 | GCCCAAAGCGGTCCACACCGCCGTCAGAGCACAG | 6840 | AQSVHTAVRAQ | 11429 | SVHTAVR | 0.342291 | -0.02887 |
| SyS705 | 2252 | GCCCAAATCACCAGCCTCATGAGCGGCGGCACAG | 6841 | AQITSLMSGAQ | 11430 | ITSLMSG | 0.342264 | -0.11737 |
| SyS706 | 2253 | GCCCAAGACCACCAACCAAATCAGCCTCGCACAG | 6842 | AQDHNQISLAQ | 11431 | DHNQISL | 0.341991 | -0.16587 |
| GS362 | 2254 | GCCCAACAAGGCCAAAGCGCCCTCAAAGCACAG | 6843 | AQQGQSALKAQ | 11432 | QGQSALK | 0.341744 | 0.009075 |
| TS146 | 2255 | GCCCAAAACAACGCCACCAGATACACCGCACAG | 6844 | AQNNATRYTAQ | 11433 | NNATRYT | 0.34159 | 0.011557 |
| SyS707 | 2256 | GCCCAATCGCGTAATACGACTTCGTGGGCACAG | 6845 | AQSRNTTSWAQ | 11434 | SRNTTSW | 0.341535 | -0.21436 |
| GS364 | 2257 | GCCCAACCTAGTAATTCGAAGCTGATTGCACAG | 6846 | AQPSNSKLIAQ | 11435 | PSNSKLI | 0.341264 | -0.05716 |
| SyS709 | 2258 | GCCCAAAAAACCGTCAGCCTCAACGACGCACAG | 6847 | AQKTVSLNDAQ | 11436 | KTVSLND | 0.341072 | 0.177223 |
| SyS710 | 2259 | GCCCAAACCCCCTCCCAGAGTCAGCGCACAG | 6848 | AQTPLPRVSAQ | 11437 | TPLPRVS | 0.340871 | -0.18284 |
| GS365 | 2260 | GCCCAACAGACTATTGCGAGTGCTTTGGCACAG | 6849 | AQQTIASALAQ | 11438 | QTIASAL | 0.340714 | -0.14779 |
| GS366 | 2261 | GCCCAACCTATTATGAAGACGACGGTTGCACAG | 6850 | AQPIMKTTVAQ | 11439 | PIMKTTV | 0.340641 | -0.111 |
| SyS711 | 2262 | GCCCAAAGTGCGGTTATTCAGGGGCATGCACAG | 6851 | AQSAVIQGHAQ | 11440 | SAVIQGH | 0.340621 | -0.08096 |
| SyS712 | 2263 | GCCCAACCGCTGTATGGTACGATGTCTGCACAG | 6852 | AQPLYGTMSAQ | 11441 | PLYGTMS | 0.34044 | -0.21325 |
| TS147 | 2264 | GCCCAAGCGAATCGGACTAAGGATTATGCACAG | 6853 | AQANRTKDYAQ | 11442 | ANRTKDY | 0.34043 | 0.212101 |
| SyS713 | 2265 | GCCCAAGTTATTCCGCAGACGGAGAGGGCACAG | 6854 | AQVIPQTERAQ | 11443 | VIPQTER | 0.34041 | -0.15132 |
| SS53 | 2266 | GCCCAAATCGTCAACGGGCCACATCAGAGCACAG | 6855 | AQIVNGHIRAQ | 11444 | IVNGHIR | 0.340404 | -0.39357 |
| SyS714 | 2267 | GCCCAAAGCAGACCCAACGAAACCACCGCACAG | 6856 | AQSRPNETTAQ | 11445 | SRPNETT | 0.340281 | 0.437826 |
| SyS716 | 2268 | GCCCAAGGGTATACTCCGGTTTCGAGGGCACAG | 6857 | AQGYTPVSRAQ | 11446 | GYTPVSR | 0.34003 | -0.22803 |
| SyS717 | 2269 | GCCCAACCTCTGCAGAGGACTATTGGGGCACAG | 6858 | AQPLQRTIGAQ | 11447 | PLQRTIG | 0.340023 | -0.17557 |
| GS367 | 2270 | GCCCAAAGCACCGGCAGCCCACCATCGCACAG | 6859 | AQSTGSPTIAQ | 11448 | STGSPTI | 0.339967 | -0.092 |
| SyS718 | 2271 | GCCCAAAGTACTATGACGGGGCTGATTGCACAG | 6860 | AQSTMTGLIAQ | 11449 | STMTGLI | 0.339737 | -0.05431 |
| GS368 | 2272 | GCCCAAATCCACGCCGTCGGCGCCGAAGCACAG | 6861 | AQIHAVGAEAQ | 11450 | IHAVGAE | 0.33972 | -0.18099 |
| SyS719 | 2273 | GCCCAAACCGCCAAGTCAGCGAACTCGCACAG | 6862 | AQTANVSELAQ | 11451 | TANVSEL | 0.33963 | -0.05039 |
| SyS720 | 2274 | GCCCAAAAACAAAAGGACATGCCCACGCACAG | 6863 | AQNKSDMPHAQ | 11452 | NKSDMPH | 0.339521 | 0.149221 |
| SyS721 | 2275 | GCCCAAAGCAACTACAACACCACGACGCACAG | 6864 | AQSNYNTHDAQ | 11453 | SNYNTHD | 0.339506 | 0.012789 |
| SyS722 | 2276 | GCCCAACCGAGTGTTACTCATCCGGCACAG | 6865 | AQPSVTHHPAQ | 11454 | PSVTHHP | 0.339089 | 0.133746 |
| GS369 | 2277 | GCCCAAAATTTGAGTCTTAAGCCGCTGGCACAG | 6866 | AQNLSLKPLAQ | 11455 | NLSLKPL | 0.338682 | -0.1774 |
| TS148 | 2278 | GCCCAACTTTATTCGAATAAGAGTAATGCACAG | 6867 | AQLYSNKSNAQ | 11456 | LYSNKSN | 0.338445 | -0.09092 |
| SyS725 | 2279 | GCCCAAGATAATGGTCTGGTTCATAGGGCACAG | 6868 | AQDNGLVHRAQ | 11457 | DNGLVHR | 0.337855 | -0.05918 |
| SyS726 | 2280 | GCCCAAATGGGCACCCTCACCATCAGCGCACAG | 6869 | AQMGTLTISAQ | 11458 | MGTLTIS | 0.337855 | -0.20103 |
| GS370 | 2281 | GCCCAAACTTTTCAGTCTGATGAGAGGCACAG | 6870 | AQTFQSDERAQ | 11459 | TFQSDER | 0.337719 | -0.16573 |

FIG. 33 (Continued)

| | | | | | | | |
|---|---|---|---|---|---|---|---|
| GS371 | 2282 | GCCCAAATCGTCACCGGCGCCTACAGAGAGCACAG | 6871 | AQIVTGAYRAQ | 11460 | IVTGAYR | 0.337298 | -0.16814 |
| SyS727 | 2283 | GCCCAAACCGTCGTCAACCCCAGCAGCGCACAG | 6872 | AQTVVNPSSAQ | 11461 | TVVNPSS | 0.337204 | 0.129144 |
| GP105 | 2284 | GCCCAAGATAATAATGTTAGGCATACGGGCACAG | 6873 | AQDNNVRHTAQ | 11462 | DNNVRHT | 0.33706 | 0.231989 |
| GS373 | 2285 | GCCCAAGATCGTTCGCAGAATTCGTTGGCACAG | 6874 | AQDRSQNSLAQ | 11463 | DRSQNSL | 0.337028 | 0.002952 |
| SyS728 | 2286 | GCCCAACATCCTCGTGCCGGCGTCTGCACAG | 6875 | AQHPPVPASAQ | 11464 | HPPVPAS | 0.336942 | 0.072962 |
| SyS729 | 2287 | GCCCAAAAATACATCACCCCCAGCAGCGCACAG | 6876 | AQKYITPSSAQ | 11465 | KYITPSS | 0.336738 | -0.12344 |
| GS374 | 2288 | GCCCAAGTGCCGGATAAGCAGGCGATGGCACAG | 6877 | AQVPDKQAMAQ | 11466 | VPDKQAM | 0.336567 | -0.02576 |
| SyS730 | 2289 | GCCCAAGTTATTGCGAAGACTGAGTATGCACAG | 6878 | AQVIAKTEYAQ | 11467 | VIAKTEY | 0.33656 | -0.04584 |
| SyS731 | 2290 | GCCCAAGGGGGCAGGCGGAGGGGCGGGGCACAG | 6879 | AQGGQAEARAQ | 11468 | GGQAEAR | 0.336557 | -0.04446 |
| SyS732 | 2291 | GCCCAACAACCCGTCCTCAACCAACCCGCACAG | 6880 | AQQPVLNQPAQ | 11469 | QPVLNQP | 0.336549 | 0.089177 |
| GS375 | 2292 | GCCCAAAATAATACTAATGAGAATCTTGCACAG | 6881 | AQNNTNENLAQ | 11470 | NNTNENL | 0.336205 | -0.15048 |
| SyS733 | 2293 | GCCCAACTAATCTGTCTCGTGTCGTCGGCACAG | 6882 | AQTNLSLSSAQ | 11471 | TNLSLSS | 0.336067 | 0.24816 |
| SyS734 | 2294 | GCCCAAGGTCAGTCGAGTGATGAGCGGGCACAG | 6883 | AQGQSSDERAQ | 11472 | GQSSDER | 0.336014 | 0.211316 |
| GS376 | 2295 | GCCCAAACCCACGCACCACCTTCGCCGCACAG | 6884 | AQTHATTFAAQ | 11473 | THATTFA | 0.335849 | -0.02171 |
| SyS736 | 2296 | GCCCAACCAGCCAACAAGACAGAAGCGGCACAG | 6885 | AQTSQQDRSAQ | 11474 | TSQQDRS | 0.335683 | -0.02651 |
| GS377 | 2297 | GCCCAAGCGTTGTTGCATCGTGAGGCGGCACAG | 6886 | AQALLHREAAQ | 11475 | ALLHREA | 0.335641 | -0.13881 |
| SyS737 | 2298 | GCCCAAAATCGAGTGTTACTGCTCTTGCACAG | 6887 | AQNPSVTALAQ | 11476 | NPSVTAL | 0.335537 | -0.07068 |
| SyS738 | 2299 | GCCCAAGTCGCCAACCTCAACAGCAGAGCACAG | 6888 | AQVANLNSRAQ | 11477 | VANLNSR | 0.335302 | -0.03973 |
| SyS739 | 2300 | GCCCAAACCATGCTCCTCGAACCCAAAGCACAG | 6889 | AQTMLLEPKAQ | 11478 | TMLLEPK | 0.335297 | -0.20955 |
| SyS740 | 2301 | GCCCAAAATGTTAGGCCTTGACTTATGCACAG | 6890 | AQNVRPSTYAQ | 11479 | NVRPSTY | 0.335144 | -0.11737 |
| GS379 | 2302 | GCCCAAGTGATTCATATTACGAATACGGCACAG | 6891 | AQVIHITNTAQ | 11480 | VIHITNT | 0.334532 | -0.12797 |
| SyS741 | 2303 | GCCCAAAGCAAGCAACCCCAGCCTCCTCACCGCACAG | 6892 | AQSNPSLLTAQ | 11481 | SNPSLLT | 0.334488 | -0.16466 |
| SyS742 | 2304 | GCCCAATATCAGGATAATGCTAGGCTTGCACAG | 6893 | AQYQDNARLAQ | 11482 | YQDNARL | 0.33435 | -0.22434 |
| SyS743 | 2305 | GCCCAAATCCAAGGCCTCACCCAGCACGCACAG | 6894 | AQIQGLTSHAQ | 11483 | IQGLTSH | 0.334337 | 0.418222 |
| GP106 | 2306 | GCCCAAACTTATAATCAGGGTAAGCAGGCACAG | 6895 | AQTYNQGKQAQ | 11484 | TYNQGKQ | 0.334287 | -0.07398 |
| GS380 | 2307 | GCCCAAGCTCCTACGGGGATGAAGCATGCACAG | 6896 | AQAPTGMKHAQ | 11485 | APTGMKH | 0.334244 | -0.16753 |
| SyS745 | 2308 | GCCCAAATGAGTGGTGAGCTTATTCGTGCACAG | 6897 | AQMSGELIRAQ | 11486 | MSGELIR | 0.333966 | -0.05676 |
| GS381 | 2309 | GCCCAAAGACTCAACACCAGCCACCTCGCACAG | 6898 | AQRLNTSHLAQ | 11487 | RLNTSHL | 0.33391 | 0.026856 |
| SyS746 | 2310 | GCCCAAGCGACGGCTCTGGGGGTGCACAG | 6899 | AQATALAAGAQ | 11488 | ATALAAG | 0.333841 | -0.19618 |
| SyS747 | 2311 | GCCCAACCTATTTCGGGGCTTAAGTCGGCACAG | 6900 | AQPISGLKSAQ | 11489 | PISGLKS | 0.333712 | -0.18245 |
| SyS748 | 2312 | GCCCAAGAGAGCGTACTTTAATCCGGCTGCACAG | 6901 | AQERTFNPAAQ | 11490 | ERTFNPA | 0.333392 | -0.01544 |
| SyS749 | 2313 | GCCCAAATGAGTAATATTTCTAGTGTGTGGCACAG | 6902 | AQMSNISSVAQ | 11491 | MSNISSV | 0.333354 | 0.062249 |

FIG. 33 (Continued)

| | | | | | | | |
|---|---|---|---|---|---|---|---|
| GS382 | 2314 | GCCCAAAGAGAGACGCCAGACTCAGCCCGCACAG | 6903 | AQRDARLSPAQ | 11492 | RDARLSP | 0.332845 | -0.01943 |
| SyS750 | 2315 | GCCCAAGACCACTACGTCAACACCAGAGCACAG | 6904 | AQDHYVNTRAQ | 11493 | DHYVNTR | 0.332785 | -0.19723 |
| SyS752 | 2316 | GCCCAACCTGGGACTGCTGCTGTCGTCTGGCACAG | 6905 | AQPGTAVRLAQ | 11494 | PGTAVRL | 0.332711 | -0.18163 |
| SyS753 | 2317 | GCCCAAGACAAAGGCACCCTCAGCGAAGCACAG | 6906 | AQDKGTLSEAQ | 11495 | DKGTLSE | 0.332541 | -0.08949 |
| GS383 | 2318 | GCCCAATCGATTCCTAGGACGGATAATGCACAG | 6907 | AQSIPRTDNAQ | 11496 | SIPRTDN | 0.332462 | -0.00974 |
| SyS754 | 2319 | GCCCAAGAGAGCCGGTTCTTCATACTGTTGCACAG | 6908 | AQEPVLHTVAQ | 11497 | EPVLHTV | 0.332214 | -0.19739 |
| GS385 | 2320 | GCCCAAGACAGAGCCATCCTCAACAGCGCACAG | 6909 | AQDRAILNSAQ | 11498 | DRAILNS | 0.332175 | -0.04121 |
| SyS755 | 2321 | GCCCAAGAAATCGGCAGCCTCAGACAAGCACAG | 6910 | AQEIGSLRQAQ | 11499 | EIGSLRQ | 0.332133 | -0.16273 |
| SyS756 | 2322 | GCCCAAGCCTTCGTCGGCGGCCACCCCGCACAG | 6911 | AQAFVGATPAQ | 11500 | AFVGATP | 0.332091 | -0.0026 |
| GS386 | 2323 | GCCCAATTCGTCCAAAACAAAGAGACGCCGCACAG | 6912 | AQFVQNKDAAQ | 11501 | FVQNKDA | 0.332078 | -0.07421 |
| SyS758 | 2324 | GCCCAAAGGGATAAAGGCGGGCCTACGGCACAG | 6913 | AQRDKAGPTAQ | 11502 | RDKAGPT | 0.331877 | 0.088605 |
| GS387 | 2325 | GCCCAACTCCTCCCCACCGCCCACAACGCACAG | 6914 | AQLLPTAHNAQ | 11503 | LLPTAHN | 0.331739 | 0.074733 |
| SyS759 | 2326 | GCCCAACCCAACGGCATCACCAGCACCGCACAG | 6915 | AQPNGITSTAQ | 11504 | PNGITST | 0.330938 | -0.07827 |
| GP108 | 2327 | GCCCAATCGGGTGTGACGAAGGGTAGTGCACAG | 6916 | AQSGVTKGSAQ | 11505 | SGVTKGS | 0.330938 | -0.07433 |
| SyS760 | 2328 | GCCCAAATGAACAGCACCATCAGCCACGCACAG | 6917 | AQMNSTISHAQ | 11506 | MNSTISH | 0.330866 | 0.28997 |
| GS389 | 2329 | GCCCAATACAAAAGCGACGTCGGCAGCGCACAG | 6918 | AQYKSDVGSAQ | 11507 | YKSDVGS | 0.330858 | -0.10092 |
| GS390 | 2330 | GCCCAACCGGTGACGCGTGTTAATCTTGCACAG | 6919 | AQPVTRVNLAQ | 11508 | PVTRVNL | 0.330856 | -0.18099 |
| SyS761 | 2331 | GCCCAAAGAAACGTCGCCACGGCCTCGCACAG | 6920 | AQRNVADGLAQ | 11509 | RNVADGL | 0.330693 | 0.111344 |
| GS391 | 2332 | GCCCAAGCTTCGGCTACTTCGATTACTGCACAG | 6921 | AQASATSITAQ | 11510 | ASATSIT | 0.330598 | -0.15766 |
| SyS762 | 2333 | GCCCAAAGCGGCACCGCCAGCAACGTCGCACAG | 6922 | AQSGTASNVAQ | 11511 | SGTASNV | 0.330558 | -0.00713 |
| SyS763 | 2334 | GCCCAACGGCAGGATCTTGGTAGTACTGCACAG | 6923 | AQRQDLGSTAQ | 11512 | RQDLGST | 0.330378 | 0.022044 |
| SyS764 | 2335 | GCCCAAGACAGCGCCCTCATCAGCAAAGCACAG | 6924 | AQDSALISKAQ | 11513 | DSALISK | 0.330309 | -0.10674 |
| SyS765 | 2336 | GCCCAAAACAACGGCCTCAACAGCGCCGCACAG | 6925 | AQNNGLNSAAQ | 11514 | NNGLNSA | 0.329752 | 0.087826 |
| SyS766 | 2337 | GCCCAAGCTGCGAGTGAGCGTCGGATGGCACAG | 6926 | AQAASERRMAQ | 11515 | AASERRM | 0.32966 | -0.15374 |
| GS393 | 2338 | GCCCAACGTCATTCTGCTGTGTGCCTGAGGCACAG | 6927 | AQRHSAVPEAQ | 11516 | RHSAVPE | 0.329584 | -0.11663 |
| GS394 | 2339 | GCCCAATATCAGGATACGAAGGGGCAGGCACAG | 6928 | AQYQDTKGQAQ | 11517 | YQDTKGQ | 0.329332 | -0.01392 |
| SyS767 | 2340 | GCCCAAAAGACTGGGTCGCTGCCTGTGGCACAG | 6929 | AQKTGSLPVAQ | 11518 | KTGSLPV | 0.329312 | -0.0962 |
| SyS768 | 2341 | GCCCAAATTGCGCGGAGTGTGTCTATGGCACAG | 6930 | AQIARSVSMAQ | 11519 | IARSVSM | 0.32924 | 0.053318 |
| SyS769 | 2342 | GCCCAACCCAGCAGCAAACTCCCCTCGCACAG | 6931 | AQPSSKLPLAQ | 11520 | PSSKLPL | 0.329108 | -0.01365 |
| SyS770 | 2343 | GCCCAAATCAACGACCAAAGAATCAGCGCACAG | 6932 | AQINDQRISAQ | 11521 | INDQRIS | 0.328822 | -0.05944 |
| GS396 | 2344 | GCCCAAGGTATTTCTGAGAAGACTTCTGCACAG | 6933 | AQGISEKTSAQ | 11522 | GISEKTS | 0.328727 | -0.03473 |
| GS397 | 2345 | GCCCAAACTAGTGCTTATACTTCGGTGGCACAG | 6934 | AQTSAYTSVAQ | 11523 | TSAYTSV | 0.328529 | -0.09069 |

FIG. 33 (Continued)

| | | | | | | | | |
|---|---|---|---|---|---|---|---|---|
| SyS771 | 2346 | GCCCAAGGCACCCTCCACAGCAGCGCCGCACAG | 6935 | AQGTLHSSAAQ | 11524 | GTLHSSA | 0.328517 | 0.041441 |
| SyS772 | 2347 | GCCCAAGCCCCCAGAGACGCCGCAGCGCACAG | 6936 | AQAPRDAASAQ | 11525 | APRDAAS | 0.328496 | -0.12465 |
| GS398 | 2348 | GCCCAAAATAATACTGCTATGAGTCTTGCACAG | 6937 | AQNNTAMSLAQ | 11526 | NNTAMSL | 0.328406 | -0.11076 |
| SyS774 | 2349 | GCCCAAATCCTCAGAGTCGCCGACGCCGCACAG | 6938 | AQILRVADAAQ | 11527 | ILRVADA | 0.328209 | 0.007753 |
| SyS775 | 2350 | GCCCAAGCCAGCGTCGCCGGCGGCCAGCGCACAG | 6939 | AQASVAGASAQ | 11528 | ASVAGAS | 0.328202 | -0.18527 |
| SyS776 | 2351 | GCCCAAAGGCGTCCTCAACGGCCAGCAAAGCACAG | 6940 | AQSVLNGSKAQ | 11529 | SVLNGSK | 0.328132 | 0.135186 |
| SyS777 | 2352 | GCCCAAATTTATCAGACGGCTTCTGCGGGCACAG | 6941 | AQIYQTASAAQ | 11530 | IYQTASA | 0.328046 | 0.09508 |
| SyS778 | 2353 | GCCCAAACCAGCGAAAGAACCCAATTCGCACAG | 6942 | AQTSERTQFAQ | 11531 | TSERTQF | 0.327984 | 0.021394 |
| SyS780 | 2354 | GCCCAAAGCACCGTCGCCCTCACCAGCGCACAG | 6943 | AQSTVALTSAQ | 11532 | STVALTS | 0.327951 | 0.008571 |
| SyP45 | 2355 | GCCCAAGGGAATACGGTGATTAATGCGGCACAG | 6944 | AQGNTVINAAQ | 11533 | GNTVINA | 0.32791 | -0.03915 |
| SyS781 | 2356 | GCCCAACCCCTCGGCAGCATCGTCACCGCACAG | 6945 | AQPLGSIVTAQ | 11534 | PLGSIVT | 0.327886 | -0.17799 |
| GS399 | 2357 | GCCCAACTCAGAATGAGCGACAGCTTCGCACAG | 6946 | AQLRMSDSFAQ | 11535 | LRMSDSF | 0.327847 | -0.16304 |
| GS400 | 2358 | GCCCAAACCAGCGAAAGCGGCACCCTCGCACAG | 6947 | AQTSESGTLAQ | 11536 | TSESGTL | 0.327847 | -0.16304 |
| SyS782 | 2359 | GCCCAAGAGGCGACGCCGGCCTGTTCGGGCACAG | 6948 | AQEATRPVRAQ | 11537 | EATRPVR | 0.327835 | -0.14041 |
| SyS783 | 2360 | GCCCAAAATAAGCAGTTTTTGGCTGATGCACAG | 6949 | AQNKQFLADAQ | 11538 | NKQFLAD | 0.327749 | -0.0825 |
| SyS784 | 2361 | GCCCAACTCACCATCAGAGACAACGTCGCACAG | 6950 | AQLTIRDNVAQ | 11539 | LTIRDNV | 0.327594 | -0.05797 |
| SyS785 | 2362 | GCCCAAGTTGGGTCTGGGCTTGCTAAGGCACAG | 6951 | AQVGSGLAKAQ | 11540 | VGSGLAK | 0.327594 | -0.13314 |
| GS401 | 2363 | GCCCAACAAAACGCCACCAACCTCATGGCACAG | 6952 | AQQNATNLMAQ | 11541 | QNATNLM | 0.327526 | -0.04297 |
| GS402 | 2364 | GCCCAATCTATGTATGCTGGGCATGAGGCACAG | 6953 | AQSMYAGHEAQ | 11542 | SMYAGHE | 0.327425 | -0.18637 |
| SyS786 | 2365 | GCCCAAATGGTCAACAGCGAAAAAGCCGCACAG | 6954 | AQMVNSEKAAQ | 11543 | MVNSEKA | 0.327321 | 0.005673 |
| GP109 | 2366 | GCCCAACGTATGAGTATGCGGTCTGATGCACAG | 6955 | AQRMSMRSDAQ | 11544 | RMSMRSD | 0.327321 | -0.07169 |
| SyS787 | 2367 | GCCCAAGCAGCAGCGGCCTCAACAAAGCACAG | 6956 | AQSSSGLNKAQ | 11545 | SSSGLNK | 0.327268 | 0.120372 |
| SyS788 | 2368 | GCCCAACAAAGCAGCGTCCTCACCCCGCACAG | 6957 | AQQSSVLTPAQ | 11546 | QSSVLTP | 0.327119 | 0.083873 |
| SyS790 | 2369 | GCCCAAACTCCTAATTTGGAGACTAGTGCACAG | 6958 | AQTPNLETSAQ | 11547 | TPNLETS | 0.326877 | -0.12871 |
| GS406 | 2370 | GCCCAAATGCGTGGTACTCTTTCGATGGCACAG | 6959 | AQMRGTLSMAQ | 11548 | MRGTLSM | 0.326812 | -0.15383 |
| SyS791 | 2371 | GCCCAAGATCATGGTGCTAGTCTTCCTGCACAG | 6960 | AQDHGASLPAQ | 11549 | DHGASLP | 0.326678 | -0.18648 |
| SyS792 | 2372 | GCCCAATCTCATTTGGCGACGCCGAAGGCACAG | 6961 | AQSHLATPKAQ | 11550 | SHLATPK | 0.326626 | -0.14162 |
| SyS793 | 2373 | GCCCAAATCTGATGCGTCGCCGCATCGGCAGGCACAG | 6962 | AQSDASHRQAQ | 11551 | SDASHRQ | 0.326591 | -0.09677 |
| SyS794 | 2374 | GCCCAAACCGGCACCGAAAGACTCAGCGCACAG | 6963 | AQTGTERLSAQ | 11552 | TGTERLS | 0.326591 | -0.09677 |
| SyS795 | 2375 | GCCCAAGCCGTCGGCCACGTCGGCCCCGCACAG | 6964 | AQAVGHVGPAQ | 11553 | AVGHVGP | 0.326533 | -0.06025 |
| SyS796 | 2376 | GCCCAACAACAAGCCAACAGGGCGTCAAAGCACAG | 6965 | AQQSQQGVKAQ | 11554 | QSQQGVK | 0.326127 | 0.155451 |
| SyS798 | 2377 | GCCCAAAATCTTACGATTAGTAATCGGGCACAG | 6966 | AQNLTISNRAQ | 11555 | NLTISNR | 0.325983 | -0.18861 |

FIG. 33 (Continued)

| | | | | | | | | |
|---|---|---|---|---|---|---|---|---|
| SyS799 | 2378 | GCCCAAGTCAGCAGCGGGCTACGAAACCGCACAG | 6967 | AQVSSGYETAQ | 11556 | VSSGYET | 0.325948 | -0.01693 |
| SyS800 | 2379 | GCCCAATCGATTTCTCCTCGTACGGCACAG | 6968 | AQSISPPRTAQ | 11557 | SISPPRT | 0.325816 | -0.0841 |
| SyS801 | 2380 | GCCCAACCCTACAACCAAAGCCCAGCGCACAG | 6969 | AQPYNQSPSAQ | 11558 | PYNQSPS | 0.325728 | -0.10729 |
| GS411 | 2381 | GCCCAAACGATGTCGTATAATACTAATGCACAG | 6970 | AQTMSYNTNAQ | 11559 | TMSYNTN | 0.325719 | -0.16035 |
| GS412 | 2382 | GCCCAAGGCGCCTACACACCGTCAGCGCACAG | 6971 | AQGAYNTVSAQ | 11560 | GAYNTVS | 0.32537 | -0.10423 |
| GS413 | 2383 | GCCCAATCGAAGGTTACGCCTCCTCTGGCACAG | 6972 | AQSKVTPPLAQ | 11561 | SKVTPPL | 0.325307 | -0.111 |
| SyS803 | 2384 | GCCCAAAGATTCAGAGAAAACGACCACGCACAG | 6973 | AQRFRENDHAQ | 11562 | RFRENDH | 0.325231 | 0.023208 |
| SyS804 | 2385 | GCCCAATTGGATACTGGGCAGCCGACGGCACAG | 6974 | AQLDTGQPTAQ | 11563 | LDTGQPT | 0.325094 | -0.12829 |
| GS414 | 2386 | GCCCAACTTCGTCGACTCGCGAGAATGCACAG | 6975 | AQLPSTPQNAQ | 11564 | LPSTPQN | 0.325044 | -0.06588 |
| SyS805 | 2387 | GCCCAAACCCTCAGCTACGTCACCAGCGCACAG | 6976 | AQTLSYVTSAQ | 11565 | TLSYVTS | 0.324951 | -0.18042 |
| SyS806 | 2388 | GCCCAAAGCACCACCGTCCTCCCGTCGCACAG | 6977 | AQSTTVLPVAQ | 11566 | STTVLPV | 0.324892 | -0.0659 |
| SyS807 | 2389 | GCCCAAATGACGCATACGCTTTGAGTGCACAG | 6978 | AQMTHTLLSAQ | 11567 | MTHTLLS | 0.324713 | -0.08142 |
| GS415 | 2390 | GCCCAAAGCACCTACAACAAAACCTTCGCACAG | 6979 | AQSTYNKTFAQ | 11568 | STYNKTF | 0.324696 | -0.13571 |
| GS416 | 2391 | GCCCAAGCGGACGTCGAGTCATACGCTGGCACAG | 6980 | AQATSSHTLAQ | 11569 | ATSSHTL | 0.324696 | -0.13571 |
| SyS808 | 2392 | GCCCAAAGACTCAACGGCACCGAACCCGCACAG | 6981 | AQRLNGTEPAQ | 11570 | RLNGTEP | 0.32462 | 0.318751 |
| SS55 | 2393 | GCCCAACAACAGCCAACACCCCACCAAAGCACAG | 6982 | AQQANTPTKAQ | 11571 | QANTPTK | 0.324608 | -0.31402 |
| SyS809 | 2394 | GCCCAAAGCGCCGTCATCAACAGCAGCGCACAG | 6983 | AQSAVINSSAQ | 11572 | SAVINSS | 0.324458 | 0.174798 |
| SyS810 | 2395 | GCCCAAAACCACGGCAACGAAGTCAAAGCACAG | 6984 | AQNHGNEVKAQ | 11573 | NHGNEVK | 0.324286 | 0.277768 |
| GS417 | 2396 | GCCCAAAAGCATCTGTCGCATGATCCGGCACAG | 6985 | AQKHLSHDPAQ | 11574 | KHLSHDP | 0.324246 | -0.0337 |
| GP110 | 2397 | GCCCAATTGGGGTCGGGTAGGATGGCTGCACAG | 6986 | AQLGSGRMAAQ | 11575 | LGSGRMA | 0.324054 | 0.229744 |
| GS418 | 2398 | GCCCAAAGCAACCAAATCACCATCGTCGCACAG | 6987 | AQSNQITIVAQ | 11576 | SNQITIV | 0.324029 | -0.0065 |
| SyS811 | 2399 | GCCCAAGGTGGTAGGGGTGTGGGTATGGCACAG | 6988 | AQGGRGVGMAQ | 11577 | GGRGVGM | 0.323942 | -0.12991 |
| SyS812 | 2400 | GCCCAATTCGTCACCGAAAGCAAAAGCGCACAG | 6989 | AQFVTESKSAQ | 11578 | FVTESKS | 0.323852 | -0.0172 |
| SyS813 | 2401 | GCCCAAAACAGCGTCCACAACGACCTCGCACAG | 6990 | AQNSVHNDLAQ | 11579 | NSVHNDL | 0.323841 | -0.12222 |
| SyS814 | 2402 | GCCCAAAGCCCCCAACAAAGCAGATACGCACAG | 6991 | AQSPQQSRYAQ | 11580 | SPQQSRY | 0.323644 | -0.10768 |
| SyS815 | 2403 | GCCCAAACTCAGCCTAATCATGATTCTGCACAG | 6992 | AQTQPNHDSAQ | 11581 | TQPNHDS | 0.323393 | -0.13686 |
| SyS816 | 2404 | GCCCAAACGAGGCTGAATGAGGTGACTGCACAG | 6993 | AQTRLNEVTAQ | 11582 | TRLNEVT | 0.323308 | 0.334916 |
| GP111 | 2405 | GCCCAAACGGCGCAGCGTACTAATGTTGCACAG | 6994 | AQTAQRTNVAQ | 11583 | TAQRTNV | 0.323198 | -0.07405 |
| GS419 | 2406 | GCCCAACCCGGCAGAAGCCCCACCACCGCACAG | 6995 | AQPGRSPTTAQ | 11584 | PGRSPTT | 0.322786 | 0.116763 |
| SyS817 | 2407 | GCCCAAGCCTACAGCGTCGTCGAGAGGCGCACAG | 6996 | AQAYSVVRGAQ | 11585 | AYSVVRG | 0.322605 | -0.20462 |
| SyS819 | 2408 | GCCCAAGTTGGTCCGGTGCTTTCTAGGGCACAG | 6997 | AQVGPVLSRAQ | 11586 | VGPVLSR | 0.322462 | -0.09823 |
| GS420 | 2409 | GCCCAAACCAAAATGGGCACCCCAACGCACAG | 6998 | AQTKMGTPNAQ | 11587 | TKMGTPN | 0.322339 | -0.18099 |

FIG. 33 (Continued)

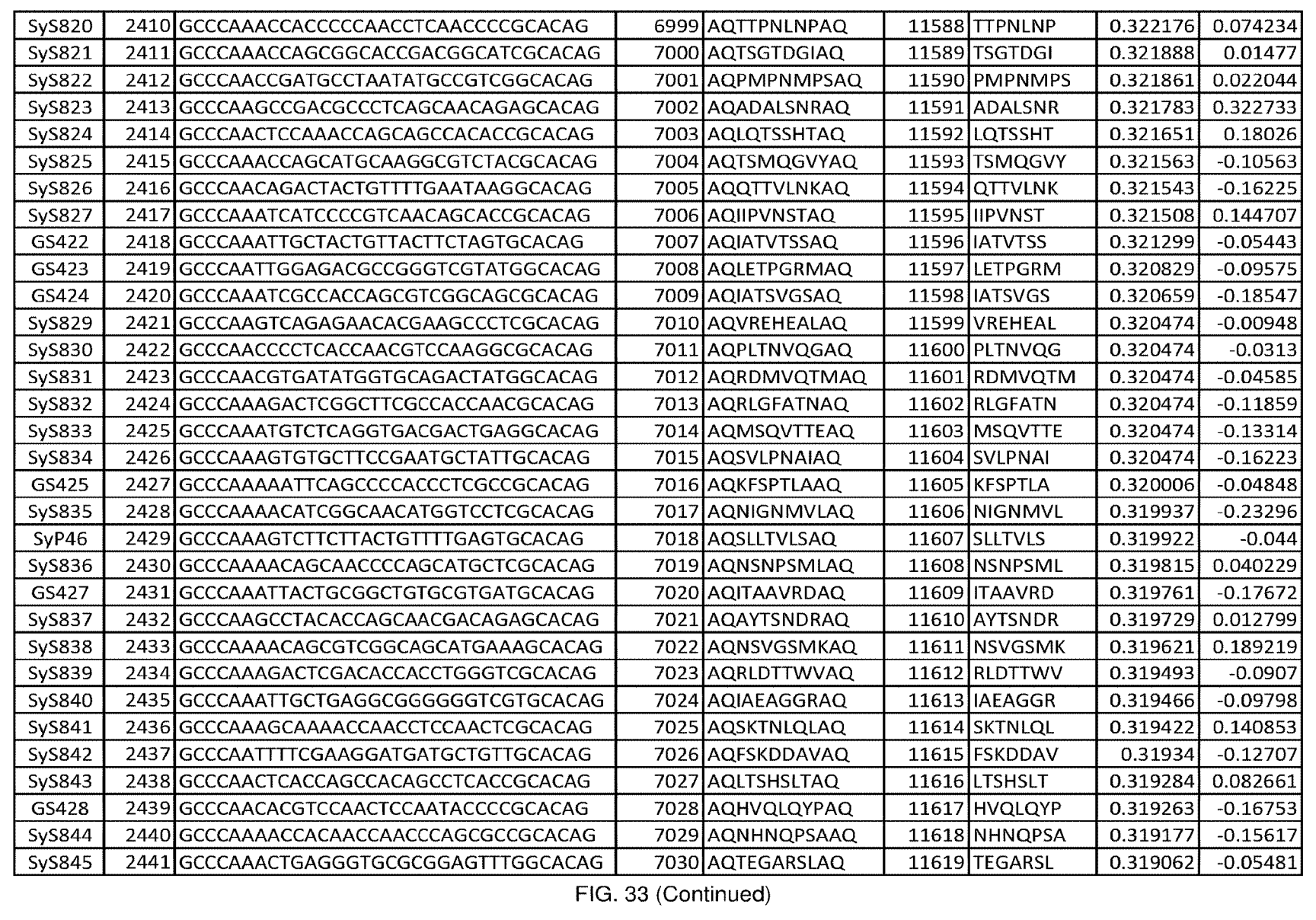

| | | | | | | | | |
|---|---|---|---|---|---|---|---|---|
| SyS820 | 2410 | GCCCAAACCACCCCCAACCTCAACCCGCACAG | 6999 | AQTTPNLNPAQ | 11588 | TTPNLNP | 0.322176 | 0.074234 |
| SyS821 | 2411 | GCCCAAACCAGCGGCACCGACGGCATCGCACAG | 7000 | AQTSGTDGIAQ | 11589 | TSGTDGI | 0.321888 | 0.01477 |
| SyS822 | 2412 | GCCCAACCGATGCCTAATATGCCGTCGGCACAG | 7001 | AQPMPNMPSAQ | 11590 | PMPNMPS | 0.321861 | 0.022044 |
| SyS823 | 2413 | GCCCAAGCCGACGCCCTCAGCAACAGAGCACAG | 7002 | AQADALSNRAQ | 11591 | ADALSNR | 0.321783 | 0.322733 |
| SyS824 | 2414 | GCCCAACTCCAAACCAGCAGCCACACCGCACAG | 7003 | AQLQTSSHTAQ | 11592 | LQTSSHT | 0.321651 | 0.18026 |
| SyS825 | 2415 | GCCCAAACCAGCATGCAAGGCGTCTACGCACAG | 7004 | AQTSMQGVYAQ | 11593 | TSMQGVY | 0.321563 | -0.10563 |
| SyS826 | 2416 | GCCCAACAGACTACTGTTTGAATAAGGCACAG | 7005 | AQQTTVLNKAQ | 11594 | QTTVLNK | 0.321543 | -0.16225 |
| SyS827 | 2417 | GCCCAAATCATCCCGTCAACAGCACCGCACAG | 7006 | AQIIPVNSTAQ | 11595 | IIPVNST | 0.321508 | 0.144707 |
| GS422 | 2418 | GCCCAAATTGCTACTGTTACTTCTAGTGCACAG | 7007 | AQIATVTSSAQ | 11596 | IATVTSS | 0.321299 | -0.05443 |
| GS423 | 2419 | GCCCAATTGGAGACGCCGGGTCGTATGGCACAG | 7008 | AQLETPGRMAQ | 11597 | LETPGRM | 0.320829 | -0.09575 |
| GS424 | 2420 | GCCCAAATCGCCACCAGCGTCGGCAGCGCACAG | 7009 | AQIATSVGSAQ | 11598 | IATSVGS | 0.320659 | -0.18547 |
| SyS829 | 2421 | GCCCAAGTCAGAGAACACGAAGCCCTCGCACAG | 7010 | AQVREHEALAQ | 11599 | VREHEAL | 0.320474 | -0.00948 |
| SyS830 | 2422 | GCCCAACCCCTCACCAACGTCCAAGGGCACAG | 7011 | AQPLTNVQGAQ | 11600 | PLTNVQG | 0.320474 | -0.0313 |
| SyS831 | 2423 | GCCCAACGTGATATGGTGCAGACTATGGCACAG | 7012 | AQRDMVQTMAQ | 11601 | RDMVQTM | 0.320474 | -0.04585 |
| SyS832 | 2424 | GCCCAAAGACTCGGCTTCGCCACCAACGCACAG | 7013 | AQRLGFATNAQ | 11602 | RLGFATN | 0.320474 | -0.11859 |
| SyS833 | 2425 | GCCCAAATGTCTCAGGTGACGACTGAGGCACAG | 7014 | AQMSQVTTEAQ | 11603 | MSQVTTE | 0.320474 | -0.13314 |
| SyS834 | 2426 | GCCCAAAGTGTGCTTCCGAATGCTATTGCACAG | 7015 | AQSVLPNAIAQ | 11604 | SVLPNAI | 0.320474 | -0.16223 |
| GS425 | 2427 | GCCCAAAAAATTCAGCCCACCCTCGCCGCACAG | 7016 | AQKFSPTLAAQ | 11605 | KFSPTLA | 0.320006 | -0.04848 |
| SyS835 | 2428 | GCCCAAAACATCGGCAACATGGTCCTCGCACAG | 7017 | AQNIGNMVLAQ | 11606 | NIGNMVL | 0.319937 | -0.23296 |
| SyP46 | 2429 | GCCCAAAGTCTCTTACTGTTTGAGTGCACAG | 7018 | AQSLLTVLSAQ | 11607 | SLLTVLS | 0.319922 | -0.044 |
| SyS836 | 2430 | GCCCAAAACAGCAACCCCAGCATGCTCGCACAG | 7019 | AQNSNPSMLAQ | 11608 | NSNPSML | 0.319815 | 0.040229 |
| GS427 | 2431 | GCCCAAATTACTGCGGCGTGTGCGTGATGCACAG | 7020 | AQITAAVRDAQ | 11609 | ITAAVRD | 0.319761 | -0.17672 |
| SyS837 | 2432 | GCCCAAGCCTACACCAGCAACGACAGAGCACAG | 7021 | AQAYTSNDRAQ | 11610 | AYTSNDR | 0.319729 | 0.012799 |
| SyS838 | 2433 | GCCCAAAACAGCGTCGGCAGCATGAAAGCACAG | 7022 | AQNSVGSMKAQ | 11611 | NSVGSMK | 0.319621 | 0.189219 |
| SyS839 | 2434 | GCCCAAAGACTCGACACCACCTGGGTCGCACAG | 7023 | AQRLDTTWVAQ | 11612 | RLDTTWV | 0.319493 | -0.0907 |
| SyS840 | 2435 | GCCCAAATTGCTGAGGCGGCGGGGGGTCGTGCACAG | 7024 | AQIAEAGGRAQ | 11613 | IAEAGGR | 0.319466 | -0.09798 |
| SyS841 | 2436 | GCCCAAAGCAAAACCAACCTCCAACTCGCACAG | 7025 | AQSKTNLQLAQ | 11614 | SKTNLQL | 0.319422 | 0.140853 |
| SyS842 | 2437 | GCCCAATTTTCGAAGGATGATGCTGTTGCACAG | 7026 | AQFSKDDAVAQ | 11615 | FSKDDAV | 0.31934 | -0.12707 |
| SyS843 | 2438 | GCCCAACTCACCAGCCACCAGAGCCTCACCGCACAG | 7027 | AQLTSHSLTAQ | 11616 | LTSHSLT | 0.319284 | 0.082661 |
| GS428 | 2439 | GCCCAACACGTCCAACTCCAATACCCCGCACAG | 7028 | AQHVQLQYPAQ | 11617 | HVQLQYP | 0.319263 | -0.16753 |
| SyS844 | 2440 | GCCCAAAACCACAACCACCAACCCAGCGCCGCACAG | 7029 | AQNHNQPSAAQ | 11618 | NHNQPSA | 0.319177 | -0.15617 |
| SyS845 | 2441 | GCCCAAACTGAGGGTGCGCGGAGTTTGGCACAG | 7030 | AQTEGARSLAQ | 11619 | TEGARSL | 0.319062 | -0.05481 |

FIG. 33 (Continued)

| ID | No. | Sequence | No. | Peptide | No. | Peptide | Value 1 | Value 2 |
|---|---|---|---|---|---|---|---|---|
| SyS846 | 2442 | GCCCAAAACCAAAGGCGACAGCAAAGTCGCACAG | 7031 | AQNQSDSKVAQ | 11620 | NQSDSKV | 0.319021 | 0.002646 |
| SyS847 | 2443 | GCCCAAGTGAGTCTTCCGCTGGCTCCGGCACAG | 7032 | AQVSLPLAPAQ | 11621 | VSLPLAP | 0.319021 | -0.17799 |
| GS429 | 2444 | GCCCAAAACAACAACCAACCTCAGCAGAGCACAG | 7033 | AQNNTNLSRAQ | 11622 | NNTNLSR | 0.318597 | 0.099602 |
| GP113 | 2445 | GCCCAATATTCGAATAGTAATAATCATGCACAG | 7034 | AQYSNSNNHAQ | 11623 | YSNSNNH | 0.31847 | -0.07259 |
| SyS848 | 2446 | GCCCAAGGCCTCGAAACCAGACTCCACGCACAG | 7035 | AQGLETRLHAQ | 11624 | GLETRLH | 0.318311 | -0.01832 |
| SyS849 | 2447 | GCCCAACTGACTACTACTGAGTCTAAGGCACAG | 7036 | AQLTTTESKAQ | 11625 | LTTTESK | 0.318126 | -0.13556 |
| SyS850 | 2448 | GCCCAAATGGGCGCCAGAATGCCCCTCGCACAG | 7037 | AQMGARMPLAQ | 11626 | MGARMPL | 0.317628 | 0.100846 |
| SyS851 | 2449 | GCCCAAAGTCATGATCATATGCTTATTGCACAG | 7038 | AQSHDHMLIAQ | 11627 | SHDHMLI | 0.317559 | -0.1792 |
| SyS852 | 2450 | GCCCAACGTACTGAGGGTTCGGATAATGCACAG | 7039 | AQRTEGSDNAQ | 11628 | RTEGSDN | 0.317519 | -0.08748 |
| SyS853 | 2451 | GCCCAAAATTTTCAGCGTGATGGGCCGGCACAG | 7040 | AQNFQRDGPAQ | 11629 | NFQRDGP | 0.317429 | -0.00904 |
| SyS854 | 2452 | GCCCAACTTTCGAATATTAATCCGCATGCACAG | 7041 | AQLSNINPHAQ | 11630 | LSNINPH | 0.317372 | -0.0216 |
| SyS855 | 2453 | GCCCAAAGCAGCAACCACCAGCAGAGCACAG | 7042 | AQSSNHTSRAQ | 11631 | SSNHTSR | 0.317335 | 0.288709 |
| SyS856 | 2454 | GCCCAAATGCACGTCAACGCCAGCCCGCACAG | 7043 | AQMHVNASPAQ | 11632 | MHVNASP | 0.317257 | 0.128729 |
| SyS857 | 2455 | GCCCAATGGGATTCGTTGGCTGCGCGGCACAG | 7044 | AQWDSLAAPAQ | 11633 | WDSLAAP | 0.317054 | -0.1295 |
| SyS858 | 2456 | GCCCAACTGGATGGTGCGCATAATGCGGCACAG | 7045 | AQLDGAHNAAQ | 11634 | LDGAHNA | 0.316943 | -0.13677 |
| GS436 | 2457 | GCCCAATCGATTAGGAGTCCGCCTCCTGCACAG | 7046 | AQSIRSPPPAQ | 11635 | SIRSPPP | 0.31688 | -0.15407 |
| GS437 | 2458 | GCCCAAAATGGGACGCTGAAGGGGTTGGCACAG | 7047 | AQNGTLKGLAQ | 11636 | NGTLKGL | 0.316732 | -0.08754 |
| SyS859 | 2459 | GCCCAATTTTATCAGGAGCAGTCTTTGGCACAG | 7048 | AQFYQEQSLAQ | 11637 | FYQEQSL | 0.316697 | -0.15132 |
| SyS860 | 2460 | GCCCAATACGACCAAAAAAGCCTCGCCGCACAG | 7049 | AQYDQKSLAAQ | 11638 | YDQKSLA | 0.316591 | -0.02956 |
| GP114 | 2461 | GCCCAACTGTCGACGAATCGTACTTTTGCACAG | 7050 | AQLSTNRTFAQ | 11639 | LSTNRTF | 0.31655 | -0.07398 |
| GS439 | 2462 | GCCCAAAAACAAACCAAGACAGCAGCGCACAG | 7051 | AQKQTQDSSAQ | 11640 | KQTQDSS | 0.316176 | -0.04007 |
| GS440 | 2463 | GCCCAATATGAGCGGGGGCCTCAGATGGCACAG | 7052 | AQYERGPQMAQ | 11641 | YERGPQM | 0.315854 | -0.17291 |
| SyS862 | 2464 | GCCCAAACCCACGCCAACAGCGTCAGAGCACAG | 7053 | AQTHANSVRAQ | 11642 | THANSVR | 0.315781 | -0.07488 |
| GS441 | 2465 | GCCCAAAGTATGAATACTAATGCTTCTGCACAG | 7054 | AQSMNTNASAQ | 11643 | SMNTNAS | 0.315733 | -0.12336 |
| SyS863 | 2466 | GCCCAACTTGATAATGAGAAGGGAGGGCACAG | 7055 | AQLDNEKGRAQ | 11644 | LDNEKGR | 0.315543 | 0.058188 |
| GS442 | 2467 | GCCCAACTCGGCCAACTCCTCCAAAGCGCACAG | 7056 | AQLGQLLQSAQ | 11645 | LGQLLQS | 0.315509 | -0.16214 |
| SyS864 | 2468 | GCCCAAATGCGGATGCCTGTTAATATGGCACAG | 7057 | AQMRMPVNMMAQ | 11646 | MRMPVNM | 0.315482 | -0.20224 |
| GS443 | 2469 | GCCCAAGGCACCAGCAACCTCCCCAGCGCACAG | 7058 | AQGTSNLPSAQ | 11647 | GTSNLPS | 0.314909 | -0.13702 |
| GS444 | 2470 | GCCCAAGAGGGGGAGATGAAGTCTCCGGCACAG | 7059 | AQEGEMKSPAQ | 11648 | EGEMKSP | 0.31482 | -0.1646 |
| SyS865 | 2471 | GCCCAACAGCTGGGGCATGATAATCGGGCACAG | 7060 | AQQLGHDNRAQ | 11649 | QLGHDNR | 0.314814 | -0.11961 |
| SyS866 | 2472 | GCCCAACTGGATGATTCTGCGGGGAGGGCACAG | 7061 | AQLDDSAGRAQ | 11650 | LDDSAGR | 0.314701 | -0.11941 |
| SyS867 | 2473 | GCCCAAAACTGGTGCTGGTAATGGGCGGGCACAG | 7062 | AQTGAGNGRAQ | 11651 | TGAGNGR | 0.314656 | -0.01667 |

FIG. 33 (Continued)

| | | | | | | | | |
|---|---|---|---|---|---|---|---|---|
| SyS868 | GCCCAAAAACACCGGCGGCCGCCATGATGGCACAG | 2474 | AQNTGAAMMAQ | 7063 | NTGAAMM | 11652 | 0.314631 | 0.055763 |
| GS446 | GCCCAAATGGGGGCGGAATACGTCTGTTGCACAG | 2475 | AQMGANTSVAQ | 7064 | MGANTSV | 11653 | 0.314385 | -0.08188 |
| SyS869 | GCCCAACCCAGCACCCACGGCGGCAGCGCACAG | 2476 | AQPSTHGGSAQ | 7065 | PSTHGGS | 11654 | 0.314357 | -0.1889 |
| SyS870 | GCCCAAATGCCTCAGTCGCAGCCGAATGCACAG | 2477 | AQMPQSQPNAQ | 7066 | MPQSQPN | 11655 | 0.31424 | 0.015982 |
| SyS871 | GCCCAATCTACTCAGGCTAGGCGACGGCACAG | 2478 | AQSTQARLTAQ | 7067 | STQARLT | 11656 | 0.314143 | -0.15374 |
| SyS872 | GCCCAAAGCGAATACCTCCTCAACCCCGCACAG | 2479 | AQSEYLLNPAQ | 7068 | SEYLLNP | 11657 | 0.314087 | -0.19618 |
| SyS873 | GCCCAAACTACTGGTCCTGGGCTGAATGCACAG | 2480 | AQTTGPGLNAQ | 7069 | TTGPGLN | 11658 | 0.314048 | 0.103567 |
| GS449 | GCCCAACCTGGGAGTTCTGGTGTCTTATGCACAG | 2481 | AQPGSSVSYAQ | 7070 | PGSSVSY | 11659 | 0.313645 | -0.14868 |
| GS450 | GCCCAATATTTTGGGTCGGCGCAGGAGGCACAG | 2482 | AQYFGSAQEAQ | 7071 | YFGSAQE | 11660 | 0.313586 | -0.17958 |
| GS451 | GCCCAAGCCGTCATCAACAACGCCACCGCACAG | 2483 | AQAVINNATAQ | 7072 | AVINNAT | 11661 | 0.313428 | -0.0842 |
| SyS874 | GCCCAAGTCGCCATGCAAGACAAAAAAGCACAG | 2484 | AQVAMQDKKAQ | 7073 | VAMQDKK | 11662 | 0.313354 | -0.14041 |
| SyS875 | GCCCAAGCGGATAATATGAATATTAAGGCACAG | 2485 | AQADNMNIKAQ | 7074 | ADNMNIK | 11663 | 0.313295 | -0.07009 |
| GP115 | GCCCAAGGCGGGGACGACTGATTCTGCACAG | 2486 | AQGRATTDSAQ | 7075 | GRATTDS | 11664 | 0.313279 | -0.07065 |
| SyS876 | GCCCAAATGAACCTCCACCTCAAAGGGCACAG | 2487 | AQMNLHLKGAQ | 7076 | MNLHLKG | 11665 | 0.313136 | 0.083677 |
| TS152 | GCCCAATCGAATCAGATTCGTGATTCGGCACAG | 2488 | AQSNQIRDSAQ | 7077 | SNQIRDS | 11666 | 0.313116 | -0.32301 |
| SyS877 | GCCCAAGTTAATGGTCAGAGTACGCCTGCACAG | 2489 | AQVNGQSTPAQ | 7078 | VNGQSTP | 11667 | 0.313037 | -0.00962 |
| SyS878 | GCCCAAATTCTTCCTCAGTTGAATTCGGCACAG | 2490 | AQILPQLNSAQ | 7079 | ILPQLNS | 11668 | 0.312954 | -0.03559 |
| SyS879 | GCCCAAGTCCAAGACAGCCTCCACTTCGCACAG | 2491 | AQVQDSLHFAQ | 7080 | VQDSLHF | 11669 | 0.312874 | 0.083873 |
| SyS880 | GCCCAAGACGTCAGCAACAGAAACAACGCACAG | 2492 | AQDVSNRNNAQ | 7081 | DVSNRNN | 11670 | 0.312493 | -0.15411 |
| GP116 | GCCCAAGATGCTAGTCATGGTTCTAGTGCACAG | 2493 | AQDASHGSSAQ | 7082 | DASHGSS | 11671 | 0.312276 | -0.07391 |
| SyS881 | GCCCAACGGGCGAGTGCTCATCCGCGGCACAG | 2494 | AQRASAHPPAQ | 7083 | RASAHPP | 11672 | 0.312043 | -0.11646 |
| SyS882 | GCCCAACCCAGCCCTCGAGCGCGACGCACAG | 2495 | AQPSLRALDAQ | 7084 | PSLRALD | 11673 | 0.311957 | -0.17678 |
| SyS883 | GCCCAAGATAAGACGCCTCCGGTTGCTGCACAG | 2496 | AQDKTPPVAAQ | 7085 | DKTPPVA | 11674 | 0.311957 | -0.17678 |
| SyS884 | GCCCAACTTAATGATGTTACGACTAGGGCACAG | 2497 | AQLNDVTTRAQ | 7086 | LNDVTTR | 11675 | 0.311619 | -0.20586 |
| SyS885 | GCCCAAGGCGCCAGCAACGCCCAAGCCGCACAG | 2498 | AQGASNAQAAQ | 7087 | GASNAQA | 11676 | 0.311537 | 0.290108 |
| SyS886 | GCCCAAAATGGGTCGCGGGATGCGTTGGCACAG | 2499 | AQNGSRDALAQ | 7088 | NGSRDAL | 11677 | 0.311371 | 0.125773 |
| GS452 | GCCCAATACGGCGTCGAAAGAATGAGCGCACAG | 2500 | AQYGVERMSAQ | 7089 | YGVERMS | 11678 | 0.311356 | -0.04604 |
| GS453 | GCCCAAGCCAAAGTGCCAGCAGCTTCGCACAG | 2501 | AQAKVASSFAQ | 7090 | AKVASSF | 11679 | 0.311335 | -0.04098 |
| SyS887 | GCCCAACATAAGCAGATTCTGTTGGATGCACAG | 2502 | AQHKQILLDAQ | 7091 | HKQILLD | 11680 | 0.311304 | -0.10069 |
| SyS888 | GCCCAAGACAGAGAATCGACAGAATCGCACAG | 2503 | AQDRANDRIAQ | 7092 | DRANDRI | 11681 | 0.311232 | 0.08751 |
| GS454 | GCCCAAAAAATGAGCACCACCATGCTCGCACAG | 2504 | AQKMSTTMLAQ | 7093 | KMSTTML | 11682 | 0.31117 | -0.1003 |
| SyS889 | GCCCAAGGCGGCGAAAACGCGTCATCGCACAG | 2505 | AQGGENGVIAQ | 7094 | GGENGVI | 11683 | 0.310602 | -0.15011 |

FIG. 33 (Continued)

| | | | | | | | | |
|---|---|---|---|---|---|---|---|---|
| SyS890 | 2506 | GCCCAAGTTACGCGAGACTCTGATTTCGGCACAG | 7095 | AQVTQTLISAQ | 11684 | VTQTLIS | 0.310505 | -0.17799 |
| SyS891 | 2507 | GCCCAACTGTATACTAAGGCTCTGATTGCACAG | 7096 | AQLYTKALIAQ | 11685 | LYTKALI | 0.310465 | -0.10161 |
| GS455 | 2508 | GCCCAAACCCTCCCGGCCACAACAGAGCACAG | 7097 | AQTLPGHNRAQ | 11686 | TLPGHNR | 0.310262 | -0.1756 |
| SyS892 | 2509 | GCCCAAGTAAGTCTGGGCTTGTGGGTGCACAG | 7098 | AQSKSGLVGAQ | 11687 | SKSGLVG | 0.310236 | 0.168736 |
| GS456 | 2510 | GCCCAACTTACTTTGAAGGATACTAGTGCACAG | 7099 | AQLTLKDTSAQ | 11688 | LTLKDTS | 0.310122 | -0.18278 |
| SyS893 | 2511 | GCCCAATGGAACGGCACCGGCGTCAGCGCACAG | 7100 | AQWNGTGVSAQ | 11689 | WNGTGVS | 0.310096 | -0.0119 |
| SS58 | 2512 | GCCCAACTCGTCCAAAACAACACCATGGCACAG | 7101 | AQLVQNNTMAQ | 11690 | LVQNNTM | 0.310057 | -0.30263 |
| SyS894 | 2513 | GCCCAACTCGCCGACAGAGGCAGCGCCGCACAG | 7102 | AQIADRGSAAQ | 11691 | IADRGSA | 0.310018 | -0.08828 |
| GS459 | 2514 | GCCCAATTGGCTTCGACGGGTGCGAATGCACAG | 7103 | AQLASTGANAQ | 11692 | LASTGAN | 0.309525 | -0.13094 |
| GS460 | 2515 | GCCCAACTTGGGCGGAATGATACTCTTGCACAG | 7104 | AQLGRNDTLAQ | 11693 | LGRNDTL | 0.3095 | -0.05896 |
| GS461 | 2516 | GCCCAAGAAGCACCAACGGCGAAGCCGCACAG | 7105 | AQRSTNGEAAQ | 11694 | RSTNGEA | 0.309188 | -0.01679 |
| GS462 | 2517 | GCCCAAGGCGGCCACCTACCAAAGAACCGCACAG | 7106 | AQGATYQRTAQ | 11695 | GATYQRT | 0.309152 | -0.12526 |
| SyS895 | 2518 | GCCCAAGGCAAAAGCCAACTCCTCATGGCACAG | 7107 | AQGKSQLLMAQ | 11696 | GKSQLLM | 0.309137 | -0.07057 |
| SyS896 | 2519 | GCCCAAAATACTGCTACGTTTTCTTCGGGCACAG | 7108 | AQNTATFSSAQ | 11697 | NTATFSS | 0.309129 | -0.04787 |
| GS463 | 2520 | GCCCAATATTCGACGACGATTTCTCCGGCACAG | 7109 | AQYSTTISPAQ | 11698 | YSTTISP | 0.30904 | -0.07316 |
| SyS897 | 2521 | GCCCAACCCAGACACAGCGTCCAAGACGCACAG | 7110 | AQPRHSVQDAQ | 11699 | PRHSVQD | 0.308961 | -0.20314 |
| GP117 | 2522 | GCCCAAAATAATAATACGAAGATGAATGCACAG | 7111 | AQNNNTKMNAQ | 11700 | NNNTKMN | 0.30893 | -0.03193 |
| GS464 | 2523 | GCCCAACTCACCGGCCACCACACCAAAGCACAG | 7112 | AQLTGHHTKAQ | 11701 | LTGHHTK | 0.308925 | -0.15855 |
| SyS899 | 2524 | GCCCAAAACGTCAGCAGCGGCCAAAGAGCACAG | 7113 | AQNVSSGQRAQ | 11702 | NVSSGQR | 0.308694 | 0.425634 |
| SS60 | 2525 | GCCCAAAGCCTCCAAGACGCCAGACTCGCACAG | 7114 | AQSLQDARLAQ | 11703 | SLQDARL | 0.308634 | -0.29859 |
| SyS900 | 2526 | GCCCAACTTAATAGGGATGGGTCGGTGGCACAG | 7115 | AQLNRDGSVAQ | 11704 | LNRDGSV | 0.308572 | -0.18648 |
| SyS901 | 2527 | GCCCAAAACAGCAACCGGAAAAACAGCACCGCACAG | 7116 | AQNSTENSTAQ | 11705 | NSTENST | 0.308538 | -0.07217 |
| SyS903 | 2528 | GCCCAAAGCCTCGTCGCCCAACCGTCGCACAG | 7117 | AQSLVAQPVAQ | 11706 | SLVAQPV | 0.308428 | -0.08008 |
| SyS904 | 2529 | GCCCAACATGCTGCTACGGTGAGTCATGCACAG | 7118 | AQHAATVSHAQ | 11707 | HAATVSH | 0.308062 | 0.032955 |
| SyS905 | 2530 | GCCCAAAATGTGTCTGTGTGCGGTTTGGCACAG | 7119 | AQNVSGARLAQ | 11708 | NVSGARL | 0.308062 | -0.04948 |
| GS466 | 2531 | GCCCAAAGAGCCGACAAAATTCGACTACGCACAG | 7120 | AQRADKFDYAQ | 11709 | RADKFDY | 0.308023 | -0.02692 |
| SyS906 | 2532 | GCCCAAAGCCAACCCGACGTCACCTACGCACAG | 7121 | AQSQPDVTYAQ | 11710 | SQPDVTY | 0.307992 | -0.127 |
| SyS907 | 2533 | GCCCAAGTTCTTACTCAGCAGACTCATGCACAG | 7122 | AQVLTQQTHAQ | 11711 | VLTQQTH | 0.307679 | 0.0148 |
| SyS908 | 2534 | GCCCAAACCGACAACAGCACCACCAGAGCACAG | 7123 | AQTDNSTTRAQ | 11712 | TDNSTTR | 0.307679 | 0.131421 |
| SyS909 | 2535 | GCCCAATATAATACTCGGTATGATGCTGCACAG | 7124 | AQYNTRYDAAQ | 11713 | YNTRYDA | 0.307506 | -0.20103 |
| SyS910 | 2536 | GCCCAAAGCGGCCAACGACGCCAGAGTCGCACAG | 7125 | AQSANDARVAQ | 11714 | SANDARV | 0.307448 | -0.03147 |
| SyS911 | 2537 | GCCCAAATCCTCACCCCCGACCTCAGAGCACAG | 7126 | AQILTPDLRAQ | 11715 | ILTPDLR | 0.307422 | -0.08464 |

FIG. 33 (Continued)

| | | | | | | | | |
|---|---|---|---|---|---|---|---|---|
| SyS912 | 2538 | GCCCAACCTAATGTGGGTGCGAGTTCGGCACAG | 7127 | AQPNVGASSAQ | 11716 | PNVGASS | 0.307375 | -0.17136 |
| SyS914 | 2539 | GCCCAACTCAGCGCCAGCCACCATCGCACAG | 7128 | AQLSASHTIAQ | 11717 | LSASHTI | 0.307038 | -0.14672 |
| SS61 | 2540 | GCCCAACCAAAGTCCTCATCGAAAAAGCACAG | 7129 | AQTKVLIEKAQ | 11718 | TKVLIEK | 0.306967 | -0.36752 |
| SyS915 | 2541 | GCCCAAATGAATACTCTTATTCCTGCGGCACAG | 7130 | AQMNTLIPAAQ | 11719 | MNTLIPA | 0.306966 | -0.05601 |
| SyS916 | 2542 | GCCCAATCTTCGAATGTGTGACTACTGCACAG | 7131 | AQSSNVVTTAQ | 11720 | SSNVVTT | 0.306697 | 0.098037 |
| SyS917 | 2543 | GCCCAAATGAACGTCAGACCCACCACCGCACAG | 7132 | AQMNVRPTTAQ | 11721 | MNVRPTT | 0.306682 | 0.085085 |
| SyS918 | 2544 | GCCCAAGATACTGGTCTTAATAATAGGGCACAG | 7133 | AQDTGLNNRAQ | 11722 | DTGLNNR | 0.306651 | 0.011783 |
| GS467 | 2545 | GCCCAAACCCTCAACAGAGACCACATGGCACAG | 7134 | AQTLNRDHMAQ | 11723 | TLNRDHM | 0.306373 | -0.09048 |
| GS469 | 2546 | GCCCAACTCCTCAGCCACCACAGCGCGCACAG | 7135 | AQLLLSHHAAQ | 11724 | LLLSHHA | 0.306247 | -0.18099 |
| SyS919 | 2547 | GCCCAAAACCCGCCATGGCCACCTTCGCACAG | 7136 | AQNPAMATFAQ | 11725 | NPAMATF | 0.305992 | -0.14768 |
| GS470 | 2548 | GCCCAAATTTCTCAGCGGATTTATGCGGCACAG | 7137 | AQISQRIYAAQ | 11726 | ISQRIYA | 0.30595 | -0.16528 |
| SyS920 | 2549 | GCCCAAACGACTGGGGTTGCTGGTAGTGCACAG | 7138 | AQTTGVAGSAQ | 11727 | TTGVAGS | 0.305896 | 0.05663 |
| SyS921 | 2550 | GCCCAATTTGGGACGTTTCCGACGCCTGCACAG | 7139 | AQFGTFPTPAQ | 11728 | FGTFPTP | 0.305776 | -0.10477 |
| SS62 | 2551 | GCCCAAAGAGGAGGCAGCGACTTCGACAGCGCACAG | 7140 | AQRGSDFDSAQ | 11729 | RGSDFDS | 0.305764 | -0.33979 |
| GS472 | 2552 | GCCCAAAGCAAAGCCAGCCTCGACAGCGCACAG | 7141 | AQSKASLDSAQ | 11730 | SKASLDS | 0.305689 | -0.08038 |
| GS473 | 2553 | GCCCAACTTCTTAATAGTCATTCTGCTGCACAG | 7142 | AQLLNSHSAAQ | 11731 | LLNSHSA | 0.305635 | 0.015974 |
| GS474 | 2554 | GCCCAAGCTAGTATTCATAAGGATATTGCACAG | 7143 | AQASIHKDIAQ | 11732 | ASIHKDI | 0.305534 | -0.1269 |
| GS475 | 2555 | GCCCAAAGCGACCCGGCAAATTCATGGCACAG | 7144 | AQSDPGKFMAQ | 11733 | SDPGKFM | 0.305528 | -0.10472 |
| SyS922 | 2556 | GCCCAAGGCACCAGCAGCGCCCAAAGAGCACAG | 7145 | AQGTSSAQRAQ | 11734 | GTSSAQR | 0.305492 | -0.05312 |
| SyS923 | 2557 | GCCCAAAGTACGAAATAGTAAGCTGGAGGCACAG | 7146 | AQSTNSKLEAQ | 11735 | STNSKLE | 0.305492 | -0.15496 |
| SyS924 | 2558 | GCCCAAAAATTTGCAGACTGTTCCGAATGCACAG | 7147 | AQNLQTVPNAQ | 11736 | NLQTVPN | 0.305492 | -0.15496 |
| GS476 | 2559 | GCCCAAGTCGTCACCCACCTCAACGCCGCACAG | 7148 | AQVVTHLNAAQ | 11737 | VVTHLNA | 0.305419 | -0.13612 |
| SyS925 | 2560 | GCCCAACTCAGCACCAGCAACAACTTCGCACAG | 7149 | AQLSTSNNFAQ | 11738 | LSTSNNF | 0.305414 | 0.115059 |
| SyS926 | 2561 | GCCCAAAACAACAGCGGCCACATCAGCGCACAG | 7150 | AQNNSGHISAQ | 11739 | NNSGHIS | 0.305094 | -0.09434 |
| SyS927 | 2562 | GCCCAAGCTACCAAGTCAACAGCGACGCACAG | 7151 | AQAYQVNSDAQ | 11740 | AYQVNSD | 0.305066 | 0.03955 |
| SyS928 | 2563 | GCCCAACAGCAGAATTATTTGAATCATGCACAG | 7152 | AQQQNYLNHAQ | 11741 | QQNYLNH | 0.304957 | -0.16223 |
| GS477 | 2564 | GCCCAATTTGCGACTACGAATACTGGGGCACAG | 7153 | AQFATTNTGAQ | 11742 | FATTNTG | 0.304891 | 0.033545 |
| GS478 | 2565 | GCCCAACTTGCGAATAAGATTGCGAATGCACAG | 7154 | AQLANKIANAQ | 11743 | LANKIAN | 0.304879 | -0.01499 |
| GS479 | 2566 | GCCCAACAAAGCTTCCAAAGAGAAGTCGCACAG | 7155 | AQQSFQREVAQ | 11744 | QSFQREV | 0.304879 | -0.14689 |
| SyS930 | 2567 | GCCCAACTGCATATTTCGGAGCCGAGGGCACAG | 7156 | AQLHISEPRAQ | 11745 | LHISEPR | 0.30455 | -0.13556 |
| GS481 | 2568 | GCCCAACGTGTGGGTGAGCGGGAGCAGGCACAG | 7157 | AQRVGEREQAQ | 11746 | RVGEREQ | 0.304522 | -0.17829 |
| SyS931 | 2569 | GCCCAAGGTTAATATTATTCAGGCGTCGGCACAG | 7158 | AQVNIIQASAQ | 11747 | VNIIQAS | 0.304499 | -0.05678 |

FIG. 33 (Continued)

| | | | | | | | | |
|---|---|---|---|---|---|---|---|---|
| SyS932 | 2570 | GCCCAAGGCGGTCGGCCTCCACAACAAAGCACAG | 7159 | AQGVGLHNKAQ | 11748 | GVGLHNK | 0.304499 | -0.10606 |
| SyS933 | 2571 | GCCCAAAATAATCCTGCGGATTCCGATTGCACAG | 7160 | AQNNPAIPIAQ | 11749 | NNPAIPI | 0.30426 | -0.01336 |
| GP118 | 2572 | GCCCAACGGCTGTCGAGTCAGGCTGTGGCACAG | 7161 | AQRLSSQAVAQ | 11750 | RLSSQAV | 0.304245 | -0.07356 |
| SyS934 | 2573 | GCCCAACACAGCAACGAACTCAGACCGCACAG | 7162 | AQHSNELRPAQ | 11751 | HSNELRP | 0.304109 | 0.131628 |
| SyS935 | 2574 | GCCCAAAGCTCGGCCCACCAACGCACAG | 7163 | AQSLGPTTNAQ | 11752 | SLGPTTN | 0.304096 | -0.09555 |
| TS154 | 2575 | GCCCAAGGTAATCAGACGAATCGTTCGGCACAG | 7164 | AQGNQTNRSAQ | 11753 | GNQTNRS | 0.303952 | -0.06046 |
| SyS936 | 2576 | GCCCAAAGTAATCCGGTGGGTAATCCGGCACAG | 7165 | AQSNPVGNPAQ | 11754 | SNPVGNP | 0.303849 | 0.006491 |
| SyS937 | 2577 | GCCCAACAAGTCCCCCCCCTCGTCCCGCACAG | 7166 | AQQVPPLVPAQ | 11755 | QVPPLVP | 0.303762 | -0.17678 |
| SyS939 | 2578 | GCCCAACTCAGCACCCCCACCCCAAGCACAG | 7167 | AQLSTPPTQAQ | 11756 | LSTPPTQ | 0.303367 | 0.011133 |
| SyS940 | 2579 | GCCCAAGTGGGTACGGAGCCGCTTTCTGCACAG | 7168 | AQVGTEPLSAQ | 11757 | VGTEPLS | 0.303367 | -0.21072 |
| GS483 | 2580 | GCCCAAAGACCGGACGCCACCAGCCACGCACAG | 7169 | AQRPDATSHAQ | 11758 | RPDATSH | 0.303361 | -0.12139 |
| GS485 | 2581 | GCCCAAGTTGAGAAGCAGATGCTTAATGCACAG | 7170 | AQVEKQMLNAQ | 11759 | VEKQMLN | 0.303278 | -0.10651 |
| SyS941 | 2582 | GCCCAATTCAAAAGCGCCAAGCACCGCACAG | 7171 | AQFKSAQATAQ | 11760 | FKSAQAT | 0.303093 | -0.09677 |
| SyS942 | 2583 | GCCCAATGGGCTTTGTCTACGGATGGGCACAG | 7172 | AQWALSTDGAQ | 11761 | WALSTDG | 0.302822 | -0.19969 |
| SyS943 | 2584 | GCCCAACTTGCTGGTCTGGCTACTAATGCACAG | 7173 | AQLAGLATNAQ | 11762 | LAGLATN | 0.302566 | -0.04978 |
| SyS944 | 2585 | GCCCAAACCCTCACCGCGCACCCCGCACAG | 7174 | AQTLTAGTPAQ | 11763 | TLTAGTP | 0.302458 | 0.051682 |
| GS486 | 2586 | GCCCAAATCCCCGTCACCAGCAGAATGGCACAG | 7175 | AQIPVTSRMAQ | 11764 | IPVTSRM | 0.302322 | -0.15669 |
| SyS945 | 2587 | GCCCAAGGAGGACGGATTATCCTAGGTCTGCACAG | 7176 | AQGTDYPRSAQ | 11765 | GTDYPRS | 0.302309 | -0.17799 |
| SyS946 | 2588 | GCCCAAGTTACGGAGCATAGTAAGTTGGCACAG | 7177 | AQVTEHSKLAQ | 11766 | VTEHSKL | 0.302301 | -0.1054 |
| GS487 | 2589 | GCCCAAAACATGAGCATGCCCGTCAAAGCACAG | 7178 | AQNMSMPVKAQ | 11767 | NMSMPVK | 0.302291 | -0.06614 |
| SyS947 | 2590 | GCCCAAAGCGTCGGCGTCGGCATGAGCGCACAG | 7179 | AQSVGVGMSAQ | 11768 | SVGVGMS | 0.302147 | -0.04842 |
| SyS948 | 2591 | GCCCAACCCAGAACGACAACGAAGGCGCACAG | 7180 | AQPRTDNEGAQ | 11769 | PRTDNEG | 0.302129 | -0.11889 |
| SyS949 | 2592 | GCCCAATTCAGCAACCCCGACAGAACCGCACAG | 7181 | AQFSNPDRTAQ | 11770 | FSNPDRT | 0.302103 | -0.03523 |
| SyS950 | 2593 | GCCCAAATGCACCTCGTCCCACCACCGCACAG | 7182 | AQMHLVPTTAQ | 11771 | MHLVPTT | 0.302085 | -0.09798 |
| SyS951 | 2594 | GCCCAAAATGCTCCTCCGGTTTCTTCTGCACAG | 7183 | AQNAPPVSSAQ | 11772 | NAPPVSS | 0.301938 | 0.008708 |
| SyS952 | 2595 | GCCCAATCGAATTTGCCTACTTTGGCGGCACAG | 7184 | AQSNLPTLAAQ | 11773 | SNLPTLA | 0.301914 | 0.035379 |
| GS490 | 2596 | GCCCAAATCATGCAAGGCATGACCACCGCACAG | 7185 | AQIMQGMTTAQ | 11774 | IMQGMTT | 0.301878 | -0.14272 |
| SyS953 | 2597 | GCCCAAAGTCGTGAGACGACGAGTCCTGCACAG | 7186 | AQSRETTSPAQ | 11775 | SRETTSP | 0.30158 | 0.041441 |
| SyS954 | 2598 | GCCCAAAACCCACCAGCTTCAGCACCGCACAG | 7187 | AQNPTSFSTAQ | 11776 | NPTSFST | 0.30158 | -0.17193 |
| SyS955 | 2599 | GCCCAAAATTTGCAGCATGGTTCGACTGCACAG | 7188 | AQNLQHGSTAQ | 11777 | NLQHGST | 0.301496 | 0.225756 |
| GS491 | 2600 | GCCCAAAATTTCATTCTGGTCATACGGCACAG | 7189 | AQNFHSGHTAQ | 11778 | NFHSGHT | 0.301283 | -0.13881 |
| GS492 | 2601 | GCCCAAACTGAGAGTGTGTATGCGGAGGGCACAG | 7190 | AQTESVYARAQ | 11779 | TESVYAR | 0.301236 | -0.15383 |

FIG. 33 (Continued)

| | | | | | | | | |
|---|---|---|---|---|---|---|---|---|
| GS493 | 2602 | GCCCAAACTAAGTCTGAGATTCCTAATGCACAG | 7191 | AQTKSEIPNAQ | 11780 | TKSEIPN | 0.301236 | -0.15383 |
| SyS956 | 2603 | GCCCAAACCAGCCTCGCCGACATGAGAGCACAG | 7192 | AQTSLADMRAQ | 11781 | TSLADMR | 0.301192 | -0.01918 |
| GS494 | 2604 | GCCCAAAGACTCAAAGCGACATCACCGCACAG | 7193 | AQRLKADITAQ | 11782 | RLKADIT | 0.301085 | -0.08801 |
| SyS957 | 2605 | GCCCAACTGAATATGAATGTTCTGGCTGCACAG | 7194 | AQLNMNVLAAQ | 11783 | LNMNVLA | 0.301014 | -0.03968 |
| GS495 | 2606 | GCCCAAAGCCTCAGACCCATCAGCGTCGCACAG | 7195 | AQSLRPISVAQ | 11784 | SLRPISV | 0.301004 | -0.15945 |
| SyS958 | 2607 | GCCCAACTCAGCGTCCAACTCGTCGAAGCACAG | 7196 | AQLSVQLVEAQ | 11785 | LSVQLVE | 0.300849 | -0.14056 |
| SyS959 | 2608 | GCCCAAAGTTTGAGGGTGTTCTTCCGGCACAG | 7197 | AQSFEGVLPAQ | 11786 | SFEGVLP | 0.300847 | -0.1792 |
| GS496 | 2609 | GCCCAAATCATCGTCGGCCTCCAACCCGCACAG | 7198 | AQIIVGLQPAQ | 11787 | IIVGLQP | 0.3008 | -0.11578 |
| GS497 | 2610 | GCCCAAGTCAGCAGCTACGAAAGACTCGCACAG | 7199 | AQVSSYERLAQ | 11788 | VSSYERL | 0.300709 | -0.12053 |
| SyS960 | 2611 | GCCCAAAGAACCAACGACGCCATCGTCGCACAG | 7200 | AQRTNDAIVAQ | 11789 | RTNDAIV | 0.300688 | 0.340159 |
| GS498 | 2612 | GCCCAATTCAGCGAACACAGAGAACTCGCACAG | 7201 | AQFSEHRELAQ | 11790 | FSEHREL | 0.300668 | -0.16304 |
| GS499 | 2613 | GCCCAAAAAGAAGCCACCGCCAACACCGCACAG | 7202 | AQKEATANTAQ | 11791 | KEATANT | 0.300598 | -0.06336 |
| SyS962 | 2614 | GCCCAACTCAGAGCCAGCAGCATCACCGTCGCACAG | 7203 | AQLRASITVAQ | 11792 | LRASITV | 0.300214 | 0.025681 |
| SyS963 | 2615 | GCCCAATGGTTGGGTATTACTGAGGCGGCACAG | 7204 | AQWLGITEAAQ | 11793 | WLGITEA | 0.300198 | -0.07373 |
| SyS964 | 2616 | GCCCAAGCAGCCAAAAGCCGCGAAGCACAG | 7205 | AQSSQKAAEAQ | 11794 | SSQKAAE | 0.300091 | -0.02263 |
| GS501 | 2617 | GCCCAAGGGTCGACTCCTGGTCTTGCTGCACAG | 7206 | AQGSTPGLAAQ | 11795 | GSTPGLA | 0.299731 | -0.12625 |
| SyS965 | 2618 | GCCCAAAAGGGGAATGCTAATGATCTTGCACAG | 7207 | AQKGNANDLAQ | 11796 | KGNANDL | 0.299619 | -0.12733 |
| SyS966 | 2619 | GCCCAAACCAGCGCCCCCCTCAAACTCGCACAG | 7208 | AQTSAPLKLAQ | 11797 | TSAPLKL | 0.299556 | -0.03494 |
| SyS967 | 2620 | GCCCAACCTGTGCAGACGAATGGGCATGCACAG | 7209 | AQPVQTNGHAQ | 11798 | PVQTNGH | 0.299313 | -0.06587 |
| SyS968 | 2621 | GCCCAAAGGCCGGCTGTGGATTCGGCTGCACAG | 7210 | AQRPAVDSAAQ | 11799 | RPAVDSA | 0.299287 | -0.04179 |
| SyS969 | 2622 | GCCCAAACCACCCTCAGCCAAAACAGAGCACAG | 7211 | AQTTLSQNRAQ | 11800 | TTLSQNR | 0.299223 | -0.05801 |
| SyS970 | 2623 | GCCCAAGTCATGACCGTCGCAGCCTCGCACAG | 7212 | AQVMTVGSLAQ | 11801 | VMTVGSL | 0.299001 | -0.07033 |
| SyS971 | 2624 | GCCCAAGCCCTCAACAAAGAAAACTGGGCACAG | 7213 | AQALNKENWAQ | 11802 | ALNKENW | 0.298989 | -0.20709 |
| SyS973 | 2625 | GCCCAACATCATCATTTGACGGGGAATGCACAG | 7214 | AQHHHLTGNAQ | 11803 | HHHLTGN | 0.298821 | -0.17259 |
| GS502 | 2626 | GCCCAAGGGATGCGGACTGTGAATATTGCACAG | 7215 | AQGMRTVNIAQ | 11804 | GMRTVNI | 0.298627 | -0.18099 |
| GS503 | 2627 | GCCCAAACTCTGAATAGTTCGGTGGCTGCACAG | 7216 | AQTLNSSVAAQ | 11805 | TLNSSVA | 0.298611 | -0.08717 |
| GS504 | 2628 | GCCCAATCTGCTTCGACGATTCTTGTTGCACAG | 7217 | AQSASTILVAQ | 11806 | SASTILV | 0.298566 | -0.16753 |
| GP119 | 2629 | GCCCAAGAGAGATGATTAGGCCTCGTGCGGCACAG | 7218 | AQEMIRPRAAQ | 11807 | EMIRPRA | 0.298415 | 0.162495 |
| SyS974 | 2630 | GCCCAAATGTCGGCGGCGAGTTATAAGGCACAG | 7219 | AQMSAASYKAQ | 11808 | MSAASYK | 0.298381 | -0.14302 |
| SyS975 | 2631 | GCCCAACATTTTACGACTGGGTCTGTTGCACAG | 7220 | AQHFTTGSVAQ | 11809 | HFTTGSV | 0.298366 | -0.02828 |
| GS505 | 2632 | GCCCAAGCTTCTCATACTATTGGGCTTGCACAG | 7221 | AQASHTIGLAQ | 11810 | ASHTIGL | 0.298317 | -0.10725 |
| GS506 | 2633 | GCCCAAAGTCGGGAGCATCAGCTGTATGCACAG | 7222 | AQSREHQLYAQ | 11811 | SREHQLY | 0.298183 | -0.11266 |

FIG. 33 (Continued)

| | | | | | | | | |
|---|---|---|---|---|---|---|---|---|
| GS507 | 2634 | GCCCAAGCTGGTACGACGGGCTCCGCTTGCACAG | 7223 | AQAGTTAPLAQ | 11812 | AGTTAPL | 0.298135 | -0.06321 |
| GS508 | 2635 | GCCCAAGGCAAAGTCAGCGGCGGCCATGGCACAG | 7224 | AQGKVSGAMAQ | 11813 | GKVSGAM | 0.298131 | -0.11524 |
| GS509 | 2636 | GCCCAAAAACTCAGCGGCGGCATGAGCGTCGCACAG | 7225 | AQKLSGMSVAQ | 11814 | KLSGMSV | 0.297895 | -0.15574 |
| GS510 | 2637 | GCCCAAGTCCTCCCCAAAGACGACGCCGCACAG | 7226 | AQVLPKDDAAQ | 11815 | VLPKDDA | 0.297661 | -0.1747 |
| SyS976 | 2638 | GCCCAACTCGCCGGCATCCTCACCACGCACAG | 7227 | AQLAGILTTAQ | 11816 | LAGILTT | 0.297605 | -0.0739 |
| SyS977 | 2639 | GCCCAAGTCGTCCCGGCCCAAACCGCACAG | 7228 | AQVVPGAQTAQ | 11817 | VVPGAQT | 0.297436 | -0.06047 |
| SyS978 | 2640 | GCCCAAGGTCAGCATTCTTATGCGCATGCACAG | 7229 | AQGQHSYAHAQ | 11818 | GQHSYAH | 0.297408 | -0.07737 |
| SyS979 | 2641 | GCCCAACATCATCTGAGTACGTCGATTGCACAG | 7230 | AQHHLSTSIAQ | 11819 | HHLSTSI | 0.297404 | -0.03102 |
| SyS980 | 2642 | GCCCAAACCCTCATCCCCCAACCCGCACAG | 7231 | AQTLIPPNPAQ | 11820 | TLIPPNP | 0.297351 | -0.14283 |
| GS511 | 2643 | GCCCAAGAGATGCATAATCCTAGGGCGGCACAG | 7232 | AQEMHNPRAAQ | 11821 | EMHNPRA | 0.297287 | -0.11417 |
| SyS982 | 2644 | GCCCAAATCGAAAACCCCCCAGAGGCGGCACAG | 7233 | AQIENPPRGAQ | 11822 | IENPPRG | 0.297181 | -0.0878 |
| SyS983 | 2645 | GCCCAAGGCCAATTCAGCGACGCCAGAGCACAG | 7234 | AQGQFSDARAQ | 11823 | GQFSDAR | 0.297111 | 0.032689 |
| SyS984 | 2646 | GCCCAAGCCGAAGCCAGCGCCAGCAGAGCACAG | 7235 | AQAEASASRAQ | 11824 | AEASASR | 0.297046 | -0.07131 |
| SyS985 | 2647 | GCCCAACTTGTTAAGGGGGATGCGAGGGCACAG | 7236 | AQLVKGDARAQ | 11825 | LVKGDAR | 0.29699 | 0.026608 |
| GS512 | 2648 | GCCCAACAGGGTCATACGCATGGGAATGCACAG | 7237 | AQQGHTHGNAQ | 11826 | QGHTHGN | 0.296975 | -0.12903 |
| SyS513 | 2649 | GCCCAACAGAAGCCTACGTCTACTTTGCACAG | 7238 | AQQKPTSTFAQ | 11827 | QKPTSTF | 0.296937 | -0.15288 |
| GS514 | 2650 | GCCCAAAAGCTTGCTGCTTGGGTGCTGCACAG | 7239 | AQKLAALGAAQ | 11828 | KLAALGA | 0.296882 | -0.17672 |
| SyS986 | 2651 | GCCCAATCGTCTGTGGATCAGATGAAGGCACAG | 7240 | AQSSVDQMKAQ | 11829 | SSVDQMK | 0.296846 | -0.08602 |
| SyS987 | 2652 | GCCCAAGGCATCGTCACCGCCCCCTCGCACAG | 7241 | AQGIVTAPLAQ | 11830 | GIVTAPL | 0.296762 | -0.16951 |
| GS515 | 2653 | GCCCAACTTTTGAAGATGCCTTCTCCTGCACAG | 7242 | AQLLKMPSPAQ | 11831 | LLKMPSP | 0.296723 | -0.12298 |
| SyS988 | 2654 | GCCCAAAATGTTGCTCATACGGTCGTGCACAG | 7243 | AQNVAHTVRAQ | 11832 | NVAHTVR | 0.2967 | -0.06524 |
| SyS989 | 2655 | GCCCAACTGATGAGTAACGAATGTGAGTGCACAG | 7244 | AQLMSTNVSAQ | 11833 | LMSTNVS | 0.29667 | 0.039016 |
| SyS990 | 2656 | GCCCAACTGTCTAATAATAATGCGCTTGCACAG | 7245 | AQLSNNNALAQ | 11834 | LSNNNAL | 0.296455 | -0.22803 |
| SyS991 | 2657 | GCCCAACTCCTCATCGGCCCCACGGGCACAG | 7246 | AQLLIGPTGAQ | 11835 | LLIGPTG | 0.296321 | -0.11131 |
| SyS517 | 2658 | GCCCAAGTCAGAAACACCATGATCAGCGCACAG | 7247 | AQVRNTMISAQ | 11836 | VRNTMIS | 0.296311 | -0.17201 |
| GS518 | 2659 | GCCCAAGGCGCCACCGGCCACCTCACCGCACAG | 7248 | AQGATGHLTAQ | 11837 | GATGHLT | 0.296311 | -0.17201 |
| GS519 | 2660 | GCCCAAATGACCGTCGGCAACCTCGGCGCACAG | 7249 | AQMTVGNLGAQ | 11838 | MTVGNLG | 0.29631 | -0.06764 |
| SyS992 | 2661 | GCCCAAAGTAATGGTCTGAATGGTTTGGCACAG | 7250 | AQSNGLNGLAQ | 11839 | SNGLNGL | 0.296065 | -0.23419 |
| SyS994 | 2662 | GCCCAACGAAGGGAATGAGAGAATGAGAGTCGTGCACAG | 7251 | AQRNENESRAQ | 11840 | RNENESR | 0.295831 | -0.08635 |
| SyP47 | 2663 | GCCCAAGGGAATGCTCGGGATGCGAGTGCACAG | 7252 | AQGNARDASAQ | 11841 | GNARDAS | 0.295799 | -0.04389 |
| SyS995 | 2664 | GCCCAAATCAGCAAACTCCTCTCCAGCGCACAG | 7253 | AQISKLLLSAQ | 11842 | ISKLLLS | 0.295612 | -0.10947 |
| GS520 | 2665 | GCCCAAAACGACACCACCAACATGAGCGCACAG | 7254 | AQNDTTNMSAQ | 11843 | NDTTNMS | 0.295587 | -0.16718 |

FIG. 33 (Continued)

| | | | | | | | | |
|---|---|---|---|---|---|---|---|---|
| SyS996 | 2666 | GCCCAAGGCCTCGAAGCCAACAAAAGGCACAG | 7255 | AQGLEANKSAQ | 11844 | GLEANKS | 0.295578 | 0.033862 |
| SyS998 | 2667 | GCCCAACATTATAGTACTGTTGGGGTGGCACAG | 7256 | AQHYSTVGVAQ | 11845 | HYSTVGV | 0.295419 | -0.19011 |
| SyS999 | 2668 | GCCCAACCTACGATTTCGGTTCTGCCTGCACAG | 7257 | AQPTISVLPAQ | 11846 | PTISVLP | 0.295257 | -0.21694 |
| SyS1000 | 2669 | GCCCAAGTCCAAACCATCGGCCACGAAGCACAG | 7258 | AQVQTIGHEAQ | 11847 | VQTIGHE | 0.295085 | -0.16397 |
| SyS1001 | 2670 | GCCCAAAAACCGAAACCGCAGCGACGGCACAG | 7259 | AQKPETASDAQ | 11848 | KPETASD | 0.294946 | -0.1036 |
| SS64 | 2671 | GCCCAAACCAACACCCCACCAGAGAGCACAG | 7260 | AQTNTPTSRAQ | 11849 | TNTPTSR | 0.294926 | -0.28124 |
| SyS1002 | 2672 | GCCCAAAGTTGACGCTTAGTTCGCATGCACAG | 7261 | AQSLTLSSHAQ | 11850 | SLTLSSH | 0.294898 | -0.14526 |
| GP120 | 2673 | GCCCAACATTATCATAGTATTCAGGCTGCACAG | 7262 | AQHYHSIQAAQ | 11851 | HYHSIQA | 0.294855 | -0.07232 |
| SyS1003 | 2674 | GCCCAATACCACGGCGAAAACGAAAGAGCACAG | 7263 | AQYHGENERAQ | 11852 | YHGENER | 0.294846 | -0.08758 |
| GS522 | 2675 | GCCCAACTGCCTCATACTGCGCCGTGTGGCACAG | 7264 | AQLPHTARVAQ | 11853 | LPHTARV | 0.294761 | -0.14958 |
| SyS1004 | 2676 | GCCCAAACCAGAGAAGGCAGCACCGGCGCACAG | 7265 | AQTREGSTGAQ | 11854 | TREGSTG | 0.294636 | -0.02281 |
| GS525 | 2677 | GCCCAAGTTGATCGTAGGGCGATGCTTGCACAG | 7266 | AQVDRRAMLAQ | 11855 | VDRRAML | 0.294282 | -0.08 |
| SyS1005 | 2678 | GCCCAAACCAGCGTCAGCGCCGTCATGGCACAG | 7267 | AQTSVSAVMAQ | 11856 | TSVSAVM | 0.29428 | -0.21679 |
| SyS1006 | 2679 | GCCCAAAGCCAAAAACTCACCGAAAAAGCACAG | 7268 | AQSQKLTEKAQ | 11857 | SQKLTEK | 0.294248 | -0.04613 |
| SyS1007 | 2680 | GCCCAAAGACTCCCCAGCCTCAGCGTCGCACAG | 7269 | AQRLPSLSVAQ | 11858 | RLPSLSV | 0.294218 | -0.049 |
| SyS1008 | 2681 | GCCCAAAGTGTTAGTGAGGGTAGTAGGGCACAG | 7270 | AQSVSEGSRAQ | 11859 | SVSEGSR | 0.294121 | -0.18245 |
| SyS1009 | 2682 | GCCCAAAGCATCCCCAGCGTCAGCGCCGCACAG | 7271 | AQSIPSVSAAQ | 11860 | SIPSVSA | 0.294121 | -0.13314 |
| GS526 | 2683 | GCCCAAACTACTAATAATGTAAGAGTGCACAG | 7272 | AQTTNNAKSAQ | 11861 | TTNNAKS | 0.294054 | -0.13141 |
| SyS1010 | 2684 | GCCCAAGGCGAGTGGGGAGGCTTCGACTGCACAG | 7273 | AQASGEASTAQ | 11862 | ASGEAST | 0.293904 | -0.11222 |
| SyS1011 | 2685 | GCCCAAGATAATAATTCGAGTATTGCTGCACAG | 7274 | AQDNNSSIAAQ | 11863 | DNNSSIA | 0.293817 | -0.21202 |
| SyS1012 | 2686 | GCCCAAGTCCACGACAACAGCAAACTCGCACAG | 7275 | AQVHDNSKLAQ | 11864 | VHDNSKL | 0.293384 | -0.0119 |
| SyS1013 | 2687 | GCCCAATCTACTTTGGCGGGTTCGGAGGCACAG | 7276 | AQSTLAGSEAQ | 11865 | STLAGSE | 0.293384 | -0.18527 |
| SyS1014 | 2688 | GCCCAACCTGAGAAGAGTCATTCGTCGGCACAG | 7277 | AQPEKSHSSAQ | 11866 | PEKSHSS | 0.293335 | 0.032955 |
| GS529 | 2689 | GCCCAACAAATGCTCAGAGCCAGCGTCGCACAG | 7278 | AQQMLRASVAQ | 11867 | QMLRASV | 0.293248 | -0.17022 |
| SyS1015 | 2690 | GCCCAAGCCCTCAGCAACAACATCACCGCACAG | 7279 | AQALSNNITAQ | 11868 | ALSNNIT | 0.293202 | 0.023276 |
| SyS1016 | 2691 | GCCCAAAGTTTGGCGAATCAGTTGCCTGCACAG | 7280 | AQSLANQLPAQ | 11869 | SLANQLP | 0.29314 | -0.10658 |
| SyS1017 | 2692 | GCCCAAGAACAAAGCAGACTCCAAACCGCACAG | 7281 | AQEQSRLQTAQ | 11870 | EQSRLQT | 0.292969 | 0.059223 |
| SyS1018 | 2693 | GCCCAAAATTTGTCTCAGAATGTTATGGCACAG | 7282 | AQNLSQNVMAQ | 11871 | NLSQNVM | 0.292952 | -0.04783 |
| SyS1019 | 2694 | GCCCAAAGCCACAAAACTCAGCAGCAGCGGCACAG | 7283 | AQSHKLSSSAQ | 11872 | SHKLSSS | 0.29295 | 0.045078 |
| GP122 | 2695 | GCCCAACCTACTAATACTAAGACGGGCGGCACAG | 7284 | AQPTNTKTAAQ | 11873 | PTNTKTA | 0.292879 | -0.0737 |
| GS530 | 2696 | GCCCAAATGAATCCGGCTACTGTGGCTGCACAG | 7285 | AQMNPATVAAQ | 11874 | MNPATVA | 0.29272 | -0.03446 |
| SyS1021 | 2697 | GCCCAAAAGATTGAGCGTACGAATTTTGCACAG | 7286 | AQKIERTNFAQ | 11875 | KIERTNF | 0.292715 | -0.1986 |

FIG. 33 (Continued)

| | | | | | | | | |
|---|---|---|---|---|---|---|---|---|
| GS532 | 2698 | GCCCAAACTAGTCCTACGTATAAGTTGGCACAG | 7287 | AQTSPTYKLAQ | 11876 | TSPTYKL | 0.292683 | -0.16394 |
| SyS1022 | 2699 | GCCCAAAGGAGTGATCATATTGATTATGCACAG | 7288 | AQRSDHIDYAQ | 11877 | RSDHIDY | 0.292545 | -0.17314 |
| GS533 | 2700 | GCCCAAACTCTTGGTCTGAATACTAATGCACAG | 7289 | AQTLGLNTNAQ | 11878 | TLGLNTN | 0.29252 | -0.08599 |
| GS534 | 2701 | GCCCAACCCCTCAGCAACCACGGCACCGCACAG | 7290 | AQPLSNHGTAQ | 11879 | PLSNHGT | 0.292259 | -0.14779 |
| SyS1023 | 2702 | GCCCAAGCCGTCAGCAGACTCCCATGGCACAG | 7291 | AQAVSRLPMAQ | 11880 | AVSRLPM | 0.292237 | -0.0617 |
| SyS1024 | 2703 | GCCCAACTCCTCACCGAAAGCAAAATGGCACAG | 7292 | AQLLTESKMAQ | 11881 | LLTESKM | 0.292116 | -0.05872 |
| GS535 | 2704 | GCCCAACATATGAGGACGGATACTGCTGCACAG | 7293 | AQHMRTDTAAQ | 11882 | HMRTDTA | 0.292093 | 0.026545 |
| SS65 | 2705 | GCCCAAAGTCTTACGGTTAATGCGGCTGCACAG | 7294 | AQSLTVNAAAQ | 11883 | SLTVNAA | 0.292051 | -0.35371 |
| SyS1025 | 2706 | GCCCAAAACCCAACGGCGTCACCGTCGCACAG | 7295 | AQNPNGVTVAQ | 11884 | NPNGVTV | 0.292021 | 0.126305 |
| GS536 | 2707 | GCCCAAACTACTAAGTTGCCGACTCTTGCACAG | 7296 | AQTTKLPTLAQ | 11885 | TTKLPTL | 0.291897 | -0.16241 |
| GS537 | 2708 | GCCCAAAATTCTACGTCGAAGCAGCTGGCACAG | 7297 | AQNSTSKQLAQ | 11886 | NSTSKQL | 0.291795 | -0.10165 |
| SyS1026 | 2709 | GCCCAAACTTTGGGGTCGTCTAATACTGCACAG | 7298 | AQTLGSSNTAQ | 11887 | TLGSSNT | 0.29177 | 0.260145 |
| SyS1027 | 2710 | GCCCAACGCGTGCGACTGATCCGCAGGCACAG | 7299 | AQPRATDPQAQ | 11888 | PRATDPQ | 0.291721 | -0.15534 |
| SyS1028 | 2711 | GCCCAAAGCTCCTCAACAAACCACCGCACAG | 7300 | AQSLLNKTTAQ | 11889 | SLLNKTT | 0.291681 | -0.03372 |
| SyS1029 | 2712 | GCCCAACAAAAAGCGACGGCAGCCCCGCACAG | 7301 | AQQKSDGSPAQ | 11890 | QKSDGSP | 0.291669 | -0.06584 |
| SyS1030 | 2713 | GCCCAAACCGTCAGCGGCTTCACCAAAGCACAG | 7302 | AQTVSGFTKAQ | 11891 | TVSGFTK | 0.291528 | -0.16386 |
| SyS1031 | 2714 | GCCCAAACCGTCCTCGTCAAAGCACCGCACAG | 7303 | AQTVLVKSTAQ | 11892 | TVLVKST | 0.291496 | -0.03529 |
| SyS1032 | 2715 | GCCCAAGGGGCTCATATTTCTAATCCTGCACAG | 7304 | AQGAHISNPAQ | 11893 | GAHISNP | 0.291472 | -0.05008 |
| SyS1033 | 2716 | GCCCAAGAACCCAGCATCCCCAGACCCGCACAG | 7305 | AQEPSIPRPAQ | 11894 | EPSIPRP | 0.291443 | -0.01064 |
| GS538 | 2717 | GCCCAAGGCACCGTCCAAGCCAGACAAGCACAG | 7306 | AQGTVQARQAQ | 11895 | GTVQARQ | 0.291432 | -0.12617 |
| GS539 | 2718 | GCCCAAAATAATCATCATAATTATGTGGATGCACAG | 7307 | AQNNHNYVDAQ | 11896 | NNHNYVD | 0.291265 | -0.18099 |
| SyS1034 | 2719 | GCCCAAAGGACGGCGAGTGTTAGTTTGGCACAG | 7308 | AQRTASVSLAQ | 11897 | RTASVSL | 0.291215 | -0.02711 |
| SyS1035 | 2720 | GCCCAAATCAGCATGGACAACCACAGAGCACAG | 7309 | AQISMDNHRAQ | 11898 | ISMDNHR | 0.291187 | -0.14425 |
| GS540 | 2721 | GCCCAAAGTGATGGGCATAATCATTCTGCACAG | 7310 | AQSDGHNHSAQ | 11899 | SDGHNHS | 0.291146 | -0.15288 |
| SyS1036 | 2722 | GCCCAAAGCGCCGGCATCGGCGGCATCGGCACAG | 7311 | AQSAGSGIGAQ | 11900 | SAGSGIG | 0.290985 | -0.22527 |
| GS541 | 2723 | GCCCAAAAAGCCACCCTCAGCGAAAAAGCACAG | 7312 | AQKATLSEKAQ | 11901 | KATLSEK | 0.290766 | -0.1747 |
| GS542 | 2724 | GCCCAAATCCACGCGCGGCGGCCAAAGAGCACAG | 7313 | AQIHAGGQRAQ | 11902 | IHAGGQR | 0.290742 | -0.07711 |
| SyS1038 | 2725 | GCCCAACTGACTCCTAGTAGTGCGAATGCACAG | 7314 | AQLTPSSANAQ | 11903 | LTPSSAN | 0.290681 | -0.11131 |
| GS543 | 2726 | GCCCAAGACGGCAAAGCTACAACCACGCACAG | 7315 | AQDGKAYNHAQ | 11904 | DGKAYNH | 0.290644 | -0.08049 |
| GS544 | 2727 | GCCCAATGGTCGGCGCAGACGATGAATGCACAG | 7316 | AQWSAQTMNAQ | 11905 | WSAQTMN | 0.290564 | -0.15855 |
| TS155 | 2728 | GCCCAAAATAGTACGCGGATTATTGTTGCACAG | 7317 | AQNSTRIIVAQ | 11906 | NSTRIIV | 0.290552 | -0.32039 |
| GS545 | 2729 | GCCCAAAAAACAGCAGCATGCTCCTCGCACAG | 7318 | AQKNSSMLLAQ | 11907 | KNSSMLL | 0.290508 | -0.18457 |

FIG. 33 (Continued)

| | | | | | | | |
|---|---|---|---|---|---|---|---|
| GS546 | 2730 | GCCCAAAGACAAGTCAGCGGCACCAGCGCACAG | 7319 | AQRQVSGTSAQ | 11908 | RQVSGTS | 0.290227 | -0.07752 |
| SyS1039 | 2731 | GCCCAACCGTCACCGGCAACAGCGACGCACAG | 7320 | AQPVTGNSDAQ | 11909 | PVTGNSD | 0.290223 | -0.13048 |
| GS548 | 2732 | GCCCAAATGTACCCCGACAGACACAGCGCACAG | 7321 | AQMYPDRHSAQ | 11910 | MYPDRHS | 0.29019 | -0.15227 |
| SyS1040 | 2733 | GCCCAAACCTACCAAATCGGCGCCGTCGCACAG | 7322 | AQTYQIGAVAQ | 11911 | TYQIGAV | 0.29007 | -0.19723 |
| GS549 | 2734 | GCCCAAAAAACCGGCAGCCTCAGCGCCGCACAG | 7323 | AQKTGSLSAAQ | 11912 | KTGSLSA | 0.289983 | -0.06165 |
| SyS1041 | 2735 | GCCCAAATCATCCCGCGCAGCAGCCCCGCACAG | 7324 | AQIIPASSPAQ | 11913 | IIPASSP | 0.289839 | 0.121455 |
| GS550 | 2736 | GCCCAAGACAACCAAGGCACCAAACACGCACAG | 7325 | AQDNQGTKHAQ | 11914 | DNQGTKH | 0.289725 | -0.03079 |
| GS551 | 2737 | GCCCAAAGCTACAAAGAAAGCCCCAGCGCACAG | 7326 | AQSYKESPSAQ | 11915 | SYKESPS | 0.28952 | -0.05844 |
| SyS1042 | 2738 | GCCCAAGCCATCATCAGCAACAGAGAGCACAG | 7327 | AQAIISNNRAQ | 11916 | AIISNNR | 0.289509 | -0.09122 |
| SyS1043 | 2739 | GCCCAAACGACCAAATCAGAACCTACGCACAG | 7328 | AQTDQIRTYAQ | 11917 | TDQIRTY | 0.289464 | -0.12291 |
| SyS1044 | 2740 | GCCCAACACAGCGCCACCAACATCGACGCACAG | 7329 | AQHSATNIDAQ | 11918 | HSATNID | 0.289436 | -0.08891 |
| SyS1045 | 2741 | GCCCAAGGCACCGTCAACATCAGCGCCGCACAG | 7330 | AQGTVNISAAQ | 11919 | GTVNISA | 0.2894 | -0.13798 |
| SyS1046 | 2742 | GCCCAAGCTGTTGTTCCGGCTATGCAGGCACAG | 7331 | AQAVVPAMQAQ | 11920 | AVVPAMQ | 0.2894 | -0.23255 |
| SyS1047 | 2743 | GCCCAAATCCCCAGAAGCGACCCCAGCGCACAG | 7332 | AQIPRSDPSAQ | 11921 | IPRSDPS | 0.289334 | 0.133056 |
| GS553 | 2744 | GCCCAAACTAAGTATACGTTGCAGAGTGCACAG | 7333 | AQTKYTLQSAQ | 11922 | TKYTLQS | 0.28888 | -0.06245 |
| SyS1050 | 2745 | GCCCAATCTCTGCGTGAGACGAGTATTGCACAG | 7334 | AQSLRETSIAQ | 11923 | SLRETSI | 0.288816 | -0.08828 |
| SyS1051 | 2746 | GCCCAAGAGGGTGATAATAAGCGGTTGGCACAG | 7335 | AQEGDNKRLAQ | 11924 | EGDNKRL | 0.288603 | -0.16397 |
| SyS1052 | 2747 | GCCCAAATCGTCAGCAGCACCAGCAGCGCACAG | 7336 | AQIVSSTSSAQ | 11925 | IVSSTSS | 0.28856 | 0.01345 |
| GS554 | 2748 | GCCCAATTGGTGAATTCTGGGGCGCATGCACAG | 7337 | AQLVNSGAHAQ | 11926 | LVNSGAH | 0.288432 | -0.09841 |
| SyS1053 | 2749 | GCCCAACGTACGTCGGATAATCAGACGGGCACAG | 7338 | AQRTSDNQTAQ | 11927 | RTSDNQT | 0.288338 | 0.057271 |
| GS555 | 2750 | GCCCAACCGACGGCAAAAGCCTCGCCGCACAG | 7339 | AQPDGKSLAAQ | 11928 | PDGKSLA | 0.288271 | -0.11074 |
| SyS1054 | 2751 | GCCCAACACACAAAAACATGCTGAAACGCACAG | 7340 | AQHKNMLETAQ | 11929 | HKNMLET | 0.288245 | -0.17678 |
| GS556 | 2752 | GCCCAACTCAGCCCGGCGTCACCGCGCACAG | 7341 | AQLSPGVTAAQ | 11930 | LSPGVTA | 0.288083 | -0.08353 |
| TS156 | 2753 | GCCCAAACCAACCACACCAGAAACACCGCACAG | 7342 | AQTNHTRNTAQ | 11931 | TNHTRNT | 0.288053 | 0.024621 |
| SyS1055 | 2754 | GCCCAACTCGGCGACAGCGAAAGAAACGCACAG | 7343 | AQLGDSERNAQ | 11932 | LGDSERN | 0.288003 | -0.13314 |
| SyS1056 | 2755 | GCCCAACTCCTCAAAATCGAACAAATGGCACAG | 7344 | AQLLKIEQMAQ | 11933 | LLKIEQM | 0.288003 | -0.17072 |
| GS557 | 2756 | GCCCAAAGCCACCTCAAAGAACACCCCGCACAG | 7345 | AQSHLKEHPAQ | 11934 | SHLKEHP | 0.287866 | -0.03141 |
| SS68 | 2757 | GCCCAACCCATCGACAACAGACAATACGCACAG | 7346 | AQPIDNRQYAQ | 11935 | PIDNRQY | 0.287402 | -0.31048 |
| SyS1058 | 2758 | GCCCAAGATATGCATTCGGGGGTGAAGGCACAG | 7347 | AQDMHSGVKAQ | 11936 | DMHSGVK | 0.287371 | -0.10493 |
| SyS1059 | 2759 | GCCCAACCTTCGTCGCCTATTCCGAATGCACAG | 7348 | AQPSSPIPNAQ | 11937 | PSSPIPN | 0.287367 | -0.19353 |
| SyS1061 | 2760 | GCCCAACTCAGCAGCACCCTCGACGACGCACAG | 7349 | AQLSSTLDDAQ | 11938 | LSSTLDD | 0.287224 | -0.19011 |
| SyS1062 | 2761 | GCCCAACCCAACACCGCCCACAGCAGCGCACAG | 7350 | AQPNTAHSSAQ | 11939 | PNTAHSS | 0.287109 | -0.03284 |

FIG. 33 (Continued)

| | | | | | | | | |
|---|---|---|---|---|---|---|---|---|
| SyS1063 | 2762 | GCCCAAGCCACCAGAGTCGACGTCATCGCACAG | 7351 | AQATRVDVIAQ | 11940 | ATRVDVI | 0.28708 | 0.115394 |
| GS558 | 2763 | GCCCAAAGCACCAACGTCACCACCGTCGCACAG | 7352 | AQSTNVTTVAQ | 11941 | STNVTTV | 0.287059 | -0.10292 |
| SyS1064 | 2764 | GCCCAATATGGTAATAATAGTTTAGTGCACAG | 7353 | AQYGNNSFSAQ | 11942 | YGNNSFS | 0.28698 | 0.020733 |
| SyS1065 | 2765 | GCCCAACCCACCGCCAAACCCATGTACGCACAG | 7354 | AQPTAKPMYAQ | 11943 | PTAKPMY | 0.28686 | -0.0907 |
| SyS1066 | 2766 | GCCCAACTCCCAACCTCCCACCATGCACAG | 7355 | AQLPNLPTIAQ | 11944 | LPNLPTI | 0.286792 | -0.17799 |
| GS560 | 2767 | GCCCAAACTAGGTTGCCGAATATTAGTGCACAG | 7356 | AQTRLPNISAQ | 11945 | TRLPNIS | 0.286766 | -0.17022 |
| GS561 | 2768 | GCCCAACATAAGCATTCTACGCAGGGTGCACAG | 7357 | AQHKHSTQGAQ | 11946 | HKHSTQG | 0.286766 | -0.17022 |
| GS562 | 2769 | GCCCAAAATGGTACGAATGGTTTTACTGCACAG | 7358 | AQNGTNGFTAQ | 11947 | NGTNGFT | 0.286695 | -0.06992 |
| SyS1067 | 2770 | GCCCAAAGCACCGACGCCATCAGATTCGCACAG | 7359 | AQSTDAIRFAQ | 11948 | STDAIRF | 0.286524 | -0.12222 |
| GS563 | 2771 | GCCCAACTGGTTCGTGATCATACGGCGGCACAG | 7360 | AQLVRDHTAAQ | 11949 | LVRDHTA | 0.286491 | -0.11663 |
| SyS1069 | 2772 | GCCCAAATCAGCCTCGGCTACAGCAAAGCACAG | 7361 | AQISLGYSKAQ | 11950 | ISLGYSK | 0.286475 | -0.21557 |
| SyS1070 | 2773 | GCCCAACTTTTTGGTTCTTCGCATACGGCACAG | 7362 | AQLFGSSHTAQ | 11951 | LFGSSHT | 0.286475 | -0.21557 |
| SyS1071 | 2774 | GCCCAAAGCACCATCACCCCAGACTCGCACAG | 7363 | AQSTITPRLAQ | 11952 | STITPRL | 0.286416 | -0.16587 |
| SyS1072 | 2775 | GCCCAACAACAGATTACTAATGGGCTGCGTGCACAG | 7364 | AQQITNGLRAQ | 11953 | QITNGLR | 0.286347 | -0.11252 |
| SyS1073 | 2776 | GCCCAAACGACCGGAGTATAATATTCGTGCACAG | 7365 | AQTTEYNIRAQ | 11954 | TTEYNIR | 0.286245 | -0.1101 |
| SyS1074 | 2777 | GCCCAAACCGACCTCGGCAGAGGCACCGCACAG | 7366 | AQTDLGRGTAQ | 11955 | TDLGRGT | 0.286128 | 0.04021 |
| GS564 | 2778 | GCCCAAGAAAGAAGCCCCACCATCCTCGCACAG | 7367 | AQERSPTILAQ | 11956 | ERSPTIL | 0.286103 | -0.17195 |
| SyS1075 | 2779 | GCCCAACATGGGGATTCTGCGAGGACTGCACAG | 7368 | AQHGDSARTAQ | 11957 | HGDSART | 0.286062 | 0.001434 |
| SyS1077 | 2780 | GCCCCAATTGAGTGTGCCTAATCAGCAGGCACAG | 7369 | AQLSVPNQQAQ | 11958 | LSVPNQQ | 0.285811 | 0.019619 |
| SyS1078 | 2781 | GCCCAAAGCGACGGCCCCGTCCCAGAGCACAG | 7370 | AQSDGPVPRAQ | 11959 | SDGPVPR | 0.285737 | -0.10136 |
| GS565 | 2782 | GCCCAAAATATGAATCATATTGCTTCTGCACAG | 7371 | AQNMNHIASAQ | 11960 | NMNHIAS | 0.28572 | -0.04994 |
| SyS1079 | 2783 | GCCCAAGTCCCAACAGCCCCAAAGAGCACAG | 7372 | AQVPNSPQRAQ | 11961 | VPNSPQR | 0.285696 | -0.06754 |
| SS70 | 2784 | GCCCAAGACAGAATGGCCAGCAGCAGAGCACAG | 7373 | AQDRMASSRAQ | 11962 | DRMASSR | 0.285607 | -0.34425 |
| SyS1080 | 2785 | GCCCAATTGCTGTCGAATTGCAGTCAGGCACAG | 7374 | AQLLSNSSQAQ | 11963 | LLSNSSQ | 0.285424 | 0.07245 |
| GS567 | 2786 | GCCCAAGAGACGCGGGTGTTGAATCATGCACAG | 7375 | AQETAVLNHAQ | 11964 | ETAVLNH | 0.285405 | -0.14868 |
| GS568 | 2787 | GCCCAAGAACAAAGAACCCCAGCCCCGCACAG | 7376 | AQEQRTPSPAQ | 11965 | EQRTPSP | 0.285349 | -0.02041 |
| SyS1081 | 2788 | GCCCAACAACACCTCAACGGCAGCATCGCACAG | 7377 | AQQHLNGSIAQ | 11966 | QHLNGSI | 0.285255 | 0.080069 |
| SyS1082 | 2789 | GCCCAAAGCGTCCTCCAAGTCGAAGGCGCACAG | 7378 | AQSVLQVEGAQ | 11967 | SVLQVEG | 0.285245 | -0.17259 |
| SyS1083 | 2790 | GCCCAATTTCTGTCGGGTACGACTAAGGCACAG | 7379 | AQFLSGTTKAQ | 11968 | FLSGTTK | 0.285183 | -0.17314 |
| SyS1085 | 2791 | GCCCAAGGTAATCCGAATGATCGGCAGGCACAG | 7380 | AQGNPNDRQAQ | 11969 | GNPNDRQ | 0.284868 | 0.038445 |
| SyS1086 | 2792 | GCCCAAACCGACAAAGCCGTCCAAATCGCACAG | 7381 | AQTDKAVQIAQ | 11970 | TDKAVQI | 0.284813 | -0.02105 |
| GS569 | 2793 | GCCCAAGAGAAGTATACGGGTTCGCCTGCACAG | 7382 | AQEKYTGSPAQ | 11971 | EKYTGSP | 0.284752 | -0.08897 |

FIG. 33 (Continued)

| | | | | | | | | |
|---|---|---|---|---|---|---|---|---|
| GS570 | 2794 | GCCCAACTCGCCGGCGAGCAGCAGAAACCTCGCACAG | 7383 | AQLAGSRNLAQ | 11972 | LAGSRNL | 0.284402 | -0.02848 |
| SyS1087 | 2795 | GCCCAAATGATCCCAGCACCAACTTCGCACAG | 7384 | AQMIPSTNFAQ | 11973 | MIPSTNF | 0.28421 | -0.0822 |
| GS572 | 2796 | GCCCAACCTTTGACGGGTTCTAGTGCTGCACAG | 7385 | AQPLTGSSAAQ | 11974 | PLTGSSA | 0.284117 | -0.10557 |
| SyS1088 | 2797 | GCCCAAAGCGTCAGCAACGCCTTCAGCGCACAG | 7386 | AQSVSNAFSAQ | 11975 | SVSNAFS | 0.284101 | -0.196 |
| GS573 | 2798 | GCCCAACAGGGGGGTCAGGCGCTTAGGGCACAG | 7387 | AQQGGQALRAQ | 11976 | QGGQALR | 0.283993 | -0.16337 |
| GS574 | 2799 | GCCCAACACCCCGGCCAAACCCTCAGCGCACAG | 7388 | AQHPGQTLSAQ | 11977 | HPGQTLS | 0.28394 | -0.15586 |
| GS575 | 2800 | GCCCAAAAGGAGTATAATACGTATAGTGCACAG | 7389 | AQKEYNTYSAQ | 11978 | KEYNTYS | 0.283589 | -0.1701 |
| SyS1089 | 2801 | GCCCAAACCCACACGCCCAACCCAGCGCACAG | 7390 | AQTHTAQPSAQ | 11979 | THTAQPS | 0.283513 | -0.14667 |
| SyS1090 | 2802 | GCCCAAATGACGCCGCAGGTTCCTGTGCACAG | 7391 | AQMTPQVPRAQ | 11980 | MTPQVPR | 0.283499 | -0.15617 |
| SyS1091 | 2803 | GCCCAAACTCGGGTTTCTAGTCTTGCGGCACAG | 7392 | AQTRVSSLAAQ | 11981 | TRVSSLA | 0.283423 | -0.15011 |
| SyS1092 | 2804 | GCCCAACACGCGACCTCAAAATCGTCGCACAG | 7393 | AQHADLKIVAQ | 11982 | HADLKIV | 0.283397 | -0.05645 |
| SyS1093 | 2805 | GCCCAAAACAGAAACACCGACACCGTCGCACAG | 7394 | AQNRNTDTVAQ | 11983 | NRNTDTV | 0.283396 | -0.01003 |
| SyS1094 | 2806 | GCCCAAGCCACAAAGACAACCACCTCGCACAG | 7395 | AQAHKDNHLAQ | 11984 | AHKDNHL | 0.283218 | -0.13192 |
| SyS1095 | 2807 | GCCCAATCTGTTCCTGTGCCTGCTGCACAG | 7396 | AQSVPVPAAAQ | 11985 | SVPVPAA | 0.283166 | -0.09997 |
| GS577 | 2808 | GCCCAACAAACCAACAGCGCCCTCATGGCACAG | 7397 | AQQTNSALMAQ | 11986 | QTNSALM | 0.283146 | -0.11549 |
| GS578 | 2809 | GCCCAACTCGGCAGAGACACCGCCTACGCACAG | 7398 | AQLGRDTAYAQ | 11987 | LGRDTAY | 0.283146 | -0.09664 |
| SyP48 | 2810 | GCCCAAAGTTCTGTTGCTCTTGTTGTTGCACAG | 7399 | AQSSVALVVAQ | 11988 | SSVALVV | 0.282934 | -0.04243 |
| GS579 | 2811 | GCCCAAATGAACGCGCCACCCAAGCACAG | 7400 | AQMNAATTQAQ | 11989 | MNAATTQ | 0.282892 | -0.11642 |
| GS581 | 2812 | GCCCAAATGGTTTCTACGGCTAAGGATGCACAG | 7401 | AQMVSTAKDAQ | 11990 | MVSTAKD | 0.282806 | -0.01428 |
| SyS1097 | 2813 | GCCCAACTGGGTCAGATGTATTCTCCGGCACAG | 7402 | AQLGQMYSPAQ | 11991 | LGQMYSP | 0.28245 | -0.19723 |
| GS583 | 2814 | GCCCAAGATTCGAAGGAGAAGCCTAATGCACAG | 7403 | AQDSKEKPNAQ | 11992 | DSKEKPN | 0.282074 | -0.18816 |
| SyS1098 | 2815 | GCCCAAAGCCCCCCGTCCAAGGCCTCGCACAG | 7404 | AQSPPVQGLAQ | 11993 | SPPVQGL | 0.28194 | -0.10889 |
| SyS1099 | 2816 | GCCCAAACTGCGTCGGATCGTTTGCCGGCACAG | 7405 | AQTASDRLPAQ | 11994 | TASDRLP | 0.281925 | -0.04427 |
| SyS1100 | 2817 | GCCCAAATCTACAGCCCCACCGTCGCACAG | 7406 | AQIYSPTTVAQ | 11995 | IYSPTTV | 0.28173 | 0.009655 |
| SyS1101 | 2818 | GCCCAAAGTCAGTCTAAGGAGCTGCGGGCACAG | 7407 | AQSQSKELRAQ | 11996 | SQSKELR | 0.28162 | -0.14795 |
| SyS1102 | 2819 | GCCCAAGGCGCCCTCAACGGCGGCGTCGCACAG | 7408 | AQGALNGGVAQ | 11997 | GALNGGV | 0.28162 | -0.09251 |
| GS585 | 2820 | GCCCAAACTATTATTAATTCGAGTAAGGCACAG | 7409 | AQTIINSSKAQ | 11998 | TIINSSK | 0.281489 | -0.18054 |
| GS586 | 2821 | GCCCAACCTGTGAGTGCTCAGCCTGTTGCACAG | 7410 | AQPVSAQPVAQ | 11999 | PVSAQPV | 0.281416 | -0.16663 |
| SyS1103 | 2822 | GCCCAATCTAATGAGGCGGTGACTAATGCACAG | 7411 | AQSNEAVTNAQ | 12000 | SNEAVTN | 0.281348 | -0.11723 |
| SyS1104 | 2823 | GCCCAAGCGAGTATGCAGATGAATCGTGCACAG | 7412 | AQASMQMNRAQ | 12001 | ASMQMNR | 0.281339 | -0.06586 |
| SyS1105 | 2824 | GCCCAAAGCGTCGGCAAAAGCGAACTCGCACAG | 7413 | AQSVGKSELAQ | 12002 | SVGKSEL | 0.281132 | 0.014504 |
| SyS1106 | 2825 | GCCCAATCTCAGGTTAATCCTTCTAGTGCACAG | 7414 | AQSQVNPSSAQ | 12003 | SQVNPSS | 0.280883 | -0.06161 |

FIG. 33 (Continued)

| | | | | | | | | |
|---|---|---|---|---|---|---|---|---|
| SyS1107 | 2826 | GCCCAAATTACGACTGATCAGCCTTTTGCACAG | 7415 | AQITTDQPFAQ | 12004 | ITTDQPF | 0.280883 | -0.16466 |
| SyS1109 | 2827 | GCCCAAAATAATGGGTCTGGTTCTTATGCACAG | 7416 | AQNNGSGSYAQ | 12005 | NNGSGSY | 0.280653 | -0.22064 |
| GS587 | 2828 | GCCCAAAACCCTCGCCAGAAGCAGCGTCGCACAG | 7417 | AQTLARSSVAQ | 12006 | TLARSSV | 0.280506 | 0.024598 |
| GS588 | 2829 | GCCCAAAACGCCAGCACCATGACCAGAGCACAG | 7418 | AQNASTMTRAQ | 12007 | NASTMTR | 0.280372 | -0.01638 |
| GP124 | 2830 | GCCCAAACGAATCAGGTGAGGTATGTTGCACAG | 7419 | AQTNQVRYVAQ | 12008 | TNQVRYV | 0.280321 | -0.06218 |
| GS589 | 2831 | GCCCAAAGCACCCAAAGCCCAACAGAGCACAG | 7420 | AQSTQSPNRAQ | 12009 | STQSPNR | 0.280294 | -0.0613 |
| GS590 | 2832 | GCCCAAGATACGGGGGCGGAGGGGTTGGCACAG | 7421 | AQDTGARGLAQ | 12010 | DTGARGL | 0.279908 | -0.09508 |
| SyS1110 | 2833 | GCCCAACCTGGTTCTCATGTGGTGGCTGCACAG | 7422 | AQPGSHVVAAQ | 12011 | PGSHVVA | 0.279813 | -0.10701 |
| SyS1112 | 2834 | GCCCAAGCCAACGGCATCGAAACCAAAGCACAG | 7423 | AQANGIETKAQ | 12012 | ANGIETK | 0.279639 | -0.14768 |
| SyS1113 | 2835 | GCCCAAGCGCATGGTCAGGTGCAGGAGGCACAG | 7424 | AQAHGQVQEAQ | 12013 | AHGQVQE | 0.279602 | -0.15374 |
| SyS1114 | 2836 | GCCCAAGCTCTGAGTCATGATCTTTCGGCACAG | 7425 | AQALSHDLSAQ | 12014 | ALSHDLS | 0.279563 | -0.15981 |
| SyS1115 | 2837 | GCCCAACTCGGCAGCAGCCTCACCGCCGCACAG | 7426 | AQLGSSLTAAQ | 12015 | LGSSLTA | 0.279545 | -0.0211 |
| SS74 | 2838 | GCCCAAGGCAACAACACCGCCAAACTCGCACAG | 7427 | AQGNNTAKLAQ | 12016 | GNNTAKL | 0.279413 | -0.32548 |
| SyS1116 | 2839 | GCCCAAAATTATGCTCAGTCGCCTTGCACAG | 7428 | AQNYAQSALAQ | 12017 | NYAQSAL | 0.279327 | -0.19011 |
| GS592 | 2840 | GCCCAAGATTCGCAGAGTAAGACTTTGCACAG | 7429 | AQDSQSKTFAQ | 12018 | DSQSKTF | 0.279314 | -0.15955 |
| TS157 | 2841 | GCCCAAACTAATCATGTTAAGTTTACGGCACAG | 7430 | AQTNHVKFTAQ | 12019 | TNHVKFT | 0.279279 | -0.09196 |
| GS593 | 2842 | GCCCAAAGCACCCCACCCCGGCCTCGCACAG | 7431 | AQSTPTHGLAQ | 12020 | STPTHGL | 0.279226 | -0.09374 |
| SyS1117 | 2843 | GCCCAAAGTGTGGGGTTGACGATGGTGGCACAG | 7432 | AQSVGLTMVAQ | 12021 | SVGLTMV | 0.279206 | -0.20224 |
| SyS1118 | 2844 | GCCCAAATTCCGAAGGGTTCTGGGGCGGCACAG | 7433 | AQIPKGSGAAQ | 12022 | IPKGSGA | 0.279091 | 0.080236 |
| GS594 | 2845 | GCCCAAACGCCCAAGCCAGAGTCCTCGCACAG | 7434 | AQTAQARVLAQ | 12023 | TAQARVL | 0.279047 | -0.1122 |
| GS595 | 2846 | GCCCAATGGCACGCCGGCAGCGTCGGCGCACAG | 7435 | AQWHAGSVGAQ | 12024 | WHAGSVG | 0.279017 | -0.09667 |
| SyS1119 | 2847 | GCCCAATCGCAGTCTCTTTGGTTGAGGCACAG | 7436 | AQSQSLLVEAQ | 12025 | SQSLLVE | 0.278987 | -0.22042 |
| SyS1120 | 2848 | GCCCAAAATAATAGTGGGCTTTGAAGGCACAG | 7437 | AQNNSGPLKAQ | 12026 | NNSGPLK | 0.278922 | -0.21078 |
| SyS1121 | 2849 | GCCCAAAGGGATAATGCTATTGAGCATGCACAG | 7438 | AQRDNAIEHAQ | 12027 | RDNAIEH | 0.278763 | -0.17259 |
| GS597 | 2850 | GCCCAAACTATGTCGAATATTACGAGGCACAG | 7439 | AQTMSNITRAQ | 12028 | TMSNITR | 0.278669 | 0.034782 |
| SyS1122 | 2851 | GCCCAACTCAGCACCCTCAGCCAAATGGCACAG | 7440 | AQLSTLSQMAQ | 12029 | LSTLSQM | 0.278541 | -0.0734 |
| GS598 | 2852 | GCCCAAGTCATGCAAAACTACGGCAGCGCACAG | 7441 | AQVMQNYGSAQ | 12030 | VMQNYGS | 0.278395 | -0.1774 |
| SyS1123 | 2853 | GCCCAAACTCATTCGGCGCAGCAGAATGCACAG | 7442 | AQTHSAQQNAQ | 12031 | THSAQQN | 0.277996 | -0.10236 |
| GS601 | 2854 | GCCCAATGCGGTTCCTCCGAATAGGAATGCACAG | 7443 | AQSVPPNRNAQ | 12032 | SVPPNRN | 0.277804 | -0.13857 |
| SyS1125 | 2855 | GCCCAATCTGTTGCGGCGAGTCCTCGTGCACAG | 7444 | AQSVAASPRAQ | 12033 | SVAASPR | 0.277759 | -0.03359 |
| SyS1127 | 2856 | GCCCAAAATAATACTTCGACGCTGCATGCACAG | 7445 | AQNNTSTLHAQ | 12034 | NNTSTLH | 0.277642 | -0.19739 |
| SyS1128 | 2857 | GCCCAAAATCTTTCTGATCATATGCCGGCACAG | 7446 | AQNLSDHMPAQ | 12035 | NLSDHMP | 0.277561 | -0.22803 |

FIG. 33 (Continued)

| | | | | | | | |
|---|---|---|---|---|---|---|---|
| GP125 | 2858 | GCCCAAGGTCTGTATGCTACGACTTCTGCACAG | 7447 | AQGLYATTSAQ | 12036 | GLYATTS | 0.277546 | 0.324596 |
| SyS1129 | 2859 | GCCCAACGTAATGGTGGTGCGAATGTTGCACAG | 7448 | AQRNGGANVAQ | 12037 | RNGGANV | 0.277332 | 0.271066 |
| SyS1130 | 2860 | GCCCAATTCCACAACCTCACCCTCAGCGCACAG | 7449 | AQFHNLTLSAQ | 12038 | FHNLTLS | 0.277251 | -0.09337 |
| SyS1131 | 2861 | GCCCAATGGAAGAGTCCTGCTGCTATTGCACAG | 7450 | AQWKSPAAIAQ | 12039 | WKSPAAI | 0.277234 | -0.14405 |
| SyS1132 | 2862 | GCCCAACCCAAAGGCCTCAGCGGCGAAGCACAG | 7451 | AQPKGLSGEAQ | 12040 | PKGLSGE | 0.277183 | 0.248416 |
| GS603 | 2863 | GCCCAATCGCATTATCAGTTGCATCCGGCACAG | 7452 | AQSHYQLHPAQ | 12041 | SHYQLHP | 0.27717 | -0.17005 |
| SyS1133 | 2864 | GCCCAACCACCTTCAGAAGCGCCCCGCACAG | 7453 | AQTTFRSAPAQ | 12042 | TTFRSAP | 0.277074 | -0.08464 |
| SyS1134 | 2865 | GCCCAATACGACGCCACCCACAGCGCCGCACAG | 7454 | AQYDATHSAAQ | 12043 | YDATHSA | 0.27674 | -0.16889 |
| GS605 | 2866 | GCCCAAAATCAGTCGGGTCCGTTGAAGGCACAG | 7455 | AQNQSGPLKAQ | 12044 | NQSGPLK | 0.276624 | -0.00392 |
| SyS1135 | 2867 | GCCCAACACACCAACATGACCAGCATGGCACAG | 7456 | AQHTNMTSMAQ | 12045 | HTNMTSM | 0.276609 | 0.123822 |
| SyS1136 | 2868 | GCCCAACATATGAAGAGTCAGCTGCCGGCACAG | 7457 | AQHMKSQLPAQ | 12046 | HMKSQLP | 0.276324 | 0.098421 |
| GS606 | 2869 | GCCCAAAAACTCCCACCATGGCCAACGCACAG | 7458 | AQKLPTMANAQ | 12047 | KLPTMAN | 0.275986 | -0.0594 |
| GS607 | 2870 | GCCCAAGTTGGGACTAATGCGAATCATGCACAG | 7459 | AQVGTNANHAQ | 12048 | VGTNANH | 0.275965 | -0.13666 |
| GP126 | 2871 | GCCCAATTGAAGACTGATCCTTTTCTGGCACAG | 7460 | AQLKTDPFLAQ | 12049 | LKTDPFL | 0.275884 | -0.07259 |
| GS608 | 2872 | GCCCAACACCTCCAACAAAACCTCACCGCACAG | 7461 | AQHLQQNLTAQ | 12050 | HLQQNLT | 0.275812 | -0.16146 |
| SyS1137 | 2873 | GCCCAAACTCAGAATAAGAATTCTCATGCACAG | 7462 | AQTQNKNSHAQ | 12051 | TQNKNSH | 0.275704 | -0.04648 |
| SS76 | 2874 | GCCCAACCCAACGCCCAAAGCCAAAGAGCACAG | 7463 | AQPNAQSQRAQ | 12052 | PNAQSQR | 0.27556 | -0.34576 |
| SyS1138 | 2875 | GCCCAAGGTAGTGGTCATTCGACTCTTGCACAG | 7464 | AQGSGHSTLAQ | 12053 | GSGHSTL | 0.275521 | -0.11616 |
| SyS1139 | 2876 | GCCCAATTGACGGGTAGGCTTGAGAAGGCACAG | 7465 | AQLTGRLEKAQ | 12054 | LTGRLEK | 0.275499 | -0.06888 |
| SyS1140 | 2877 | GCCCAACCCAGCAGAAACGCCAGCCTCGCACAG | 7466 | AQPSRNASLAQ | 12055 | PSRNASL | 0.275483 | -0.0216 |
| GS610 | 2878 | GCCCAAGTTTTAGGACGTCGGATCTTGCACAG | 7467 | AQVFRTSDLAQ | 12056 | VFRTSDL | 0.275429 | -0.12297 |
| GS611 | 2879 | GCCCAAATCGCCAGCACCTACAGCAGCGCACAG | 7468 | AQIASTYSSAQ | 12057 | IASTYSS | 0.275379 | 0.042246 |
| SyS1141 | 2880 | GCCCAAACCATCAACCACGCCACCAGCGCACAG | 7469 | AQTINHATSAQ | 12058 | TINHATS | 0.275307 | 0.060839 |
| SyS1142 | 2881 | GCCCAAGCTATGAATAATCGTGCTCATGCACAG | 7470 | AQAMNNRAHAQ | 12059 | AMNNRAH | 0.275089 | -0.19723 |
| GS612 | 2882 | GCCCAATCGCATCATGAGCAGGTTTCTGCACAG | 7471 | AQSHHEQVSAQ | 12060 | SHHEQVS | 0.274982 | -0.12807 |
| SyS1143 | 2883 | GCCCAATCGGGGGTTACTAGTAAGCTTGCACAG | 7472 | AQSGVTSKLAQ | 12061 | SGVTSKL | 0.274938 | -0.12208 |
| SyS1144 | 2884 | GCCCAAGTGTTTACTAATGATGTGCCTGCACAG | 7473 | AQVFTNDVPAQ | 12062 | VFTNDVP | 0.274934 | -0.14041 |
| SyS1145 | 2885 | GCCCAAGCTGCGGTGTTGGTGGCTCCGGCACAG | 7474 | AQAAVLVAPAQ | 12063 | AAVLVAP | 0.274757 | -0.22434 |
| GS613 | 2886 | GCCCAACCCACGGCCAGATACCTGCCGGCACAG | 7475 | AQPTAGRYLAQ | 12064 | PTAGRYL | 0.274712 | -0.18816 |
| GS614 | 2887 | GCCCAACATCTTAATTCGCAGAATATGGCACAG | 7476 | AQHLNSQNMAQ | 12065 | HLNSQNM | 0.274394 | -0.04601 |
| SyS1146 | 2888 | GCCCAACCCAACGTCGGGCAGAGCACAG | 7477 | AQPNPNVGRAQ | 12066 | PNPNVGR | 0.274299 | 0.025701 |
| SyS1147 | 2889 | GCCCAAGCTAGTGAGAATCTTCGTTCGGCACAG | 7478 | AQASENLRSAQ | 12067 | ASENLRS | 0.2742 | -0.12824 |

FIG. 33 (Continued)

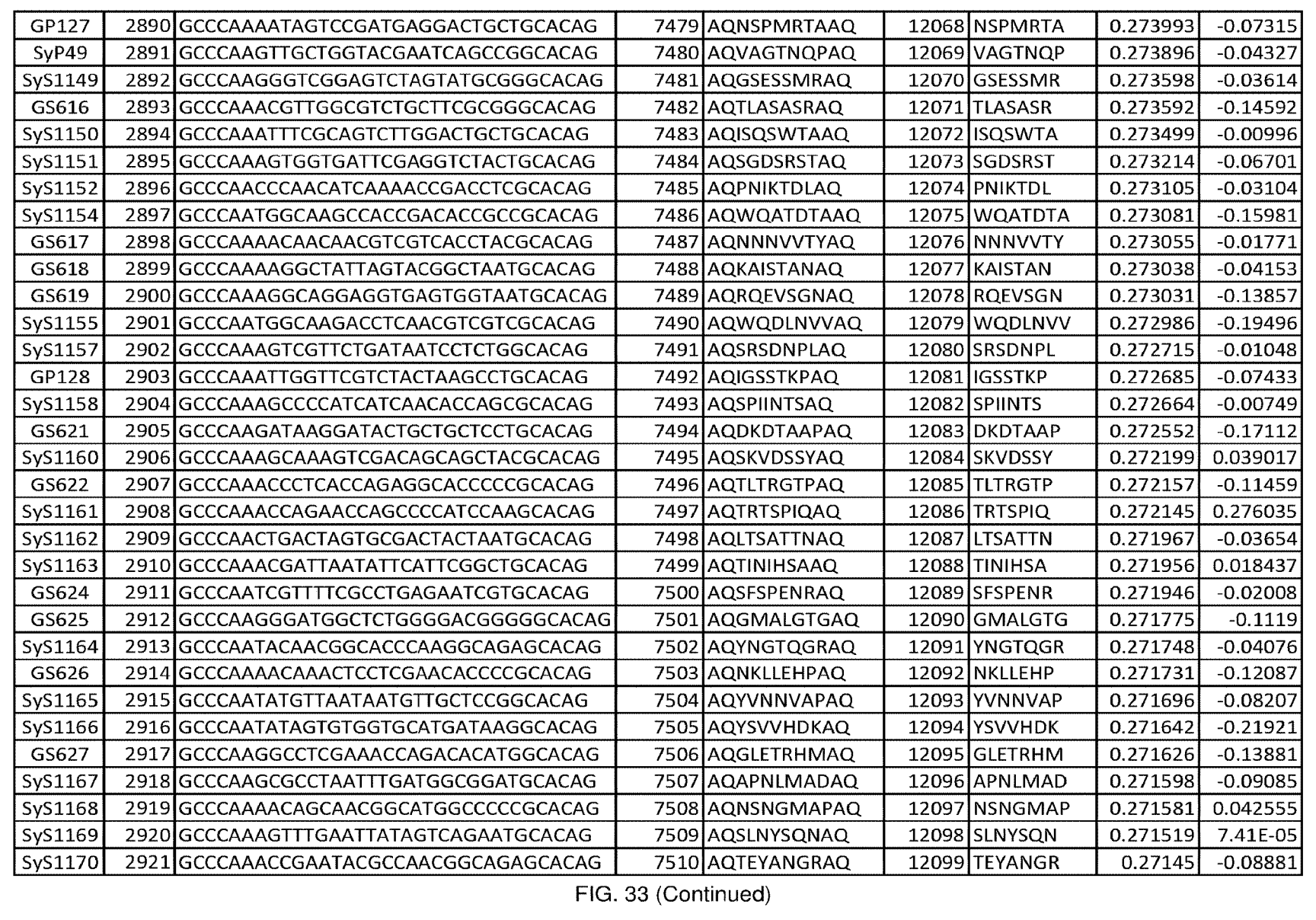

| | | | | | | | | |
|---|---|---|---|---|---|---|---|---|
| GP127 | 2890 | GCCCAAAATAGTCCGATGAGGACTGCTGCACAG | 7479 | AQNSPMRTAAQ | 12068 | NSPMRTA | 0.273993 | -0.07315 |
| SyP49 | 2891 | GCCCAAGTTGCTGGTACGAATCAGCGGCACAG | 7480 | AQVAGTNQPAQ | 12069 | VAGTNQP | 0.273896 | -0.04327 |
| SyS1149 | 2892 | GCCCAAACGTTGGCGTCTGCTTCGCGGGCACAG | 7481 | AQGSESSMRAQ | 12070 | GSESSMR | 0.273598 | -0.03614 |
| GS616 | 2893 | GCCCAAATTTCGCAGTCTTGGACTGCTGCACAG | 7482 | AQTLASASRAQ | 12071 | TLASASR | 0.273592 | -0.14592 |
| SyS1150 | 2894 | GCCCAAAGTGGTGATTCGAGGTCTACTGCACAG | 7483 | AQISQSWTAAQ | 12072 | ISQSWTA | 0.273499 | -0.00996 |
| SyS1151 | 2895 | GCCCAAAGTGGTGATTCGAGGTCTACTGCACAG | 7484 | AQSGDSRSTAQ | 12073 | SGDSRST | 0.273214 | -0.06701 |
| SyS1152 | 2896 | GCCCAACCCAACATCAAAACCGACCTCGCACAG | 7485 | AQPNIKTDLAQ | 12074 | PNIKTDL | 0.273105 | -0.03104 |
| SyS1154 | 2897 | GCCCAATGGCAAGCACCGACACCGCCGCACAG | 7486 | AQWQATDTAAQ | 12075 | WQATDTA | 0.273081 | -0.15981 |
| GS617 | 2898 | GCCCAAAACAACAACGTCGTCACCTAGGCACAG | 7487 | AQNNNVVTYAQ | 12076 | NNNVVTY | 0.273055 | -0.01771 |
| GS618 | 2899 | GCCCAAAAGGCTATTAGTACGGCTAATGCACAG | 7488 | AQKAISTANAQ | 12077 | KAISTAN | 0.273038 | -0.04153 |
| GS619 | 2900 | GCCCAAAGGCAGGAGGTGAGTGGTAATGCACAG | 7489 | AQRQEVSGNAQ | 12078 | RQEVSGN | 0.273031 | -0.13857 |
| SyS1155 | 2901 | GCCCAATGGCAAGACCTCAACGTCGTCGCACAG | 7490 | AQWQDLNVVAQ | 12079 | WQDLNVV | 0.272986 | -0.19496 |
| SyS1157 | 2902 | GCCCAAAGTCGTTCTGATAATCCTCTGGCACAG | 7491 | AQSRSDNPLAQ | 12080 | SRSDNPL | 0.272715 | -0.01048 |
| GP128 | 2903 | GCCCAAAATTGGTTCGTTCGTTACTAAGCCTGCACAG | 7492 | AQIGSSTKPAQ | 12081 | IGSSTKP | 0.272685 | -0.07433 |
| SyS1158 | 2904 | GCCCAAAGCCCCATCATCAACACCAGCGCACAG | 7493 | AQSPIINTSAQ | 12082 | SPIINTS | 0.272664 | -0.00749 |
| GS621 | 2905 | GCCCAAGATAAGGATACTGCTGCTCCTGCACAG | 7494 | AQDKDTAAPAQ | 12083 | DKDTAAP | 0.272552 | -0.17112 |
| SyS1160 | 2906 | GCCCAAAGCAAAGTCGACAGCAGCTACGCCACAG | 7495 | AQSKVDSSYAQ | 12084 | SKVDSSY | 0.272199 | 0.039017 |
| GS622 | 2907 | GCCCAAACCCTCACCAGAGGCACCCCGCACAG | 7496 | AQTLTRGTPAQ | 12085 | TLTRGTP | 0.272157 | -0.11459 |
| SyS1161 | 2908 | GCCCAAACCAGAACCAGCCCCATCCAAGCACAG | 7497 | AQTRTSPIQAQ | 12086 | TRTSPIQ | 0.272145 | 0.276035 |
| SyS1162 | 2909 | GCCCAACTGACTAGTGCGACTACTAATGCACAG | 7498 | AQLTSATTNAQ | 12087 | LTSATTN | 0.271967 | -0.03654 |
| SyS1163 | 2910 | GCCCAAACGATTAATATTCATTCGGCTGCACAG | 7499 | AQTINIHSAAQ | 12088 | TINIHSA | 0.271956 | 0.018437 |
| GS624 | 2911 | GCCCAATCGTTTCGCCTGAGAATCGTGCACAG | 7500 | AQSFSPENRAQ | 12089 | SFSPENR | 0.271946 | -0.02008 |
| GS625 | 2912 | GCCCAAGGGATGGCTCTGGGGACGGGGGCACAG | 7501 | AQGMALGTGAQ | 12090 | GMALGTG | 0.271775 | -0.1119 |
| SyS1164 | 2913 | GCCCAATACAACGGCACCAAGGCAGAGCACAG | 7502 | AQYNGTQGRAQ | 12091 | YNGTQGR | 0.271748 | -0.04076 |
| GS626 | 2914 | GCCCAAAACAAACTCCTCGAACACCCCGCACAG | 7503 | AQNKLLEHPAQ | 12092 | NKLLEHP | 0.271731 | -0.12087 |
| SyS1165 | 2915 | GCCCAATATGTTAATAATGTTGCTCCGGCACAG | 7504 | AQYVNNVAPAQ | 12093 | YVNNVAP | 0.271696 | -0.08207 |
| SyS1166 | 2916 | GCCCAATATAGTGGTGCATGATAAGGCACAG | 7505 | AQYSVVHDKAQ | 12094 | YSVVHDK | 0.271642 | -0.21921 |
| GS627 | 2917 | GCCCAAGGCCTCGAAACCAGACACATGGCACAG | 7506 | AQGLETRHMAQ | 12095 | GLETRHM | 0.271626 | -0.13881 |
| SyS1167 | 2918 | GCCCAAGCGCCTAATTTGATGGCGGATGCACAG | 7507 | AQAPNLMADAQ | 12096 | APNLMAD | 0.271598 | -0.09085 |
| SyS1168 | 2919 | GCCCAAAACAGCAACGGCATGGCCCCGCACAG | 7508 | AQNSNGMAPAQ | 12097 | NSNGMAP | 0.271581 | 0.042555 |
| SyS1169 | 2920 | GCCCAAAGTTTGAATTATATAGTCAGAATGCACAG | 7509 | AQSLNYSQNAQ | 12098 | SLNYSQN | 0.271519 | 7.41E-05 |
| SyS1170 | 2921 | GCCCAAAACCGAATACGCCAACGGCAGAGCACAG | 7510 | AQTEYANGRAQ | 12099 | TEYANGR | 0.27145 | -0.08881 |

FIG. 33 (Continued)

| | | | | | | | | |
|---|---|---|---|---|---|---|---|---|
| GP129 | 2922 | GCCCAACCTCTTGGGCATGTTAGGTCTGCACAG | 7511 | AQPLGHVRSAQ | 12100 | PLGHVRS | 0.271369 | 0.161673 |
| GS628 | 2923 | GCCCAACTTCGGGATTCGCCGGGGCTGGCACAG | 7512 | AQLRDSPGLAQ | 12101 | LRDSPGL | 0.271307 | -0.1747 |
| SyS1171 | 2924 | GCCCAAGTTATTAGGTCGAATACTCATGCACAG | 7513 | AQVIRSNTHAQ | 12102 | VIRSNTH | 0.271216 | -0.15781 |
| SyS1172 | 2925 | GCCCAAGCGTCGGTGAGTAATCTTTCGGCACAG | 7514 | AQASVSNLSAQ | 12103 | ASVSNLS | 0.271028 | -0.12012 |
| SyS1173 | 2926 | GCCCAATGGGCCCAAAGAACCAGCCAAGCACAG | 7515 | AQWAQRTSQAQ | 12104 | WAQRTSQ | 0.271025 | -0.17382 |
| GS630 | 2927 | GCCCAAAACGACAAAGGCATGAGCAGAGCACAG | 7516 | AQNDKGMSRAQ | 12105 | NDKGMSR | 0.270989 | -0.07517 |
| GP130 | 2928 | GCCCAACAGAATGATACTCGTAATTATGCACAG | 7517 | AQQNDTRNYAQ | 12106 | QNDTRNY | 0.270955 | -0.07273 |
| SyS1174 | 2929 | GCCCAAGGCGAAGTCGCCGGCAGACTCGCACAG | 7518 | AQGEVAGRLAQ | 12107 | GEVAGRL | 0.270924 | -0.02281 |
| SyS1175 | 2930 | GCCCAAACCACCACCAACACCGTCAGCGCACAG | 7519 | AQTTTNTVSAQ | 12108 | TTTNTVS | 0.270848 | -0.1792 |
| SyS1176 | 2931 | GCCCAACCGGTTATGTCGAATAAGGATGCACAG | 7520 | AQPVMSNKDAQ | 12109 | PVMSNKD | 0.270622 | -0.13314 |
| GS632 | 2932 | GCCCAAAACGGGCGGCACCACCTTCATCGCACAG | 7521 | AQNGGTTFIAQ | 12110 | NGGTTFI | 0.270379 | -0.12521 |
| SyS1177 | 2933 | GCCCAAGTTTGAAGACTACGGCTATTGCACAG | 7522 | AQVLKTTAIAQ | 12111 | VLKTTAI | 0.270139 | -0.19133 |
| SyS1178 | 2934 | GCCCAACCCCACGGCGTCGGCAGCGCCGCACAG | 7523 | AQPHGVGSAAQ | 12112 | PHGVGSA | 0.27008 | -0.03489 |
| GS635 | 2935 | GCCCAATCTAATGCGCATCCTCTGGCTGCACAG | 7524 | AQSNAHPLAAQ | 12113 | SNAHPLA | 0.270011 | -0.17958 |
| SyS1179 | 2936 | GCCCAAAAAAGCACCAGCCTCGACCCCGCACAG | 7525 | AQKSTSLDPAQ | 12114 | KSTSLDP | 0.269961 | -0.05312 |
| SyS1180 | 2937 | GCCCAATTCAACAAAACCAACGACATGGCACAG | 7526 | AQFNKTNDMAQ | 12115 | FNKTNDM | 0.269911 | 0.039016 |
| SyS1181 | 2938 | GCCCAACACCAAACCAGCGAACTCAGAGCACAG | 7527 | AQHQTSELRAQ | 12116 | HQTSELR | 0.269505 | -0.13316 |
| SyS1182 | 2939 | GCCCAATGGGCCAAAGTCCTCGACAAAGCACAG | 7528 | AQWAKVLDKAQ | 12117 | WAKVLDK | 0.269376 | -0.18042 |
| GS637 | 2940 | GCCCAAATGAGCAGCAACAACAAAAGCGCACAG | 7529 | AQMSSNNKSAQ | 12118 | MSSNNKS | 0.26924 | -0.10804 |
| GS638 | 2941 | GCCCAAGATGGTACTCATTTGAAGCTGGCACAG | 7530 | AQDGTHLKLAQ | 12119 | DGTHLKL | 0.269216 | -0.12903 |
| SyS1183 | 2942 | GCCCAAACGGTTATTAGTGATCAGAGGGCACAG | 7531 | AQTVISDQRAQ | 12120 | TVISDQR | 0.269208 | -0.23296 |
| GS639 | 2943 | GCCCAAATGCACAGCCAACTCCTCCCCGCACAG | 7532 | AQMHSQLLPAQ | 12121 | MHSQLLP | 0.269185 | -0.16394 |
| GP131 | 2944 | GCCCAATCGTCTTATGGGACTGCGGCGGCACAG | 7533 | AQSSYGTAAAQ | 12122 | SSYGTAA | 0.269078 | -0.07134 |
| SyS1184 | 2945 | GCCCAAGTGTTGTCTACGATGGCTGTTGCACAG | 7534 | AQVLSTMAVAQ | 12123 | VLSTMAV | 0.269054 | -0.01394 |
| GS640 | 2946 | GCCCAATGCGCTTCGAATTTTGCGTCTGCACAG | 7535 | AQSASNFASAQ | 12124 | SASNFAS | 0.268964 | -0.14715 |
| GS642 | 2947 | GCCCAAAGTAAGGCTGGTCTGAGTGATGCACAG | 7536 | AQSKAGLSDAQ | 12125 | SKAGLSD | 0.268902 | -0.06703 |
| GS643 | 2948 | GCCCAAATTAATCGGATTGTTAGTGGGGCACAG | 7537 | AQINRIVSGAQ | 12126 | INRIVSG | 0.268902 | -0.0141 |
| SyS1185 | 2949 | GCCCAAAAAACTCGACACCCCGGCAAAGCACAG | 7538 | AQKLDTPGKAQ | 12127 | KLDTPGK | 0.268816 | -0.14647 |
| GS644 | 2950 | GCCCAAATGGATCGTATTGTTAAGATGGCACAG | 7539 | AQMDRIVKMAQ | 12128 | MDRIVKM | 0.268718 | -0.16125 |
| SyS1186 | 2951 | GCCCAAAGAGAAAGAAGCACCGACGCCGCACAG | 7540 | AQRERSTDAAQ | 12129 | RERSTDA | 0.26861 | 0.020477 |
| GS645 | 2952 | GCCCAACTCAGAGACTGGCACCGCCACGCACAG | 7541 | AQLRDSTGHAQ | 12130 | LRDSTGH | 0.268608 | -0.08258 |
| SyS1187 | 2953 | GCCCAAATGAGAGGCCAAGGCGTCCACGCACAG | 7542 | AQMRGQGVHAQ | 12131 | MRGQGVH | 0.268511 | 0.013557 |

FIG. 33 (Continued)

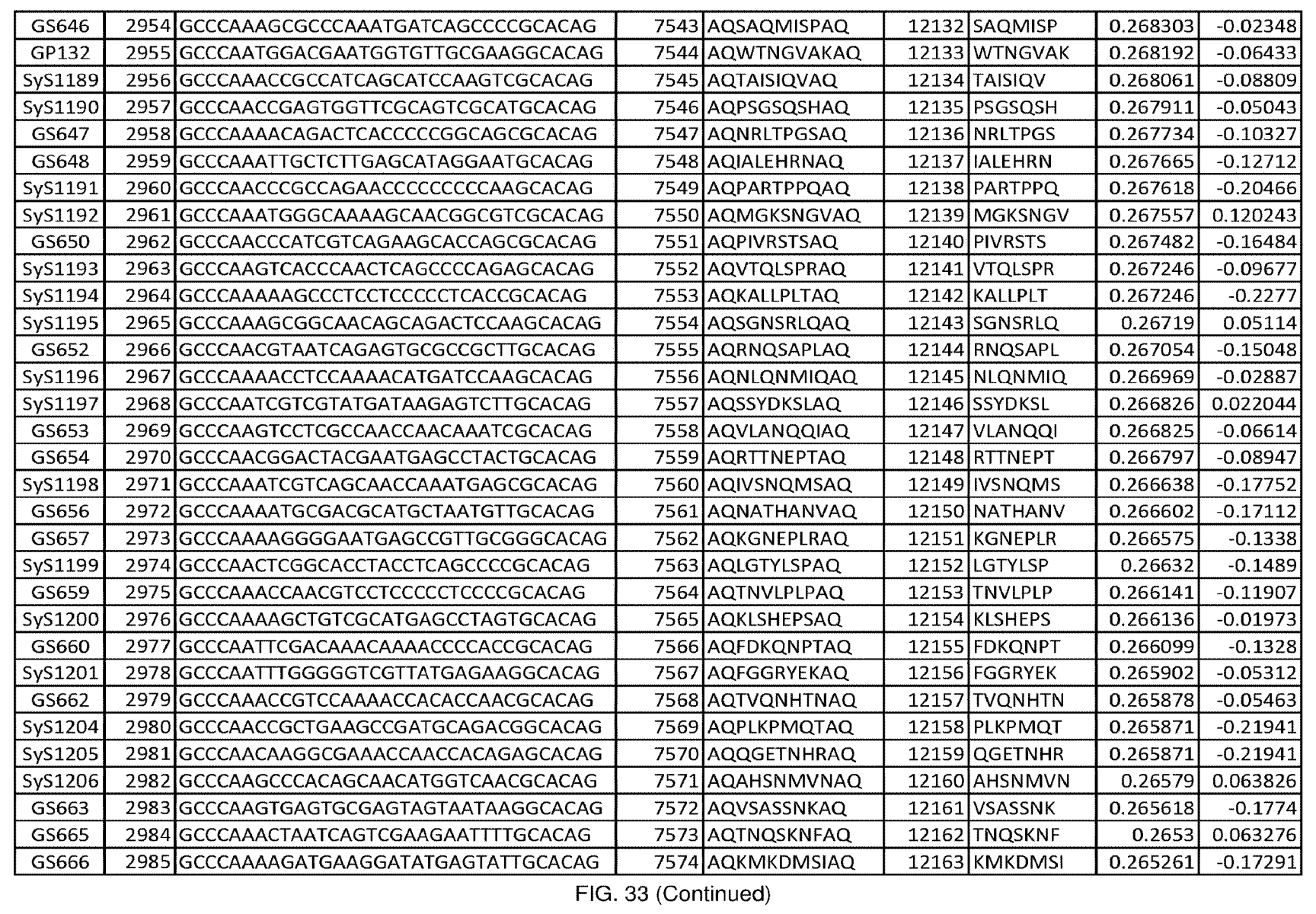

| | | | | | | | | |
|---|---|---|---|---|---|---|---|---|
| GS646 | 2954 | GCCCAAAGGCGCCCAAAATGATCAGCCCGCACAG | 7543 | AQSAQMISPAQ | 12132 | SAQMISP | 0.268303 | -0.02348 |
| GP132 | 2955 | GCCCAATGGACGAATGGTGTTGCGAAGGCACAG | 7544 | AQWTNGVAKAQ | 12133 | WTNGVAK | 0.268192 | -0.06433 |
| SyS1189 | 2956 | GCCCAAACCGCCATCAGCATCCAAGTCGCACAG | 7545 | AQTAISIQVAQ | 12134 | TAISIQV | 0.268061 | -0.08809 |
| SyS1190 | 2957 | GCCCAACCGAGTGGTTCGCGAGTGCCATGCACAG | 7546 | AQPSGSQSHAQ | 12135 | PSGSQSH | 0.267911 | -0.05043 |
| GS647 | 2958 | GCCCAAAACAGACTCACCCCGGCAGCGGCACAG | 7547 | AQNRLTPGSAQ | 12136 | NRLTPGS | 0.267734 | -0.10327 |
| GS648 | 2959 | GCCCAAATTGCTCTTGAGCATAGGAATGCACAG | 7548 | AQIALEHRNAQ | 12137 | IALEHRN | 0.267665 | -0.12712 |
| SyS1191 | 2960 | GCCCAACCGCCAGAAACCCCCCAAGCACAG | 7549 | AQPARTPPQAQ | 12138 | PARTPPQ | 0.267618 | -0.20466 |
| SyS1192 | 2961 | GCCCAAATGGGCAAAAGCAACGGCGTCGCACAG | 7550 | AQMGKSNGVAQ | 12139 | MGKSNGV | 0.267557 | 0.120243 |
| GS650 | 2962 | GCCCAACCATCGTCAGAAGCACCAGCGCACAG | 7551 | AQPIVRSTSAQ | 12140 | PIVRSTS | 0.267482 | -0.16484 |
| SyS1193 | 2963 | GCCCAAGTCACCCAACTCAGCCCCAGAGCACAG | 7552 | AQVTQLSPRAQ | 12141 | VTQLSPR | 0.267246 | -0.09677 |
| SyS1194 | 2964 | GCCCAAAAAGCCCTCCTCCCCTCACCGCACAG | 7553 | AQKALLPLTAQ | 12142 | KALLPLT | 0.267246 | -0.2277 |
| SyS1195 | 2965 | GCCCAAAGCGGCAACAGCAGACTCCAAGCACAG | 7554 | AQSGNSRLQAQ | 12143 | SGNSRLQ | 0.26719 | 0.05114 |
| GS652 | 2966 | GCCCAACGTAATCAGAGTGCGCGCGCTTGCACAG | 7555 | AQRNQSAPLAQ | 12144 | RNQSAPL | 0.267054 | -0.15048 |
| SyS1196 | 2967 | GCCCAAAAACCTCCAAAACATGATCCAAGCACAG | 7556 | AQNLQNMIQAQ | 12145 | NLQNMIQ | 0.266969 | -0.02887 |
| SyS1197 | 2968 | GCCCAATCGTCGTATGATAAGAGTCTTGCACAG | 7557 | AQSSYDKSLAQ | 12146 | SSYDKSL | 0.266826 | 0.022044 |
| GS653 | 2969 | GCCCAAGTCCTCGCCAACCAACAAATCGCACAG | 7558 | AQVLANQQIAQ | 12147 | VLANQQI | 0.266825 | -0.06614 |
| GS654 | 2970 | GCCCAACGGACTACGAATGAGCCTACTGCACAG | 7559 | AQRTTNEPTAQ | 12148 | RTTNEPT | 0.266797 | -0.08947 |
| SyS1198 | 2971 | GCCCAAATCGTCAGCAACCAAATGAGCGCACAG | 7560 | AQIVSNQMSAQ | 12149 | IVSNQMS | 0.266638 | -0.17752 |
| GS656 | 2972 | GCCCAAAATGCGACGCATGCTAATGTTGCACAG | 7561 | AQNATHANVAQ | 12150 | NATHANV | 0.266602 | -0.17112 |
| GS657 | 2973 | GCCCAAAAGGGGAATGAGCCGTTGCGGGCACAG | 7562 | AQKGNEPLRAQ | 12151 | KGNEPLR | 0.266575 | -0.1338 |
| SyS1199 | 2974 | GCCCAACTCGGCCACCTACCTCAGCCCGCACAG | 7563 | AQLGTYLSPAQ | 12152 | LGTYLSP | 0.26632 | -0.1489 |
| GS659 | 2975 | GCCCAAACCAACGTCCTCCCCCGCACAG | 7564 | AQTNVLPLPAQ | 12153 | TNVLPLP | 0.266141 | -0.11907 |
| SyS1200 | 2976 | GCCCAAAAGCTGTCGCATGAGCCTAGTGCACAG | 7565 | AQKLSHEPSAQ | 12154 | KLSHEPS | 0.266136 | -0.01973 |
| GS660 | 2977 | GCCCAATTCGACAAAACCCACCGCACAG | 7566 | AQFDKQNPTAQ | 12155 | FDKQNPT | 0.266099 | -0.1328 |
| SyS1201 | 2978 | GCCCAATTTGGGGGTCGTTATGAGAAGGCACAG | 7567 | AQFGGRYEKAQ | 12156 | FGGRYEK | 0.265902 | -0.05312 |
| GS662 | 2979 | GCCCAAACCGTCCAAAACCAACGCACAG | 7568 | AQTVQNHTNAQ | 12157 | TVQNHTN | 0.265878 | -0.05463 |
| SyS1204 | 2980 | GCCCAACCGCTGAAGCCGATGCAGACGGCACAG | 7569 | AQPLKPMQTAQ | 12158 | PLKPMQT | 0.265871 | -0.21941 |
| SyS1205 | 2981 | GCCCAACAGGCGAAACAACCACAGAGCACAG | 7570 | AQQGETNHRAQ | 12159 | QGETNHR | 0.265871 | -0.21941 |
| SyS1206 | 2982 | GCCCAAGCCCACAGCAACAACATGGTCAACGCACAG | 7571 | AQAHSNMVNAQ | 12160 | AHSNMVN | 0.26579 | 0.063826 |
| GS663 | 2983 | GCCCAAGTGAGTGCGAGTAGTAATAAGGCACAG | 7572 | AQVSASSNKAQ | 12161 | VSASSNK | 0.265618 | -0.1774 |
| GS665 | 2984 | GCCCAAACTAATCAGTCGGAAGAATTTTGCACAG | 7573 | AQTNQSKNFAQ | 12162 | TNQSKNF | 0.2653 | 0.063276 |
| GS666 | 2985 | GCCCAAAAGATGAAGGATATGAGTATTGCACAG | 7574 | AQKMKDMSIAQ | 12163 | KMKDMSI | 0.265261 | -0.17291 |

FIG. 33 (Continued)

| | | | | | | | | |
|---|---|---|---|---|---|---|---|---|
| SyS1209 | 2986 | GCCCAACACCCAGCGGGCAGCACCCTCGCACAG | 7575 | AQHPSGSTLAQ | 12164 | HPSGSTL | 0.265242 | -0.09127 |
| SyS1210 | 2987 | GCCCAAATTAAGGATACTGTTTCTGTGGGCACAG | 7576 | AQIKDTVSGAQ | 12165 | IKDTVSG | 0.265119 | -0.06613 |
| GS668 | 2988 | GCCCAAATGAACACCCTCACCAACGTCGCACAG | 7577 | AQMNTLTNVAQ | 12166 | MNTLTNV | 0.264894 | -0.09087 |
| SyS1211 | 2989 | GCCCAAACTGATAGTGCTCCGCATCCGGCACAG | 7578 | AQTDSAPHPAQ | 12167 | TDSAPHP | 0.264791 | -0.12222 |
| SyS1212 | 2990 | GCCCAACCCAGACCCGTCAGCAACGGCGCACAG | 7579 | AQPRPVSNGAQ | 12168 | PRPVSNG | 0.264764 | -0.02466 |
| SyS1213 | 2991 | GCCCAATCTGTTGATAGGCGGCGCCGCAGGCACAG | 7580 | AQSVDRRPQAQ | 12169 | SVDRRPQ | 0.264728 | -0.0604 |
| GS670 | 2992 | GCCCAAATGGATTCTCCTATTAGGAATGCACAG | 7581 | AQMDSPIRNAQ | 12170 | MDSPIRN | 0.264655 | -0.15766 |
| GS671 | 2993 | GCCCAAGCTACGCGTATGAGTATTCCTGCACAG | 7582 | AQATRMSIPAQ | 12171 | ATRMSIP | 0.264401 | -0.16932 |
| SyS1214 | 2994 | GCCCAAAACGTCCCACCAGCCTCCCGCACAG | 7583 | AQNVPTSLPAQ | 12172 | NVPTSLP | 0.264383 | 0.102058 |
| SyS1215 | 2995 | GCCCAAAGCCTCAGAATCGAAAGCAAAGCACAG | 7584 | AQSLRIESKAQ | 12173 | SLRIESK | 0.264383 | -0.12829 |
| GS673 | 2996 | GCCCAAAACAGCGGCAACACCCTCGGCGCACAG | 7585 | AQNSGNTLGAQ | 12174 | NSGNTLG | 0.264155 | -0.1119 |
| SyS1216 | 2997 | GCCCAACGGTTGGATCATGCTAGTATTGCACAG | 7586 | AQRLDHASIAQ | 12175 | RLDHASI | 0.264068 | -0.07051 |
| SyS1217 | 2998 | GCCCAAAGCCACCTCGTCGTCAGCGCCGCACAG | 7587 | AQSHLVVSAAQ | 12176 | SHLVVSA | 0.263941 | -0.22064 |
| SyS1218 | 2999 | GCCCAACCCGCCAGCCCCAGAAGCCACGCACAG | 7588 | AQPASPRSHAQ | 12177 | PASPRSH | 0.263752 | -0.19618 |
| SyS1219 | 3000 | GCCCAAAACCACCACCCTCGTCCCCCGCACAG | 7589 | AQNHTLVPPAQ | 12178 | NHTLVPP | 0.263502 | -0.06767 |
| SyS1220 | 3001 | GCCCAAATGCAGATGACGGGGACTGCTGCACAG | 7590 | AQMQMTGTAAQ | 12179 | MQMTGTA | 0.26338 | 0.109806 |
| SyS1221 | 3002 | GCCCAAAATACTCAGGCGAATCCGAGGGCACAG | 7591 | AQNTQANPRAQ | 12180 | NTQANPR | 0.263187 | 0.026893 |
| GS675 | 3003 | GCCCAAACCAGAGACCTCAACGCCATCGCACAG | 7592 | AQTRDLNAIAQ | 12181 | TRDLNAI | 0.263161 | -0.06205 |
| SyS1222 | 3004 | GCCCAAACCGACGCCAGCAGCCCCTTCGCACAG | 7593 | AQTDASSPFAQ | 12182 | TDASSPF | 0.263114 | -0.20224 |
| SyS1223 | 3005 | GCCCAAGCTGATCAGAGGACCGGAAGGCACAG | 7594 | AQADQRQPKAQ | 12183 | ADQRQPK | 0.263076 | -0.0037 |
| SyS1224 | 3006 | GCCCAAGCCGTCAACCCAACTACGCCGCACAG | 7595 | AQAVNPNYAAQ | 12184 | AVNPNYA | 0.262974 | -0.0907 |
| SyS1225 | 3007 | GCCCAACTGACTGCGTCTACGAATGTTCGGGCACAG | 7596 | AQLTATNVRAQ | 12185 | LTATNVR | 0.262845 | 0.030087 |
| SyS1226 | 3008 | GCCCAATTGACTGCGTCTACTTATTCGGCACAG | 7597 | AQLTASTYSAQ | 12186 | LTASTYS | 0.262777 | -0.16344 |
| SyS1227 | 3009 | GCCCAAGGGTGCGTGATAATTCTGTGGCACAG | 7598 | AQGSRDNSVAQ | 12187 | GSRDNSV | 0.262777 | -0.21921 |
| SyS1228 | 3010 | GCCCAAACTGATACTCAGAATCGGCTTGCACAG | 7599 | AQTDTQNRLAQ | 12188 | TDTQNRL | 0.262725 | -0.15534 |
| GS676 | 3011 | GCCCAAAATAGTACGGTTAATACGGGTGCACAG | 7600 | AQNSTVNTGAQ | 12189 | NSTVNTG | 0.262505 | -0.14811 |
| SyS1229 | 3012 | GCCCAATTGTCTCATGCGATGCGTTCTGCACAG | 7601 | AQLSHAMRSAQ | 12190 | LSHAMRS | 0.262482 | -0.18042 |
| SyS1230 | 3013 | GCCCAACGGCTGCCGATGACTACTATGGCACAG | 7602 | AQRLPMTTMAQ | 12191 | RLPMTTM | 0.262441 | -0.04775 |
| SyS1231 | 3014 | GCCCAACTCTACCACGAAAGCCAAACGCGCACAG | 7603 | AQLYHESQTAQ | 12192 | LYHESQT | 0.262338 | -0.18614 |
| SyS1232 | 3015 | GCCCAAATTTTGCATCAGAGTTCGACTGCACAG | 7604 | AQILHQSSTAQ | 12193 | ILHQSST | 0.262234 | 0.103448 |
| GS677 | 3016 | GCCCAAACCAGCTTCGCCACCCAAACCGCACAG | 7605 | AQTSLATQTAQ | 12194 | TSLATQT | 0.262228 | -0.11907 |
| GS678 | 3017 | GCCCAAAGAACCCCACCCTCACCGTCGCACAG | 7606 | AQRTPTLTVAQ | 12195 | RTPTLTV | 0.262188 | -0.1338 |

FIG. 33 (Continued)

| | | | | | | | |
|---|---|---|---|---|---|---|---|
| GS679 | 3018 | GCCCAAGCTACGCGCGTGAGAGTCGTACGGCACAG | 7607 | AQATRESRTAQ | 12196 | ATRESRT | 0.262188 | -0.1338 |
| SyS1233 | 3019 | GCCCAATTGTCTGAGAGTCTGCGGATTGCACAG | 7608 | AQLSESLRIAQ | 12197 | LSESLRI | 0.262085 | -0.13071 |
| SyS1234 | 3020 | GCCCAAAGGCGTCACCGGCGGCATGGTCGCACAG | 7609 | AQSVTGGMVAQ | 12198 | SVTGGMV | 0.261982 | 0.275265 |
| SyS1235 | 3021 | GCCCAACCCAGAACCAGCAGCGACAGCAACGCACAG | 7610 | AQPRTSDSNAQ | 12199 | PRTSDSN | 0.261751 | 0.100471 |
| GS680 | 3022 | GCCCAAGTTCATTCTACGGTTACGTCGGCACAG | 7611 | AQVHSTVTSAQ | 12200 | VHSTVTS | 0.261737 | -0.09477 |
| SyS1236 | 3023 | GCCCAAGGCACCACAACATGAACCACCTGCACAG | 7612 | AQGTNMNHLAQ | 12201 | GTNMNHL | 0.261685 | -0.07009 |
| SyS1237 | 3024 | GCCCAAATGAAGGCTGAGTTGTATGGCGGCACAG | 7613 | AQMKAELYAAQ | 12202 | MKAELYA | 0.261535 | -0.02039 |
| GS681 | 3025 | GCCCAACTCAGAAGCCCAGCGTCGACGCACAG | 7614 | AQLRSPSVDAQ | 12203 | LRSPSVD | 0.261426 | 0.021615 |
| SyS1238 | 3026 | GCCCAAACCAACAGCCCCAATTCCCGCACAG | 7615 | AQTNSPQFPAQ | 12204 | TNSPQFP | 0.261388 | 0.019965 |
| TS158 | 3027 | GCCCAAAATAATTCGCTTAGGTCGAATGCACAG | 7616 | AQNNSLRSNAQ | 12205 | NNSLRSN | 0.261381 | -0.10273 |
| GS682 | 3028 | GCCCAAGACAGCCACATGGGCAAATACGCACAG | 7617 | AQDSHMGKYAQ | 12206 | DSHMGKY | 0.261318 | -0.11556 |
| SyS1239 | 3029 | GCCCAAGTTAATTCGATGACGCCGGGCACAG | 7618 | AQVNSMTPRAQ | 12207 | VNSMTPR | 0.261313 | 0.013095 |
| SyS1240 | 3030 | GCCCAACTCGCCCCCATCAGCCTCAACGCACAG | 7619 | AQLAPISLNAQ | 12208 | LAPISLN | 0.261307 | -0.03736 |
| SyS1241 | 3031 | GCCCAAAATATGCCGAGTATTATGCAGGCACAG | 7620 | AQNMPSIMQAQ | 12209 | NMPSIMQ | 0.261198 | -0.19254 |
| TS159 | 3032 | GCCCAAGGGAATATGATTAAGGTGGCGGCACAG | 7621 | AQGNMIKVAAQ | 12210 | GNMIKVA | 0.261132 | -0.28624 |
| SyS1242 | 3033 | GCCCAAACCGGCGTCAGCCTCCAAGTCGCACAG | 7622 | AQTGVSLQVAQ | 12211 | TGVSLQV | 0.261129 | -0.23133 |
| SyS1243 | 3034 | GCCCAACCTCAGTTTAATACTGCGCTCGGCACAG | 7623 | AQPQFNTASAQ | 12212 | PQFNTAS | 0.261076 | -0.14283 |
| SyS1244 | 3035 | GCCCAAACGGAGGCGTATAGGAATACTGCACAG | 7624 | AQTEAYRNTAQ | 12213 | TEAYRNT | 0.261 | -0.18163 |
| SyS1245 | 3036 | GCCCAACTTATGAAGGCTGATACTGTGGCACAG | 7625 | AQLMKADTVAQ | 12214 | LMKADTV | 0.260947 | -0.04342 |
| GS683 | 3037 | GCCCAAAATCATAAGGAGTTTATGCTTGCACAG | 7626 | AQNHKEFMLAQ | 12215 | NHKEFML | 0.260914 | -0.14906 |
| GS684 | 3038 | GCCCAATTGAATGGCGACTTTGACTGTGGCACAG | 7627 | AQLNGTLTVAQ | 12216 | LNGTLTV | 0.26088 | -0.1462 |
| GS686 | 3039 | GCCCAAACTGCGAAGATTTTGACGATGGCACAG | 7628 | AQTAKILTMAQ | 12217 | TAKILTM | 0.260811 | -0.17112 |
| SyS1246 | 3040 | GCCCAACTCAGAGACAGCCTCCCGTCGCACAG | 7629 | AQLRDSLPVAQ | 12218 | LRDSLPV | 0.260626 | 0.104246 |
| SyS1247 | 3041 | GCCCAACTCAAAGGCGGCGACAGCTGGGCACAG | 7630 | AQLKGGDSWAQ | 12219 | LKGGDSW | 0.260615 | -0.12208 |
| GS687 | 3042 | GCCCAAAAAACCGTCGACATCATGGGCGCACAG | 7631 | AQKTVDIMGAQ | 12220 | KTVDIMG | 0.260533 | -0.09485 |
| GS688 | 3043 | GCCCAACTCAACATGGGCAAATGAAAGCACAG | 7632 | AQLNMGQMKAQ | 12221 | LNMGQMK | 0.260458 | -0.09755 |
| SyS1248 | 3044 | GCCCAAAGCGTCCCCAGCCTCGACAGAGCACAG | 7633 | AQSVPSLDRAQ | 12222 | SVPSLDR | 0.260448 | -0.05185 |
| SyS1249 | 3045 | GCCCAACAGCTGTTGGGGACGAGTAAGGCACAG | 7634 | AQQLLGTSKAQ | 12223 | QLLGTSK | 0.260344 | -0.23296 |
| SyS1250 | 3046 | GCCCAAATGAATCCTAAGCATGGTCTGGCACAG | 7635 | AQMNPKHGLAQ | 12224 | MNPKHGL | 0.260327 | -0.18769 |
| SyS1251 | 3047 | GCCCAATCTCCGGAGGGTTCTCTGAAGGCACAG | 7636 | AQSPEGSLKAQ | 12225 | SPEGSLK | 0.260327 | -0.18769 |
| SyS1252 | 3048 | GCCCAAGCGAATATGCCGAATTCTGGGCACAG | 7637 | AQANMPNSRAQ | 12226 | ANMPNSR | 0.260318 | -0.08035 |
| SyS1253 | 3049 | GCCCAAGCCTACATCAGCAGCGGCGTCGCACAG | 7638 | AQAYISSGVAQ | 12227 | AYISSGV | 0.260028 | -0.08758 |

FIG. 33 (Continued)

| | | | | | | | | |
|---|---|---|---|---|---|---|---|---|
| GS690 | 3050 | GCCCAAGAGAAAGAGGGCAGCCAAGCCAAGCCAAGCCACAG | 7639 | AQERGSQANAQ | 12228 | ERGSQAN | 0.260015 | -0.16304 |
| GS691 | 3051 | GCCCAAGGTCATGATAGGCTGAGTCCGGCACAG | 7640 | AQGHDRLSPAQ | 12229 | GHDRLSP | 0.259905 | -0.06434 |
| GS692 | 3052 | GCCCAAACGAGTAATGTGACTGGTACTGCACAG | 7641 | AQTSNVTGTAQ | 12230 | TSNVTGT | 0.259758 | -0.10244 |
| GS693 | 3053 | GCCCAACTCACCCACCACGTCGGCGTCGCACAG | 7642 | AQLTHNVGVAQ | 12231 | LTHNVGV | 0.259654 | -0.0842 |
| GS694 | 3054 | GCCCAAGGGAGGAGGATGGGGTGGCTAAGGCACAG | 7643 | AQREDGVAKAQ | 12232 | REDGVAK | 0.2595 | -0.1774 |
| SyS1254 | 3055 | GCCCAACCCGCGACGGCTACAAACTCGCACAG | 7644 | AQPADGYKLAQ | 12233 | PADGYKL | 0.259383 | 0.021493 |
| GS697 | 3056 | GCCCAACAACTCGACGCGCCACCAGAGCCGCACAG | 7645 | AQQLDATRAAQ | 12234 | QLDATRA | 0.259246 | -0.02679 |
| GS698 | 3057 | GCCCAAGTGACTGGTATGACGACTCGTGCACAG | 7646 | AQVTGMTTRAQ | 12235 | VTGMTTR | 0.259241 | -0.1747 |
| SyS1255 | 3058 | GCCCAATCGGATAGTCGGACGTATGAGGCACAG | 7647 | AQSDSRTYEAQ | 12236 | SDSRTYE | 0.25915 | -0.12829 |
| SyS1259 | 3059 | GCCCAAGTTGAGCCGCTGAAGCCGGATGCACAG | 7648 | AQVEPLKPDAQ | 12237 | VEPLKPD | 0.258734 | -0.17799 |
| SyS1260 | 3060 | GCCCAAGGCGTCCTCGCCAGCAACAGAGCACAG | 7649 | AQGVLASNRAQ | 12238 | GVLASNR | 0.258676 | -0.15411 |
| SyS1262 | 3061 | GCCCAAATGGGCGAAAGAATGAGCATCGCACAG | 7650 | AQMGERMSIAQ | 12239 | MGERMSI | 0.258443 | -0.05797 |
| SyS1263 | 3062 | GCCCAATTTACGAAGACTGAGGATTTGGCACAG | 7651 | AQFTKTEDLAQ | 12240 | FTKTEDL | 0.258323 | -0.0551 |
| SyS1264 | 3063 | GCCCAAGTCAAAAACACCGAACTCCTCGCACAG | 7652 | AQVKNTELLAQ | 12241 | VKNTELL | 0.258283 | 0.073327 |
| GS700 | 3064 | GCCCAAACTGTTACGAGTACGGTGGTGGCACAG | 7653 | AQTVTSTVVAQ | 12242 | TVTSTVV | 0.258274 | -0.18637 |
| SyS1267 | 3065 | GCCCAAGCCAAATACGGCGACCCCACCGCACAG | 7654 | AQAKYGDPTAQ | 12243 | AKYGDPT | 0.257892 | 0.222899 |
| GS701 | 3066 | GCCCAAACCAGCGACAGACTCCTCGGCGCACAG | 7655 | AQTSDRLLGAQ | 12244 | TSDRLLG | 0.257859 | -0.13666 |
| GS702 | 3067 | GCCCAAGTCGTTGGGAATACTAAGATGGCACAG | 7656 | AQAVGNTKMAQ | 12245 | AVGNTKM | 0.25783 | -0.13952 |
| GS704 | 3068 | GCCCACCAACAGACGTATAATAAGATGGATGCACAG | 7657 | AQQTYNKMDAQ | 12246 | QTYNKMD | 0.257666 | -0.05596 |
| GS706 | 3069 | GCCCAAGCGTGGGCTAGTCAGTCTTCGGCACAG | 7658 | AQAWASQSSAQ | 12247 | AWASQSS | 0.25724 | -0.14779 |
| SyS1269 | 3070 | GCCCAAAATGCGTTTCTTACTGGTGGGGCACAG | 7659 | AQNAFLTGGAQ | 12248 | NAFLTGG | 0.257171 | -0.20103 |
| SyS1270 | 3071 | GCCCAAAGCATCGGGCAGACAAATACACCGCACAG | 7660 | AQSIGDKYTAQ | 12249 | SIGDKYT | 0.257047 | -0.09127 |
| GS707 | 3072 | GCCCAATCGAATCATCATCATACTGGGGCACAG | 7661 | AQSNHHHTGAQ | 12250 | SNHHHTG | 0.256757 | -0.11758 |
| GS708 | 3073 | GCCCAAATCACCAACAAACCCATGACCGCACAG | 7662 | AQITNKPMTAQ | 12251 | ITNKPMT | 0.256656 | -0.13702 |
| SS84 | 3074 | GCCCAACTCAGCGGCCAAGTCAGCAACGCACAG | 7663 | AQLSGQVSNAQ | 12252 | LSGQVSN | 0.256425 | -0.35654 |
| GS709 | 3075 | GCCCAAAATAGTATGTCGGGGCATTTGGCACAG | 7664 | AQNSMSGHLAQ | 12253 | NSMSGHL | 0.256275 | -0.14334 |
| SyS1271 | 3076 | GCCCAACCTGCGGTGCATGGTTATGCTGCACAG | 7665 | AQPAVHGYAAQ | 12254 | PAVHGYA | 0.256274 | -0.20709 |
| GS710 | 3077 | GCCCAACTCATGAGAACCAAACAACACCGCACAG | 7666 | AQLMRTKQPAQ | 12255 | LMRTKQP | 0.256142 | -0.14906 |
| SyS1272 | 3078 | GCCCAAGCAGCCTCGCCGTCAACAAAGCACAG | 7667 | AQSSLAVNKAQ | 12256 | SSLAVNK | 0.256141 | -0.07737 |
| SyS1273 | 3079 | GCCCAAAATACGCAGTCGGAGCCTCGTGCACAG | 7668 | AQNTQSEPRAQ | 12257 | NTQSEPR | 0.2561 | 0.127962 |
| SyS1275 | 3080 | GCCCAAGATCATCTGGTTAGTGTTCCTGCACAG | 7669 | AQDHLVSVPAQ | 12258 | DHLVSVP | 0.256044 | -0.19107 |
| SyS1276 | 3081 | GCCCAATGGGCCACCAGCACCCACGACGCACAG | 7670 | AQWATSTHDAQ | 12259 | WATSTHD | 0.256044 | -0.18121 |

FIG. 33 (Continued)

| | | | | | | | | |
|---|---|---|---|---|---|---|---|---|
| SyS1277 | 3082 | GCCCAACCCCAACAACAACCATCGGGCACAG | 7671 | AQPQQQPIGAQ | 12260 | PQQQPIG | 0.256044 | -0.21571 |
| SyS1278 | 3083 | GCCCAAAGCCTCAGCAGCACCCACAGCGACGCACAG | 7672 | AQSLSTHSDAQ | 12261 | SLSTHSD | 0.255878 | -0.0507 |
| SyS1279 | 3084 | GCCCAAGGCAGCATGGCCGCCAGAAGCGCACAG | 7673 | AQGSMAARSAQ | 12262 | GSMAARS | 0.2558 | -0.12101 |
| GS711 | 3085 | GCCCAAGCCCCGGCATGACCGCCAGAGCACAG | 7674 | AQAPGMTARAQ | 12263 | APGMTAR | 0.255662 | -0.16623 |
| SyS1280 | 3086 | GCCCAAGTCCTGCCAACATGACCGCCGCACAG | 7675 | AQVLANMTAAQ | 12264 | VLANMTA | 0.255612 | 0.070331 |
| SyS1281 | 3087 | GCCCAACTCACCAAACAAGAGAAGCGCCGCACAG | 7676 | AQLTKQESAAQ | 12265 | LTKQESA | 0.255528 | -0.09434 |
| SyS1282 | 3088 | GCCCAAGGCGCCAACAGCGGCGGCGTCGCACAG | 7677 | AQGANSGGVAQ | 12266 | GANSGGV | 0.255503 | 0.080739 |
| SyS1283 | 3089 | GCCCAACAGAGTGAGCCGAAGCGTCCTGCACAG | 7678 | AQQSEPKRPAQ | 12267 | QSEPKRP | 0.255307 | -0.11616 |
| SyS1284 | 3090 | GCCCAAGTCCACGGCGAAAGAAGCGTCGCACAG | 7679 | AQVHGERSVAQ | 12268 | VHGERSV | 0.255229 | 0.018407 |
| SyS1285 | 3091 | GCCCAAGGCCATCAGACTGCTGCTTTCTGCACAG | 7680 | AQAHQTAASAQ | 12269 | AHQTAAS | 0.255147 | -0.17557 |
| GP133 | 3092 | GCCCAAGTTCGGGAGGATGCAGACGGCGGGCACAG | 7681 | AQVREMQTAAQ | 12270 | VREMQTA | 0.255121 | -0.07329 |
| GS713 | 3093 | GCCCAAGTCGCCCCCAGCGCCCTCCACGCACAG | 7682 | AQVAPSALHAQ | 12271 | VAPSALH | 0.255035 | -0.16842 |
| SyS1286 | 3094 | GCCCAAAGTGTTGGTCATCATAATATGGCACAG | 7683 | AQSVGHHNMAQ | 12272 | SVGHHNM | 0.254967 | -0.18648 |
| SyS1287 | 3095 | GCCCAATTCCTCACCCAAGGCGACGTCGCACAG | 7684 | AQFLTQGDVAQ | 12273 | FLTQGDV | 0.254933 | -0.11838 |
| SyS1288 | 3096 | GCCCAATTCAGCACCCAATTCCAACACGCACAG | 7685 | AQFSTQFQHAQ | 12274 | FSTQFQH | 0.254806 | -0.14302 |
| GP134 | 3097 | GCCCAACAGAATACGACGCGGTCGAATGCACAG | 7686 | AQQNTTRSNAQ | 12275 | QNTTRSN | 0.254756 | 0.347693 |
| SyS1289 | 3098 | GCCCAACCCGCCGTCACCAGCATCGCCGCACAG | 7687 | AQPAVTSIAAQ | 12276 | PAVTSIA | 0.254579 | -0.07092 |
| SyS1290 | 3099 | GCCCAAGGCCAGCACCAACAACTACGTCGCACAG | 7688 | AQASTNTYVAQ | 12277 | ASTNTYV | 0.254465 | 0.185493 |
| SyS1291 | 3100 | GCCCAATCGACGGCTACGCCTACGTCGGCACAG | 7689 | AQSTATPTSAQ | 12278 | STATPTS | 0.254392 | -0.19723 |
| GS714 | 3101 | GCCCAACATTTAATAGGACGTCGCCTGCACAG | 7690 | AQHFNRTSPAQ | 12279 | HFNRTSP | 0.254355 | -0.04208 |
| SyS1294 | 3102 | GCCCAAAGCGTCGCCGGCATGCTCCCCGCACAG | 7691 | AQSVAGMLPAQ | 12280 | SVAGMLP | 0.254355 | -0.14405 |
| SyS1295 | 3103 | GCCCAACCTATGAGTTCTGAGAGTAGTGCACAG | 7692 | AQPMSSESSAQ | 12281 | PMSSESS | 0.25434 | -0.20216 |
| SyS1296 | 3104 | GCCCAAAGCCTCGCCCAGCACCACCGTCGCACAG | 7693 | AQSLASTTVAQ | 12282 | SLASTTV | 0.254318 | -0.00463 |
| SyS1297 | 3105 | GCCCAAACTTCTACTCCTGCTCAGGTTGCACAG | 7694 | AQTSTPAQVAQ | 12283 | TSTPAQV | 0.254198 | 0.05736 |
| SyS1298 | 3106 | GCCCAAAGTCTGACGCGGCGCAGCCTGCACAG | 7695 | AQSLTAQQPAQ | 12284 | SLTAQQP | 0.254112 | -0.01576 |
| GS715 | 3107 | GCCCAAAGTGGTCGTGTGCCTGTGGCTGCACAG | 7696 | AQSGRVPVAAQ | 12285 | SGRVPVA | 0.254016 | -0.18816 |
| GS716 | 3108 | GCCCAACTCGACGCCGCCAAAAGCCTCGCACAG | 7697 | AQLDAAKSLAQ | 12286 | LDAAKSL | 0.253973 | -0.14151 |
| GS717 | 3109 | GCCCAAAACTTCGCCAACAAAAACGTCGCACAG | 7698 | AQNFANKNVAQ | 12287 | NFANKNV | 0.25395 | 0.011201 |
| GS718 | 3110 | GCCCAAGGCCCCGGCCCAGCGTCACCCCGCCACAG | 7699 | AQGPASVTPAQ | 12288 | GPASVTP | 0.253945 | -0.05651 |
| SyS1299 | 3111 | GCCCAATATTCTCGGGAGGCGACGAATGCACAG | 7700 | AQYSREATNAQ | 12289 | YSREATN | 0.253828 | 0.015982 |
| SyS1300 | 3112 | GCCCAAACCGGCAGCAGCTTCGCCATGGCACAG | 7701 | AQTGSSFAMAQ | 12290 | TGSSFAM | 0.25367 | -0.1344 |
| SyS1301 | 3113 | GCCCAAGGGATTAAGGGGGATCCGGTTGCACAG | 7702 | AQGIKGDPVAQ | 12291 | GIKGDPV | 0.253653 | -0.05918 |

FIG. 33 (Continued)

| | | | | | | | |
|---|---|---|---|---|---|---|---|
| SyS1302 | 3114 | GCCCAAGTCACCAGCACCAGCACGCCGCACAG | 7703 | AQVTSTSHAAQ | 12292 | VTSTSHA | 0.253643 | 0.149339 |
| SyS1303 | 3115 | GCCCAAACCAGCCAAAACAACCTCAGAGCACAG | 7704 | AQTSQNNIRAQ | 12293 | TSQNNIR | 0.253347 | -0.04388 |
| GS719 | 3116 | GCCCAAATGAGACAAGAGGGCTCAGGCACAG | 7705 | AQMRQEGLSAQ | 12294 | MRQEGLS | 0.253321 | -0.14238 |
| SyS1304 | 3117 | GCCCAACTCAACCTCAACGCCATCGCCGCACAG | 7706 | AQLNLNAIAAQ | 12295 | LNLNAIA | 0.253187 | -0.10853 |
| SyS1305 | 3118 | GCCCAAGTAAGAATGAGGGGCCTACTGCACAG | 7707 | AQSKNEGPTAQ | 12296 | SKNEGPT | 0.253158 | -0.05578 |
| SyS1306 | 3119 | GCCCAAGATTCTCGTTCTACGACTAATGCACAG | 7708 | AQDSRSTTNAQ | 12297 | DSRSTTN | 0.252881 | 0.072962 |
| SyS1307 | 3120 | GCCCAAAGCACCGGCGACGCCCTCAGAGCACAG | 7709 | AQSTGDALRAQ | 12298 | STGDALR | 0.252785 | 0.062357 |
| SyS1308 | 3121 | GCCCAAATTAATAAGCCTGGTACGCCTGCACAG | 7710 | AQINKPGTPAQ | 12299 | INKPGTP | 0.25278 | 0.014889 |
| SyS1309 | 3122 | GCCCAAGTTTCGGCTCCTTGAATATTGCACAG | 7711 | AQVSAPLNIAQ | 12300 | VSAPLNI | 0.252695 | -0.23618 |
| GP135 | 3123 | GCCCAAGTTTCTTGGGTTCGCTTGCGGCACAG | 7712 | AQVSLGSLAAQ | 12301 | VSLGSLA | 0.252596 | 0.083569 |
| SyS1310 | 3124 | GCCCAACTCAACCACATCAACGAAAAAGCACAG | 7713 | AQLNHINEKAQ | 12302 | LNHINEK | 0.252494 | -0.00166 |
| SyS1311 | 3125 | GCCCAAAAGTCGGTGACGATTCTTTCGGCACAG | 7714 | AQKSVTILSAQ | 12303 | KSVTILS | 0.252487 | -0.19375 |
| GS722 | 3126 | GCCCAATCTAATGTGTCGTCGCTTGTTGCACAG | 7715 | AQSNVSSLVAQ | 12304 | SNVSSLV | 0.252289 | -0.12894 |
| GS723 | 3127 | GCCCAATTTTCGCAGACTGTTGGGGGGGCACAG | 7716 | AQFSQTVGGAQ | 12305 | FSQTVGG | 0.252132 | -0.0379 |
| GS724 | 3128 | GCCCAACGTCCGTCTATTACGCATGATGCACAG | 7717 | AQRPSITHDAQ | 12306 | RPSITHD | 0.252097 | -0.13761 |
| SyS1314 | 3129 | GCCCAAAGACAAGAAAGCACCACCCTCGCACAG | 7718 | AQRQESTTLAQ | 12307 | RQESTTL | 0.252004 | -0.07737 |
| SyS1315 | 3130 | GCCCAAGGGCCTTATGTGACTCCTCAGGCACAG | 7719 | AQGPYVTPQAQ | 12308 | GPYVTPQ | 0.251887 | 0.023256 |
| SyS1316 | 3131 | GCCCAAAACGGCCTCGTCACCACGCGCGCACAG | 7720 | AQNGLVTTAAQ | 12309 | NGLVTTA | 0.251887 | -0.01918 |
| SyS1317 | 3132 | GCCCAACACGCCGGCAACGTCCCCGGCGCACAG | 7721 | AQHAGNVPGAQ | 12310 | HAGNVPG | 0.251887 | -0.1889 |
| SyS1318 | 3133 | GCCCAACCCATGGGCAACAACCTCGTCGCACAG | 7722 | AQPMGNNLVAQ | 12311 | PMGNNLV | 0.251827 | -0.23296 |
| SyS1319 | 3134 | GCCCAAGTCTACAACGACAGAAGCCACGCACAG | 7723 | AQVYNDRSHAQ | 12312 | VYNDRSH | 0.251746 | -0.03526 |
| GS725 | 3135 | GCCCAAACCCACAAAGAAAGCGGGTACGCACAG | 7724 | AQTHKESGYAQ | 12313 | THKESGY | 0.251703 | -0.06465 |
| SyS1320 | 3136 | GCCCAAGGCATGAACAGCGTTCTCCTCGCACAG | 7725 | AQGMNSVLLAQ | 12314 | GMNSVLL | 0.25156 | -0.15738 |
| GS726 | 3137 | GCCCAATACCTCGAAAACCAATACAGCGCACAG | 7726 | AQYLENQYSAQ | 12315 | YLENQYS | 0.251521 | -0.17291 |
| GP137 | 3138 | GCCCAATCTATTACGTCGAGGCCTAATGCACAG | 7727 | AQSITSRPNAQ | 12316 | SITSRPN | 0.251405 | -0.02611 |
| GS727 | 3139 | GCCCAAAGCCACCAAAAACACCGCCAGAGCACAG | 7728 | AQSHQNTARAQ | 12317 | SHQNTAR | 0.251208 | -0.15138 |
| GS728 | 3140 | GCCCAACGTTTGGTTCAGTCTGCGGAGGCACAG | 7729 | AQRLVQSAEAQ | 12318 | RLVQSAE | 0.251117 | -0.12998 |
| SyS1321 | 3141 | GCCCAATACCCCAAAAGCGCCACCAACGCACAG | 7730 | AQYPKSATNAQ | 12319 | YPKSATN | 0.250939 | -0.04706 |
| SyS1322 | 3142 | GCCCAAATTAATTCTTCTCCGCCGCTGGCACAG | 7731 | AQINSSPPLAQ | 12320 | INSSPPL | 0.250894 | -0.20462 |
| GS729 | 3143 | GCCCAAACTCAGAATCTGGCGGGTGGTGCACAG | 7732 | AQTQNLAGGAQ | 12321 | TQNLAGG | 0.250713 | -0.13682 |
| SyS1323 | 3144 | GCCCAATTTCCAAGTCGCGCCAAAGACAGAGCACAG | 7733 | AQFQVAKDRAQ | 12322 | FQVAKDR | 0.250692 | 0.020536 |
| GS731 | 3145 | GCCCAACGGCTGAGTGGTAATCAGAATGCACAG | 7734 | AQRLSGNQNAQ | 12323 | RLSGNQN | 0.250664 | 0.025382 |

FIG. 33 (Continued)

| SyS1324 | 3146 | GCCCAAACTACGGATCGGGTGTCGCATGCACAG | 7735 | AQTTDRVSHAQ | 12324 | TTDRVSH | 0.250526 | 0.007999 |
|---|---|---|---|---|---|---|---|---|
| SyS1325 | 3147 | GCCCAAACTGCTACTGTGACGGCTCGGGCACAG | 7736 | AQTATVTARAQ | 12325 | TATVTAR | 0.250464 | -0.16039 |
| SyS1326 | 3148 | GCCCAACTCAGCATGATGAGGCGACAAAGCACAG | 7737 | AQLSMMSDKAQ | 12326 | LSMMSDK | 0.250432 | -0.15808 |
| GS733 | 3149 | GCCCAAACTCTGATTCAGACTAGTCCGGCACAG | 7738 | AQTLIQTSPAQ | 12327 | TLIQTSP | 0.250263 | -0.14429 |
| SyS1327 | 3150 | GCCCAACCGATGCATATTACGAATGCTGCACAG | 7739 | AQPMHITNAAQ | 12328 | PMHITNA | 0.250148 | -0.22434 |
| GS734 | 3151 | GCCCAAACCGTCGGCCAACCGCCCACGCACAG | 7740 | AQTVGQPAHAQ | 12329 | TVGQPAH | 0.25007 | -0.08134 |
| SyS1328 | 3152 | GCCCAAGAAGACAAAGACGTCAGACTCGCACAG | 7741 | AQEDKDVRLAQ | 12330 | EDKDVRL | 0.249926 | -0.22926 |
| GS735 | 3153 | GCCCAAATGAAGGTTGCGCAGCCTATGGCACAG | 7742 | AQMKVAQPMAQ | 12331 | MKVAQPM | 0.249854 | -0.12039 |
| SyS1329 | 3154 | GCCCAAGTGGGGGTGCCTAATCTGCCGGCACAG | 7743 | AQVGVPNLPAQ | 12332 | VGVPNLP | 0.24985 | -0.07803 |
| SyS1330 | 3155 | GCCCAAGGCGCCGCTGAGTAGTGATCCGGCACAG | 7744 | AQAPLSSDPAQ | 12333 | APLSSDP | 0.249809 | -0.13798 |
| GS737 | 3156 | GCCCAATTCCTCCACGCGTCGACGCGCACAG | 7745 | AQFLHASVDAQ | 12334 | FLHASVD | 0.249673 | -0.17919 |
| GS738 | 3157 | GCCCAACCTACTGTGGGGACGTATATTGCACAG | 7746 | AQPTVGTYIAQ | 12335 | PTVGTYI | 0.249673 | -0.1765 |
| GS739 | 3158 | GCCCAAGAGCCTCTGCATAGGAATTCTGCACAG | 7747 | AQEPLHRNSAQ | 12336 | EPLHRNS | 0.249673 | -0.1442 |
| GS740 | 3159 | GCCCAAGCCAGCACCGTCACCGTCGAAGCACAG | 7748 | AQASTVTVEAQ | 12337 | ASTVTVE | 0.249673 | -0.18727 |
| GS741 | 3160 | GCCCAAGCCCCAGAATCGACAACGCCGCACAG | 7749 | AQAPRIDNAAQ | 12338 | APRIDNA | 0.249673 | -0.05537 |
| GS744 | 3161 | GCCCAAATATCGTGATTCGGCTGCTCCTGCACAG | 7750 | AQYRDSAAPAQ | 12339 | YRDSAAP | 0.249343 | -0.13666 |
| SyS1332 | 3162 | GCCCAACTCACCCAAAACGCCAGCGTGCACAG | 7751 | AQLTQNASVAQ | 12340 | LTQNASV | 0.249317 | -0.0022 |
| SyS1335 | 3163 | GCCCAATTGAGTGCTCGTTTGACGACTGCACAG | 7752 | AQLSARLTTAQ | 12341 | LSARLTT | 0.24914 | -0.09677 |
| SS87 | 3164 | GCCCAAAACGGCAAAAGCAGCGACAAAGCACAG | 7753 | AQNGKSSDKAQ | 12342 | NGKSSDK | 0.249118 | -0.28649 |
| SyS1336 | 3165 | GCCCAAGCGCTGGTGAAGGATACTACTGCACAG | 7754 | AQALVKDTTAQ | 12343 | ALVKDTT | 0.248993 | -0.14405 |
| SyS1337 | 3166 | GCCCAAATGCTCGTCACCACCGGCGAAGCACAG | 7755 | AQMLVTTGEAQ | 12344 | MLVTTGE | 0.248845 | -0.13932 |
| SyS1338 | 3167 | GCCCAAGGCGGCAACCCAGCTACGCCGCACAG | 7756 | AQSGNPSYAAQ | 12345 | SGNPSYA | 0.248803 | -0.02317 |
| SyS1339 | 3168 | GCCCAAGTCATCACCGGCGGCATGAGCGCACAG | 7757 | AQVITGGMSAQ | 12346 | VITGGMS | 0.248801 | 0.075387 |
| SyS1340 | 3169 | GCCCAACTCGAACCCAACGTCCAAACCGCACAG | 7758 | AQLEPNVQTAQ | 12347 | LEPNVQT | 0.248763 | -0.19133 |
| SyS1341 | 3170 | GCCCAAAGATTCAGCGAAGTCACCCCCGCACAG | 7759 | AQRFSEVTPAQ | 12348 | RFSEVTP | 0.248692 | 0.100649 |
| GS745 | 3171 | GCCCAAGATCCGGGGAAGGCGAGTCTGGCACAG | 7760 | AQDPGKASLAQ | 12349 | DPGKASL | 0.248503 | -0.07157 |
| SyS1343 | 3172 | GCCCAAATCGCCCACGAAAGCACCGACGCACAG | 7761 | AQIAHESTDAQ | 12350 | IAHESTD | 0.248487 | -0.15595 |
| GS748 | 3173 | GCCCAATATCCTAGTAATTCTATGCATGCACAG | 7762 | AQYPSNSMHAQ | 12351 | YPSNSMH | 0.248436 | -0.05512 |
| SyS1345 | 3174 | GCCCAAGAGCACCACCCCCCAGCGGCGCACAG | 7763 | AQSTTPPSGAQ | 12352 | STTPPSG | 0.248285 | -0.18648 |
| SyS1346 | 3175 | GCCCAAGTTGAGCAGAATTCTAAGAATGCACAG | 7764 | AQVEQNSKNAQ | 12353 | VEQNSKN | 0.248285 | -0.18648 |
| GS749 | 3176 | GCCCAAAACGATTGCGGGTCGGCTTGTGTGGCACAG | 7765 | AQTIAGRLVAQ | 12354 | TIAGRLV | 0.248255 | -0.15097 |
| GS750 | 3177 | GCCCAAGCTAGGCATACGGGGTGAGATGGCACAG | 7766 | AQARHTGEMAQ | 12355 | ARHTGEM | 0.24798 | -0.11854 |

FIG. 33 (Continued)

| | | | | | | | | |
|---|---|---|---|---|---|---|---|---|
| GS751 | 3178 | GCCCAACAGCATCTGCCGAATCATATTGCACAG | 7767 | AQQHLPNHIAQ | 12356 | QHLPNHI | 0.2479 | -0.16932 |
| GS752 | 3179 | GCCCAAACTACTATGGGGACTTATCCTGCACAG | 7768 | AQTTMGTYPAQ | 12357 | TTMGTYP | 0.247856 | -0.17201 |
| SyS1347 | 3180 | GCCCAAACCGAAAGCGTCATGCCCAGAGCACAG | 7769 | AQTESVMPRAQ | 12358 | TESVMPR | 0.247776 | -0.09369 |
| SyS1348 | 3181 | GCCCAAGGCGCCAAACCCAGCAACGACGCACAG | 7770 | AQGAKPSNDAQ | 12359 | GAKPSND | 0.247643 | 0.125092 |
| SyS1349 | 3182 | GCCCAAGCCGTCAGCAGCGACATGAGCGCACAG | 7771 | AQAVSSDMSAQ | 12360 | AVSSDMS | 0.2476 | -0.16102 |
| SyS1350 | 3183 | GCCCAACACAGCCCCCAACTCGGCGGCGCACAG | 7772 | AQHSPQLGGAQ | 12361 | HSPQLGG | 0.247571 | -0.12465 |
| SyS1351 | 3184 | GCCCAATTGTATACTAATCCTAATACTGCACAG | 7773 | AQLYTNPNTAQ | 12362 | LYTNPNT | 0.247527 | -0.17382 |
| SyS1352 | 3185 | GCCCAAACCGTCGCCCTCAACATGGCCGCACAG | 7774 | AQTVALNMAAQ | 12363 | TVALNMA | 0.247496 | -0.02465 |
| GS754 | 3186 | GCCCAACAGCGGGTTCCTGCTTATCAGGCACAG | 7775 | AQQRVPAYQAQ | 12364 | QRVPAYQ | 0.247403 | -0.14564 |
| SyS1353 | 3187 | GCCCAAAGTGATGTTTCTAAGGTTTATGCACAG | 7776 | AQSDVSKVYAQ | 12365 | SDVSKVY | 0.247354 | -0.11668 |
| SyS1354 | 3188 | GCCCAATCGAATACGGGGGAGCAGGTTGCACAG | 7777 | AQSNTGEQVAQ | 12366 | SNTGEQV | 0.247184 | -0.19254 |
| SyS1355 | 3189 | GCCCAATTCACCACCGGCCTCAACCACGCACAG | 7778 | AQFTTGLNHAQ | 12367 | FTTGLNH | 0.247139 | -0.09374 |
| SyS1356 | 3190 | GCCCAAAACGACACACCAATACAAACACGCACAG | 7779 | AQNDTQYKHAQ | 12368 | NDTQYKH | 0.247109 | -0.10786 |
| SyS1357 | 3191 | GCCCAAGTCCACGACGTCAAAGGCATCGCACAG | 7780 | AQVHDVKGIAQ | 12369 | VHDVKGI | 0.247033 | 0.063895 |
| GS756 | 3192 | GCCCAATATGGTGGTAGGGATAGTTATGCACAG | 7781 | AQYGGRDSYAQ | 12370 | YGGRDSY | 0.246964 | -0.09066 |
| SyS1358 | 3193 | GCCCAACATAGTACTGCGACTACTCATGCACAG | 7782 | AQHSTATTHAQ | 12371 | HSTATTH | 0.246866 | -0.15132 |
| SyS1360 | 3194 | GCCCAACCTTCGCCTACTACTCGGACTGCACAG | 7783 | AQPSPTTRTAQ | 12372 | PSPTTRT | 0.246802 | -0.21694 |
| SyS1361 | 3195 | GCCCAAGGGCATGCGGGAGGCGGGATGGCACAG | 7784 | AQGHAEAAMAQ | 12373 | GHAEAAM | 0.246802 | -0.16027 |
| SyS1362 | 3196 | GCCCAAAGCCTCAGCACCAGACCCGTCGCACAG | 7785 | AQSLSTRPVAQ | 12374 | SLSTRPV | 0.24675 | -0.01949 |
| GS757 | 3197 | GCCCAATCTCCGGTGCCTGGTAAGCCTGCACAG | 7786 | AQSPVPGKPAQ | 12375 | SPVPGKP | 0.246636 | -0.15138 |
| GS758 | 3198 | GCCCAAACCAGAATCACACGCCCCCTGCACAG | 7787 | AQTRINSPLAQ | 12376 | TRINSPL | 0.246552 | -0.07422 |
| SyS1363 | 3199 | GCCCAAGAGTCTACGTATGCGAAGCTGGCACAG | 7788 | AQESTYAKLAQ | 12377 | ESTYAKL | 0.246443 | -0.12586 |
| SyS1364 | 3200 | GCCCAACAAATCAACCAAGGCACCAGAGCACAG | 7789 | AQQINQGTRAQ | 12378 | QINQGTR | 0.246362 | 0.115808 |
| GS759 | 3201 | GCCCAAGGCAGCAGAACCGGCAGCATCGCACAG | 7790 | AQGSRTGSIAQ | 12379 | GSRTGSI | 0.24628 | -0.05088 |
| SyS1365 | 3202 | GCCCAAGGGAATGCTTCTTGGTCTGGCTGCACAG | 7791 | AQGNASWSAAQ | 12380 | GNASWSA | 0.246249 | 0.006225 |
| SyS1366 | 3203 | GCCCAAGCGGCTCATGATATTGGTAAGGCACAG | 7792 | AQAAHDIGKAQ | 12381 | AAHDIGK | 0.2462 | -0.14162 |
| GS760 | 3204 | GCCCAAAAGGATAGGCCTTTTGTGGAGGCACAG | 7793 | AQKDRPFVEAQ | 12382 | KDRPFVE | 0.246199 | -0.16753 |
| SyS1367 | 3205 | GCCCAACTCCCCACCAAACCCTTCGCACAG | 7794 | AQLPHTKPFAQ | 12383 | LPHTKPF | 0.246181 | -0.02281 |
| SyS1368 | 3206 | GCCCAACCTGGGAAGGGTGTGTCTCTTGCACAG | 7795 | AQPGKGVSLAQ | 12384 | PGKGVSL | 0.246139 | 0.157066 |
| SyS1369 | 3207 | GCCCAAGACAGACAAAACGCCAGCGCCGCACAG | 7796 | AQDRQNASAAQ | 12385 | DRQNASA | 0.246065 | -0.07979 |
| SyS1370 | 3208 | GCCCAAGTCCAACCCAGCCTCAGCGTCGCACAG | 7797 | AQVQPSLSVAQ | 12386 | VQPSLSV | 0.246042 | -0.08582 |
| SyS1371 | 3209 | GCCCAAAAGCCTACGCCGATTGAGTTTGCACAG | 7798 | AQKPTPIEFAQ | 12387 | KPTPIEF | 0.246004 | -0.1986 |

FIG. 33 (Continued)

| | | | | | | | | |
|---|---|---|---|---|---|---|---|---|
| SyS1372 | 3210 | GCCCAACTGCTTCATGATATGAAGAGTGCACAG | 7799 | AQLLHDMKSAQ | 12388 | LLHDMKS | 0.245942 | 0.000193 |
| SyS1373 | 3211 | GCCCAAAACAGCGACAGAACCCTCAGCGCACAG | 7800 | AQNSDRTLSAQ | 12389 | NSDRTLS | 0.245806 | -0.17998 |
| SyS1374 | 3212 | GCCCAAAAGGTTGGGCATGGGTTAATGCACAG | 7801 | AQKVGHGFNAQ | 12390 | KVGHGFN | 0.24575 | -0.23173 |
| GS761 | 3213 | GCCCAAACGAAGCCTGCGGTTAGTTTTGCACAG | 7802 | AQTKPAVSFAQ | 12391 | TKPAVSF | 0.245736 | -0.16051 |
| SyS1375 | 3214 | GCCCAAGCTATGACGAATATTCCGAAGGCACAG | 7803 | AQAMTNIPKAQ | 12392 | AMTNIPK | 0.245618 | -0.13316 |
| GS762 | 3215 | GCCCAATTTTCGCATATGTCTTTGCCGGCACAG | 7804 | AQFSHMSLPAQ | 12393 | FSHMSLP | 0.245614 | -0.18368 |
| SyS1376 | 3216 | GCCCAAGGGTCTGTGCGGGATAATCCGGCACAG | 7805 | AQGSVRDNPAQ | 12394 | GSVRDNP | 0.245593 | -0.19375 |
| GS763 | 3217 | GCCCAAGTAGTTCGCAGGGGCCGACTGCACAG | 7806 | AQSSSQGPTAQ | 12395 | SSSQGPT | 0.24552 | -0.10423 |
| GP139 | 3218 | GCCCAACTTGTGGGGCGGCCGGTTACGGCACAG | 7807 | AQLVGRPVTAQ | 12396 | LVGRPVT | 0.245491 | -0.07301 |
| SyS1377 | 3219 | GCCCAAATCAACTACGGCGTCAAAAAGCACAG | 7808 | AQINYGVQKAQ | 12397 | INYGVQK | 0.245326 | 0.004509 |
| SyS1378 | 3220 | GCCCAAATTAATAAGGATAATAATCAGGCACAG | 7809 | AQINKDNNQAQ | 12398 | INKDNNQ | 0.245119 | -0.081 |
| SyS1379 | 3221 | GCCCAAAGTGGTCAGTCTTCTGCTATGGCACAG | 7810 | AQSGQSSAMAQ | 12399 | SGQSSAM | 0.245048 | -0.00536 |
| GS765 | 3222 | GCCCAAGAATACAACAGCACCAAACTCGCACAG | 7811 | AQEYNSTKLAQ | 12400 | EYNSTKL | 0.244968 | 0.026789 |
| SyS1381 | 3223 | GCCCAATTTATGACGCTGGAGCGGGGGGCACAG | 7812 | AQFMTLERAAQ | 12401 | FMTLERA | 0.244739 | -0.20466 |
| GS766 | 3224 | GCCCAATTCGGCAAGACTACGTCAACGCACAG | 7813 | AQFGKDYVNAQ | 12402 | FGKDYVN | 0.244671 | -0.06664 |
| SyS1382 | 3225 | GCCCAACTCCTCCGGCGGCACCCCGCACAG | 7814 | AQLLLGGTPAQ | 12403 | LLLGGTP | 0.244645 | -0.15288 |
| GS767 | 3226 | GCCCAAACCACCACCTACACCAGAAACGCACAG | 7815 | AQTTYTRNAQ | 12404 | TTYTRN | 0.244598 | -0.0132 |
| GP140 | 3227 | GCCCAAGATCGGGGTATGCGGGGGGCTGCACAG | 7816 | AQDRGMRGAAQ | 12405 | DRGMRGA | 0.24456 | -0.07273 |
| GS769 | 3228 | GCCCAAGCGGTTTCGGGTACGCGTACGGCACAG | 7817 | AQAVSGTRTAQ | 12406 | AVSGTRT | 0.244519 | -0.05607 |
| SS88 | 3229 | GCCCAAAACTTCAGCGGCGTGCCAAAGCACAG | 7818 | AQNFSGVAKAQ | 12407 | NFSGVAK | 0.24428 | -0.34565 |
| GS770 | 3230 | GCCCAAGATCGGAATAATAGTATTTCGGCACAG | 7819 | AQDRNNSISAQ | 12408 | DRNNSIS | 0.244033 | -0.1765 |
| GS771 | 3231 | GCCCAAATCCCCAAAGACCCCTCGACGCACAG | 7820 | AQIPQRPLDAQ | 12409 | IPQRPLD | 0.244033 | -0.1424 |
| GP141 | 3232 | GCCCAACCTGCTGCGAATCAGTATGTTGCACAG | 7821 | AQPAANQYVAQ | 12410 | PAANQYV | 0.243833 | 0.318489 |
| GS772 | 3233 | GCCCAATACAGCGGCACCGCCATCGAGCACAG | 7822 | AQYSGTAIRAQ | 12411 | YSGTAIR | 0.243671 | -0.06766 |
| GS773 | 3234 | GCCCAATGGGTTCAGCGGACTGAGAGTGCACAG | 7823 | AQWVQRTESAQ | 12412 | WVQRTES | 0.243512 | -0.17768 |
| SyS1385 | 3235 | GCCCAACCCAAAGACGCGGCCATCGCACAG | 7824 | AQPKDGGAIAQ | 12413 | PKDGGAI | 0.243472 | -0.17259 |
| SyS1386 | 3236 | GCCCAACTTGCTACTCCGCAGGAGGAGGCACAG | 7825 | AQLATPQEEAQ | 12414 | LATPQEE | 0.243453 | -0.23618 |
| GS774 | 3237 | GCCCAACTGAATAGTCCGGTTATGGCGGCACAG | 7826 | AQLNSPVMAAQ | 12415 | LNSPVMA | 0.243434 | -0.14048 |
| GP142 | 3238 | GCCCAAGGGGCTACTGGGACGAGGGGCTGCACAG | 7827 | AQGATGTRAAQ | 12416 | GATGTRA | 0.243373 | -0.01961 |
| SyS1387 | 3239 | GCCCAACGGACGGATGTGCGGGACGAATGCACAG | 7828 | AQRTDVRTNAQ | 12417 | RTDVRTN | 0.243327 | -0.18527 |
| SyS1388 | 3240 | GCCCAAAGAAACCTCGCCCACCCTACGCACAG | 7829 | AQRNLAHPYAQ | 12418 | RNLAHPY | 0.243327 | -0.18527 |
| SyS1389 | 3241 | GCCCAACTCAGCACCAGCTACACAGCCACGCACAG | 7830 | AQLSTSYSTAQ | 12419 | LSTSYST | 0.243288 | -0.15981 |

FIG. 33 (Continued)

| | | | | | | | |
|---|---|---|---|---|---|---|---|
| SyS1390 | 3242 | GCCCAAGGCGGTCAACCAAACCGCCAGAGAGCACAG | 7831 | AQGVNQTARAQ | 12420 | GVNQTAR | 0.243276 | -0.08615 |
| SyS1391 | 3243 | GCCCAACTTCCGGCTAGTTCGGCTAGGGCACAG | 7832 | AQIPASSARAQ | 12421 | LPASSAR | 0.243214 | -0.08645 |
| SyS1392 | 3244 | GCCCAACAACTCTACAGCGTCAACGCCGCACAG | 7833 | AQQLYSVNAAQ | 12422 | QLYSVNA | 0.243023 | -0.15496 |
| SyS1393 | 3245 | GCCCAAGTTGGGACGTATACTGCTACGGCACAG | 7834 | AQVGTYTATAQ | 12423 | VGTYTAT | 0.243023 | -0.18042 |
| GS775 | 3246 | GCCCAAGAAGAGCATGACCGTCATCGAAGCACAG | 7835 | AQRSMTVIEAQ | 12424 | RSMTVIE | 0.242977 | -0.15669 |
| SyS1394 | 3247 | GCCCAATTTGGGCGTGGTGATACGGGGTGCACAG | 7836 | AQFGRGDTGAQ | 12425 | FGRGDTG | 0.242909 | 0.104483 |
| SyS1395 | 3248 | GCCCAAGCCGCGGCAGAAGCAACCCCGCACAG | 7837 | AQAAGRSNPAQ | 12426 | AAGRSNP | 0.242903 | 0.079024 |
| GS776 | 3249 | GCCCAAATGCCTCAGTCGAGTCTTGCTGCACAG | 7838 | AQMPQSSLAAQ | 12427 | MPQSSLA | 0.242838 | -0.16718 |
| SyS1397 | 3250 | GCCCAACCGTCTAAGCATGAGCGGGTATGCACAG | 7839 | AQPSKHERYAQ | 12428 | PSKHERY | 0.242467 | -0.20586 |
| SyS1399 | 3251 | GCCCAATTGTTTGATTCTTCTAAGACTGCACAG | 7840 | AQLFDSSKTAQ | 12429 | LFDSSKT | 0.242166 | -0.06487 |
| GS779 | 3252 | GCCCAAAGCCCCAACCAGACTCAGCGCACAG | 7841 | AQSPQPRLSAQ | 12430 | SPQPRLS | 0.242119 | -0.1774 |
| SyS1400 | 3253 | GCCCAAAGAAGAACCGACGTCGAAAACGCACAG | 7842 | AQRRPDVENAQ | 12431 | RRPDVEN | 0.242029 | -0.04446 |
| GS780 | 3254 | GCCCAACCGATGGGTAGTGCGGGGTAGTGCACAG | 7843 | AQPMGSAGSAQ | 12432 | PMGSAGS | 0.241931 | -0.10709 |
| GS781 | 3255 | GCCCAATGGAGCACCGGCATGACCAGCGCACAG | 7844 | AQWSTGMTSAQ | 12433 | WSTGMTS | 0.241931 | -0.10709 |
| SyS1401 | 3256 | GCCCAAGGCCTCGTCAGAAACGGCGTCGCACAG | 7845 | AQGLVRNGVAQ | 12434 | GLVRNGV | 0.241887 | 0.011133 |
| SyS1402 | 3257 | GCCCAAGAGGGGTCGTATAGTACGTCTCGCACAG | 7846 | AQEGSYSTSAQ | 12435 | EGSYSTS | 0.241562 | -0.07279 |
| SyS1403 | 3258 | GCCCAAGCCACCAGCATGCTCACCCACGCACAG | 7847 | AQATSMLTHAQ | 12436 | ATSMLTH | 0.241541 | -0.18163 |
| SyS1404 | 3259 | GCCCAAGCAACCACCACCGGCCCCCCAGCGCACAG | 7848 | AQSTTGPPSAQ | 12437 | STTGPPS | 0.241416 | -0.00061 |
| SyS1405 | 3260 | GCCCAACGTGGGGCGTCGGTGTCTATGGCACAG | 7849 | AQRGASVSMAQ | 12438 | RGASVSM | 0.241293 | -0.17678 |
| SyS1406 | 3261 | GCCCAAGTCCACGAACACGGCGCCAGCGCACAG | 7850 | AQVHEHGASAQ | 12439 | VHEHGAS | 0.241293 | -0.20709 |
| GS783 | 3262 | GCCCAACATTCTCCTTCTCAGCCGAGGGCACAG | 7851 | AQHSPSQPRAQ | 12440 | HSPSQPR | 0.241239 | -0.18816 |
| SyS1407 | 3263 | GCCCAAGGCATCGGCCAAAACACCGCCGCACAG | 7852 | AQGIGQNTAAQ | 12441 | GIGQNTA | 0.240916 | 0.12394 |
| SyS1408 | 3264 | GCCCAACACAGAGTCGAAAAACAGCTACGCACAG | 7853 | AQHRVENSYAQ | 12442 | HRVENSY | 0.240897 | -0.13677 |
| GS785 | 3265 | GCCCAAACTGAGTTTAAGCCTCCGTCGGCACAG | 7854 | AQTEFKPPSAQ | 12443 | TEFKPPS | 0.240856 | -0.16051 |
| SyS1409 | 3266 | GCCCAATATGGTAATTTGGGGGTTAATGCACAG | 7855 | AQYGNLGVNAQ | 12444 | YGNLGVN | 0.240623 | -0.09677 |
| SyS1410 | 3267 | GCCCAACTCACCAGAGTCCTCACCGGCGCACAG | 7856 | AQLTRVLTGAQ | 12445 | LTRVLTG | 0.240472 | -0.09192 |
| SyS1411 | 3268 | GCCCAAATGAAAAACAGCAACGGCGCCGCACAG | 7857 | AQMKNSNGAAQ | 12446 | MKNSNGA | 0.240422 | -0.05676 |
| GS788 | 3269 | GCCCAAGGCACCCAAACCCACCTCCAAGCACAG | 7858 | AQGTQTHLQAQ | 12447 | GTQTHLQ | 0.24023 | -0.15766 |
| SyS1412 | 3270 | GCCCAAAATGCGCTTGCTAGGACGATGGCACAG | 7859 | AQNALARTMAQ | 12448 | NALARTM | 0.240048 | -0.14768 |
| GS789 | 3271 | GCCCAAAATAATTCTATGCAGACGGTGGCACAG | 7860 | AQNNSMQTVAQ | 12449 | NNSMQTV | 0.24002 | -0.16035 |
| GS790 | 3272 | GCCCAACAACAAGGCAACGGCCAGAAGCGCACAG | 7861 | AQQQGNGRSAQ | 12450 | QQGNGRS | 0.239981 | -0.06255 |
| GS791 | 3273 | GCCCAACTCACCAAAAGCCAAGGCTACGCACAG | 7862 | AQLTKSQGYAQ | 12451 | LTKSQGY | 0.239958 | -0.05367 |

FIG. 33 (Continued)

| | | | | | | | |
|---|---|---|---|---|---|---|---|
| SyS1413 | 3274 | GCCCAAGCCCCGCCGAACCCAAAACCGCACAG | 7863 | AQAPAEPKTAQ | 12452 | APAEPKT | 0.239917 | -0.07252 |
| SyS1415 | 3275 | GCCCAATATAGTAATCAGGTGAGTAATGCACAG | 7864 | AQYSNQVSNAQ | 12453 | YSNQVSN | 0.23984 | -0.17799 |
| GS792 | 3276 | GCCCAAACTCGTACGGGGTTTTCTCCTGCACAG | 7865 | AQTRTGFSPAQ | 12454 | TRTGFSP | 0.23983 | -0.09659 |
| SyS1416 | 3277 | GCCCAACCCGTCTACAAAACCGACGACGCACAG | 7866 | AQPVYKTDDAQ | 12455 | PVYKTDD | 0.23942 | 0.109874 |
| SyS1417 | 3278 | GCCCAATCTGATAGGCGGCTCCTGAGGCACAG | 7867 | AQSDRPAPEAQ | 12456 | SDRPAPE | 0.239322 | -0.20345 |
| GS796 | 3279 | GCCCAAGTTCAGGAGAAGTCGAGGCCTGCACAG | 7868 | AQVQEKSRPAQ | 12457 | VQEKSRP | 0.239154 | -0.05489 |
| SyS1418 | 3280 | GCCCAAAGCGGGCGGCCTCACCGAAAGAGCACAG | 7869 | AQSGGLTERAQ | 12458 | SGGLTER | 0.238974 | 0.018624 |
| GS797 | 3281 | GCCCAAAGCGGCGGCGGCACCAGAGAAGGCGCACAG | 7870 | AQSGGTREGAQ | 12459 | SGGTREG | 0.238968 | -0.17195 |
| GS798 | 3282 | GCCCAAGCCGTCCCGGCGAAACCAGAGCACAG | 7871 | AQAVPGETRAQ | 12460 | AVPGETR | 0.238881 | -0.10872 |
| SyS1419 | 3283 | GCCCAACCGCGGCGGCGGAGAGGATGTATGCACAG | 7872 | AQPRPERMYAQ | 12461 | PRPERMY | 0.238847 | -0.23376 |
| SyS1420 | 3284 | GCCCAAAGCAACGGCAACATCAGCAGAGCACAG | 7873 | AQSNGNISRAQ | 12462 | SNGNISR | 0.23868 | 0.07724 |
| GS799 | 3285 | GCCCAAGCCAGAACCGAAAGAAACCAAGCACAG | 7874 | AQARTERNQAQ | 12463 | ARTERNQ | 0.238676 | -0.07152 |
| SyS1421 | 3286 | GCCCAAAGTCCTCAGCAGTTTCGAAGGCACAG | 7875 | AQSPQQFSKAQ | 12464 | SPQQFSK | 0.238555 | -0.16766 |
| SyS1422 | 3287 | GCCCAAAGCACCGGCCCCTTCCCCCAAGCACAG | 7876 | AQSTGPFPQAQ | 12465 | STGPFPQ | 0.238506 | -0.2268 |
| GS800 | 3288 | GCCCAAGCCAACATCGGCACCAGCACGCACAG | 7877 | AQANIGTSTAQ | 12466 | ANIGTST | 0.238473 | -0.1462 |
| SyS1423 | 3289 | GCCCAATACAGAGACAACACCAGCGGCGCACAG | 7878 | AQYRDNTSGAQ | 12467 | YRDNTSG | 0.238378 | -0.04463 |
| SyS1424 | 3290 | GCCCAAGTGCAGACTAGGTCTCCGATGGCACAG | 7879 | AQVQTRSPMAQ | 12468 | VQTRSPM | 0.238378 | -0.13435 |
| SyS1425 | 3291 | GCCCAAATCCACACCAGCATCGTCGACGCACAG | 7880 | AQIHTSIVDAQ | 12469 | IHTSIVD | 0.238378 | -0.1792 |
| GS801 | 3292 | GCCCAAATGACTCGGACTAGTAGTGAGGCACAG | 7881 | AQMTRTSSEAQ | 12470 | MTRTSSE | 0.23833 | -0.08134 |
| SyP51 | 3293 | GCCCAACCGTCGAATTTTCCTGGGTCTGCACAG | 7882 | AQPSNFPGSAQ | 12471 | PSNFPGS | 0.238303 | -0.0398 |
| SyS1426 | 3294 | GCCCAAATGATCGGCGGCACCCAAAGCGCACAG | 7883 | AQMIGGTQSAQ | 12472 | MIGGTQS | 0.238168 | -0.21921 |
| SyS1427 | 3295 | GCCCAAAAGCTTGATAAGCATGAGTCTGCACAG | 7884 | AQKLDKHESAQ | 12473 | KLDKHES | 0.238069 | -0.16951 |
| SyS1428 | 3296 | GCCCAACTTACGAGTAGTAATAGTGCTGCACAG | 7885 | AQLTSSNSAAQ | 12474 | LTSSNSA | 0.23749 | -0.09555 |
| GS805 | 3297 | GCCCAAAGTACTCGTGATACTCATTTTGCACAG | 7886 | AQSTRDTHFAQ | 12475 | STRDTHF | 0.237351 | -0.04196 |
| GS808 | 3298 | GCCCAAGATACGTTGAAGGGTGTTAGGGCACAG | 7887 | AQDTLKAVRAQ | 12476 | DTLKAVR | 0.237261 | -0.17201 |
| GS809 | 3299 | GCCCAACAGCGTAATCCGTCGCTTCATGCACAG | 7888 | AQQRNPSLHAQ | 12477 | QRNPSLH | 0.237261 | -0.14151 |
| SyS1430 | 3300 | GCCCAATCGGGTGATGGGAATCGTTCGGCACAG | 7889 | AQSGDGNRSAQ | 12478 | SGDGNRS | 0.237239 | 0.28722 |
| SyS1431 | 3301 | GCCCAAGGCGTCTACAAAACCCTCCACGCACAG | 7890 | AQGVYKTLHAQ | 12479 | GVYKTLH | 0.236906 | -0.18042 |
| GS812 | 3302 | GCCCAAATTAATTCGAATCAGGTGAGTGCACAG | 7891 | AQINSNQVSAQ | 12480 | INSNQVS | 0.236622 | -0.1774 |
| SyS1432 | 3303 | GCCCAACACTACAACGAACACATGACCGCACAG | 7892 | AQHYNEHMTAQ | 12481 | HYNEHMT | 0.236614 | -0.05689 |
| SyS1433 | 3304 | GCCCAAACTGTGCAGGTTCGTGATCGGGCACAG | 7893 | AQTVQVRDRAQ | 12482 | TVQVRDR | 0.236461 | -0.06516 |
| TS162 | 3305 | GCCCAAGGCAACGACATCAGAGAAGCAGAGCACAG | 7894 | AQGNDIRSRAQ | 12483 | GNDIRSR | 0.236352 | 0.106582 |

FIG. 33 (Continued)

| | | | | | | | | |
|---|---|---|---|---|---|---|---|---|
| SyS1434 | 3306 | GCCCAAGTCAGCGTCAGCATGGGCCCGCACAG | 7895 | AQVSVSMGPAQ | 12484 | VSVSMGP | 0.236036 | -0.02892 |
| SyS1436 | 3307 | GCCCAATTCAAAACCAACATCAGCGCGCACAG | 7896 | AQFKTNISAAQ | 12485 | FKTNISA | 0.235866 | -0.12707 |
| SyS1438 | 3308 | GCCCAATTTCCGAAGGTGGAGAGGTATGCACAG | 7897 | AQFPKVERYAQ | 12486 | FPKVERY | 0.235735 | -0.23296 |
| SyS1439 | 3309 | GCCCAACTTAGTAAGTTTCAGACTACGGCACAG | 7898 | AQLSKFQTTAQ | 12487 | LSKFQTT | 0.235498 | -0.19723 |
| SyS1442 | 3310 | GCCCAAAGCCTCATGAACAGCAGAAGCGCACAG | 7899 | AQSLMNSRSAQ | 12488 | SLMNSRS | 0.235263 | -0.09106 |
| SyP52 | 3311 | GCCCAAGGGCGTGGGGTGCTGGAGTCTGCACAG | 7900 | AQGRGVLESAQ | 12489 | GRGVLES | 0.235143 | -0.04392 |
| GS814 | 3312 | GCCCAACCTAATGGGTCGCAGATGATTGCACAG | 7901 | AQPNGSQMIAQ | 12490 | PNGSQMI | 0.235069 | -0.1756 |
| SyS1443 | 3313 | GCCCAACCCACCGTCGGCAACAGCTACGCACAG | 7902 | AQPTVGNSYAQ | 12491 | PTVGNSY | 0.234983 | 0.010187 |
| SyS1444 | 3314 | GCCCAAAGCAGCGACATCATGAAAGCCGCACAG | 7903 | AQSSDIMKAAQ | 12492 | SSDIMKA | 0.234776 | -0.13314 |
| GS816 | 3315 | GCCCAACTGATGACTAGTAGTGCTGGTCGTGCACAG | 7904 | AQLMTSAGRAQ | 12493 | LMTSAGR | 0.234691 | -0.17829 |
| SyS1447 | 3316 | GCCCAACCCGCCATGAGCAGCAGCAGAGCACAG | 7905 | AQPAMSSSRAQ | 12494 | PAMSSSR | 0.234552 | 0.036927 |
| GS817 | 3317 | GCCCAACGTGATAAGGCGATTTCGACGGCACAG | 7906 | AQRDKAISTAQ | 12495 | RDKAIST | 0.234493 | -0.08025 |
| GS818 | 3318 | GCCCAATTGACTTTGAAGCAGGGGATTGCACAG | 7907 | AQLTLKQGIAQ | 12496 | LTLKQGI | 0.234404 | -0.1433 |
| GS819 | 3319 | GCCCAATCTCATGCTAATGGGTTTAGTGCACAG | 7908 | AQSHANGFSAQ | 12497 | SHANGFS | 0.234293 | -0.18099 |
| SyS1449 | 3320 | GCCCAACCGAATTGAAGGCTCCGCAGGCACAG | 7909 | AQPNLKAPQAQ | 12498 | PNLKAPQ | 0.233974 | -0.18769 |
| SyS1450 | 3321 | GCCCAAAGCTACGGCAGAGAAGTCAGAGCACAG | 7910 | AQSYGREVRAQ | 12499 | SYGREVR | 0.233931 | -0.18284 |
| SyS1451 | 3322 | GCCCAAAACGACACCCAAAGCCCCAAAGCACAG | 7911 | AQNDTQSPKAQ | 12500 | NDTQSPK | 0.233816 | -0.16829 |
| SyS1452 | 3323 | GCCCAAGACGAAAGAGCCCCAAACACGCACAG | 7912 | AQDERAPKHAQ | 12501 | DERAPKH | 0.233748 | -0.15859 |
| GS820 | 3324 | GCCCAAAACGGCAGACCCATGGGCATGGCACAG | 7913 | AQNGRPMGMAQ | 12502 | NGRPMGM | 0.233736 | -0.12617 |
| GS821 | 3325 | GCCCAACATACTCAGTCTGTGACTATGGCACAG | 7914 | AQHTQSVTMAQ | 12503 | HTQSVTM | 0.233699 | -0.16125 |
| SyS1453 | 3326 | GCCCAAAACAACTTCAACGCCAGCCTCGCACAG | 7915 | AQNNFNASLAQ | 12504 | NNFNASL | 0.23358 | -0.1295 |
| SyS1454 | 3327 | GCCCAAGAATACCTCAAAGGCAGCGCGCACAG | 7916 | AQEYLKGSAAQ | 12505 | EYLKGSA | 0.23358 | -0.1295 |
| GS822 | 3328 | GCCCAATCTAAGACGCCTGATATGTTGGCACAG | 7917 | AQSKTPDMLAQ | 12506 | SKTPDML | 0.233472 | -0.15138 |
| SyS1455 | 3329 | GCCCAAGTCAACACCGGCCACGTCAGAGCACAG | 7918 | AQVNTGHVRAQ | 12507 | VNTGHVR | 0.23344 | -0.13454 |
| GS823 | 3330 | GCCCAAGGTTCTCAGTCGGATGCGGTGCACAG | 7919 | AQGSQSDARAQ | 12508 | GSQSDAR | 0.233353 | -0.0985 |
| SyS1456 | 3331 | GCCCAATCTTTGACTTTTCTAAGGATGCACAG | 7920 | AQSLTFSKDAQ | 12509 | SLTFSKD | 0.233165 | -0.15904 |
| SyS1457 | 3332 | GCCCAAAACGCCCTCGAAAGCAGAATGGCACAG | 7921 | AQNALESRMAQ | 12510 | NALESRM | 0.233165 | -0.18121 |
| SyS1458 | 3333 | GCCCAAAACGGCATCGCCAGAGAACCCGCACAG | 7922 | AQNGIAREPAQ | 12511 | NGIAREP | 0.233148 | 0.030787 |
| SyS1459 | 3334 | GCCCAAAACCTCGTCAGCGTCAGCACCGCACAG | 7923 | AQNLVSVSTAQ | 12512 | NLVSVST | 0.232787 | -0.21694 |
| SyS1461 | 3335 | GCCCAAGACATGCTCAGCTACAAACCCGCACAG | 7924 | AQDMLSYKPAQ | 12513 | DMLSYKP | 0.232747 | 0.049327 |
| SyS1463 | 3336 | GCCCAAAGAAGCACCGACAGCATGACCGCACAG | 7925 | AQRSTDSMTAQ | 12514 | RSTDSMT | 0.232649 | 0.12732 |
| SyS1464 | 3337 | GCCCAAGAGATGAATCATAGTCTTTCTGCACAG | 7926 | AQEMNHSLSAQ | 12515 | EMNHSLS | 0.232545 | -0.18614 |

FIG. 33 (Continued)

| | | | | | | | | |
|---|---|---|---|---|---|---|---|---|
| GS827 | 3338 | GCCCAAGCCCTCAGCAAAGAAGCCAGCGCACAG | 7927 | AQALSKEASAQ | 12516 | ALSKEAS | 0.232439 | -0.11949 |
| SyS1465 | 3339 | GCCCAAAACGGCCACACGCGGCCAAGCACAG | 7928 | AQNGHNMSQAQ | 12517 | NGHNMSQ | 0.232428 | -0.00948 |
| SyS1466 | 3340 | GCCCAAACACCGCGGAAGCCACCAGAGCACAG | 7929 | AQTTAEATRAQ | 12518 | TTAEATR | 0.232428 | -0.03372 |
| SyS1467 | 3341 | GCCCAAAGAGAAAGCGCCCACCACAACGCACAG | 7930 | AQRESAHHNAQ | 12519 | RESAHHN | 0.232428 | -0.12586 |
| SyS1469 | 3342 | GCCCAAATGTTACGGGGAATGGGCAGGCACAG | 7931 | AQMFTGNGQAQ | 12520 | MFTGNGQ | 0.232428 | -0.218 |
| SyS1470 | 3343 | GCCCAACATCTTCAGACGCGCCGGCTGCACAG | 7932 | AQHLQTPPAAQ | 12521 | HLQTPPA | 0.232331 | -0.2305 |
| SyS1471 | 3344 | GCCCAATCGCTTGTGGGTCAGGGTAAGGCACAG | 7933 | AQSLVGQGKAQ | 12522 | SLVGQGK | 0.232298 | -0.09584 |
| SyS1472 | 3345 | GCCCAACTCCCCTCACCCCATCGCCGCACAG | 7934 | AQIPLTPIAAQ | 12523 | LPLTPIA | 0.232279 | 0.019127 |
| GS828 | 3346 | GCCCAAGCTATGAAGCAGTCGTCTATTGCACAG | 7935 | AQAMKQSSIAQ | 12524 | AMKQSSI | 0.232051 | -0.12341 |
| GS829 | 3347 | GCCCAATATCCTACGAATGTGAAGTCGGCACAG | 7936 | AQYPTNVKSAQ | 12525 | YPTNVKS | 0.232018 | 0.099106 |
| SyS1473 | 3348 | GCCCAAAGCAACAGCCTCCCCAGCAGAGCACAG | 7937 | AQSNSLPSRAQ | 12526 | SNSLPSR | 0.231997 | -0.06106 |
| GS830 | 3349 | GCCCAACCGACGGCGGCTACTGGGACGGCACAG | 7938 | AQPTAATGTAQ | 12527 | PTAATGT | 0.231918 | -0.16528 |
| GS831 | 3350 | GCCCAAATCGCCCAAAACGGCCCCGGCGCACAG | 7939 | AQIAQNGPGAQ | 12528 | IAQNGPG | 0.231887 | -0.12998 |
| SyS1475 | 3351 | GCCCAAACTACTCATCAGCTTACTCCGGCACAG | 7940 | AQTTHQLTPAQ | 12529 | TTHQLTP | 0.231805 | 0.179914 |
| SyS1476 | 3352 | GCCCAACTTATTCCTGCGAGGGATGTGGCACAG | 7941 | AQLIPARDVAQ | 12530 | LIPARDV | 0.231788 | -0.0519 |
| SyS1477 | 3353 | GCCCAAAAAATCGCCCACGGCGACATCGCACAG | 7942 | AQKIAHGDIAQ | 12531 | KIAHGDI | 0.231565 | -0.05433 |
| SyS1478 | 3354 | GCCCAAGCCAGACCCCAAAGCGACAAAGCACAG | 7943 | AQARPQSDKAQ | 12532 | ARPQSDK | 0.231506 | 0.192363 |
| SyS1479 | 3355 | GCCCAACCCAGACCCAACGTCCTCGAGCACAG | 7944 | AQPRPNVLDAQ | 12533 | PRPNVLD | 0.231372 | 0.138428 |
| GS833 | 3356 | GCCCAACTCAACAAAGGCAGCAGCAACGCACAG | 7945 | AQLNKGSSNAQ | 12534 | LNKGSSN | 0.231355 | -0.0385 |
| GS834 | 3357 | GCCCAACGGGTTTATAATGGTGATCTGGCACAG | 7946 | AQRVYNGDLAQ | 12535 | RVYNGDL | 0.231254 | -0.14048 |
| SyS1481 | 3358 | GCCCAAACCGTCCCGCCAACAGCAGCGCACAG | 7947 | AQTVPANSSAQ | 12536 | TVPANSS | 0.231245 | -0.13677 |
| SyS1482 | 3359 | GCCCAACCAGACACACCAGCCTCACCGCACAG | 7948 | AQTRHTSLTAQ | 12537 | TRHTSLT | 0.231191 | -0.14647 |
| SS95 | 3360 | GCCCAAAATCATGCGGTGACGAATTCTGCACAG | 7949 | AQNHAVTNSAQ | 12538 | NHAVTNS | 0.231161 | -0.29794 |
| SyS1483 | 3361 | GCCCAATTGGCGTCGCATTCTACGCTTGCACAG | 7950 | AQLASHSTLAQ | 12539 | LASHSTL | 0.231132 | -0.15617 |
| GS836 | 3362 | GCCCAAGTGCGCCTTCAAAAGCGGCATCGCACAG | 7951 | AQVAFKSGIAQ | 12540 | VAFKSGI | 0.231125 | -0.13792 |
| SyS1484 | 3363 | GCCCAAAGAGTCGGCCCGAAAGCAGCGGCACAG | 7952 | AQRVGPESSAQ | 12541 | RVGPESS | 0.231067 | -0.16587 |
| GS838 | 3364 | GCCCAAGCCCCAGCAACGTCCACCGCACAG | 7953 | AQAPSNVHTAQ | 12542 | APSNVHT | 0.231055 | -0.05067 |
| SyS1485 | 3365 | GCCCAAACTAGGTCGGAGGTGATGAAGGCACAG | 7954 | AQTRSEVMKAQ | 12543 | TRSEVMK | 0.230872 | -0.19011 |
| GS839 | 3366 | GCCCAATTGAAGGAGCAGCATGGTGGGGCACAG | 7955 | AQLKEQHGGAQ | 12544 | LKEQHGG | 0.230779 | -0.18009 |
| SP37 | 3367 | GCCCAAAAGGCGGAGTCGCATGCGACGGCACAG | 7956 | AQKAESHATAQ | 12545 | KAESHAT | 0.230702 | -0.0491 |
| SyS1486 | 3368 | GCCCAATATAGGACGGATATGCTGAGTGCACAG | 7957 | AQYRTDMLSAQ | 12546 | YRTDMLS | 0.230667 | -0.20955 |
| GS841 | 3369 | GCCCAAGATACGCAGGGGAGGAGGATGCGGGCACAG | 7958 | AQDTQGRMRAQ | 12547 | DTQGRMR | 0.230611 | -0.10327 |

FIG. 33 (Continued)

| | | | | | | | | |
|---|---|---|---|---|---|---|---|---|
| GS842 | 3370 | GCCCAATGTCTTCCTAAGGGTTGTACGGCACAG | 7959 | AQCLPKGCTAQ | 12548 | CLPKGCT | 0.230518 | -0.15097 |
| SyS1487 | 3371 | GCCCAAGGCAGCCCACCGTCGTCCACGCACAG | 7960 | AQGSPTVVHAQ | 12549 | GSPTVVH | 0.230363 | -0.07403 |
| SyS1488 | 3372 | GCCCAATTGTCGCTTTCTACGCAGAGGGCACAG | 7961 | AQLSLSTQRAQ | 12550 | LSLSTQR | 0.230358 | -0.10005 |
| GS843 | 3373 | GCCCAAAAACATGGCCCAAAACGCCAGAGCACAG | 7962 | AQNMAQNARAQ | 12551 | NMAQNAR | 0.230121 | -0.1462 |
| GS845 | 3374 | GCCCAACTCAGCACCAACGTCCTCCTCGCACAG | 7963 | AQLSTNVLLAQ | 12552 | LSTNVLL | 0.229919 | -0.16573 |
| GS846 | 3375 | GCCCAAACTTCGCCTGTTATTCGTACTGCACAG | 7964 | AQTSPVIRTAQ | 12553 | TSPVIRT | 0.229823 | -0.17386 |
| SyS1490 | 3376 | GCCCAACCTAGTGCTGGTCATGTTTGGCACAG | 7965 | AQPSAGHVLAQ | 12554 | PSAGHVL | 0.229391 | -0.18648 |
| GS849 | 3377 | GCCCAACTGTCTGGTACGGCTACTTCGGCACAG | 7966 | AQLSGTATSAQ | 12555 | LSGTATS | 0.229374 | -0.16909 |
| SyS1491 | 3378 | GCCCAAACGGGTAATCGAATCGGACTGCACAG | 7967 | AQTGNPNPTAQ | 12556 | TGNPNPT | 0.229306 | -0.17998 |
| SyS1492 | 3379 | GCCCAACAATTCGAACACAGCCTCCCCGCACAG | 7968 | AQQFEHSLPAQ | 12557 | QFEHSLP | 0.229163 | -0.03857 |
| SyS1493 | 3380 | GCCCAACTCACCCGGCCAAATCAGAGCACAG | 7969 | AQLTPGQIRAQ | 12558 | LTPGQIR | 0.229124 | 0.08066 |
| GS850 | 3381 | GCCCAACTGATGAATGCGAAGACGACGGCACAG | 7970 | AQLMNAKTTAQ | 12559 | LMNAKTT | 0.22906 | -0.06983 |
| SyS1494 | 3382 | GCCCAACAAAGAGACACCAACATGGCCGCACAG | 7971 | AQQRDTNMAAQ | 12560 | QRDTNMA | 0.228811 | 0.109343 |
| SyS1495 | 3383 | GCCCAAAACCTCCTCGAAATCGGCAGAGCACAG | 7972 | AQNILEIGRAQ | 12561 | NILEIGR | 0.228652 | -0.22042 |
| SyS1496 | 3384 | GCCCAAGACGTCAAAGACAAACAAATCGCACAG | 7973 | AQDVKDKQIAQ | 12562 | DVKDKQI | 0.228561 | -0.08214 |
| GS851 | 3385 | GCCCAAGTGACTATTTCGAATAAGCCTGCACAG | 7974 | AQVTISNKPAQ | 12563 | VTISNKP | 0.228495 | -0.06638 |
| SyS1497 | 3386 | GCCCAAAGCACCCCCATCAACAGCAGAGCACAG | 7975 | AQSTPINSRAQ | 12564 | STPINSR | 0.228369 | -0.10161 |
| SyS1499 | 3387 | GCCCAAGGCACCCACGGCCTCACCAGCGCACAG | 7976 | AQGTHGLTSAQ | 12565 | GTHGLTS | 0.228217 | 0.021364 |
| SyS1500 | 3388 | GCCCAACAGTCTCCGGGGATGATTCATGCACAG | 7977 | AQQSPGMIHAQ | 12566 | QSPGMIH | 0.228178 | -0.10536 |
| SyS1501 | 3389 | GCCCAACAAAACCGGCCCGTTCCTCAGCGCACAG | 7978 | AQQTGPVLSAQ | 12567 | QTGPVLS | 0.2281 | -0.17799 |
| GS853 | 3390 | GCCCAAACTTATGTGTCGTCGGTCCGGCACAG | 7979 | AQTYVSSGPAQ | 12568 | TYVSSGP | 0.228034 | -0.07561 |
| SyS1502 | 3391 | GCCCAAACCAGCACCCTCCCAGACTCGCACAG | 7980 | AQTSTLPRLAQ | 12569 | TSTLPRL | 0.227986 | -0.21571 |
| SyS1503 | 3392 | GCCCAATACACCCACAAAGACAACGACGCACAG | 7981 | AQYTHKDNDAQ | 12570 | YTHKDND | 0.227932 | -0.20709 |
| SyS1504 | 3393 | GCCCAACTCGGCGCCCAAAGCACCCTCGCACAG | 7982 | AQLGAQSTLAQ | 12571 | LGAQSTL | 0.227857 | -0.18769 |
| SyS1505 | 3394 | GCCCAATTGGCGCAGGTTAGGCTGCTGCACAG | 7983 | AQLAQVRPAAQ | 12572 | LAQVRPA | 0.227792 | -0.01727 |
| GS854 | 3395 | GCCCAAGGCAGGAGAGTCGTCGCCAGCAACGCACAG | 7984 | AQGRVVASNAQ | 12573 | GRVVASN | 0.227751 | -0.11202 |
| TS165 | 3396 | GCCCAAAGTAATCGGGTTAGGGATCTTGCACAG | 7985 | AQSNRVRDLAQ | 12574 | SNRVRDL | 0.227718 | -0.09285 |
| SyS1506 | 3397 | GCCCAAGAGAAAGAGACAGAGAGAAAAACTCGCACAG | 7986 | AQERDREKLAQ | 12575 | ERDREKL | 0.227632 | -0.12947 |
| GS855 | 3398 | GCCCAAAAGTCTGGACGAGTTCTACTGCACAG | 7987 | AQKSGTSSTAQ | 12576 | KSGTSST | 0.227463 | -0.16214 |
| SyS1507 | 3399 | GCCCAAGCTGGTCAGAGTACTATTTATGCACAG | 7988 | AQAGQSTIYAQ | 12577 | AGQSTIY | 0.227436 | -0.20224 |
| GS856 | 3400 | GCCCAAGAGTTTTCGCAGCCGAGGCTGGCACAG | 7989 | AQEFSQPRLAQ | 12578 | EFSQPRL | 0.22738 | -0.18245 |
| GS857 | 3401 | GCCCAAAACGTATGCGAGGTCGGATAAGGCACAG | 7990 | AQTYARSDKAQ | 12579 | TYARSDK | 0.227253 | -0.11091 |

FIG. 33 (Continued)

| | | | | | | | | |
|---|---|---|---|---|---|---|---|---|
| GS859 | 3402 | GCCCAAGGCAAATTCAACGGCCACACCGCACAG | 7991 | AQGKFNGHTAQ | 12580 | GKFNGHT | 0.227141 | -0.07202 |
| GS860 | 3403 | GCCCAACGGTTGATTAGTAGTAATGGGAATGCACAG | 7992 | AQRLISNGNAQ | 12581 | RLISNGN | 0.227083 | -0.13571 |
| GS861 | 3404 | GCCCAATTGAAGGAGTCGTTGGGGCCTGCACAG | 7993 | AQLKESLGPAQ | 12582 | LKESLGP | 0.226974 | -0.14811 |
| GS862 | 3405 | GCCCAAAACAGACACACCCTGCCGTCGCACAG | 7994 | AQNRHTLAVAQ | 12583 | NRHTLAV | 0.226794 | -0.18188 |
| GS863 | 3406 | GCCCAAAGAGACACCAGACTCAGCGCCGCACAG | 7995 | AQRDTRLSAAQ | 12584 | RDTRLSA | 0.226714 | -0.14334 |
| GS864 | 3407 | GCCCAAGTCAGCAGCAGACTCGGCAGCATCGCACAG | 7996 | AQVSRLGSIAQ | 12585 | VSRLGSI | 0.226686 | -0.12988 |
| GS865 | 3408 | GCCCAATTGACTACGTCGGTGATTTCGGCACAG | 7997 | AQLTTSVISAQ | 12586 | LTTSVIS | 0.226678 | -0.17291 |
| SyS1509 | 3409 | GCCCAATTTAAGGGGGTGGCTCATATTGCACAG | 7998 | AQFKGVAHIAQ | 12587 | FKGVAHI | 0.226637 | -0.1792 |
| GS866 | 3410 | GCCCAAAAGACGACGGAGGCTCTTCCTGCACAG | 7999 | AQKTTEALPAQ | 12588 | KTTEALP | 0.226561 | -0.15574 |
| SyS1510 | 3411 | GCCCAACGTAATCAGCATGATACTACTGCACAG | 8000 | AQRNQHDTTAQ | 12589 | RNQHDTT | 0.226461 | -0.1307 |
| SyS1511 | 3412 | GCCCAAAATAAGCTTCTGCCTCGTAGTGCACAG | 8001 | AQNKLLPRSAQ | 12590 | NKLLPRS | 0.226387 | -0.15657 |
| GS867 | 3413 | GCCCAAGTCAACAGCCACGAAAGAGCCGCACAG | 8002 | AQVNSHERAAQ | 12591 | VNSHERA | 0.226374 | -0.16814 |
| GS868 | 3414 | GCCCAAGCGAAGGGTAGTCTGAAATATGGCACAG | 8003 | AQAKGSLNMAQ | 12592 | AKGSLNM | 0.22628 | -0.08549 |
| SyS1512 | 3415 | GCCCAAGTTAAGACTAAGACTGATCGGGTTCTGGCACAG | 8004 | AQVKTDRVLAQ | 12593 | VKTDRVL | 0.226235 | -0.04586 |
| SyS1513 | 3416 | GCCCAACCGGTTCGGATCAGATTAGGGCACAG | 8005 | AQPRSDQIRAQ | 12594 | PRSDQIR | 0.226105 | -0.21694 |
| GS869 | 3417 | GCCCAAAACAGAGTCGGCACCGAAAGAGCACAG | 8006 | AQNRVGTERAQ | 12595 | NRVGTER | 0.226048 | -0.00622 |
| SyS1514 | 3418 | GCCCAAGGCGTCCCCACCGCACCGCACAG | 8007 | AQGVPTAGTAQ | 12596 | GVPTAGT | 0.226045 | -0.22557 |
| GS870 | 3419 | GCCCAAAGCCTCATGAAACAAAGCCACGCACAG | 8008 | AQSLMKQSHAQ | 12597 | SLMKQSH | 0.225961 | -0.13881 |
| GS871 | 3420 | GCCCAAGGCACCAGCAACATCATGGCACAG | 8009 | AQGTSSNIMAQ | 12598 | GTSSNIM | 0.225838 | -0.14143 |
| SyS1515 | 3421 | GCCCAACTTCGGAGTGATATTAGTACTGCACAG | 8010 | AQLRSDISTAQ | 12599 | LRSDIST | 0.225835 | -0.09082 |
| GS872 | 3422 | GCCCAAATGACCACCGCAGAGACCTCGCACAG | 8011 | AQMTTGRDLAQ | 12600 | MTTGRDL | 0.225564 | -0.06321 |
| SyS1516 | 3423 | GCCCAAAGTGGTTGCGAATAGTTATGCACAG | 8012 | AQSGVANSYAQ | 12601 | SGVANSY | 0.225464 | -0.10606 |
| SyS1517 | 3424 | GCCCAAGCGGTTCCGTCTTATAATAATGCACAG | 8013 | AQAVPSYNNAQ | 12602 | AVPSYNN | 0.225384 | -0.18728 |
| GS873 | 3425 | GCCCAACTCAACGGCGGCAACAGCCCCGCACAG | 8014 | AQLNGGNSPAQ | 12603 | LNGGNSP | 0.225327 | -0.11997 |
| GS874 | 3426 | GCCCAAAACAGCAGCACCAGCAGTGGGCACAG | 8015 | AQNSHSTSWAQ | 12604 | NSHSTSW | 0.225327 | -0.17291 |
| GS875 | 3427 | GCCCAAATGTATCATACGGGGCAGGTGGCACAG | 8016 | AQMYHTGQVAQ | 12605 | MYHTGQV | 0.22518 | -0.15855 |
| GS876 | 3428 | GCCCAAAGAGACAAAACTCTACATCGCCGCACAG | 8017 | AQRDKLYIAAQ | 12606 | RDKLYIA | 0.225179 | -0.14429 |
| SyS1518 | 3429 | GCCCAAAGGAAGTCGGAGGCGGTTCTTGCACAG | 8018 | AQRKSEAVLAQ | 12607 | RKSEAVL | 0.225067 | -0.14768 |
| SyP53 | 3430 | GCCCAACATAAGGGTATTCAGGTGATTGCACAG | 8019 | AQHKGIQVIAQ | 12608 | HKGIQVI | 0.224991 | -0.04221 |
| GP146 | 3431 | GCCCAAATTGGGAAGGATGCTCCGAAGGCACAG | 8020 | AQIGKDAPKAQ | 12609 | IGKDAPK | 0.224985 | -0.06655 |
| SyS1519 | 3432 | GCCCAAAGCCTCGCCGGCCTCCAAGACGCACAG | 8021 | AQSLAGLQDAQ | 12610 | SLAGLQD | 0.22498 | 0.118922 |
| SyS1520 | 3433 | GCCCAATTTAGGGTGTCTGTTGCTGAGGCACAG | 8022 | AQFRVSVAEAQ | 12611 | FRVSVAE | 0.22497 | -0.2305 |

FIG. 33 (Continued)

| | | | | | | | | |
|---|---|---|---|---|---|---|---|---|
| SyS1521 | 3434 | GCCCAAACCCACACAAAGAACACAGCATCGCACAG | 8023 | AQTHKEHSIAQ | 12612 | THKEHSI | 0.2249 | -0.06105 |
| SyS1522 | 3435 | GCCCAAAACAGCAACCACCACTACAGAGCACACAG | 8024 | AQNSNHTYRAQ | 12613 | NSNHTYR | 0.224808 | -0.22285 |
| SyS1523 | 3436 | GCCCAATTTAATGGGGTTCGTACGGTGGCACAG | 8025 | AQFNGVRTVAQ | 12614 | FNGVRTV | 0.224692 | -0.12465 |
| GS878 | 3437 | GCCCAACACATGGGCATGAGAGACGGCGCACAG | 8026 | AQHMGMRDGAQ | 12615 | HMGMRDG | 0.22465 | -0.16125 |
| SyS1524 | 3438 | GCCCAAGGGCAGCAGTCTATGGCGGTGGCACAG | 8027 | AQGQQSMAVAQ | 12616 | GQQSMAV | 0.224648 | -0.1923 |
| GS879 | 3439 | GCCCAATGGTGCGAGTCAGGTTAATCGTGCACAG | 8028 | AQWSSQVNRAQ | 12617 | WSSQVNR | 0.224293 | -0.16432 |
| SyS1525 | 3440 | GCCCAAGGTTGCCATGTTGGGGATGCCGGCACAG | 8029 | AQGSHVGMPAQ | 12618 | GSHVGMP | 0.224189 | -0.1392 |
| GP147 | 3441 | GCCCAAAAGGGGTCGTTGACTGCTAGTGCACAG | 8030 | AQKGSLTASAQ | 12619 | KGSLTAS | 0.224166 | -0.06794 |
| SyS1526 | 3442 | GCCCAAGGCGCCCAAAGCAACATCGTCGCACAG | 8031 | AQGAQSNIVAQ | 12620 | GAQSNIV | 0.224129 | -0.07858 |
| GS880 | 3443 | GCCCAAAATGATTATAATCATACGCGTGCACAG | 8032 | AQNDYNHTRAQ | 12621 | NDYNHTR | 0.224097 | -0.18547 |
| GS881 | 3444 | GCCCAACAAATCAACCCAGCAGCGTCGCACAG | 8033 | AQQINPSSVAQ | 12622 | QINPSSV | 0.224097 | -0.17829 |
| GS882 | 3445 | GCCCAAGCGTTGCGTGGTGCGTCTAATGCACAG | 8034 | AQALRGASNAQ | 12623 | ALRGASN | 0.224097 | -0.17112 |
| SyS1527 | 3446 | GCCCAAAGTGCTTCGACTATGTCGTTTGCACAG | 8035 | AQSASTMSFAQ | 12624 | SASTMSF | 0.223975 | -0.13887 |
| GS883 | 3447 | GCCCAACTCAGCAGCAACAACAACGCACACAG | 8036 | AQLSSNNNNAQ | 12625 | LSSNNNN | 0.223961 | -0.10614 |
| GS884 | 3448 | GCCCAATCTACGACGCTGGCGTCGAAGGCACAG | 8037 | AQSTTLASKAQ | 12626 | STTLASK | 0.223954 | -0.1411 |
| GS885 | 3449 | GCCCAACACAGAATGCTCGACGGCGTCGCACAG | 8038 | AQHRMLDGVAQ | 12627 | HRMLDGV | 0.223938 | -0.15478 |
| SyS1528 | 3450 | GCCCAAAGCAGCGAAAGCAGCACCCCGCACAG | 8039 | AQSSESSTPAQ | 12628 | SSESSTP | 0.223912 | -0.17678 |
| GS886 | 3451 | GCCCAATTGTATGATTCTAGTCATAGTGCACAG | 8040 | AQLYDSSHSAQ | 12629 | LYDSSHS | 0.223828 | -0.13594 |
| SyS1529 | 3452 | GCCCAAGGTAATTATAATTTGAGTGTGGCACAG | 8041 | AQGNYNLSVAQ | 12630 | GNYNLSV | 0.223824 | -0.18808 |
| GS887 | 3453 | GCCCAAATGCATAATGTTGCTACGGTGGCACAG | 8042 | AQMHNVATVAQ | 12631 | MHNVATV | 0.223778 | -0.12132 |
| SyS1530 | 3454 | GCCCAAACCAACTACGGCGACAGCGTCGCACAG | 8043 | AQTNYGDSVAQ | 12632 | TNYGDSV | 0.223637 | -0.06038 |
| SyS1531 | 3455 | GCCCAAAATCGTGGGGAGGATGCGCGGGCACAG | 8044 | AQNRGEDARAQ | 12633 | NRGEDAR | 0.223622 | 0.017796 |
| GS889 | 3456 | GCCCAATTTGGTAAGACGGCGGCTACTGCACAG | 8045 | AQFGKTAATAQ | 12634 | FGKTAAT | 0.223612 | -0.1451 |
| GS890 | 3457 | GCCCAAAATACGAAGGTTAATACTGAGGCACAG | 8046 | AQNTKVNTEAQ | 12635 | NTKVNTE | 0.223612 | -0.1451 |
| GS891 | 3458 | GCCCAAGTCACCGGCCACCTCAGCAGCGCACAG | 8047 | AQVTGHLSSAQ | 12636 | VTGHLSS | 0.223553 | -0.15945 |
| SyS1532 | 3459 | GCCCAAGTGGCTACTTCGCATTTGAAGGCACAG | 8048 | AQVATSHLKAQ | 12637 | VATSHLK | 0.223491 | -0.21436 |
| SyS1533 | 3460 | GCCCAATACACACCCCGGCAGCGACAGAGCACAG | 8049 | AQYTPGSDRAQ | 12638 | YTPGSDR | 0.223431 | -0.03541 |
| SyS1534 | 3461 | GCCCAAGGCTTCACCAGCCGTCACCCAGCGCACAG | 8050 | AQGFTVTHAQ | 12639 | GFTVTH | 0.223406 | -0.15859 |
| SyS1535 | 3462 | GCCCAAGCCGCGCCACCAGCACCACCGCACAG | 8051 | AQAAATSTTAQ | 12640 | AAATSTT | 0.223334 | -0.08247 |
| SyS1536 | 3463 | GCCCAAGCGAATATTCATGTTCATGGTGCACAG | 8052 | AQANIHVHGAQ | 12641 | ANIHVHG | 0.223187 | -0.13556 |
| SyS1537 | 3464 | GCCCAATATAGTTTGCGGGGTAATGATGCACAG | 8053 | AQYSLRGNDAQ | 12642 | YSLRGND | 0.223187 | -0.16344 |
| SyS1538 | 3465 | GCCCAAATTGATCAGATTGTGCAGCGTGCACAG | 8054 | AQIDQIVQRAQ | 12643 | IDQIVQR | 0.223187 | -0.19133 |

FIG. 33 (Continued)

| ID | No. | DNA Sequence | No. | Peptide | No. | Peptide | Value | Value |
|---|---|---|---|---|---|---|---|---|
| SyS1539 | 3466 | GCCCAATTCAACAGCGACCTCGCCATGGCACAG | 8055 | AQFNSDLAMAQ | 12644 | FNSDLAM | 0.223187 | -0.19133 |
| SyS1540 | 3467 | GCCCAAAATATGGAGTGCGCAGCGTTATGCACAG | 8056 | AQNMESQRYAQ | 12645 | NMESQRY | 0.223135 | -0.2231 |
| SyP54 | 3468 | GCCCAACCGCTTCTAGTTCGGCTTTCGGCACAG | 8057 | AQPLSSSLSAQ | 12646 | PLSSSLS | 0.222938 | -0.04335 |
| SyS1541 | 3469 | GCCCAACAGGGTACGCTTCATGCTGAGGCACAG | 8058 | AQQGTLHAEAQ | 12647 | QGTLHAE | 0.222917 | -0.19618 |
| SyS1542 | 3470 | GCCCAACCGACAGAGCCACGCCCTCGCACAG | 8059 | AQPDRATALAQ | 12648 | PDRATAL | 0.222911 | -0.1344 |
| SyS1543 | 3471 | GCCCAAGCCAACGGCAAAATCCAACTCGCACAG | 8060 | AQANGKIQLAQ | 12649 | ANGKIQL | 0.22286 | 0.163533 |
| SyS1545 | 3472 | GCCCAATACAGCAAAGACAGAGCACGACGGCACAG | 8061 | AQYSKDRHDAQ | 12650 | YSKDRHD | 0.22263 | 0.135905 |
| SyS1546 | 3473 | GCCCAAGACAGCACCAGCAGAGCCTGGGCACAG | 8062 | AQDSTSRAWAQ | 12651 | DSTSRAW | 0.222511 | -0.22891 |
| SyS1547 | 3474 | GCCCAAGGCCTCAGCGTCGCCATCCCGCACAG | 8063 | AQGLSVAIPAQ | 12652 | GLSVAIP | 0.222511 | -0.22891 |
| SyS1548 | 3475 | GCCCAATCGTATCTTACTAATCATGTGGCACAG | 8064 | AQSYLTNHVAQ | 12653 | SYLTNHV | 0.222327 | -0.20588 |
| SyS1550 | 3476 | GCCCAAGTTATTACGCATAATATGCCTGCACAG | 8065 | AQVITHNMPAQ | 12654 | VITHNMP | 0.222221 | -0.13192 |
| GS894 | 3477 | GCCCAAAACAGAACCCACGTCCCCAAGCACAG | 8066 | AQNRTHVPQAQ | 12655 | NRTHVPQ | 0.222189 | -0.10995 |
| GS895 | 3478 | GCCCAACTCCAAACCACCAGAGCCGTCGCACAG | 8067 | AQLQTTRAVAQ | 12656 | LQTTRAV | 0.222058 | 0.00505 |
| SyS1551 | 3479 | GCCCAAGCCCCAAGCGTCGACGTCGCACAG | 8068 | AQAPNAIDVAQ | 12657 | APNAIDV | 0.222003 | -0.13677 |
| GS896 | 3480 | GCCCAAGTCAGAGACAACACCGTCTACGCACAG | 8069 | AQVRDNTVYAQ | 12658 | VRDNTVY | 0.221995 | -0.14143 |
| SyS1552 | 3481 | GCCCAAACTCGTATTGGGACGTCGTTGGCACAG | 8070 | AQTRIGTSLAQ | 12659 | TRIGTSL | 0.221747 | -0.01731 |
| SyS1553 | 3482 | GCCCAAACCCTCACCAGCGGCAACGTCGCACAG | 8071 | AQTLTSGNVAQ | 12660 | TLTSGNV | 0.221657 | 0.075338 |
| GS897 | 3483 | GCCCAACATCTTGATACTATGCGGGGTGCACAG | 8072 | AQHLDTMRGAQ | 12661 | HLDTMRG | 0.221624 | -0.14743 |
| GS898 | 3484 | GCCCAACTCAGCAGCACCACCCTCAACGCACAG | 8073 | AQLSSTTLNAQ | 12662 | LSSTTLN | 0.221499 | -0.10327 |
| TS166 | 3485 | GCCCAAGTTCAGAGTAATAATATTACGACGTCTCGCACAG | 8074 | AQVQSNRTNAQ | 12663 | VQSNRTN | 0.221422 | -0.26117 |
| SyS1554 | 3486 | GCCCAAAATAATAATATTACGACGTCTTGGCACAG | 8075 | AQNNNITTSAQ | 12664 | NNNITTS | 0.221339 | -0.15304 |
| GS899 | 3487 | GCCCAAGTCGGCACCGCGCCGGCAAACTCGCACAG | 8076 | AQVGTAGKLAQ | 12665 | VGTAGKL | 0.221334 | -0.1471 |
| SyS1555 | 3488 | GCCCAACCCGCCATCAGCACCGACCACGCACAG | 8077 | AQPAISTDHAQ | 12666 | PAISTDH | 0.22129 | -0.17435 |
| GP148 | 3489 | GCCCAAAGTAATCTGGGTAATGTGCCGGCACAG | 8078 | AQSNLGNVPAQ | 12667 | SNLGNVP | 0.22117 | -0.04186 |
| SyS1556 | 3490 | GCCCAACAACAAAACCAAAGCAGATTCACCGCACAG | 8079 | AQQNQSRFTAQ | 12668 | QNQSRFT | 0.221076 | 0.133629 |
| GS900 | 3491 | GCCCAAGCTTCTAAGGGTATGACGTTGGCACAG | 8080 | AQASKGMTLAQ | 12669 | ASKGMTL | 0.221024 | -0.11947 |
| SyS1557 | 3492 | GCCCAAGCCACCGCGCCAAGACAAAACCGCACAG | 8081 | AQATAQDKTAQ | 12670 | ATAQDKT | 0.220998 | -0.14056 |
| SS100 | 3493 | GCCCAATGGGACAGCAGCAGCGTCAGAGCACAG | 8082 | AQWDSSSVRAQ | 12671 | WDSSSVR | 0.220864 | -0.36436 |
| SyS1558 | 3494 | GCCCAAACGAATGGTAGTGAGAAGAAGTGCACAG | 8083 | AQTNGSEKSAQ | 12672 | TNGSEKS | 0.220858 | -0.11495 |
| SyS1560 | 3495 | GCCCAATCTGCTGAGAATCATACGTATGCACAG | 8084 | AQSAENHTYAQ | 12673 | SAENHTY | 0.220753 | -0.21202 |
| SyS1561 | 3496 | GCCCAAAGCGTCCCCAAGCCTACCAAGCACAG | 8085 | AQSVPQAYQAQ | 12674 | SVPQAYQ | 0.220753 | -0.23296 |
| SyS1562 | 3497 | GCCCAAAAAGACTACGTCGTCACCAACGCACAG | 8086 | AQKDYVVTNAQ | 12675 | KDYVVTN | 0.220753 | -0.23296 |

FIG. 33 (Continued)

| | | | | | | | | |
|---|---|---|---|---|---|---|---|---|
| SyS1563 | 3498 | GCCCAAGTCGTCCAAATGAAACAAACCGCACAG | 8087 | AQVVQMKQTAQ | 12676 | VVQMKQT | 0.220688 | -0.18405 |
| GS901 | 3499 | GCCCAAGAGAACCCTCAGCCTCACCGCCGCACAG | 8088 | AQRTLSLTAAQ | 12677 | RTLSLTA | 0.220684 | -0.171 |
| GS902 | 3500 | GCCCAAAACACCGTCGTCGGCAGCAGCGCACAG | 8089 | AQNTVVGSSAQ | 12678 | NTVVGSS | 0.220539 | -0.15192 |
| GS903 | 3501 | GCCCAATCTTTGAATAGTCCGACGACTGCACAG | 8090 | AQSLNSPTTAQ | 12679 | SLNSPTT | 0.220388 | -0.12331 |
| SyS1564 | 3502 | GCCCAAACCACCGGCATGGACGTCAAAGCACAG | 8091 | AQTTGMDVKAQ | 12680 | TTGMDVK | 0.220289 | -0.06566 |
| GS907 | 3503 | GCCCAAAACAACAGAGACACCACCAACGCACAG | 8092 | AQNNRDTTNAQ | 12681 | NNRDTTN | 0.220068 | -0.11907 |
| GS908 | 3504 | GCCCAATGGGGCAACTACACCCCACCGCACAG | 8093 | AQWGNYTPTAQ | 12682 | WGNYTPT | 0.220016 | -0.16842 |
| SyS1565 | 3505 | GCCCAAGGGATTACGGCGTTCTGATACTGCACAG | 8094 | AQGITRSDTAQ | 12683 | GITRSDT | 0.219828 | -0.01242 |
| GS910 | 3506 | GCCCAACACATCCTCAGAACCCCGAAGCACAG | 8095 | AQHILRTPEAQ | 12684 | HILRTPE | 0.219735 | -0.1756 |
| GS911 | 3507 | GCCCAACGTTCTGCTAGTGTGGAGAATGCACAG | 8096 | AQRSASVENAQ | 12685 | RSASVEN | 0.219721 | -0.14524 |
| SyS1568 | 3508 | GCCCAAAGCCTCAGCCTCGGCAAAGGCGCACAG | 8097 | AQSLSLGKGAQ | 12686 | SLSLGKG | 0.219525 | -0.0022 |
| SyS1570 | 3509 | GCCCAAAAAGAGAAGTCGTCGGCGACGCACAG | 8098 | AQKREVVGDAQ | 12687 | KREVVGD | 0.219431 | -0.0561 |
| SyS1571 | 3510 | GCCCAAATCCAACCAGCAACCACGAAGCACAG | 8099 | AQIQPSNHEAQ | 12688 | IQPSNHE | 0.219421 | -0.16223 |
| GS912 | 3511 | GCCCAAATGAATCTGGGTAATGCGCCGGCACAG | 8100 | AQMNLGNAPAQ | 12689 | MNLGNAP | 0.219412 | -0.18278 |
| SyS1572 | 3512 | GCCCAACAGCCGAATAATACTAATAGTGCACAG | 8101 | AQQPNNTNSAQ | 12690 | QPNNTNS | 0.219392 | -0.15739 |
| GS914 | 3513 | GCCCAACTCCAAAGCATGGTCCAAGGCGCACAG | 8102 | AQLQSMVQGAQ | 12691 | LQSMVQG | 0.219195 | -0.14779 |
| SyS1573 | 3514 | GCCCAACATGGTAATACTACTTCGACTGCACAG | 8103 | AQHGNTTSTAQ | 12692 | HGNTTST | 0.219043 | -0.04692 |
| SyS1576 | 3515 | GCCCAAATCCAAAGCACCGTCACCCTGCACAG | 8104 | AQIQSTVTLAQ | 12693 | IQSTVTL | 0.218993 | -0.14672 |
| SyS1577 | 3516 | GCCCAAGACGACAGACAAGGCCCCAGAGCACAG | 8105 | AQDDRQGPRAQ | 12694 | DDRQGPR | 0.218992 | -0.13071 |
| SyS1578 | 3517 | GCCCAACAGACGGCTACGAATATTCTGGCACAG | 8106 | AQQTATNILAQ | 12695 | QTATNIL | 0.218912 | -0.22649 |
| GS915 | 3518 | GCCCAACGGCAGCATGCGGATACTGTTGCACAG | 8107 | AQRQHADTVAQ | 12696 | RQHADTV | 0.218828 | -0.10831 |
| GS916 | 3519 | GCCCAAACTAGGTCGGAGAGTTCTCTGGCACAG | 8108 | AQTRSESSLAQ | 12697 | TRSESSL | 0.218795 | -0.16718 |
| GS917 | 3520 | GCCCAACGTGGGCATGATGATCCGGCTGTGGCACAG | 8109 | AQRGHDPAVAQ | 12698 | RGHDPAV | 0.218795 | -0.16718 |
| SyS1579 | 3521 | GCCCAAAGCACCAGCCAAACGACCTCGCACAG | 8110 | AQSTSQTDLAQ | 12699 | STSQTDL | 0.218784 | -0.10958 |
| SyS1580 | 3522 | GCCCAAGTCAGCACCAGCGCCGTCCTCGCACAG | 8111 | AQVSTSAVLAQ | 12700 | VSTSAVL | 0.218614 | -0.10842 |
| SyS1581 | 3523 | GCCCAAAGCATGCCCCCGGAAAGATTCGCACAG | 8112 | AQSMPPERFAQ | 12701 | SMPPERF | 0.218531 | -0.14302 |
| SS104 | 3524 | GCCCAAGTCACCAGCGCGCCACCCGTCGCACAG | 8113 | AQVTSAHPVAQ | 12702 | VTSAHPV | 0.218414 | -0.35519 |
| SyS1582 | 3525 | GCCCAAACCAGCAGACAGTCGGCCTGCACAG | 8114 | AQTSRQVGLAQ | 12703 | TSRQVGL | 0.218414 | -0.08585 |
| SyS1583 | 3526 | GCCCAAACTCCGAAGTTTCTTATGAGGCACAG | 8115 | AQTPKFSYEAQ | 12704 | TPKFSYE | 0.218414 | -0.23133 |
| GS918 | 3527 | GCCCAAAACAGAATGGCCAGCACCATGGCACAG | 8116 | AQNRMASTMAQ | 12705 | NRMASTM | 0.218278 | -0.15766 |
| SyS1584 | 3528 | GCCCAACTCCTCGACAACACCAGACCCGCACAG | 8117 | AQLLDNTRPAQ | 12706 | LLDNTRP | 0.218247 | 0.036592 |
| GS919 | 3529 | GCCCAATTGACGACTATTCCTAGTACTGCACAG | 8118 | AQLTTIPSTAQ | 12707 | LTTIPST | 0.218243 | -0.16932 |

FIG. 33 (Continued)

| | | | | | | | |
|---|---|---|---|---|---|---|---|
| TS168 | 3530 | GCCCAAGCCAACAGAATCAGAGACAACGCACAG | 8119 | AQANRIRDNAQ | 12708 | ANRIRDN | 0.218215 | -0.03931 |
| SyS1585 | 3531 | GCCCAACCCAGAGACATCCAAAGAACCGCACAG | 8120 | AQPRDIQRTAQ | 12709 | PRDIQRT | 0.218142 | -0.00772 |
| GP149 | 3532 | GCCCAAATGCCTCATGGGCTTAAGAATGCACAG | 8121 | AQMPHGLKNAQ | 12710 | MPHGLKN | 0.218113 | -0.06725 |
| SyS1586 | 3533 | GCCCAACCTTTTACGCAGAATCATCTTGCACAG | 8122 | AQPFTQNHLAQ | 12711 | PFTQNHL | 0.218077 | -0.16344 |
| SyS1587 | 3534 | GCCCAAAATGCGAATGGTAATACTCGTGCACAG | 8123 | AQNANGNTRAQ | 12712 | NANGNTR | 0.218042 | -0.18163 |
| GS920 | 3535 | GCCCAACTGGCTTATTCTACGTCGGCGGCACAG | 8124 | AQLAYSTSAAQ | 12713 | LAYSTSA | 0.217974 | 0.000834 |
| GS921 | 3536 | GCCCAAACCGACAGATACAACATCAAAGCACAG | 8125 | AQTDRYNIKAQ | 12714 | TDRYNIK | 0.217916 | -0.16484 |
| GS922 | 3537 | GCCCAATATGTTACTAGTGCTGAGCATGCACAG | 8126 | AQYVTSAEHAQ | 12715 | YVTSAEH | 0.217839 | -0.1765 |
| GS923 | 3538 | GCCCAAAGTCATCAGCAGACTACGGTTGCACAG | 8127 | AQSHQQTTVAQ | 12716 | SHQQTTV | 0.217682 | -0.10921 |
| SyS1588 | 3539 | GCCCAACTTAATATGCAGACGAGGGGGCACAG | 8128 | AQLNMQTRGAQ | 12717 | LNMQTRG | 0.217651 | -0.01433 |
| GS925 | 3540 | GCCCAATACACCCCCAACTCAAAAGCGCACAG | 8129 | AQYTPQLKSAQ | 12718 | YTPQLKS | 0.217643 | -0.17958 |
| SyS1589 | 3541 | GCCCAACAGATTAATGGTCAGGTTATTGCACAG | 8130 | AQQINGQVIAQ | 12719 | QINGQVI | 0.217561 | -0.20466 |
| GS926 | 3542 | GCCCAAACGCGTGAGGGTGTGTTGCCTGCACAG | 8131 | AQTREGVLPAQ | 12720 | TREGVLP | 0.217502 | -0.13952 |
| SyS1591 | 3543 | GCCCAAGTTCATCAGTCGGTGCCGCTGGCACAG | 8132 | AQVHQSVPLAQ | 12721 | VHQSVPL | 0.217352 | -0.17314 |
| SyS1592 | 3544 | GCCCAACCGTATTCGATGGGGCATCCTGCACAG | 8133 | AQPYSMGHPAQ | 12722 | PYSMGHP | 0.217352 | -0.17314 |
| GS927 | 3545 | GCCCAAGGCACCAAAACCCACAGCCTCGCACAG | 8134 | AQGTKTHSLAQ | 12723 | GTKTHSL | 0.217339 | -0.14906 |
| SyS1595 | 3546 | GCCCAAACGCTGACTACGGGGTCGAAGGCACAG | 8135 | AQTLTTGSKAQ | 12724 | TLTTGSK | 0.217166 | -0.04194 |
| GS928 | 3547 | GCCCAATTTACGATTGGTGTTACGGGGGCACAG | 8136 | AQFTIGVTGAQ | 12725 | FTIGVTG | 0.21713 | -0.0827 |
| GS930 | 3548 | GCCCAACTCAGCAGCCACAACCACAACGCACAG | 8137 | AQLSSHNHNAQ | 12726 | LSSHNHN | 0.216901 | -0.13284 |
| SyS1596 | 3549 | GCCCAAACGGCAAAATGCCCCTCGAAGCACAG | 8138 | AQTGKMPLEAQ | 12727 | TGKMPLE | 0.216862 | -0.14056 |
| GS931 | 3550 | GCCCAAACTGCGAATCCTCATGCGACTGCACAG | 8139 | AQTANPHATAQ | 12728 | TANPHAT | 0.216859 | -0.04999 |
| SyS1597 | 3551 | GCCCAACACGACAGCGTCGCCAGCGCACAG | 8140 | AQHDSVASSAQ | 12729 | HDSVASS | 0.216844 | -0.154 |
| GS932 | 3552 | GCCCAAACGCGTGCGGATGTGTTGATGGCACAG | 8141 | AQTRADVLMAQ | 12730 | TRADVLM | 0.216806 | -0.13761 |
| GS933 | 3553 | GCCCAAGCTAATCATGCTTCTAATGCGGCACAG | 8142 | AQANHASNAAQ | 12731 | ANHASNA | 0.216449 | -0.09199 |
| SyS1599 | 3554 | GCCCAAAGCCACACATCGTCGGCGTCGAAGCACAG | 8143 | AQSHIVGVEAQ | 12732 | SHIVGVE | 0.216347 | 0.074638 |
| GS934 | 3555 | GCCCAATACACCGCCCAAAAAACCAGGCACAG | 8144 | AQYTAQKTSAQ | 12733 | YTAQKTS | 0.2162 | -0.16573 |
| SyS1600 | 3556 | GCCCAATTGCCTGCTGTGCAGAAGATGGCACAG | 8145 | AQLPAVQKMAQ | 12734 | LPAVQKM | 0.216175 | -0.12465 |
| SyS1601 | 3557 | GCCCAATCTGGTATTCAGACGGCTAAGGCACAG | 8146 | AQSGIQTAKAQ | 12735 | SGIQTAK | 0.215988 | -0.14283 |
| GS935 | 3558 | GCCCAAGATCCGGTGAAGATTGGTCATGCACAG | 8147 | AQDPVKIGHAQ | 12736 | DPVKIGH | 0.215963 | -0.16125 |
| GS936 | 3559 | GCCCAAAGTCAGACTATGAGTAAGAGTGCACAG | 8148 | AQSQTMSKSAQ | 12737 | SQTMSKS | 0.215809 | -0.07639 |
| SyS1602 | 3560 | GCCCAAAGCCTCACCCCACCAAACATCGCACAG | 8149 | AQSLTPTNIAQ | 12738 | SLTPTNI | 0.215809 | -0.0396 |
| GS937 | 3561 | GCCCAATATCTTAATAATACGAATTCTGCACAG | 8150 | AQYLNNTNSAQ | 12739 | YLNNTNS | 0.215545 | -0.18054 |

FIG. 33 (Continued)

| | | | | | | | |
|---|---|---|---|---|---|---|---|
| GS938 | 3562 | GCCCAAATGACCAGAATGAGCCAAAACGCACAG | AQMTRMSQNAQ | 12740 | MTRMSQN | 0.215545 | -0.18054 |
| GS939 | 3563 | GCCCAAGTCAACCAAAGCCTCAGCAGAGCACAG | AQVNQSLSRAQ | 12741 | VNQSLSR | 0.215514 | -0.03828 |
| GS940 | 3564 | GCCCAAGAACCGTCACCGAACAGAGAGCACAG | AQRTVTDNRAQ | 12742 | RTVTDNR | 0.21543 | -0.10655 |
| SyS1603 | 3565 | GCCCAAATTACTGGGGTGTTTGCTAATGCACAG | AQITGVFANAQ | 12743 | ITGVFAN | 0.215212 | -0.05959 |
| SyS1604 | 3566 | GCCCAATCGCTGGGCTGAGTAGGGTTGCACAG | AQSPGLSRVAQ | 12744 | SPGLSRV | 0.215048 | -0.09636 |
| GP151 | 3567 | GCCCAAGTGGTGAATCCTCAGACTAGGGCACAG | AQVVNPQTRAQ | 12745 | VVNPQTR | 0.214905 | -0.06586 |
| SyS1606 | 3568 | GCCCAATGGAGCCAAAGCCTCAGCGCCGCACAG | AQWSQSLSAAQ | 12746 | WSQSLSA | 0.214764 | -0.14405 |
| SyS1607 | 3569 | GCCCAACCCAGAGACGCCAGCAACGACGCACAG | AQPRDASNDAQ | 12747 | PRDASND | 0.214659 | -0.20224 |
| GS942 | 3570 | GCCCAATACACCAGCATGACGAATTCGCACAG | AQYTSMTEFAQ | 12748 | YTSMTEF | 0.214654 | -0.17112 |
| SS106 | 3571 | GCCCAAAACAACAGCCCCAGCCCAGAGCACAG | AQNNSPSPRAQ | 12749 | NNSPSPR | 0.214625 | -0.35665 |
| SyS1608 | 3572 | GCCCAAAAACAGCCTCAGCCACGGCGACGCACAG | AQNSLSHGDAQ | 12750 | NSLSHGD | 0.21457 | -0.10404 |
| SyS1609 | 3573 | GCCCAAAGAGTCGCCGGCGAAATGGCCGCACAG | AQRVAGEMAAQ | 12751 | RVAGEMA | 0.214459 | 0.040653 |
| GS943 | 3574 | GCCCAAGGTATTGGGTCTAGGGAGCTTGCACAG | AQGIGSRELAQ | 12752 | GIGSREL | 0.214321 | -0.1462 |
| SyS1610 | 3575 | GCCCAATATGTTAGTCGTATTCGTGATGCACAG | AQYVSRIRDAQ | 12753 | YVSRIRD | 0.214067 | -0.19375 |
| SyS1611 | 3576 | GCCCAATACCCCAGCCCAACGACAACGCACAG | AQYPSPNDNAQ | 12754 | YPSPNDN | 0.213993 | -0.16708 |
| SyS1612 | 3577 | GCCCAACTTCAGAGGACGGGCATAATGCACAG | AQLQRTAHNAQ | 12755 | LQRTAHN | 0.213963 | -0.15374 |
| SyS1613 | 3578 | GCCCAACTCGACAGCCTCAGCAGACACGCACAG | AQLDSLSRHAQ | 12756 | LDSLSRH | 0.213963 | -0.15374 |
| GS945 | 3579 | GCCCAAACCAAAATCAGCGCGGAGCGCACAG | AQTKISAGSAQ | 12757 | TKISAGS | 0.21391 | -0.10628 |
| SyS1614 | 3580 | GCCCAAAAAGACAACAGCCCCGTCGTCGCACAG | AQKDNSPVVAQ | 12758 | KDNSPVV | 0.213893 | -0.11374 |
| SyS1615 | 3581 | GCCCAAACCGGCCAAGGCAGCAGCCTCGCACAG | AQTGQGSSLAQ | 12759 | TGQGSSL | 0.213721 | -0.16397 |
| SyS1617 | 3582 | GCCCAAGATACGCATCTGAGTCGTCATGCACAG | AQDTHLSRHAQ | 12760 | DTHLSRH | 0.213534 | -0.21194 |
| SyS1618 | 3583 | GCCCAAGATATTGTTAGGAGGCAGGCTGCACAG | AQDIVRRQAAQ | 12761 | DIVRRQA | 0.213267 | -0.03009 |
| SyS1619 | 3584 | GCCCAAGCTATGAAGTATGCGCAGACTGCACAG | AQAMKYAQTAQ | 12762 | AMKYAQT | 0.213114 | -0.15011 |
| SyS1620 | 3585 | GCCCAAAGGCTGGCTGATCAGCATCCGGCACAG | AQRLADQHPAQ | 12763 | RLADQHP | 0.213086 | -0.20093 |
| SyS1621 | 3586 | GCCCAAGCTCCTGATAGTACTCGGATGGCACAG | AQAPDSTRMAQ | 12764 | APDSTRM | 0.213044 | 0.014524 |
| SyS1622 | 3587 | GCCCAAAGTCGGGTTTCTTCCTTCTTCGGCACAG | AQSRVSPSSAQ | 12765 | SRVSPSS | 0.213013 | 0.008275 |
| GS949 | 3588 | GCCCAAGTGCATGGTCAGGGTGAGCCTGCACAG | AQVHGQGEPAQ | 12766 | VHGQGEP | 0.212959 | -0.1765 |
| SyS1623 | 3589 | GCCCAAATGAGAGACAGCAGCAGCAGAGCACAG | AQMRDSSTRAQ | 12767 | MRDSSTR | 0.21283 | 0.073268 |
| GS951 | 3590 | GCCCAATGGCCCAACACCAACACCGCACAG | AQWPQHTNTAQ | 12768 | WPQHTNT | 0.212527 | -0.15855 |
| GS952 | 3591 | GCCCAAGTCGGCAGCTACCCGTCACCGCACAG | AQVGSYPVTAQ | 12769 | VGSYPVT | 0.21252 | 0.007456 |
| SyS1625 | 3592 | GCCCAAACTGCGACTCAGGGGCTAATGCACAG | AQTATQGANAQ | 12770 | TATQGAN | 0.212372 | -0.07076 |
| SyS1626 | 3593 | GCCCAAAAGAATAATAAGTATGGATAGTGCACAG | AQKNNSMDSAQ | 12771 | KNNSMDS | 0.212366 | -0.12084 |

FIG. 33 (Continued)

| | | | | | | | | |
|---|---|---|---|---|---|---|---|---|
| SyS1628 | 3594 | GCCCAACACACCAACGCCGTCAAAGAGAGCACAG | 8183 | AQHTNAVKEAQ | 12772 | HTNAVKE | 0.212319 | 0.211829 |
| GS953 | 3595 | GCCCAACTTCATTCGGTGACTACGCCGGCACAG | 8184 | AQLHSVTTPAQ | 12773 | LHSVTTP | 0.212166 | -0.0828 |
| SyS1629 | 3596 | GCCCAAGCCCGCGGCAACAAAACTTCGCACAG | 8185 | AQAPGQQNFAQ | 12774 | APGQQNF | 0.212026 | 0.059715 |
| GS955 | 3597 | GCCCAATCTTATACTAATCGTACTATGGCACAG | 8186 | AQSYTNRTMAQ | 12775 | SYTNRTM | 0.211833 | -0.0714 |
| SyS1632 | 3598 | GCCCAATCGGGTCAGAGTAATACGAAGGCACAG | 8187 | AQSGQSNTKAQ | 12776 | SGQSNTK | 0.211749 | -0.18984 |
| SyS1633 | 3599 | GCCCAAGACAGCTACAGAGCCCAAAGCGCACAG | 8188 | AQDSYRAQSAQ | 12777 | DSYRAQS | 0.211749 | -0.02105 |
| SyS1634 | 3600 | GCCCAAATGTATAAGCATAATTCTGATGCACAG | 8189 | AQMYKHNSDAQ | 12778 | MYKHNSD | 0.211732 | -0.06767 |
| GS957 | 3601 | GCCCAAAGCCTCGCCATGGTCAACCCCGCACAG | 8190 | AQSLAMVNPAQ | 12779 | SLAMVNP | 0.211678 | -0.17768 |
| SyS1635 | 3602 | GCCCAACCCTCACCAGCAAAAGCATGGCACAG | 8191 | AQPLTSKSMAQ | 12780 | PLTSKSM | 0.211599 | 0.023996 |
| GS958 | 3603 | GCCCAACTCGGCGCCCAACCCACCCCGCACAG | 8192 | AQLGAQPTPAQ | 12781 | LGAQPTP | 0.211205 | -0.15955 |
| GS959 | 3604 | GCCCAAGAAGGCAACCAAAAAACCCAAGCACAG | 8193 | AQEGNQKPQAQ | 12782 | EGNQKPQ | 0.211139 | -0.18637 |
| SyP56 | 3605 | GCCCAACAGGTTCGGCCGGGTGCTCATGCACAG | 8194 | AQQVRPGAHAQ | 12783 | QVRPGAH | 0.211056 | -0.04396 |
| GS962 | 3606 | GCCCAAAGCGGCAACATCACCGCCATGGCACAG | 8195 | AQSGNITAMAQ | 12784 | SGNITAM | 0.210967 | -0.16842 |
| SyS1637 | 3607 | GCCCAAAAACGACACAGCAAAATCGCCGAAGCACAG | 8196 | AQNDSKIAEAQ | 12785 | NDSKIAE | 0.210955 | -0.2305 |
| SyS1638 | 3608 | GCCCAAATCATGAAAAACGAACACAACGCACAG | 8197 | AQIMKNEHNAQ | 12786 | IMKNEHN | 0.210886 | -0.16102 |
| GS963 | 3609 | GCCCAACTTTGACGAATACTGATCGGGCACAG | 8198 | AQLLTNTDRAQ | 12787 | LLTNTDR | 0.210857 | -0.16432 |
| SyS1640 | 3610 | GCCCAAGATACGGCGCAGAGTCGTAATGCACAG | 8199 | AQDTAQSRNAQ | 12788 | DTAQSRN | 0.210588 | 0.341933 |
| SyS1641 | 3611 | GCCCAAATTGATCATGGTAAGACGAATGCACAG | 8200 | AQIDHGKTNAQ | 12789 | IDHGKTN | 0.210574 | -0.15253 |
| GS964 | 3612 | GCCCAAACCAGCCCAGAAGCCTCCTCGCACAG | 8201 | AQTSPRSLLAQ | 12790 | TSPRSLL | 0.210515 | -0.15764 |
| GS965 | 3613 | GCCCAATCGAATCCTCGGGATTCTAGTGCACAG | 8202 | AQSNPRDSSAQ | 12791 | SNPRDSS | 0.210308 | -0.12807 |
| SyS1643 | 3614 | GCCCAAATCATGCAAAGCATCCAAAACGCACAG | 8203 | AQIMQSIQNAQ | 12792 | IMQSIQN | 0.210287 | -0.14405 |
| GS966 | 3615 | GCCCAAAAAGTCAGCCCCAGCACCGCACAG | 8204 | AQKVSPSSTAQ | 12793 | KVSPSST | 0.210279 | -0.06417 |
| SyS1645 | 3616 | GCCCAAACCGGCCCCAGCCTCGCACAG | 8205 | AQTGPSPSLAQ | 12794 | TGPSPSL | 0.210228 | -0.17505 |
| SyS1646 | 3617 | GCCCAAGGCGGCGCCGCAGAGCCCAAGCCGCACAG | 8206 | AQGAARAQAAAQ | 12795 | GAARAQA | 0.210219 | 0.035379 |
| GS967 | 3618 | GCCCAAAAGTTTCAGTCTCCTGAGCCTGCACAG | 8207 | AQKFQSPEPAQ | 12796 | KFQSPEP | 0.210082 | -0.18009 |
| SyS1647 | 3619 | GCCCAAATGGCGACGAATTCGACGGAGGCACAG | 8208 | AQMATNSTEAQ | 12797 | MATNSTE | 0.210073 | -0.15738 |
| GS968 | 3620 | GCCCAAAACGTCCTCACCAACATCAGCGCACAG | 8209 | AQNVLTNISAQ | 12798 | NVLTNIS | 0.210069 | -0.17386 |
| SS112 | 3621 | GCCCAAAAGAATGGTATGAATTTGGTGGCACAG | 8210 | AQKNGMNLVAQ | 12799 | KNGMNLV | 0.210013 | -0.32377 |
| SyS1649 | 3622 | GCCCAAACTCTACGCAGCCTTCTAGTGCACAG | 8211 | AQTPTQPSSAQ | 12800 | TPTQPSS | 0.209867 | -0.19254 |
| SyS1650 | 3623 | GCCCAAACTAAGGAGCTTGTTATTCATGCACAG | 8212 | AQTKELVIHAQ | 12801 | TKELVIH | 0.209867 | -0.19254 |
| SyS1651 | 3624 | GCCCAAATCATGAACCAAAGCGTCCAAGCACAG | 8213 | AQIMNQSVQAQ | 12802 | IMNQSVQ | 0.209715 | -0.03979 |
| SyS1653 | 3625 | GCCCAAGTGTCTAATGCTAGGGATAAGGCACAG | 8214 | AQVSNARDKAQ | 12803 | VSNARDK | 0.209549 | -0.14041 |

FIG. 33 (Continued)

| | | | | | | | | |
|---|---|---|---|---|---|---|---|---|
| TS169 | 3626 | GCCCAAAGTAATCATACGCGGTCGTATGCACAG | 8215 | AQSNHTRSYAQ | 12804 | SNHTRSY | 0.20947 | -0.21368 |
| GS971 | 3627 | GCCCAACACCACGACAGACTCAACCCGCACAG | 8216 | AQHTDRLNPAQ | 12805 | HTDRLNP | 0.209344 | -0.14238 |
| SyS1654 | 3628 | GCCCAAGCGCCCCAGCATGAGCGACGGCACAG | 8217 | AQAAPSMSDAQ | 12806 | AAPSMSD | 0.209262 | -0.17557 |
| GS972 | 3629 | GCCCAATTTCGAATACGCATGCTTGGCACAG | 8218 | AQFSNTHALAQ | 12807 | FSNTHAL | 0.209156 | -0.17381 |
| SyS1655 | 3630 | GCCCAAGCTCATGATCTGCATCGTGTGGCACAG | 8219 | AQAHDLHRVAQ | 12808 | AHDLHRV | 0.209091 | -0.17998 |
| SyS1656 | 3631 | GCCCAACTTCAGGTTAATCATGTGGCGGCACAG | 8220 | AQLQVNHVAAQ | 12809 | LQVNHVA | 0.209057 | -0.14526 |
| SyS1657 | 3632 | GCCCAAAGCGGCCCCAACCTCAGCAGAGCACAG | 8221 | AQSGPNLSRAQ | 12810 | SGPNLSR | 0.209039 | 0.179343 |
| GS974 | 3633 | GCCCAAACTTATACGTGCGACGCCTGGTGCACAG | 8222 | AQTYTSTPGAQ | 12811 | TYTSTPG | 0.209033 | -0.13253 |
| GS975 | 3634 | GCCCAATATGGTACTCCTCCTTCGACGGCACAG | 8223 | AQYGTPPSTAQ | 12812 | YGTPPST | 0.209029 | -0.11621 |
| SyS1658 | 3635 | GCCCAATATGGTGTGAGTTCGGGTAGTGCACAG | 8224 | AQYGVSSGSAQ | 12813 | YGVSSGS | 0.209 | -0.07131 |
| SyS1659 | 3636 | GCCCAACCCACCAGAGACCTCATGAGCGCACAG | 8225 | AQPTRDLMSAQ | 12814 | PTRDLMS | 0.209 | -0.16708 |
| SyS1660 | 3637 | GCCCAAAAGATTGATGCGATGACGCAGGCACAG | 8226 | AQKIDAMTQAQ | 12815 | KIDAMTQ | 0.208964 | -0.12454 |
| GS976 | 3638 | GCCCAAAGAATCGGCACCAGCGAAGTCGCACAG | 8227 | AQRIGTSEVAQ | 12816 | RIGTSEV | 0.208937 | -0.10921 |
| GS977 | 3639 | GCCCAATTTGATCCTCCTTCAGTCGTCGGCACAG | 8228 | AQFDPLQSSAQ | 12817 | FDPLQSS | 0.208624 | -0.13472 |
| SyS1662 | 3640 | GCCCAACTCCTCCACCACGTCGAAGTCGCACAG | 8229 | AQLLHHVEVAQ | 12818 | LLHHVEV | 0.208542 | -0.15011 |
| GS978 | 3641 | GCCCAAGTCACCCTCGGCAACAGCGTCGCACAG | 8230 | AQVTLGNSVAQ | 12819 | VTLGNSV | 0.208389 | -0.14524 |
| SyS1663 | 3642 | GCCCAACTCCTCAACGACAGAAGCGTCGCACAG | 8231 | AQLLNDRSVAQ | 12820 | LLNDRSV | 0.208296 | -0.09749 |
| GS979 | 3643 | GCCCAATTCGTCGACAGAGAGACCCCAAGCACAG | 8232 | AQFVDRRPQAQ | 12821 | FVDRRPQ | 0.207955 | -0.00471 |
| SyS1664 | 3644 | GCCCAAACGAATGTGACTACGACGACGGCACAG | 8233 | AQTNVTTTTAQ | 12822 | TNVTTTT | 0.207819 | -0.05555 |
| SyS1665 | 3645 | GCCCAAGACGAAACCAACAACAAAGATGGGCACAG | 8234 | AQDETNKRWAQ | 12823 | DETNKRW | 0.207819 | -0.20709 |
| SyS1666 | 3646 | GCCCAAACGTCGACGTCTGCTATTCGGGCACAG | 8235 | AQTSTSAIRAQ | 12824 | TSTSAIR | 0.207608 | -0.1626 |
| SyS1668 | 3647 | GCCCAAGGCACCAGAGAGTCCAAGGCGCACAG | 8236 | AQGTSRVQGAQ | 12825 | GTSRVQG | 0.207468 | 0.069325 |
| SyS1669 | 3648 | GCCCAACTCAACACCATGGCCCTCCCGCACAG | 8237 | AQLNTMALPAQ | 12826 | LNTMALP | 0.207441 | -0.15981 |
| SyS1671 | 3649 | GCCCAAAGTACTCATGCGACTGATAGGGCACAG | 8238 | AQSTHATDRAQ | 12827 | STHATDR | 0.207437 | 0.052678 |
| SyS1672 | 3650 | GCCCAACACCACGGCGTCACCAGCGGCGCACAG | 8239 | AQHHGVTSGAQ | 12828 | HHGVTSG | 0.207346 | -0.13809 |
| SyS1674 | 3651 | GCCCAAGGCCTCATGGCCAACAACCCGCACAG | 8240 | AQGLMANNPAQ | 12829 | GLMANNP | 0.207257 | -0.19723 |
| SyS1675 | 3652 | GCCCAAGGGTCTTCGTCTAATTCGTTTGCACAG | 8241 | AQGSSSNSFAQ | 12830 | GSSSNSF | 0.207096 | -0.03155 |
| GS985 | 3653 | GCCCAAAGAGAAAAAATGACCCTCCTCGCACAG | 8242 | AQREKMTLLAQ | 12831 | REKMTLL | 0.207031 | -0.18368 |
| SyS1676 | 3654 | GCCCAAAGCCCCGTCAGCAGCGACAGCGCACAG | 8243 | AQSPVSSDSAQ | 12832 | SPVSSDS | 0.206943 | -0.18954 |
| SyS1679 | 3655 | GCCCAAGACGTCGCCCACAAAGACAGAGCACAG | 8244 | AQDVAHKDRAQ | 12833 | DVAHKDR | 0.206739 | -0.10729 |
| SyS1680 | 3656 | GCCCAAAGTATGGTTTCTAATATTGCGGCACAG | 8245 | AQSMVSNIAAQ | 12834 | SMVSNIA | 0.206728 | -0.08096 |
| GS986 | 3657 | GCCCAAAATGATGCATAATATGCAGTCTGCACAG | 8246 | AQMMHNMMQSAQ | 12835 | MMHNMQS | 0.20664 | -0.13284 |

FIG. 33 (Continued)

| | | | | | | | | |
|---|---|---|---|---|---|---|---|---|
| GS987 | 3658 | GCCCAAGTGTGTGAATTCTTCTCGGATGGCACAG | 8247 | AQVSNSSRMAQ | 12836 | VSNSSRM | 0.206658 | -0.16842 |
| GS988 | 3659 | GCCCAATATACGGCTACTAAGGCGAGTGCACAG | 8248 | AQYTATKASAQ | 12837 | YTATKAS | 0.206493 | -0.1442 |
| GS989 | 3660 | GCCCAAAGCACCAGCGGCGGCGTCAGAGCACAG | 8249 | AQSTSGGVRAQ | 12838 | STSGGVR | 0.206367 | -0.11215 |
| SyS1681 | 3661 | GCCCAATTTACTAGGGCTGAGCCTGCGGCACAG | 8250 | AQFTRAEPAAQ | 12839 | FTRAEPA | 0.206339 | -0.13071 |
| SyS1682 | 3662 | GCCCAACCTATTACGAGGGGTACTATTGCACAG | 8251 | AQPITRGTIAQ | 12840 | PITRGTI | 0.206234 | -0.16951 |
| SyS1683 | 3663 | GCCCAATACCACAACAGCATGCTCGGCGCACAG | 8252 | AQYHNSMLGAQ | 12841 | YHNSMLG | 0.206136 | -0.11374 |
| GP153 | 3664 | GCCCAAAGTAATAGTCGGGTAATGCTGCACAG | 8253 | AQSNSPGNAAQ | 12842 | SNSPGNA | 0.205916 | -0.06579 |
| GS990 | 3665 | GCCCAACAAAAAGGCGTCCAACTCCCCGCACAG | 8254 | AQQKGVQLPAQ | 12843 | QKGVQLP | 0.205912 | -0.01992 |
| GS991 | 3666 | GCCCAACGTAGTGAGACTAATAATACTGCACAG | 8255 | AQRSETNNTAQ | 12844 | RSETNNT | 0.205906 | -0.18637 |
| SyS1685 | 3667 | GCCCAAGTGGATCAGATGCTGGCTCCTGCACAG | 8256 | AQVDQMLAPAQ | 12845 | VDQMLAP | 0.205805 | -0.19133 |
| GS992 | 3668 | GCCCAACAACAAACCAGACACCAGCATGGCACAG | 8257 | AQQTRHTSMAQ | 12846 | QTRHTSM | 0.205758 | -0.12266 |
| SyS1686 | 3669 | GCCCAAATGCACGCCGACAGAGCCCTGCACAG | 8258 | AQMHADRALAQ | 12847 | MHADRAL | 0.205735 | -0.12963 |
| GS994 | 3670 | GCCCAATGCGACTACGCATGCTCCTAAGGCACAG | 8259 | AQSTTHAPKAQ | 12848 | STTHAPK | 0.205535 | -0.12148 |
| SyS1687 | 3671 | GCCCAATCTAATCAGACTATTATGACGGCACAG | 8260 | AQSNQTIMTAQ | 12849 | SNQTIMT | 0.205491 | -0.16587 |
| GS995 | 3672 | GCCCAAGTTTCTTCGCCTTCTGGTCTGGCACAG | 8261 | AQVSSPSGLAQ | 12850 | VSSPSGL | 0.205479 | -0.14665 |
| SyS1689 | 3673 | GCCCAAAAAGAGGGCGAAGAAATGGTCGCACAG | 8262 | AQKRGEEMVAQ | 12851 | KRGEEMV | 0.205315 | -0.19477 |
| SyS1690 | 3674 | GCCCAACAGGATAGTGGGAATAGTTATGCACAG | 8263 | AQQDSGNSYAQ | 12852 | QDSGNSY | 0.205249 | -0.21315 |
| SyS1691 | 3675 | GCCCAAAGCCACGCCACCACCGGCGGCCACAG | 8264 | AQSHATTGGAQ | 12853 | SHATTGG | 0.205059 | -0.19618 |
| SyS1693 | 3676 | GCCCAAAAGTCGAGTGAGACGTCTCATGCACAG | 8265 | AQKLSETSHAQ | 12854 | KLSETSH | 0.205006 | -0.21448 |
| SyS1694 | 3677 | GCCCAACTTAATTATAAGGAGGGCGCCGGCACAG | 8266 | AQLNYKEAPAQ | 12855 | LNYKEAP | 0.204978 | -0.18769 |
| SyS1695 | 3678 | GCCCAAAGCGTCGACAGCGTCAGACTCGCACAG | 8267 | AQSVDSVRLAQ | 12856 | SVDSVRL | 0.20496 | -0.08842 |
| SyS1697 | 3679 | GCCCAACAACCAAGTCATCCAAACGCACAG | 8268 | AQQPNVIQTAQ | 12857 | QPNVIQT | 0.204872 | 0.059518 |
| GS996 | 3680 | GCCCAACGTATGACTAATTTGCAGACTGCACAG | 8269 | AQRMTNLQTAQ | 12858 | RMTNLQT | 0.20474 | -0.17863 |
| SyS1698 | 3681 | GCCCAAGCCACCCCGGCGGCAGCGGGCACAG | 8270 | AQATPGGSGAQ | 12859 | ATPGGSG | 0.204721 | -0.15374 |
| SyS1699 | 3682 | GCCCAAGACGTCAACAGCATGAGCAGCACAG | 8271 | AQDVNSMSSAQ | 12860 | DVNSMSS | 0.204599 | -0.23419 |
| SyS1700 | 3683 | GCCCAATTGCCTCGTAGTCATCTTGATGCACAG | 8272 | AQLPRSHLDAQ | 12861 | LPRSHLD | 0.204525 | -0.13316 |
| SyS1701 | 3684 | GCCCAACCCGCCCCCAGATACGACAAAGCACAG | 8273 | AQPAPRYDKAQ | 12862 | PAPRYDK | 0.204501 | -0.09014 |
| SyS1703 | 3685 | GCCCAAAGAAACTACAGCGACAAAGACGCACAG | 8274 | AQRNYSDKDAQ | 12863 | RNYSDKD | 0.204317 | 0.088722 |
| SyS1704 | 3686 | GCCCAAAGTGAGAATCTTTGAGTCGTGCACAG | 8275 | AQSENLLSRAQ | 12864 | SENLLSR | 0.204317 | -0.20951 |
| GS997 | 3687 | GCCCAAAGTAGTCTTAATATGAAGGATGCACAG | 8276 | AQSSLNMKDAQ | 12865 | SSLNMKD | 0.204292 | -0.11279 |
| GS998 | 3688 | GCCCAAAGCGACAAAGAATACGGCAGAGCACAG | 8277 | AQSDKEYGRAQ | 12866 | SDKEYGR | 0.204204 | -0.15001 |
| GS999 | 3689 | GCCCAATACGTCAGCCAAAGCGGCATGGCACAG | 8278 | AQYVSQSGMAQ | 12867 | YVSQSGM | 0.204064 | -0.17672 |

FIG. 33 (Continued)

| | | | | | | | | |
|---|---|---|---|---|---|---|---|---|
| GS1000 | 3690 | GCCCAAAACGTCGTCAGCGTCAGACAAGCACAG | 8279 | AQNVVSVRQAQ | 12868 | NVVSVRQ | 0.204038 | -0.16753 |
| SyS1705 | 3691 | GCCCAAACGGGTAAGGAGGGTCGGACTGCACAG | 8280 | AQTGKEGRTAQ | 12869 | TGKEGRT | 0.203988 | -0.05387 |
| GS1001 | 3692 | GCCCAATTTAAGAATACTGTGGCGACTGCACAG | 8281 | AQFKNTVATAQ | 12870 | FKNTVAT | 0.203984 | -0.13702 |
| SyS1706 | 3693 | GCCCAAGGCAGCAGAGAACCCAGCAGCGCACAG | 8282 | AQGSREPSSAQ | 12871 | GSREPSS | 0.203966 | -0.2268 |
| SyS1707 | 3694 | GCCCAAAGAGAAAAAGTCAGCACCCCGCACAG | 8283 | AQREKVSTPAQ | 12872 | REKVSTP | 0.20368 | 0.088388 |
| GP154 | 3695 | GCCCAACAGGAGCCTGCTAGGCATAATGCACAG | 8284 | AQQEPARHNAQ | 12873 | QEPARHN | 0.203631 | -0.07336 |
| GS1002 | 3696 | GCCCAAACTAGTCATTCGAATGGTCGTGCACAG | 8285 | AQTSHSNGRAQ | 12874 | TSHSNGR | 0.203484 | -0.09149 |
| SyS1708 | 3697 | GCCCAAGGACCTCAGCAGCCCCAAAATGGCACAG | 8286 | AQDLSSPKMAQ | 12875 | DLSSPKM | 0.203432 | -0.06161 |
| SyS1709 | 3698 | GCCCAACTGCCACCACCCCAAACCCGCACAG | 8287 | AQLATTPKPAQ | 12876 | LATTPKP | 0.203432 | -0.11253 |
| SyS1710 | 3699 | GCCCAAAGGCGCCCAACGTCAGCCTGCACAG | 8288 | AQSGPNVSLAQ | 12877 | SGPNVSL | 0.203432 | -0.16344 |
| SyS1711 | 3700 | GCCCAACCCGTCTACAACGCAGCCCGCACAG | 8289 | AQPVYNASPAQ | 12878 | PVYNASP | 0.203401 | -0.21941 |
| SyS1712 | 3701 | GCCCAAAATTCTACTACTTGGTGATGGCACAG | 8290 | AQNSTTLVMAQ | 12879 | NSTTLVM | 0.203291 | -0.10908 |
| SyS1713 | 3702 | GCCCAAAGAAACGCCGTCGTCAGCATGGCACAG | 8291 | AQRNAVVSMAQ | 12880 | RNAVVSM | 0.203173 | -0.1307 |
| SP38 | 3703 | GCCCAAAAGGATCTTCTGGCTAAGCTTGCACAG | 8292 | AQKDILAKLAQ | 12881 | KDILAKL | 0.203052 | -0.0513 |
| SyS1715 | 3704 | GCCCAACCCCACGAAGGCAGCAGCAGAGCACAG | 8293 | AQPHEGSSRAQ | 12882 | PHEGSSR | 0.202954 | -0.08343 |
| SyS1716 | 3705 | GCCCAACGGGATACGGTTTCGCGTTATGCACAG | 8294 | AQRDTVSRYAQ | 12883 | RDTVSRY | 0.20293 | -0.15411 |
| SyS1717 | 3706 | GCCCAAGGCCAAGCCGCGCCAAGGCCACGCACAG | 8295 | AQGQAAQGHAQ | 12884 | GQAAQGH | 0.202823 | -0.14283 |
| SyS1718 | 3707 | GCCCAAGGGCTGAGACTGCTCATGTGGCACAG | 8296 | AQRAETAHVAQ | 12885 | RAETAHV | 0.202798 | -0.15132 |
| SyS1720 | 3708 | GCCCAAGAAAACAGAACCGTCCCACCGCACAG | 8297 | AQENRTVPTAQ | 12886 | ENRTVPT | 0.202755 | 0.23929 |
| GS1004 | 3709 | GCCCAAAGTAGTAATGATGCGAGGGTGGCACAG | 8298 | AQSSNDARVAQ | 12887 | SSNDARV | 0.202721 | -0.1747 |
| SyS1721 | 3710 | GCCCAACCCGGCCAAGTCGACAGAAGAGCACAG | 8299 | AQPGQVDRRAQ | 12888 | PGQVDRR | 0.202674 | -0.18527 |
| SyS1723 | 3711 | GCCCAAGGCCCGGCGCCAACACCGCACAG | 8300 | AQGPGANTTAQ | 12889 | GPGANTT | 0.202623 | -0.17752 |
| SyS1724 | 3712 | GCCCAAATGCCGAAAACCTCAAAGAAGCACAG | 8301 | AQMPENLKEAQ | 12890 | MPENLKE | 0.202544 | -0.21072 |
| GS1005 | 3713 | GCCCAAACGAATGCGGTGGCTTCTAATGCACAG | 8302 | AQTNAVASNAQ | 12891 | TNAVASN | 0.202544 | -0.12235 |
| GS1006 | 3714 | GCCCAATACGGCAAAATGCGAACTCTACGCACAG | 8303 | AQYGKIELYAQ | 12892 | YGKIELY | 0.202395 | -0.17919 |
| SyS1725 | 3715 | GCCCAAAAATCGAATGGTACGGGTTTTGCACAG | 8304 | AQNPNGTGFAQ | 12893 | NPNGTGF | 0.202346 | -0.1784 |
| GS1007 | 3716 | GCCCAATCTCGGAATACTATGGGTTCGGCACAG | 8305 | AQSRNTMGSAQ | 12894 | SRNTMGS | 0.202244 | -0.11377 |
| GS1008 | 3717 | GCCCAACCGAGTCATGGATTACGGCTGCACAG | 8306 | AQPSHGITAAQ | 12895 | PSHGITA | 0.202231 | -0.10748 |
| SyS1726 | 3718 | GCCCAATTGGAGACGCTGAGGGGGCCTGCACAG | 8307 | AQLETLRGPAQ | 12896 | LETLRGP | 0.202095 | -0.0594 |
| SyS1727 | 3719 | GCCCAAGATCGTTCTCCTGATATTAGGGCACAG | 8308 | AQDRSPDIRAQ | 12897 | DRSPDIR | 0.202025 | -0.19723 |
| SyS1728 | 3720 | GCCCAAAAGGATTTGGCGTCTGCGAAGGCACAG | 8309 | AQKDLASAKAQ | 12898 | KDLASAK | 0.201927 | -0.22803 |
| SyS1729 | 3721 | GCCCAAATCACCAGCCACGGCAACAGCGCACAG | 8310 | AQITSHGNSAQ | 12899 | ITSHGNS | 0.201888 | 0.12116 |

FIG. 33 (Continued)

| ID | Num | DNA Sequence | Num | Protein | Num | Peptide | Value 1 | Value 2 |
|---|---|---|---|---|---|---|---|---|
| GS1009 | 3722 | GCCCAACATTCTAAGATGCCTTCTACGGCACAG | 8311 | AQHSKMPSTAQ | 12900 | HSKMPST | 0.201887 | -0.16214 |
| GS1010 | 3723 | GCCCAAATTGCGACTTTTACGACGGCGGCACAG | 8312 | AQIATFTTAAQ | 12901 | IATFTTA | 0.201795 | -0.08442 |
| SyS1730 | 3724 | GCCCAAGCGGCGTCTGGGTATCTTAATGCACAG | 8313 | AQAASGYLNAQ | 12902 | AASGYLN | 0.201793 | -0.1986 |
| SyS1731 | 3725 | GCCCAAGATAGTGTTAGGCCGGCTATTGCACAG | 8314 | AQDSVRPAIAQ | 12903 | DSVRPAI | 0.201702 | -0.20709 |
| SyS1732 | 3726 | GCCCAAAGACTCAGCGAAGAAATGAGAGCACAG | 8315 | AQRLSEEMRAQ | 12904 | RLSEEMR | 0.201693 | -0.22434 |
| SyS1733 | 3727 | GCCCAACTCCCATCAGCGCCACCGAAGCACAG | 8316 | AQLPISATEAQ | 12905 | LPISATE | 0.201693 | -0.22434 |
| SyS1734 | 3728 | GCCCAATCTAATGTGGCGGCTCAGATGGCACAG | 8317 | AQSNVAAQMAQ | 12906 | SNVAAQM | 0.2016 | -0.21557 |
| SyS1735 | 3729 | GCCCAATATCAGTCGCTGATTTCTGAGGCACAG | 8318 | AQYQSLISEAQ | 12907 | YQSLISE | 0.2016 | -0.21557 |
| SyS1737 | 3730 | GCCCAATATCAGAGTGGGTATGATAAGGCACAG | 8319 | AQYQSGYDKAQ | 12908 | YQSGYDK | 0.201403 | -0.07145 |
| SyS1738 | 3731 | GCCCAACTCAGAACCGGCGAACTCACCGCACAG | 8320 | AQLRTGELTAQ | 12909 | LRTGELT | 0.201143 | -0.02579 |
| SyS1739 | 3732 | GCCCAACCGGCGACGAATAATATGCGGGCACAG | 8321 | AQPATNNMRAQ | 12910 | PATNNMR | 0.201063 | -0.21325 |
| SyS1740 | 3733 | GCCCAAGTCAGCAGCAGCAAATTCAGCGCACAG | 8322 | AQVSSSKFSAQ | 12911 | VSSSKFS | 0.201033 | -0.08585 |
| SyS1741 | 3734 | GCCCAAACTACGCTGCTTGATAAGGCTGCACAG | 8323 | AQTTLLDKAAQ | 12912 | TTLLDKA | 0.201033 | -0.19496 |
| SyS1742 | 3735 | GCCCAAAGCCCGCCCTCCACCCAGCGACACAG | 8324 | AQSPALHPSAQ | 12913 | SPALHPS | 0.201033 | -0.19496 |
| SyS1743 | 3736 | GCCCAATTCAACCACCACAGAACCGACGCACAG | 8325 | AQFNHNRTDAQ | 12914 | FNHNRTD | 0.200936 | -0.13686 |
| GS1013 | 3737 | GCCCAAGCCGAAAAAACCGCCAACGGCGCACAG | 8326 | AQAEKTANGAQ | 12915 | AEKTANG | 0.200841 | -0.1756 |
| GS1014 | 3738 | GCCCAAAATCTGCGTGTGACGGCTTCGGCACAG | 8327 | AQNLRVTASAQ | 12916 | NLRVTAS | 0.200801 | -0.08207 |
| GS1015 | 3739 | GCCCAAATGAAGGATGGGTCGCGGATTGCACAG | 8328 | AQMKDGSRIAQ | 12917 | MKDGSRI | 0.200699 | -0.14334 |
| SyS1744 | 3740 | GCCCAAAGAATCGGCGCCAACGCACCGCACAG | 8329 | AQRIGANATAQ | 12918 | RIGANAT | 0.200534 | 0.065728 |
| GS1018 | 3741 | GCCCAAGCCAACCTCACCCCAACAGAGCACAG | 8330 | AQANLTPNRAQ | 12919 | ANLTPNR | 0.20043 | -0.18009 |
| SyP58 | 3742 | GCCCAATCGGTGTCTGTGATAAGAGTCATGCACAG | 8331 | AQSVSDKSHAQ | 12920 | SVSDKSH | 0.200325 | -0.03907 |
| SyS1745 | 3743 | GCCCAATACAGCACCCTCCACCGCCGCACAG | 8332 | AQYSTLHTAAQ | 12921 | YSTLHTA | 0.200268 | 0.146915 |
| SyS1747 | 3744 | GCCCAAACGAAGTTTGGTGGTATTCAGGCACAG | 8333 | AQTKFGGIQAQ | 12922 | TKFGGIQ | 0.200153 | 0.040003 |
| GS1019 | 3745 | GCCCAAGACATCCCCAAAGGCAGCAGCGCACAG | 8334 | AQDIPKGSSAQ | 12923 | DIPKGSS | 0.200135 | -0.13523 |
| SyS1748 | 3746 | GCCCAAATCTCCCCAGCAGCAGCCAAGCACAG | 8335 | AQILPSSSQAQ | 12924 | ILPSSSQ | 0.200107 | 0.034167 |
| GS1020 | 3747 | GCCCAAGTCAGCCAAACCACCAGCAGCGCACAG | 8336 | AQVSQTTSSAQ | 12925 | VSQTTSS | 0.200008 | -0.11818 |
| SyS1750 | 3748 | GCCCAAACGATTCATCTGCATAAGGATGCACAG | 8337 | AQTIHLHKDAQ | 12926 | TIHLHKD | 0.199958 | -0.13314 |
| SyS1754 | 3749 | GCCCAAGTCACCGACAGAGTCGGCAACGGCACAG | 8338 | AQVTDRVGNAQ | 12927 | VTDRVGN | 0.199795 | -0.1792 |
| SyP59 | 3750 | GCCCAACTGCCTGCTCGCGGCTGTAATGCACAG | 8339 | AQLPARAANAQ | 12928 | LPARAAN | 0.199763 | -0.04316 |
| SyS1755 | 3751 | GCCCAACAACACCCAAAGCATGACCGTCGCACAG | 8340 | AQHTQSMTVAQ | 12929 | HTQSMTV | 0.199748 | 0.113433 |
| SyS1756 | 3752 | GCCCAACTCCTCAACAGCAGCCAACTCGCACAG | 8341 | AQLLNSSQLAQ | 12930 | LLNSSQL | 0.199713 | -0.01322 |
| SyS1757 | 3753 | GCCCAAAGAAACAGCGAACTCAGAGCCGCACAG | 8342 | AQRNSELRAAQ | 12931 | RNSELRA | 0.199623 | -0.1344 |

FIG. 33 (Continued)

| | | | | | | | | |
|---|---|---|---|---|---|---|---|---|
| SyS1758 | 3754 | GCCCAACAGAAGTCTCCGAATGGTCTGGCACAG | 8343 | AQQKSPNGLAQ | 12932 | QKSPNGL | 0.199418 | -0.01019 |
| SyS1759 | 3755 | GCCCAAAAAGCGGCGACCACCTCACCGCACAG | 8344 | AQKSGDHLTAQ | 12933 | KSGDHLT | 0.199256 | -0.10889 |
| TS171 | 3756 | GCCCAAGGGAATCGGACTACGAGTAGTGCACAG | 8345 | AQGNRTTSSAQ | 12934 | GNRTTSS | 0.199229 | -0.1942 |
| SyS1760 | 3757 | GCCCAAATGGTCGCCCTCACCGTCGGCGCACAG | 8346 | AQMVALTVGAQ | 12935 | MVALTVG | 0.19916 | -0.17557 |
| SyS1761 | 3758 | GCCCAACTCAGCAGCAACAGCCCCAGAGCACAG | 8347 | AQLSSNSPRAQ | 12936 | LSSNSPR | 0.199055 | 0.023543 |
| SyS1762 | 3759 | GCCCAAGCTTCGAATAATCAGACGTATGCACAG | 8348 | AQASNNQTYAQ | 12937 | ASNNQTY | 0.199003 | -0.05924 |
| GS1025 | 3760 | GCCCAAAAACAACATCGTCACCAGCGCACAG | 8349 | AQNNIVTTSAQ | 12938 | NNIVTTS | 0.19875 | -0.15317 |
| GS1026 | 3761 | GCCCAACACGACACCAAAAAACCCATGGCACAG | 8350 | AQHDTKKPMAQ | 12939 | HDTKKPM | 0.198636 | -0.1338 |
| SyS1765 | 3762 | GCCCAAATTAATACGGCTAGTTATAAGGCACAG | 8351 | AQINTASYKAQ | 12940 | INTASYK | 0.198495 | -0.10647 |
| SyS1766 | 3763 | GCCCAAAGTGGTATGGTTAGTATGTCGGCACAG | 8352 | AQSGMVSMSAQ | 12941 | SGMVSMS | 0.19837 | -0.10161 |
| SyS1768 | 3764 | GCCCAACTCGTCACCGCCAGCGCCAGAGCACAG | 8353 | AQLVTASARAQ | 12942 | LVTASAR | 0.198271 | -0.12079 |
| GS1028 | 3765 | GCCCAAAGCAGAGCCCCAGCGCCATGGCACAG | 8354 | AQSRAPSAMAQ | 12943 | SRAPSAM | 0.198243 | -0.1747 |
| SyS1769 | 3766 | GCCCAAAACAACAACAACCAAAAAGTCTACGCACAG | 8355 | AQNNNQKVYAQ | 12944 | NNNQKVY | 0.197983 | -0.11345 |
| SyS1770 | 3767 | GCCCAAACTAGTGTGGTTGCTAATCCTGCACAG | 8356 | AQTSVVANPAQ | 12945 | TSVVANP | 0.197975 | -0.02461 |
| SyS1771 | 3768 | GCCCAAGGCAACGCCGGCCCCAGCCTCGCACAG | 8357 | AQGNAGPSLAQ | 12946 | GNAGPSL | 0.197961 | -0.17382 |
| SyS1772 | 3769 | GCCCAATACAGCACCAGCTCGAACTCGCACAG | 8358 | AQYSTSLELAQ | 12947 | YSTSLEL | 0.197917 | -0.23419 |
| SyS1773 | 3770 | GCCCAACCGTCTAATCCGCCTAAGGAGGCACAG | 8359 | AQPSNPPKEAQ | 12948 | PSNPPKE | 0.197834 | -0.10324 |
| SyS1774 | 3771 | GCCCAAACTAATTCTAAGCCTTCGTGGGCACAG | 8360 | AQTNSKPSWAQ | 12949 | TNSKPSW | 0.197791 | -0.2305 |
| SyS1775 | 3772 | GCCCAATCGATTGATCGGCAGCAGCTTGCACAG | 8361 | AQSIDRQQLAQ | 12950 | SIDRQQL | 0.19771 | -0.16273 |
| GS1030 | 3773 | GCCCAAAACAAAGCGGCCCGCCAGCGCACAG | 8362 | AQNKAGPASAQ | 12951 | NKAGPAS | 0.197681 | -0.08173 |
| GS1031 | 3774 | GCCCAAAGCATGACCAACAGAGAGCGCACAG | 8363 | AQSMTTNRSAQ | 12952 | SMTTNRS | 0.197629 | -0.14958 |
| SyS1776 | 3775 | GCCCAAGGCAACAGCGCCGTCAACTCGCACAG | 8364 | AQGNSAVQLAQ | 12953 | GNSAVQL | 0.197614 | -0.09127 |
| GS1032 | 3776 | GCCCAAAGAAGCAGCGACGTCAACACCGCACAG | 8365 | AQRSSDVNTAQ | 12954 | RSSDVNT | 0.197531 | -0.12807 |
| SyS1777 | 3777 | GCCCAACACACAACGGCGTCCAAAGCGTCGCACAG | 8366 | AQHNGVQSVAQ | 12955 | HNGVQSV | 0.197468 | 0.173685 |
| SyS1778 | 3778 | GCCCAAGAAAAAGACCACGGCATGGCCGCACAG | 8367 | AQEKDHGMAAQ | 12956 | EKDHGMA | 0.197362 | -0.12344 |
| SyS1779 | 3779 | GCCCAATACAGACTCCCGACGGGCAGAGCACAG | 8368 | AQYRLPDGRAQ | 12957 | YRLPDGR | 0.197255 | -0.21202 |
| SyS1780 | 3780 | GCCCAAAGCAGCAGAGAACTCAGACTCGCACAG | 8369 | AQSSRELRLAQ | 12958 | SSRELRL | 0.197138 | -0.13192 |
| SyS1782 | 3781 | GCCCAAAACCAAGTCGAAAGCAGAGTCGCACAG | 8370 | AQNQVESRVAQ | 12959 | NQVESRV | 0.196941 | -0.11838 |
| SyS1783 | 3782 | GCCCAAGCCCTCCACAGCGTCCCCAAAGCACAG | 8371 | AQALHSVPKAQ | 12960 | ALHSVPK | 0.196939 | -0.11574 |
| SyS1784 | 3783 | GCCCAAACTGGTCCTAGTACGGTGCCGGCACAG | 8372 | AQTGPSTVPAQ | 12961 | TGPSTVP | 0.196935 | -0.09919 |
| SyS1785 | 3784 | GCCCAAGAGAACCCCTCGGCGTCCACCCCGCACAG | 8373 | AQEPLGVHPAQ | 12962 | EPLGVHP | 0.196915 | -0.19723 |
| GS1036 | 3785 | GCCCAAAACCAGAACCGACACCACCAACGCACAG | 8374 | AQTRTDTTNAQ | 12963 | TRTDTTN | 0.196745 | -0.08049 |

FIG. 33 (Continued)

| | | | | | | | |
|---|---|---|---|---|---|---|---|
| GS1037 | 3786 | GCCCAAAGGCCACAACCTCACCGCCGACGCACAG | 8375 | AQSHNLTADAQ | 12964 | SHNLTAD | 0.196727 | -0.15855 |
| SyS1787 | 3787 | GCCCAAAACGTCAGAAGAGAGACGACACCGCACAG | 8376 | AQNVRRDDTAQ | 12965 | NVRRDDT | 0.196487 | -0.11616 |
| SyS1788 | 3788 | GCCCAATTCGCCGCCAACCTCGTCGCCGCACAG | 8377 | AQFAANLVAAQ | 12966 | FAANLVA | 0.196427 | -0.13677 |
| SyS1790 | 3789 | GCCCAAATCGGCGCGCCAAGCCAGAATGGCACAG | 8378 | AQIGAQARMAQ | 12967 | IGAQARM | 0.19619 | -0.15288 |
| SyS1791 | 3790 | GCCCAAAATTCTATGTCTAAGGCTTATGCACAG | 8379 | AQNSMSKAYAQ | 12968 | NSMSKAY | 0.196153 | -0.1986 |
| GS1039 | 3791 | GCCCAAAACGTCAACAAAGACAGAGTCGCACAG | 8380 | AQNVNKDRVAQ | 12969 | NVNKDRV | 0.196068 | -0.1442 |
| GS1040 | 3792 | GCCCAATCTTTCAGGGTTCGGCTAGGGCACAG | 8381 | AQSFQGSARAQ | 12970 | SFQGSAR | 0.196025 | -0.06362 |
| GS1041 | 3793 | GCCCAAGCCAACAGCGACCACATCCACGCACAG | 8382 | AQANSDHIHAQ | 12971 | ANSDHIH | 0.196025 | -0.13792 |
| GS1042 | 3794 | GCCCAAGTCAGCCTCGCCAGCAAAAGGCACAG | 8383 | AQVSLASKSAQ | 12972 | VSLASKS | 0.195985 | -0.13164 |
| SyS1793 | 3795 | GCCCAACCCAAAGACAGAGCCACCAGCGCACAG | 8384 | AQPKDRATSAQ | 12973 | PKDRATS | 0.195973 | -0.13314 |
| SyS1794 | 3796 | GCCCAAGTTCGGTCGCAGAGTGATTCGGCACAG | 8385 | AQVRSQSDSAQ | 12974 | VRSQSDS | 0.195812 | -0.12101 |
| SyS1795 | 3797 | GCCCAACTTGGTAATTCGGTGTTAAGGCACAG | 8386 | AQLGNSVFKAQ | 12975 | LGNSVFK | 0.195693 | -0.10483 |
| SyS1796 | 3798 | GCCCAAAGCACCAAAGAAAGCCCAAAGCACAG | 8387 | AQSTKESPKAQ | 12976 | STKESPK | 0.195693 | -0.23173 |
| SyS1797 | 3799 | GCCCAACTCCAACCACCACCTTCAGCGCACAG | 8388 | AQLQPTTFSAQ | 12977 | LQPTTFS | 0.195693 | -0.23173 |
| SyS1798 | 3800 | GCCCAACCCATGCACACCGCCATGGTCGCACAG | 8389 | AQPMHTAMVAQ | 12978 | PMHTAMV | 0.195687 | -0.14162 |
| SyS1799 | 3801 | GCCCAAGTGTTTGCTCATATGGTCTTGCACAG | 8390 | AQVFAHTGLAQ | 12979 | VFAHTGL | 0.195535 | -0.2277 |
| GS1044 | 3802 | GCCCAACAAAAGCCACCAGCATCCACGCACAG | 8391 | AQQKATSIHAQ | 12980 | QKATSIH | 0.195419 | -0.1338 |
| SyS1800 | 3803 | GCCCAAGGTTCTAAGTGTCGGATAATCTGGCACAG | 8392 | AQGSKSDNLAQ | 12981 | GSKSDNL | 0.195377 | -0.15011 |
| SyS1801 | 3804 | GCCCAAAGCGGCCACCAACGTCGTCAGCGCACAG | 8393 | AQSGTNVVSAQ | 12982 | SGTNVVS | 0.195376 | -0.20955 |
| SyS1802 | 3805 | GCCCAAACCAAACTCACCACCCTCAGCGCACAG | 8394 | AQTKLTTLSAQ | 12983 | TKLTTLS | 0.195251 | -0.19846 |
| SyS1803 | 3806 | GCCCAACCCATCCTCCACCAAATCGCACAG | 8395 | AQPILHNQIAQ | 12984 | PILHNQI | 0.195237 | -0.13798 |
| SyS1804 | 3807 | GCCCAAGTCACCAACACCCATCAAACCCGCACAG | 8396 | AQVTNPIKPAQ | 12985 | VTNPIKP | 0.195213 | -0.19477 |
| SyS1805 | 3808 | GCCCAAACCAACCGCCCTCCACATGAAAGCACAG | 8397 | AQTNALHMKAQ | 12986 | TNALHMK | 0.195213 | -0.19477 |
| SyS1806 | 3809 | GCCCAAGTCGCCCACGCCTACCCGCGCACAG | 8398 | AQVAHAYPAAQ | 12987 | VAHAYPA | 0.195206 | 0.067049 |
| SyS1807 | 3810 | GCCCAAGCTGAGCATGTGTCTTGGTCCTGCACAG | 8399 | AQAEHGLGPAQ | 12988 | AEHGLGP | 0.195111 | -0.20345 |
| GS1045 | 3811 | GCCCAAATGAACAAATACAGCCCGCGCACAG | 8400 | AQMNKYSPAAQ | 12989 | MNKYSPA | 0.195101 | -0.14689 |
| SyS1808 | 3812 | GCCCAACCATGCAAGACAGACTCACCGCACAG | 8401 | AQTMQDRLTAQ | 12990 | TMQDRLT | 0.19501 | -0.12978 |
| SyS1809 | 3813 | GCCCAAGGCGTCAAAATCCTCAACAGCGCACAG | 8402 | AQGVKILNSAQ | 12991 | GVKILNS | 0.194998 | -0.11374 |
| GS1046 | 3814 | GCCCAAGCGCAGAATAAGATGACGAGTGCACAG | 8403 | AQAQNKMTSAQ | 12992 | AQNKMTS | 0.194978 | -0.14048 |
| SyS1810 | 3815 | GCCCAAACCAGCGCCCTCACCGACATCGCACAG | 8404 | AQTSALTDIAQ | 12993 | TSALTDI | 0.194946 | -0.19133 |
| SyS1811 | 3816 | GCCCAAGACCTCAGACACGCCGACATCGCACAG | 8405 | AQDLRHADIAQ | 12994 | DLRHADI | 0.194916 | -0.14647 |
| GP158 | 3817 | GCCCAACAGAATAAGGCGTTGACGGTGGCACAG | 8406 | AQQNKALTVAQ | 12995 | QNKALTV | 0.194813 | -0.07426 |

FIG. 33 (Continued)

| | | | | | | | |
|---|---|---|---|---|---|---|---|
| SyS1812 | 3818 | GCCCAAACTCAGGGGATTACGATTGTGGCACAG | 8407 | AQTQGITIVAQ | 12996 | TQGITIV | 0.194803 | -0.1792 |
| GS1047 | 3819 | GCCCAAACGGCGACTATTCTTGTCGTGGGGCACAG | 8408 | AQTATILSGAQ | 12997 | TATILSG | 0.194742 | -0.11376 |
| GP159 | 3820 | GCCCAATTTGCGGGCGAGTAATATTTCTGCACAG | 8409 | AQFAASNISAQ | 12998 | FAASNIS | 0.194572 | -0.07232 |
| SyS1814 | 3821 | GCCCAACGTAATACTATGGAGACTATGGCACAG | 8410 | AQRNTMETMAQ | 12999 | RNTMETM | 0.194502 | -0.19981 |
| GS1049 | 3822 | GCCCAAAGTTCTGGTACTAGTTATAGTGCACAG | 8411 | AQSSGTSYSAQ | 13000 | SSGTSYS | 0.194467 | -0.1765 |
| SyS1815 | 3823 | GCCCAAGCCAACCACGGCCTCAACGCCGCACAG | 8412 | AQANHGLNAAQ | 13001 | ANHGLNA | 0.194455 | 0.086643 |
| GS1050 | 3824 | GCCCAAATGCTGTCGAATTCGCGTAGTGCACAG | 8413 | AQMLSNSRSAQ | 13002 | MLSNSRS | 0.194307 | -0.13666 |
| SyS1816 | 3825 | GCCCAAGCTGCGATTCATGCGACGCCTGCACAG | 8414 | AQAAIHATPAQ | 13003 | AAIHATP | 0.194234 | -0.23255 |
| SyS1817 | 3826 | GCCCAATGGCAGTCGTTTGCGTCGGCGGGCACAG | 8415 | AQWQSFASAAQ | 13004 | WQSFASA | 0.194234 | -0.23255 |
| SyS1818 | 3827 | GCCCAAATGGGTGGGAATTCGAGTACGGCACAG | 8416 | AQMGGNSSTAQ | 13005 | MGGNSST | 0.194111 | -0.01311 |
| SyS1819 | 3828 | GCCCAAAAGACGGATTTGGGCGCAGCATGCACAG | 8417 | AQKTDLAQHAQ | 13006 | KTDLAQH | 0.194111 | -0.15132 |
| TS172 | 3829 | GCCCAAGTCAACACCACCAGATTCAGCGCACAG | 8418 | AQVNTTRFSAQ | 13007 | VNTTRFS | 0.19409 | -0.31218 |
| SyS1821 | 3830 | GCCCAAAATGTGCATGCTCATCAGGCTGCACAG | 8419 | AQNVHAHQAAQ | 13008 | NVHAHQA | 0.193921 | -0.11495 |
| GS1051 | 3831 | GCCCAAGGCGCCATGAGCATCCAAACCGCACAG | 8420 | AQGAMSIQTAQ | 13009 | GAMSIQT | 0.193889 | -0.10282 |
| GS1052 | 3832 | GCCCAAGCTCGGGGTCCGACGATTGTTGCACAG | 8421 | AQARGPTIVAQ | 13010 | ARGPTIV | 0.193777 | -0.18099 |
| GS1055 | 3833 | GCCCAAACGATGCATAGTAAGTCGGATGCACAG | 8422 | AQTMHSKSDAQ | 13011 | TMHSKSD | 0.193462 | -0.16035 |
| GS1056 | 3834 | GCCCAAACGGTTACGCAGACTACTCAGGCACAG | 8423 | AQTVTQTTQAQ | 13012 | TVTQTTQ | 0.193371 | -0.16663 |
| GS1057 | 3835 | GCCCAAGGCAACAACAACAGCCTCACCGCACAG | 8424 | AQGNTNSLTAQ | 13013 | GNTNSLT | 0.193295 | -0.04686 |
| GS1058 | 3836 | GCCCAAAGAGTCATCGCCAGCGTCAACGCACAG | 8425 | AQRVIASVNAQ | 13014 | RVIASVN | 0.193253 | -0.15001 |
| SyS1823 | 3837 | GCCCAACCCAGCAGCGGCAACAGCGAAGCACAG | 8426 | AQPSSGNSEAQ | 13015 | PSSGNSE | 0.193165 | -0.03781 |
| GS1059 | 3838 | GCCCAACAGCCGCATGGTTTTACGGCTGCACAG | 8427 | AQQPHGFTAAQ | 13016 | QPHGFTA | 0.19311 | -0.08893 |
| GS1060 | 3839 | GCCCAAACGACTGGTACCAACATGAGAGCACAG | 8428 | AQTTGTNMRAQ | 13017 | TTGTNMR | 0.192999 | -0.1586 |
| SyS1825 | 3840 | GCCCAATTCACCAGACTCGAAGACAGAGCACAG | 8429 | AQFTRLEDRAQ | 13018 | FTRLEDR | 0.192838 | -0.12829 |
| GS1061 | 3841 | GCCCAAGACAGAGAGCCCGCCCACACCGCACAG | 8430 | AQDRSPAHTAQ | 13019 | DRSPAHT | 0.192801 | -0.06749 |
| SyS1827 | 3842 | GCCCAACACGTCCACAACACCGTCCCGCACAG | 8431 | AQHVHNTVPAQ | 13020 | HVHNTVP | 0.192711 | -0.04938 |
| SS118 | 3843 | GCCCAAATGAACACCGGCACCAAAGCACAG | 8432 | AQMNTTGTKAQ | 13021 | MNTTGTK | 0.192667 | -0.30576 |
| SyS1828 | 3844 | GCCCAATTCGCCACCCAAACCATCGCCGCACAG | 8433 | AQFATQTIAAQ | 13022 | FATQTIA | 0.192606 | 0.020831 |
| GS1062 | 3845 | GCCCAAGTCAGCGGCAACATCCCCGTCGCACAG | 8434 | AQVSGNIPVAQ | 13023 | VSGNIPV | 0.192554 | -0.1774 |
| GS1063 | 3846 | GCCCAAGACGGCAGAAACATCGCCCCGCACAG | 8435 | AQDGRNIAPAQ | 13024 | DGRNIAP | 0.192531 | -0.10292 |
| SyS1829 | 3847 | GCCCAAATGCTCCCCACCGTCAACAGAGCACAG | 8436 | AQMLPTVNRAQ | 13025 | MLPTVNR | 0.192494 | -0.11361 |
| GS1064 | 3848 | GCCCAACCTACTACTAATGTGCTTGGTGCACAG | 8437 | AQPTTNVLGAQ | 13026 | PTTNVLG | 0.192456 | -0.15676 |
| SyS1830 | 3849 | GCCCAACGGGAGATGCATGGTACTCTTGCACAG | 8438 | AQREMHGTLAQ | 13027 | REMHGTL | 0.192442 | -0.13677 |

FIG. 33 (Continued)

| | | | | | | | | |
|---|---|---|---|---|---|---|---|---|
| GS1066 | 3850 | GCCCAATCTCCGTATTCGACTCGTCCGGCACAG | 8439 | AQSPYSTRPAQ | 13028 | SPYSTRP | 0.192371 | -0.15517 |
| SyS1832 | 3851 | GCCCAATACAACATGAACACCGAAATGGCACAG | 8440 | AQYNMNTEMAQ | 13029 | YNMNTEM | 0.192365 | -0.17314 |
| SyS1833 | 3852 | GCCCAAGGGGCGGCGTATGGGTCATTCGGCACAG | 8441 | AQGARMGHSAQ | 13030 | GARMGHS | 0.192225 | -0.07252 |
| SyS1834 | 3853 | GCCCAATTCAGCCCCGGCTACGTCCCCGCACAG | 8442 | AQFSPGYVPAQ | 13031 | FSPGYVP | 0.192168 | -0.09677 |
| SyS1835 | 3854 | GCCCAACAGCAGCATATTCCTCCTTCTGCACAG | 8443 | AQQQHIPPSAQ | 13032 | QQHIPPS | 0.191995 | -0.18984 |
| GS1067 | 3855 | GCCCAACTCAGCACCAGCCTCAGCCCCGCACAG | 8444 | AQLSTSLSPAQ | 13033 | LSTSLSP | 0.191963 | -0.10041 |
| SyS1836 | 3856 | GCCCAAGTTAATGGGATTAAGGAGTATGCACAG | 8445 | AQVNGIKEYAQ | 13034 | VNGIKEY | 0.191891 | -0.081 |
| SyP60 | 3857 | GCCCAAGGTGTGCGGACTGAGCCGATGGCACAG | 8446 | AQGVRTEPMAQ | 13035 | GVRTEPM | 0.191789 | -0.0406 |
| SyS1837 | 3858 | GCCCAAAGAAACAACGACAGCCTCACCGCACAG | 8447 | AQRNNDSLTAQ | 13036 | RNNDSLT | 0.191786 | 0.1054 |
| SyS1838 | 3859 | GCCCAATTTAATGCGTCTCCTAAGTTGGCACAG | 8448 | AQFNASPKLAQ | 13037 | FNASPKL | 0.191776 | -0.19375 |
| SyS1839 | 3860 | GCCCAAGGCCTCACCAGCACCACCGCACAG | 8449 | AQGLTTSTTAQ | 13038 | GLTTSTT | 0.191776 | -0.19375 |
| SyS1840 | 3861 | GCCCAAATGATCAGAGGCACCAGCAGCGCACAG | 8450 | AQMIRGTSSAQ | 13039 | MIRGTSS | 0.191749 | -0.11737 |
| SyS1841 | 3862 | GCCCAAACTAAGCTTGTGGCTACTGTGGCACAG | 8451 | AQTKLVATVAQ | 13040 | TKLVATV | 0.191661 | -0.21941 |
| SyS1842 | 3863 | GCCCAAGTGAGTCGGCAGTTTGAGCCGGCACAG | 8452 | AQVSRQFEPAQ | 13041 | VSRQFEP | 0.191661 | -0.21941 |
| SyS1843 | 3864 | GCCCAAAATGGTGATAGTTTGCGTCCTGCACAG | 8453 | AQNGDSLRPAQ | 13042 | NGDSLRP | 0.191643 | -0.05025 |
| SyS1844 | 3865 | GCCCAAACCCAAAACCTCAGCAGCCACGCACAG | 8454 | AQTQNLSSHAQ | 13043 | TQNLSSH | 0.191633 | 0.003465 |
| SyS1845 | 3866 | GCCCAAACCGTCACCGGCAGCCTCGTCGCACAG | 8455 | AQTVTGSLVAQ | 13044 | TVTGSLV | 0.191556 | -0.15374 |
| SyS1846 | 3867 | GCCCAAGGCAGAGGCCCCGAAGCCCAAGCACAG | 8456 | AQGRGPEAQAQ | 13045 | GRGPEAQ | 0.191398 | 0.062377 |
| GS1068 | 3868 | GCCCAACCCAGAAACGTCGGCCTCGAAGCACAG | 8457 | AQPRNVGLEAQ | 13046 | PRNVGLE | 0.191325 | -0.0842 |
| SyS1847 | 3869 | GCCCAATTCAACAGCAGCATCCCCACCGCACAG | 8458 | AQFNSSIPTAQ | 13047 | FNSSIPT | 0.191319 | 0.002066 |
| SyS1848 | 3870 | GCCCAAGGTAATCAGCAGCATTCTTCTGCACAG | 8459 | AQGNQQHSSAQ | 13048 | GNQQHSS | 0.191216 | 0.020615 |
| GS1069 | 3871 | GCCCAACCCATCACCAACGGCAGCTTCGGCACAG | 8460 | AQPITNGSFAQ | 13049 | PITNGSF | 0.191188 | -0.13074 |
| GS1070 | 3872 | GCCCAAGTTCAGCGTACTCCGCTTACTGCACAG | 8461 | AQVQRTPLTAQ | 13050 | VQRTPLT | 0.191121 | -0.18054 |
| GS1071 | 3873 | GCCCAAACGCCTTATGCTGGTAGGGCTGCACAG | 8462 | AQTPYAGRAAQ | 13051 | TPYAGRA | 0.19095 | -0.10831 |
| SyS1849 | 3874 | GCCCAACTGGCTCTGTCTAATCGTACGGCACAG | 8463 | AQLALSNRTAQ | 13052 | LALSNRT | 0.190717 | -0.17259 |
| SyS1850 | 3875 | GCCCAAGGTCAGATGGCTACTGGTCTGGCACAG | 8464 | AQGQMATGLAQ | 13053 | GQMATGL | 0.190704 | -0.13866 |
| SyS1852 | 3876 | GCCCAATCTAATCCTGCGACTACTACTGCACAG | 8465 | AQSNPATTTAQ | 13054 | SNPATTT | 0.190655 | -0.11859 |
| GS1074 | 3877 | GCCCAAGGGCGGACTACTAGTGATAGTGCACAG | 8466 | AQGRTTSDSAQ | 13055 | GRTTSDS | 0.190613 | -0.09357 |
| GS1075 | 3878 | GCCCAAAGCAGAGCTCACCAGCCTGGGCACAG | 8467 | AQSRLTSLGAQ | 13056 | SRLTSLG | 0.19049 | -0.12819 |
| SyS1853 | 3879 | GCCCAACACATCTTTCTACGCCGGATTTGGCACAG | 8468 | AQHLSTPDLAQ | 13057 | HLSTPDL | 0.190472 | -0.18737 |
| SyS1854 | 3880 | GCCCAAATGCCTCATGCTCCGACTTCGGCACAG | 8469 | AQMPHAPTSAQ | 13058 | MPHAPTS | 0.190411 | -0.14283 |
| GS1076 | 3881 | GCCCAAGTTGCGGGGTATGTTGACGCATGCACAG | 8470 | AQVAGMLTHAQ | 13059 | VAGMLTH | 0.190345 | -0.17672 |

FIG. 33 (Continued)

| | | | | | | | | |
|---|---|---|---|---|---|---|---|---|
| GS1077 | 3882 | GCCCAAGTCGCCAGCCAAAAACTCAAGCGCACAG | 8471 | AQVASQKLNAQ | 13060 | VASQKLN | 0.190288 | -0.13094 |
| SyS1856 | 3883 | GCCCAAACCCAAAGCATGACCAGCAGAGCACAG | 8472 | AQTQSMTSRAQ | 13061 | TQSMTSR | 0.190241 | -0.02852 |
| GS1079 | 3884 | GCCCAACCCATCAGCACCATGAGCCTCGCACAG | 8473 | AQPISTMSLAQ | 13062 | PISTMSL | 0.19008 | -0.1765 |
| SyS1857 | 3885 | GCCCAAGCCCAACTCAACAGCGCCGGCGCACAG | 8474 | AQAQLNSAGAQ | 13063 | AQLNSAG | 0.190056 | -0.1392 |
| SyS1858 | 3886 | GCCCAACACCTCCCAAATACGAACACGCACAG | 8475 | AQHLPKYEHAQ | 13064 | HLPKYEH | 0.190056 | -0.1392 |
| GS1080 | 3887 | GCCCAAGGGGTGCAGGCTGTTGTTGGGTGCACAG | 8476 | AQGVQAVVGAQ | 13065 | GVQAVVG | 0.189947 | -0.15647 |
| SyS1859 | 3888 | GCCCAAGGCGACACCCAATACGCCAGAGCACAG | 8477 | AQGDTQYARAQ | 13066 | GDTQYAR | 0.189923 | -0.1792 |
| SyS1860 | 3889 | GCCCAAGCCAGCCAGCCCCCTCGTCATGAGCGCACAG | 8478 | AQASPLVMSAQ | 13067 | ASPLVMS | 0.189788 | -0.033 |
| SyS1861 | 3890 | GCCCAAAGCAACGCCGGCATGAGCAAAGCACAG | 8479 | AQSNAGMSKAQ | 13068 | SNAGMSK | 0.189781 | -0.07895 |
| SyS1862 | 3891 | GCCCAAAGAAGCGTCAGCGCCGTCCCCGCACAG | 8480 | AQRSVSAVPAQ | 13069 | RSVSAVP | 0.189731 | -0.22064 |
| SyS1863 | 3892 | GCCCAACCCAGCTACCACAAAAGCCCCGCACAG | 8481 | AQPSYHKSPAQ | 13070 | PSYHKSP | 0.189731 | -0.15164 |
| GS1081 | 3893 | GCCCAACATCAGTTTACTAGTTCTGCGGCACAG | 8482 | AQHQFTSSAAQ | 13071 | HQFTSSA | 0.189638 | -0.13792 |
| SyS1865 | 3894 | GCCCAAAACCAAAGCCCCATCGGCGCCGCACAG | 8483 | AQNQSPIGAAQ | 13072 | NQSPIGA | 0.189626 | -0.22434 |
| SyS1866 | 3895 | GCCCAAGGTGCGGCTGGGATGTGCGGGGGCACAG | 8484 | AQGAAGMSRAQ | 13073 | GAAGMSR | 0.189609 | -0.04299 |
| GS1082 | 3896 | GCCCAAACGGTGAAGACGTATAGTGCGGGCACAG | 8485 | AQTVKTYSAAQ | 13074 | TVKTYSA | 0.189603 | 0.055302 |
| SyS1867 | 3897 | GCCCAACTCAGCATGACCAGCCAAATGGCACAG | 8486 | AQLSMTSQMAQ | 13075 | LSMTSQM | 0.189571 | -0.09374 |
| SyS1868 | 3898 | GCCCAAGGCCTCAGCCCCACCTTCGGCGCACAG | 8487 | AQGLSPTFGAQ | 13076 | GLSPTFG | 0.189515 | -0.16273 |
| GS1083 | 3899 | GCCCAAATGGACACCGTCATGAAAGGCGCACAG | 8488 | AQMDTVMKGAQ | 13077 | MDTVMKG | 0.189386 | -0.16663 |
| GS1085 | 3900 | GCCCAACGTGATAAGATTTCTACGTATGCACAG | 8489 | AQRDKISTYAQ | 13078 | RDKISTY | 0.189205 | -0.18099 |
| SyS1870 | 3901 | GCCCAAGACAGCAACAGCTACGTCAGAGCACAG | 8490 | AQDSNSYVRAQ | 13079 | DSNSYVR | 0.189097 | -0.18121 |
| SyS1872 | 3902 | GCCCAAAGCCTCAAAAGCAGCCCCTTCGCACAG | 8491 | AQSLKSSPFAQ | 13080 | SLKSSPF | 0.189004 | -0.19981 |
| GS1088 | 3903 | GCCCAACTTGATCGTACTGCGAAGCCTGCACAG | 8492 | AQLDRTAKPAQ | 13081 | LDRTAKP | 0.188806 | -0.15676 |
| SyS1873 | 3904 | GCCCAACCGTCGAGGGCTCCGGATCCTGCACAG | 8493 | AQPSRAPDPAQ | 13082 | PSRAPDP | 0.188784 | -0.10614 |
| SyS1874 | 3905 | GCCCAATACCTCAACCAAATCAGAAGCGCACAG | 8494 | AQYLNQIRSAQ | 13083 | YLNQIRS | 0.188662 | -0.10889 |
| GS1090 | 3906 | GCCCAACAAAACAGAAGCGTCGTCGAAGCACAG | 8495 | AQQNRSVVEAQ | 13084 | QNRSVVE | 0.188647 | -0.14238 |
| GS1091 | 3907 | GCCCAACAGGAGTCTATGGTTAAGTATGCACAG | 8496 | AQQESMVKYAQ | 13085 | QESMVKY | 0.188647 | -0.17958 |
| GS1092 | 3908 | GCCCAAAAGCTGTCGCAGGAGAGTAATGCACAG | 8497 | AQKLSQESNAQ | 13086 | KLSQESN | 0.18854 | -0.13253 |
| SyS1875 | 3909 | GCCCAACGTGGTACTATGGAGCATGATGCACAG | 8498 | AQRGTMEHDAQ | 13087 | RGTMEHD | 0.188451 | -0.18042 |
| SyS1878 | 3910 | GCCCAACAGTCGGGTCCTGGGATTGTGGCACAG | 8499 | AQQSGPGIVAQ | 13088 | QSGPGIV | 0.188217 | -0.2083 |
| SyS1879 | 3911 | GCCCAACTCAACCAAGGCGACCTCCTCGCACAG | 8500 | AQLNQGDLLAQ | 13089 | LNQGDLL | 0.188212 | -0.21078 |
| SyS1880 | 3912 | GCCCAAGCCCAAAACCATCGGCACCGCACAG | 8501 | AQAKTIGSTAQ | 13090 | AKTIGST | 0.188109 | -0.10161 |
| SyS1881 | 3913 | GCCCAAGACAGCGGCAACAGAACCAGCGCACAG | 8502 | AQDSGNRTSAQ | 13091 | DSGNRTS | 0.187878 | -0.11374 |

FIG. 33 (Continued)

| | | | | | | | | |
|---|---|---|---|---|---|---|---|---|
| SyS1882 | 3914 | GCCCAACTCAGCCACCAGCTTCGCACAG | 8503 | AQLSHSTSFAQ | 13092 | LSHSTSF | 0.187878 | -0.11374 |
| GS1094 | 3915 | GCCCAAGGTGATTTTTCGTCGAAGCAGGCACAG | 8504 | AQGDFSSKQAQ | 13093 | GDFSSKQ | 0.187866 | -0.03656 |
| GP160 | 3916 | GCCCAAGATCATAGTAATGCGTATCGTGCACAG | 8505 | AQDHSNAYRAQ | 13094 | DHSNAYR | 0.187845 | -0.07058 |
| SyS1883 | 3917 | GCCCAAGTTCCGACTGATCGTCCTCGTGCACAG | 8506 | AQVPTDRPRAQ | 13095 | VPTDRPR | 0.187817 | -0.22042 |
| SyS1884 | 3918 | GCCCAAAGCATGCAACTCATCAACGAAGCACAG | 8507 | AQSMQLINEAQ | 13096 | SMQLINE | 0.187817 | -0.22042 |
| GS1095 | 3919 | GCCCAATACGCCAACAGCGTCGGCCTCGCACAG | 8508 | AQYANSVGLAQ | 13097 | YANSVGL | 0.187791 | -0.11279 |
| SyS1885 | 3920 | GCCCAAGTCTACCTCGCCAGCGGCGGCGCACAG | 8509 | AQVYLASGGAQ | 13098 | VYLASGG | 0.187783 | -0.22187 |
| SyS1886 | 3921 | GCCCAACTCATCCCCGTCACCAGCGTCGCACAG | 8510 | AQLIPVTSVAQ | 13099 | LIPVTSV | 0.187768 | -0.20466 |
| SyS1888 | 3922 | GCCCAAGGCAACATGAACAGCAGAACCGCACAG | 8511 | AQGNMNSRTAQ | 13100 | GNMNSRT | 0.18734 | -0.07494 |
| SyS1889 | 3923 | GCCCAAAGCCACAACGACAGCAGAAGCCTCGCACAG | 8512 | AQSHNDRSLAQ | 13101 | SHNDRSL | 0.18734 | -0.13798 |
| SyS1890 | 3924 | GCCCAACATAGGATTCCTACGGCTGGGGCACAG | 8513 | AQHRIPTAGAQ | 13102 | HRIPTAG | 0.18734 | -0.18527 |
| SyS1891 | 3925 | GCCCAAATGGGCAAAGACTACACCCACGCACAG | 8514 | AQMGKDYTHAQ | 13103 | MGKDYTH | 0.187325 | -0.18984 |
| SyS1893 | 3926 | GCCCAATCTCATGCGAGTACTCCTATTGCACAG | 8515 | AQSHASTPIAQ | 13104 | SHASTPI | 0.18723 | -0.16041 |
| GS1098 | 3927 | GCCCAACTCAACAGCCAAACCAGAAGCGCACAG | 8516 | AQLNSQTRSAQ | 13105 | LNSQTRS | 0.18719 | -0.08992 |
| SyS1894 | 3928 | GCCCAACGGACGCTGAGTGATAGTGTGGCACAG | 8517 | AQRTLSDSVAQ | 13106 | RTLSDSV | 0.187066 | -0.11859 |
| SyS1895 | 3929 | GCCCAACTTACGACTGCTAAGACGTTTGCACAG | 8518 | AQLTTAKTFAQ | 13107 | LTTAKTF | 0.187043 | -0.19723 |
| GS1099 | 3930 | GCCCAAAGAATCGTCGGCAGCCAGCGCACAG | 8519 | AQRIVGSTSAQ | 13108 | RIVGSTS | 0.187032 | -0.05357 |
| SyS1897 | 3931 | GCCCAAACCAAAACCCTGCCCCTCCACGCACAG | 8520 | AQTKTLALHAQ | 13109 | TKTLALH | 0.187025 | -0.15011 |
| SyS1898 | 3932 | GCCCAATGGGAAGTCCCCGCCAGAAACGCACAG | 8521 | AQWEVPARNAQ | 13110 | WEVPARN | 0.186968 | -0.18163 |
| SyS1899 | 3933 | GCCCAAATTTCTAATCCGGCGATTGCTGCACAG | 8522 | AQISNPAIAAQ | 13111 | ISNPAIA | 0.186968 | -0.18163 |
| GS1101 | 3934 | GCCCAATTGGGGGCTTCGCAGACTTCTGCACAG | 8523 | AQLGASQTSAQ | 13112 | LGASQTS | 0.186895 | -0.14143 |
| GS1103 | 3935 | GCCCAACTCAGCACCAACAGCGTCGCACAG | 8524 | AQLSTHNSVAQ | 13113 | LSTHNSV | 0.186848 | -0.02926 |
| GS1104 | 3936 | GCCCAAAGACACACCGACATGCGACACCGCACAG | 8525 | AQRHTDIDTAQ | 13114 | RHTDIDT | 0.186832 | -0.14779 |
| SyP61 | 3937 | GCCCAAGGGAGGCCGGTTATTGCGGCGGCACAG | 8526 | AQGRPVIAAAQ | 13115 | GRPVIAA | 0.186825 | -0.04411 |
| SyS1900 | 3938 | GCCCAAGCCAACCTCAGAGACGGCGTCGCACAG | 8527 | AQANLRDGVAQ | 13116 | ANLRDGV | 0.186763 | -0.13071 |
| GS1105 | 3939 | GCCCAAGTTCAGTCTCCGTCGATTACGGCACAG | 8528 | AQVQSPSITAQ | 13117 | VQSPSIT | 0.186748 | -0.17201 |
| SyS1901 | 3940 | GCCCAATTCACCAGCGGCAGCCACCTCGCACAG | 8529 | AQFTSGSHLAQ | 13118 | FTSGSHL | 0.18672 | -0.14647 |
| GS1106 | 3941 | GCCCAACCTCTTCAGCAGTCGGGTCATGCACAG | 8530 | AQPLQQSGHAQ | 13119 | PLQQSGH | 0.186526 | -0.09792 |
| SyS1902 | 3942 | GCCCAAGCCAGAGTCGCCACCACCCTCGCACAG | 8531 | AQARVATTLAQ | 13120 | ARVATTL | 0.186427 | -0.14283 |
| GS1108 | 3943 | GCCCAACCCGGCAGACAAAACGACGCCGCACAG | 8532 | AQPGRQNDAAQ | 13121 | PGRQNDA | 0.186248 | -0.1214 |
| SyS1905 | 3944 | GCCCAAAAATACAGCACCACCCATCGCACAG | 8533 | AQKYSSTAIAQ | 13122 | KYSSTAI | 0.186114 | -0.03736 |
| SyS1906 | 3945 | GCCCAACACAGCACCCACTACATCGCCGCACAG | 8534 | AQHSTHYIAAQ | 13123 | HSTHYIA | 0.186051 | -0.15496 |

FIG. 33 (Continued)

| | | | | | | | | |
|---|---|---|---|---|---|---|---|---|
| SyS1907 | 3946 | GCCCAACACCCCTCAACGCCCTCCCGCACAG | 8535 | AQQPLINALPAQ | 13124 | QPLINALP | 0.185989 | 0.064654 |
| GS1109 | 3947 | GCCCAAAAACCCAAGAAACCGGCAACGCACAG | 8536 | AQKTQETGNAQ | 13125 | KTQETGN | 0.185973 | -0.16035 |
| SyS1908 | 3948 | GCCCAAGTGAGTTGTCTGGCCATGCGGCACAG | 8537 | AQSELSRHAAQ | 13126 | SELSRHA | 0.18587 | 0.08751 |
| GS1110 | 3949 | GCCCAAGGCCCCAAAACCATCAGCACCGCACAG | 8538 | AQGPKTISTAQ | 13127 | GPKTIST | 0.18578 | -0.09587 |
| GS1111 | 3950 | GCCCAAGTCATAGTATTGTGAATCCGGCACAG | 8539 | AQSHSIVNPAQ | 13128 | SHSIVNP | 0.18578 | -0.1765 |
| SyS1909 | 3951 | GCCCAACATTCGAATACTGTGAGTTCGGCACAG | 8540 | AQHSNTVSSAQ | 13129 | HSNTVSS | 0.18577 | 0.232173 |
| SyS1910 | 3952 | GCCCAAGTCGCCGGCCTCACCGTCCAAGCACAG | 8541 | AQVAGLTVQAQ | 13130 | VAGLTVQ | 0.185758 | 0.055989 |
| GS1112 | 3953 | GCCCAAGCCAACCCGGCCTGCCAACGCACAG | 8542 | AQANPGLANAQ | 13131 | ANPGLAN | 0.185473 | -0.16663 |
| SyS1912 | 3954 | GCCCAAGCAGCGGTCAAATGACCCTCGCACAG | 8543 | AQASVQMTLAQ | 13132 | ASVQMTL | 0.185379 | -0.2305 |
| SyS1913 | 3955 | GCCCAACTCGTCACCGCCCAAGGCCCCGCACAG | 8544 | AQLVTAQGPAQ | 13133 | LVTAQGP | 0.185303 | -0.10115 |
| GP161 | 3956 | GCCCAAACTACGCGGTTATACTTCGCGGCACAG | 8545 | AQTTRYTSPAQ | 13134 | TTRYTSP | 0.185249 | -0.07433 |
| SyS1914 | 3957 | GCCCAAATGGACACCGACAAACCCAGAGCACAG | 8546 | AQMDTDKPRAQ | 13135 | MDTDKPR | 0.185204 | -0.14405 |
| SS121 | 3958 | GCCCAAGGCACCCAGCGTCCAAGACAGAGCACAG | 8547 | AQGTSVQDRAQ | 13136 | GTSVQDR | 0.185176 | -0.37486 |
| GS1113 | 3959 | GCCCAAAGAGCCAGCCCCAACAATACGCACAG | 8548 | AQRASPQQYAQ | 13137 | RASPQQY | 0.185058 | -0.15478 |
| SyS1915 | 3960 | GCCCAAGTCAGCAGCGAACACAGAATCGCACAG | 8549 | AQVSSEHRIAQ | 13138 | VSSEHRI | 0.184992 | 0.003859 |
| GS1114 | 3961 | GCCCAAAGCAACATGAAAATCCAACCGCACAG | 8550 | AQSNMKIQPAQ | 13139 | SNMKIQP | 0.184985 | -0.09183 |
| SyS1916 | 3962 | GCCCAAAACCTCAGAATCGAACCCATGGCACAG | 8551 | AQNLRIEPMAQ | 13140 | NLRIEPM | 0.18494 | -0.08585 |
| SyS1917 | 3963 | GCCCAACCCACCGAAAGCCTCAGAGTCGCACAG | 8552 | AQPTESLRVAQ | 13141 | PTESLRV | 0.184782 | -0.20955 |
| GP162 | 3964 | GCCCAAACTAATAGGGGTCTTGCTCTTGCACAG | 8553 | AQTNRGLALAQ | 13142 | TNRGLAL | 0.184678 | -0.05599 |
| SyS1920 | 3965 | GCCCAACATGAGAAGACGGCGTATATTGCACAG | 8554 | AQHEKTAYIAQ | 13143 | HEKTAYI | 0.184498 | -0.15657 |
| SyS1921 | 3966 | GCCCAAAATGTTATTTCTAAGAATTTGGCACAG | 8555 | AQNVISKNLAQ | 13144 | NVISKNL | 0.184372 | -0.22649 |
| SyP62 | 3967 | GCCCAAGGACGGCGGGGTTTCGTCGGCACAG | 8556 | AQGTAGFSSAQ | 13145 | GTAGFSS | 0.184333 | -0.04152 |
| SyS1922 | 3968 | GCCCAAATTGCGCAGATGGGGGTTAAGGCACAG | 8557 | AQIAQMGVKAQ | 13146 | IAQMGVK | 0.184332 | -0.18861 |
| SyS1923 | 3969 | GCCCAAACTTCTAAGGATGTGAAGGATGCACAG | 8558 | AQTSKDVKDAQ | 13147 | TSKDVKD | 0.184281 | -0.18769 |
| SyS1924 | 3970 | GCCCAAATCATCGGCGCCAGAGACATCGCACAG | 8559 | AQIIGARDIAQ | 13148 | IIGARDI | 0.18425 | -0.16829 |
| SyS1925 | 3971 | GCCCAACTTAGGGATACGGGTCTTGGGGCACAG | 8560 | AQLRDTGLGAQ | 13149 | LRDTGLG | 0.184224 | -0.1489 |
| SyS1926 | 3972 | GCCCAACTCAGCAACAGCCTCGGCCAAGCACAG | 8561 | AQLSNSLGQAQ | 13150 | LSNSLGQ | 0.184171 | 0.126572 |
| GS1116 | 3973 | GCCCAAAACGTCCTCAACAGCAGAGGCGCACAG | 8562 | AQNVLNSRGAQ | 13151 | NVLNSRG | 0.18417 | -0.17958 |
| GS1117 | 3974 | GCCCAATTTAGGGGTAGTGGTAGTCCGGCACAG | 8563 | AQFRGSGSPAQ | 13152 | FRGSGSP | 0.18417 | -0.17958 |
| GS1118 | 3975 | GCCCAAAATCCGGAGTTGCCGCGTCAGGCACAG | 8564 | AQNPELPRQAQ | 13153 | NPELPRQ | 0.184111 | -0.16932 |
| GS1119 | 3976 | GCCCAAACGTCTAGTTCGTTTAAGGAGGCACAG | 8565 | AQTSSSFKEAQ | 13154 | TSSSFKE | 0.184043 | -0.14524 |
| SyS1928 | 3977 | GCCCAAAACAGAGAATACATGACCCACGCACAG | 8566 | AQNREYMTHAQ | 13155 | NREYMTH | 0.183973 | -0.18405 |

FIG. 33 (Continued)

| | | | | | | | | |
|---|---|---|---|---|---|---|---|---|
| SyP63 | 3978 | GCCCAAACGCCTGGTGTTGCGCATCCTGCACAG | 8567 | AQTPGVAHPAQ | 13156 | TPGVAHP | 0.183725 | -0.04392 |
| SyS1931 | 3979 | GCCCAAACGCAGTCTTCGGAGGGGCCTGCACAG | 8568 | AQTQSSEGPAQ | 13157 | TQSSEGP | 0.183702 | -0.19969 |
| GS1120 | 3980 | GCCCAAAGGGGTGAGCCGATTGTGTCGGCACAG | 8569 | AQRGEPIVSAQ | 13158 | RGEPIVS | 0.183678 | -0.17577 |
| GS1121 | 3981 | GCCCAATCGCTTACGTCTCTGAATTCTGCACAG | 8570 | AQSLTSLNSAQ | 13159 | SLTSLNS | 0.183678 | -0.14143 |
| SyS1933 | 3982 | GCCCAAACGGTGTTGCATACGAGGCAGGCACAG | 8571 | AQTVLHTRQAQ | 13160 | TVLHTRQ | 0.183603 | -0.06701 |
| SyS1934 | 3983 | GCCCAATTGTCGAAGTCGGGTGCGGATGCACAG | 8572 | AQLSKSGADAQ | 13161 | LSKSGAD | 0.183472 | -0.12577 |
| SyS1935 | 3984 | GCCCAAGCCAACGGCAACCAAAGCCTCGCACAG | 8573 | AQANGNQSLAQ | 13162 | ANGNQSL | 0.183416 | 0.105951 |
| SyS1936 | 3985 | GCCCAATTCGTCACCAGCAGCAGCGGCGCACAG | 8574 | AQFVTSSSGAQ | 13163 | FVTSSSG | 0.183382 | 0.086298 |
| SyP64 | 3986 | GCCCAAGGTGCGAATAATCATACGCGTGCACAG | 8575 | AQGANNHTRAQ | 13164 | GANNHTR | 0.183354 | -0.04236 |
| SyS1937 | 3987 | GCCCAACACGCCAGCGACGTCAACAACGCACAG | 8576 | AQHASDVNNAQ | 13165 | HASDVNN | 0.183281 | -0.23173 |
| GS1123 | 3988 | GCCCAAGGCCACCACACCAGCACCCGCACAG | 8577 | AQGHHTSDPAQ | 13166 | GHHTSDP | 0.183067 | -0.17381 |
| SyS1939 | 3989 | GCCCAAGACAAAAACCCGGCGTCCACGCACAG | 8578 | AQDKNPGVHAQ | 13167 | DKNPGVH | 0.182966 | -0.15011 |
| SyS1940 | 3990 | GCCCAATCGAGGAATTCGCATATTGAGGCACAG | 8579 | AQSRNSHIEAQ | 13168 | SRNSHIE | 0.182829 | -0.00548 |
| SyS1941 | 3991 | GCCCAACAGGCGAGTTCTGATCATGTTGCACAG | 8580 | AQQASSDHVAQ | 13169 | QASSDHV | 0.182736 | -0.1889 |
| GS1125 | 3992 | GCCCAACTCAGAGACACCCCTACAACGCACAG | 8581 | AQLRDTPYNAQ | 13170 | LRDTPYN | 0.182726 | -0.18188 |
| GS1126 | 3993 | GCCCAAAGTTGGCTGCGACGAGGGATGCACAG | 8582 | AQSLAATRDAQ | 13171 | SLAATRD | 0.182549 | -0.12807 |
| SyS1942 | 3994 | GCCCAAGGCCACGTCAACAACGCCGTCGCACAG | 8583 | AQGHVNNAVAQ | 13172 | GHVNNAV | 0.182493 | -0.12331 |
| SyS1943 | 3995 | GCCCAATTGGTGGGCTTACGACGCGGGGCACAG | 8584 | AQIGGLTTRAQ | 13173 | IGGLTTR | 0.18241 | -0.12143 |
| GS1127 | 3996 | GCCCAAAGCAAAGAAAGAAAACGGCCAAGCACAG | 8585 | AQSKERNGQAQ | 13174 | SKERNGQ | 0.182404 | -0.12617 |
| GS1128 | 3997 | GCCCAATTGAATAGTGGTTCTTCTGCACAG | 8586 | AQLNSGSSAAQ | 13175 | LNSGSSA | 0.182404 | -0.16432 |
| SyS1944 | 3998 | GCCCAAACCATGAGCACCACCTACGAAGCACAG | 8587 | AQTMSTTYEAQ | 13176 | TMSTTYE | 0.182396 | -0.10816 |
| GS1129 | 3999 | GCCCAAGGCGCCGACAACAGAGATCAGCGCACAG | 8588 | AQGADNRISAQ | 13177 | GADNRIS | 0.182324 | -0.17022 |
| SyS1945 | 4000 | GCCCAAACCCAAAACAACCAACGGCGACGTCGCACAG | 8589 | AQTQNNGDVAQ | 13178 | TQNNGDV | 0.18227 | -0.20466 |
| GP163 | 4001 | GCCCAAAATGGTCCGTCTGTGCTGAGTGCACAG | 8590 | AQNGPSVLSAQ | 13179 | NGPSVLS | 0.182231 | 0.090896 |
| SyS1946 | 4002 | GCCCAAACGGCTCTTCGGGATGTGGGTGCACAG | 8591 | AQTALRDVGAQ | 13180 | TALRDVG | 0.182226 | 0.09096 |
| SyS1947 | 4003 | GCCCAAAGGACTATGGGGACGACTATGGCACAG | 8592 | AQRTMGTTMAQ | 13181 | RTMGTTM | 0.182133 | 0.002686 |
| GS1131 | 4004 | GCCCAAACGAGGGGTACGACTGTGGAGGCACAG | 8593 | AQTRGTTVEAQ | 13182 | TRGTTVE | 0.182067 | 0.079797 |
| GS1132 | 4005 | GCCCAAACCGTCAGCAGAGTCCAAGTCGCACAG | 8594 | AQTVSRVQVAQ | 13183 | TVSRVQV | 0.181971 | -0.16842 |
| SyS1948 | 4006 | GCCCAAAGGCTGGAATACTAGTGCGGATGCACAG | 8595 | AQRLDTSADAQ | 13184 | RLDTSAD | 0.181959 | -0.1344 |
| GS1133 | 4007 | GCCCAACTCATGACCAAAGGCCTCGTCGCACAG | 8596 | AQLMTKGLVAQ | 13185 | LMTKGLV | 0.181936 | -0.17829 |
| SyS1949 | 4008 | GCCCAACCCATGAGAATGCAAACCGCCGCACAG | 8597 | AQPMRMQTAAQ | 13186 | PMRMQTA | 0.181912 | -0.17998 |
| SyS1950 | 4009 | GCCCAAGTGGTGCTGGGGAGTACTTTCTGCACAG | 8598 | AQVVLGSTSAQ | 13187 | VVLGSTS | 0.181893 | -0.13192 |

FIG. 33 (Continued)

| | | | | | | | | |
|---|---|---|---|---|---|---|---|---|
| GS1135 | 4010 | GCCCAATCTAATAATGGGAATGGTCATGCACAG | 8599 | AQSNNGNGHAQ | 13188 | SNNGNGH | 0.181861 | -0.17863 |
| SyS1951 | 4011 | GCCCAAAGAGGCCCGACCTCCTCAACGCACAG | 8600 | AQRGPDLLNAQ | 13189 | RGPDLLN | 0.181699 | -0.12829 |
| SyS1952 | 4012 | GCCCAAGGTTTAATAGTATGAAGCCTGCACAG | 8601 | AQGFNSMKPAQ | 13190 | GFNSMKP | 0.181699 | -0.17435 |
| SyS1953 | 4013 | GCCCAACTCAACAGCAACCCATGAACGCACAG | 8602 | AQLNSNPMNAQ | 13191 | LNSNPMN | 0.181699 | -0.17435 |
| GS1136 | 4014 | GCCCAACTCAGCAACAGAGTCAAAGCGCACAG | 8603 | AQLSNRVQSAQ | 13192 | LSNRVQS | 0.181602 | -0.07962 |
| GS1137 | 4015 | GCCCAAAGCAGAATGGAAGGCACCGTCGCACAG | 8604 | AQSRMEGTVAQ | 13193 | SRMEGTV | 0.181451 | -0.1451 |
| SyS1955 | 4016 | GCCCAAAGCGAACAATACGTCAGAGTCGCACAG | 8605 | AQSEQYVRVAQ | 13194 | SEQYVRV | 0.181394 | -0.16643 |
| GS1138 | 4017 | GCCCAAAGTAATCTTGCGAATCAGCCTGCACAG | 8606 | AQSNLANQPAQ | 13195 | SNLANQP | 0.1813 | -0.16484 |
| GP164 | 4018 | GCCCAAGTGAGTATGCAGAGGCCGACGGCACAG | 8607 | AQVSMQRPTAQ | 13196 | VSMQRPT | 0.181294 | -0.06864 |
| SyS1956 | 4019 | GCCCAATTTCATGGTCAGGGTATGTCTGCACAG | 8608 | AQFHGQGMSAQ | 13197 | FHGQGMS | 0.181291 | -0.14405 |
| SyS1959 | 4020 | GCCCAAACGGGCGCCATCAACGCCCCGCACAG | 8609 | AQTGAINAPAQ | 13198 | TGAINAP | 0.181162 | -0.21202 |
| SyS1960 | 4021 | GCCCAAAACGCTGTTTAAGAATGGTCCTGCACAG | 8610 | AQTLFKNGPAQ | 13199 | TLFKNGP | 0.181097 | -0.21315 |
| SyS1961 | 4022 | GCCCAAGTGGTGCCTATTTGACGAATGCACAG | 8611 | AQVVPISTNAQ | 13200 | VVPISTN | 0.181026 | -0.16344 |
| GS1140 | 4023 | GCCCAAGCAAAGGCACCGCCCTGTCGCACAG | 8612 | AQAKGTALVAQ | 13201 | AKGTALV | 0.180981 | -0.16304 |
| SyS1962 | 4024 | GCCCAAAGGGATACTGTGCAGGTGTATGCACAG | 8613 | AQRDTVQVYAQ | 13202 | RDTVQVY | 0.180851 | -0.21571 |
| GS1141 | 4025 | GCCCAACTCGGCACCAAAGCCACCCACGCACAG | 8614 | AQLGTKATHAQ | 13203 | LGTKATH | 0.180672 | -0.16125 |
| SyS1964 | 4026 | GCCCAAGACAACGTCAGAGTCACCGCCGCACAG | 8615 | AQDNVRVTAAQ | 13204 | DNVRVTA | 0.180658 | 0.019619 |
| SP40 | 4027 | GCCCAAACGAGGCCTGGGTCGCATACTGCACAG | 8616 | AQTRPGSHTAQ | 13205 | TRPGSHT | 0.180609 | -0.05314 |
| SyS1965 | 4028 | GCCCAAGCTCAGTTGGCTCCTCGTGCGGCACAG | 8617 | AQAQLAPRAAQ | 13206 | AQLAPRA | 0.180606 | -0.19846 |
| GP165 | 4029 | GCCCAATCTACTACTATGCGGACGTGCTGGCACAG | 8618 | AQSTMRTSLAQ | 13207 | STMRTSL | 0.1806 | 0.12275 |
| SP41 | 4030 | GCCCAAATGAATCAGACTTCTGCTAAGGCACAG | 8619 | AQMNQTSAKAQ | 13208 | MNQTSAK | 0.180557 | -0.05178 |
| SyS1966 | 4031 | GCCCAAAGCAGAAGCAGCCCACCATCGCACAG | 8620 | AQSRSSPTIAQ | 13209 | SRSSPTI | 0.180499 | -0.01734 |
| GS1142 | 4032 | GCCCAAAGCGCCCTCAACCAATACCCGCACAG | 8621 | AQSALNQYPAQ | 13210 | SALNQYP | 0.180451 | -0.08545 |
| GS1143 | 4033 | GCCCAAATCAGCAACCACCACCAGAAACGCACAG | 8622 | AQISTTTRNAQ | 13211 | ISTTTRN | 0.180379 | -0.13952 |
| GS1144 | 4034 | GCCCAATCTCGTGATACGCCGAGTGGTGCCACAG | 8623 | AQSRDTPSGAQ | 13212 | SRDTPSG | 0.18029 | -0.0879 |
| SyS1967 | 4035 | GCCCAAAAACTTCAACAACAAGGCCTCGCACAG | 8624 | AQNFNKQGLAQ | 13213 | NFNKQGL | 0.180248 | -0.06663 |
| SyS1968 | 4036 | GCCCAACCTAGTAATACGTCTTCGGTTGCACAG | 8625 | AQPSNTSSVAQ | 13214 | PSNTSSV | 0.180178 | -0.2231 |
| SS127 | 4037 | GCCCAAAACTGTTAGTACGAATGCGAGGGCACAG | 8626 | AQTVSTNARAQ | 13215 | TVSTNAR | 0.180153 | -0.35824 |
| GS1145 | 4038 | GCCCAAAAACATGAGCCAAACCGTCGCCGCACAG | 8627 | AQNMSQTVAAQ | 13216 | NMSQTVA | 0.180083 | -0.15766 |
| GS1146 | 4039 | GCCCAAATTGGGAAGAGTTCTACTCCTGCACAG | 8628 | AQIGKSSTPAQ | 13217 | IGKSSTP | 0.179902 | -0.11877 |
| GS1147 | 4040 | GCCCAAAGAGAGAAACCGAAACCGGCAGAGCACAG | 8629 | AQRETETGRAQ | 13218 | RETETGR | 0.179896 | -0.13189 |
| SyS1969 | 4041 | GCCCAACCTTATACTCCGCTGACTGGTGCACAG | 8630 | AQPYTPLTGAQ | 13219 | PYTPLTG | 0.179831 | -0.19496 |

FIG. 33 (Continued)

| | | | | | | | | |
|---|---|---|---|---|---|---|---|---|
| SyS1970 | 4042 | GCCCAAGCCGAATACAACACCGGCGGTCGCACAG | 8631 | AQAEYNTGVAQ | 13220 | AEYNTGV | 0.179673 | -0.16466 |
| SyS1971 | 4043 | GCCCAAGGCAGAAACGCCGAAACCAGAGCACAG | 8632 | AQGRNAETRAQ | 13221 | GRNAETR | 0.17963 | -0.04562 |
| GS1149 | 4044 | GCCCAAACGTTTAATCATACTACTGATGCACAG | 8633 | AQTFNHTTDAQ | 13222 | TFNHTTD | 0.179619 | -0.17768 |
| GS1150 | 4045 | GCCCAAACCCACCTCAGCACCCTCGGCGCACAG | 8634 | AQTHLSTLGAQ | 13223 | THLSTLG | 0.179495 | -0.06913 |
| GS1151 | 4046 | GCCCAACTTAAGGGTATTAGTCAGCATGCACAG | 8635 | AQLKGISQHAQ | 13224 | LKGISQH | 0.17936 | -0.12235 |
| SyS1974 | 4047 | GCCCAATATTCTAGTGGTATGGTATGACGGCACAG | 8636 | AQYSSGMTTAQ | 13225 | YSSGMTT | 0.17933 | -0.09037 |
| SyS1975 | 4048 | GCCCAAACGGCTATTACGATGACTAGTGCACAG | 8637 | AQTAITMTSAQ | 13226 | TAITMTS | 0.179201 | -0.00948 |
| SyS1976 | 4049 | GCCCAAAGAGGCAACGAACTCAACACCGCACAG | 8638 | AQRGNELNTAQ | 13227 | RGNELNT | 0.179161 | -0.06646 |
| SyS1977 | 4050 | GCCCAAGTCGTCAGCAGCCAAATGGCCGCACAG | 8639 | AQVVSSQMAAQ | 13228 | VVSSQMA | 0.179109 | -0.03159 |
| SyS1978 | 4051 | GCCCAACACCAACACGAAAACATGGTCGCACAG | 8640 | AQHQHENMVAQ | 13229 | HQHENMV | 0.179092 | -0.15927 |
| SyS1980 | 4052 | GCCCAAAGCTTCGGCGGCGTCCCAAAGCACAG | 8641 | AQSFGGVPKAQ | 13230 | SFGGVPK | 0.179027 | -0.08158 |
| GS1153 | 4053 | GCCCAATTGATGCGTGATAGTAAGTCTGCACAG | 8642 | AQLMRDSKSAQ | 13231 | LMRDSKS | 0.17901 | -0.11654 |
| GS1154 | 4054 | GCCCAAATGAGAAACCAACCTCAGCATGGCACAG | 8643 | AQMRTNLSMAQ | 13232 | MRTNLSM | 0.179008 | -0.17381 |
| SyS1981 | 4055 | GCCCAACCGAATAATCCTGTGGTGCCTGCACAG | 8644 | AQPNNPVVPAQ | 13233 | PNNPVVP | 0.179008 | -0.18042 |
| GP167 | 4056 | GCCCAAAGGGTTAGTCAGTCTATGGGTGCACAG | 8645 | AQRVSQSMGAQ | 13234 | RVSQSMG | 0.17897 | -0.07391 |
| SyS1982 | 4057 | GCCCAAGCTGAGGGTCCTCAGAAGACGGGCACAG | 8646 | AQAEGPQKTAQ | 13235 | AEGPQKT | 0.178923 | -0.05601 |
| SyS1983 | 4058 | GCCCAACTTAATTCTGTGGTTCATACGGCACAG | 8647 | AQLNSVVHTAQ | 13236 | LNSVVHT | 0.17892 | -0.01781 |
| GS1155 | 4059 | GCCCAACTGTTGACGTTGAATTCGGCTGCACAG | 8648 | AQLLTLNSAAQ | 13237 | LLTLNSA | 0.178886 | -0.16814 |
| SyS1985 | 4060 | GCCCAAACGCTTGCCTCCTCGGAGGGATGCACAG | 8649 | AQTLAPRRDAQ | 13238 | TLAPRRD | 0.178476 | -0.16951 |
| GS1159 | 4061 | GCCCAAAGAGTCGCCAACCCCGCCACCGCACAG | 8650 | AQRVANPATAQ | 13239 | RVANPAT | 0.178389 | -0.12177 |
| SyS1986 | 4062 | GCCCAATTGCCGGATCCTAGGTTGCAGGCACAG | 8651 | AQLPDPRLQAQ | 13240 | LPDPRLQ | 0.178351 | -0.1063 |
| SyS1987 | 4063 | GCCCAAAAAATGGACGTTCGGCGAAGCCGCACAG | 8652 | AQKMDVGEAAQ | 13241 | KMDVGEA | 0.178194 | -0.22434 |
| SyS1988 | 4064 | GCCCAAGGTCGTCTCTATGGTTATGGCACAG | 8653 | AQGPSPMVMAQ | 13242 | GPSPMVM | 0.178194 | -0.22434 |
| GS1160 | 4065 | GCCCAAGGCACCAACAAAGCCACCGCCGCACAG | 8654 | AQGTNKATAAQ | 13243 | GTNKATA | 0.178061 | -0.05206 |
| GS1161 | 4066 | GCCCAACTCAGCGCCCAGGCACCACCGCACAG | 8655 | AQLSAHGTTAQ | 13244 | LSAHGTT | 0.178024 | -0.18009 |
| GS1162 | 4067 | GCCCAAACAGCAGAGATACAACAGCCGCCGCACAG | 8656 | AQTSRYNSAAQ | 13245 | TSRYNSA | 0.177853 | -0.16663 |
| GS1989 | 4068 | GCCCAAGGCCCCAACAGCAGCTTCAAAGCACAG | 8657 | AQGPNSSFKAQ | 13246 | GPNSSFK | 0.177775 | -0.16273 |
| GS1163 | 4069 | GCCCAAAGTGTTGGGAGGGCTCCGATTGCACAG | 8658 | AQSVGRAPIAQ | 13247 | SVGRAPI | 0.177653 | -0.14715 |
| SyS1990 | 4070 | GCCCAATTTCAGGGTGAGAAGACGTGGGCACAG | 8659 | AQFQGEKTWAQ | 13248 | FQGEKTW | 0.177633 | -0.06462 |
| SyS1991 | 4071 | GCCCAAACCAGCAGCGCCAGAACCATCGCACAG | 8660 | AQTSSARTIAQ | 13249 | TSSARTI | 0.177546 | -0.07616 |
| SyS1992 | 4072 | GCCCAAGCTGAGCGTACTGGGACTGCGGCACAG | 8661 | AQAERTGTAAQ | 13250 | AERTGTA | 0.177482 | -0.16643 |
| GS1164 | 4073 | GCCCAACTCAACCTCGGCACCCCCAAAGCACAG | 8662 | AQLNLGTPKAQ | 13251 | LNLGTPK | 0.177441 | -0.17672 |

FIG. 33 (Continued)

| | | | | | | | | |
|---|---|---|---|---|---|---|---|---|
| GP168 | 4074 | GCCCAAGCTGCGCCGGTTGGGTCTAGGGCACAG | 8663 | AQAAPVGSRAQ | 13252 | AAPVGSR | 0.177438 | 0.019689 |
| GS1165 | 4075 | GCCCAAATGAGACAAGCCAACCACCCGCACAG | 8664 | AQMRQANHPAQ | 13253 | MRQANHP | 0.177418 | -0.10804 |
| SyS1993 | 4076 | GCCCAAGCAGCAGCAGGCGGTGATGTGCTGGCACAG | 8665 | AQEQQRDVLAQ | 13254 | EQQRDVL | 0.177373 | -0.18368 |
| SyS1994 | 4077 | GCCCAACCCAAAAGCGACGAACTCACCGCACAG | 8666 | AQPKSDELTAQ | 13255 | PKSDELT | 0.177331 | -0.23173 |
| SyS1995 | 4078 | GCCCAAAATGCTCGTGTTCAGGAGACTGCACAG | 8667 | AQNARVQETAQ | 13256 | NARVQET | 0.177294 | 0.036888 |
| SyS1996 | 4079 | GCCCAAACTACGGTTGCTACTCAGTCGGCACAG | 8668 | AQTTVATQSAQ | 13257 | TTVATQS | 0.177266 | -0.08132 |
| SyS1997 | 4080 | GCCCAAACCGAAGTCAGCCACAGACCGGCACAG | 8669 | AQTEVSHRPAQ | 13258 | TEVSHRP | 0.177079 | -0.13314 |
| SyS1998 | 4081 | GCCCAAAGCAGCACCGTCAAAAACGTCGGCACAG | 8670 | AQSSTVKNVAQ | 13259 | SSTVKNV | 0.177072 | 0.041757 |
| SyS1999 | 4082 | GCCCAAAATCGACAGCCACCTCAACAGAGCACAG | 8671 | AQIDSHLNRAQ | 13260 | IDSHLNR | 0.176954 | -0.05133 |
| SyS2000 | 4083 | GCCCAAGGTTCGACTCAGCTGAGTCTGGCACAG | 8672 | AQGSTQLSLAQ | 13261 | GSTQLSL | 0.17695 | -0.03737 |
| GS1170 | 4084 | GCCCAAGACGGGCAGCCCGCCACCAAAGCACAG | 8673 | AQDGSPATKAQ | 13262 | DGSPATK | 0.17691 | -0.18637 |
| SyS2001 | 4085 | GCCCAACAAACCGGCAACAGCCAAGCCGCACAG | 8674 | AQQTGNSQAAQ | 13263 | QTGNSQA | 0.176685 | -0.02351 |
| SyS2002 | 4086 | GCCCAAAGACAAGAGCGTCAACGTCAGCGCACAG | 8675 | AQRQDVNVSAQ | 13264 | RQDVNVS | 0.176645 | -0.22187 |
| GS1172 | 4087 | GCCCAACTCGACTACGGCGGTCAAAAGCGCACAG | 8676 | AQLDYGVKSAQ | 13265 | LDYGVKS | 0.176625 | -0.01607 |
| SyS2003 | 4088 | GCCCAAGGTTCTCGTCCTGAGGCGCCGGCACAG | 8677 | AQGSRPEAPAQ | 13266 | GSRPEAP | 0.176327 | -0.1489 |
| SyS2004 | 4089 | GCCCAATGGAGCAACATGACCGCCGCCGCACAG | 8678 | AQWSNMTAAAQ | 13267 | WSNMTAA | 0.176285 | 0.188706 |
| GP171 | 4090 | GCCCAAACTAATACTACTCGGATTTCTGCACAG | 8679 | AQTNTTRISAQ | 13268 | TNTTRIS | 0.176104 | 0.234131 |
| SyS2007 | 4091 | GCCCAACCTTATGCGGAGAGGCAGGCTGCACAG | 8680 | AQPYAERQAAQ | 13269 | PYAERQA | 0.175875 | -0.12869 |
| SyS2008 | 4092 | GCCCAAACCAGCAGCGCCACCGTCCTCGCACAG | 8681 | AQTSSATVLAQ | 13270 | TSSATVL | 0.175872 | -0.08332 |
| SyS2009 | 4093 | GCCCAAGCGCAGACTGATTTTAGGCAGGCACAG | 8682 | AQAQTDFRQAQ | 13271 | AQTDFRQ | 0.175789 | -0.17557 |
| GS1173 | 4094 | GCCCAAAACAGCGGCAACGAACAGCAGCGCACAG | 8683 | AQNSGNEHSAQ | 13272 | NSGNEHS | 0.175772 | -0.17919 |
| SyS2010 | 4095 | GCCCAAAAAGCCGCTGATTAATGCTACTGCACAG | 8684 | AQKPLINATAQ | 13273 | KPLINAT | 0.175674 | -0.17193 |
| SyS2011 | 4096 | GCCCAAATGGGGAGTTCGTCGGCGTTTGCACAG | 8685 | AQMGSSSAFAQ | 13274 | MGSSSAF | 0.175674 | -0.17193 |
| GS1174 | 4097 | GCCCAAATTGGTAATAAGACGAGTCTGGCACAG | 8686 | AQIGNKTSLAQ | 13275 | IGNKTSL | 0.175642 | -0.13523 |
| SyS2012 | 4098 | GCCCAAGCGCCACACCGCCCCAAAGCACAG | 8687 | AQAANTAPKAQ | 13276 | AANTAPK | 0.17558 | -0.10142 |
| GS1175 | 4099 | GCCCAACTCGTCGACCAAAGAGCCACGGCACAG | 8688 | AQLVDQRATAQ | 13277 | LVDQRAT | 0.175514 | -0.1774 |
| SyS2015 | 4100 | GCCCAACAAGTCAAACTCGGCAGCACCGCACAG | 8689 | AQQVKLGSTAQ | 13278 | QVKLGST | 0.175457 | -0.21315 |
| GS1176 | 4101 | GCCCAACTCACCAGCAACACCCACGTCGCACAG | 8690 | AQLTSNTHVAQ | 13279 | LTSNTHV | 0.175385 | -0.05777 |
| GS1177 | 4102 | GCCCAAGTCTACAGCGCCATCAACAAAGCACAG | 8691 | AQVYSAINKAQ | 13280 | VYSAINK | 0.175251 | -0.17386 |
| SyS2017 | 4103 | GCCCAAAGAGCCAACGGCAGCGACCTCGCACAG | 8692 | AQRANGSDLAQ | 13281 | RANGSDL | 0.17502 | 0.012701 |
| SyS2018 | 4104 | GCCCAAAACCTCAAAAGCCAAACCGAAGCACAG | 8693 | AQNLKSQTEAQ | 13282 | NLKSQTE | 0.174966 | -0.12454 |
| SyS2019 | 4105 | GCCCAAAGCTACGGCAACGAAATCAGAGAGCACAG | 8694 | AQSYGNEIRAQ | 13283 | SYGNEIR | 0.174809 | 0.068074 |

FIG. 33 (Continued)

| | | | | | | | | |
|---|---|---|---|---|---|---|---|---|
| SyS2020 | 4106 | GCCCAACTCACCAGAGGGCGGCCATCGGCGCACAG | 8695 | AQLTRGAIGAQ | 13284 | LTRGAIG | 0.174654 | -0.13192 |
| GS1178 | 4107 | GCCCAACCCATCAGAACCGTCGACACCGCACAG | 8696 | AQPIRTVDTAQ | 13285 | PIRTVDT | 0.174634 | -0.12446 |
| SyS2021 | 4108 | GCCCAACGGAGTATGCCTGATGGTTCGGCACAG | 8697 | AQRSMPDGSAQ | 13286 | RSMPDGS | 0.174629 | -0.18769 |
| GS1179 | 4109 | GCCCAAACCGCCCACACCGGCCCCCTCGCACAG | 8698 | AQTAHTGPLAQ | 13287 | TAHTGPL | 0.174581 | -0.15288 |
| SP42 | 4110 | GCCCAATCGCAGGGGAGTCCGCTTTCGGCACAG | 8699 | AQSQGSPLSAQ | 13288 | SQGSPLS | 0.174469 | -0.0526 |
| SyS2022 | 4111 | GCCCAACTCCAAGCCATCGCCCACAGCGCACAG | 8700 | AQLQAIAHSAQ | 13289 | LQAIAHS | 0.174346 | -0.17678 |
| SyS2024 | 4112 | GCCCAAGGCAACAGCCTCAGCACCAGCGCACAG | 8701 | AQGNSLSTSAQ | 13290 | GNSLSTS | 0.174173 | -0.2268 |
| GS1180 | 4113 | GCCCAACTCACCCACAGAGAAGCCGAAGCACAG | 8702 | AQLTHREAFAQ | 13291 | LTHREAF | 0.174167 | -0.06761 |
| GS1181 | 4114 | GCCCAAACGTTGCATCTGGCGAAGGAGGCACAG | 8703 | AQTLHLAKEAQ | 13292 | TLHLAKE | 0.174141 | -0.16663 |
| GS1182 | 4115 | GCCCAAAAACATCAGCAGCAGGGCAAAGCACAG | 8704 | AQNISSSGKAQ | 13293 | NISSSGK | 0.174056 | -0.08647 |
| SyS2026 | 4116 | GCCCAAGGCAGACACATGGTCATGGAAGCACAG | 8705 | AQGRHMVMEAQ | 13294 | GRHMVME | 0.173999 | -0.09555 |
| GS1183 | 4117 | GCCCAAGGTGAGAGGTTTGGGGGGCCTGCACAG | 8706 | AQGERFGGPAQ | 13295 | GERFGGP | 0.173807 | -0.18009 |
| SyS2027 | 4118 | GCCCAATATAGTGGGTCTTCTACTAAGGCACAG | 8707 | AQYSGSSTKAQ | 13296 | YSGSSTK | 0.173744 | -0.09789 |
| SyS2028 | 4119 | GCCCAAAAGGAGTCTGTTAGTGCGAATGCACAG | 8708 | AQKESVSANAQ | 13297 | KESVSAN | 0.173712 | -0.006 |
| SyS2030 | 4120 | GCCCAAATTACGAGTGATGGGAAGCCGGCACAG | 8709 | AQITSDGKPAQ | 13298 | ITSDGKP | 0.173449 | 0.031329 |
| SyS2031 | 4121 | GCCCAAGGTCATGATGCGCGTGTGGTTGCACAG | 8710 | AQGHDARVVAQ | 13299 | GHDARVV | 0.173427 | 0.011182 |
| SyS2032 | 4122 | GCCCAAACCAGCAGCAACGGCGTCAGAGCACAG | 8711 | AQTSSNGVRAQ | 13300 | TSSNGVR | 0.173427 | 0.042989 |
| GS1184 | 4123 | GCCCAAAATCATCAGAATCGGTCTTTGGCACAG | 8712 | AQNHQNRSLAQ | 13301 | NHQNRSL | 0.173427 | -0.18245 |
| GS1185 | 4124 | GCCCAACGGGTTCCGGAGCAGAATGTGGCACAG | 8713 | AQRVPEQNVAQ | 13302 | RVPEQNV | 0.173385 | -0.18054 |
| GS1186 | 4125 | GCCCAAAGCGCCCAACTCAGAAGCAGCGCACAG | 8714 | AQSAQLRSSAQ | 13303 | SAQLRSS | 0.173344 | -0.17863 |
| GS1187 | 4126 | GCCCAACACGCCAAAAGCGAAACCTACGCACAG | 8715 | AQHAKSETYAQ | 13304 | HAKSETY | 0.173305 | -0.17672 |
| SyS2033 | 4127 | GCCCAACTCCTCACCCAAGTCGAAACGCACAG | 8716 | AQLLTQVETAQ | 13305 | LLTQVET | 0.173298 | -0.12503 |
| SyS2034 | 4128 | GCCCAAACCAAACCGCCGACACCTACGCACAG | 8717 | AQTKTADTYAQ | 13306 | TKTADTY | 0.173226 | 0.171999 |
| SyS2035 | 4129 | GCCCAAGTTATGCCTGCTACGTTGAGTGCACAG | 8718 | AQVMPATLSAQ | 13307 | VMPATLS | 0.173152 | -0.19254 |
| GS1188 | 4130 | GCCCAATACCAAGCCAACAACCTCATCGCACAG | 8719 | AQYQANNLIAQ | 13308 | YQANNLI | 0.17301 | -0.15955 |
| SyS2036 | 4131 | GCCCAAGTCAGAGTCCCGACAGCAGCGCACAG | 8720 | AQVRVPDSSAQ | 13309 | VRVPDSS | 0.172979 | -0.09411 |
| SyS2037 | 4132 | GCCCAACACCAACCGGCAGCGGCTTCGCACAG | 8721 | AQHQTGSGFAQ | 13310 | HQTGSGF | 0.172861 | -0.04462 |
| SyS2038 | 4133 | GCCCAAAGTGCTACGTTGAGTGGGTATGCACAG | 8722 | AQSATLSGYAQ | 13311 | SATLSGY | 0.172673 | -0.16344 |
| GS1189 | 4134 | GCCCAAAATGGTTCTGCGACCACCTACGCACAG | 8723 | AQNGSATYSAQ | 13312 | NGSATYS | 0.172618 | 0.021489 |
| GS1190 | 4135 | GCCCAAAGCACCAGACCCTCACCGCACAG | 8724 | AQSTRPTLTAQ | 13313 | STRPTLT | 0.172526 | -0.15048 |
| SyS2039 | 4136 | GCCCAAAGACCCGCGACGTCAGCCAAGCACAG | 8725 | AQRPADVSQAQ | 13314 | RPADVSQ | 0.172441 | -0.14526 |
| GS1191 | 4137 | GCCCAAAGCCACCTCAGCAGCACCGGCGCACAG | 8726 | AQSHLSSTGAQ | 13315 | SHLSSTG | 0.172433 | -0.18637 |

FIG. 33 (Continued)

| | | | | | | | | |
|---|---|---|---|---|---|---|---|---|
| GS1192 | 4138 | GCCCAAGCTAATCAGTCTTATGATCGGGCACAG | 8727 | AQANQSYDRAQ | 13316 | ANQSYDR | 0.172433 | -0.18637 |
| SyS2040 | 4139 | GCCCAAAGCAGCGGCGACAGAACCGCGCACAG | 8728 | AQSSGDRTAAQ | 13317 | SSGDRTA | 0.172372 | -0.21448 |
| SyS2041 | 4140 | GCCCAAAGGCAGCGGTCCCGGCTCAACGCACAG | 8729 | AQGSVPGLNAQ | 13318 | GSVPGLN | 0.172134 | -0.22803 |
| SyS2043 | 4141 | GCCCAACTCGTCACCATCCACAGCGCCGCACAG | 8730 | AQLVTIHSAAQ | 13319 | LVTIHSA | 0.171906 | -0.22285 |
| SyS2044 | 4142 | GCCCAACCTCAGCATGAGACTACGCTGGCACAG | 8731 | AQPQHETTLAQ | 13320 | PQHETTL | 0.171807 | -0.21557 |
| SyS2046 | 4143 | GCCCAACCGACGAGAGTCGGCGCAGTATGCACAG | 8732 | AQPTKSAQYAQ | 13321 | PTKSAQY | 0.171667 | -0.11931 |
| GS1194 | 4144 | GCCCAAAAAAGACCCCGTCCTCGGCGCACACAG | 8733 | AQKKDPVLGAQ | 13322 | KKDPVLG | 0.171636 | -0.17919 |
| SyS2047 | 4145 | GCCCAATTTAGGGTTGGTCCGTCTGCTGCACAG | 8734 | AQFRVGPSAAQ | 13323 | FRVGPSA | 0.171598 | -0.19739 |
| SyS2048 | 4146 | GCCCAAACCAGCAGCGGCCACGCCGTCGCACAG | 8735 | AQTSSGHAVAQ | 13324 | TSSGHAV | 0.17151 | -0.12824 |
| SyS2049 | 4147 | GCCCAACGTGTTGGTGAGGCTAGGATGGCACAG | 8736 | AQRVGEARMAQ | 13325 | RVGEARM | 0.171462 | -0.18284 |
| SyS2050 | 4148 | GCCCAACGTGTTACGTCGCCTTCTAAGGCACAG | 8737 | AQRVTSPSKAQ | 13326 | RVTSPSK | 0.171402 | -0.17557 |
| SyS2051 | 4149 | GCCCAAGATAGGATGCCTTCTACGATTGCACAG | 8738 | AQDRMPSTIAQ | 13327 | DRMPSTI | 0.171373 | -0.17193 |
| SyS2052 | 4150 | GCCCAACAAGGGCGACACCAGCAGACACGCACAG | 8739 | AQQGDTSKHAQ | 13328 | QGDTSKH | 0.171295 | -0.16102 |
| GS1195 | 4151 | GCCCAAAGCACCAGCAGCAACAGAGCCGCACAG | 8740 | AQSTSSNRAAQ | 13329 | STSSNRA | 0.171266 | -0.12044 |
| GS1196 | 4152 | GCCCAAAAGGTGCCTACGGGTTATACGGCACAG | 8741 | AQKVPTGYTAQ | 13330 | KVPTGYT | 0.171266 | -0.14334 |
| SyS2053 | 4153 | GCCCAATTCAAAGGCCAAAGAAACGACGCACAG | 8742 | AQFKGQRNDAQ | 13331 | FKGQRND | 0.171225 | -0.15011 |
| SyS2055 | 4154 | GCCCAAGGTAATCATTTGGGGAATGAGGCACAG | 8743 | AQGNHLGNEAQ | 13332 | GNHLGNE | 0.170544 | -0.18245 |
| SyS2056 | 4155 | GCCCAAGCAGCAGCAAAGCTTCGAACTCGCACAG | 8744 | AQASKSFELAQ | 13333 | ASKSFEL | 0.170464 | -0.08466 |
| SyS2057 | 4156 | GCCCAAACCGTCAGAGACACCACCAGAGCACAG | 8745 | AQTVRDTTRAQ | 13334 | TVRDTTR | 0.170442 | 0.262057 |
| GS1199 | 4157 | GCCCAAAAGGTTAGTCGAATACTCTTGCACAG | 8746 | AQKVSPNTLAQ | 13335 | KVSPNTL | 0.170349 | -0.16484 |
| GS1201 | 4158 | GCCCAAGGCAGAACCCCGAAAGCTACGCACAG | 8747 | AQGRTPESYAQ | 13336 | GRTPESY | 0.16998 | -0.18368 |
| SyS2058 | 4159 | GCCCAACAGGTGTCGGGGGTTAGGACGGCACAG | 8748 | AQQVSGVRTAQ | 13337 | QVSGVRT | 0.169959 | -0.11859 |
| SyS2059 | 4160 | GCCCAATACACCGGCATCAGCACCAGCGCACAG | 8749 | AQYTGISTSAQ | 13338 | YTGISTS | 0.169959 | -0.13314 |
| SyS2060 | 4161 | GCCCAACAAACGCGAACCCACAAAGCACAG | 8750 | AQQTAEPHKAQ | 13339 | QTAEPHK | 0.169959 | -0.16223 |
| SyS2061 | 4162 | GCCCAACTTGGTCCTGTGGGTTCTCCGGCACAG | 8751 | AQLGPVGSPAQ | 13340 | LGPVGSP | 0.169959 | -0.16587 |
| SyS2062 | 4163 | GCCCAAGCCAGAGACGACGACACCGACGCACAG | 8752 | AQARDDSTDAQ | 13341 | ARDDSTD | 0.169959 | -0.22042 |
| SyS2063 | 4164 | GCCCAAAATTTTAAGCATAGTGAGGTGGCACAG | 8753 | AQNFKHSEVAQ | 13342 | NFKHSEV | 0.169959 | -0.22042 |
| GS1202 | 4165 | GCCCAAATTACTACTCCTCTGCAGGCGGCACAG | 8754 | AQITTPLQAAQ | 13343 | ITTPLQA | 0.169823 | -0.18188 |
| SyS2066 | 4166 | GCCCAACCCATGAGCAGCAGAGAAAGAGCACAG | 8755 | AQPMSSRERAQ | 13344 | PMSSRER | 0.169722 | -0.10113 |
| GS1204 | 4167 | GCCCAAGTCGAAAAACGGCAAAGGCCTCGCACAG | 8756 | AQVENGKGLAQ | 13345 | VENGKGL | 0.169651 | -0.13239 |
| SyS2067 | 4168 | GCCCAAACCAGCAACAGCCTCGCCGCACAG | 8757 | AQTSNSGLAAQ | 13346 | TSNSGLA | 0.169432 | -0.02428 |
| SyS2068 | 4169 | GCCCAAGGCAACAGCCTGCCAACCCCGCACAG | 8758 | AQGNSLANPAQ | 13347 | GNSLANP | 0.169287 | -0.15041 |

FIG. 33 (Continued)

| | | | | | | | | |
|---|---|---|---|---|---|---|---|---|
| SS131 | 4170 | GCCCAAGCCAGCAACGAAGCCCACGCCGCACAG | 8759 | AQASNEAHAAQ | 13348 | ASNEAHA | 0.169245 | -0.37022 |
| GS1207 | 4171 | GCCCAAGGCCTCGCCGCGCAGCACCCCGCACAG | 8760 | AQGLAGSTPAQ | 13349 | GLAGSTP | 0.169127 | -0.18245 |
| SyS2069 | 4172 | GCCCAAGTCCCGCCCCCGGCAGATACGCACAG | 8761 | AQVPAPGRYAQ | 13350 | VPAPGRY | 0.169081 | -0.19353 |
| GS1208 | 4173 | GCCCAAGCCAGCGACAGACTCATCGCCGCACAG | 8762 | AQASDRLIAAQ | 13351 | ASDRLIA | 0.168842 | -0.14151 |
| GS1209 | 4174 | GCCCAAATCAGCACCTGGCAAACCCAAGCACAG | 8763 | AQISTWQTQAQ | 13352 | ISTWQTQ | 0.168829 | -0.1447 |
| SyS2070 | 4175 | GCCCAAATCACCAGCGGCGCCACCGTCGCACAG | 8764 | AQITSGATVAQ | 13353 | ITSGATV | 0.168795 | -0.1344 |
| GS1210 | 4176 | GCCCAACTTGCGAAGGCGAGTAATGTTGCACAG | 8765 | AQLAKASNVAQ | 13354 | LAKASNV | 0.168765 | -0.10613 |
| SyS2071 | 4177 | GCCCAACCGCGAGGGGACGTTTGGGAGTGCACAG | 8766 | AQPQGTFGSAQ | 13355 | PQGTFGS | 0.168707 | -0.1489 |
| SyS2072 | 4178 | GCCCAAATTGTTCGGCGCCGAATAGTGCACAG | 8767 | AQIVRPPNSAQ | 13356 | IVRPPNS | 0.168685 | -0.15253 |
| SyS2073 | 4179 | GCCCAAACCAGCCACCTCACCAGCGCCGCACAG | 8768 | AQTSHLTSAAQ | 13357 | TSHLTSA | 0.16862 | -0.07746 |
| SyS2075 | 4180 | GCCCAACTCCACCCGAAACCATGAGAGCACAG | 8769 | AQLHPETMRAQ | 13358 | LHPETMR | 0.168589 | -0.16708 |
| SyS2076 | 4181 | GCCCAAGTCCTCCACGACACCAGATACGCACAG | 8770 | AQVLHDTRYAQ | 13359 | VLHDTRY | 0.168547 | -0.14967 |
| SS132 | 4182 | GCCCAAGTCAGCAACACCCCCCAGAGGCGCACAG | 8771 | AQVSNPPRGAQ | 13360 | VSNPPRG | 0.168542 | -0.36117 |
| GS1211 | 4183 | GCCCAAGAGCCTCTGATGACTAGGCCTGCACAG | 8772 | AQEPLMTRPAQ | 13361 | EPLMTRP | 0.168414 | -0.16214 |
| GS1212 | 4184 | GCCCAAGACAGAGTCAGCAGCCACGCACAG | 8773 | AQDRVSSSHAQ | 13362 | DRVSSSH | 0.168392 | 0.004781 |
| GP175 | 4185 | GCCCAAACTAAGACTGGTCATTCGAGTGCACAG | 8774 | AQTKTGHSSAQ | 13363 | TKTGHSS | 0.168367 | -0.07287 |
| GS1213 | 4186 | GCCCAATGCTGTCTATTCTCCTGTTACTGCACAG | 8775 | AQSSYSPVTAQ | 13364 | SSYSPVT | 0.168316 | -0.08904 |
| GS1214 | 4187 | GCCCAAAAACCAACCTCCAAAACAACGCACAG | 8776 | AQKPNLQNNAQ | 13365 | KPNLQNN | 0.168309 | -0.10113 |
| SyS2077 | 4188 | GCCCAACTCAAAAGCCCCCCGGCATCGCACAG | 8777 | AQLKSPPGIAQ | 13366 | LKSPPGI | 0.168269 | -0.20345 |
| SyS2078 | 4189 | GCCCAAGGGATGCAGCTGGGGATGCCGGCACAG | 8778 | AQGMQLGMPAQ | 13367 | GMQLGMP | 0.168244 | -0.00148 |
| SyS2079 | 4190 | GCCCACACATCAGGCGAATCTTACGTTGGCACAG | 8779 | AQHQANLTLAQ | 13368 | HQANLTL | 0.168142 | -0.21436 |
| GS1215 | 4191 | GCCCAAACTGGTCATCCTACGACTGCGGCACAG | 8780 | AQTGHPTTAAQ | 13369 | TGHPTTA | 0.168138 | -0.09841 |
| GS1216 | 4192 | GCCCAATTCATCGGCAGCCACCTCGGCGCACAG | 8781 | AQFIGSHLGAQ | 13370 | FIGSHLG | 0.168096 | -0.14906 |
| SyS2081 | 4193 | GCCCAAAGGAATGAGAGGAGTAATGGGCGGCACAG | 8782 | AQRNESNGPAQ | 13371 | RNESNGP | 0.167998 | -0.2305 |
| SyS2082 | 4194 | GCCCAAAAGATTGAGACGAATGGTAATGCACAG | 8783 | AQKIETNGNAQ | 13372 | KIETNGN | 0.167998 | -0.21078 |
| SyS2083 | 4195 | GCCCAATATCTTCAGAATGGTGTTGTTGCACAG | 8784 | AQYLQNGVVAQ | 13373 | YLQNGVV | 0.167795 | -0.04255 |
| SyS2084 | 4196 | GCCCAAAGACCCGGCATGCTCGGCACCGCACAG | 8785 | AQRPGMLGTAQ | 13374 | RPGMLGT | 0.167685 | -0.12829 |
| SyS2085 | 4197 | GCCCAATTGACGCAGATTGGGACTGCTGCACAG | 8786 | AQLTQIGTAAQ | 13375 | LTQIGTA | 0.167589 | -0.03508 |
| GS1218 | 4198 | GCCCAAAACGAAGACGTCCAAAGAGCCGCACAG | 8787 | AQNEDVQRAAQ | 13376 | NEDVQRA | 0.1675 | -0.13213 |
| SyS2086 | 4199 | GCCCAACATTTGGCTGATCAGAGTCGTGCACAG | 8788 | AQHLADQSRAQ | 13377 | HLADQSR | 0.167422 | -0.00573 |
| SyS2087 | 4200 | GCCCAATTGGGTAATGATACGGTGAGGGCACAG | 8789 | AQLGNDTVRAQ | 13378 | LGNDTVR | 0.167404 | -0.15374 |
| SyS2091 | 4201 | GCCCAAAAACAACCACCACGTCCCCCCGCACAG | 8790 | AQNNHHVPPAQ | 13379 | NNHHVPP | 0.167167 | 0.019492 |

FIG. 33 (Continued)

| | | | | | | | | |
|---|---|---|---|---|---|---|---|---|
| GS1220 | 4202 | GCCCAAGACAAAGCCGGCACCCTCAGCGGCACAG | 8791 | AQDKAGTLSAQ | 13380 | DKAGTLS | 0.167139 | -0.12171 |
| SyS2093 | 4203 | GCCCAACGTACTAAGAGAATGAGTCGATGGCACAG | 8792 | AQRTKNESMAQ | 13381 | RTKNESM | 0.167044 | -0.1792 |
| SyS2094 | 4204 | GCCCAATTTAATGTTGTGCGTGGTGATGGCACAG | 8793 | AQFNVVRGDAQ | 13382 | FNVVRGD | 0.167044 | -0.1792 |
| SyS2095 | 4205 | GCCCAAATCGTCAGAGAGGCATGAACCAAGCACAG | 8794 | AQIVRGMNQAQ | 13383 | IVRGMNQ | 0.166951 | -0.18861 |
| SyS2096 | 4206 | GCCCAACAACACACCCCACCCTCAACGCACAG | 8795 | AQQHTPTLNAQ | 13384 | QHTPTLN | 0.166887 | -0.19846 |
| GS1222 | 4207 | GCCCAAAGCCTCGGCAAAGAACCCCTCGCACAG | 8796 | AQSLGKEPLAQ | 13385 | SLGKEPL | 0.166818 | -0.16484 |
| SyS2097 | 4208 | GCCCAAAGCAGCAGCGGCCTCAACGCACAG | 8797 | AQSSGHGLNAQ | 13386 | SSGHGLN | 0.166803 | 0.1418 |
| GS1223 | 4209 | GCCCAACGGATTAATAGTGATTCTACTGCACAG | 8798 | AQRINSDSTAQ | 13387 | RINSDST | 0.16679 | -0.12903 |
| SyS2098 | 4210 | GCCCAAAATCCGCATAATCATCCTGTTGCACAG | 8799 | AQNPHNHPVAQ | 13388 | NPHNHPV | 0.166789 | -0.19375 |
| SyS2100 | 4211 | GCCCAATCGCATAAGCCGTCGACGGTTGCACAG | 8800 | AQSHKPSTVAQ | 13389 | SHKPSTV | 0.166718 | -0.19739 |
| SyS2101 | 4212 | GCCCAAAGCAGCATGAGCCACCTACGCACAG | 8801 | AQSSMSTTYAQ | 13390 | SSMSTTY | 0.166718 | -0.19739 |
| SyS2102 | 4213 | GCCCAAGGTGCTGCTGTCTTCTAATCCTGCACAG | 8802 | AQGAAASNPAQ | 13391 | GAAASNP | 0.166693 | -0.11859 |
| GS1224 | 4214 | GCCCAAATGAACCAAAGAGAACAAAAAGCACAG | 8803 | AQMNQREQKAQ | 13392 | MNQREQK | 0.166658 | -0.16125 |
| SyS2103 | 4215 | GCCCAATCGTATCCTAGTAATCCGGGGCACAG | 8804 | AQSYPSNPRAQ | 13393 | SYPSNPR | 0.166484 | -0.2083 |
| SyS2104 | 4216 | GCCCAACTGCGTGATTTTGTGACTGATGCACAG | 8805 | AQLRDFVTDAQ | 13394 | LRDFVTD | 0.166484 | -0.2083 |
| GS1225 | 4217 | GCCCAAAACAACACCGTCATGAGAAGCGCACAG | 8806 | AQNNTVMRSAQ | 13395 | NNTVMRS | 0.166403 | 0.078355 |
| SyS2105 | 4218 | GCCCAACTCAGCCCAGAAAATACATCGCACAG | 8807 | AQLSPRKYIAQ | 13396 | LSPRKYI | 0.166309 | -0.21557 |
| SyS2106 | 4219 | GCCCAACACATCAGACCCCAGCCCGGCACAG | 8808 | AQHIRPPSPAQ | 13397 | HIRPPSP | 0.166309 | -0.21557 |
| SyS2107 | 4220 | GCCCAACCTTATGTGTCGACTACTGCGGCACAG | 8809 | AQPYVSTTAAQ | 13398 | PYVSTTA | 0.166295 | -0.20216 |
| SyS2108 | 4221 | GCCCAAGTCAACCACGGCAGCCCACCGCACAG | 8810 | AQVNHGSPTAQ | 13399 | VNHGSPT | 0.166263 | -0.07616 |
| SyS2109 | 4222 | GCCCAAAGTGGTTATCTTAATGGTGCGGCACAG | 8811 | AQSGYLNGAAQ | 13400 | SGYLNGA | 0.166181 | -0.21202 |
| SyS2110 | 4223 | GCCCAAAGTCGGGAGAGACGTCTGATGCACAG | 8812 | AQSRERTSDAQ | 13401 | SRERTSD | 0.166115 | -0.01918 |
| GS1227 | 4224 | GCCCAAACCCACAGCGTCACCAGAAGCGCACAG | 8813 | AQTHSVTRSAQ | 13402 | THSVTRS | 0.166033 | -0.10592 |
| GS1228 | 4225 | GCCCAACTTGTTGCGAATAAGAATGGGGCACAG | 8814 | AQLVANKNAAQ | 13403 | LVANKNA | 0.16597 | -0.12426 |
| GS1229 | 4226 | GCCCAAAATTTTACGGATCGTGCTACTGCACAG | 8815 | AQNFTDRATAQ | 13404 | NFTDRAT | 0.165948 | -0.16337 |
| SyS2111 | 4227 | GCCCAATATAGGACGAGTACTTTGGCGGCACAG | 8816 | AQYRTSTLAAQ | 13405 | YRTSTLA | 0.165933 | -0.09069 |
| GS1230 | 4228 | GCCCAACACGTCATGAACAAACAAGCCGCACAG | 8817 | AQHVMNKQAAQ | 13406 | HVMNKQA | 0.165928 | -0.14151 |
| SyS2112 | 4229 | GCCCAAGCCACCAACACCCGCACCGGCACAG | 8818 | AQATNNPASAQ | 13407 | ATNNPAS | 0.1659 | -0.23012 |
| SyS2113 | 4230 | GCCCAAACCATCATGAAAGCCCAAACCGCACAG | 8819 | AQTIMKAQTAQ | 13408 | TIMKAQT | 0.1659 | 0.100294 |
| SyS2114 | 4231 | GCCCAAGGCATGAGCACCATGACCCCGCACAG | 8820 | AQGMSTMTPAQ | 13409 | GMSTMTP | 0.165745 | -0.07802 |
| GS1231 | 4232 | GCCCAAGGCACCCCATCTACAAACAAGCACAG | 8821 | AQGTPIYKQAQ | 13410 | GTPIYKQ | 0.165686 | -0.18188 |
| SyS2115 | 4233 | GCCCAAAATGGTACGTTGGAGAAGGGCGGCACAG | 8822 | AQNGTLEKAAQ | 13411 | NGTLEKA | 0.165659 | -0.05555 |

FIG. 33 (Continued)

| | | | | | | | | |
|---|---|---|---|---|---|---|---|---|
| SyS2116 | 4234 | GCCCAAAGCAACGAAAGAACCATCCCGCACAG | 8823 | AQSNERTIPAQ | 13412 | SNERTIP | 0.165594 | -0.1198 |
| SyS2117 | 4235 | GCCCAAATTCCGGTGTCTATTCAGGCTGCACAG | 8824 | AQIPVSIQAAQ | 13413 | IPVSIQA | 0.165516 | -0.17998 |
| SyS2118 | 4236 | GCCCAAAACCTCAAAGAGAAGGCCCGCACAG | 8825 | AQNLQREGPAQ | 13414 | NLQREGP | 0.165401 | -0.00546 |
| GS1234 | 4237 | GCCCAAGGGAGGGTGGTAAGTCTAATGCACAG | 8826 | AQGEGGKSNAQ | 13415 | GEGGKSN | 0.165262 | -0.17672 |
| SyS2119 | 4238 | GCCCAATTGCAGGGTAATGGGAGGAATGCACAG | 8827 | AQLQGNGRNAQ | 13416 | LQGNGRN | 0.165238 | -0.13798 |
| GS1236 | 4239 | GCCCAACTCGTCAGCAGCACCAGCGAAGCACAG | 8828 | AQLVSSTSEAQ | 13417 | LVSSTSE | 0.165149 | -0.17863 |
| SyS2120 | 4240 | GCCCAAAGCCTCGCCGGCAACACCACCGCACAG | 8829 | AQSLAGNTTAQ | 13418 | SLAGNTT | 0.165128 | -0.11547 |
| SyS2122 | 4241 | GCCCAATTGACTGTTGGTAATAATGTGGCACAG | 8830 | AQLTVGNNVAQ | 13419 | LTVGNNV | 0.164995 | -0.1489 |
| SyS2123 | 4242 | GCCCAAAGCATCCTCACCAGAGACAGGCACAG | 8831 | AQSILTRDSAQ | 13420 | SILTRDS | 0.164909 | -0.15253 |
| SyS2124 | 4243 | GCCCAAGTTCTTGTTGATTCGCGTGCGGCACAG | 8832 | AQVLVDSRAAQ | 13421 | VLVDSRA | 0.164849 | -0.20588 |
| SyS2125 | 4244 | GCCCAAGGCGTCGCCAGCACCACCGCACAG | 8833 | AQGVASTTTAQ | 13422 | GVASTTT | 0.164819 | -0.15617 |
| SyS2126 | 4245 | GCCCAACACGGCGCCAACCTCAGCGTCGCACAG | 8834 | AQHGANLSVAQ | 13423 | HGANLSV | 0.164788 | -0.05676 |
| SyS2127 | 4246 | GCCCAATCGTTAATCAGCGTCTGTTGCACAG | 8835 | AQSFNQPSVAQ | 13424 | SFNQPSV | 0.164762 | -0.04976 |
| GS1238 | 4247 | GCCCAACTCAACCAAACCAAAGAGTCGCACAG | 8836 | AQLNQNQRVAQ | 13425 | LNQNQRV | 0.164752 | -0.15317 |
| SyS2128 | 4248 | GCCCAAAGAATCGACAGCCAAGACACCGCACAG | 8837 | AQRIDSQDTAQ | 13426 | RIDSQDT | 0.164726 | -0.20951 |
| GS1239 | 4249 | GCCCAAACCGTCCCCGGCAGACCCAGCGCACAG | 8838 | AQTVPGRPSAQ | 13427 | TVPGRPS | 0.164623 | -0.14779 |
| SyS2130 | 4250 | GCCCAACGTGAGCCGAATAATACGAGTGCACAG | 8839 | AQREPNNTSAQ | 13428 | REPNNTS | 0.164588 | -0.05033 |
| SyS2131 | 4251 | GCCCAAGAAGAATGACCATGCACGCCGGCACAG | 8840 | AQERMTMHAAQ | 13429 | ERMTMHA | 0.164489 | -0.12101 |
| GS1240 | 4252 | GCCCAAATTGCTATTCAGAATGATCGGGCACAG | 8841 | AQIAIQNDRAQ | 13430 | IAIQNDR | 0.164441 | -0.14603 |
| SyS2132 | 4253 | GCCCAACTTGGGGCTCAGTCTATTCGGCACAG | 8842 | AQLGAQSISAQ | 13431 | LGAQSIS | 0.164426 | -0.17072 |
| SS136 | 4254 | GCCCAAGCAGGGGGATAAGACGTATGTTGCACAG | 8843 | AQAGDKTYVAQ | 13432 | AGDKTYV | 0.164227 | -0.35249 |
| SyS2135 | 4255 | GCCCAAATGAATAGGACTGGGTATACTGCACAG | 8844 | AQMNRTAYTAQ | 13433 | MNRTAYT | 0.164206 | -0.17799 |
| SyS2136 | 4256 | GCCCAAGCGCTGCCTGGGGGTCTTATGGCACAG | 8845 | AQALPGGLMAQ | 13434 | ALPGGLM | 0.164168 | -0.22406 |
| GS1241 | 4257 | GCCCAACTCAAAAACCACGACACCACCGCACAG | 8846 | AQLKNHDTTAQ | 13435 | LKNHDTT | 0.164164 | -0.02897 |
| SyS2138 | 4258 | GCCCAACCCCTCAACTACGCCCTCGAAGCACAG | 8847 | AQPLNYALEAQ | 13436 | PLNYALE | 0.164085 | -0.2231 |
| SyS2139 | 4259 | GCCCAAAGCAAACAAATGCACAACGACGCACAG | 8848 | AQSKQMHNDAQ | 13437 | SKQMHND | 0.163943 | -0.14283 |
| SyS2140 | 4260 | GCCCAAACGGCGCATACGACTCCTTTTGCACAG | 8849 | AQTAHTTPFAQ | 13438 | TAHTTPF | 0.163842 | -0.14647 |
| SyS2141 | 4261 | GCCCAACTCAAAAACGGGCGACAGCCAAGCACAG | 8850 | AQLKTGDSQAQ | 13439 | LKTGDSQ | 0.163842 | -0.14647 |
| SyS2142 | 4262 | GCCCAATATTCTACGACGGCTGAGTATGCACAG | 8851 | AQYSTTAEYAQ | 13440 | YSTTAEY | 0.163781 | -0.19107 |
| SyP66 | 4263 | GCCCAACCGCTGGATCGGACGGGTGAGGCACAG | 8852 | AQPLDRTGEAQ | 13441 | PLDRTGE | 0.163769 | -0.04278 |
| SyS2144 | 4264 | GCCCAAGGCCCCGGCGAAGTCAAAATCGCACAG | 8853 | AQGPGEVKIAQ | 13442 | GPGEVKI | 0.163669 | -0.17505 |
| GS1243 | 4265 | GCCCAACTCAGAAAACCTCGACCTCAACGCACAG | 8854 | AQLRNLDLNAQ | 13443 | LRNLDLN | 0.163512 | -0.09845 |

FIG. 33 (Continued)

| | | | | | | | | |
|---|---|---|---|---|---|---|---|---|
| SyS2145 | 4266 | GCCCAACTGGGGTCTACTTTGACTAAGGCACAG | 8855 | AQLGSTLTKAQ | 13444 | LGSTLTK | 0.163495 | -0.14302 |
| GS1244 | 4267 | GCCCAATTGAGGCCTGTGAGTGAGCATGCACAG | 8856 | AQIRPVSEHAQ | 13445 | LRPVSEH | 0.1634 | -0.16842 |
| GS1245 | 4268 | GCCCAAAGTAGGAGTCTGACTGAGATGGCACAG | 8857 | AQSRSLTEMAQ | 13446 | SRSLTEM | 0.163369 | -0.17577 |
| SyS2147 | 4269 | GCCCAAAACGGCCTCAGCACCACCATGGCACAG | 8858 | AQNGLSTTMAQ | 13447 | NGLSTTM | 0.163348 | -0.16889 |
| GS1247 | 4270 | GCCCAACATGATAAGACGTATGCGATGGCACAG | 8859 | AQHDKTYAMAQ | 13448 | HDKTYAM | 0.163317 | -0.16304 |
| SyS2148 | 4271 | GCCCAAGTTCCGTCGGATAAGATGCGTGCACAG | 8860 | AQVPSDKMRAQ | 13449 | VPSDKMR | 0.163313 | -0.2268 |
| SyS2149 | 4272 | GCCCAAGGCGCCCACAACCTCCTCACCGCACAG | 8861 | AQGAHNLLTAQ | 13450 | GAHNLLT | 0.163277 | -0.20345 |
| GS1248 | 4273 | GCCCAAAGCACCAGCACCACCATGGTCATGGCACAG | 8862 | AQSTSTMVMMAQ | 13451 | STSTMVM | 0.163265 | -0.11218 |
| SS137 | 4274 | GCCCAAAAACATGGCCCACGAAAGCAAAGCACAG | 8863 | AQNMAHESKAQ | 13452 | NMAHESK | 0.163246 | -0.34932 |
| SyS2151 | 4275 | GCCCAATATCTTGGGGTGGGTGCTACTGCACAG | 8864 | AQYLGVGATAQ | 13453 | YLGVGAT | 0.163021 | -0.17193 |
| SyS2152 | 4276 | GCCCAAGCCAGCGAATACAACCAACACGCACAG | 8865 | AQASEYNQHAQ | 13454 | ASEYNQH | 0.162953 | -0.21072 |
| SyS2153 | 4277 | GCCCAAAGAGCCGAAGGGCGACAAAATCGCACAG | 8866 | AQRAEGDKIAQ | 13455 | RAEGDKI | 0.162815 | -0.18861 |
| SyS2154 | 4278 | GCCCAATCTAGTGGTAGTAGTTTTCATGCACAG | 8867 | AQSSGSSFHAQ | 13456 | SSGSSFH | 0.162597 | -0.218 |
| SyS2155 | 4279 | GCCCAATGGGGCAAAGAATACACCGGCGCACAG | 8868 | AQWGKEYTGAQ | 13457 | WGKEYTG | 0.162268 | -0.12824 |
| SyS2156 | 4280 | GCCCAACCTGCTTCGGGGGCTATGCCTGCACAG | 8869 | AQPASGAMPAQ | 13458 | PASGAMP | 0.16218 | 0.044005 |
| SyS2158 | 4281 | GCCCAAAGGGGGCGGTTGTTGTGGCTGCACAG | 8870 | AQRGAVVVAAQ | 13459 | RGAVVVA | 0.161915 | -0.16587 |
| GS1249 | 4282 | GCCCAAGTGATGATGCAGAATCATGCTGCACAG | 8871 | AQVMMQNHAAQ | 13460 | VMMQNHA | 0.161911 | -0.12712 |
| GS1250 | 4283 | GCCCAACAAGACAGACTCCAAAGCAGAGCACAG | 8872 | AQQDRLQSRAQ | 13461 | QDRLQSR | 0.161891 | -0.14906 |
| SyS2159 | 4284 | GCCCAAGGTCATGCTGCGTTTCTGTGGCACAG | 8873 | AQGHAAVSVAQ | 13462 | GHAAVSV | 0.161865 | 0.031161 |
| SyS2160 | 4285 | GCCCAAGACAAAACGACAGCACCCCGCACAG | 8874 | AQDKTDSTPAQ | 13463 | DKTDSTP | 0.161817 | -0.20216 |
| GP176 | 4286 | GCCCAAGTGCCTCCGACTTCTTTTACTGCACAG | 8875 | AQVPPTSFTAQ | 13464 | VPPTSFT | 0.161782 | -0.06149 |
| GS1251 | 4287 | GCCCAAGTCGGCCCAACGCCCAACAGCACACAG | 8876 | AQVGPNAQHAQ | 13465 | VGPNAQH | 0.16174 | -0.06577 |
| SyS2161 | 4288 | GCCCAACATCATGGTCGGGGCTGATACTGCACAG | 8877 | AQHHGRADTAQ | 13466 | HHGRADT | 0.161642 | -0.23419 |
| GS1253 | 4289 | GCCCAACATGTTAATATGGGTCCGGCGGCACAG | 8878 | AQHVNMGPAAQ | 13467 | HVNMGPA | 0.161627 | -0.1747 |
| SyS2162 | 4290 | GCCCAACACGCCACCAAAGAAACCAGCGCACAG | 8879 | AQHATKETSAQ | 13468 | HATKETS | 0.161604 | -0.17998 |
| SyS2163 | 4291 | GCCCAATTGGCTACGGGTGTGAGTAATGCACAG | 8880 | AQLATGVSNAQ | 13469 | LATGVSN | 0.161594 | -0.07794 |
| SyS2164 | 4292 | GCCCAAAGCCTCGGCAGCTACCCCACCGCACAG | 8881 | AQSLGSYPTAQ | 13470 | SLGSYPT | 0.1614 | -0.11737 |
| SyS2165 | 4293 | GCCCAAGGCAGCAAAGCCTACGTCGGGGCACAG | 8882 | AQGSKAYVGAQ | 13471 | GSKAYVG | 0.161272 | -0.12101 |
| SyS2167 | 4294 | GCCCAACAAGACAGAATGAGCGTCAACGCACAG | 8883 | AQQDRMSVNAQ | 13472 | QDRMSVN | 0.161186 | -0.18954 |
| SyS2168 | 4295 | GCCCAATGGTCGGATTCTCTGAGGGATGCACAG | 8884 | AQWSDSLRDAQ | 13473 | WSDSLRD | 0.161166 | -0.21194 |
| SyS2169 | 4296 | GCCCAAACGAAGGTGCCTATGACTCAGGCACAG | 8885 | AQTKVPMTQAQ | 13474 | TKVPMTQ | 0.161135 | -0.08946 |
| SyS2170 | 4297 | GCCCAATCTCCGTTGTCTGATCGGTTGGCACAG | 8886 | AQSPLSDRLAQ | 13475 | SPLSDRL | 0.161094 | -0.18405 |

FIG. 33 (Continued)

| | | | | | | | | |
|---|---|---|---|---|---|---|---|---|
| SyS2171 | 4298 | GCCCAACTGTATGGTAGTTCGGTTGTTGCACAG | 8887 | AQLYGSSVVAQ | 13476 | LYGSSVV | 0.161094 | -0.18405 |
| SyS2172 | 4299 | GCCCAACCGACGCAGACTGTTAGTTCGGCACAG | 8888 | AQPTQTVSSAQ | 13477 | PTQTVSS | 0.161094 | -0.18405 |
| GP178 | 4300 | GCCCAACTGAATAAGCTGCTTGGGGCGGCACAG | 8889 | AQLNKLLGAAQ | 13478 | LNKLLGA | 0.160777 | 0.340925 |
| SyS2173 | 4301 | GCCCAACATTCTAATCAGGAGCCTCGGCACAG | 8890 | AQHSNQEPRAQ | 13479 | HSNQEPR | 0.160633 | -0.17106 |
| SyS2174 | 4302 | GCCCAAAACGGCGCCAGCATCCACAGCGCACAG | 8891 | AQNGASIHSAQ | 13480 | NGASIHS | 0.16061 | 0.144677 |
| SyS2175 | 4303 | GCCCAACTCAGCCAACAAAGACTCCAAGCACAG | 8892 | AQLSQQRLQAQ | 13481 | LSQQRLQ | 0.160413 | -0.02302 |
| GS1258 | 4304 | GCCCAACTCCCCACGGCACCATGAACGCACAG | 8893 | AQLPHGTMNAQ | 13482 | LPHGTMN | 0.160361 | -0.12536 |
| SyS2176 | 4305 | GCCCAAAGCAGCCCGACGCCAAATACGCACAG | 8894 | AQSSPDAKYAQ | 13483 | SSPDAKY | 0.160306 | -0.1986 |
| GS1259 | 4306 | GCCCAATTCCACACCCCGCCGCAAGCGCACAG | 8895 | AQFHTPAGNAQ | 13484 | FHTPAGN | 0.160249 | -0.13792 |
| SyS2177 | 4307 | GCCCAAAGAACCACCGCCAACAGCCTCGCACAG | 8896 | AQRTTANSLAQ | 13485 | RTTANSL | 0.16022 | -0.09434 |
| SyS2178 | 4308 | GCCCAATTGGATAAGACTATTCCTCAGGCACAG | 8897 | AQLDKTIPQAQ | 13486 | LDKTIPQ | 0.160087 | -0.20224 |
| SyS2179 | 4309 | GCCCAATGGCAAGGCAACAGACAAGCCGCACAG | 8898 | AQWQGNRQAAQ | 13487 | WQGNRQA | 0.160025 | -0.07373 |
| SyS2181 | 4310 | GCCCAAGGGTATGGTACGATTACGCCTGCACAG | 8899 | AQGYGTITPAQ | 13488 | GYGTITP | 0.159821 | -0.02887 |
| GS1260 | 4311 | GCCCAAATGAGAGAACAACAAAGCCGCACAG | 8900 | AQMREQNKAAQ | 13489 | MREQNKA | 0.15981 | -0.17201 |
| SyS2183 | 4312 | GCCCAAAACCTCGCCGGCCTCACCGGCGCACAG | 8901 | AQNLAGLTGAQ | 13490 | NLAGLTG | 0.159698 | -0.16889 |
| SyS2184 | 4313 | GCCCAATGGTTTAAGGCTGGGAGTGTGCACAG | 8902 | AQWFKAGSAAQ | 13491 | WFKAGSA | 0.159617 | -0.20951 |
| SyS2185 | 4314 | GCCCAAATCAACGTCGCCCCCTACAAAGCACAG | 8903 | AQINVAPYKAQ | 13492 | INVAPYK | 0.159555 | -0.16102 |
| SyS2186 | 4315 | GCCCAAGGGGTGCATTCGAATGGTCAGGCACAG | 8904 | AQGVHSNGQAQ | 13493 | GVHSNGQ | 0.159514 | -0.10739 |
| SyS2187 | 4316 | GCCCAAATGAGCGCCAGCACCAACACCGCACAG | 8905 | AQMSASTNTAQ | 13494 | MSASTNT | 0.15942 | -0.1344 |
| GS1263 | 4317 | GCCCAAGGCAGCCACAACGCCAAGGGCGCACAG | 8906 | AQGSHNAQGAQ | 13495 | GSHNAQG | 0.159285 | -0.08901 |
| SyS2189 | 4318 | GCCCAAATCAGCGCCGTCCCCAAAAACGCACAG | 8907 | AQISAVPKNAQ | 13496 | ISAVPKN | 0.159253 | -0.17875 |
| SyS2190 | 4319 | GCCCAAGCCGGGCATGCAAAACGCACAG | 8908 | AQAGGGMQNAQ | 13497 | AGGGMQN | 0.159207 | -0.1198 |
| SyS2191 | 4320 | GCCCAACTCCTCAACACCACCAGCACCGCACAG | 8909 | AQLLNTTSTAQ | 13498 | LLNTTST | 0.159024 | 0.011774 |
| SyS2192 | 4321 | GCCCAAACTAATACTGTGAGTGCTAGTGCACAG | 8910 | AQTNTVSASAQ | 13499 | TNTVSAS | 0.158935 | 0.332609 |
| SyS2193 | 4322 | GCCCAACAGTTGTCTCCGATTGTTAATTTGGCACAG | 8911 | AQQLSPIAMAQ | 13500 | QLSPIAM | 0.158902 | -0.19618 |
| GS1264 | 4323 | GCCCAACTTACTCGTACGTCGGTGGATGCACAG | 8912 | AQAPRGVNLAQ | 13501 | APRGVNL | 0.158854 | -0.18149 |
| SyS2194 | 4324 | GCCCAACTGGGGCAGAAGGGCCTACTGCACAG | 8913 | AQLTRTSVDAQ | 13502 | LTRTSVD | 0.158821 | -0.01311 |
| SyS2195 | 4325 | GCCCAACTGGGGCAGAAGGGCCTACTGCACAG | 8914 | AQLGQKAPTAQ | 13503 | LGQKAPT | 0.158804 | -0.1069 |
| SyS2196 | 4326 | GCCCAAAAGAATGCCGCGCCTCTGACGGCACAG | 8915 | AQKNAPPLTAQ | 13504 | KNAPPLT | 0.158756 | -0.21694 |
| SyS2197 | 4327 | GCCCAAGTCAGAAACGCCGTCCACGCCGCACAG | 8916 | AQVRNAVHAAQ | 13505 | VRNAVHA | 0.158629 | -0.12577 |
| SyS2198 | 4328 | GCCCAAATCAGACACATGGACGCCCCGCACAG | 8917 | AQIRHMDAPAQ | 13506 | IRHMDAP | 0.158527 | -0.1792 |
| SyS2200 | 4329 | GCCCAAGGTGCTCCTTTGGTTGCTACTGCACAG | 8918 | AQGAPLVATAQ | 13507 | GAPLVAT | 0.15843 | -0.17629 |

FIG. 33 (Continued)

| | | | | | | | | |
|---|---|---|---|---|---|---|---|---|
| SyS2201 | 4330 | GCCCAATCTGATCATAATGCTCGTGGGGCACAG | AQSDHNARGAQ | 8919 | SDHNARG | 13508 | 0.158426 | -0.15859 |
| SyS2202 | 4331 | GCCCAAATCAGCGACACCTCCACTACGCACAG | AQISDTLHYAQ | 8920 | ISDTLHY | 13509 | 0.158424 | -0.08821 |
| GS1266 | 4332 | GCCCAAAACAACAGAGGCAGCATCAGCGCACAG | AQNNRGSISAQ | 8921 | NNRGSIS | 13510 | 0.158422 | -0.05843 |
| GS1267 | 4333 | GCCCAACAACAAGAGAAAGAGACGGCGTCGCACAG | AQQRERDGVAQ | 8922 | QRERDGV | 13511 | 0.158316 | -0.10804 |
| SyS2203 | 4334 | GCCCAAAGTAAGCAGGATGTGCTGTGCACAG | AQSKQDVRAAQ | 8923 | SKQDVRA | 13512 | 0.158297 | -0.18284 |
| SyS2204 | 4335 | GCCCAAAACAGCGCAGACTCAACGTCGCACAG | AQNSGRLNVAQ | 8924 | NSGRLNV | 13513 | 0.158284 | -0.17013 |
| SyS2205 | 4336 | GCCCAAGGCCCAGCGTCGAAAGCAACGCACAG | AQGPSVESNAQ | 8925 | GPSVESN | 13514 | 0.158284 | -0.23296 |
| GS1268 | 4337 | GCCCAATTGCTTTCTTCTTCGCCTTCTGCACAG | AQLLSSSPSAQ | 8926 | LLSSSPS | 13515 | 0.158261 | -0.16394 |
| SyS2206 | 4338 | GCCCAAAAAGTCCTCGTCAGCGGCAGCGCACAG | AQKVLVSGSAQ | 8927 | KVLVSGS | 13516 | 0.158127 | -0.20709 |
| SyS2207 | 4339 | GCCCAAGATGTGCGGAATACTATTGCTGCACAG | AQDVRNTIAAQ | 8928 | DVRNTIA | 13517 | 0.158027 | -0.07579 |
| GS1270 | 4340 | GCCCAACATAAGTTGGTGACGAAGGATGCACAG | AQHKLVTKDAQ | 8929 | HKLVTKD | 13518 | 0.157915 | -0.1747 |
| GS1271 | 4341 | GCCCAACCGTATGTTTCGGGTGTTCCTGCACAG | AQPYVSGVPAQ | 8930 | PYVSGVP | 13519 | 0.157885 | -0.11277 |
| SyS2209 | 4342 | GCCCAAAACGACTAAGGCTTCGTTTACTGCACAG | AQTTKASFTAQ | 8931 | TTKASFT | 13520 | 0.15776 | -0.17998 |
| GS1272 | 4343 | GCCCAAACCCCCACGGCCCCGACGCGGCACAG | AQTPHGPDAAQ | 8932 | TPHGPDA | 13521 | 0.157568 | -0.18368 |
| SyS2210 | 4344 | GCCCAAGATTATCGTCAGACTGATCATGCACAG | AQDYRQTDHAQ | 8933 | DYRQTDH | 13522 | 0.157547 | -0.17314 |
| SyS2211 | 4345 | GCCCAACACAGCCCCAAACCGACCACGCACAG | AQHSPKPDHAQ | 8934 | HSPKPDH | 13523 | 0.157547 | -0.19375 |
| SyS2212 | 4346 | GCCCAAGCGTATGGTCAGGTGCCTCTGCACAG | AQAYGQVPPAQ | 8935 | AYGQVPP | 13524 | 0.157393 | -0.07373 |
| SyS2213 | 4347 | GCCCAAGCAACCAAGGCCTCGCCGGGGCACAG | AQSNQGLAGAQ | 8936 | SNQGLAG | 13525 | 0.157367 | -0.11495 |
| SyS2214 | 4348 | GCCCAAATCAACAGCCCCATCGGCAACGCACAG | AQINSPIGNAQ | 8937 | INSPIGN | 13526 | 0.157315 | -0.09779 |
| SyS2215 | 4349 | GCCCAACAAAACCAAATCATGAGCGGGGCACAG | AQQNQIMSGAQ | 8938 | QNQIMSG | 13527 | 0.157275 | -0.19739 |
| SyS2216 | 4350 | GCCCAAGTCTACCAAGGCAACCAAAACGCACAG | AQVYQGNQNAQ | 8939 | VYQGNQN | 13528 | 0.157122 | -0.05314 |
| GS1273 | 4351 | GCCCAAGGCAGCAACAGCGACCACCGCACAG | AQGSNSQHTAQ | 8940 | GSNSQHT | 13529 | 0.156944 | -0.11091 |
| SyS2217 | 4352 | GCCCAAAAAGCAGGAGCCGTCGGATAGGGCACAG | AQKQEPSDRAQ | 8941 | KQEPSDR | 13530 | 0.156938 | -0.14283 |
| GS1274 | 4353 | GCCCAACACAGAAGCAGCAGCCCGCCGCACAG | AQHRSSPAAAQ | 8942 | HRSSPAA | 13531 | 0.156784 | -0.15945 |
| SyS2219 | 4354 | GCCCAAAATGAGGGGAATTCGATGAAGGCACAG | AQNEGNSMKAQ | 8943 | NEGNSMK | 13532 | 0.156665 | -0.08967 |
| GS1277 | 4355 | GCCCAAAGACCCGACAAAGGCCCATGGCACAG | AQRPDKGPMAQ | 8944 | RPDKGPM | 13533 | 0.156399 | -0.15764 |
| SyS2222 | 4356 | GCCCAAGCGATTGTGTCTCATCCGCTGGCACAG | AQAIVSHPLAQ | 8945 | AIVSHPL | 13534 | 0.156109 | -0.19805 |
| GS1279 | 4357 | GCCCAAACCCAAGGCGAAAGACCCGTCGCACAG | AQTQGERPVAQ | 8946 | TQGERPV | 13535 | 0.156022 | -0.17386 |
| SyS2225 | 4358 | GCCCAATACGTCAACAGCGCCCCCAAAGCACAG | AQYVNSAPKAQ | 8947 | YVNSAPK | 13536 | 0.155853 | -0.17799 |
| GS1280 | 4359 | GCCCAACCTTCGGGGACTTCGATTGTGGCACAG | AQPSGTSIVAQ | 8948 | PSGTSIV | 13537 | 0.155836 | -0.17919 |
| SyS2226 | 4360 | GCCCAAAGCGTCGGCGGCCAACAGAGAAGCGCACAG | AQSVGANRSAQ | 8949 | SVGANRS | 13538 | 0.155529 | -0.18491 |
| SyS2227 | 4361 | GCCCAATCTGCGCATTTTAATCATTCGGGCACAG | AQSAHFNHSAQ | 8950 | SAHFNHS | 13539 | 0.155529 | -0.18491 |

FIG. 33 (Continued)

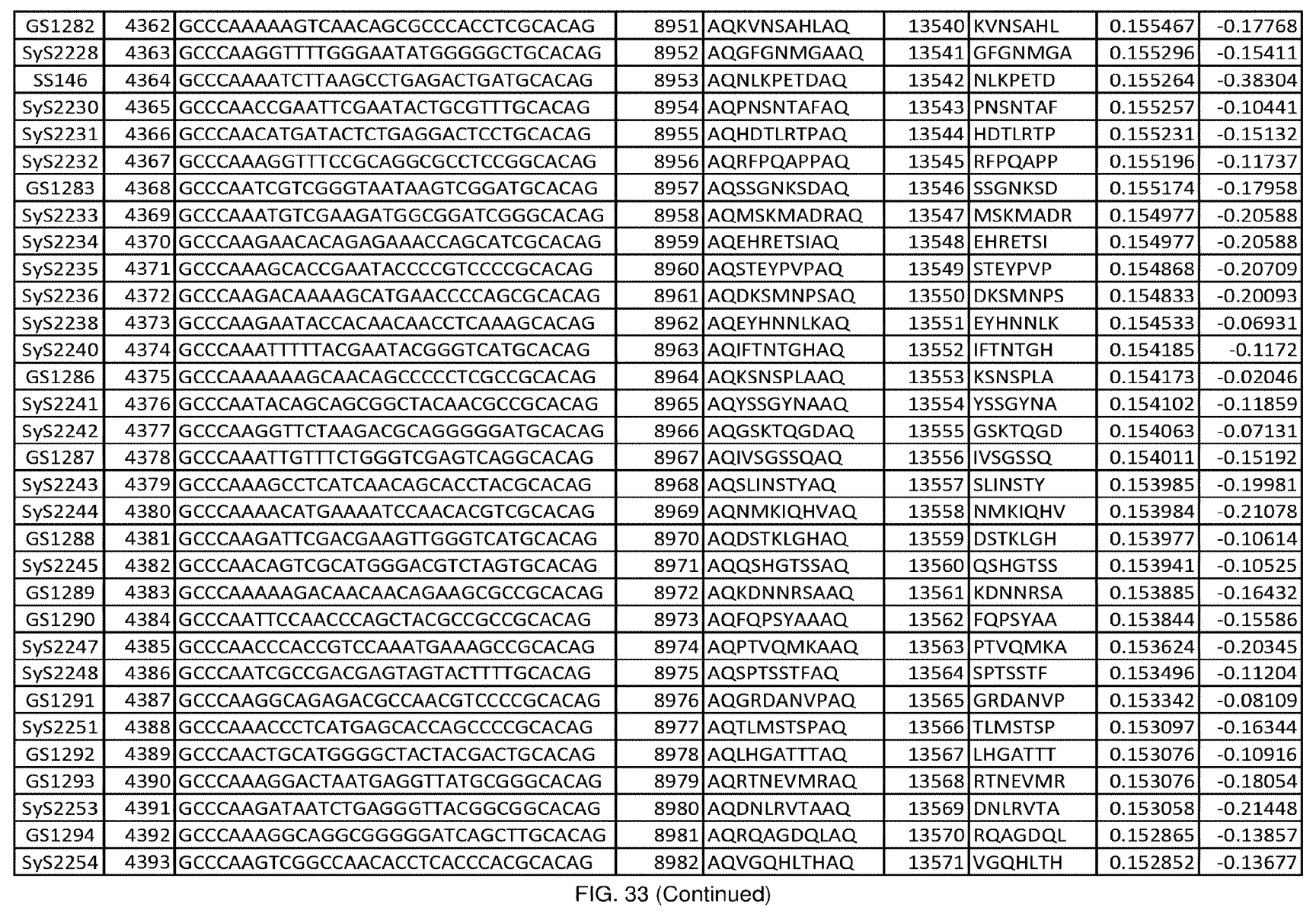

| | | | | | | | |
|---|---|---|---|---|---|---|---|
| GS1282 | 4362 | GCCCAAAAAGTCAACAGCGCCACCTGCACAG | 8951 | AQKVNSAHLAQ | 13540 | KVNSAHL | 0.155467 | -0.17768 |
| SyS2228 | 4363 | GCCCAAGGTTTTGGGAATATGGGGGCTGCACAG | 8952 | AQGFGNMGAAQ | 13541 | GFGNMGA | 0.155296 | -0.15411 |
| SS146 | 4364 | GCCCAAAATCTTAAGCCTGAATACTGCGTTTGCACAG | 8953 | AQNLKPETDAQ | 13542 | NLKPETD | 0.155264 | -0.38304 |
| SyS2230 | 4365 | GCCCAACCGAATTCGAATACTCTGAGGACTCCTGCACAG | 8954 | AQPNSNTAFAQ | 13543 | PNSNTAF | 0.155257 | -0.10441 |
| SyS2231 | 4366 | GCCCAACATGATACTCTGAGGACTCCTGCACAG | 8955 | AQHDTLRTPAQ | 13544 | HDTLRTP | 0.155231 | -0.15132 |
| SyS2232 | 4367 | GCCCAAAGGTTTCCGCAGGCGCCTCCGGCACAG | 8956 | AQRFPQAPPAQ | 13545 | RFPQAPP | 0.155196 | -0.11737 |
| GS1283 | 4368 | GCCCAATCGTCGGGTAATAAGTCGGATGCACAG | 8957 | AQSSGNKSDAQ | 13546 | SSGNKSD | 0.155174 | -0.17958 |
| SyS2233 | 4369 | GCCCAAATGTCGAAGATGGCGGATCGGGCACAG | 8958 | AQMSKMADRAQ | 13547 | MSKMADR | 0.154977 | -0.20588 |
| SyS2234 | 4370 | GCCCAAGAACACAGAGAAACCAGCATCGCACAG | 8959 | AQEHRETSIAQ | 13548 | EHRETSI | 0.154977 | -0.20588 |
| SyS2235 | 4371 | GCCCAAAGCACCGAATACCCCGTCCCCGCACAG | 8960 | AQSTEYPVPAQ | 13549 | STEYPVP | 0.154868 | -0.20709 |
| SyS2236 | 4372 | GCCCAAGACAAAAGCATGAACCCCAGCGCACAG | 8961 | AQDKSMNPSAQ | 13550 | DKSMNPS | 0.154833 | -0.20093 |
| SyS2238 | 4373 | GCCCAAGAATACCACAACAACCTCAAAGCACAG | 8962 | AQEYHNNLKAQ | 13551 | EYHNNLK | 0.154533 | -0.06931 |
| SyS2240 | 4374 | GCCCAAATTTTTACGAATACGGGTCATGCACAG | 8963 | AQIFTNTGHAQ | 13552 | IFTNTGH | 0.154185 | -0.1172 |
| GS1286 | 4375 | GCCCAAAAAAGCAACAGCCCCTCGCCGCACAG | 8964 | AQKSNSPLAAQ | 13553 | KSNSPLA | 0.154173 | -0.02046 |
| SyS2241 | 4376 | GCCCAATACAGCAGCGGCTACAACGCCGCACAG | 8965 | AQYSSGYNAAQ | 13554 | YSSGYNA | 0.154102 | -0.11859 |
| SyS2242 | 4377 | GCCCAAGGTTCTAAGACGCAGGGGATGCACAG | 8966 | AQGSKTQGDAQ | 13555 | GSKTQGD | 0.154063 | -0.07131 |
| GS1287 | 4378 | GCCCAAATTGTTTCTGGGTCGAGTCAGGCACAG | 8967 | AQIVSGSSQAQ | 13556 | IVSGSSQ | 0.154011 | -0.15192 |
| SyS2243 | 4379 | GCCCAAAGCCTCATCAACAGCACCTACGCACAG | 8968 | AQSLINSTYAQ | 13557 | SLINSTY | 0.153985 | -0.19981 |
| SyS2244 | 4380 | GCCCAAAACATGAAAATCCAACACGTCGCACAG | 8969 | AQNMKIQHVAQ | 13558 | NMKIQHV | 0.153984 | -0.21078 |
| GS1288 | 4381 | GCCCAAGATTCGACGAAGTTGGGTCATGCACAG | 8970 | AQDSTKLGHAQ | 13559 | DSTKLGH | 0.153977 | -0.10614 |
| SyS2245 | 4382 | GCCCAACAGTCGCATGGGACGTCTAGTGCACAG | 8971 | AQQSHGTSSAQ | 13560 | QSHGTSS | 0.153941 | -0.10525 |
| GS1289 | 4383 | GCCCAAAAGACAACAACAGAGAAGCGCCGCACAG | 8972 | AQKDNNRSAAQ | 13561 | KDNNRSA | 0.153885 | -0.16432 |
| GS1290 | 4384 | GCCCAATTCCAACCCAGCTACGCCGCGCACAG | 8973 | AQFQPSYAAAQ | 13562 | FQPSYAA | 0.153844 | -0.15586 |
| SyS2247 | 4385 | GCCCAACCACCGTCCAAATGAAAGCCGCACAG | 8974 | AQPTVQMKAAQ | 13563 | PTVQMKA | 0.153624 | -0.20345 |
| SyS2248 | 4386 | GCCCAATCGCGACGAGTAGTACTTTTGCACAG | 8975 | AQSPTSSTFAQ | 13564 | SPTSSTF | 0.153496 | -0.11204 |
| GS1291 | 4387 | GCCCAAGGCAGAGACGCCAACGTCCCCGCACAG | 8976 | AQGRDANVPAQ | 13565 | GRDANVP | 0.153342 | -0.08109 |
| SyS2251 | 4388 | GCCCAAACCCTCATGAGCACCAGCCCCGCACAG | 8977 | AQTLMSTSPAQ | 13566 | TLMSTSP | 0.153097 | -0.16344 |
| GS1292 | 4389 | GCCCAACTGCATGGGCTACTACGACTGCACAG | 8978 | AQLHGATTTAQ | 13567 | LHGATTT | 0.153076 | -0.10916 |
| GS1293 | 4390 | GCCCAAAGGACTAATGAGGTTATGCGGGCACAG | 8979 | AQRTNEVMRAQ | 13568 | RTNEVMR | 0.153076 | -0.18054 |
| SyS2253 | 4391 | GCCCAAGATAATCTGAGGGTTACGGCGGCACAG | 8980 | AQDNLRVTAAQ | 13569 | DNLRVTA | 0.153058 | -0.21448 |
| GS1294 | 4392 | GCCCAAAGGCAGGGGGGGATCAGCTTGCACAG | 8981 | AQRQAGDQLAQ | 13570 | RQAGDQL | 0.152865 | -0.13857 |
| SyS2254 | 4393 | GCCCAAGTCGGCCAACACCTCACCCACGCACAG | 8982 | AQVGQHLTHAQ | 13571 | VGQHLTH | 0.152852 | -0.13677 |

FIG. 33 (Continued)

| | | | | | | | | |
|---|---|---|---|---|---|---|---|---|
| SyS2255 | 4394 | GCCCAACTCAGCGCGCCAGCGGCATCGCACAG | 8983 | AQLSAASGIAQ | 13572 | LSAASGI | 0.152829 | -0.16497 |
| SyS2256 | 4395 | GCCCAAAGCAGCCACAACGGCTTCATCGCACAG | 8984 | AQSSHNGFIAQ | 13573 | SSHNGFI | 0.152739 | -0.14425 |
| GS1296 | 4396 | GCCCAAAACGCCACCAGACAATACAGCGCACAG | 8985 | AQNATRQYSAQ | 13574 | NATRQYS | 0.152256 | -0.06882 |
| GS1297 | 4397 | GCCCAAGTCAGCAGCAGACAAAGCCTCGGCGCACAG | 8986 | AQVSRQSLGAQ | 13575 | VSRQSLG | 0.152253 | -0.15676 |
| SyS2259 | 4398 | GCCCAAGACGTCGTCAAACCCACGGCGCACAG | 8987 | AQDVVKPHGAQ | 13576 | DVVKPHG | 0.152101 | -0.10404 |
| SyS2260 | 4399 | GCCCAAGGGATTGGGGGTATTAGTTCTGCACAG | 8988 | AQGIGGISSAQ | 13577 | GIGGISS | 0.152077 | -0.00277 |
| SyS2262 | 4400 | GCCCAAACTAATAATAGTCTGCGTGAGGCACAG | 8989 | AQTNNSLREAQ | 13578 | TNNSLRE | 0.151972 | -0.02172 |
| SyS2263 | 4401 | GCCCAAAGCGTACGGCTTCGGCGCTGGCACAG | 8990 | AQTRTASALAQ | 13579 | TRTASAL | 0.15196 | -0.08332 |
| SyS2264 | 4402 | GCCCAAACTACGACGGCTCCGAGTCCGGCACAG | 8991 | AQTTTAPSPAQ | 13580 | TTTAPSP | 0.151942 | 0.097476 |
| SyS2265 | 4403 | GCCCAAAACGCCAGCATGAGCAGCATCGCACAG | 8992 | AQNASMSSIAQ | 13581 | NASMSSI | 0.151936 | 0.127665 |
| SyS2266 | 4404 | GCCCAAACCCAACCCACAGAGGCCTCGCACAG | 8993 | AQTQPHRGLAQ | 13582 | TQPHRGL | 0.151921 | -0.20466 |
| SyS2267 | 4405 | GCCCAAAGACTCGACCACCACAGCAGCGCACAG | 8994 | AQRLDHHSSAQ | 13583 | RLDHHSS | 0.151906 | -0.2305 |
| SyS2268 | 4406 | GCCCAAGAAAAACACCACCAGAATCGCCGCACAG | 8995 | AQENTTRIAAQ | 13584 | ENTTRIA | 0.151859 | 0.202781 |
| GS1299 | 4407 | GCCCAAAGCCTCAGAGGCAACGAAGCCGCACAG | 8996 | AQSLRGNEAAQ | 13585 | SLRGNEA | 0.151754 | -0.16718 |
| GS1300 | 4408 | GCCCAACCTAATGTTCCTTCGCATTCTGCACAG | 8997 | AQPNVPSHSAQ | 13586 | PNVPSHS | 0.15171 | -0.18278 |
| SyS2269 | 4409 | GCCCAAGGGATGCCTTTGATGAAGATGGCACAG | 8998 | AQGMPLMKMAQ | 13587 | GMPLMKM | 0.151503 | -0.2083 |
| SyS2270 | 4410 | GCCCACAGAAGACTGAGCGGACGGTTGCACAG | 8999 | AQQKTERTVAQ | 13588 | QKTERTV | 0.15144 | -0.03374 |
| SyS2271 | 4411 | GCCCAAAACCACACACCACCAGCAGCGCACAG | 9000 | AQNHTNHSSAQ | 13589 | NHTNHSS | 0.151411 | -0.16829 |
| GS1302 | 4412 | GCCCAAGGGGCTGGGGAATAGGTCTGCTGCACAG | 9001 | AQGLGNRSAAQ | 13590 | GLGNRSA | 0.15133 | -0.17958 |
| GS1303 | 4413 | GCCCAAGGAACCTCGACAAAGAGGCCTCGCACAG | 9002 | AQDLDKRGLAQ | 13591 | DLDKRGL | 0.151278 | -0.07669 |
| SyS2273 | 4414 | GCCCAACTCACCAACGCCCAACCGACGCACAG | 9003 | AQLTNAQPDAQ | 13592 | LTNAQPD | 0.151194 | -0.21571 |
| SyS2275 | 4415 | GCCCAAACGAAGCCTGATTATCTGGTTGCACAG | 9004 | AQTKPDYLVAQ | 13593 | TKPDYLV | 0.151065 | -0.15859 |
| SyS2276 | 4416 | GCCCAAAAGTTGCAGTTGCATGAGGTTGCACAG | 9005 | AQKLQLHEVAQ | 13594 | KLQLHEV | 0.150883 | -0.08921 |
| SyS2277 | 4417 | GCCCAAACGTCTGTGACGATTTCGAGTGCACAG | 9006 | AQTSVTISSAQ | 13595 | TSVTISS | 0.150853 | -0.08154 |
| SyS2278 | 4418 | GCCCAAAATTCGAGTAATAGGCGTGAGGCACAG | 9007 | AQNSSNRAEAQ | 13596 | NSSNRAE | 0.150815 | -0.09555 |
| GS1304 | 4419 | GCCCAACTCGAACACGGCACCAGAATCGCACAG | 9008 | AQLEHGTRIAQ | 13597 | LEHGTRI | 0.150746 | -0.07792 |
| GS1305 | 4420 | GCCCAAACCCTCCAAATGAGAGAACACGCACAG | 9009 | AQTLQMREHAQ | 13598 | TLQMREH | 0.150701 | -0.13475 |
| GS1306 | 4421 | GCCCAAGGCAGCCCCAAACCGCACAG | 9010 | AQGSPTAQTAQ | 13599 | GSPTAQT | 0.150489 | -0.15945 |
| SyS2280 | 4422 | GCCCAAATAAGGGGCAGACGCTTACTGCACAG | 9011 | AQNKGQTLTAQ | 13600 | NKGQTLT | 0.150205 | -0.20588 |
| SyS2281 | 4423 | GCCCAATCGGTGGGTCATCGGGATATGGCACAG | 9012 | AQSVGHRDMAQ | 13601 | SVGHRDM | 0.150092 | -0.15617 |
| GS1308 | 4424 | GCCCAAAGAGACAAAAGCAGCATGCACACCGCACAG | 9013 | AQRDKSSMHAQ | 13602 | RDKSSMH | 0.149802 | -0.13189 |
| SyS2283 | 4425 | GCCCAAGTCAGCGTCATCAACAACACCGCACAG | 9014 | AQVSVINNTAQ | 13603 | VSVINNT | 0.14972 | -0.11447 |

FIG. 33 (Continued)

| | | | | | | | | |
|---|---|---|---|---|---|---|---|---|
| SyS2284 | 4426 | GCCCAACTTCCTAATTCTGCTTTAGTGCACAG | 9015 | AQLPNSAFSAQ | 13604 | LPNSAFS | 0.149676 | -0.02892 |
| GS1309 | 4427 | GCCCAACGTACGGTGTCTACGGATGATGCACAG | 9016 | AQRTVSTDDAQ | 13605 | RTVSTDD | 0.149671 | -0.18368 |
| GS1310 | 4428 | GCCCAACTCATGGACAGAATGGCCAGCGCACAG | 9017 | AQLMDRMASAQ | 13606 | LMDRMAS | 0.149549 | -0.14121 |
| SyS2285 | 4429 | GCCCAACGAGTGGGTTTAATACTTTGGCACAG | 9018 | AQPSGFNTLAQ | 13607 | PSGFNTL | 0.149506 | -0.21078 |
| SyS2286 | 4430 | GCCCAAAAAAGCGCCCAACCCATGAGCGCACAG | 9019 | AQKSAQPMSAQ | 13608 | KSAQPMS | 0.149458 | -0.11374 |
| SyS2287 | 4431 | GCCCAAACCGGCCTCAGCGTCCAAAAGCACAG | 9020 | AQTGLSVQKAQ | 13609 | TGLSVQK | 0.149458 | -0.23618 |
| SyS2288 | 4432 | GCCCAACACGGCTTCCCGGCCCCGCACAG | 9021 | AQHGFPAGPAQ | 13610 | HGFPAGP | 0.149413 | -0.19981 |
| SyS2289 | 4433 | GCCCAAAGCTACGAAGCCGTCGGCATCGCACAG | 9022 | AQSYEAVGIAQ | 13611 | SYEAVGI | 0.149397 | -0.13594 |
| SyS2290 | 4434 | GCCCAAAACCGCCAAAGGCGTCCTCAGCGCACAG | 9023 | AQTAKGVLSAQ | 13612 | TAKGVLS | 0.149081 | -0.22649 |
| SS153 | 4435 | GCCCAAGGGCGCCAGCACCCACAACGCCGCACAG | 9024 | AQGASTHNAAQ | 13613 | GASTHNA | 0.149034 | -0.40725 |
| SyS2291 | 4436 | GCCCAAATCATCAAAGAAATCCCGCCGCACAG | 9025 | AQIIKEIPAAQ | 13614 | IIKEIPA | 0.149013 | -0.16708 |
| GS1313 | 4437 | GCCCAAAAACCACGTCATCAGCAACGGGCACAG | 9026 | AQNHVISNGAQ | 13615 | NHVISNG | 0.148941 | -0.12903 |
| SyS2293 | 4438 | GCCCAATACACCAACATGGCCGGCGTCGCACAG | 9027 | AQYTNMAGVAQ | 13616 | YTNMAGV | 0.148928 | -0.14405 |
| SyS2294 | 4439 | GCCCAATTCAACAGAATCGGCGGCGGCGCACAG | 9028 | AQFNRIGAGAQ | 13617 | FNRIGAG | 0.14886 | -0.12101 |
| SyS2295 | 4440 | GCCCAATGGAGCACCATGATGAAAAGCGCACAG | 9029 | AQWSTMMKSAQ | 13618 | WSTMMKS | 0.148757 | -0.21679 |
| SyS2296 | 4441 | GCCCAAACCGCCCCGCCAACCACGTCGCACAG | 9030 | AQTAPANHVAQ | 13619 | TAPANHV | 0.148692 | 0.040594 |
| SyS2298 | 4442 | GCCCAAATGCATGGGGGTTCGGAGCTGGCACAG | 9031 | AQMHGGSELAQ | 13620 | MHGGSEL | 0.148583 | -0.18737 |
| GS1314 | 4443 | GCCCAAATGAGTAGGAGGATGGGGGGTGGCGCACAG | 9032 | AQMSRMGVAAQ | 13621 | MSRMGVA | 0.148576 | -0.1774 |
| GS1315 | 4444 | GCCCAAACTCGGATTAGTGAGGTTCTTGCACAG | 9033 | AQTRISEVLAQ | 13622 | TRISEVL | 0.148534 | -0.1313 |
| SyS2299 | 4445 | GCCCAAAGCGGCCCCGGCCTCAGAACCGCACAG | 9034 | AQSGPGLRTAQ | 13623 | SGPGLRT | 0.148397 | -0.13798 |
| GS1316 | 4446 | GCCCAAGATAAGCGTCATCATGCGGAGGCACAG | 9035 | AQDKRHHAEAQ | 13624 | DKRHHAE | 0.148387 | -0.10709 |
| SyS2300 | 4447 | GCCCAATTGACGGCAGAATGATCGGCCTGCACAG | 9036 | AQLTQNDRPAQ | 13625 | LTQNDRP | 0.148385 | -0.19353 |
| GS1317 | 4448 | GCCCAAAGCGTCACCAGCCACGTCGCACAG | 9037 | AQSVTTSHVAQ | 13626 | SVTTSHV | 0.148348 | -0.17919 |
| SyS2301 | 4449 | GCCCAAATGCTCACCGGCGGCACCAACGCACAG | 9038 | AQMLTGGTNAQ | 13627 | MLTGGTN | 0.148306 | -0.17259 |
| SyS2302 | 4450 | GCCCAAGACAACGTCGCCAACGCCGGCGCACAG | 9039 | AQDNVANAGAQ | 13628 | DNVANAG | 0.148252 | -0.125 |
| SyS2303 | 4451 | GCCCAAATGACCACCAACAGCATCGCCGCACAG | 9040 | AQMTTNSIAAQ | 13629 | MTTNSIA | 0.148226 | -0.22042 |
| SyS2304 | 4452 | GCCCAAATGCGTACGCAGTCTCTGTCGGCACAG | 9041 | AQMRTQSLSAQ | 13630 | MRTQSLS | 0.14815 | 0.030244 |
| GS1318 | 4453 | GCCCAATACGGCAGCTTCACCGGCCAAGCACAG | 9042 | AQYGSFTGQAQ | 13631 | YGSFTGQ | 0.148082 | -0.14334 |
| GS1320 | 4454 | GCCCAAGGCCCATGTGCTCCTCAAAGCCGCACAG | 9043 | AQGPMLLKAAQ | 13632 | GPMLLKA | 0.148051 | -0.16753 |
| SyS2305 | 4455 | GCCCAAATGACCCAAAAAGCCCCGTCGCACAG | 9044 | AQMTQKAPVAQ | 13633 | MTQKAPV | 0.147926 | -0.03714 |
| GS1321 | 4456 | GCCCAAAGCGCCAACGCCCACCAAACTCGCACAG | 9045 | AQSANATKLAQ | 13634 | SANATKL | 0.147918 | -0.10232 |
| SyS2306 | 4457 | GCCCAATTCAACGGCAGCCTCGCCATGGCACAG | 9046 | AQFNGSLAMAQ | 13635 | FNGSLAM | 0.147866 | -0.14302 |

FIG. 33 (Continued)

| | | | | | | | | |
|---|---|---|---|---|---|---|---|---|
| SyS2308 | 4458 | GCCCAAATTGTTAATGCTAAGCTTACTGCACAG | 9047 | AQIVNAKLTAQ | 13636 | IVNAKLT | 0.147749 | -0.20103 |
| SyS2310 | 4459 | GCCCAAATGTTCAGCGGCCTCCAAGCCGCACAG | 9048 | AQMFSGLQAAQ | 13637 | MFSGLQA | 0.147689 | -0.23296 |
| GS1322 | 4460 | GCCCAAGTGATTATCGGGTGAATGGTGCACAG | 9049 | AQVDYRVNGAQ | 13638 | VDYRVNG | 0.147677 | -0.16241 |
| SyS2311 | 4461 | GCCCAACTGGCTTCGGCTGGTAATGGTGCACAG | 9050 | AQLASAGNGAQ | 13639 | LASAGNG | 0.147593 | -0.07841 |
| GS1323 | 4462 | GCCCAACGTGATCTTCATTCTAAGGATGCACAG | 9051 | AQRDLHSKDAQ | 13640 | RDLHSKD | 0.147554 | -0.17958 |
| SyS2313 | 4463 | GCCCAAAGCCACGTCAGCAGAACCGCGGCACAG | 9052 | AQSHVSRTAAQ | 13641 | SHVSRTA | 0.147511 | 0.008708 |
| SyS2314 | 4464 | GCCCAAACCCCGTCCAAAGCCTCAGCGCACAG | 9053 | AQTPVQSLSAQ | 13642 | TPVQSLS | 0.147458 | -0.1444 |
| SyS2315 | 4465 | GCCCAATACCTCAACGGCAGCGAACTCGCACAG | 9054 | AQYLNGSELAQ | 13643 | YLNGSEL | 0.147331 | -0.1489 |
| SyS2316 | 4466 | GCCCAACCTGCTTTGAAGACTCATGAGGCACAG | 9055 | AQPALKTHEAQ | 13644 | PALKTHE | 0.14732 | 0.228732 |
| GS1324 | 4467 | GCCCAAAATAAGTCTCTGACTTCTGATGCACAG | 9056 | AQNKSLTSDAQ | 13645 | NKSLTSD | 0.147304 | -0.16432 |
| GS1325 | 4468 | GCCCAATATAATGCTACTAAGTCGAGTGCACAG | 9057 | AQYNATKSSAQ | 13646 | YNATKSS | 0.147262 | -0.13189 |
| GS1326 | 4469 | GCCCAAATGCGGGATAAGAGTCATGATGCACAG | 9058 | AQMRDKSHDAQ | 13647 | MRDKSHD | 0.147262 | -0.13189 |
| SyS2318 | 4470 | GCCCAACACAGAACCGAAGGCAAAACGCACAG | 9059 | AQHRTEGQNAQ | 13648 | HRTEGQN | 0.147163 | -0.041 |
| SyS2319 | 4471 | GCCCAACTCCACAAACCGACGAATTCGCACAG | 9060 | AQLHKPDEFAQ | 13649 | LHKPDEF | 0.147149 | -0.14672 |
| SyS2320 | 4472 | GCCCAAATTGCTGCGAGGCCTCCTTCGGCACAG | 9061 | AQIAARPPSAQ | 13650 | IAARPPS | 0.14708 | -0.16223 |
| SyS2321 | 4473 | GCCCAAACGCCTACGCATTATTCTCATGCACAG | 9062 | AQTPTHYSHAQ | 13651 | TPTHYSH | 0.14708 | -0.19496 |
| GP183 | 4474 | GCCCAATCGACTTTTTCGGCTGATAGGGCACAG | 9063 | AQSTFSADRAQ | 13652 | STFSADR | 0.147035 | -0.07197 |
| SyP68 | 4475 | GCCCAACAGTCGGTGCAGGTGACGGCTGCACAG | 9064 | AQQSVQVTAAQ | 13653 | QSVQVTA | 0.146995 | -0.04053 |
| SyS2322 | 4476 | GCCCAACTCGACAGCAGCAGAAACAGAGCACAG | 9065 | AQLDSSRNRAQ | 13654 | LDSSRNR | 0.146928 | -0.18527 |
| GS1327 | 4477 | GCCCAAAGACAACCCAAAGCACCGTCGCACAG | 9066 | AQRQPQSTVAQ | 13655 | RQPQSTV | 0.146727 | -0.01889 |
| SyS2323 | 4478 | GCCCAAAGAGTGCGACGACGGCGTCAGAGCACAG | 9067 | AQRVDDGVRAQ | 13656 | RVDDGVR | 0.146717 | -0.07779 |
| GS1328 | 4479 | GCCCAAAAAATCACCAACACTTACAGCGCACAG | 9068 | AQKITNTYSAQ | 13657 | KITNTYS | 0.146679 | -0.1481 |
| GS1329 | 4480 | GCCCAACCTGGGAAGGCGACTCCTGCACAG | 9069 | AQPGKATPPAQ | 13658 | PGKATPP | 0.146646 | -0.15317 |
| GS1330 | 4481 | GCCCAATTCAGCACCCCACACCCCCGCACAG | 9070 | AQFSTHTPPAQ | 13659 | FSTHTPP | 0.146343 | -0.13761 |
| SyS2324 | 4482 | GCCCAACTCGCCCCAACATGAGACTCGCACAG | 9071 | AQLAPNMRLAQ | 13660 | LAPNMRL | 0.146185 | -0.21194 |
| SS154 | 4483 | GCCCAAAACCTCCCAGAACCAACGTCGCACAG | 9072 | AQNLPRTNVAQ | 13661 | NLPRTNV | 0.146169 | -0.35701 |
| GS1331 | 4484 | GCCCAAGAGACGAGTAATGTGAATCGTGCACAG | 9073 | AQETSNVNRAQ | 13662 | ETSNVNR | 0.14611 | -0.18188 |
| SyS2325 | 4485 | GCCCAAGGCAGCACCGACCACAGACTCGCACAG | 9074 | AQGSTDHRLAQ | 13663 | GSTDHRL | 0.145928 | -0.13071 |
| SS155 | 4486 | GCCCAAGTCAACACCGCCGCGCCATGCACAG | 9075 | AQVNTAMPAAQ | 13664 | VNTAMPA | 0.145614 | -0.40725 |
| GS1335 | 4487 | GCCCAAATGGTTGCTCGGGATCAGAATGCACAG | 9076 | AQMVARDQNAQ | 13665 | MVARDQN | 0.145535 | -0.13881 |
| SyS2328 | 4488 | GCCCAAAAAAACAACCCGTCCTCCACGCACAG | 9077 | AQKNNPVLHAQ | 13666 | KNNPVLH | 0.145436 | -0.18984 |
| GS1337 | 4489 | GCCCAAGATTCGACGACGGTTAGGCTTGCACAG | 9078 | AQDSTTVRLAQ | 13667 | DSTTVRL | 0.145378 | -0.10767 |

FIG. 33 (Continued)

| | | | | | | | | |
|---|---|---|---|---|---|---|---|---|
| SyS2329 | 4490 | GCCCAAAAACTCAACGTCATGAACGACGCACAG | 9079 | AQKLNVMNDAQ | 13668 | KLNVMND | 0.145256 | -0.15738 |
| GS1339 | 4491 | GCCCAAAGCCTCAGAGACAAAAGCGCCGCACAG | 9080 | AQSLRDKNAAQ | 13669 | SLRDKNA | 0.145231 | -0.18727 |
| SyS2330 | 4492 | GCCCAAGGTGTTGGTAATAGTCTGAGTGCACAG | 9081 | AQGVGNSLSAQ | 13670 | GVGNSLS | 0.145202 | -0.01482 |
| SyS2332 | 4493 | GCCCAATTCAGCAAAACCAACTTCAACGCACAG | 9082 | AQFSKTNFNAQ | 13671 | FSKTNFN | 0.145119 | -0.22557 |
| GS1342 | 4494 | GCCCAAGCTAATCGGCCTTCGCTGCTGCACAG | 9083 | AQANRPSLPAQ | 13672 | ANRPSLP | 0.144885 | -0.0877 |
| GS1343 | 4495 | GCCCAAGACAGCAAACCAACAGAGTCGCACAG | 9084 | AQDSQTNRVAQ | 13673 | DSQTNRV | 0.144816 | -0.09307 |
| SyS2333 | 4496 | GCCCAAATTTGACGTCGTCCGGTTGCACAG | 9085 | AQISTSSPVAQ | 13674 | ISTSSPV | 0.144754 | -0.12222 |
| SyS2334 | 4497 | GCCCAAATCCTCAAAATCACCGAAGGCGCACAG | 9086 | AQILKITEGAQ | 13675 | ILKITEG | 0.144609 | -0.14918 |
| GS1344 | 4498 | GCCCAATTTCGTCGGCGTCTGAGATTGCACAG | 9087 | AQFRPASEIAQ | 13676 | FRPASEI | 0.144534 | -0.13935 |
| SyS2335 | 4499 | GCCCAAAAAAAGACAGCGAACCCCTCGCACAG | 9088 | AQKKDSEPLAQ | 13677 | KKDSEPL | 0.144431 | 0.01409 |
| SyS2336 | 4500 | GCCCAAAACGCCAGACCCCTCACCGCGCACAG | 9089 | AQNARPLTAAQ | 13678 | NARPLTA | 0.144383 | -0.05797 |
| SyS2338 | 4501 | GCCCAAAAGGCGGGCTAGGATGGAGACTGCACAG | 9090 | AQKAARMETAQ | 13679 | KAARMET | 0.144286 | -0.10236 |
| SyS2340 | 4502 | GCCCAACACGCCAACGTCAGCAGCAGAGAGCACAG | 9091 | AQHANVSSRAQ | 13680 | HANVSSR | 0.144111 | -0.14672 |
| SyS2341 | 4503 | GCCCAAACCAGCACCACCCAAACCAGCGCACAG | 9092 | AQTSTTQTSAQ | 13681 | TSTTQTS | 0.144008 | -0.21448 |
| SyS2342 | 4504 | GCCCAAGTGCGTTGTCGCTGAGTCCGGCACAG | 9093 | AQSALSLSPAQ | 13682 | SALSLSP | 0.143867 | -0.11439 |
| SyS2343 | 4505 | GCCCAAGCTAATGTTCAGATTCAGTCGGCACAG | 9094 | AQANVQIQSAQ | 13683 | ANVQIQS | 0.143839 | -0.19739 |
| GS1346 | 4506 | GCCCAAACCCCAGCAGCAACAGCCTCGCACAG | 9095 | AQTPSSNSLAQ | 13684 | TPSSNSL | 0.143816 | -0.14429 |
| SyS2345 | 4507 | GCCCAAACGATGACGGGGCCTGGTCATGCACAG | 9096 | AQTMTGPGHAQ | 13685 | TMTGPGH | 0.143627 | -0.14425 |
| SyS2346 | 4508 | GCCCAAATTACTGCTCAGATTACGAATGCACAG | 9097 | AQITAQITNAQ | 13686 | ITAQITN | 0.143574 | -0.22064 |
| SyS2348 | 4509 | GCCCAACTTCCTAATCCTTCGTCTCGGGCACAG | 9098 | AQLPNPSSRAQ | 13687 | LPNPSSR | 0.143468 | -0.19723 |
| SyS2349 | 4510 | GCCCAAAAGATGGGGACTATGACGCCTGCACAG | 9099 | AQKMGTMTPAQ | 13688 | KMGTMTP | 0.143411 | -0.08828 |
| GS1347 | 4511 | GCCCAATACACCAACGGCAGAATCAACGCACAG | 9100 | AQYTNGRINAQ | 13689 | YTNGRIN | 0.143337 | -0.13284 |
| SyS2350 | 4512 | GCCCAAGATGGGAGTAATGTGGTGAAGGCACAG | 9101 | AQDGSNVVKAQ | 13690 | DGSNVVK | 0.143302 | -0.21202 |
| GS1348 | 4513 | GCCCAACTCCCCTCAGCATCCCGCGCACAG | 9102 | AQLPLSIPAAQ | 13691 | LPLSIPA | 0.143269 | -0.17481 |
| GS1349 | 4514 | GCCCAAGAAAGCAGACTCAGCAGCAGCACAG | 9103 | AQESRLSSSAQ | 13692 | ESRLSSS | 0.143208 | -0.16814 |
| SyS2351 | 4515 | GCCCAAATGAGTCCTTCTCGGGGTAATGCACAG | 9104 | AQMSPSRGNAQ | 13693 | MSPSRGN | 0.143199 | -0.13677 |
| SyS2352 | 4516 | GCCCAAAGCGTCCACGCCGCCAAACAAGCACAG | 9105 | AQSVHAAKQAQ | 13694 | SVHAAKQ | 0.143145 | -0.14647 |
| SyS2353 | 4517 | GCCCAAGCGTTTTCTAGTGGTACTTCGGCACAG | 9106 | AQAFSSGTSAQ | 13695 | AFSSGTS | 0.143125 | 0.020339 |
| GS1350 | 4518 | GCCCAAACTGGGTGGTCTCCTTCGCCTGCACAG | 9107 | AQTGWSPSPAQ | 13696 | TGWSPSP | 0.143107 | -0.15478 |
| SyS2354 | 4519 | GCCCAAGCGTCGCATAGTGCGAGTGGTGCACAG | 9108 | AQASHSASGAQ | 13697 | ASHSASG | 0.143021 | -0.23012 |
| GS1353 | 4520 | GCCCAAGTCACCCCAGAAGCCCCTCGCACAG | 9109 | AQVTPRSPLAQ | 13698 | VTPRSPL | 0.142958 | -0.12807 |
| GS1354 | 4521 | GCCCAAACTGAGCGTGATACTAGTCGTGCACAG | 9110 | AQTERDTSRAQ | 13699 | TERDTSR | 0.142958 | -0.1159 |

FIG. 33 (Continued)

| | | | | | | | | |
|---|---|---|---|---|---|---|---|---|
| SyS2355 | 4522 | GCCCAATACACCCTCACGGCACCACCGCACAG | 9111 | AQYTLTGTTAQ | 13700 | YTLTGTT | 0.142869 | -0.18527 |
| SyS2356 | 4523 | GCCCAAGACCTCAGAGTCAGCAGAGACGCACAG | 9112 | AQDLRVSRDAQ | 13701 | DLRVSRD | 0.142848 | -0.13071 |
| SyS2357 | 4524 | GCCCAACTTATTGCGTGCGATACGGCGGGCACAG | 9113 | AQLIASHTAAQ | 13702 | LIASHTA | 0.142848 | -0.13071 |
| SyS2358 | 4525 | GCCCAACAGCGTTCTGAGAATTCGCATGCACAG | 9114 | AQQRSENSHAQ | 13703 | QRSENSH | 0.142835 | -0.08424 |
| GS13355 | 4526 | GCCCAAAGTGCGAGTAATCAGACTTATGCACAG | 9115 | AQSASNQTYAQ | 13704 | SASNQTY | 0.142747 | -0.17005 |
| SyS2360 | 4527 | GCCCAATTGGAGAAGGTGCTGCAGCGGCACAG | 9116 | AQLEKVLQPAQ | 13705 | LEKVLQP | 0.142579 | -0.23296 |
| SyS2361 | 4528 | GCCCAAAATAGTGGTCCGTTGGTGATTGCACAG | 9117 | AQNSGPLVIAQ | 13706 | NSGPLVI | 0.142353 | -0.17829 |
| SyS2362 | 4529 | GCCCAAGGCACCATCCACAGCCCGTCGCACAG | 9118 | AQGTIHSPVAQ | 13707 | GTIHSPV | 0.142285 | -0.23376 |
| SyS2363 | 4530 | GCCCAAAACAAAAACGGGGAAGTCCTCGCACAG | 9119 | AQNKNGEVLAQ | 13708 | NKNGEVL | 0.142243 | -0.13686 |
| SyS2364 | 4531 | GCCCAACCCATGAACGAAAGAGAAAGAGCACAG | 9120 | AQPMNERERAQ | 13709 | PMNERER | 0.1422 | -0.1986 |
| SyS2366 | 4532 | GCCCAAGGCAGCAACAACCTCCACCCGCACAG | 9121 | AQGSNNLHPAQ | 13710 | GSNNLHP | 0.141901 | -0.14768 |
| SyS2367 | 4533 | GCCCAAATGAGCCTCCACGCCAAAGCGCACAG | 9122 | AQMSLHAKSAQ | 13711 | MSLHAKS | 0.141901 | -0.18284 |
| SyS2368 | 4534 | GCCCAACAAGAAAAAGCCCTCGCCAGAGCACAG | 9123 | AQQEKALARAQ | 13712 | QEKALAR | 0.141841 | -0.08342 |
| SP45 | 4535 | GCCCAAGATCGTAGTACGCATGCTAAGGCACAG | 9124 | AQDRSTHAKAQ | 13713 | DRSTHAK | 0.141804 | -0.05361 |
| SyS2369 | 4536 | GCCCAAATTGTGAGGGGTGATACGTCTGCACAG | 9125 | AQIVRGDTSAQ | 13714 | IVRGDTS | 0.141804 | -0.2305 |
| GS13359 | 4537 | GCCCAAAGCAGCGGCGGCATGAACGAAGCACAG | 9126 | AQSSGGMNEAQ | 13715 | SSGGMNE | 0.141777 | -0.17386 |
| SyS2370 | 4538 | GCCCAAAGTTGCATGTCGTGTTGAGGCTGCACAG | 9127 | AQKLHAVEAAQ | 13716 | KLHAVEA | 0.141757 | -0.19254 |
| SyS2371 | 4539 | GCCCAAATGTTCGCCGAAGGCACCGTCGCACAG | 9128 | AQMFAEGTVAQ | 13717 | MFAEGTV | 0.14166 | -0.18984 |
| GS13360 | 4540 | GCCCAAACCCTCGGCAGAGTCCCCAAGCACAG | 9129 | AQTLGRVPQAQ | 13718 | TLGRVPQ | 0.141609 | -0.12235 |
| GS13361 | 4541 | GCCCAACTCCTCGGCAACAAAGACAAAGCACAG | 9130 | AQLLGNKDKAQ | 13719 | LLGNKDK | 0.141569 | -0.13971 |
| GS13362 | 4542 | GCCCAAAGAGTCAACACCAGCACGACGCACAG | 9131 | AQRVNTSTDAQ | 13720 | RVNTSTD | 0.141559 | 0.158617 |
| SyS2372 | 4543 | GCCCAACCCCAAGGCGTCAGCCCGCCGCACAG | 9132 | AQPQGVSPAAQ | 13721 | PQGVSPA | 0.14153 | -0.18121 |
| SyS2373 | 4544 | GCCCAAGGCGCCGTCTCCAGCAAAGCCGCACAG | 9133 | AQGAVLSKAAQ | 13722 | GAVLSKA | 0.14147 | -0.14056 |
| SyS2374 | 4545 | GCCCAACTCGGCCACGCGCCACCAGCGCACAG | 9134 | AQLGHAATSAQ | 13723 | LGHAATS | 0.141412 | -0.21194 |
| SyS2375 | 4546 | GCCCAAAGCGGCTTCAGCAGCACGCCGCACAG | 9135 | AQSGFSSTAAQ | 13724 | SGFSSTA | 0.141288 | -0.12331 |
| SyS2376 | 4547 | GCCCAATTGGTGAATCAGCCTCAGTCGGCACAG | 9136 | AQLVNQPQSAQ | 13725 | LVNQPQS | 0.141288 | -0.12331 |
| GS13366 | 4548 | GCCCAAGGTCGTGCGGAGGTGGGGATTGCACAG | 9137 | AQGRAEVGIAQ | 13726 | GRAEVGI | 0.141255 | -0.16932 |
| GS13369 | 4549 | GCCCAAGTCCTGCGCCACCAAAAACAGCGCACAG | 9138 | AQVLATKNSAQ | 13727 | VLATKNS | 0.140992 | -0.15764 |
| SyS2378 | 4550 | GCCCAACAGGCTCATGCGTTTGCGGATGCACAG | 9139 | AQQAHAFADAQ | 13728 | QAHAFAD | 0.140963 | -0.20588 |
| SyS2379 | 4551 | GCCCAAAACCTCGACACCGTCAAAACCGCACAG | 9140 | AQNLDTVKTAQ | 13729 | NLDTVKT | 0.140932 | -0.21941 |
| SyS2380 | 4552 | GCCCAACGTCCGCAGACTCTGCCGAATGCACAG | 9141 | AQRPQTLPNAQ | 13730 | RPQTLPN | 0.140903 | -0.17013 |
| SyS2381 | 4553 | GCCCAAAACCCCAGAAACAGCCCCACCGCACAG | 9142 | AQNPRNSPTAQ | 13731 | NPRNSPT | 0.140813 | -0.1392 |

FIG. 33 (Continued)

| | | | | | | | |
|---|---|---|---|---|---|---|---|
| SyS2382 | 4554 | GCCCAACACATGTGCAGATGGATGCGGATGCACAG | AQHVQMDADAQ | 13732 | HVQMDAD | 0.140761 | -0.1071 |
| GS1371 | 4555 | GCCCAAACTTATCGGACTGAGCGGTGGCACAG | AQTYRTEPVAQ | 13733 | TYRTEPV | 0.14075 | -0.18099 |
| SyS2383 | 4556 | GCCCAACCGGCCTCGTCAACATGAGCGCACAG | AQPGLVNMSAQ | 13734 | PGLVNMS | 0.140733 | -0.21557 |
| SyS2384 | 4557 | GCCCAAAGCCTCAGCCAAGCCCCGCCGCACAG | AQSLSQGPAAQ | 13735 | SLSQGPA | 0.14057 | -0.10768 |
| SyS2385 | 4558 | GCCCAACTGGGTGCTTCTGGTTATACGGCACAG | AQLGASGYTAQ | 13736 | LGASGYT | 0.14047 | -0.22527 |
| SyS2386 | 4559 | GCCCAAAGGCGCCGTCACCACCATGCCGCACAG | AQSAVTTMPAQ | 13737 | SAVTTMP | 0.14044 | -0.23419 |
| GP186 | 4560 | GCCCAAAAGGTGAATGCTGAGCTTCTTGCACAG | AQKVNAELLAQ | 13738 | KVNAELL | 0.140309 | -0.07287 |
| SyS2387 | 4561 | GCCCAACCGTTTACGCCTAAGTTGAGTGCACAG | AQPFTPKLSAQ | 13739 | PFTPKLS | 0.140302 | -0.20951 |
| GS1372 | 4562 | GCCCAAATGAGAAGCACCAACGCCAGCGCACAG | AQMRSTNASAQ | 13740 | MRSTNAS | 0.140251 | -0.14868 |
| SyS2388 | 4563 | GCCCAAGTGATGTATGCGCGTGGGGATGCACAG | AQVMYARGDAQ | 13741 | VMYARGD | 0.140081 | -0.11698 |
| GS1373 | 4564 | GCCCAACGGGTTGGTAGTACGATGCAGGCACAG | AQRVGSTMQAQ | 13742 | RVGSTMQ | 0.140075 | -0.16146 |
| SP47 | 4565 | GCCCAATTGACGGTGGCGGTTGAGACTGCACAG | AQLTVAVETAQ | 13743 | LTVAVET | 0.139972 | -0.05361 |
| SyS2390 | 4566 | GCCCAATGGACTAATTCTGGTAGTTCTGCACAG | AQWTNSGSSAQ | 13744 | WTNSGSS | 0.139811 | -0.18769 |
| GS1374 | 4567 | GCCCAACACGCCATGAGAGGCACCGGCGCACAG | AQHAMRGTGAQ | 13745 | HAMRGTG | 0.139811 | -0.16842 |
| SyS2391 | 4568 | GCCCAACACCAGAACGTCAGAGGCAGCGCACAG | AQHQDVRGSAQ | 13746 | HQDVRGS | 0.139527 | -0.18861 |
| GS1375 | 4569 | GCCCAAAGCTTCCAAAGAGAAATCCCGCACAG | AQSFQREIPAQ | 13747 | SFQREIP | 0.13934 | -0.09891 |
| GS1377 | 4570 | GCCCAACTCCAAAGAGCGCCCTCAACGCACAG | AQLQRAALNAQ | 13748 | LQRAALN | 0.1391 | -0.16528 |
| SyS2392 | 4571 | GCCCAAGGCGACGCCACCATCAGACCGCACAG | AQSDATIRPAQ | 13749 | SDATIRP | 0.139008 | 0.01549 |
| GS1378 | 4572 | GCCCAACAAATGAGCACCGGCAGAGTCGCACAG | AQQMSTGRVAQ | 13750 | QMSTGRV | 0.13898 | -0.10908 |
| GS1379 | 4573 | GCCCAAAGAAGCACCCAAGCCATCCCGCACAG | AQRSTQAIPAQ | 13751 | RSTQAIP | 0.138749 | -0.15766 |
| SyS2395 | 4574 | GCCCAACAAATCAGAGACGCCAACGCGCACAG | AQQIRDANAAQ | 13752 | QIRDANA | 0.138593 | -0.14056 |
| GS1382 | 4575 | GCCCAACTCCACACCAGCCTACGCACAG | AQLHTSNAYAQ | 13753 | LHTSNAY | 0.138339 | -0.18368 |
| SS160 | 4576 | GCCCAATCTTCTGGGCTGGGGACGCCTGCACAG | AQSSGLGTPAQ | 13754 | SSGLGTP | 0.138099 | -0.36216 |
| SyS2396 | 4577 | GCCCAAGAGCCACAAACCCGTCAGAGACGCACAG | AQDHKPVRDAQ | 13755 | DHKPVRD | 0.138062 | -0.16708 |
| GS1383 | 4578 | GCCCAAATGAAACTCGTCAGCGTCGGCGCACAG | AQMKLVSVGAQ | 13756 | MKLVSVG | 0.138012 | -0.12152 |
| SyS2397 | 4579 | GCCCAAGGTGAGCAGAGTCTTAAGGCGGCACAG | AQGEQSLKAAQ | 13757 | GEQSLKA | 0.137822 | -0.16102 |
| GS1385 | 4580 | GCCCAAATGACCAGCGGCACCAACGGCGCACAG | AQMTSGTNGAQ | 13758 | MTSGTNG | 0.137741 | -0.16304 |
| SyS2398 | 4581 | GCCCAACATGGGCTAAGGGTGTTGTTGCACAG | AQHAAKGVVAQ | 13759 | HAAKGVV | 0.137688 | -0.1392 |
| SyS2401 | 4582 | GCCCAAAGCAGCAGAGACAAAGAACCCGCACAG | AQSSRQNEPAQ | 13760 | SSRQNEP | 0.137659 | -0.23012 |
| SyS2402 | 4583 | GCCCAAGCCCTCATCAACAGACCCAACGCACAG | AQALINRPNAQ | 13761 | ALINRPN | 0.137501 | -0.08183 |
| SyS2403 | 4584 | GCCCAATTGAGGTCTTCATGGCGTCTGCACAG | AQLRSSMASAQ | 13762 | LRSSMAS | 0.137488 | -0.17072 |
| SyS2404 | 4585 | GCCCAAAATAATGAGTATTCGAAGCTGGCACAG | AQNNEYSKLAQ | 13763 | NNEYSKL | 0.137304 | -0.13033 |

FIG. 33 (Continued)

| | | | | | | | |
|---|---|---|---|---|---|---|---|
| GS1386 | 4586 | GCCCAAACTGGGCGTTTGAATGGGGAGGCACAG | 9175 | AQTGRLNGEAQ | 13764 | TGRLNGE | 0.137105 | -0.15001 |
| GS1387 | 4587 | GCCCAAACCAACAGCCACGCACCGTCAGAGCACAG | 9176 | AQTNSHAVRAQ | 13765 | TNSHAVR | 0.137064 | -0.10066 |
| SyS2406 | 4588 | GCCCAAATCGTCACCAACCACAGCCACGCACAG | 9177 | AQIVTNHSHAQ | 13766 | IVTNHSH | 0.136985 | 0.018624 |
| GS1388 | 4589 | GCCCAAGCCCTCACCAGAGACATCACCGCACAG | 9178 | AQALTRDITAQ | 13767 | ALTRDIT | 0.136966 | -0.10929 |
| SyS2407 | 4590 | GCCCAAGGCATCGCCAACCAAGGCGTCGCACAG | 9179 | AQGIANQGVAQ | 13768 | GIANQGV | 0.136871 | -0.02727 |
| GP188 | 4591 | GCCCAAAATACTGTGCGTTCTCAGCAGGCACAG | 9180 | AQNTVRSQQAQ | 13769 | NTVRSQQ | 0.136631 | -0.07079 |
| SyS2409 | 4592 | GCCCAAATGGAGAATTCGAATAAGGCTGCACAG | 9181 | AQMENSNKAAQ | 13770 | MENSNKA | 0.136602 | -0.21078 |
| SyS2410 | 4593 | GCCCAAGGTACGGTTAGGGTGCAGGCTGCACAG | 9182 | AQGTVRVQAAQ | 13771 | GTVRVQA | 0.136485 | -0.00948 |
| SyS2411 | 4594 | GCCCAAACCACCAGCCACCTCATCGACGCACAG | 9183 | AQTTSHLIDAQ | 13772 | TTSHLID | 0.136485 | -0.16223 |
| GS1389 | 4595 | GCCCAAGGTACGCAGGGCGCATCAGGGTGCACAG | 9184 | AQGTQAHQGAQ | 13773 | GTQAHQG | 0.13647 | -0.00419 |
| GS1390 | 4596 | GCCCAAAAAATGAGCGCGCAGCAGCGTCGCACAG | 9185 | AQKMSASSVAQ | 13774 | KMSASSV | 0.136227 | -0.15586 |
| SyS2414 | 4597 | GCCCAAAGCCTCAAAGTCAACCCGGCGCACAG | 9186 | AQSLKVNPGAQ | 13775 | SLKVNPG | 0.136211 | -0.22164 |
| GP189 | 4598 | GCCCAATCGACTGGGACGTCTACTCTTGCACAG | 9187 | AQSTGTSTLAQ | 13776 | STGTSTL | 0.136041 | 0.207438 |
| SyS2415 | 4599 | GCCCAAGTTTGACGAATCGTGAGCAGGCACAG | 9188 | AQVLTNREQAQ | 13777 | VLTNREQ | 0.135897 | -0.05665 |
| SyS2416 | 4600 | GCCCAACTCGACGTCAGCAGAACCCTCGCACAG | 9189 | AQLDVSRTLAQ | 13778 | LDVSRTL | 0.135826 | -0.18769 |
| SyS2417 | 4601 | GCCCAATCGTTGGGACTGAGAGTCGTGCACAG | 9190 | AQSFGTESRAQ | 13779 | SFGTESR | 0.135821 | 0.273431 |
| SyS2418 | 4602 | GCCCAACAGCTTGCGAAGGGAATTATGCACAG | 9191 | AQQLAKGNYAQ | 13780 | QLAKGNY | 0.135676 | -0.22557 |
| SyS2419 | 4603 | GCCCAAGCCAAAAACGACCCAGAGCCGCACAG | 9192 | AQAKNDPRAAQ | 13781 | AKNDPRA | 0.135675 | 0.015165 |
| SyS2420 | 4604 | GCCCAACTCACCCAAGTCGGCGGCACCGCACAG | 9193 | AQLTQVGGTAQ | 13782 | LTQVGGT | 0.135637 | -0.18163 |
| SyS2421 | 4605 | GCCCAAAAGCAGAATACTTCTCTGGCACAG | 9194 | AQKQNTTSLAQ | 13783 | KQNTTSL | 0.135601 | -0.23133 |
| SyS2423 | 4606 | GCCCAACTTTCGACTAGGGCTGAGGATGCACAG | 9195 | AQLSTRAEDAQ | 13784 | LSTRAED | 0.135448 | -0.23419 |
| GS1394 | 4607 | GCCCAAACCGTCCCCAACATCCCCATGGCACAG | 9196 | AQTVPNIPMAQ | 13785 | TVPNIPM | 0.135363 | -0.15317 |
| GS1395 | 4608 | GCCCAAAATTCGTTGTCTAAGCTGTCGGCACAG | 9197 | AQNSLSKLSAQ | 13786 | NSLSKLS | 0.13513 | -0.00256 |
| SyS2424 | 4609 | GCCCAAATGAATGAGCATCAGATGAAGGCACAG | 9198 | AQMNEHQMKAQ | 13787 | MNEHQMK | 0.135017 | -0.20339 |
| GS1396 | 4610 | GCCCAAGACGTCAAAGGCCACCAAAGCGCACAG | 9199 | AQDVKGHQSAQ | 13788 | DVKGHQS | 0.135013 | -0.096 |
| SyS2427 | 4611 | GCCCAAGACGTCAGCGTCCAAAAAGACGCACAG | 9200 | AQDVSLQKDAQ | 13789 | DVSLQKD | 0.134944 | -0.11931 |
| GS1397 | 4612 | GCCCAAACCAGACCCAGCGGCACCTACGCACAG | 9201 | AQTRPSGTYAQ | 13790 | TRPSGTY | 0.134868 | -0.16932 |
| SyS2429 | 4613 | GCCCAAGTTAAGGGGCCGGATTCTCTTGCACAG | 9202 | AQVKGPDSLAQ | 13791 | VKGPDSL | 0.134815 | -0.1792 |
| SyS2430 | 4614 | GCCCAAAACCACCAGCAGTCTACGAACTCGCACAG | 9203 | AQNHSSYELAQ | 13792 | NHSSYEL | 0.13473 | -0.14526 |
| SyS2431 | 4615 | GCCCAAACCGTCAGAACCCCTCATCGCACAG | 9204 | AQTVRTPLIAQ | 13793 | TVRTPLI | 0.134668 | -0.23497 |
| SyS2432 | 4616 | GCCCAAGCCAGCATCGACACGACCAACACGCACAG | 9205 | AQASIDSQHAQ | 13794 | ASIDSQH | 0.134524 | -0.20093 |
| GS1401 | 4617 | GCCCAAGATCAGAGAAGAATTCTGGGCATGCACAG | 9206 | AQDQKNSGHAQ | 13795 | DQKNSGH | 0.134505 | -0.18054 |

FIG. 33 (Continued)

| | | | | | | | | |
|---|---|---|---|---|---|---|---|---|
| SyS2434 | 4618 | GCCCAACTGACACCAACAACAAAGCCGCACAG | 9207 | AQLDTNNKAAQ | 13796 | LDTNNKA | 0.134292 | 0.171043 |
| GP190 | 4619 | GCCCAAGCGGAGTGCTCATGCGCAGGTTGCACAG | 9208 | AQASAHAQVAQ | 13797 | ASAHAQV | 0.134161 | 0.132411 |
| GS1403 | 4620 | GCCCAAGACAGCGGCAAACAACGACGCACAG | 9209 | AQDSGKHNDAQ | 13798 | DSGKHND | 0.134104 | -0.17919 |
| GS1404 | 4621 | GCCCAACTTAATCGGAATAGTGGTATGGCACAG | 9210 | AQLNRNSGMAQ | 13799 | LNRNSGM | 0.134006 | -0.08579 |
| SyS2436 | 4622 | GCCCAACCCACCATGCTCCCGACAAAGCACAG | 9211 | AQPTMLPDKAQ | 13800 | PTMLPDK | 0.133981 | -0.21818 |
| GS1406 | 4623 | GCCCAAAGCACCCAAGTCAGCAACTACGCACAG | 9212 | AQSTQVSNYAQ | 13801 | STQVSNY | 0.133756 | -0.10556 |
| SyS2439 | 4624 | GCCCAATCTAATCAGACGCTGATGAGTGCACAG | 9213 | AQSNQTLMSAQ | 13802 | SNQTLMS | 0.133656 | -0.2268 |
| GS1407 | 4625 | GCCCAAAGAAAACCCGGCAGCACCAGCGCACAG | 9214 | AQRNPGSTSAQ | 13803 | RNPGSTS | 0.133603 | -0.05879 |
| GS1409 | 4626 | GCCCAACGTATGGCTCAGGGTTATAGTGCACAG | 9215 | AQRMAQGYSAQ | 13804 | RMAQGYS | 0.133569 | -0.1747 |
| SyS2441 | 4627 | GCCCAACAGGTTATGCGTCAGAGTAGTGCACAG | 9216 | AQQVMRQSSAQ | 13805 | QVMRQSS | 0.133377 | -0.22649 |
| SyS2442 | 4628 | GCCCAAAAGAATACGACGGTTAGTGATGCACAG | 9217 | AQKNTTVSDAQ | 13806 | KNTTVSD | 0.133377 | -0.22649 |
| SyS2443 | 4629 | GCCCAAACGGCAAAACCGCAGAGACGCACAG | 9218 | AQTGKTARDAQ | 13807 | TGKTARD | 0.133287 | -0.17382 |
| SyS2444 | 4630 | GCCCAAATCCTCAGAAACCCTCACGAAGCACAG | 9219 | AQILRTLTEAQ | 13808 | ILRTLTE | 0.133244 | -0.12829 |
| GS1411 | 4631 | GCCCAAAGACTCGACAACGCGGCATGGCACAG | 9220 | AQRLDNAGMAQ | 13809 | RLDNAGM | 0.133189 | -0.08971 |
| SyS2445 | 4632 | GCCCAAAGTGGTACTGGTAGGCAGCAGGCACAG | 9221 | AQSGTGRQQAQ | 13810 | SGTGRQQ | 0.133033 | -0.1101 |
| SyS2447 | 4633 | GCCCAACTCGGCAAAGACACCTTCAGCGCACAG | 9222 | AQLGKDTFSAQ | 13811 | LGKDTFS | 0.132869 | -0.1242 |
| GS1413 | 4634 | GCCCAACGGTATGATGGGTCTGTGGCTGCACAG | 9223 | AQRYDGSVAAQ | 13812 | RYDGSVA | 0.132847 | -0.13504 |
| SyS2448 | 4635 | GCCCAGGCCCACTACCCGCCAGCACCGCACAG | 9224 | AQAHYPASTAQ | 13813 | AHYPAST | 0.132836 | -0.14405 |
| SyS2449 | 4636 | GCCCAAAAAGCAACGGCAGCCCCTCGCACAG | 9225 | AQKSNGSPLAQ | 13814 | KSNGSPL | 0.132749 | -0.09137 |
| SyS2450 | 4637 | GCCCAAAGAGACCTGTCTTCTCACCAAAGCACAG | 9226 | AQRDLVLTKAQ | 13815 | RDLVLTK | 0.132711 | -0.13986 |
| SyS2451 | 4638 | GCCCAACCAGCAACCCGCAACATGGCACAG | 9227 | AQTSNPGNMAQ | 13816 | TSNPGNM | 0.132642 | -0.18405 |
| GS1414 | 4639 | GCCCAATTGCCGAGGCCGAGTAATACGGCACAG | 9228 | AQLPRPSNTAQ | 13817 | LPRPSNT | 0.132631 | -0.16573 |
| SyS2452 | 4640 | GCCCAAACCGGCGGCGGCAGCTTCAGCGCACAG | 9229 | AQTGGGSFSAQ | 13818 | TGGGSFS | 0.132596 | 0.004539 |
| SyS2454 | 4641 | GCCCAATACCCCAACAAAGAACTCAGCGCACAG | 9230 | AQYPNKELSAQ | 13819 | YPNKELS | 0.132195 | -0.06134 |
| SyS2456 | 4642 | GCCCAAACGATGGTGCATCAGGAGTCTGCACAG | 9231 | AQTMVHQESAQ | 13820 | TMVHQES | 0.132057 | -0.01475 |
| SyS2457 | 4643 | GCCCAAGTTAATAGTAATAATTCGATGGCACAG | 9232 | AQVNSNNSMAQ | 13821 | VNSNNSM | 0.132035 | -0.11468 |
| GS1416 | 4644 | GCCCAAAACGGCGTCACGTCACCCCCGCACAG | 9233 | AQNGVHVTPAQ | 13822 | NGVHVTP | 0.132015 | -0.04532 |
| SyS2458 | 4645 | GCCCAAGCCAAATACCTCAACAGCAACGCACAG | 9234 | AQAKYLNSNAQ | 13823 | AKYLNSN | 0.131997 | -0.13316 |
| SyS2460 | 4646 | GCCCAAGGTATGACGAAGAATGGTGGGGCACAG | 9235 | AQGMTKNGGAQ | 13824 | GMTKNGG | 0.131765 | 0.019619 |
| SyS2461 | 4647 | GCCCAACGGCGCGTGATGAGGGTATGGCACAG | 9236 | AQRARDEGMAQ | 13825 | RARDEGM | 0.131684 | -0.09036 |
| GS1418 | 4648 | GCCCAAGTCCCAGCCCCGGCGCCACCGCACAG | 9237 | AQVPSPGATAQ | 13826 | VPSPGAT | 0.131628 | -0.18188 |
| GS1419 | 4649 | GCCCAAAAAACCCAACTCGGCCAAATGGCACAG | 9238 | AQKTQLGQMAQ | 13827 | KTQLGQM | 0.131628 | -0.18188 |

FIG. 33 (Continued)

| | | | | | | |
|---|---|---|---|---|---|---|
| SyS2462 | 4650 | GCCCAATCTACTTCGACGATTCAGCGGCACAG | 9239 AQSTSTIQPAQ | 13828 STSTIQP | 0.131508 | -0.12707 |
| SyS2463 | 4651 | GCCCAACGTAAGGAGAATGCTAGTTATGCACAG | 9240 AQRKENASYAQ | 13829 RKENASY | 0.131186 | -0.19739 |
| SyS2464 | 4652 | GCCCAACTGACGAATCATGGGAATGTTGCACAG | 9241 AQLTNHGNVAQ | 13830 LTNHGNV | 0.131105 | -0.11468 |
| SyS2465 | 4653 | GCCCAACTCGACAACGTCCACAGCCACGCACAG | 9242 AQLDNVHSHAQ | 13831 LDNVHSH | 0.131105 | -0.20339 |
| SyS2466 | 4654 | GCCCAACCCACCATGGCCGTCACCCCGCACAG | 9243 AQPTMAVTPAQ | 13832 PTMAVTP | 0.131105 | -0.22557 |
| SyS2467 | 4655 | GCCCAAAAGCCTGAGCGTACTGAGGCGGCACAG | 9244 AQKPERTEAAQ | 13833 KPERTEA | 0.131079 | -0.17314 |
| GS1420 | 4656 | GCCCAAACCGGCGACAGAAAAGGGGCGCACAG | 9245 AQTGDRKSGAQ | 13834 TGDRKSG | 0.131063 | -0.16623 |
| GS1421 | 4657 | GCCCAAGCTAAGCATACTTCGTTTCCTGCACAG | 9246 AQAKHTSFPAQ | 13835 AKHTSFP | 0.131036 | -0.171 |
| GS1422 | 4658 | GCCCAAGGGTTGGTTGCGTCGTTGGGGGCACAG | 9247 AQGLVASLGAQ | 13836 GLVASLG | 0.131036 | -0.171 |
| SyS2468 | 4659 | GCCCAATCTGTTCCTAGGTCGGAGTTGGCACAG | 9248 AQSVPRSELAQ | 13837 SVPRSEL | 0.130804 | -0.11824 |
| GS1425 | 4660 | GCCCAAGCTGAGAGGATTGGTATGGGGTGCACAG | 9249 AQAERIGMGAQ | 13838 AERIGMG | 0.130715 | -0.04864 |
| SyP69 | 4661 | GCCCAATCTCTGGTTCGGCAGTCTGATGCACAG | 9250 AQSLVRQSDAQ | 13839 SLVRQSD | 0.130711 | -0.04411 |
| SyS2470 | 4662 | GCCCAACACGTCAAAGCCAACCCATCGCACAG | 9251 AQHVKANPIAQ | 13840 HVKANPI | 0.130681 | -0.20093 |
| SyS2473 | 4663 | GCCCAAGTCGTCGACACCCTCAAAAACGCACAG | 9252 AQVVDTLKNAQ | 13841 VVDTLKN | 0.130632 | -0.11957 |
| SyS2474 | 4664 | GCCCAACAGATTCCTTATAATTCGTCGGCACAG | 9253 AQQIPYNSSAQ | 13842 QIPYNSS | 0.130617 | 0.06558 |
| SyS2475 | 4665 | GCCCAAGCTGATCATTCTATGCATGTTGCACAG | 9254 AQADHSMHVAQ | 13843 ADHSMHV | 0.130612 | -0.2231 |
| SyS2476 | 4666 | GCCCAAAACCACGTCACCGCCCAAGCGCACAG | 9255 AQNHVTAQAAQ | 13844 NHVTAQA | 0.130454 | -0.0399 |
| GS1429 | 4667 | GCCCAACCAACTTCACCAAAGCGGCGCACAG | 9256 AQTNFTKSGAQ | 13845 TNFTKSG | 0.130388 | 0.51224 |
| SyS2477 | 4668 | GCCCAATATGGTCATTCGATGACTAATGCACAG | 9257 AQYGHSMTNAQ | 13846 YGHSMTN | 0.130368 | -0.17678 |
| SyS2479 | 4669 | GCCCAAATGAGACCGGACCTCAAAACGCACAG | 9258 AQMRPDLKTAQ | 13847 MRPDLKT | 0.130368 | -0.23133 |
| SyS2480 | 4670 | GCCCAAGGCCCGGCACCAGCTTCAAAGCACAG | 9259 AQGPGTSFKAQ | 13848 GPGTSFK | 0.130368 | -0.23133 |
| SyS2481 | 4671 | GCCCAAGTTCTACGACTCCTGGGCTTGCACAG | 9260 AQSSTTPGLAQ | 13849 SSTTPGL | 0.130295 | -0.09714 |
| SS170 | 4672 | GCCCAATCGGTGAAGGCTAATCCTACTGCACAG | 9261 AQSVKANPTAQ | 13850 SVKANPT | 0.130019 | -0.37951 |
| GS1430 | 4673 | GCCCAAACCCCACCGTCTTCACCCCGCACAG | 9262 AQTPTVFTPAQ | 13851 TPTVFTP | 0.129999 | -0.15574 |
| GP193 | 4674 | GCCCAAATGCTGCCTAGTCCTGGGTCGGCACAG | 9263 AQMLPSPGSAQ | 13852 MLPSPGS | 0.129923 | -0.06982 |
| GS1432 | 4675 | GCCCAAAACTTCGACTACGGCAAACCCGCACAG | 9264 AQNFDYAKPAQ | 13853 NFDYAKP | 0.129793 | -0.15945 |
| SyS2482 | 4676 | GCCCAAACCCTCAACACCAGCCCCATGGCACAG | 9265 AQTLNTSPMAQ | 13854 TLNTSPM | 0.129754 | -0.11431 |
| SyS2483 | 4677 | GCCCAAAACCAACAGCCCCAAAAGCACCGCACAG | 9266 AQTNSPKSTAQ | 13855 TNSPKST | 0.129681 | -0.17136 |
| SyS2484 | 4678 | GCCCAAGTCACCCCGGCAGATACAGGCACAG | 9267 AQVTPGRYSAQ | 13856 VTPGRYS | 0.129681 | -0.17136 |
| SyS2485 | 4679 | GCCCAAACCAGAGTCAGCAACCTGACGCACAG | 9268 AQTRVSNLDAQ | 13857 TRVSNLD | 0.129667 | 0.015982 |
| GS1433 | 4680 | GCCCAAAGTCATGGTCCTGATAGGACGGCACAG | 9269 AQSHGPDRTAQ | 13858 SHGPDRT | 0.129608 | -0.18278 |
| SyS2488 | 4681 | GCCCAAAATATTCATACGGCTACGACTGCACAG | 9270 AQNIHTATTAQ | 13859 NIHTATT | 0.12948 | -0.21072 |

FIG. 33 (Continued)

| ID | No. | Sequence | No. | Sequence | No. | Pep | Val1 | Val2 |
|---|---|---|---|---|---|---|---|---|
| SyS2490 | 4682 | GCCCAATTGCTTCCGCAGACTACGCTTGCACAG | 9271 | AQLLPQTTLAQ | 13860 | LLPQTTL | 0.129383 | -0.05215 |
| SyS2491 | 4683 | GCCCAACGTACTAATGATACTTCGGCGGCACAG | 9272 | AQRTNDTSAAQ | 13861 | RTNDTSA | 0.12914 | -0.15534 |
| GS1435 | 4684 | GCCCAAGAAAGAAACGGGCAGCCACGAAGCACAG | 9273 | AQERNGSHEAQ | 13862 | ERNGSHE | 0.129106 | -0.14524 |
| GS1436 | 4685 | GCCCAAAACACCAGAGAAGCCTTCATCGCACAG | 9274 | AQNTREAFIAQ | 13863 | NTREAFI | 0.129068 | -0.15676 |
| GS1437 | 4686 | GCCCAAGTCGGCCAATACGCAGCCCGCACAG | 9275 | AQVGQYASPAQ | 13864 | VGQYASP | 0.129006 | 0.012421 |
| GS1438 | 4687 | GCCCAAGTCGCGAAACCGGCAGAACCGCGCACAG | 9276 | AQVAETGRTAQ | 13865 | VAETGRT | 0.128986 | -0.17672 |
| GS1439 | 4688 | GCCCAAATGAGCGCCGGGCAGCAACAGCGCACAG | 9277 | AQMSAGSNSAQ | 13866 | MSAGSNS | 0.128951 | -0.17381 |
| SyS2492 | 4689 | GCCCAACTCAGCCCCAAAAACGCCCAAGCACAG | 9278 | AQLSPKNAQAQ | 13867 | LSPKNAQ | 0.128916 | -0.17799 |
| SyS2497 | 4690 | GCCCAAGCGGGCACCAGCCAACTCCCGCACAG | 9279 | AQSGTSQLPAQ | 13868 | SGTSQLP | 0.128594 | -0.19969 |
| SS171 | 4691 | GCCCAAAGACTCCAAGACACAAACCCCAAGCACAG | 9280 | AQRLQDKPQAQ | 13869 | RLQDKPQ | 0.12854 | -0.41153 |
| SyS2498 | 4692 | GCCCAAAACGTCCCCAGAAGCAGCGTCGCACAG | 9281 | AQNVPRSSVAQ | 13870 | NVPRSSV | 0.128415 | -0.15738 |
| SyS2500 | 4693 | GCCCAAGCCCTCGGCAGCCCCAGACCCGCACAG | 9282 | AQALGSPRPAQ | 13871 | ALGSPRP | 0.128407 | -0.13686 |
| SyS2501 | 4694 | GCCCAAGCGAAGGAGCCTATGAGTGCGGCACAG | 9283 | AQAKEPMSAAQ | 13872 | AKEPMSA | 0.128223 | -0.19723 |
| GS1441 | 4695 | GCCCAAGCCGTCAGCGGCGCCCACGCACAG | 9284 | AQAVSGAAHAQ | 13873 | AVSGAAH | 0.128127 | -0.15781 |
| SyS2502 | 4696 | GCCCAATACAACAACACAAAGCGCCGCCGCACAG | 9285 | AQYNNKSAAAQ | 13874 | YNNKSAA | 0.12811 | -0.15904 |
| SyS2503 | 4697 | GCCCAACAAGTCAGCGTCAGAAACCTCGCACAG | 9286 | AQQVSVRNLAQ | 13875 | QVSVRNL | 0.12807 | -0.18769 |
| SyS2504 | 4698 | GCCCAAAGGGGTACTCATCCTCCGGCTGCACAG | 9287 | AQKGTHPPAAQ | 13876 | KGTHPPA | 0.12807 | -0.18769 |
| GS1442 | 4699 | GCCCAACAGTATCCTAATAGTAAGGTTGCACAG | 9288 | AQQYPNSKVAQ | 13877 | QYPNSKV | 0.128026 | -0.16623 |
| SyS2505 | 4700 | GCCCAACAACATAATGCTTCGAATTCTGGGGCACAG | 9289 | AQHNASNSGAQ | 13878 | HNASNSG | 0.127942 | -0.14283 |
| SyS2507 | 4701 | GCCCAAGAACTCAACCCAAATTCATCGCACAG | 9290 | AQELNPKFIAQ | 13879 | ELNPKFI | 0.127896 | -0.19981 |
| SyS2508 | 4702 | GCCCAATCGCGTGAGACTCCTGGGACTGCACAG | 9291 | AQSRETPGTAQ | 13880 | SRETPGT | 0.127851 | 0.095109 |
| SyS2509 | 4703 | GCCCAAAATTTAAGCCGCAGAATGAGGCACAG | 9292 | AQNFKPQNEAQ | 13881 | NFKPQNE | 0.127738 | -0.18121 |
| SyS2510 | 4704 | GCCCAAGCTATGACTTCGGGGGTCGGCGGCACAG | 9293 | AQAMTSGSAAQ | 13882 | AMTSGSA | 0.127637 | -0.16708 |
| GS1443 | 4705 | GCCCAAAAGGATCCGAGGAGTACGTTGGCACAG | 9294 | AQKDPRSTLAQ | 13883 | KDPRSTL | 0.127399 | -0.16842 |
| GS1444 | 4706 | GCCCAAGACAGAGAGGCACCAGAACCGTCGCACAG | 9295 | AQDRGTRTVAQ | 13884 | DRGTRTV | 0.127399 | -0.16842 |
| GS1445 | 4707 | GCCCAAAGCCTCGCCAGAAACAACGTCGCACAG | 9296 | AQSLARNNVAQ | 13885 | SLARNNV | 0.127397 | -0.15097 |
| SyS2511 | 4708 | GCCCAAGCCATCAGATTCAACGAACCCGCACAG | 9297 | AQAIRFNEPAQ | 13886 | AIRFNEP | 0.127317 | -0.23012 |
| SyS2512 | 4709 | GCCCAACAACACAGATTTGAGGGAGCCGGTGGCACAG | 9298 | AQQHHIATPAQ | 13887 | QHHIATP | 0.127284 | 0.014485 |
| GS1447 | 4710 | GCCCAACAACTGTTGTTAATAAGCTTAGTGCACAG | 9299 | AQQILREPVAQ | 13888 | QILREPV | 0.127158 | -0.17291 |
| GS1448 | 4711 | GCCCAAACTGTTGTTAATAAGCTTAGTGCACAG | 9300 | AQTVVNKLSAQ | 13889 | TVVNKLS | 0.127158 | -0.17291 |
| SyS2513 | 4712 | GCCCAAAGAGAGACAACACCACCAAATTCGCACAG | 9301 | AQRDNTTKFAQ | 13890 | RDNTTKF | 0.127154 | 0.054334 |
| SyS2515 | 4713 | GCCCAAAGCCTCCTCAGCACCCCTCGGCGCACAG | 9302 | AQSLLSTLGAQ | 13891 | SLLSTLG | 0.127046 | -0.22803 |

FIG. 33 (Continued)

| | | | | | | | | |
|---|---|---|---|---|---|---|---|---|
| SyS2516 | 4714 | GCCCAAGGCCAAGTCCCGTCACCAGAGCACAG | 9303 | AQGQVPVTRAQ | 13892 | GQVPVTR | 0.126817 | -0.1319 |
| SyS2517 | 4715 | GCCCAAATCCAAAACAGCCTCATGCCGCACAG | 9304 | AQIQNSLMPAQ | 13893 | IQNSLMP | 0.126654 | -0.0084 |
| GP194 | 4716 | GCCCAACAGCATAATACGCAGAATACTGCACAG | 9305 | AQQHNTQNTAQ | 13894 | QHNTQNT | 0.126648 | -0.07218 |
| SyS2518 | 4717 | GCCCAAGTCGGCCCCACCATGACCCACGCACAG | 9306 | AQVGPTMTHAQ | 13895 | VGPTMTH | 0.126491 | -0.15781 |
| GS1450 | 4718 | GCCCAAACCAACGTCACCATGGCCAGAGCACAG | 9307 | AQTNVTMARAQ | 13896 | TNVTMAR | 0.126427 | -0.17481 |
| GS1451 | 4719 | GCCCAAAGGCGCCCACTTCACCGGCACCGCACAG | 9308 | AQSAHFTGTAQ | 13897 | SAHFTGT | 0.126427 | -0.17481 |
| GS1453 | 4720 | GCCCAAAGATACAGCGTCAACGACAAAGCACAG | 9309 | AQRYSVNDKAQ | 13898 | RYSVNDK | 0.126337 | -0.17201 |
| SyS2519 | 4721 | GCCCAAGTCTACAAAAGCGCCGACCCCGCACAG | 9310 | AQVYKSADPAQ | 13899 | VYKSADP | 0.126276 | -0.13556 |
| SyS2521 | 4722 | GCCCAAGTCCACACCGCCCTCCCATGGCACAG | 9311 | AQVHTALPMAQ | 13900 | VHTALPM | 0.126124 | -0.17435 |
| SyS2522 | 4723 | GCCCAAACTATTAGTAGTGCTGGTATTGCACAG | 9312 | AQTISSAGIAQ | 13901 | TISSAGI | 0.126033 | -0.07473 |
| GS1455 | 4724 | GCCCAAAGGTTGCCTTCGACTCAGGCGGCACAG | 9313 | AQRLPSTQAAQ | 13902 | RLPSTQA | 0.126016 | -0.12848 |
| SyS2523 | 4725 | GCCCAAAGCCAAGAAAGAGCCATGAGCGCACAG | 9314 | AQSQERAMSAQ | 13903 | SQERAMS | 0.125872 | -0.20709 |
| GS1456 | 4726 | GCCCAAATGAATCAGCTTGCGAATCCTGCACAG | 9315 | AQMNQLANPAQ | 13904 | MNQLANP | 0.125837 | -0.12712 |
| SyS2524 | 4727 | GCCCAATTTGGGGCGACTAGTGGGCAGGCACAG | 9316 | AQFGATSGQAQ | 13905 | FGATSGQ | 0.12559 | -0.11323 |
| SyS2525 | 4728 | GCCCAAACGCTTCTTCGTTCTCCTGCTGCACAG | 9317 | AQTLLRSPAAQ | 13906 | TLLRSPA | 0.125488 | -0.14526 |
| GS1457 | 4729 | GCCCAACTTAGGTCGAATGTGTCGAATGCACAG | 9318 | AQLRSNVSNAQ | 13907 | LRSNVSN | 0.125352 | -0.12087 |
| GS1458 | 4730 | GCCCAAATCGCCAACAGCCAAGCGCCGCACAG | 9319 | AQIANSQAAAQ | 13908 | IANSQAA | 0.125352 | -0.10113 |
| TS177 | 4731 | GCCCAATCTAATCGTATTGTGCCTGTTGCACAG | 9320 | AQSNRIVPVAQ | 13909 | SNRIVPV | 0.125315 | -0.25713 |
| GP197 | 4732 | GCCCAATCTCCGAATCCTTCTAATGCGGCACAG | 9321 | AQSPNPSNAAQ | 13910 | SPNPSNA | 0.125295 | -0.0703 |
| SyS2526 | 4733 | GCCCAAAAATGGGACAGCGCCAACGAAGCACAG | 9322 | AQKWDSANEAQ | 13911 | KWDSANE | 0.125284 | -0.10361 |
| SyS2527 | 4734 | GCCCAAGCTTCGTCGTCAGGGTGAGGCTGCACAG | 9323 | AQASRQGEAAQ | 13912 | ASRQGEA | 0.125259 | -0.10404 |
| SyS2528 | 4735 | GCCCAAGTTCCTGGGAATAGTCCTCATGCACAG | 9324 | AQVPGNSPHAQ | 13913 | VPGNSPH | 0.125198 | -0.15738 |
| SyS2529 | 4736 | GCCCAAAGCGCCACCACCAACAGCGTCGCACAG | 9325 | AQSATTNSVAQ | 13914 | SATTNSV | 0.125189 | 0.067512 |
| SyS2530 | 4737 | GCCCAACACATCGGCGCCAGACAAGTCGCACAG | 9326 | AQHIGARQVAQ | 13915 | HIGARQV | 0.125155 | -0.15904 |
| GS1462 | 4738 | GCCCAACTTACGGATCGTTCTCCTATGGCACAG | 9327 | AQLTDRSPMAQ | 13916 | LTDRSPM | 0.125019 | -0.13728 |
| SyS2531 | 4739 | GCCCAAAATCCGACGCAGGCTGTTTTGGCACAG | 9328 | AQNPTQAVLAQ | 13917 | NPTQAVL | 0.124871 | -0.21679 |
| GS1464 | 4740 | GCCCAAACCAAAAACGAAACCGGCACCGCACAG | 9329 | AQTKNETGTAQ | 13918 | TKNETGT | 0.124832 | -0.05823 |
| SyS2533 | 4741 | GCCCAACTCACCGCCACCCTCACCAGCGCACAG | 9330 | AQLTATLTSAQ | 13919 | LTATLTS | 0.124607 | -0.2268 |
| SyS2535 | 4742 | GCCCAATATAAGGCTAGTTATGCTGCGGGCACAG | 9331 | AQYKASYAAAQ | 13920 | YKASYAA | 0.124548 | -0.07814 |
| SyS2536 | 4743 | GCCCAAACTCTTCCTGATAAGGTGTCGGCACAG | 9332 | AQTLPDKVSAQ | 13921 | TLPDKVS | 0.124499 | -0.18163 |
| SyS2537 | 4744 | GCCCAAAATAATCATATTCCTTGGCTGCACAG | 9333 | AQNNHIPLAAQ | 13922 | NNHIPLA | 0.12448 | -0.10087 |
| SyS2538 | 4745 | GCCCAATCTAATCTGACGGTCTAATCCTGCACAG | 9334 | AQSNLTSNPAQ | 13923 | SNLTSNP | 0.124443 | 0.020734 |

FIG. 33 (Continued)

| | | | | | | | | |
|---|---|---|---|---|---|---|---|---|
| SS177 | 4746 | GCCCAACAACAACAAAACGACAGAAACGCCGCACAG | 9335 | AQQQNDRNAAQ | 13924 | QQNDRNA | 0.124316 | -0.33917 |
| SyS2540 | 4747 | GCCCAAATGCTCAGCACCAACAGAAGCGCACAG | 9336 | AQMLSTNRSAQ | 13925 | MLSTNRS | 0.124294 | -0.18769 |
| SyS2541 | 4748 | GCCCAAATCACCAGCGCCACCCTCAGCGCACAG | 9337 | AQITSATLSAQ | 13926 | ITSATLS | 0.124242 | -0.22434 |
| GS1465 | 4749 | GCCCAAGTCGACGCCATGCAAAGACCCGCACAG | 9338 | AQVDAMQRPAQ | 13927 | VDAMQRP | 0.124217 | -0.16051 |
| GS1466 | 4750 | GCCCAAAGAGAAGCCAACTACGCCAGCGCACAG | 9339 | AQREANYASAQ | 13928 | REANYAS | 0.124095 | -0.18368 |
| GS1467 | 4751 | GCCCAACGTAGTAATAATGCTGATCTGGCACAG | 9340 | AQRSNNADLAQ | 13929 | RSNNADL | 0.12408 | -0.18054 |
| SyS2542 | 4752 | GCCCAAGGCCTCGACAAAATGGGCAGCGCACAG | 9341 | AQGLDKMGSAQ | 13930 | GLDKMGS | 0.124074 | -0.00826 |
| GS1468 | 4753 | GCCCAATTCACCACCAGCCACGCCCCGCACAG | 9342 | AQFTTSHAPAQ | 13931 | FTTSHAP | 0.123988 | -0.13761 |
| GS1469 | 4754 | GCCCAAGACAAAAGCGTCAAATTCGCCGCACAG | 9343 | AQDKSVKFAAQ | 13932 | DKSVKFA | 0.123988 | -0.13761 |
| SyS2544 | 4755 | GCCCAACACGCCAAAAAAGAACTCCAAGCACAG | 9344 | AQHAKKELQAQ | 13933 | HAKKELQ | 0.123802 | -0.22042 |
| SyS2546 | 4756 | GCCCAAGTCGAAAGCAAAGGCGCCAGCGCACAG | 9345 | AQVESKGASAQ | 13934 | VESKGAS | 0.123704 | 0.11358 |
| GS1470 | 4757 | GCCCAAAAAACCGCCCCCAGCATGGGCGCACAG | 9346 | AQKTAPSMGAQ | 13935 | KTAPSMG | 0.123698 | -0.14537 |
| GS1471 | 4758 | GCCCAAGGCCTCAGAACCGACAACAGAGCACAG | 9347 | AQGLRTDNRAQ | 13936 | GLRTDNR | 0.123641 | -0.1476 |
| SyS2548 | 4759 | GCCCAACGTATTGCGGGGATAATCCTGCACAG | 9348 | AQRIAGNNPAQ | 13937 | RIAGNNP | 0.123582 | -0.1295 |
| GS1472 | 4760 | GCCCAAAAAGACCCCCACCAGTCGTCGCACAG | 9349 | AQKDPHQVVAQ | 13938 | KDPHQVV | 0.123524 | -0.16241 |
| SyS2549 | 4761 | GCCCAAGAGCAGACTCCGCATAATTCGGCACAG | 9350 | AQEQTPHNSAQ | 13939 | EQTPHNS | 0.123505 | -0.22649 |
| SyS2550 | 4762 | GCCCAAGGGCTGGATAAGGGGAATTGGGCACAG | 9351 | AQGLDKGNWAQ | 13940 | GLDKGNW | 0.12349 | -0.08183 |
| SyS2551 | 4763 | GCCCAACCTTCGAATGGGAATTATTCGGCACAG | 9352 | AQPSNGNYSAQ | 13941 | PSNGNYS | 0.123474 | -0.17072 |
| SyS2552 | 4764 | GCCCAAGGCAGACCCGGCATCGGCAGCGCACAG | 9353 | AQGRPGIGSAQ | 13942 | GRPGIGS | 0.123474 | -0.17072 |
| SyS2553 | 4765 | GCCCAAAGGACGTCTCTGGGGTGTCGGCACAG | 9354 | AQRTSPGVSAQ | 13943 | RTSPGVS | 0.123431 | -0.18737 |
| SyS2554 | 4766 | GCCCAAGTCAACGCCAGCCTCATCAGCGCACAG | 9355 | AQVNASLISAQ | 13944 | VNASLIS | 0.123431 | -0.18737 |
| SyS2555 | 4767 | GCCCAAAAAACCAGCAACCTCCAAGCACAG | 9356 | AQKTSTNLQAQ | 13945 | KTSTNLQ | 0.1234 | -0.13556 |
| SyS2556 | 4768 | GCCCAAATGGATATGAAGCAGAATATGGCACAG | 9357 | AQMDMKQNMAAQ | 13946 | MDMKQNM | 0.123199 | -0.09592 |
| SyS2557 | 4769 | GCCCAAGATCTTAATGGGATTAATGTTGCACAG | 9358 | AQDLNGINVAQ | 13947 | DLNGINV | 0.12317 | -0.17988 |
| GS1475 | 4770 | GCCCAACGTACGCCTCCGAGTTTTGAGGCACAG | 9359 | AQRTPPSFEAQ | 13948 | RTPPSFE | 0.122987 | -0.12067 |
| SyS2559 | 4771 | GCCCAAGACTTCCACGACAGAAAAGGGCGCACAG | 9360 | AQDFHDRKGAQ | 13949 | DFHDRKG | 0.122909 | -0.13314 |
| GS1476 | 4772 | GCCCAACTCCACACCCAAACCGCACAG | 9361 | AQLHTQTQTAQ | 13950 | LHTQTQT | 0.122656 | -0.17381 |
| SyS2561 | 4773 | GCCCAACTCGGCGCCAGCAACAACGCCGCACAG | 9362 | AQLGASNNAAQ | 13951 | LGASNNA | 0.122644 | -0.09068 |
| SyS2562 | 4774 | GCCCAAATCGCCAGCGTCCCCAGAGACGCACAG | 9363 | AQIASVPRDAQ | 13952 | IASVPRD | 0.122568 | -0.22803 |
| SyS2563 | 4775 | GCCCAAAAAGCAAAGACGTCGGCGACGCACAG | 9364 | AQKAKDVGDAQ | 13953 | KAKDVGD | 0.122492 | -0.14548 |
| SyS2564 | 4776 | GCCCAAAGCGCCTTCGCCGCCAAACAAGCACAG | 9365 | AQSAFAAKQAQ | 13954 | SAFAAKQ | 0.122374 | -0.11616 |
| SyS2565 | 4777 | GCCCAAGTCTACCAAGGCCAACACCTCGCACAG | 9366 | AQVYQGQHLAQ | 13955 | VYQGQHL | 0.12237 | -0.19353 |

FIG. 33 (Continued)

| | | | | | | | | |
|---|---|---|---|---|---|---|---|---|
| SyS2567 | 4778 | GCCCAATACCTCCCGCGCCAGCAGCGCACAG | 9367 | AQYLPAASSAQ | 13956 | YLPAASS | 0.122028 | -0.15738 |
| SyS2568 | 4779 | GCCCAAAGCCCCAGCACCGTCATCAGCGCACAG | 9368 | AQSPSTVISAQ | 13957 | SPSTVIS | 0.121889 | -0.22164 |
| SyS2569 | 4780 | GCCCAAGGCACCAACAAACCCCGACGCACAG | 9369 | AQGTNKPPDAQ | 13958 | GTNKPPD | 0.121621 | -0.22064 |
| SyS2570 | 4781 | GCCCAAGAAAGCACCGGCGCCATCAGAGCACAG | 9370 | AQESTGAIRAQ | 13959 | ESTGAIR | 0.121621 | -0.22064 |
| SS180 | 4782 | GCCCAACTCATGAACACCATCGCCGCACAG | 9371 | AQLMNTTIAAQ | 13960 | LMNTTIA | 0.121608 | -0.32745 |
| GS1478 | 4783 | GCCCAAATGGCGGGTGTTGCTCAGCCTGCACAG | 9372 | AQMAGVAQPAQ | 13961 | MAGVAQP | 0.121335 | -0.18637 |
| SyS2573 | 4784 | GCCCAACGGCCGGAGCTTAAGCGTGAGGCACAG | 9373 | AQRPELKREAQ | 13962 | RPELKRE | 0.121162 | -0.20466 |
| SyS2574 | 4785 | GCCCAAAAAGCCCAAGACACCCCCACCGCACAG | 9374 | AQKAQDTPTAQ | 13963 | KAQDTPT | 0.121141 | -0.07163 |
| GS1480 | 4786 | GCCCAAAGCACCAACCACCAGCACCAGCGCACAG | 9375 | AQSTNHSTSAQ | 13964 | STNHSTS | 0.120864 | -0.17291 |
| GS1481 | 4787 | GCCCAATTCCCCAGAACCACCACCGACGCACAG | 9376 | AQFPRTTTDAQ | 13965 | FPRTTTD | 0.120827 | -0.11818 |
| SyS2576 | 4788 | GCCCAATCGCGTGCTCATAATTGGGATGCACAG | 9377 | AQSRAHNLDAQ | 13966 | SRAHNLD | 0.120812 | -0.23173 |
| SyS2577 | 4789 | GCCCAACGTACTATTCAGGAGGGGATTGCACAG | 9378 | AQRTIQEGIAQ | 13967 | RTIQEGI | 0.120812 | -0.23173 |
| GS1482 | 4790 | GCCCAAGGCGGCAAAAGCTTCGCCCAAGCACAG | 9379 | AQGGKSFAQAQ | 13968 | GGKSFAQ | 0.120713 | -0.18054 |
| SyS2578 | 4791 | GCCCAAGGCAGACCCAGCAGCACCCAAGCACAG | 9380 | AQGRPSSTQAQ | 13969 | GRPSSTQ | 0.120696 | -0.01043 |
| SyS2579 | 4792 | GCCCAAAACCCCTCAACACCAGCACCGCACAG | 9381 | AQNPLNTSTAQ | 13970 | NPLNTST | 0.120592 | -0.13772 |
| GS1483 | 4793 | GCCCAAGAAAACCTCAGCAACGGCAGAGCACAG | 9382 | AQENLSNGRAQ | 13971 | ENLSNGR | 0.120537 | -0.0855 |
| GP199 | 4794 | GCCCAAGAGAATACTATTCGGATGAGTGCACAG | 9383 | AQENTIRMSAQ | 13972 | ENTIRMS | 0.12044 | -0.07273 |
| SyS2582 | 4795 | GCCCAACCCCCAGAAGCATGCCCATGGCACAG | 9384 | AQPPRSMPMAQ | 13973 | PPRSMPM | 0.120421 | -0.16466 |
| SyS2583 | 4796 | GCCCAACTCCTCAGCAGCAACCTCCCGCACAG | 9385 | AQLLSSNLPAQ | 13974 | LLSSNLP | 0.120362 | -0.09427 |
| SyS2586 | 4797 | GCCCAAAGAGTCCAAAGCCTCAACGAAGCACAG | 9386 | AQRVQSLNEAQ | 13975 | RVQSLNE | 0.120212 | -0.06599 |
| SyS2588 | 4798 | GCCCAACCGAGGAGGGCGCAGGATGATGCACAG | 9387 | AQPRRAQDDAQ | 13976 | PRRAQDD | 0.119774 | -0.17678 |
| SyS2589 | 4799 | GCCCAACAAGGCAACGTCGGCGCGCACAG | 9388 | AQQGNVNVGAQ | 13977 | QGNVNVG | 0.11977 | -0.05616 |
| GS1484 | 4800 | GCCCAAAGCGGCGAAACCCTCAGAGGCGCACAG | 9389 | AQSGETLRGAQ | 13978 | SGETLRG | 0.119683 | -0.05248 |
| SyS2590 | 4801 | GCCCAACACGTCAGCCACAACACCGACGCACAG | 9390 | AQHVSHNTDAQ | 13979 | HVSHNTD | 0.119543 | -0.20093 |
| SyS2592 | 4802 | GCCCAATTTGGTGGGGGGTCGCTGGTTGCACAG | 9391 | AQFGGGSLVAQ | 13980 | FGGGSLV | 0.119216 | -0.10883 |
| SyS2593 | 4803 | GCCCAACCCAGCCTCAGAAGCGAAGGCGCACAG | 9392 | AQPSLRSEGAQ | 13981 | PSLRSEG | 0.119011 | -0.00524 |
| SS186 | 4804 | GCCCAAGTGCGTAGTGAGAATGGTGTGGCACAG | 9393 | AQVRSENGVAQ | 13982 | VRSENGV | 0.118723 | -0.33991 |
| SyS2594 | 4805 | GCCCAAACCCTCAAAGTCACCGGCGACGCACAG | 9394 | AQTLKVTGDAQ | 13983 | TLKVTGD | 0.118628 | -0.14041 |
| SyS2595 | 4806 | GCCCAAGTCCCCAAAGTCTACCTGGACGCACAG | 9395 | AQVPKVYLDAQ | 13984 | VPKVYLD | 0.118518 | -0.16766 |
| SyS2597 | 4807 | GCCCAAACTAGTATGCGGAATACGGAGGCACAG | 9396 | AQTSMRNTEAQ | 13985 | TSMRNTE | 0.118368 | -0.09192 |
| GS1486 | 4808 | GCCCAAGGCTACAGCAGCGGCAGCATGGCACAG | 9397 | AQGYSHGSMAQ | 13986 | GYSHGSM | 0.118333 | -0.05276 |
| SyS2598 | 4809 | GCCCAAGCCACCTTCCCGAAAAACAAGCACAG | 9398 | AQATFPEKQAQ | 13987 | ATFPEKQ | 0.118306 | -0.18614 |

FIG. 33 (Continued)

| | | | | | | | | |
|---|---|---|---|---|---|---|---|---|
| SyS2599 | 4810 | GCCCAAACCGGCCCCACCCAGGCACGGCACGCACAG | 9399 | AQTGPTHGTAQ | 13988 | TGPTHGT | 0.118306 | -0.18614 |
| GS1490 | 4811 | GCCCAAACCAACGACAGACACGCCCCGCACGCACAG | 9400 | AQTNDRHAPAQ | 13989 | TNDRHAP | 0.118185 | -0.1451 |
| SyS2600 | 4812 | GCCCAAGAGACACCTCGCGCAGCGTCGACGCACAG | 9401 | AQRHLASVDAQ | 13990 | RHLASVD | 0.118181 | -0.22803 |
| SyS2601 | 4813 | GCCCAAAATATGATTCAGCCTAGTAATGCACAG | 9402 | AQNMIQPSNAQ | 13991 | NMIQPSN | 0.118011 | -0.22406 |
| GS1492 | 4814 | GCCCAAAACCTCAGCGGCAGCCCGCGCACAG | 9403 | AQNLSGSPAAQ | 13992 | NLSGSPA | 0.117908 | -0.11652 |
| SyS2602 | 4815 | GCCCAACAAACGTCGGCCCCTCCCCGCACAG | 9404 | AQQTVGPLPAQ | 13993 | QTVGPLP | 0.117854 | -0.21557 |
| SyS2604 | 4816 | GCCCAAGTCGGCCACCTCAGCAGAGACGGCACAG | 9405 | AQVGHLSRDAQ | 13994 | VGHLSRD | 0.117641 | -0.03829 |
| SyS2605 | 4817 | GCCCAACAAAACTTCAACGCCGGCCACGCACAG | 9406 | AQQNFNAGHAQ | 13995 | QNFNAGH | 0.117535 | -0.0709 |
| GS1493 | 4818 | GCCCAACTCACCGGCGCGCCGCCAGAGTCGCACAG | 9407 | AQLTGAARVAQ | 13996 | LTGAARV | 0.117519 | -0.17919 |
| GS1494 | 4819 | GCCCAAGGGACTCGTCCGACTGCGACGGCACAG | 9408 | AQGTRPTATAQ | 13997 | GTRPTAT | 0.117449 | -0.15669 |
| SyS2607 | 4820 | GCCCAAATGCCCTCAGCGTCGCCCCGCACAG | 9409 | AQMPLSVAPAQ | 13998 | MPLSVAP | 0.116992 | -0.1392 |
| GS1495 | 4821 | GCCCAAGACAGAGTCCAACAATTCAGCGCACAG | 9410 | AQDRVQQFSAQ | 13999 | DRVQQFS | 0.11689 | -0.16146 |
| SyS2610 | 4822 | GCCCAAAACAACGACACCAGCACCAAAGCACAG | 9411 | AQNNDTSTKAQ | 14000 | NNDTSTK | 0.116554 | -0.23419 |
| SyS2611 | 4823 | GCCCAACCTTCGAAGAATACTCATATTGCACAG | 9412 | AQPSKNTHIAQ | 14001 | PSKNTHI | 0.116554 | -0.23419 |
| SyS2612 | 4824 | GCCCAACCTTTTAAGGCTGATGTTACGGCACAG | 9413 | AQPFKADVTAQ | 14002 | PFKADVT | 0.116512 | -0.20224 |
| SyS2613 | 4825 | GCCCAACCTAAGACTCCTACTTATGTGGCACAG | 9414 | AQPKTPTYVAQ | 14003 | PKTPTYV | 0.116298 | -0.20586 |
| SyS2614 | 4826 | GCCCAACTCACCAACATGACCACCCCGCACAG | 9415 | AQLTNMTTPAQ | 14004 | LTNMTTP | 0.116179 | 0.069335 |
| SyS2615 | 4827 | GCCCAAGGTAGTAAGGTGCATCTTTCTGCACAG | 9416 | AQGSKVHLSAQ | 14005 | GSKVHLS | 0.116046 | -0.22527 |
| SyS2616 | 4828 | GCCCAATCTATTCCGGGTTATAATAATGCACAG | 9417 | AQSIPGYNNAQ | 14006 | SIPGYNN | 0.116006 | -0.21679 |
| GS1497 | 4829 | GCCCAAATGAAAACCGCGAAAGCTACGCACAG | 9418 | AQMKTAESYAQ | 14007 | MKTAESY | 0.115832 | -0.1756 |
| SyS2618 | 4830 | GCCCAAAACGGCGACAGAGACTCCTCAACGCACAG | 9419 | AQNGDRLLNAQ | 14008 | NGDRLLN | 0.115647 | 0.03466 |
| SS189 | 4831 | GCCCAAGGCACCACCCCCAGCCTCGCACAG | 9420 | AQGTTHTSLAQ | 14009 | GTTHTSL | 0.11558 | -0.38281 |
| GS1499 | 4832 | GCCCAACTCGGCCCCAGCACCCAAAGCGCACAG | 9421 | AQLGPSTQSAQ | 14010 | LGPSTQS | 0.115388 | -0.14619 |
| SyS2619 | 4833 | GCCCAAATGAACGCCCTCACCGACAAAGCACAG | 9422 | AQMNALTDKAQ | 14011 | MNALTDK | 0.115181 | -0.16027 |
| SyS2620 | 4834 | GCCCAAAGCAGCAAAGAAATCAGCCTGCACAG | 9423 | AQSSKEISLAQ | 14012 | SSKEISL | 0.114992 | -0.07231 |
| SyS2621 | 4835 | GCCCAACTCGACAACGGCACCACCAGAGCACAG | 9424 | AQLDNGTTRAQ | 14013 | LDNGTTR | 0.114827 | -0.15288 |
| SyS2622 | 4836 | GCCCAACGTGTGAATTTAATTCGGATGCACAG | 9425 | AQRVNFNSDAQ | 14014 | RVNFNSD | 0.114822 | -0.20345 |
| SyS2623 | 4837 | GCCCAAAACATGCAAGCCATCAGCAACGCACAG | 9426 | AQNMQAISNAQ | 14015 | NMQAISN | 0.114811 | -0.08155 |
| SyS2624 | 4838 | GCCCAAAACAACACCAACCCCAGAAGCATCGCACAG | 9427 | AQNTNPRSIAQ | 14016 | NTNPRSI | 0.114545 | 0.005791 |
| SyS2625 | 4839 | GCCCAAAAAATCAACAGCAACAGCCCGCACAG | 9428 | AQKINSNSPAQ | 14017 | KINSNSP | 0.114472 | -0.07131 |
| GS1501 | 4840 | GCCCAAGTCCCCTCGGCAAAGCCAGCGCACAG | 9429 | AQVPLGKASAQ | 14018 | VPLGKAS | 0.114441 | -0.18637 |
| SyS2628 | 4841 | GCCCAACGGCTGAATCATAATTCGCCTGCACAG | 9430 | AQRLNHNSPAQ | 14019 | RLNHNSP | 0.11425 | -0.20216 |

FIG. 33 (Continued)

| | | | | | | | | |
|---|---|---|---|---|---|---|---|---|
| GS1502 | 4842 | GCCCAACAACTCAACACGTCCTCCCGCACAG | 9431 | AQQLNTVLPAQ | 14020 | QLNTVLP | 0.114132 | -0.18054 |
| SyS2630 | 4843 | GCCCAAGAGACAGCTTCGGCAAAAGCCTCGCACAG | 9432 | AQDSFGKSLAQ | 14021 | DSFGKSL | 0.114045 | -0.16643 |
| SyS2631 | 4844 | GCCCAAAAGCCGCCTAAGTTGGTTGATGCACAG | 9433 | AQKPPKLVDAQ | 14022 | KPPKLVD | 0.113972 | -0.17314 |
| GS1504 | 4845 | GCCCAACAAATCACCGTCGGCAAACCCGCACAG | 9434 | AQQITVGKPAQ | 14023 | QITVGKP | 0.113906 | -0.15574 |
| GS1505 | 4846 | GCCCAACAACACCCCACGGCCAACAAGCACAG | 9435 | AQQHPHGQQAQ | 14024 | QHPHGQQ | 0.113842 | -0.16214 |
| SyS2633 | 4847 | GCCCAAACTTCGACTAATATGGCGGCTGCACAG | 9436 | AQTSTNMAAAQ | 14025 | TSTNMAA | 0.113622 | -0.04892 |
| SyS2634 | 4848 | GCCCAACAAGGCGGCCTCGCCGTCGTCGCACAG | 9437 | AQQGGLAVVAQ | 14026 | QGGLAVV | 0.113622 | -0.15657 |
| GS1507 | 4849 | GCCCAAGGGAGGGGTAGTCTTCCGTTTGCACAG | 9438 | AQGRGSLPFAQ | 14027 | GRGSLPF | 0.113603 | -0.18816 |
| SyS2637 | 4850 | GCCCAAAGCGGCAAACCCGCAGCGAAGCACAG | 9439 | AQSGKPASEAQ | 14028 | SGKPASE | 0.113257 | -0.18245 |
| GS1508 | 4851 | GCCCAACGGTCTCGTTAGTGTGAATTCTGCACAG | 9440 | AQRSVSVNSAQ | 14029 | RSVSVNS | 0.11314 | -0.18245 |
| SyS2638 | 4852 | GCCCAAGACAGAGGGCGGCGTCGTCGCCGCACAG | 9441 | AQDRGGVVAAQ | 14030 | DRGGVVA | 0.113119 | -0.20466 |
| SyS2639 | 4853 | GCCCAAGGTCGTGAGACTGGTTTTCGGCACAG | 9442 | AQGRETGFSAQ | 14031 | GRETGFS | 0.112987 | -0.21315 |
| SyS2640 | 4854 | GCCCAACAGATTGTTCCGTCGAATCCGGCACAG | 9443 | AQQIVPSNPAQ | 14032 | QIVPSNP | 0.112987 | -0.21315 |
| SyP73 | 4855 | GCCCAAACGACGTTGGGTCATAGTAGTTATTCACAG | 9444 | AQTTLGHSYSQ | 14033 | TTLGHSY | 0.11285 | -0.03826 |
| SyS2642 | 4856 | GCCCAAAGCAGAGAATTCCAACTCGCCGCACAG | 9445 | AQSREFQLAAQ | 14034 | SREFQLA | 0.112786 | -0.15738 |
| GS1510 | 4857 | GCCCAAGGCAGAGACCACAACATCGGGCGCACAG | 9446 | AQGRDHNIGAQ | 14035 | GRDHNIG | 0.112781 | -0.17386 |
| TS179 | 4858 | GCCCAATCGAATAATTCTCGGCCGAATGCACAG | 9447 | AQSNNSRPNAQ | 14036 | SNNSRPN | 0.112766 | -0.14993 |
| SyS2643 | 4859 | GCCCAAAAAACCAAAGCAGGACCTCGCACAG | 9448 | AQKNQSSDLAQ | 14037 | KNQSSDL | 0.11276 | 0.0834 |
| SyS2644 | 4860 | GCCCAACCCAACGACAGAGCCCACGGCGCACAG | 9449 | AQPNDRAHGAQ | 14038 | PNDRAHG | 0.112742 | -0.19375 |
| SyS2645 | 4861 | GCCCAAGCTCTGACTAGGACTCAGTCTGCACAG | 9450 | AQALTRTQSAQ | 14039 | ALTRTQS | 0.11269 | -0.10041 |
| SyS2647 | 4862 | GCCCAAATGAGACGCCCCAGCGACAAAGCACAG | 9451 | AQMRPPSDKAQ | 14040 | MRPPSDK | 0.112599 | -0.20224 |
| TS180 | 4863 | GCCCAAACGAATTCGACTACGAAGTCGGCACAG | 9452 | AQTNSTTKSAQ | 14041 | TNSTTKS | 0.112569 | -0.20873 |
| SyS2648 | 4864 | GCCCAAGGCAGACACGGCATGACCGCCGCACAG | 9453 | AQGRHGMTAAQ | 14042 | GRHGMTA | 0.112548 | -0.08222 |
| GS1511 | 4865 | GCCCAAGTCAGCACATCAGCGCCGCACAG | 9454 | AQVSHISPAAQ | 14043 | VSHISPA | 0.112496 | -0.13761 |
| GS1512 | 4866 | GCCCAAAAGGTTACTAGTAATAGTTCGGCACAG | 9455 | AQKVTSNSSAQ | 14044 | KVTSNSS | 0.112386 | -0.16241 |
| SyS2649 | 4867 | GCCCAAATGTACGGCCCGGCGCAGCGCACAG | 9456 | AQMYGPGASAQ | 14045 | MYGPGAS | 0.112262 | -0.19133 |
| GS1514 | 4868 | GCCCAAGTCCTCAGAAGCAACACCCCGCACAG | 9457 | AQVLRSNTPAQ | 14046 | VLRSNTP | 0.112217 | -0.12617 |
| SyS2650 | 4869 | GCCCAAAATAGTAGTTCTAGTAATAAGGCACAG | 9458 | AQNSSSSNKAQ | 14047 | NSSSSNK | 0.112213 | -0.20989 |
| SyS2652 | 4870 | GCCCAAAGCACCGAAAAAAGCACCAGCGCACAG | 9459 | AQSTEKSTSAQ | 14048 | STEKSTS | 0.11211 | -0.0765 |
| GS1516 | 4871 | GCCCAAAACACCACCAAAGGCAACAAAGGCGCACAG | 9460 | AQNTNGNKGAQ | 14049 | NTNGNKG | 0.112014 | -0.18149 |
| GP205 | 4872 | GCCCAAATTACGACTAATCTGGGGGGCGGCACAG | 9461 | AQITTNLGAAQ | 14050 | ITTNLGA | 0.111979 | -0.07377 |
| GS1517 | 4873 | GCCCAAATCCAAAAACCCCAAAGCAGCGCACAG | 9462 | AQIQKPQSSAQ | 14051 | IQKPQSS | 0.111935 | -0.18457 |

FIG. 33 (Continued)

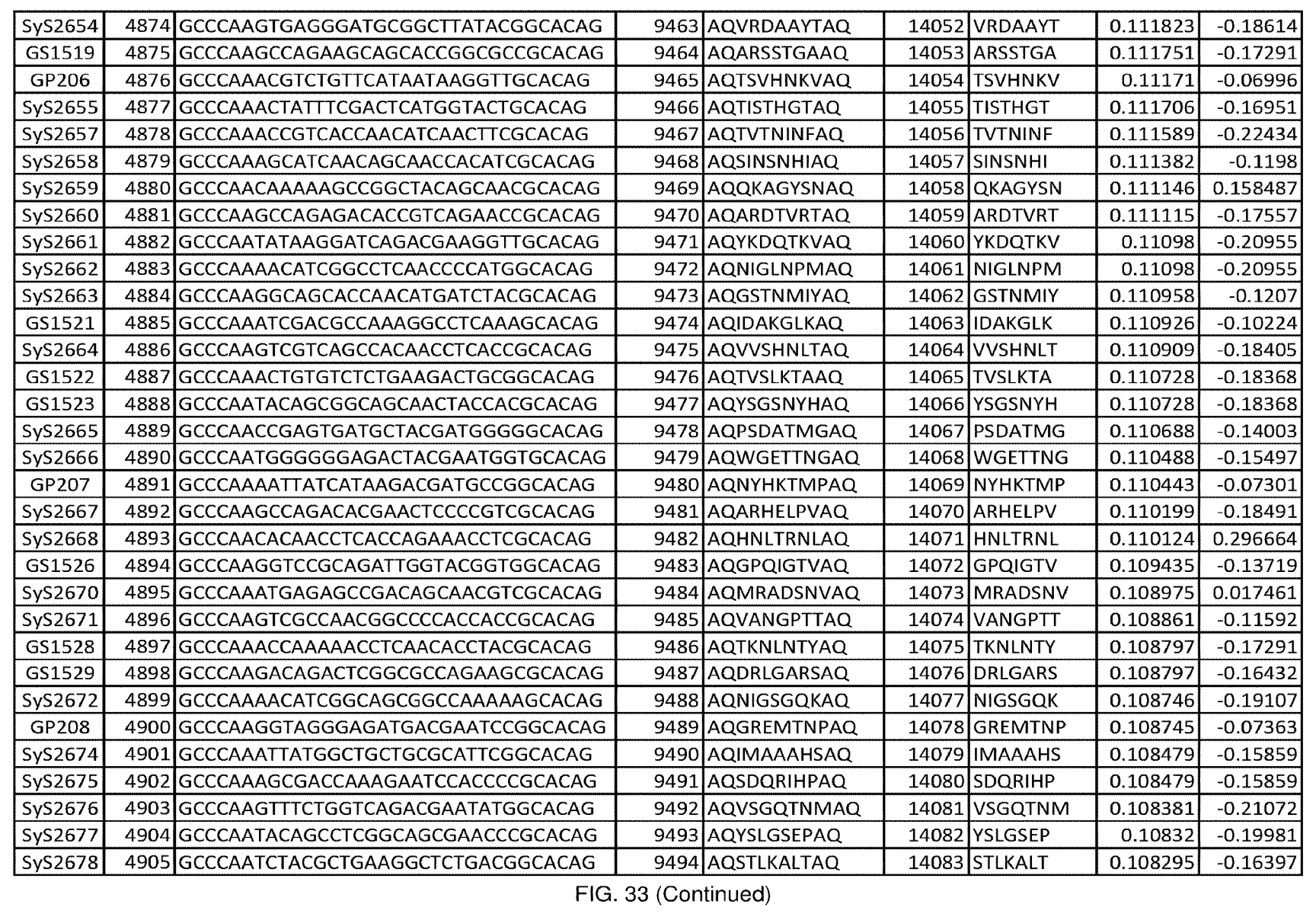

| | | | | | | | | |
|---|---|---|---|---|---|---|---|---|
| SyS2654 | 4874 | GCCCAAGTGAGGGATGCGGCTTATACGGCACAG | 9463 | AQVRDAAYTAQ | 14052 | VRDAAYT | 0.111823 | -0.18614 |
| GS1519 | 4875 | GCCCAAGCCAGAAGCAGCACCGGCGCCGCACAG | 9464 | AQARSSTGAAQ | 14053 | ARSSTGA | 0.111751 | -0.17291 |
| GP206 | 4876 | GCCCAAACGTCTGTTCATAATAAGGTTGCACAG | 9465 | AQTSVHNKVAQ | 14054 | TSVHNKV | 0.11171 | -0.06996 |
| SyS2655 | 4877 | GCCCAAACTATTCGACTCATGGTACTGCACAG | 9466 | AQTISTHGTAQ | 14055 | TISTHGT | 0.111706 | -0.16951 |
| SyS2657 | 4878 | GCCCAAACCGTCACCAACATCAACTTCGCACAG | 9467 | AQTVTNINFAQ | 14056 | TVTNINF | 0.111589 | -0.22434 |
| SyS2658 | 4879 | GCCCAAGCATCAACAGCAACCACATCGCACAG | 9468 | AQSINSNHIAQ | 14057 | SINSNHI | 0.111382 | -0.1198 |
| SyS2659 | 4880 | GCCCAACAAAAGCCGGCTACAGCAACGCACAG | 9469 | AQQKAGYSNAQ | 14058 | QKAGYSN | 0.111146 | 0.158487 |
| SyS2660 | 4881 | GCCCAAGCCAGAGACACCGTCAGAACCGCACAG | 9470 | AQARDTVRTAQ | 14059 | ARDTVRT | 0.111115 | -0.17557 |
| SyS2661 | 4882 | GCCCAATATAAGGATCAGACGAAGGTTGCACAG | 9471 | AQYKDQTKVAQ | 14060 | YKDQTKV | 0.11098 | -0.20955 |
| SyS2662 | 4883 | GCCCAAAAACATCGGCCTCAACCCCATGGCACAG | 9472 | AQNIGLNPMAQ | 14061 | NIGLNPM | 0.11098 | -0.20955 |
| SyS2663 | 4884 | GCCCAAGGCAGCACCAACATGATCTACGCACAG | 9473 | AQGSTNMIYAQ | 14062 | GSTNMIY | 0.110958 | -0.1207 |
| GS1521 | 4885 | GCCCAAATCGACGCCAAAGGCCTCAAAGCACAG | 9474 | AQIDAKGLKAQ | 14063 | IDAKGLK | 0.110926 | -0.10224 |
| SyS2664 | 4886 | GCCCAAGTCGTCAGCCACAACCTCACCGCACAG | 9475 | AQVVSHNLTAQ | 14064 | VVSHNLT | 0.110909 | -0.18405 |
| GS1522 | 4887 | GCCCAAACTGTGTCTCTGAAGACTGCGGCACAG | 9476 | AQTVSLKTAAQ | 14065 | TVSLKTA | 0.110728 | -0.18368 |
| GS1523 | 4888 | GCCCAATACAGCGGCAGCAACTACCACGCACAG | 9477 | AQYSGSNYHAQ | 14066 | YSGSNYH | 0.110728 | -0.18368 |
| SyS2665 | 4889 | GCCCAACCGAGTGATGCTACGATGGGGGCACAG | 9478 | AQPSDATMGAQ | 14067 | PSDATMG | 0.110688 | -0.14003 |
| SyS2666 | 4890 | GCCCAATGGGGGGAGACTACGAATGGTGCGGCACAG | 9479 | AQWGETTNGAQ | 14068 | WGETTNG | 0.110488 | -0.15497 |
| GP207 | 4891 | GCCCAAAATTATCATAAGACGATGCCGGCACAG | 9480 | AQNYHKTMPAQ | 14069 | NYHKTMP | 0.110443 | -0.07301 |
| SyS2667 | 4892 | GCCCAAGCCAGACACGAACTCCCGTCGCACAG | 9481 | AQARHELPVAQ | 14070 | ARHELPV | 0.110199 | -0.18491 |
| SyS2668 | 4893 | GCCCAACACACAACCTCACCAGAAACCTCGCACAG | 9482 | AQHNLTRNLAQ | 14071 | HNLTRNL | 0.110124 | 0.296664 |
| GS1526 | 4894 | GCCCAAGGTCCGCAGATTGGTACGGTGGCACAG | 9483 | AQGPQIGTVAQ | 14072 | GPQIGTV | 0.109435 | -0.13719 |
| SyS2670 | 4895 | GCCCAAATGAGAGCCGACAGCAAGTCGCACAG | 9484 | AQMRADSNVAQ | 14073 | MRADSNV | 0.108975 | 0.017461 |
| SyS2671 | 4896 | GCCCAAGTCGCCAACGCCCCACCACCGCACAG | 9485 | AQVANGPTTAQ | 14074 | VANGPTT | 0.108861 | -0.11592 |
| GS1528 | 4897 | GCCCAAACCAAAAACCTCAACACCTACGCACAG | 9486 | AQTKNLNTYAQ | 14075 | TKNLNTY | 0.108797 | -0.17291 |
| GS1529 | 4898 | GCCCAAGACAGACTCGGCGCGCCAGAAGCGCACAG | 9487 | AQDRLGARSAQ | 14076 | DRLGARS | 0.108797 | -0.16432 |
| SyS2672 | 4899 | GCCCAAAAACATCGGCAGCGGCCAAAAAGCACAG | 9488 | AQNIGSGQKAQ | 14077 | NIGSGQK | 0.108746 | -0.19107 |
| GP208 | 4900 | GCCCAAGGTAGGGAGATGACGAATCCGGCACAG | 9489 | AQGREMTNPAQ | 14078 | GREMTNP | 0.108745 | -0.07363 |
| SyS2674 | 4901 | GCCCAAATTATGGCTGCTGCGCATTCGGCACAG | 9490 | AQIMAAAHSAQ | 14079 | IMAAAHS | 0.108479 | -0.15859 |
| SyS2675 | 4902 | GCCCAAAGGCACCAAAGAATCCACCCCGCACAG | 9491 | AQSDQRIHPAQ | 14080 | SDQRIHP | 0.108479 | -0.15859 |
| SyS2676 | 4903 | GCCCAAGTTTCTGGTCAGACGAATATGGCACAG | 9492 | AQVSGQTNMMAQ | 14081 | VSGQTNM | 0.108381 | -0.21072 |
| SyS2677 | 4904 | GCCCAATACAGCTCGGGCAGCGAACCCGCACAG | 9493 | AQYSLGSEPAQ | 14082 | YSLGSEP | 0.10832 | -0.19981 |
| SyS2678 | 4905 | GCCCAATCTACGCTGAAAGGCTCTGACGGCACAG | 9494 | AQSTLKALTAQ | 14083 | STLKALT | 0.108295 | -0.16397 |

FIG. 33 (Continued)

| | | | | | | | |
|---|---|---|---|---|---|---|---|
| SyS2679 | 4906 | GCCCAAAGGCGCCTCATCCCCAGCCCGCACAG | 9495 | AQSALIPSPAQ | 14084 | SALIPSP | 0.108266 | -0.1889 |
| GS1530 | 4907 | GCCCAAACCAGCCAGCCGGCAACCAAGCACAG | 9496 | AQTSQAGNQAQ | 14085 | TSQAGNQ | 0.108221 | -0.05787 |
| GS1531 | 4908 | GCCCAAACACGCCAGCCTCCCATCGCACAG | 9497 | AQKHASLPIAQ | 14086 | KHASLPI | 0.108122 | -0.15676 |
| GS1532 | 4909 | GCCCAACTCGACCAACTCACCAAAAACGCACAG | 9498 | AQLDQLTKNAQ | 14087 | LDQLTKN | 0.108122 | -0.15676 |
| SyS2680 | 4910 | GCCCAAATGGCCAGAAGCACCGACAGAGCACAG | 9499 | AQMARSTDRAQ | 14088 | MARSTDR | 0.108107 | -0.14526 |
| SyS2681 | 4911 | GCCCAAAGTTATAATCATCATATTGAGAAGGCACAG | 9500 | AQSYNHIEKAQ | 14089 | SYNHIEK | 0.108002 | -0.23012 |
| SS193 | 4912 | GCCCAAGTCAACCACATCCAACCCATGGCACAG | 9501 | AQVNHIQPMAQ | 14090 | VNHIQPM | 0.107975 | -0.33355 |
| GS1533 | 4913 | GCCCAAAGCAGAGCCGAACCCAAACTCGCACAG | 9502 | AQSRAEPKLAQ | 14091 | SRAEPKL | 0.10781 | -0.16394 |
| GS1534 | 4914 | GCCCAAGCCAGCCACATCGCCAACAGCGCACAG | 9503 | AQASHIGNSAQ | 14092 | ASHIGNS | 0.107759 | -0.18637 |
| SyS2682 | 4915 | GCCCAACATCAGGGTTTGCGAGTGCTGCACAG | 9504 | AQHQGFASAAQ | 14093 | HQGFASA | 0.107489 | 0.012345 |
| SyS2684 | 4916 | GCCCAAGAGGGTAAGTCTATTATGCCGGCACAG | 9505 | AQEGKSIMPAQ | 14094 | EGKSIMP | 0.107301 | -0.20709 |
| SyS2685 | 4917 | GCCCAACTCACCGGCATGCACAGCACCGCACAG | 9506 | AQLTGMHSTAQ | 14095 | LTGMHST | 0.107301 | -0.20709 |
| SyS2686 | 4918 | GCCCAAAGTAATCCTAGTACTATTCATGCACAG | 9507 | AQSNPSTIHAQ | 14096 | SNPSTIH | 0.107232 | -0.12873 |
| SyS2688 | 4919 | GCCCAAAGCAGAGACCAACCACCAGCGCACAG | 9508 | AQSRDQPTSAQ | 14097 | SRDQPTS | 0.107118 | -0.18163 |
| SyS2689 | 4920 | GCCCAAAAAACCGCGAACCCTACACCGCACAG | 9509 | AQKTAEPYTAQ | 14098 | KTAEPYT | 0.107074 | -0.18491 |
| SyS2690 | 4921 | GCCCAAATTGGTTCTAATCCTGATAAGGCACAG | 9510 | AQIGSNPDKAQ | 14099 | IGSNPDK | 0.107034 | -0.21436 |
| SyS2691 | 4922 | GCCCAACTCGCCAGCACCTTCAGCCCGCACAG | 9511 | AQLASTFSPAQ | 14100 | LASTFSP | 0.107031 | -0.17998 |
| SyS2692 | 4923 | GCCCAACTTGTTAGGCTTAATACTTCTGCACAG | 9512 | AQLVRLNTSAQ | 14101 | LVRLNTS | 0.106997 | -0.22527 |
| SyP76 | 4924 | GCCCAATTTCAGGATCTGCGTGCGCAAGCACAG | 9513 | AQFQDLRAQAQ | 14102 | FQDLRAQ | 0.10698 | -0.03979 |
| GS1537 | 4925 | GCCCAAATCAGCCACAGCCCCAAACGCACAG | 9514 | AQISHSPQTAQ | 14103 | ISHSPQT | 0.106884 | -0.171 |
| SyS2693 | 4926 | GCCCAATTCCAAGACGGCCAAAGAGAAGCACAG | 9515 | AQFQDGQREAQ | 14104 | FQDGQRE | 0.106797 | -0.11297 |
| SyS2694 | 4927 | GCCCAAGACACCAGAGAAGCCTTCAGAGCACAG | 9516 | AQDTREAFRAQ | 14105 | DTREAFR | 0.106757 | -0.1792 |
| SyS2695 | 4928 | GCCCAATTGGTTGCTGATGCGCGTCCTGCACAG | 9517 | AQLVADARPAQ | 14106 | LVADARP | 0.106656 | -0.20103 |
| GS1540 | 4929 | GCCCAAAGCTTCAGCAGCGGCGGCGGGCACAG | 9518 | AQSFSSGAGAQ | 14107 | SFSSGAG | 0.10653 | -0.08043 |
| SyS2696 | 4930 | GCCCAAGATGTGTTGACTGGGAAGAGTGCACAG | 9519 | AQDVLTGKSAQ | 14108 | DVLTGKS | 0.106522 | -0.15496 |
| SyS2697 | 4931 | GCCCAAAAAGATGGTGTTGAATAATGCTGCACAG | 9520 | AQKMVLNNAAQ | 14109 | KMVLNNA | 0.106481 | -0.17225 |
| SyS2698 | 4932 | GCCCAACGGAAGATTGATACGATGTCTGCACAG | 9521 | AQRKIDTMSAQ | 14110 | RKIDTMS | 0.106265 | -0.13872 |
| GS1541 | 4933 | GCCCAAATGTCTCAGGTGATTACTGGGGCACAG | 9522 | AQMSQVITGAQ | 14111 | MSQVITG | 0.106232 | -0.1439 |
| GP212 | 4934 | GCCCAAACGTATAGGGATACGCGGAATACTGCACAG | 9523 | AQTYDTRNTAQ | 14112 | TYDTRNT | 0.106211 | -0.06295 |
| SyS2699 | 4935 | GCCCAATATAGGGATGGTTTCGGGTAGTGCACAG | 9524 | AQYRDGSGSAQ | 14113 | YRDGSGS | 0.105987 | 0.014681 |
| GS1542 | 4936 | GCCCAAGGGAATATTAGTCCTGCGGGGGCACAG | 9525 | AQGNISPAGAQ | 14114 | GNISPAG | 0.105627 | -0.18149 |
| SyS2700 | 4937 | GCCCAAAAAGCCGGCCCTCAGCGCCACAG | 9526 | AQKAGLGLSAQ | 14115 | KAGLGLS | 0.105529 | -0.21571 |

FIG. 33 (Continued)

| | | | | | | | |
|---|---|---|---|---|---|---|---|
| GP214 | 4938 | GCCCAACGTCATGTGGAGAAGGATACTGCACAG | 9527 | AQRHVEKDTAQ | 14116 | RHVEKDT | 0.105492 | -0.07433 |
| GS1543 | 4939 | GCCCAAAAGAAGTCAGAGCCAACGCCGCACAG | 9528 | AQKEVRANAAQ | 14117 | KEVRANA | 0.105404 | -0.15764 |
| SyS2701 | 4940 | GCCCAAGAGAGTAAGCCTTCTGCGGCACAG | 9529 | AQESKPLPAAQ | 14118 | ESKPLPA | 0.105201 | -0.21557 |
| SyS2702 | 4941 | GCCCAAACGTTGAGTCATAATAGTATGGCACAG | 9530 | AQTLSHNSMAQ | 14119 | TLSHNSM | 0.105046 | 0.006619 |
| SyS2703 | 4942 | GCCCAAGTCGGCAGTCACCGTCAGCGCACAG | 9531 | AQVGSYTVSAQ | 14120 | VGSYTVS | 0.105013 | -0.22649 |
| SyS2704 | 4943 | GCCCAACAAAGCGCCACCAGCCTCACGCACAG | 9532 | AQQSATSLTAQ | 14121 | QSATSLT | 0.104841 | -0.06501 |
| GS1546 | 4944 | GCCCAACACGCCAACGGCCTCAGAGACGCACAG | 9533 | AQHANGLRDAQ | 14122 | HANGLRD | 0.104497 | -0.15955 |
| GS1547 | 4945 | GCCCAAAGAATGAGCCACGACAGCCCGCACAG | 9534 | AQRMSHDSPAQ | 14123 | RMSHDSP | 0.104494 | -0.18637 |
| SyS2705 | 4946 | GCCCAAAAGCATAGTGGTCTTGAGTCTGCACAG | 9535 | AQKHSGLESAQ | 14124 | KHSGLES | 0.104319 | -0.17314 |
| SyS2707 | 4947 | GCCCAAAAACTCAGCACCGCCATCGAAGCACAG | 9536 | AQKLSTAIEAQ | 14125 | KLSTAIE | 0.103851 | -0.06923 |
| SyS2708 | 4948 | GCCCAAAACAGCAAACAACTCCTCTCGCACAG | 9537 | AQNSKQLLLAQ | 14126 | NSKQLLL | 0.10377 | -0.20709 |
| SyS2709 | 4949 | GCCCAATCGCTTCATAATAATCGTGTGGCACAG | 9538 | AQSLHNNRVAQ | 14127 | SLHNNRV | 0.103655 | -0.12587 |
| SyS2710 | 4950 | GCCCAAAGCGCCGACAGAAGCATCACCGCACAG | 9539 | AQSADRSITAQ | 14128 | SADRSIT | 0.103582 | -0.14162 |
| SyS2711 | 4951 | GCCCAACCCACCGGCAGACCCAGAAGCACAG | 9540 | AQPTGRPQEAQ | 14129 | PTGRPQE | 0.103492 | -0.1792 |
| SyS2712 | 4952 | GCCCAAAAGACTGTTCAGGAGCCTTTGGCACAG | 9541 | AQKTVQEPLAQ | 14130 | KTVQEPL | 0.10347 | -0.22926 |
| SyS2715 | 4953 | GCCCAAAGCACCAAAGCCCTCAGCAACGCACAG | 9542 | AQSTKALSNAQ | 14131 | STKALSN | 0.103085 | -0.13677 |
| GS1551 | 4954 | GCCCAAAGCAACCAAAGCACCAGAAGCGCACAG | 9543 | AQSNQSTRSAQ | 14132 | SNQSTRS | 0.103015 | -0.15138 |
| SyS2716 | 4955 | GCCCAAGGTGTTGAGGGGAGTTCGCGGGGCACAG | 9544 | AQGVEGSSRAQ | 14133 | GVEGSSR | 0.102975 | -0.21436 |
| SyS2717 | 4956 | GCCCAACTCCACCAAGGCCCCAGCAGCGCACAG | 9545 | AQLHQGPSSAQ | 14134 | LHQGPSS | 0.102855 | -0.099 |
| GS1552 | 4957 | GCCCAAGTCGACACGACAGAAACGTCGTCGCACAG | 9546 | AQVDSRNVVAQ | 14135 | VDSRNVV | 0.102836 | -0.118 |
| SyS2718 | 4958 | GCCCAACTTGGGAAGCAGACGGCTTTGGCACAG | 9547 | AQLGKQTALAQ | 14136 | LGKQTAL | 0.102831 | -0.1615 |
| SyS2719 | 4959 | GCCCAAAGGCGGCAACAGAACCAACATGGCACAG | 9548 | AQSGNRTNMAQ | 14137 | SGNRTNM | 0.102775 | 0.06214 |
| GS1553 | 4960 | GCCCAAGTCAAAGGCTACGCCAGCACCGCACAG | 9549 | AQVKGYASTAQ | 14138 | VKGYAST | 0.102753 | -0.16051 |
| SyS2720 | 4961 | GCCCAAGCTTCTGTTAGTTCGTCGAGTGCACAG | 9550 | AQASVSSSSAQ | 14139 | ASVSSSS | 0.102658 | 0.00519 |
| SyS2722 | 4962 | GCCCAACTCCAACTCAAAAGCGGCATGGCACAG | 9551 | AQLQLKSGMAQ | 14140 | LQLKSGM | 0.102481 | -0.07053 |
| SyS2723 | 4963 | GCCCAAGATATGCGTGCGTCTGGGAGTGCACAG | 9552 | AQDMRASGSAQ | 14141 | DMRASGS | 0.102358 | -0.19107 |
| GP216 | 4964 | GCCCAATTGACTGCTACGCTGCCTTATGCACAG | 9553 | AQLTATLPYAQ | 14142 | LTATLPY | 0.102226 | -0.0676 |
| GS1555 | 4965 | GCCCAAAGTAATGCTCCTAATTCGTATGCACAG | 9554 | AQSNAPNSYAQ | 14143 | SNAPNSY | 0.102094 | -0.10049 |
| SyS2726 | 4966 | GCCCAAAAAGTCGAAAGCAGCAGAGCCGCACAG | 9555 | AQKVESSRAAQ | 14144 | KVESSRA | 0.102054 | -0.20586 |
| GS1556 | 4967 | GCCCAATGGAGCAACAGCACCACCGTCGCACAG | 9556 | AQWSNSTTVAQ | 14145 | WSNSTTV | 0.10196 | -0.17381 |
| GP217 | 4968 | GCCCAATCTCTTATTCATACGGCGTCCTGCACAG | 9557 | AQSLIHTRPAQ | 14146 | SLIHTRP | 0.101865 | -0.0719 |
| SyS2727 | 4969 | GCCCAAACGCTTTCTAGTCCTCATAATGCACAG | 9558 | AQTLSSPHNAQ | 14147 | TLSSPHN | 0.101849 | -0.22042 |

FIG. 33 (Continued)

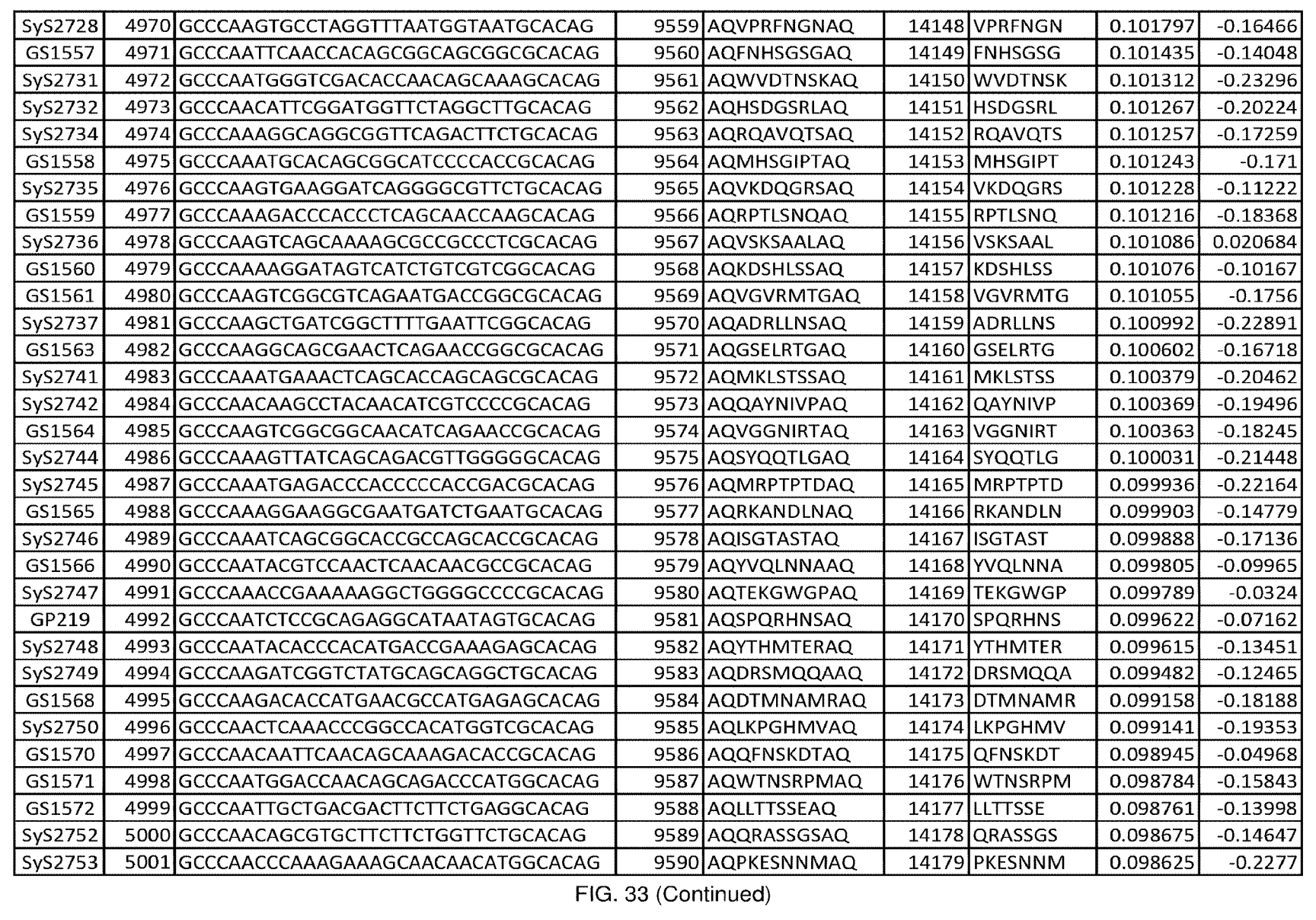

| | | | | | | | | |
|---|---|---|---|---|---|---|---|---|
| SyS2728 | 4970 | GCCCAAGTGCCTAGGTTTAATGGTAATGCACAG | 9559 | AQVPRFNGNAQ | 14148 | VPRFNGN | 0.101797 | -0.16466 |
| GS1557 | 4971 | GCCCAATTCAACCACAGCGGCAGCGGCGCACAG | 9560 | AQFNHSGSGAQ | 14149 | FNHSGSG | 0.101435 | -0.14048 |
| SyS2731 | 4972 | GCCCAATGGGTCGACACCAACAGCAAAGCACAG | 9561 | AQWVDTNSKAQ | 14150 | WVDTNSK | 0.101312 | -0.23296 |
| SyS2732 | 4973 | GCCCAACATTCGGATGGTTCTAGGCTTGCACAG | 9562 | AQHSDGSRLAQ | 14151 | HSDGSRL | 0.101267 | -0.20224 |
| SyS2734 | 4974 | GCCCAAAGGCAGGCGGTTCAGACTTCTGCACAG | 9563 | AQRQAVQTSAQ | 14152 | RQAVQTS | 0.101257 | -0.17259 |
| GS1558 | 4975 | GCCCAAATGCACAGCGGCATCCCCACCGCACAG | 9564 | AQMHSGIPTAQ | 14153 | MHSGIPT | 0.101243 | -0.171 |
| SyS2735 | 4976 | GCCCAAGTGAAGGATCAGGGGCGTTCTGCACAG | 9565 | AQVKDQGRSAQ | 14154 | VKDQGRS | 0.101228 | -0.11222 |
| GS1559 | 4977 | GCCCAAAGACCCACCCTCAGCAACCAAGCACAG | 9566 | AQRPTLSNQAQ | 14155 | RPTLSNQ | 0.101216 | -0.18368 |
| SyS2736 | 4978 | GCCCAAGTCAGCAAAAGCGCCGCCCTCGCACAG | 9567 | AQVSKSAALAQ | 14156 | VSKSAAL | 0.101086 | 0.020684 |
| GS1560 | 4979 | GCCCAAAAGGATAGTCATCTGTCGTCGGCACAG | 9568 | AQKDSHLSSAQ | 14157 | KDSHLSS | 0.101076 | -0.10167 |
| GS1561 | 4980 | GCCCAAGTCGGCGTCAGAATGACCGGCGCACAG | 9569 | AQVGVRMTGAQ | 14158 | VGVRMTG | 0.101055 | -0.1756 |
| SyS2737 | 4981 | GCCCAAGCTGATCGGCTTTTGAATTCGGCACAG | 9570 | AQADRLLNSAQ | 14159 | ADRLLNS | 0.100992 | -0.22891 |
| GS1563 | 4982 | GCCCAAGGCAGCGAACTCAGAACCGGCGGCACAG | 9571 | AQGSELRTGAQ | 14160 | GSELRTG | 0.100602 | -0.16718 |
| SyS2741 | 4983 | GCCCAAAATGAAACTCAGCACCAGCAGCGCACAG | 9572 | AQMKLSTSSAQ | 14161 | MKLSTSS | 0.100379 | -0.20462 |
| SyS2742 | 4984 | GCCCAACAACAGCCTACAACATCGTCCCCGCACAG | 9573 | AQQAYNIVPAQ | 14162 | QAYNIVP | 0.100369 | -0.19496 |
| GS1564 | 4985 | GCCCAAGTCGGGCGGCAACATCAGAACCGCACAG | 9574 | AQVGGNIRTAQ | 14163 | VGGNIRT | 0.100363 | -0.18245 |
| SyS2744 | 4986 | GCCCAAAGTTATCAGACAGACGTTGGGGCACAG | 9575 | AQSYQQTLGAQ | 14164 | SYQQTLG | 0.100031 | -0.21448 |
| SyS2745 | 4987 | GCCCAAAATGAGAACCCACCCCACGACGCACAG | 9576 | AQMRPTPTDAQ | 14165 | MRPTPTD | 0.099936 | -0.22164 |
| GS1565 | 4988 | GCCCAAAGGAAGGGCGAATGATCTGAATGCACAG | 9577 | AQRKANDLNAQ | 14166 | RKANDLN | 0.099903 | -0.14779 |
| SyS2746 | 4989 | GCCCAAAATCAGCGGCCACCGCCAGCACCGCACAG | 9578 | AQISGTASTAQ | 14167 | ISGTAST | 0.099888 | -0.17136 |
| GS1566 | 4990 | GCCCAATACGTCCAACTCAACACGCCGCACAG | 9579 | AQYVQLNNAAQ | 14168 | YVQLNNA | 0.099805 | -0.09965 |
| SyS2747 | 4991 | GCCCAAACCGAAAAAGGCTGGGGCCCCGCACAG | 9580 | AQTEKGWGPAQ | 14169 | TEKGWGP | 0.099789 | -0.0324 |
| GP219 | 4992 | GCCCAATCTCCGCAGAGGCATAATAGTGCACAG | 9581 | AQSPQRHNSAQ | 14170 | SPQRHNS | 0.099622 | -0.07162 |
| SyS2748 | 4993 | GCCCAATACACCCACCATGACCGAAAGAGCACAG | 9582 | AQYTHMTERAQ | 14171 | YTHMTER | 0.099615 | -0.13451 |
| SyS2749 | 4994 | GCCCAAGATCGGTCTATGCAGCAGGCTGCACAG | 9583 | AQDRSMQQAAQ | 14172 | DRSMQQA | 0.099482 | -0.12465 |
| GS1568 | 4995 | GCCCAAGACACCATGAACGCCATGAGAGCACAG | 9584 | AQDTMNAMRAQ | 14173 | DTMNAMR | 0.099158 | -0.18188 |
| SyS2750 | 4996 | GCCCAACTCAAACCCGGCCACATGGTCGCACAG | 9585 | AQLKPGHMVAQ | 14174 | LKPGHMV | 0.099141 | -0.19353 |
| GS1570 | 4997 | GCCCAACAATTCAACAGCAAAGACACCGCACAG | 9586 | AQQFNSKDTAQ | 14175 | QFNSKDT | 0.098945 | -0.04968 |
| GS1571 | 4998 | GCCCAATGGACCAACAGCAGAGACCCCATGGCACAG | 9587 | AQWTNSRPMAQ | 14176 | WTNSRPM | 0.098784 | -0.15843 |
| GS1572 | 4999 | GCCCAACATTGCTGACGACTTCTTCTGAGGCACAG | 9588 | AQLLTTSSEAQ | 14177 | LLTTSSE | 0.098761 | -0.13998 |
| SyS2752 | 5000 | GCCCAACAGCGTGCTTCTTCTGGTTCTGCACAG | 9589 | AQQRASSGSAQ | 14178 | QRASSGS | 0.098675 | -0.14647 |
| SyS2753 | 5001 | GCCCAACCCAAAGAAAGCAACAACATGGCACAG | 9590 | AQPKESNNMAQ | 14179 | PKESNNM | 0.098625 | -0.2277 |

FIG. 33 (Continued)

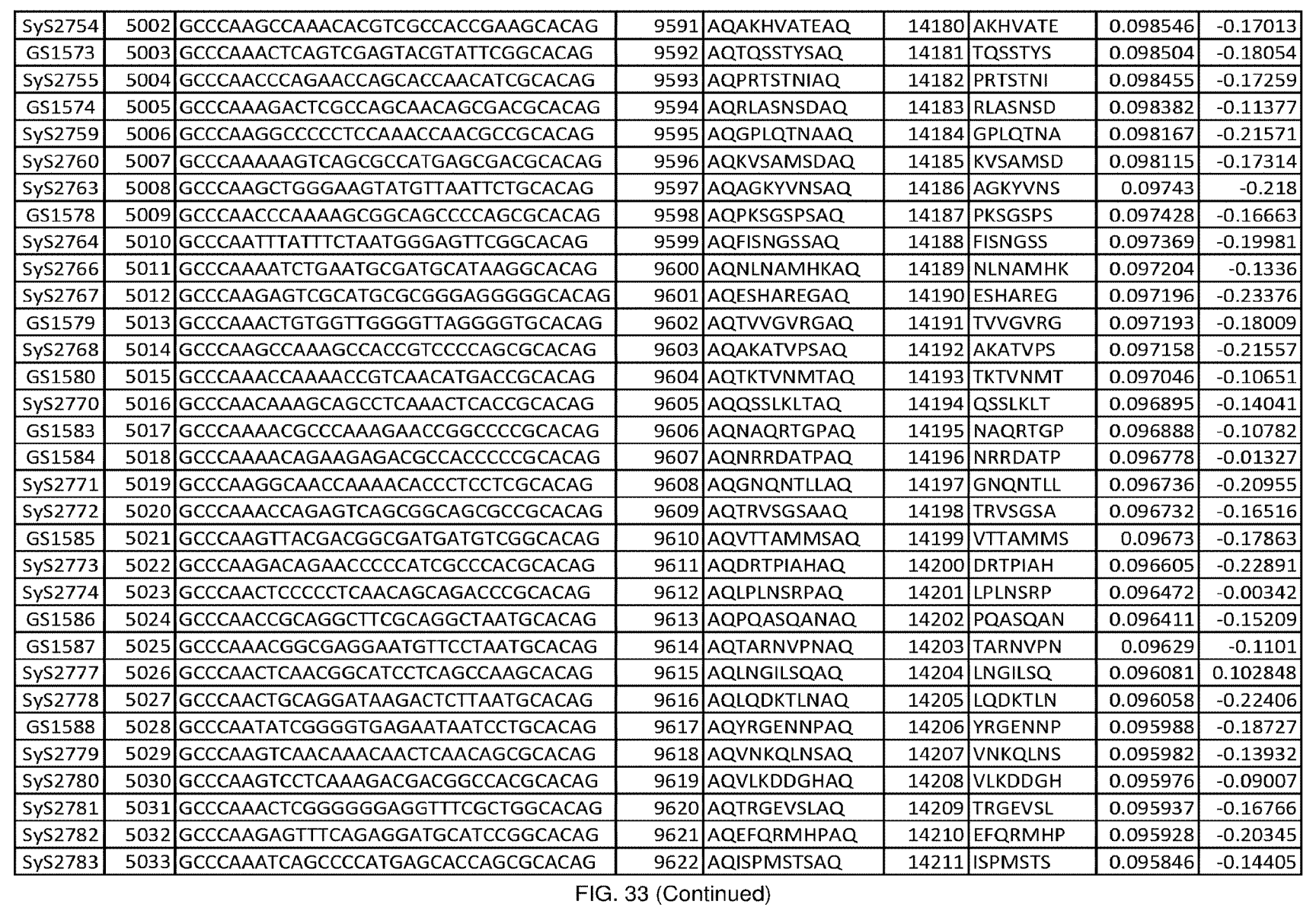

| | | | | | | | | |
|---|---|---|---|---|---|---|---|---|
| SyS2754 | 5002 | GCCCAAGCCAAACACGTCGCCACCGAAGCACAG | 9591 | AQAKHVATEAQ | 14180 | AKHVATE | 0.098546 | -0.17013 |
| GS1573 | 5003 | GCCCAAACTCAGTCGAGTACGTATTCGGCACAG | 9592 | AQTQSSTYSAQ | 14181 | TQSSTYS | 0.098504 | -0.18054 |
| SyS2755 | 5004 | GCCCAAACCAGAACCAGCAACAACATCGCACAG | 9593 | AQPRTSTNIAQ | 14182 | PRTSTNI | 0.098455 | -0.17259 |
| GS1574 | 5005 | GCCCAAAGACTCGCCAGCAACAGCGACGCACAG | 9594 | AQRLASNSDAQ | 14183 | RLASNSD | 0.098382 | -0.11377 |
| SyS2759 | 5006 | GCCCAAGGCCCCTCCAAACCAACGCCGCACAG | 9595 | AQGPLQTNAAQ | 14184 | GPLQTNA | 0.098167 | -0.21571 |
| SyS2760 | 5007 | GCCCAAAAAGTCAGCGCCATGAGCGACGCACAG | 9596 | AQKVSAMSDAQ | 14185 | KVSAMSD | 0.098115 | -0.17314 |
| SyS2763 | 5008 | GCCCAAGCTGGGAAGTATGTTAATTCTGCACAG | 9597 | AQAGKYVNSAQ | 14186 | AGKYVNS | 0.09743 | -0.218 |
| GS1578 | 5009 | GCCCAACCCAAAAGCGGCAGCCCCAGCGCACAG | 9598 | AQPKSGSPSAQ | 14187 | PKSGSPS | 0.097428 | -0.16663 |
| SyS2764 | 5010 | GCCCAATTTATTTCTAATGGGAGTTCGGCACAG | 9599 | AQFISNGSSAQ | 14188 | FISNGSS | 0.097369 | -0.19981 |
| SyS2766 | 5011 | GCCCAAAATCTGAATGCGATGCATAAGGCACAG | 9600 | AQNLNAMHKAQ | 14189 | NLNAMHK | 0.097204 | -0.1336 |
| SyS2767 | 5012 | GCCCAAGAGTCGCATGCGGGGAGGGGGCACAG | 9601 | AQESHAREGAQ | 14190 | ESHAREG | 0.097196 | -0.23376 |
| GS1579 | 5013 | GCCCAAACTGTGGTTGGGGTTAGGGGTGCACAG | 9602 | AQTVVGVRGAQ | 14191 | TVVGVRG | 0.097193 | -0.18009 |
| SyS2768 | 5014 | GCCCAAGCCAAAGCCACCGTCCCCAGCGCACAG | 9603 | AQAKATVPSAQ | 14192 | AKATVPS | 0.097158 | -0.21557 |
| GS1580 | 5015 | GCCCAACCAACAAAACCGTCAACATGACCGCACAG | 9604 | AQTKTVNMTAQ | 14193 | TKTVNMT | 0.097046 | -0.10651 |
| SyS2770 | 5016 | GCCCAACAAAGCAGCCTCAAACTCACCGCACAG | 9605 | AQQSSLKLTAQ | 14194 | QSSLKLT | 0.096895 | -0.14041 |
| GS1583 | 5017 | GCCCAAAAGCCCAAAGAACCGGCCCCGCACAG | 9606 | AQNAQRTGPAQ | 14195 | NAQRTGP | 0.096888 | -0.10782 |
| GS1584 | 5018 | GCCCAAAACAGAGAGACGCCACCCCGCACAG | 9607 | AQNRRDATPAQ | 14196 | NRRDATP | 0.096778 | -0.01327 |
| SyS2771 | 5019 | GCCCAAGGCAACCAAAACACCCTCCTGCACAG | 9608 | AQGNQNTLLAQ | 14197 | GNQNTLL | 0.096736 | -0.20955 |
| SyS2772 | 5020 | GCCCAAACCAGAGTCAGCGGCAGCGCCGCACAG | 9609 | AQTRVSGSAAQ | 14198 | TRVSGSA | 0.096732 | -0.16516 |
| GS1585 | 5021 | GCCCAAGTTACGACGGCGGATGATGTCGGCACAG | 9610 | AQVTTAMMSAQ | 14199 | VTTAMMS | 0.09673 | -0.17863 |
| SyS2773 | 5022 | GCCCAAGACAGAACCCCATGCGCCACGCACAG | 9611 | AQDRTPIAHAQ | 14200 | DRTPIAH | 0.096605 | -0.22891 |
| SyS2774 | 5023 | GCCCAACTCCCCTCAACAGCAGACCCGCACAG | 9612 | AQLPLNSRPAQ | 14201 | LPLNSRP | 0.096472 | -0.00342 |
| GS1586 | 5024 | GCCCAACCGCAGGCTTCGCAGGCTAATGCACAG | 9613 | AQPQASQANAQ | 14202 | PQASQAN | 0.096411 | -0.15209 |
| GS1587 | 5025 | GCCCAAACGGCGAGGAATGTTCCTAATGCACAG | 9614 | AQTARNVPNAQ | 14203 | TARNVPN | 0.09629 | -0.1101 |
| SyS2777 | 5026 | GCCCAACTCAACGGCATCCTCAGCCAAGCACAG | 9615 | AQLNGILSQAQ | 14204 | LNGILSQ | 0.096081 | 0.102848 |
| SyS2778 | 5027 | GCCCAACTGCAGGATAAGACTCTTAATGCACAG | 9616 | AQLQDKTLNAQ | 14205 | LQDKTLN | 0.096058 | -0.22406 |
| GS1588 | 5028 | GCCCAATATCGGGGTGAGAATAATCCTGCACAG | 9617 | AQYRGENNPAQ | 14206 | YRGENNP | 0.095988 | -0.18727 |
| SyS2779 | 5029 | GCCCAAGTCAACAAACAACTCAACAGCGCACAG | 9618 | AQVNKQLNSAQ | 14207 | VNKQLNS | 0.095982 | -0.13932 |
| SyS2780 | 5030 | GCCCAAGTCCTCAAAGACGACGGCCACGCACAG | 9619 | AQVLKDDGHAQ | 14208 | VLKDDGH | 0.095976 | -0.09007 |
| SyS2781 | 5031 | GCCCAAACTCGGGGGGGAGGTTTCGCTGGCACAG | 9620 | AQTRGEVSLAQ | 14209 | TRGEVSL | 0.095937 | -0.16766 |
| SyS2782 | 5032 | GCCCAAGAGTTTCAGAGGATGCATCCGGCACAG | 9621 | AQEFQRMHPAQ | 14210 | EFQRMHP | 0.095928 | -0.20345 |
| SyS2783 | 5033 | GCCCAAAATCAGCCCCATGAGCACCAGCGCACAG | 9622 | AQISPMSTSAQ | 14211 | ISPMSTS | 0.095846 | -0.14405 |

FIG. 33 (Continued)

| | | | | | | | | |
|---|---|---|---|---|---|---|---|---|
| SyS2784 | 5034 | GCCCAACTCGGCCACGACCACGCCACCGCACAG | 9623 | AQLGHDHATAQ | 14212 | LGHDHAT | 0.0958 | -0.22164 |
| GS1590 | 5035 | GCCCAACTCAGCCCGGCCCCCAACAAGCACAG | 9624 | AQLSPGPQQAQ | 14213 | LSPGPQQ | 0.095745 | -0.171 |
| GP221 | 5036 | GCCCAAAAGTTTAGGGGGGAGGAGCCTGCACAG | 9625 | AQKFRGEEPAQ | 14214 | KFRGEEP | 0.095692 | -0.06711 |
| GS1591 | 5037 | GCCCAACAGGGTTCTCGTCTGGCTTCGGCACAG | 9626 | AQQGSRLASAQ | 14215 | QGSRLAS | 0.095684 | -0.16753 |
| SyS2786 | 5038 | GCCCAATGGGAGCGGTTCTCAGTTGTCTGCACAG | 9627 | AQWERSQLSAQ | 14216 | WERSQLS | 0.095581 | -0.20093 |
| SyS2787 | 5039 | GCCCAACAGCAGAAGGCGGCTAATGGGGCACAG | 9628 | AQQQKAANGAQ | 14217 | QQKAANG | 0.095548 | -0.01243 |
| SyS2788 | 5040 | GCCCAATATACGCTGAGTCTGAGTAGTGCACAG | 9629 | AQYTLSLSSAQ | 14218 | YTLSLSS | 0.095427 | -0.20339 |
| SyS2789 | 5041 | GCCCAAGGCCTCATCCCAACAACAGCGCACAG | 9630 | AQGLIPNNSAQ | 14219 | GLIPNNS | 0.095235 | -0.23173 |
| SyS2790 | 5042 | GCCCAAAGCGTCCCGTCAGCAGAACCGCACAG | 9631 | AQSVPVSRTAQ | 14220 | SVPVSRT | 0.095224 | -0.08979 |
| SP51 | 5043 | GCCCAAAATAAGCAGCAGTCTCAGACGGCACAG | 9632 | AQNKQQSQTAQ | 14221 | NKQQSQT | 0.095031 | -0.04883 |
| SyS2792 | 5044 | GCCCAAAGCAAACACAGCGTCCAAGTCGCACAG | 9633 | AQSKHSVQVAQ | 14222 | SKHSVQV | 0.095008 | -0.01372 |
| GS1592 | 5045 | GCCCAAAATCGTCCTTCTCAGCAGGGGGCACAG | 9634 | AQNRPSQQGAQ | 14223 | NRPSQQG | 0.094956 | -0.08958 |
| SyS2793 | 5046 | GCCCAACAAGAATACAGAAACACCCTCGCACAG | 9635 | AQQEYRNTLAQ | 14224 | QEYRNTL | 0.094903 | -0.17072 |
| SyS2794 | 5047 | GCCCAATTCGAAAGAGACAGAATGGGCGCACAG | 9636 | AQFERDRMGAQ | 14225 | FERDRMG | 0.094881 | -0.19133 |
| SyS2795 | 5048 | GCCCAAGCACCAGCAGCAACCTCAGCGCACAG | 9637 | AQSTSSNLSAQ | 14226 | STSSNLS | 0.094566 | -0.23012 |
| SyS2796 | 5049 | GCCCAAAGAAGCCTCGAAGGCATCGTCGCACAG | 9638 | AQRSLEGIVAQ | 14227 | RSLEGIV | 0.094566 | -0.23012 |
| SyS2797 | 5050 | GCCCAAGGCAACAGCAGCAGACTCGACCCGCACAG | 9639 | AQGNSRLDPAQ | 14228 | GNSRLDP | 0.094522 | -0.12222 |
| GS1594 | 5051 | GCCCAAATCGACACCATCGGCAAAGCCGCACAG | 9640 | AQIDTIGKAAQ | 14229 | IDTIGKA | 0.094385 | -0.15766 |
| SyS2799 | 5052 | GCCCAACTGGATCATACGAGTCGTGCGGCACAG | 9641 | AQLDHTSRAAQ | 14230 | LDHTSRA | 0.094325 | -0.18405 |
| SyS2800 | 5053 | GCCCAATGGGCCAAACCAACAGCAGCGCACAG | 9642 | AQWGQTNSSAQ | 14231 | WGQTNSS | 0.094236 | -0.10601 |
| GS1596 | 5054 | GCCCAAGCGCGGGGTAATCTGTGAGTGCACAG | 9643 | AQARGNLSSAQ | 14232 | ARGNLSS | 0.094135 | -0.14906 |
| SyS2801 | 5055 | GCCCAAGACAACATGAAACTCCACGTCGCACAG | 9644 | AQDNMKLHVAQ | 14233 | DNMKLHV | 0.094093 | -0.22527 |
| SyS2802 | 5056 | GCCCAAGAAAAAACCCACAAAGTACGCACAG | 9645 | AQEKTQQSYAQ | 14234 | EKTQQSY | 0.094009 | -0.08103 |
| GS1597 | 5057 | GCCCAATCGAATGGTTGGCGCGGAATGCACAG | 9646 | AQSNGLARNAQ | 14235 | SNGLARN | 0.093844 | -0.16118 |
| GS1598 | 5058 | GCCCAAGTCGTCAGCACAGACCCGCCGCACAG | 9647 | AQVVSHRPAAQ | 14236 | VVSHRPA | 0.093796 | -0.17112 |
| SyS2803 | 5059 | GCCCAAAGTTTGGGTGTTAGTCGGAATGCACAG | 9648 | AQSLGVSRNAQ | 14237 | SLGVSRN | 0.093666 | -0.06472 |
| SyS2804 | 5060 | GCCCAAGACCACAGCCACGGCAGAGACGCACAG | 9649 | AQDHSHGRDAQ | 14238 | DHSHGRD | 0.093446 | -0.218 |
| SyP78 | 5061 | GCCCAATCGACTCATCAGGTGGCGAATGCACAG | 9650 | AQSTHQVANAQ | 14239 | STHQVAN | 0.093182 | -0.0423 |
| SyS2806 | 5062 | GCCCAAAATCAGAGTGCGAGTAGTGCGCACAG | 9651 | AQNQSASSRAQ | 14240 | NQSASSR | 0.09291 | -0.16223 |
| SyS2807 | 5063 | GCCCAAGTCACCGTCGGCAGCCACATGGCACAG | 9652 | AQVTVGSHMAQ | 14241 | VTVGSHM | 0.092881 | -0.13936 |
| SyS2808 | 5064 | GCCCAAAGCAGCAACATCGCCCAAAACGCACAG | 9653 | AQSSNIAQNAQ | 14242 | SSNIAQN | 0.092827 | -0.11131 |
| GP222 | 5065 | GCCCAATTGAATGAGAGATGGCTACTCCTGCACAG | 9654 | AQLNEMATPAQ | 14243 | LNEMATP | 0.092632 | -0.071 |

FIG. 33 (Continued)

| | | | | | | | | |
|---|---|---|---|---|---|---|---|---|
| GS1600 | 5066 | GCCCAAAGCACCAAAATCGAAAGAGACGCACAG | 9655 | AQSTKIERDAQ | 14244 | STKIERD | 0.092384 | -0.16337 |
| SyS2811 | 5067 | GCCCAAAACCTCGTCGACGCCAGAATCGCACAG | 9656 | AQNLVDARIAQ | 14245 | NLVDARI | 0.092338 | -0.20345 |
| GS1601 | 5068 | GCCCAATACAGCACCGGCAAAGACGCCGCACAG | 9657 | AQYSTGKDAAQ | 14246 | YSTGKDA | 0.092318 | -0.16663 |
| SyS2812 | 5069 | GCCCAAACCCAAGGCATCGTCACCAGCGCACAG | 9658 | AQTQGIVTSAQ | 14247 | TQGIVTS | 0.092249 | -0.22187 |
| SyS2813 | 5070 | GCCCAATCTTTTGGGGCTACGAGTTGGCACAG | 9659 | AQSFGATSLAQ | 14248 | SFGATSL | 0.092013 | -0.22434 |
| SyP79 | 5071 | GCCCAAACTGCGGGGGATGTCTTCGCGGGCACAG | 9660 | AQTAGMSSRAQ | 14249 | TAGMSSR | 0.091732 | -0.03931 |
| SyS2815 | 5072 | GCCCAAAGAGACAACAGCCTCATCCCCGCACAG | 9661 | AQRDNSLIPAQ | 14250 | RDNSLIP | 0.091477 | -0.06762 |
| SyS2816 | 5073 | GCCCAAAAGACTAATGCTGATTATGGGGCACAG | 9662 | AQKTNADYGAQ | 14251 | KTNADYG | 0.09146 | -0.13314 |
| GS1602 | 5074 | GCCCAAGTCAACCCCACAGAACCATGGCACAG | 9663 | AQVNPHRTMAQ | 14252 | VNPHRTM | 0.091294 | -0.14811 |
| GS1603 | 5075 | GCCCAAGATATTCGTGGGAGGCCTACTGCACAG | 9664 | AQDIRGRPTAQ | 14253 | DIRGRPT | 0.091275 | -0.16528 |
| SyS2818 | 5076 | GCCCAACGTGAGGTTTCGAGTACTTCTGCACAG | 9665 | AQREVSSTSAQ | 14254 | REVSSTS | 0.091098 | -0.0482 |
| SyS2819 | 5077 | GCCCAAGTCAGCCAAGGCACCAGAGTCGCACAG | 9666 | AQVSQGTRVAQ | 14255 | VSQGTRV | 0.091058 | -0.12344 |
| SyS2820 | 5078 | GCCCAAAAGACGCCTATTATGCATGCGGGCACAG | 9667 | AQKTPIMHAAQ | 14256 | KTPIMHA | 0.090778 | -0.14647 |
| GP224 | 5079 | GCCCAACTGGAGTCGCGGGATACGGTTGCACAG | 9668 | AQLESRDTVAQ | 14257 | LESRDTV | 0.090555 | -0.07426 |
| SyS2822 | 5080 | GCCCAAGTCCTCAACAGCAGCATGACCGCACAG | 9669 | AQVLNSSMTAQ | 14258 | VLNSSMT | 0.090547 | -0.22064 |
| GS1605 | 5081 | GCCCAATTTCGGACTGTGACGCAGGCGGCACAG | 9670 | AQFRTVTQAAQ | 14259 | FRTVTQA | 0.090305 | -0.15001 |
| SyS2823 | 5082 | GCCCAAACCGGCGCCATGAACATGACCGCACAG | 9671 | AQTGAMNMTAQ | 14260 | TGAMNMT | 0.09021 | 0.113384 |
| GS1606 | 5083 | GCCCAATTGAAGACTCAGAATTATTCTGCACAG | 9672 | AQLKTQNYSAQ | 14261 | LKTQNYS | 0.090046 | -0.18457 |
| GS1607 | 5084 | GCCCAACAGAAGACGATGTTGACTGCTGCACAG | 9673 | AQQKTMLTAAQ | 14262 | QKTMLTA | 0.089785 | -0.10968 |
| SyS2824 | 5085 | GCCCAAAGTAATATTATTGGTTCGGATGCACAG | 9674 | AQSNIIGSDAQ | 14263 | SNIIGSD | 0.089711 | -0.20562 |
| SyS2825 | 5086 | GCCCAATGCGTGTCGGTTTCGGTTTCGAAGATGGCACAG | 9675 | AQSVSVSKMAQ | 14264 | SVSVSKM | 0.089669 | -0.22042 |
| SyS2826 | 5087 | GCCCAAGCGGCCAGGTTCGCATGCTGCACAG | 9676 | AQAAQVSHAAQ | 14265 | AAQVSHA | 0.089533 | -0.18284 |
| SyS2827 | 5088 | GCCCAAATTAATGTGGTTGAGAAGGCTGCACAG | 9677 | AQINVVEKAAQ | 14266 | INVVEKA | 0.089471 | -0.14819 |
| SyS2829 | 5089 | GCCCAAATGCTCAGAGGGGACCTCCCGCACAG | 9678 | AQMLRGDLPAQ | 14267 | MLRGDLP | 0.089436 | -0.18245 |
| SyS2830 | 5090 | GCCCAAAACCTCCCACCATGCCAACCCGCACAG | 9679 | AQNLPTMQPAQ | 14268 | NLPTMQP | 0.089402 | -0.21557 |
| SyS2831 | 5091 | GCCCAATTCCAAGACAAAATCAACAGAGCACAG | 9680 | AQFQDKINRAQ | 14269 | FQDKINR | 0.089402 | -0.21557 |
| GS1609 | 5092 | GCCCAAAGCAGACAAACCATGAAACCGCACAG | 9681 | AQSRQTIETAQ | 14270 | SRQTIET | 0.089312 | -0.12392 |
| SyS2833 | 5093 | GCCCAACTCCACAGCAAACTCAACGGGCACAG | 9682 | AQLHSKLNGAQ | 14271 | LHSKLNG | 0.089225 | -0.17557 |
| SyS2834 | 5094 | GCCCAAACCCCAGCGCCAGCAACATGGCACAG | 9683 | AQTPSASNMAQ | 14272 | TPSASNM | 0.089132 | -0.23296 |
| GS1611 | 5095 | GCCCAAGCTAATACGGCTATTAGGACTGCACAG | 9684 | AQANTAIRTAQ | 14273 | ANTAIRT | 0.088865 | -0.18637 |
| GS1612 | 5096 | GCCCAAAGCCCCTACACACCAAAAACGCACAG | 9685 | AQSPYNQNNAQ | 14274 | SPYNQNN | 0.088563 | -0.18009 |
| SyS2835 | 5097 | GCCCAATCGGGGAAGCAGCAGACGACTGCACAG | 9686 | AQSGKQQTTAQ | 14275 | SGKQQTT | 0.088368 | -0.06888 |

FIG. 33 (Continued)

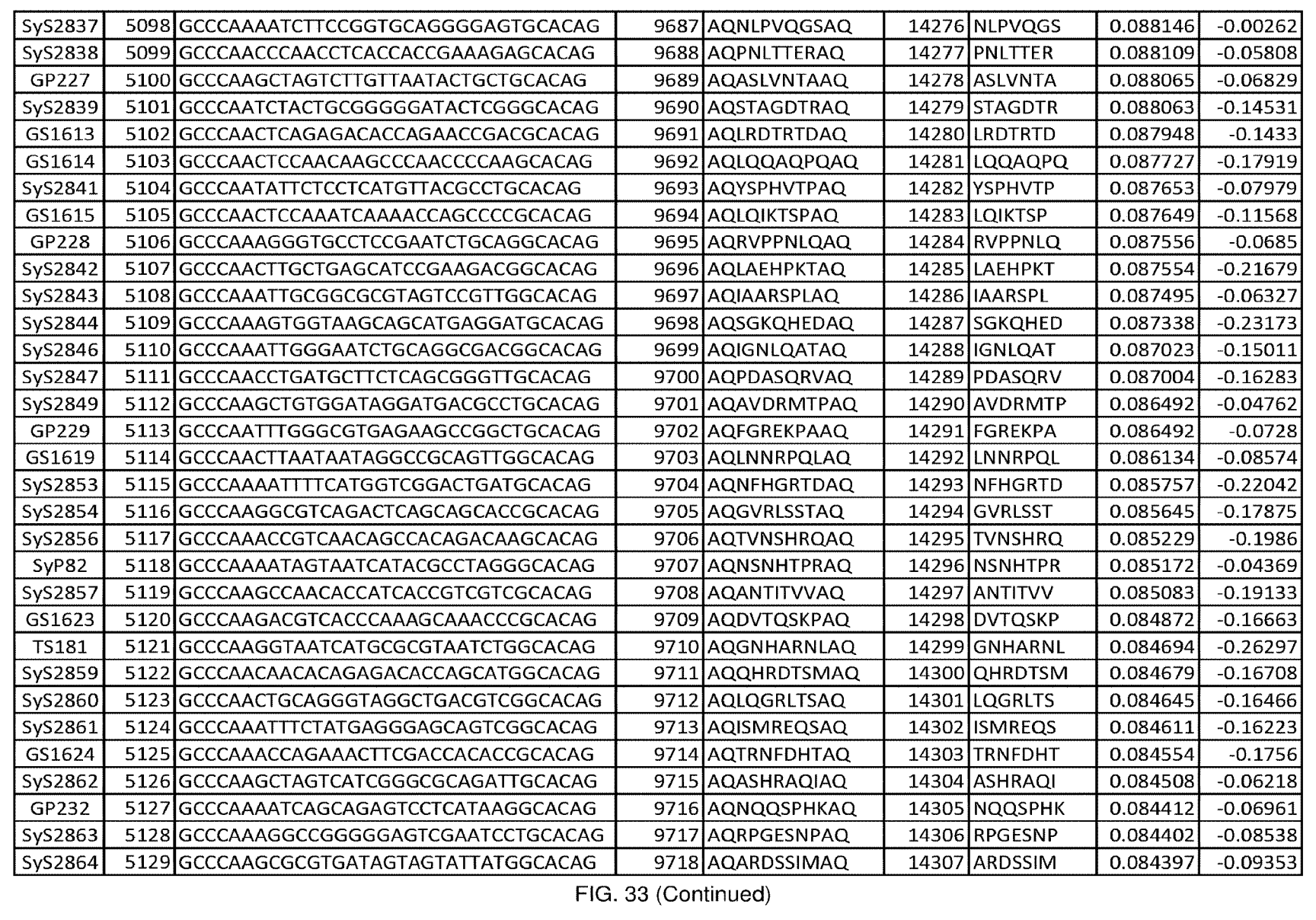

| | | | | | | | | |
|---|---|---|---|---|---|---|---|---|
| SyS2837 | 5098 | GCCCAAAATCTTCCGGTGCAGGGGAGTGCACAG | 9687 | AQNLPVQGSAQ | 14276 | NLPVQGS | 0.088146 | -0.00262 |
| SyS2838 | 5099 | GCCCAACCCAACCTCACCACGGAAAGAGCACAG | 9688 | AQPNLTTERAQ | 14277 | PNLTTER | 0.088109 | -0.05808 |
| GP227 | 5100 | GCCCAAGCTAGTCTTGTTAATACTGCTGCACAG | 9689 | AQASLVNTAAQ | 14278 | ASLVNTA | 0.088065 | -0.06829 |
| SyS2839 | 5101 | GCCCAATCTACTGCGGGGGATACTCGGGCACAG | 9690 | AQSTAGDTRAQ | 14279 | STAGDTR | 0.088063 | -0.14531 |
| GS1613 | 5102 | GCCCAACTCAGAGACACCAGAACCGACGGCACAG | 9691 | AQLRDTRTDAQ | 14280 | LRDTRTD | 0.087948 | -0.1433 |
| GS1614 | 5103 | GCCCAACTCCAACAAGCCCAACCCCAAGCACAG | 9692 | AQLQQAQPQAQ | 14281 | LQQAQPQ | 0.087727 | -0.17919 |
| SyS2841 | 5104 | GCCCAATATTCTCCTCATGTTACGCCTGCACAG | 9693 | AQYSPHVTPAQ | 14282 | YSPHVTP | 0.087653 | -0.07979 |
| GS1615 | 5105 | GCCCAACTCCAAATCAAAACCAGCCCGCACAG | 9694 | AQLQIKTSPAQ | 14283 | LQIKTSP | 0.087649 | -0.11568 |
| GP228 | 5106 | GCCCAAAGGGTGCCTCCGAATCTGCAGGCACAG | 9695 | AQRVPPNLQAQ | 14284 | RVPPNLQ | 0.087556 | -0.0685 |
| SyS2842 | 5107 | GCCCAACTTGCTGAGCATCCGAAGACGGCACAG | 9696 | AQLAEHPKTAQ | 14285 | LAEHPKT | 0.087554 | -0.21679 |
| SyS2843 | 5108 | GCCCAAATTGCGGCGCGTAGTCCGTTGGCACAG | 9697 | AQIAARSPLAQ | 14286 | IAARSPL | 0.087495 | -0.06327 |
| SyS2844 | 5109 | GCCCAAAGTGGTAAGCAGCATGAGGATGCACAG | 9698 | AQSGKQHEDAQ | 14287 | SGKQHED | 0.087338 | -0.23173 |
| SyS2846 | 5110 | GCCCAAATTGGGAATCTGCAGGCGACGGCACAG | 9699 | AQIGNLQATAQ | 14288 | IGNLQAT | 0.087023 | -0.15011 |
| SyS2847 | 5111 | GCCCAACCTGATGCTTCTCAGCGGGTTGCACAG | 9700 | AQPDASQRVAQ | 14289 | PDASQRV | 0.087004 | -0.16283 |
| SyS2849 | 5112 | GCCCAAGCTGTGGATAGGATGACGCCTGCACAG | 9701 | AQAVDRMTPAQ | 14290 | AVDRMTP | 0.086492 | -0.04762 |
| GP229 | 5113 | GCCCAATTTGGGCGTGAGAAGCCGGCTGCACAG | 9702 | AQFGREKPAAQ | 14291 | FGREKPA | 0.086492 | -0.0728 |
| GS1619 | 5114 | GCCCAACTTAATAATAGGCCGCAGTTGGCACAG | 9703 | AQLNNRPQLAQ | 14292 | LNNRPQL | 0.086134 | -0.08574 |
| SyS2853 | 5115 | GCCCAAAATTTTCATGGTCGGACTGATGCACAG | 9704 | AQNFHGRTDAQ | 14293 | NFHGRTD | 0.085757 | -0.22042 |
| SyS2854 | 5116 | GCCCAAGGCGTCAGACTCAGCGACACCGCACAG | 9705 | AQGVRLSSTAQ | 14294 | GVRLSST | 0.085645 | -0.17875 |
| SyS2856 | 5117 | GCCCAAACCGTCAACAGCACAGACAAGCACAG | 9706 | AQTVNSHRQAQ | 14295 | TVNSHRQ | 0.085229 | -0.1986 |
| SyP82 | 5118 | GCCCAAAATAGTAATCATACGCCTAGGGCACAG | 9707 | AQNSNHTPRAQ | 14296 | NSNHTPR | 0.085172 | -0.04369 |
| SyS2857 | 5119 | GCCCAAGCCAACACCATCACCGTCGTCGCACAG | 9708 | AQANTITVVAQ | 14297 | ANTITVV | 0.085083 | -0.19133 |
| GS1623 | 5120 | GCCCAAGACGTCACCCAAAGCAAACCCGCACAG | 9709 | AQDVTQSKPAQ | 14298 | DVTQSKP | 0.084872 | -0.16663 |
| TS181 | 5121 | GCCCAAGGTAATCATGCGGGTAATCTGGCACAG | 9710 | AQGNHARNLAQ | 14299 | GNHARNL | 0.084694 | -0.26297 |
| SyS2859 | 5122 | GCCCAACAACAGAGACACCAGCATATGGCACAG | 9711 | AQQHRDTSMAQ | 14300 | QHRDTSM | 0.084679 | -0.16708 |
| SyS2860 | 5123 | GCCCAACTGCAGGGTAGGCTGACGTCGGCACAG | 9712 | AQLQGRLTSAQ | 14301 | LQGRLTS | 0.084645 | -0.16466 |
| SyS2861 | 5124 | GCCCAAATTTCTATGAGGGAGCAGTCGGCACAG | 9713 | AQISMREQSAQ | 14302 | ISMREQS | 0.084611 | -0.16223 |
| GS1624 | 5125 | GCCCAAACCAGAAACTTCGACCACCGCACAG | 9714 | AQTRNFDHTAQ | 14303 | TRNFDHT | 0.084554 | -0.1756 |
| SyS2862 | 5126 | GCCCAAGCTAGTAATCAGCAGAGTCCTCATGGCACAG | 9715 | AQASHRAQIAQ | 14304 | ASHRAQI | 0.084508 | -0.06218 |
| GP232 | 5127 | GCCCAAAATCAGCAGAGTCCTCATAAGGCACAG | 9716 | AQNQQSPHKAQ | 14305 | NQQSPHK | 0.084412 | -0.06961 |
| SyS2863 | 5128 | GCCCAAAGGCCGGGGGAGTCGAATCCTGCACAG | 9717 | AQRPGESNPAQ | 14306 | RPGESNP | 0.084402 | -0.08538 |
| SyS2864 | 5129 | GCCCAAGCGCGTGATAGTAGTATTATGGCACAG | 9718 | AQARDSSIMAQ | 14307 | ARDSSIM | 0.084397 | -0.09353 |

FIG. 33 (Continued)

| | | | | | | | | |
|---|---|---|---|---|---|---|---|---|
| GS1625 | 5130 | GCCCAAACCGGCATGAGCACCCAAGTCGCACAG | 9719 | AQTGMSTQVAQ | 14308 | TGMSTQV | 0.084373 | -0.1586 |
| SyS2865 | 5131 | GCCCAAATGGGTGTGAAGGCGGATATTGCACAG | 9720 | AQMGVKADIAQ | 14309 | MGVKADI | 0.084327 | 0.025771 |
| SyS2866 | 5132 | GCCCAACAATTCAAAGGCATCACCCAAGCACAG | 9721 | AQQFKGITQAQ | 14310 | QFKGITQ | 0.084326 | -0.01044 |
| SyS2867 | 5133 | GCCCAACACAACAACAGCCCACCCACGCACAG | 9722 | AQHNNSPTHAQ | 14311 | HNNSPTH | 0.084074 | -0.23618 |
| SyS2868 | 5134 | GCCCAAGACAGCAACTTCACCGCGCGCACAG | 9723 | AQDSNFTSAAQ | 14312 | DSNFTSA | 0.083991 | -0.23133 |
| SyP83 | 5135 | GCCCAAGCGGTTCCGCATATGGGTACGGCACAG | 9724 | AQAVPHMGTAQ | 14313 | AVPHMGT | 0.083983 | -0.04282 |
| SyS2869 | 5136 | GCCCAAGTCGTCAGCCCCAACCTCATGGCACAG | 9725 | AQVVSPNLMAQ | 14314 | VVSPNLM | 0.083952 | -0.22891 |
| SyS2870 | 5137 | GCCCAACCCTTCCCCAAAACCCTCGACGCACAG | 9726 | AQPFPKTLDAQ | 14315 | PFPKTLD | 0.08395 | -0.19353 |
| GP233 | 5138 | GCCCAACAGAGTGCGGGTCTTGCGGAGGCACAG | 9727 | AQQSAGLAEAQ | 14316 | QSAGLAE | 0.083906 | -0.07245 |
| GS1627 | 5139 | GCCCAAGGCAAAGCCCACGACCTCGCCGCACAG | 9728 | AQGKAHDLAAQ | 14317 | GKAHDLA | 0.083898 | -0.17672 |
| GS1629 | 5140 | GCCCAACAAAGAATCAGCACCAACGCCGCACAG | 9729 | AQQRISTNAAQ | 14318 | QRISTNA | 0.083603 | -0.08402 |
| SyS2872 | 5141 | GCCCAATGGCTCACCACCGGCAGCAGCGCACAG | 9730 | AQWLTTGSSAQ | 14319 | WLTTGSS | 0.083427 | -0.22064 |
| SyS2873 | 5142 | GCCCAATACAGAGCCCAAGGCCCCCTCGCACAG | 9731 | AQYRAQGPLAQ | 14320 | YRAQGPL | 0.083416 | -0.18284 |
| SyS2874 | 5143 | GCCCAAGTGATGAAGAGGTATGATGAGGCACAG | 9732 | AQVMKRYDEAQ | 14321 | VMKRYDE | 0.083375 | -0.17799 |
| GS1631 | 5144 | GCCCAACTCGAATACAGCCAAAGAGACGCACAG | 9733 | AQLEYSQRDAQ | 14322 | LEYSQRD | 0.083359 | -0.18368 |
| SyS2876 | 5145 | GCCCAACTCCAAAAAGTCCACCTCGGCGCACAG | 9734 | AQLQKVHLGAQ | 14323 | LQKVHLG | 0.083283 | -0.16587 |
| GP234 | 5146 | GCCCAACGTTCTCATTCCATCCTTCGGCACAG | 9735 | AQRSHSHPSAQ | 14324 | RSHSHPS | 0.083166 | -0.07405 |
| SyS2878 | 5147 | GCCCAACACACTTCACCAGCACCGGCGCACAG | 9736 | AQHTFTSTGAQ | 14325 | HTFTSTG | 0.082801 | -0.06161 |
| GS1632 | 5148 | GCCCAATCTGTTGGTAGTGGTCCTGGTGCACAG | 9737 | AQSVGSGPGAQ | 14326 | SVGSGPG | 0.082658 | -0.1765 |
| SyS2880 | 5149 | GCCCAACAAAGCTTCAACGGCAGCAACGCACAG | 9738 | AQQSFNGSNAQ | 14327 | QSFNGSN | 0.08265 | -0.22557 |
| SyS2881 | 5150 | GCCCAAGTCACCGCCATCAGAGGCGCCGCACAG | 9739 | AQVTAIRGAAQ | 14328 | VTAIRGA | 0.082407 | -0.14105 |
| GS1634 | 5151 | GCCCAATTGGGAAGAGTCTTATAGTGCACAG | 9740 | AQLGKTSYSAQ | 14329 | LGKTSYS | 0.082225 | -0.12353 |
| SyS2882 | 5152 | GCCCAAAGCTACGATGGCGATGGCTTCTGCACAG | 9741 | AQSTMAMASAQ | 14330 | STMAMAS | 0.082049 | -0.13139 |
| SyS2883 | 5153 | GCCCAAGCTTCTGGTAGGTCTTCTGTGCACAG | 9742 | AQASGRSSAAQ | 14331 | ASGRSSA | 0.081913 | -0.13556 |
| SyS2884 | 5154 | GCCCAAGGCAGAACCCCCGCGGTCGAAGCACAG | 9743 | AQGRTPAVEAQ | 14332 | GRTPAVE | 0.081913 | -0.14283 |
| SyS2885 | 5155 | GCCCAAGGCAGAATCGACGTCAGCAGCGCACAG | 9744 | AQGRIDVSSAQ | 14333 | GRIDVSS | 0.081913 | -0.16223 |
| SyS2886 | 5156 | GCCCAAACCCCCAAAGTCAACAGCAGCGCACAG | 9745 | AQTPKVNSSAQ | 14334 | TPKVNSS | 0.081913 | -0.18648 |
| SyS2887 | 5157 | GCCCAAAGTGTTCGGAATTCGACTACTGCACAG | 9746 | AQSVRNSTTAQ | 14335 | SVRNSTT | 0.081913 | -0.1986 |
| SyS2888 | 5158 | GCCCAAGTTAATGGTGCTCAGCAGATTGCACAG | 9747 | AQVNGAQQIAQ | 14336 | VNGAQQI | 0.081913 | -0.20588 |
| SyS2889 | 5159 | GCCCAAAACAGAGCCGAAAGCTTCAGAGCACAG | 9748 | AQNRAESFRAQ | 14337 | NRAESFR | 0.081913 | -0.22042 |
| SyS2891 | 5160 | GCCCAACAACGACAGCCAGCGTCAGAGCACAG | 9749 | AQHDRASVRAQ | 14338 | HDRASVR | 0.081913 | -0.22285 |
| GS1637 | 5161 | GCCCAAGACAGCCCCAGCAGAGGCAGAGCACAG | 9750 | AQDSPSRGRAQ | 14339 | DSPSRGR | 0.081895 | -0.13812 |

FIG. 33 (Continued)

| | | | | | |
|---|---|---|---|---|---|
| GS1638 | GCCCAAAGCAACAACATCCACAGCAAAGCACAG | 5162 | AQSNNIIHSKAQ | 14340 | SNNIIHSK | 0.081895 | -0.13812 |
| GS1639 | GCCCAAATCAACAACACATCGTCATCCCGCACAG | 5163 | AQINNIVIPAQ | 14341 | INNIVIP | 0.081806 | -0.18149 |
| GS1640 | GCCCAAATTCGGAGTTCTGATGAGACGGCACAG | 5164 | AQIRSSDETAQ | 14342 | IRSSDET | 0.081637 | -0.17201 |
| SyS2893 | GCCCAAAACATGCCCAGCTCGTCGCCGCACACAG | 5165 | AQNMPSLVAAQ | 14343 | NMPSLVA | 0.081507 | -0.07591 |
| GP235 | GCCCAAAATAGGACGGCTGGAGTCTATTGCACAG | 5166 | AQNRTLESIAQ | 14344 | NRTLESI | 0.081383 | -0.06975 |
| SyS2894 | GCCCAACCCAACAACAACAACCAACCGCACAG | 5167 | AQPQHNNQPAQ | 14345 | PQHNNQP | 0.081218 | -0.05341 |
| GS1643 | GCCCAACTCGGCTACAACGCCCACCCGCACAG | 5168 | AQLGYNAHPAQ | 14346 | LGYNAHP | 0.080886 | -0.12719 |
| SyS2897 | GCCCAACTCAAACACCAATACGACGGCGCACAG | 5169 | AQIKHQYDGAQ | 14347 | LKHQYDG | 0.080743 | -0.13435 |
| GS1644 | GCCCAACACTACAGCCCCACCAGAGAAGCACAG | 5170 | AQHYSPTREAQ | 14348 | HYSPTRE | 0.08058 | -0.13312 |
| GS1646 | GCCCAAAGCTACAGAAGCACCAGCGACGCACAG | 5171 | AQSYRSTSDAQ | 14349 | SYRSTSD | 0.080284 | -0.106 |
| SyS2898 | GCCCAAGTTACGCCTACTGCGGCTCTTGCACAG | 5172 | AQVTPTAALAQ | 14350 | VTPTAAL | 0.080182 | -0.22926 |
| SyS2899 | GCCCAATTGGAGCAGCGGTATAGTTCTGCACAG | 5173 | AQLEQRYSSAQ | 14351 | LEQRYSS | 0.080126 | -0.21194 |
| SyS2900 | GCCCAAATGAATAATATTAGGCAGTCTGCACAG | 5174 | AQMNNIRQSAQ | 14352 | MNNIRQS | 0.080126 | -0.21194 |
| GS1647 | GCCCAAAGTAGTCGTAATGATGCTTCTGCACAG | 5175 | AQSSRNDASAQ | 14353 | SSRNDAS | 0.079783 | -0.10036 |
| SyS2902 | GCCCAAGGCACCGACAGAAAACCCTTCGCACAG | 5176 | AQGTDRKPFAQ | 14354 | GTDRKPF | 0.07975 | -0.21202 |
| SyS2903 | GCCCAAAGAGTCAACAAAGAAGACAGAGCACAG | 5177 | AQRVNKEDRAQ | 14355 | RVNKEDR | 0.079514 | -0.2231 |
| SyS2904 | GCCCAAACCGGCAGAAGCCTCGCCACCGCACAG | 5178 | AQTGRSLATAQ | 14356 | TGRSLAT | 0.079216 | -0.16466 |
| SyS2905 | GCCCAAATGAAGTCTTCGACGTCGAATGCACAG | 5179 | AQMKSSTSNAQ | 14357 | MKSSTSN | 0.07906 | -0.22557 |
| GS1651 | GCCCAAAGACACGACCTCGCCAGCAACGCACAG | 5180 | AQRHDLASNAQ | 14358 | RHDLASN | 0.078859 | -0.16909 |
| SyS2906 | GCCCAATTGATGGCGGGTGTCTACTCCGGCACAG | 5181 | AQLMAVSTPAQ | 14359 | LMAVSTP | 0.078782 | -0.09648 |
| SyS2907 | GCCCAAAGAGAGAAGGCATCTACACCCTGCACAG | 5182 | AQREGIYTLAQ | 14360 | REGIYTL | 0.078638 | -0.1783 |
| SyS2910 | GCCCAAGACAACAAAGGCAGCCTCAGCGCACAG | 5183 | AQDNKGSLSAQ | 14361 | DNKGSLS | 0.078127 | -0.14438 |
| SyS2914 | GCCCAAAAGGCCAAGTCACCCACGGCGCACAG | 5184 | AQKGQVTHGAQ | 14362 | KGQVTHG | 0.077531 | -0.22434 |
| SyS2915 | GCCCAAAGTAAGACTCTGAATAATCTTGCACAG | 5185 | AQSKTLNNLAQ | 14363 | SKTLNNL | 0.077419 | -0.06551 |
| SyS2916 | GCCCAAAGGAATCCGCAGGTTCCTACTGCACAG | 5186 | AQRNPQVPTAQ | 14364 | RNPQVPT | 0.076921 | -0.20224 |
| SS210 | GCCCAAAGTGCGAATGCGTCTAATACTGCACAG | 5187 | AQSANASNTAQ | 14365 | SANASNT | 0.076865 | -0.34975 |
| GS1654 | GCCCAAGGCTACATGAAACCCGCCATCGCACAG | 5188 | AQGYMKPAIAQ | 14366 | GYMKPAI | 0.076811 | -0.13236 |
| SyS2917 | GCCCAAAGCAGCCACCAGGCACGGCCCACCGCACAG | 5189 | AQSSHGPTPAQ | 14367 | SSHGPTP | 0.076743 | -0.15738 |
| GS1655 | GCCCAAAGCAAGCACCAGAAACCCCCCAAGCACAG | 5190 | AQSTRNPPQAQ | 14368 | STRNPPQ | 0.076738 | -0.17386 |
| GS1656 | GCCCAACTCAACAGAATCAACGAACAAGCACAG | 5191 | AQLNRINEQAQ | 14369 | LNRINEQ | 0.076662 | -0.15138 |
| SyS2918 | GCCCAAGGGCGCCGCCAAAAGCCAAAACGCACAG | 5192 | AQGAAKSQNAQ | 14370 | GAAKSQN | 0.076533 | -0.22064 |
| SyS2919 | GCCCAACTCCCCACCCTCCACGCCCCGCACAG | 5193 | AQLPTLHGPAQ | 14371 | LPTLHGP | 0.076416 | -0.16951 |

FIG. 33 (Continued)

| | | | | | | | | |
|---|---|---|---|---|---|---|---|---|
| SyS2920 | 5194 | GCCCAAGTCCCAGCACCATCAAAGGGCGCACAG | 9783 | AQVPSTIKGAQ | 14372 | VPSTIKG | 0.076072 | -0.06158 |
| GS1658 | 5195 | GCCCAAACGTCGTCTATGCGGGAGTCGGCACAG | 9784 | AQTSSMRESAQ | 14373 | TSSMRES | 0.076046 | -0.15574 |
| SyS2921 | 5196 | GCCCAACTCATGAGCAGCAACAACGCCGCACAG | 9785 | AQLMSSNNAAQ | 14374 | LMSSNNA | 0.076028 | 0.036405 |
| SyS2922 | 5197 | GCCCAAGCCAAAACCCAAAGCGCCACCGCACAG | 9786 | AQAKTQSATAQ | 14375 | AKTQSAT | 0.076006 | -0.23173 |
| SyS2923 | 5198 | GCCCAAAAGGAGGGGCAGTCTAGGTATGCACAG | 9787 | AQKEGQSRYAQ | 14376 | KEGQSRY | 0.076006 | -0.23173 |
| SyS2924 | 5199 | GCCCAAAAAGTCAACAGCAGCGGCCACCGCACAG | 9788 | AQKVNSSATAQ | 14377 | KVNSSAT | 0.075872 | -0.15657 |
| GS1659 | 5200 | GCCCAAAGAACCACCAGCCTCGTCGCCGCACAG | 9789 | AQRTTSLVAAQ | 14378 | RTTSLVA | 0.075859 | -0.16814 |
| GS1660 | 5201 | GCCCAAATGACTAATCAGAGTGCGCATGCACAG | 9790 | AQMTNQSAHAQ | 14379 | MTNQSAH | 0.075702 | -0.09086 |
| GS1661 | 5202 | GCCCAACCCCACATCAGAGGCGAAAACGCACAG | 9791 | AQPHIRGENAQ | 14380 | PHIRGEN | 0.075512 | -0.1774 |
| SyS2925 | 5203 | GCCCAAAGAACCCAAAGCAGCATCAGCGCACAG | 9792 | AQRTQSSISAQ | 14381 | RTQSSIS | 0.075407 | -0.11999 |
| SyS2927 | 5204 | GCCCAAATGTTTACGACGACGGGTGCGGCACAG | 9793 | AQMFTTGAAQ | 14382 | MFTTGA | 0.075331 | 0.191298 |
| GS1662 | 5205 | GCCCAAAGCAACATCAAACTCATGGCCGCACAG | 9794 | AQSNIKLMAAQ | 14383 | SNIKLMA | 0.075323 | -0.15001 |
| GS1663 | 5206 | GCCCAATCGACTCAGGGTACTCGGGATGCACAG | 9795 | AQSTQGTRDAQ | 14384 | STQGTRD | 0.075323 | -0.17577 |
| SyS2929 | 5207 | GCCCAAATTTTGTCGGGGCGTAATGGTGCACAG | 9796 | AQILSGRNGAQ | 14385 | ILSGRNG | 0.07519 | -0.16587 |
| GP238 | 5208 | GCCCAAGGGCTGAAGGTGTCTGGGTCTGCACAG | 9797 | AQGLKVSGSAQ | 14386 | GLKVSGS | 0.075124 | -0.0719 |
| GS1666 | 5209 | GCCCAAACCGGCGCCAACCTCCCAACGCACAG | 9798 | AQTGANLPNAQ | 14387 | TGANLPN | 0.074952 | -0.18368 |
| SyS2933 | 5210 | GCCCAATACAGCCTCAGCATGCCCAACGCACAG | 9799 | AQYSLSMPNAQ | 14388 | YSLSMPN | 0.074455 | -0.19846 |
| SyS2934 | 5211 | GCCCAAACTTTTGAGAGGAAGGCTGCGGCACAG | 9800 | AQTFERKAAAQ | 14389 | TFERKAA | 0.07445 | -0.18527 |
| GS1667 | 5212 | GCCCAACTCGGCAGAGCCAGCAGCGTCGCACAG | 9801 | AQLGRASSVAQ | 14390 | LGRASSV | 0.074286 | -0.18637 |
| SyS2936 | 5213 | GCCCAAAGAACCAAAACCAGCGACGGCGCACAG | 9802 | AQRTKTSDGAQ | 14391 | RTKTSDG | 0.074203 | -0.15738 |
| SyS2937 | 5214 | GCCCAACTCAACCCCACCTCGGCCCGCACAG | 9803 | AQLNPHLGPAQ | 14392 | LNPHLGP | 0.074203 | -0.15738 |
| SyS2938 | 5215 | GCCCAAATCATGCCCAACACAACCATGGCACAG | 9804 | AQIMPNNTMAQ | 14393 | IMPNNTM | 0.074133 | -0.1923 |
| SyS2940 | 5216 | GCCCAACATAAGAGTGATAGTGGTTATGCACAG | 9805 | AQHKSDSGYAQ | 14394 | HKSDSGY | 0.073819 | -0.10745 |
| GS1670 | 5217 | GCCCAAGGATCGGCTGAATAAGAATAGTGCACAG | 9806 | AQDRLNKNSAQ | 14395 | DRLNKNS | 0.073374 | -0.03379 |
| GS1671 | 5218 | GCCCAAATGAGCGGCGGCGGCAGCAAAGCACAG | 9807 | AQMSGGSSKAQ | 14396 | MSGGSSK | 0.073582 | -0.18547 |
| GS1673 | 5219 | GCCCAACAGCGTGAGCAGGGGAATGCTGCACAG | 9808 | AQQREQGNAAQ | 14397 | QREQGNA | 0.073506 | -0.07984 |
| SyS2941 | 5220 | GCCCAAGGTGGTGGTAATGTGACGTCGGCACAG | 9809 | AQGGGNVTSAQ | 14398 | GGGNVTS | 0.073363 | -0.11899 |
| GP239 | 5221 | GCCCAAAATCTGAAGAATGCGGTATGTTGCACAG | 9810 | AQNLKNAYVAQ | 14399 | NLKNAYV | 0.073205 | -0.06961 |
| SyS2942 | 5222 | GCCCAAAGCAAGAGCAAAAACGACAGACCCGGCGCACAG | 9811 | AQSKNDRPGAQ | 14400 | SKNDRPG | 0.073138 | -0.12344 |
| SyS2943 | 5223 | GCCCAAAGAGAGGCAGCGGCCAAGAACATCGCACAG | 9812 | AQRGSGQDIAQ | 14401 | RGSGQDI | 0.0731 | -0.15374 |
| SyS2944 | 5224 | GCCCAAGTCGGCAGCAACACCAGCTACGCACAG | 9813 | AQVGSNTSYAQ | 14402 | VGSNTSY | 0.073063 | -0.03729 |
| SyS2946 | 5225 | GCCCAAGCCCCAGAATCGGCAGCACCGCACAG | 9814 | AQSPRIGSTAQ | 14403 | SPRIGST | 0.072976 | -0.21436 |

FIG. 33 (Continued)

| | | | | | | | | |
|---|---|---|---|---|---|---|---|---|
| SyS2947 | 5226 | GCCCAAGGTACTTTGAAGGAGACTAGTGCACAG | 9815 | AQGTLKETSAQ | 14404 | GTLKETS | 0.072976 | -0.21436 |
| SyS2948 | 5227 | GCCCAAAGCATCCAAAGAACCGTCGCCGCACAG | 9816 | AQSIQRTVAAQ | 14405 | SIQRTVA | 0.072957 | -0.12829 |
| SyS2950 | 5228 | GCCCAAGAGAGGCGAAAGCAACGGCACCGCACAG | 9817 | AQRGESNGTAQ | 14406 | RGESNGT | 0.072864 | -0.13071 |
| SyS2951 | 5229 | GCCCAAGAACCCAGCAACGCCAGAGTCGCACAG | 9818 | AQEPSNARVAQ | 14407 | EPSNARV | 0.072852 | -0.21448 |
| GS1674 | 5230 | GCCCAAAGCCAAGCCACCATGAACAAAGCACAG | 9819 | AQSQATMNKAAQ | 14408 | SQATMNK | 0.072824 | -0.03657 |
| SyS2952 | 5231 | GCCCAAGCCCAAGGCACCAGCACCACCGCACAG | 9820 | AQAQGTSTTAQ | 14409 | AQGTSTT | 0.072774 | 0.021058 |
| SyS2953 | 5232 | GCCCAATACATGAGCAAAAACAACCTCGCACAG | 9821 | AQYMSKNNLAQ | 14410 | YMSKNNL | 0.072703 | -0.08453 |
| GP241 | 5233 | GCCCAAAATACGACGAATATGTCGAAGGCACAG | 9822 | AQNTTNMSKAQ | 14411 | NTTNMSK | 0.072684 | -0.06642 |
| GS1675 | 5234 | GCCCAATCGAAGGCTTCTAAGACTGAGGCACAG | 9823 | AQSKASKTEAQ | 14412 | SKASKTE | 0.072653 | -0.15764 |
| SyS2955 | 5235 | GCCCAAATGGCTGGTTCTATTGTTACTGCACAG | 9824 | AQMAGSIVTAQ | 14413 | MAGSIVT | 0.072511 | -0.22164 |
| SyS2956 | 5236 | GCCCAAGTGAATTCGAGTCAGACTCCTGCACAG | 9825 | AQVNSSQTPAQ | 14414 | VNSSQTP | 0.07248 | -0.17875 |
| SyP88 | 5237 | GCCCAAACTCGTAGTGCTTCTTCTTGATGCACAG | 9826 | AQTRSALLDAQ | 14415 | TRSALLD | 0.07245 | -0.03959 |
| SyS2958 | 5238 | GCCCAAGGGATTAGTTATTCGCCTTCTGCACAG | 9827 | AQGISYSPSAQ | 14416 | GISYSPS | 0.072408 | -0.17433 |
| SyS2959 | 5239 | GCCCAACATGGGAGGGAGGTTCCGCCAGGCACAG | 9828 | AQHGREVPQAQ | 14417 | HGREVPQ | 0.07239 | 0.073051 |
| GS1677 | 5240 | GCCCAAACCAGAAGCGCCGACAACAGAGCACAG | 9829 | AQTRSADNRAQ | 14418 | TRSADNR | 0.072342 | -0.09862 |
| SyS2962 | 5241 | GCCCAATCTGGGAATTCGTCGCGTGGTGCACAG | 9830 | AQSGNSSRGAQ | 14419 | SGNSSRG | 0.0723 | -0.20216 |
| SyS2963 | 5242 | GCCCAAACGACGAAGGGGAATCCTTCGGCACAG | 9831 | AQTTKGNPSAQ | 14420 | TTKGNPS | 0.071966 | -0.20345 |
| GS1679 | 5243 | GCCCAAGAACATGAGAAGCACCAGAGACGCACAG | 9832 | AQDMRSTRDAQ | 14421 | DMRSTRD | 0.071824 | -0.16842 |
| SyS2964 | 5244 | GCCCAACTGGGTAATTCGTTGCCGGCTGCACAG | 9833 | AQLGNSLPAAQ | 14422 | LGNSLPA | 0.071809 | -0.02082 |
| GS1680 | 5245 | GCCCAATTGACTAGTATGTCGATTCCTGCACAG | 9834 | AQLTSMSIPAQ | 14423 | LTSMSIP | 0.071702 | -0.1756 |
| SyS2967 | 5246 | GCCCAAGGCACCCACATCAAACAAGCCGCACAG | 9835 | AQGTHIKQAAQ | 14424 | GTHIKQA | 0.071536 | -0.18527 |
| GS1681 | 5247 | GCCCAAACTCAGGGTCGTATTGTTAGTGCACAG | 9836 | AQTQGRIVSAQ | 14425 | TQGRIVS | 0.071228 | -0.1296 |
| SyS2970 | 5248 | GCCCAACTCGGCGGCAACAACACCCTCGCACAG | 9837 | AQLGGNNTLAQ | 14426 | LGGNNTL | 0.071141 | -0.11838 |
| SyS2971 | 5249 | GCCCAAATGTCTGCGAATAATGGTCGTGCACAG | 9838 | AQMSANNGRAQ | 14427 | MSANNGR | 0.071102 | -0.0887 |
| GP242 | 5250 | GCCCAAGTTACTAATCCGATGAGTGCGGCACAG | 9839 | AQVTNPMSAAQ | 14428 | VTNPMSA | 0.070957 | -0.07086 |
| SyS2972 | 5251 | GCCCAAGAGGCTTATAAGTCTACGTCGGCACAG | 9840 | AQEAYKSTSAQ | 14429 | EAYKSTS | 0.070916 | -0.17193 |
| SyS2975 | 5252 | GCCCAAAGACCCAACAACCAAGGCCAAGCACAG | 9841 | AQRPNNQGQAQ | 14430 | RPNNQGQ | 0.070759 | -0.15288 |
| SyS2976 | 5253 | GCCCAAATGAATTTTGCGGGTAGTGGTGCACAG | 9842 | AQMNFAGSGAQ | 14431 | MNFAGSG | 0.07066 | -0.13071 |
| GP243 | 5254 | GCCCAAAAGACTAATCATAGTTCGTCTGCACAG | 9843 | AQKTNHSSSAQ | 14432 | KTNHSSS | 0.070635 | -0.06975 |
| SyS2977 | 5255 | GCCCAAAATGGGTATGGGTCGCAGACGGCACAG | 9844 | AQNGYGSQTAQ | 14433 | NGYGSQT | 0.070529 | -0.0094 |
| SyS2978 | 5256 | GCCCAAAAAACCGGCCACCAATTCACCGCACAG | 9845 | AQKTGHQFTAQ | 14434 | KTGHQFT | 0.070429 | -0.21818 |
| SyS2979 | 5257 | GCCCAAACCGCCAGAACCCTCCAACTCGCACAG | 9846 | AQTARTLQLAQ | 14435 | TARTLQL | 0.070336 | -0.1247 |

FIG. 33 (Continued)

| | | | | | | | |
|---|---|---|---|---|---|---|---|
| SS213 | GCCCAACAAGCCAGCACCACCAAATCGCACAG | 9847 | AQQASTTQIAQ | 14436 | QASTTQI | 0.070288 | -0.3987 |
| SyS2980 | GCCCAAACTGCTTTTGATACGCCGTGGTGCACAG | 9848 | AQTAFDTRGAQ | 14437 | TAFDTRG | 0.070216 | -0.0582 |
| SyS2981 | GCCCAAGTCAACAGCCACGTCGCCAGAGCACAG | 9849 | AQVNSHVARAQ | 14438 | VNSHVAR | 0.070107 | 0.01137 |
| SyS2983 | GCCCAAAGTCCGCTTCATTCTAATACGGCACAG | 9850 | AQSPLHSNTAQ | 14439 | SPLHSNT | 0.069894 | -0.20951 |
| SyS2984 | GCCCAACTCAGCAGAGTCACCATCAACGCACAG | 9851 | AQLSRVTINAQ | 14440 | LSRVTIN | 0.069886 | -0.1307 |
| SyS2987 | GCCCAAACTACTGCAGCATAATGTGGATTCGGCACAG | 9852 | AQTQHNVDSAQ | 14441 | TQHNVDS | 0.069682 | -0.21448 |
| SyS2988 | GCCCAAACCTTCCAAACCAGCAACAGCGCACAG | 9853 | AQTFQTSNSAQ | 14442 | TFQTSNS | 0.069368 | 0.003859 |
| SyS2989 | GCCCAAAGTAATCATGTTAGTGTTAATGCACAG | 9854 | AQSNHVSVNAQ | 14443 | SNHVSVN | 0.069358 | -0.15496 |
| SyS2990 | GCCCAAATGCTCCACAGCAGCATCACCGCACAG | 9855 | AQMLHSSITAQ | 14444 | MLHSSIT | 0.069253 | -0.2231 |
| GS1685 | GCCCAACTGAAGGCTACTGATGGGTCGGCACAG | 9856 | AQLKATDGSAQ | 14445 | LKATDGS | 0.068961 | -0.16753 |
| GS1686 | GCCCAACTCGGCAACATGCACAACATGGCACAG | 9857 | AQLGNMHNMAQ | 14446 | LGNMHNM | 0.068637 | -0.10508 |
| SyS2993 | GCCCAAATCAACAGACTCATCAGCGGCGCACAG | 9858 | AQINRLISGAQ | 14447 | INRLISG | 0.068598 | 0.031034 |
| SyS2994 | GCCCAAACCAGAAGCAACCTCGCCAGCGCACAG | 9859 | AQTRSNLASAQ | 14448 | TRSNLAS | 0.068554 | -0.15288 |
| SyS2995 | GCCCAACATTCGAATGGTGTTAGGGGGGCACAG | 9860 | AQHSNGVRGAQ | 14449 | HSNGVRG | 0.06839 | -0.09686 |
| SyS2997 | GCCCAAGCCGGCAACCCCAGAGAAAAAGCACAG | 9861 | AQAGNPREKAQ | 14450 | AGNPREK | 0.068322 | -0.12337 |
| SyS2999 | GCCCAAAGAGCCAGAGACGTCGACGAAGCACAG | 9862 | AQRARDVDEAQ | 14451 | RARDVDE | 0.067899 | -0.17678 |
| SS217 | GCCCAAGTCAGCAACGGCCCCAGCCTCGCACAG | 9863 | AQVSNGPSLAQ | 14452 | VSNGPSL | 0.067877 | -0.37204 |
| GS1687 | GCCCAAGCGAATCAGAGGGGTGTTGGGGCACAG | 9864 | AQANQRGVGAQ | 14453 | ANQRGVG | 0.067791 | -0.14599 |
| GS1688 | GCCCAAATGAGAAGCGAAACCCTCAACGCACAG | 9865 | AQMRSETLNAQ | 14454 | MRSETLN | 0.06777 | -0.171 |
| GS1689 | GCCCAAAAACCCAGCAGCCAACTCCTCGCACAG | 9866 | AQKPSSQLLAQ | 14455 | KPSSQLL | 0.067749 | -0.10538 |
| SyS3000 | GCCCAAAGCCTCAGACCCCAGCAGAGCACAG | 9867 | AQSLRPHDRAQ | 14456 | SLRPHDR | 0.067635 | -0.23376 |
| SyS3002 | GCCCAAGGTTCGAATGCTTCGAAGTATGCACAG | 9868 | AQGSNASKYAQ | 14457 | GSNASKY | 0.067496 | -0.09073 |
| GS1690 | GCCCAAACCAACAGAGACCTCGGCCCCGCACAG | 9869 | AQTNRDLGPAQ | 14458 | TNRDLGP | 0.067362 | -0.23618 |
| SyS3004 | GCCCAATGGGGTCTACTGCGGGTGCTGCACAG | 9870 | AQWGSTAGAAQ | 14459 | WGSTAGA | 0.067211 | -0.14795 |
| SyS3005 | GCCCAAATCAGCGGCGCGGCGACAGAACCGCACAG | 9871 | AQISGADRTAQ | 14460 | ISGADRT | 0.067202 | -0.06067 |
| SyS3007 | GCCCAAAGCGCCGTCAGAAGCCCATCGCACAG | 9872 | AQSAVRSPIAQ | 14461 | SAVRSPI | 0.067136 | -0.18648 |
| GS1693 | GCCCAAAGAGTCAGCCACACGAAACCGCACAG | 9873 | AQRVSHTETAQ | 14462 | RVSHTET | 0.066771 | -0.12188 |
| SyS3008 | GCCCAAAAAGCCAACAGCCAAATCACCGCACAG | 9874 | AQKANSQITAQ | 14463 | KANSQIT | 0.066615 | -0.2268 |
| SyS3009 | GCCCAACCGAGTGTGTATCGTGAGCCTGCACAG | 9875 | AQPSVYREPAQ | 14464 | PSVYREP | 0.066506 | -0.19375 |
| SyS3010 | GCCCAAACCACCAACTTCGTCACCAGCGCACAG | 9876 | AQTTNFVTSAQ | 14465 | TTNFVTS | 0.066487 | -0.196 |
| SyS3011 | GCCCAAAACCTCATGCCCACCGACAGAGCACAG | 9877 | AQNLMPTDRAQ | 14466 | NLMPTDR | 0.066443 | -0.0508 |
| GS1695 | GCCCAACCAACCACCGGCCAGCAAGCACAG | 9878 | AQTNHTGSQAQ | 14467 | TNHTGSQ | 0.066407 | -0.16304 |

FIG. 33 (Continued)

| | | | | | | | | |
|---|---|---|---|---|---|---|---|---|
| GS1696 | 5290 | GCCCAACACTGGAACGGCACCAACCCGCACAG | 9879 | AQHWNGTNPAQ | 14468 | HWNGTNP | 0.066366 | -0.10986 |
| GS1697 | 5291 | GCCCAACATAAGTCTATTGGTCAGGAGGCACAG | 9880 | AQHKSIGQEAQ | 14469 | HKSIGQE | 0.066155 | -0.17768 |
| SyS3012 | 5292 | GCCCAAACTCGGCCGATTCCGATTAGTGCACAG | 9881 | AQTRPIPISAQ | 14470 | TRPIPIS | 0.065601 | -0.18769 |
| SyS3013 | 5293 | GCCCAAAACCCGGCATGAGCAGAATGGCACAG | 9882 | AQNPGMSRMAQ | 14471 | NPGMSRM | 0.065579 | -0.20345 |
| SyS3015 | 5294 | GCCCAAATTGCTAATCGGGTGTCGCCTGCACAG | 9883 | AQIANRVSPAQ | 14472 | IANRVSP | 0.065325 | -0.21325 |
| GP244 | 5295 | GCCCAAACGGCGGTTGGCGAATCAGAAGGCACAG | 9884 | AQTALANQKAQ | 14473 | TALANQK | 0.065317 | 0.093523 |
| SyS3016 | 5296 | GCCCAAACTTCGCTTTCTTCTTCTGCTGCACAG | 9885 | AQTSLSSSAAQ | 14474 | TSLSSSA | 0.06508 | -0.17118 |
| GS1700 | 5297 | GCCCAAGCTTTGACTGGTAATATGTCGGCACAG | 9886 | AQALTGNMSAQ | 14475 | ALTGNMS | 0.064735 | -0.13712 |
| GS1701 | 5298 | GCCCAAATGCAGAGAGAAGAATGTGCCGGCACAG | 9887 | AQMQTKNVPAQ | 14476 | MQTKNVP | 0.064729 | -0.16432 |
| GP246 | 5299 | GCCCAACAGGCGACTAAGACTAATGTTGCACAG | 9888 | AQQATKTNVAQ | 14477 | QATKTNV | 0.064527 | -0.07329 |
| GS1702 | 5300 | GCCCAACTCCACACCACCAGCAGCGTGCACAG | 9889 | AQLHTTSSVAQ | 14478 | LHTTSSV | 0.064309 | -0.06184 |
| GS1703 | 5301 | GCCCAATACGTCCAAAGCAGCAGCAACGCACAG | 9890 | AQYVQSSSNAQ | 14479 | YVQSSSN | 0.064226 | -0.18368 |
| SyS3017 | 5302 | GCCCAAACGATGAAGATTCGTACTGAGGCACAG | 9891 | AQTMKIRTEAQ | 14480 | TMKIRTE | 0.063807 | -0.19133 |
| SyS3019 | 5303 | GCCCAAAAGAGTCATTCGCCTGGGTCGGCACAG | 9892 | AQKSHSPGSAQ | 14481 | KSHSPGS | 0.063552 | -0.19375 |
| GP248 | 5304 | GCCCAAAAGGCGGTGGATCCTCCGAATGCACAG | 9893 | AQKAVDPPNAQ | 14482 | KAVDPPN | 0.06345 | -0.07301 |
| SyS3021 | 5305 | GCCCAAAATGCTCCTCCTATGAGTCCTGCACAG | 9894 | AQNAPPMSPAQ | 14483 | NAPPMSP | 0.063019 | -0.21194 |
| SyS3022 | 5306 | GCCCAAATCAACAAAAATGTTCACCCCGCACAG | 9895 | AQINKMFTPAQ | 14484 | INKMFTP | 0.062922 | -0.18245 |
| GS1704 | 5307 | GCCCAATATGTCTAAGGCGACTTTGGGTGCACAG | 9896 | AQYAKATLGAQ | 14485 | YAKATLG | 0.062788 | -0.15955 |
| GS1705 | 5308 | GCCCAACATCTTGCGCGCTCCGTCTGAGGCACAG | 9897 | AQHLARPSEAQ | 14486 | HLARPSE | 0.062657 | -0.14328 |
| SyS3024 | 5309 | GCCCAACAACTCAACAGCGACAGAAACGCACAG | 9898 | AQQLNSDRNAQ | 14487 | QLNSDRN | 0.062537 | -0.17678 |
| SyS3026 | 5310 | GCCCAAATGAGGCCTGATACTAGTTATGCACAG | 9899 | AQMRPDTSYAQ | 14488 | MRPDTSY | 0.061794 | -0.07565 |
| SyS3027 | 5311 | GCCCAAGGGCGTCGCCATGAGCAGGGCGCACAG | 9900 | AQGVAMSSGAQ | 14489 | GVAMSSG | 0.061421 | -0.22187 |
| SyS3028 | 5312 | GCCCAAGGTCATTCTAGGCCTGATCGGGCACAG | 9901 | AQGHSRPDRAQ | 14490 | GHSRPDR | 0.061217 | -0.21315 |
| SyS3029 | 5313 | GCCCAAGTCTTCCAAGCCACCAGAACCGCACAG | 9902 | AQVFQATRTAQ | 14491 | VFQATRT | 0.06105 | -0.14842 |
| SyP91 | 5314 | GCCCAAACTTCGTTGACGTCGTATACTGCACAG | 9903 | AQTSLTSYTAQ | 14492 | TSLTSYT | 0.06097 | -0.04186 |
| SyS3032 | 5315 | GCCCAAAAACTCAACACCGGCGACATCGCACAG | 9904 | AQKLNTGDIAQ | 14493 | KLNTGDI | 0.06088 | -0.09377 |
| GS1708 | 5316 | GCCCAAAGAACCAACGAAACCATCGTCGCACAG | 9905 | AQRTNETIVAQ | 14494 | RTNETIV | 0.060773 | -0.10144 |
| SyS3033 | 5317 | GCCCAAAGACTCCAAAACAGCACCCCCGCACAG | 9906 | AQRLQNSTPAQ | 14495 | RLQNSTP | 0.060769 | -0.14526 |
| SyS3036 | 5318 | GCCCAAACGTGCGGCTTACTAGTGGGGCACAG | 9907 | AQTSRLTSGAQ | 14496 | TSRLTSG | 0.060537 | -0.18284 |
| SyS3037 | 5319 | GCCCAAAGCAACACCACCTTCAGCGCGCACAG | 9908 | AQSNTTFSAAQ | 14497 | SNTTFSA | 0.060537 | -0.218 |
| SyS3038 | 5320 | GCCCAAGACCAAAGAAGCAGCCGCCGCACAG | 9909 | AQDQRSSPAAQ | 14498 | DQRSSPA | 0.060474 | 0.074204 |
| GS1709 | 5321 | GCCCAAGTTGGGAGTGGTGGGTCTCGTGCACAG | 9910 | AQVGSGGSRAQ | 14499 | VGSGGSR | 0.060342 | -0.18149 |

FIG. 33 (Continued)

| | | | | | | |
|---|---|---|---|---|---|---|
| SyS3039 | 5322 | GCCCAAAGAAGCACCAACGCCCCAAGCGCACAG | 9911 | AQRSTNAPNAQ | 14500 RSTNAPN | 0.060253 | -0.18527 |
| GP249 | 5323 | GCCCAAATGGCGGGTCAGCAGCGGTTGGCACAG | 9912 | AQMAGQQRLAQ | 14501 MAGQQRL | 0.060214 | -0.07405 |
| GS1710 | 5324 | GCCCAAATTAGGAATTCTGCTCCTCTGCACAG | 9913 | AQIRNSAPPAQ | 14502 IRNSAPP | 0.060006 | -0.16753 |
| SyS3040 | 5325 | GCCCAACTGTCGACTAAGAGTTTAATGCACAG | 9914 | AQLSTKSFNAQ | 14503 LSTKSFN | 0.059895 | -0.0596 |
| GS1711 | 5326 | GCCCAATGGCGCGGGGTCGATTACTGCGGCACAG | 9915 | AQWPGSITAAQ | 14504 WPGSITA | 0.059836 | -0.1026 |
| SS224 | 5327 | GCCCAAACCGGCGGCGTCCACGCCCAAGCACAG | 9916 | AQTGGVHAQAQ | 14505 TGGVHAQ | 0.059719 | -0.36534 |
| GS1713 | 5328 | GCCCAATCTGAGAGGTCGTCTATGGCTGCACAG | 9917 | AQSERSSMAAQ | 14506 SERSSMA | 0.059554 | -0.17386 |
| SyS3042 | 5329 | GCCCAATTTCAGAATGGTCGGAATAATGCACAG | 9918 | AQFQNGRNNAQ | 14507 FQNGRNN | 0.05943 | -0.22527 |
| SyS3045 | 5330 | GCCCAAGGCGGCAGCAGACTCCCCAAGCACAG | 9919 | AQGGSRLPQAQ | 14508 GGSRLPQ | 0.059246 | 0.005703 |
| SyS3047 | 5331 | GCCCAAGGCGGCAACAGCCTCAGCGTCGCACAG | 9920 | AQGGNSLSVAQ | 14509 GGNSLSV | 0.058708 | -0.19739 |
| SyS3048 | 5332 | GCCCAATCGAAGAAGATTGATCATGGTGCACAG | 9921 | AQSKKIDHGAQ | 14510 SKKIDHG | 0.058708 | -0.19739 |
| SyS3049 | 5333 | GCCCAATATCGTGATACGTTGGCGGCTGCACAG | 9922 | AQYRDTLAAAQ | 14511 YRDTLAA | 0.05864 | -0.10104 |
| GS1715 | 5334 | GCCCAACTCCACAGCGGGCGAAAGAAACGCACAG | 9923 | AQLHSGERNAQ | 14512 LHSGERN | 0.058356 | -0.13213 |
| SyS3050 | 5335 | GCCCAAATTATGCCTCATGGTTCGCCTGCACAG | 9924 | AQIMPHGSPAQ | 14513 IMPHGSP | 0.05825 | -0.17629 |
| SyS3051 | 5336 | GCCCAAACCGCCAGAACCCTCAACATGGCACAG | 9925 | AQTARTLNMAQ | 14514 TARTLNM | 0.05825 | -0.12147 |
| SyP93 | 5337 | GCCCAAGCTAGTGTTCAGGGCATAGTGCACAG | 9926 | AQASVQGHSAQ | 14515 ASVQGHS | 0.058222 | -0.04362 |
| SyS3054 | 5338 | GCCCAATTGAATAATGCTGGGAGGGCGGCACAG | 9927 | AQLNNAGRAAQ | 14516 LNNAGRA | 0.058102 | -0.20216 |
| SyS3056 | 5339 | GCCCAAGGCCTCAGAGGCAGCCACGCGCACAG | 9928 | AQGLRGSHAAQ | 14517 GLRGSHA | 0.058027 | -0.15011 |
| SyS3057 | 5340 | GCCCAATTTGTGCGTGATTCTTATTCGGCACAG | 9929 | AQFVRDSYSAQ | 14518 FVRDSYS | 0.057988 | -0.1214 |
| GS1716 | 5341 | GCCCAAGGCAGATTCACCGGCACCGAAGCACAG | 9930 | AQGRFTGTEAQ | 14519 GRFTGTE | 0.057942 | -0.17577 |
| SP53 | 5342 | GCCCAACGTCAGAATCCGATTGAGCTTGCACAG | 9931 | AQRQNPIELAQ | 14520 RQNPIEL | 0.057876 | -0.05124 |
| SyS3058 | 5343 | GCCCAAGTCAGAGAGACAAATTCGGCACCGCACAG | 9932 | AQVRDKFGTAQ | 14521 VRDKFGT | 0.057761 | -0.15253 |
| GS1717 | 5344 | GCCCAACTCCCCAGCAACAGCAACAGAGCACAG | 9933 | AQLPSNSNRAQ | 14522 LPSNSNR | 0.057489 | -0.18547 |
| SyS3061 | 5345 | GCCCAAGTCAGACAAGAAACACACCAGCGCACAG | 9934 | AQVRQEHTSAQ | 14523 VRQEHTS | 0.057485 | -0.13639 |
| SyS3062 | 5346 | GCCCAAATCAGACTACAGCAAAGCAACACCGCACAG | 9935 | AQIRQGPTNAQ | 14524 IRQGPTN | 0.057472 | -0.22434 |
| SyS3063 | 5347 | GCCCAAGACTACAGCAAAAGCAACACCGCACAG | 9936 | AQDYSKSNTAQ | 14525 DYSKSNT | 0.057421 | -0.11995 |
| SyS3064 | 5348 | GCCCAAATGTCGAATGTTAATGTTTCGGCACAG | 9937 | AQMSNVNVSAQ | 14526 MSNVNVS | 0.057014 | -0.22891 |
| SyS3066 | 5349 | GCCCAAATGAGCAGCGGCAGAAGCCTCGCACAG | 9938 | AQMSSGRSLAQ | 14527 MSSGRSL | 0.056536 | -0.21194 |
| SyS3067 | 5350 | GCCCAAGGCCTCAGAGACATCAGAGCGCACAG | 9939 | AQGLRDIRAAQ | 14528 GLRDIRA | 0.056134 | -0.21436 |
| SyS3068 | 5351 | GCCCAACTGATTTCTGCTCATAAGGGTGCACAG | 9940 | AQLISAHKGAQ | 14529 LISAHKG | 0.056125 | -0.18984 |
| SyS3069 | 5352 | GCCCAACCCATCAACACCACCGCGCCGCACAG | 9941 | AQPINTHAAAQ | 14530 PINTHAA | 0.055919 | -0.03722 |
| SyS3070 | 5353 | GCCCAAATGCCTCATGTGGGGAATGCTGCACAG | 9942 | AQMPHVGNAAQ | 14531 MPHVGNA | 0.055761 | -0.196 |

FIG. 33 (Continued)

| | | | | | | | |
|---|---|---|---|---|---|---|---|
| SyS3071 | 5354 | GCCCAATATGGTTCTTCTGCGATTAATGCACAG | 9943 | AQYGSSAINAQ | 14532 | YGSSAIN | 0.055471 | -0.22557 |
| SyS3073 | 5355 | GCCCAACATGCTTCTATGCCTAGTTCTGCACAG | 9944 | AQHASMPSSAQ | 14533 | HASMPSS | 0.055168 | -0.08783 |
| SyS3074 | 5356 | GCCCAATTTGGGGAGAATGCTCGTTTGCACAG | 9945 | AQFGENARFAQ | 14534 | FGENARF | 0.055162 | -0.131 |
| SyS3076 | 5357 | GCCCAATCTAGGCATGATTTGCCTTCTGCACAG | 9946 | AQSRHDLPSAQ | 14535 | SRHDLPS | 0.055032 | -0.20224 |
| SyS3077 | 5358 | GCCCAACGGTCGCAGGGTGCGAATATGGCACAG | 9947 | AQRSQGANMAQ | 14536 | RSQGANM | 0.054873 | -0.14214 |
| SyS3078 | 5359 | GCCCAAGCCAACAGCAACAGCCACAGCGCACAG | 9948 | AQANSNSHSAQ | 14537 | ANSNSHS | 0.054709 | 0.06627 |
| GP255 | 5360 | GCCCAACAGGCTAGGCAGAATCAGGGTGCACAG | 9949 | AQQARQNQGAQ | 14538 | QARQNQG | 0.054577 | -0.06905 |
| GS1723 | 5361 | GCCCAAGGTGTGGCTAGTAATACGACGGCACAG | 9950 | AQGVASNTTAQ | 14539 | GVASNTT | 0.054331 | -0.12484 |
| GS1724 | 5362 | GCCCAAAAGTATAGTTCTTCTCAGAGTGCACAG | 9951 | AQKYSSSQSAQ | 14540 | KYSSSQS | 0.054225 | -0.16528 |
| SyS3081 | 5363 | GCCCAAAGCGCCAAAACCCTCAACACCGCACAG | 9952 | AQSAKTLNTAQ | 14541 | SAKTLNT | 0.054008 | -0.06036 |
| SyS3082 | 5364 | GCCCAAGGCATCAGAACCAACGCCGCACAG | 9953 | AQGIRTTNAAQ | 14542 | GIRTTNA | 0.053754 | -0.12222 |
| GP257 | 5365 | GCCCAAATGAATACGACGATTAATAGGGCACAG | 9954 | AQMNTTINRAQ | 14543 | MNTTINR | 0.053729 | -0.06843 |
| SyS3083 | 5366 | GCCCAACTCAAAAACACCAGCCTCCCGCACAG | 9955 | AQLKNTSLPAQ | 14544 | LKNTSLP | 0.053711 | -0.19254 |
| GS1725 | 5367 | GCCCAAACTAATCGTGCTGCTACGATGGCACAG | 9956 | AQTNRAATMAQ | 14545 | TNRAATM | 0.053552 | -0.07849 |
| SyS3084 | 5368 | GCCCAACACGGCTACCCAAGTCCCGCACAG | 9957 | AQHGYPNVPAQ | 14546 | HGYPNVP | 0.053161 | -0.20955 |
| SyS3085 | 5369 | GCCCAATGGGGCTACAGAGGCGCCGAAGCACAG | 9958 | AQWGYRGAEAQ | 14547 | WGYRGAE | 0.053019 | -0.20683 |
| SyS3086 | 5370 | GCCCAACTCCTCGTCACCAACACCAGCGCACAG | 9959 | AQLLVTNTSAQ | 14548 | LLVTNTS | 0.052911 | -0.20586 |
| SP54 | 5371 | GCCCAAAAGAATCGTCTTCCTCCTGATGCACAG | 9960 | AQKNRLPPDAQ | 14549 | KNRLPPD | 0.052816 | -0.05331 |
| GP259 | 5372 | GCCCAATATCGTTCGCAGGAGCATCCGGCACAG | 9961 | AQYRSQEHPAQ | 14550 | YRSQEHP | 0.052745 | -0.07356 |
| GS1728 | 5373 | GCCCAACACGGCGGGCAGAGTCAGCCCGCACAG | 9962 | AQHGGRVSPAQ | 14551 | HGGRVSP | 0.052674 | -0.08274 |
| SP55 | 5374 | GCCCAAGGCAGAATAGGCTTGCTTCGGCACAG | 9963 | AQGQNRLASAQ | 14552 | GQNRLAS | 0.052585 | -0.05282 |
| GS1729 | 5375 | GCCCAACAGTCGGTTTCTGCTACGAGGGCACAG | 9964 | AQQSVSATRAQ | 14553 | QSVSATR | 0.052569 | -0.11912 |
| GS1730 | 5376 | GCCCAACAACAAGACCCATCCCCAAGCCGCACAG | 9965 | AQQRPIPQAAQ | 14554 | QRPIPQA | 0.052511 | -0.09282 |
| GP260 | 5377 | GCCCAACAGAGAGGGCGGATTGGTATTGGAGGCACAG | 9966 | AQQRAIGIEAQ | 14555 | QRAIGIE | 0.052081 | -0.06454 |
| GS1731 | 5378 | GCCCAATTTGGGCCATGTGGTGGTATTAATGCACAG | 9967 | AQFGHVGINAQ | 14556 | FGHVGIN | 0.052078 | -0.15412 |
| SyS3088 | 5379 | GCCCAATTTGAGCATGTTCGTTCGGAGGCACAG | 9968 | AQFEHVRSEAQ | 14557 | FEHVRSE | 0.051845 | -0.23618 |
| SyS3089 | 5380 | GCCCAAAAAGCGTCACCAGCAACACCGCACAG | 9969 | AQKSVTSNTAQ | 14558 | KSVTSNT | 0.051777 | -0.061 |
| SyS3090 | 5381 | GCCCAACTCACCGGCAACGTCACCGCCGCACAG | 9970 | AQLTGNVTAAQ | 14559 | LTGNVTA | 0.051576 | -0.21448 |
| GS1732 | 5382 | GCCCAAAATCATGCGCAGGGTAAGAGTGTTGCACAG | 9971 | AQNHAYPSAAQ | 14560 | NHAYPSA | 0.051489 | -0.16034 |
| SyS3091 | 5383 | GCCCAAATGCCGCAGGGTAAGAGTGTTGCACAG | 9972 | AQMPQGKSVAQ | 14561 | MPQGKSV | 0.051435 | -0.18163 |
| SyS3092 | 5384 | GCCCAACTCAGAACCGCCGCCACCAGCGCACAG | 9973 | AQLRTAATSAQ | 14562 | LRTAATS | 0.051386 | -0.23012 |
| SyS3095 | 5385 | GCCCAAGATTCTCAGCATCGGGTTTCTGCACAG | 9974 | AQDSQHRVSAQ | 14563 | DSQHRVS | 0.05101 | -0.15253 |

FIG. 33 (Continued)

| | | | | | | | | |
|---|---|---|---|---|---|---|---|---|
| SyS3096 | 5386 | GCCCAATTCCTCAACGAACACACCGTGCACAG | 9975 | AQFLNEHTVAQ | 14564 | FLNEHTV | 0.050937 | -0.10186 |
| SyS3098 | 5387 | GCCCAAAACAGCACCGGCACCAGCATGGCACAG | 9976 | AQNSTGTSMAQ | 14565 | NSTGTSM | 0.050651 | -0.03019 |
| SyP98 | 5388 | GCCCAACACATAGTCCTCCTATGTCGGCGGCACAG | 9977 | AQHSPPMSAAQ | 14566 | HSPPMSA | 0.05057 | -0.0435 |
| SyS3099 | 5389 | GCCCAATTGATGTCGCAGCGTCCTACGGCACAG | 9978 | AQLMSQRPTAQ | 14567 | LMSQRPT | 0.050441 | -0.22649 |
| SyS3100 | 5390 | GCCCAAAACACCAACGTCAACCCCCGCACAG | 9979 | AQNTNVNPPAQ | 14568 | NTNVNPP | 0.050347 | -0.18042 |
| SyS3104 | 5391 | GCCCAATGGGGTGGTTATTCTTCGGGTGCACAG | 9980 | AQWGGYSSAAQ | 14569 | WGGYSSA | 0.050081 | -0.2231 |
| GS1733 | 5392 | GCCCAATACAGCCTCAACCCAGCGGCGGCACAG | 9981 | AQYSLNPSGAQ | 14570 | YSLNPSG | 0.050057 | -0.05463 |
| GS1734 | 5393 | GCCCAAAAGAAAGCAAAGACAAGAGAGTCGCACAG | 9982 | AQKESKDRVAQ | 14571 | KESKDRV | 0.050049 | -0.18054 |
| SyS3105 | 5394 | GCCCAAAAGCTGGTGTGCAGTCCTGATGCACAG | 9983 | AQKLVSSPDAQ | 14572 | KLVSSPD | 0.049827 | -0.16829 |
| SyS3106 | 5395 | GCCCAAAACACCGCCAGCCACAACGCCGCACAG | 9984 | AQNTASHNAAQ | 14573 | NTASHNA | 0.049827 | -0.16829 |
| SyS3107 | 5396 | GCCCAAGACATGAGCAACAAAACCTACGCACAG | 9985 | AQDMSNKTYAQ | 14574 | DMSNKTY | 0.049793 | -0.19133 |
| SyS3108 | 5397 | GCCCAACTCGTCCACAAAGACTTCCCGCACAG | 9986 | AQLVHKDFPAQ | 14575 | LVHKDFP | 0.049712 | -0.21571 |
| SyS3109 | 5398 | GCCCAAAAACCGCCCTCGCCCAAAACGCACAG | 9987 | AQKPALAQNAQ | 14576 | KPALAQN | 0.049542 | -0.23296 |
| GS1735 | 5399 | GCCCAAGGCAACGCGCCAACCAGCAAAGCACAG | 9988 | AQGNAQPSKAQ | 14577 | GNAQPSK | 0.049521 | -0.09141 |
| SyS3110 | 5400 | GCCCAAAGAGTCGCCCACACCGAAAACGCACAG | 9989 | AQRVAHTENAQ | 14578 | RVAHTEN | 0.049496 | -0.10715 |
| SyS3111 | 5401 | GCCCAAGTTTCTGCGTCTTTATGGGGGCACAG | 9990 | AQVSASFMAAQ | 14579 | VSASFMA | 0.049437 | -0.02125 |
| SyS3112 | 5402 | GCCCAACGGGGTGCTGACGGCTGATGCTGCACAG | 9991 | AQRVLTADAAQ | 14580 | RVLTADA | 0.049329 | -0.08038 |
| GS1737 | 5403 | GCCCAACCGTCGTCGGCCACAAACAAGCACAG | 9992 | AQTVVGTKQAQ | 14581 | TVVGTKQ | 0.049239 | -0.16241 |
| SyS3113 | 5404 | GCCCAACTTGCGAGGACGCAGCCTTCTGCACAG | 9993 | AQLARTQPSAQ | 14582 | LARTQPS | 0.049237 | -0.21679 |
| GS1738 | 5405 | GCCCAAATGTCAGTAGTCATTCTGCTGCACAG | 9994 | AQMSSSHSAAQ | 14583 | MSSSHSA | 0.049163 | -0.17768 |
| GP261 | 5406 | GCCCAACCGTCTTCGAAGTCTCCGTCGGCACAG | 9995 | AQPSSKSPSAQ | 14584 | PSSKSPS | 0.049142 | -0.0728 |
| GP262 | 5407 | GCCCAATATTCTGGTGCGATGTCGGTGGCACAG | 9996 | AQYSGAMSVAQ | 14585 | YSGAMSV | 0.049076 | -0.06114 |
| SyS3114 | 5408 | GCCCAACCGCCGCCTACGAAGTCGTATGCACAG | 9997 | AQPPPTKSYAQ | 14586 | PPPTKSY | 0.048985 | -0.00892 |
| SyP100 | 5409 | GCCCAATCTGCGCGCATGCTACGACGGCACAG | 9998 | AQSAPHATTAQ | 14587 | SAPHATT | 0.048581 | -0.04347 |
| SyS3116 | 5410 | GCCCAAGCTTCTAAGCCTATGGTTGCTGCACAG | 9999 | AQASKPMVAAQ | 14588 | ASKPMVA | 0.04844 | -0.2277 |
| SyS3117 | 5411 | GCCCAAACCCTCACCTACGGCGACAGAGCACAG | 10000 | AQTLTYGDRAQ | 14589 | TLTYGDR | 0.048421 | -0.20709 |
| SyS3118 | 5412 | GCCCAAGCCAGAAGCGACAGCAAAGACGCACAG | 10001 | AQARSDSKDAQ | 14590 | ARSDSKD | 0.048221 | -0.17505 |
| SyS3119 | 5413 | GCCCAAATGAGCAAAGCCGCCAGCCTCGCACAG | 10002 | AQMSKAASLAQ | 14591 | MSKAASL | 0.047752 | -0.19496 |
| SyS3121 | 5414 | GCCCAAAGCACCCACACCAGCGCCGTCGCACAG | 10003 | AQSTHTSAVAQ | 14592 | STHTSAV | 0.047188 | -0.1233 |
| GS1742 | 5415 | GCCCAAACTGCTCGTCTTCAGGATGGTGCACAG | 10004 | AQTARLQDGAQ | 14593 | TARLQDG | 0.047164 | -0.13739 |
| SyS3122 | 5416 | GCCCAAAGAACCCGTCCTCGGCCAACCCGCACAG | 10005 | AQRPVLGQPAQ | 14594 | RPVLGQP | 0.047021 | -0.22649 |
| SyS3123 | 5417 | GCCCAAGCCAGCTTCAAAACCGAAGTCGCACAG | 10006 | AQASFKTEVAQ | 14595 | ASFKTEV | 0.046975 | -0.08471 |

FIG. 33 (Continued)

| | | | | | | | | |
|---|---|---|---|---|---|---|---|---|
| GS1743 | 5418 | GCCCAAGTCACCAGAACCGTCAACGCCGCACAG | 10007 | AQVTRTVNAAQ | 14596 | VTRTVNA | 0.046915 | -0.16663 |
| SyS3125 | 5419 | GCCCAAGACCACGCCAGAAGCGGCGGCGCACAG | 10008 | AQDHARSGGAQ | 14597 | DHARSGG | 0.046836 | -0.21571 |
| GS1744 | 5420 | GCCCAAGACGACGCATTTGACGCGGTGAGTGCACAG | 10009 | AQTTHLTVSAQ | 14598 | TTHLTVS | 0.046543 | -0.10586 |
| SyS3126 | 5421 | GCCCAAGTCCCAAAAGCAACGGCACCGCACAG | 10010 | AQVPKSNGTAQ | 14599 | VPKSNGT | 0.046485 | -0.16708 |
| SyS3127 | 5422 | GCCCAAGACTCGGCGTCGGCCCGAAGCACAG | 10011 | AQRLGVGPEAQ | 14600 | RLGVGPE | 0.046192 | -0.17557 |
| SyS3128 | 5423 | GCCCAAAACAACAGACAAACCAGCGACGACGCACAG | 10012 | AQNNRQTSDAQ | 14601 | NNRQTSD | 0.046184 | -0.14302 |
| SyS3129 | 5424 | GCCCAAAGATTCACCAACAACAAGAAGCCGCACAG | 10013 | AQRFTNNEAAQ | 14602 | RFTNNEA | 0.045922 | 0.054373 |
| SyS3131 | 5425 | GCCCAAAGTTCGCATCAGATGCGGGGGGCACAG | 10014 | AQSSHQMRGAQ | 14603 | SSHQMRG | 0.045403 | -0.18648 |
| GS1745 | 5426 | GCCCAAACTACGATGGGGACGATGTTGGCACAG | 10015 | AQTTMGTMLAQ | 14604 | TTMGTML | 0.044961 | -0.14435 |
| SyS3133 | 5427 | GCCCAAACCAACGGCGGCGTCCCCATCGCACAG | 10016 | AQTNGGVPIAQ | 14605 | TNGGVPI | 0.04489 | -0.09496 |
| SyS3135 | 5428 | GCCCAAAAAAGCAACGAAGGCAACGGCGGCACAG | 10017 | AQKSNEGNGAQ | 14606 | KSNEGNG | 0.044718 | -0.06873 |
| SyS3137 | 5429 | GCCCAAAACGTCGCCATGACCACCCTCGCACAG | 10018 | AQNVAMTTLAQ | 14607 | NVAMTTL | 0.044662 | 0.069739 |
| SyS3138 | 5430 | GCCCAATACAGCGGCCACACCCCCATGGCACAG | 10019 | AQYSGHTPMAQ | 14608 | YSGHTPM | 0.044417 | 0.00379 |
| GP266 | 5431 | GCCCAAGGTACTCCGAATCGGGGCTGGCACAG | 10020 | AQGTPNRALAQ | 14609 | GTPNRAL | 0.0441 | -0.06683 |
| SyS3141 | 5432 | GCCCAAAGAAGCGGCCCACCCACCCGCCACAG | 10021 | AQRSGPTQPAQ | 14610 | RSGPTQP | 0.043925 | -0.19375 |
| SyS3142 | 5433 | GCCCAAATCTTCAACCTCAAACAAGACGCACAG | 10022 | AQIFNLKQDAQ | 14611 | IFNLKQD | 0.043579 | -0.0447 |
| SyS3143 | 5434 | GCCCAACACGCCATGAGCCTCAGCCCGCACAG | 10023 | AQHAMSLSPAQ | 14612 | HAMSLSP | 0.04335 | -0.14871 |
| SyS3144 | 5435 | GCCCAAGGCGAAAGCATGCTCAGAGAAGCACAG | 10024 | AQSESMLREAQ | 14613 | SESMLRE | 0.043343 | 0.006658 |
| SyS3146 | 5436 | GCCCAACTCCCCAGACCCCCCAAGCCGCACAG | 10025 | AQLPRPPQAAQ | 14614 | LPRPPQA | 0.043059 | -0.22187 |
| GP268 | 5437 | GCCCAACTTGGTCTTGGGGCTTTGTCTGCACAG | 10026 | AQLGLGALSAQ | 14615 | LGLGALS | 0.042709 | -0.07245 |
| SyS3148 | 5438 | GCCCAAATTCCTAAGTCGGCGGATATTGCACAG | 10027 | AQIPKSADIAQ | 14616 | IPKSADI | 0.042447 | -0.09151 |
| SyS3150 | 5439 | GCCCAAGCTCAGTCGTTGCGTACTATGGCACAG | 10028 | AQAQSLRTMAQ | 14617 | AQSLRTM | 0.042077 | -0.19113 |
| SyP103 | 5440 | GCCCAAATGCTTACTAGTTCGTTGGATGCACAG | 10029 | AQMLTSSLDAQ | 14618 | MLTSSLD | 0.041856 | -0.03909 |
| SyS3151 | 5441 | GCCCAAATCTACAGAGACAACGAAAGAGCACAG | 10030 | AQIYRDNERAQ | 14619 | IYRDNER | 0.041758 | -0.20345 |
| SyS3155 | 5442 | GCCCAAAGCCCCCCACCATGCCGCCGCACAG | 10031 | AQSPPTMPAAQ | 14620 | SPPTMPA | 0.041298 | -0.18769 |
| SyS3156 | 5443 | GCCCAACCTATGAGGAGTGGTACGCCTGCACAG | 10032 | AQPMRSGTPAQ | 14621 | PMRSGTP | 0.041276 | -0.10941 |
| GS1750 | 5444 | GCCCAACTCCTCAGCAAAAGCAGCGAAGCACAG | 10033 | AQLLSKSSEAQ | 14622 | LLSKSSE | 0.041269 | 0.009441 |
| SyS3157 | 5445 | GCCCAAACCGCCAACTTCCAAGAAAGAGCACAG | 10034 | AQTANFQERAQ | 14623 | TANFQER | 0.041022 | -0.22406 |
| GS1751 | 5446 | GCCCAAAGCGGCAACAGACACCCGTCACCGCACAG | 10035 | AQSGNRPVTAQ | 14624 | SGNRPVT | 0.040905 | -0.17381 |
| SyS3158 | 5447 | GCCCAACTGAATCAGGTTGATAGTCGTGCACAG | 10036 | AQLNQVDSRAQ | 14625 | LNQVDSR | 0.040817 | -0.14836 |
| SyS3159 | 5448 | GCCCAAATTACGCCGAGTTCTAGTAAGGCACAG | 10037 | AQITPSSSKAQ | 14626 | ITPSSSK | 0.040646 | -0.20224 |
| SyS3160 | 5449 | GCCCAAGATGTTTCGCTTACTAAGGCGGCACAG | 10038 | AQDVSLTKAAQ | 14627 | DVSLTKA | 0.040618 | -0.17351 |

FIG. 33 (Continued)

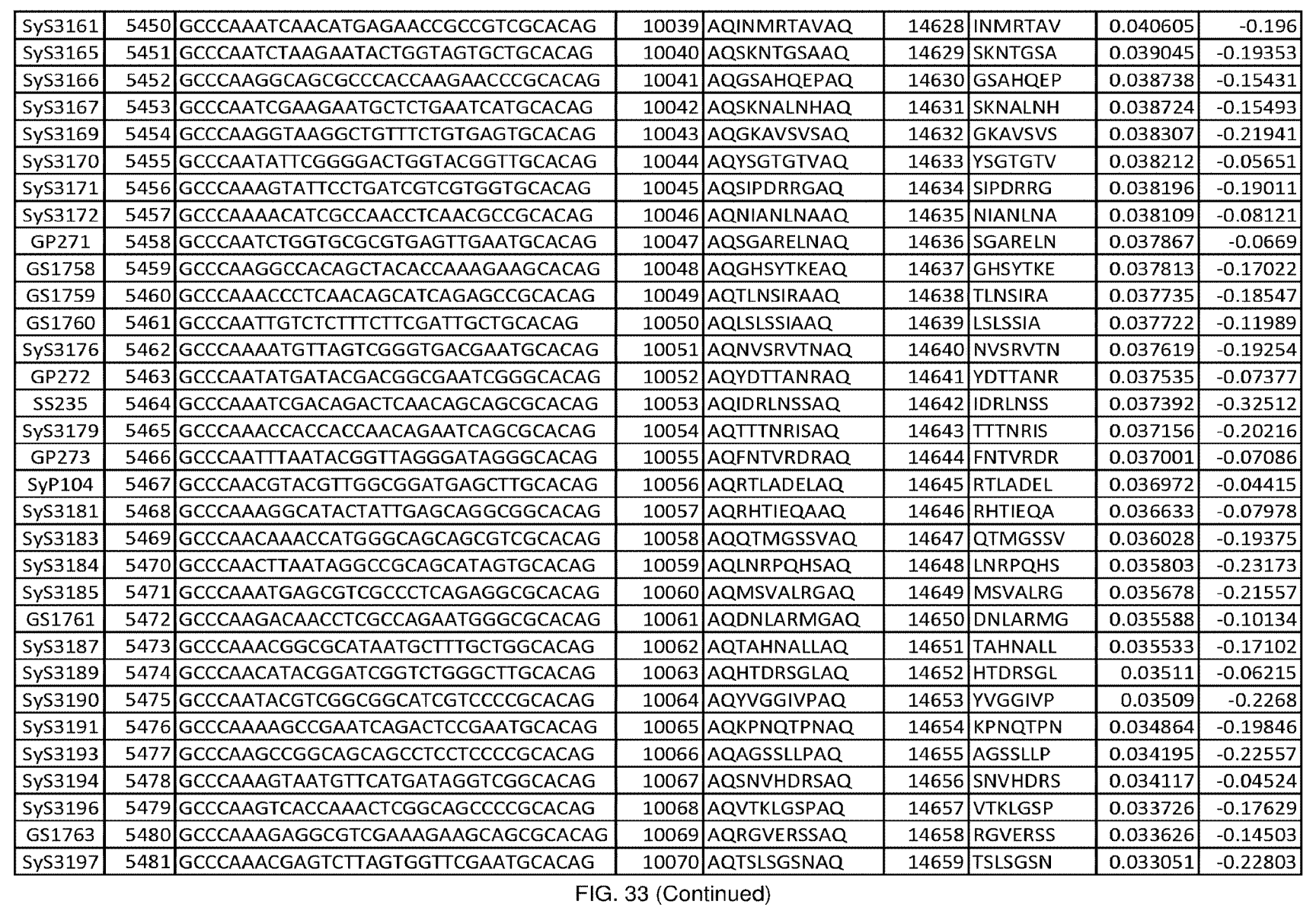

| | | | | | | | | |
|---|---|---|---|---|---|---|---|---|
| SyS3161 | 5450 | GCCCAAATCAACACATGAGAACCGCCGTCGCACAG | 10039 | AQINMRTAVAQ | 14628 | INMRTAV | 0.040605 | -0.196 |
| SyS3165 | 5451 | GCCCAATCTAAGAATACTGGTAGTGCTGCACAG | 10040 | AQSKNTGSAAQ | 14629 | SKNTGSA | 0.039045 | -0.19353 |
| SyS3166 | 5452 | GCCCAAGGCAGCGCCCACCAAGAACCGCACAG | 10041 | AQGSAHQEPAQ | 14630 | GSAHQEP | 0.038738 | -0.15431 |
| SyS3167 | 5453 | GCCCAATCGAAGAATGCTCTGAATCATGCACAG | 10042 | AQSKNALNHAQ | 14631 | SKNALNH | 0.038724 | -0.15493 |
| SyS3169 | 5454 | GCCCAAGGTAAGGCTGTTTCTGTGAGTGCACAG | 10043 | AQGKAVSVSAQ | 14632 | GKAVSVS | 0.038307 | -0.21941 |
| SyS3170 | 5455 | GCCCAATATTCGGGGACTGGTACGGTTGCACAG | 10044 | AQYSGTGTVAQ | 14633 | YSGTGTV | 0.038212 | -0.05651 |
| SyS3171 | 5456 | GCCCAAAGTATTCCTGATCGTCGTGGTGCACAG | 10045 | AQSIPDRRGAQ | 14634 | SIPDRRG | 0.038196 | -0.19011 |
| SyS3172 | 5457 | GCCCAAAACATCGCCAACCTCAACGCCGCACAG | 10046 | AQNIANLNAAQ | 14635 | NIANLNA | 0.038109 | -0.08121 |
| GP271 | 5458 | GCCCAATCTGGTGCGGTGAGTTGAATGCACAG | 10047 | AQSGARELNAQ | 14636 | SGARELN | 0.037867 | -0.0669 |
| GS1758 | 5459 | GCCCAAGGCCACAGCTACACCAAGAAGCACAG | 10048 | AQGHSYTKEAQ | 14637 | GHSYTKE | 0.037813 | -0.17022 |
| GS1759 | 5460 | GCCCAAACCCTCAACAGCATCAGAGCCGCACAG | 10049 | AQTLNSIRAAQ | 14638 | TLNSIRA | 0.037735 | -0.18547 |
| GS1760 | 5461 | GCCCAATTGTCTCTTCTTCGATTGCTGCACAG | 10050 | AQLSLSSIAAQ | 14639 | LSLSSIA | 0.037722 | -0.11989 |
| SyS3176 | 5462 | GCCCAAAATGTTAGTCGGGTGACGAATGCACAG | 10051 | AQNVSRVTNAQ | 14640 | NVSRVTN | 0.037619 | -0.19254 |
| GP272 | 5463 | GCCCAATATGATACGGACAGGCGAATCGGGCACAG | 10052 | AQYDTTANRAQ | 14641 | YDTTANR | 0.037535 | -0.07377 |
| SS235 | 5464 | GCCCAAATCGACAGACTCAACAGCAGCGCACAG | 10053 | AQIDRLNSSAQ | 14642 | IDRLNSS | 0.037392 | -0.32512 |
| SyS3179 | 5465 | GCCCAAACCACCACCAACAGAATCAGCGCACAG | 10054 | AQTTTNRISAQ | 14643 | TTTNRIS | 0.037156 | -0.20216 |
| GP273 | 5466 | GCCCAATTTAATACGGTTAGGGATAGGGCACAG | 10055 | AQFNTVRDRAQ | 14644 | FNTVRDR | 0.037001 | -0.07086 |
| SyP104 | 5467 | GCCCAACGTACGTTGGCGGATGAGCTTGCACAG | 10056 | AQRTLADELAQ | 14645 | RTLADEL | 0.036972 | -0.04415 |
| SyS3181 | 5468 | GCCCAAAGGCATACTATTGAGCAGGCGGCACAG | 10057 | AQRHTIEQAAQ | 14646 | RHTIEQA | 0.036633 | -0.07978 |
| SyS3183 | 5469 | GCCCAACAAACCATGGGCAGCAGCGTCGCACAG | 10058 | AQQTMGSSVAQ | 14647 | QTMGSSV | 0.036028 | -0.19375 |
| SyS3184 | 5470 | GCCCAACTTAATAGGCCGCAGCATAGTGCACAG | 10059 | AQINRPQHSAQ | 14648 | LNRPQHS | 0.035803 | -0.23173 |
| SyS3185 | 5471 | GCCCAAATGAGCGTCGCCCTCAGAGGCGCACAG | 10060 | AQMSVALRGAQ | 14649 | MSVALRG | 0.035678 | -0.21557 |
| GS1761 | 5472 | GCCCAAGACAACCTCGCCAGAATGGGCGCACAG | 10061 | AQDNLARMGAQ | 14650 | DNLARMG | 0.035588 | -0.10134 |
| SyS3187 | 5473 | GCCCAAACGGCGCATAATGCTTTGCTGGCACAG | 10062 | AQTAHNALLAQ | 14651 | TAHNALL | 0.035533 | -0.17102 |
| SyS3189 | 5474 | GCCCAACAACATACGGATCGGCGGCATCGCACAG | 10063 | AQHTDRSGLAQ | 14652 | HTDRSGL | 0.03511 | -0.06215 |
| SyS3190 | 5475 | GCCCAATACGTCGGGCGGCATCGTCCCGCACAG | 10064 | AQYVGGIVPAQ | 14653 | YVGGIVP | 0.03509 | -0.2268 |
| SyS3191 | 5476 | GCCCAAAAGCCGAATCAGACTCCGAATGCACAG | 10065 | AQKPNQTPNAQ | 14654 | KPNQTPN | 0.034864 | -0.19846 |
| SyS3193 | 5477 | GCCCAAGCCGGCAGCAGCCTCCTCCCCGCACAG | 10066 | AQAGSSLLPAQ | 14655 | AGSSLLP | 0.034195 | -0.22557 |
| SyS3194 | 5478 | GCCCAAAGTAATGTTCATGATAGGTCGGCACAG | 10067 | AQSNVHDRSAQ | 14656 | SNVHDRS | 0.034117 | -0.04524 |
| SyS3196 | 5479 | GCCCAAAGTCACCAAACTCGGCAGCCCGCACAG | 10068 | AQVTKLGSPAQ | 14657 | VTKLGSP | 0.033726 | -0.17629 |
| GS1763 | 5480 | GCCCAAAGAGGGCGTCGAAAGAAGCAGCGCACAG | 10069 | AQRGVERSSAQ | 14658 | RGVERSS | 0.033626 | -0.14503 |
| SyS3197 | 5481 | GCCCAAAACGAGTCTTAGTGGTTCGAATGCACAG | 10070 | AQTSLSGSNAQ | 14659 | TSLSGSN | 0.033051 | -0.22803 |

FIG. 33 (Continued)

| | | | | | | | |
|---|---|---|---|---|---|---|---|
| SyS3198 | 5482 | GCCCAACTCAGCCTCAGCACCAACAACGCACAG | 10071 | AQLSLSTNNAQ | 14660 | LSLSTNN | 0.03277 | -0.20588 |
| GS1766 | 5483 | GCCCAACTCGGCCAAATCACCAGACCGCACAG | 10072 | AQLGQITRPAQ | 14661 | LGQITRP | 0.032735 | -0.13666 |
| SyS3199 | 5484 | GCCCAAAATGCGTCTCCTGGGAGTAGTGCACAG | 10073 | AQNASPGSSAQ | 14662 | NASPGSS | 0.032455 | -0.15335 |
| SyS3200 | 5485 | GCCCAAATGAAGGCGAATAGTCTTTCGGCACAG | 10074 | AQMKANSLSAQ | 14663 | MKANSLS | 0.032347 | -0.16951 |
| SyS3201 | 5486 | GCCCAACATAAGGGGATGGCGAATTCGGCACAG | 10075 | AQHKGMANSAQ | 14664 | HKGMANS | 0.032108 | -0.14425 |
| GS1769 | 5487 | GCCCAAGGCAGAAACAACTACCCGACGCACAG | 10076 | AQGRNNYPDAQ | 14665 | GRNNYPD | 0.031842 | -0.09188 |
| SyS3204 | 5488 | GCCCAACTCCCGACCAAAAATGGCAAGCACAG | 10077 | AQLPDQKWQAQ | 14666 | LPDQKWQ | 0.031415 | -0.21325 |
| SyS3206 | 5489 | GCCCAAGGCGTCAACAACAGAGGCAGCGCACAG | 10078 | AQGVNNRGSAQ | 14667 | GVNNRGS | 0.0313 | 0.063353 |
| GS1771 | 5490 | GCCCAAAACAGAAATCGGCATGCAACCGCACAG | 10079 | AQNRIGMQPAQ | 14668 | NRIGMQP | 0.031094 | -0.07541 |
| SyS3208 | 5491 | GCCCAAGAGAAGGTGCCGAGTCTGAATGCACAG | 10080 | AQEKVPSLNAQ | 14669 | EKVPSLN | 0.031014 | -0.23012 |
| GS1772 | 5492 | GCCCAAGGCAGAGACAGCAGCAACCCGCACAG | 10081 | AQGRDSSNPAQ | 14670 | GRDSSNP | 0.030896 | -0.10468 |
| SyS3209 | 5493 | GCCCAAACGGCAGACCCAACCTCATGGCACAG | 10082 | AQTGRPNLMAQ | 14671 | TGRPNLM | 0.030687 | -0.22649 |
| SyS3212 | 5494 | GCCCAAGTGCGCGGCAGAAGCCCATGCACAG | 10083 | AQVAGRSPMAQ | 14672 | VAGRSPM | 0.030511 | -0.16344 |
| SyS3213 | 5495 | GCCCAACTCCCCACGTCAGCGTCCCGCACAG | 10084 | AQLPHVSVPAQ | 14673 | LPHVSVP | 0.030241 | -0.19618 |
| SyS3214 | 5496 | GCCCAACTCAGAACCGGCAGCTTCGCCGCACAG | 10085 | AQLRTGSFAAQ | 14674 | LRTGSFA | 0.029936 | -0.16587 |
| SyS3216 | 5497 | GCCCAAGGCGGGTGTTTCTAGTGGGAGTGCACAG | 10086 | AQAGVSSGSAQ | 14675 | AGVSSGS | 0.029244 | -0.14892 |
| GS1773 | 5498 | GCCCAATGGAGAGACAGCGGCCACGGCGCACAG | 10087 | AQWRDSGHGAQ | 14676 | WRDSGHG | 0.029219 | -0.16663 |
| SyS3217 | 5499 | GCCCAAAGCTTCGGCAACGACCGTCGCACAG | 10088 | AQSFGNRPVAQ | 14677 | SFGNRPV | 0.029098 | -0.20093 |
| SyS3218 | 5500 | GCCCAAAAAGTCAGCCACAACGGCGACGCACAG | 10089 | AQKVSHNGDAQ | 14678 | KVSHNGD | 0.029043 | -0.13435 |
| SyS3220 | 5501 | GCCCAAAACACCCCCTACGTCCAAGCACAG | 10090 | AQNTPPYVQAQ | 14679 | NTPPYVQ | 0.028913 | -0.09322 |
| SyS3222 | 5502 | GCCCAAAAGAAGGATAATAATCAGCCGCACAG | 10091 | AQKKDNNQPAQ | 14680 | KKDNNQP | 0.028636 | -0.07058 |
| GS1774 | 5503 | GCCCAAACTATTAAGTCTTTGCCTGTGGCACAG | 10092 | AQTIKSLPVAQ | 14681 | TIKSLPV | 0.028464 | -0.08628 |
| GS1775 | 5504 | GCCCAAATTAATGCGATGCGTCGCAGGCACAG | 10093 | AQINAMRSQAQ | 14682 | INAMRSQ | 0.028288 | -0.12055 |
| SyS3223 | 5505 | GCCCAAGGCAACAGCATCGCCAAAGGCGCACAG | 10094 | AQGNSIAKGAQ | 14683 | GNSIAKG | 0.028156 | -0.14283 |
| GP279 | 5506 | GCCCAAGTTACTACTCCTAAGGCTTTGCACAG | 10095 | AQVTTPKAFAQ | 14684 | VTTPKAF | 0.028102 | -0.07259 |
| SyS3224 | 5507 | GCCCAAGGCAGCGTCGCCGGCAGAGAGCACAG | 10096 | AQGSVAGSRAQ | 14685 | GSVAGSR | 0.028078 | -0.18614 |
| GS1777 | 5508 | GCCCAAAGTGCTAATAATGCTCCTAAGGCACAG | 10097 | AQSANNAPKAQ | 14686 | SANNAPK | 0.027939 | -0.14408 |
| GS1778 | 5509 | GCCCAAGGCAACGACTCAACCCCTCCCGCACAG | 10098 | AQDRLNPLPAQ | 14687 | DRLNPLP | 0.027045 | -0.07977 |
| GS1779 | 5510 | GCCCAAAGAAGAAACCACCACCGACGTCGCACAG | 10099 | AQRNQPTDVAQ | 14688 | RNQPTDV | 0.026888 | -0.09709 |
| SyS3227 | 5511 | GCCCAAACCCAAGTCGGCAGCGGCCCCGCACAG | 10100 | AQTQVGSGPAQ | 14689 | TQVGSGP | 0.026786 | 0.288018 |
| GS1780 | 5512 | GCCCAACTGAGTCAGGTTTCGGAGGCCGGCACAG | 10101 | AQLSQVSRPAQ | 14690 | LSQVSRP | 0.02663 | -0.1747 |
| SyS3228 | 5513 | GCCCAAAACGGCGCCAACCTTCCAAATGGCACAG | 10102 | AQNGANLQMAQ | 14691 | NGANLQM | 0.026629 | -0.03438 |

FIG. 33 (Continued)

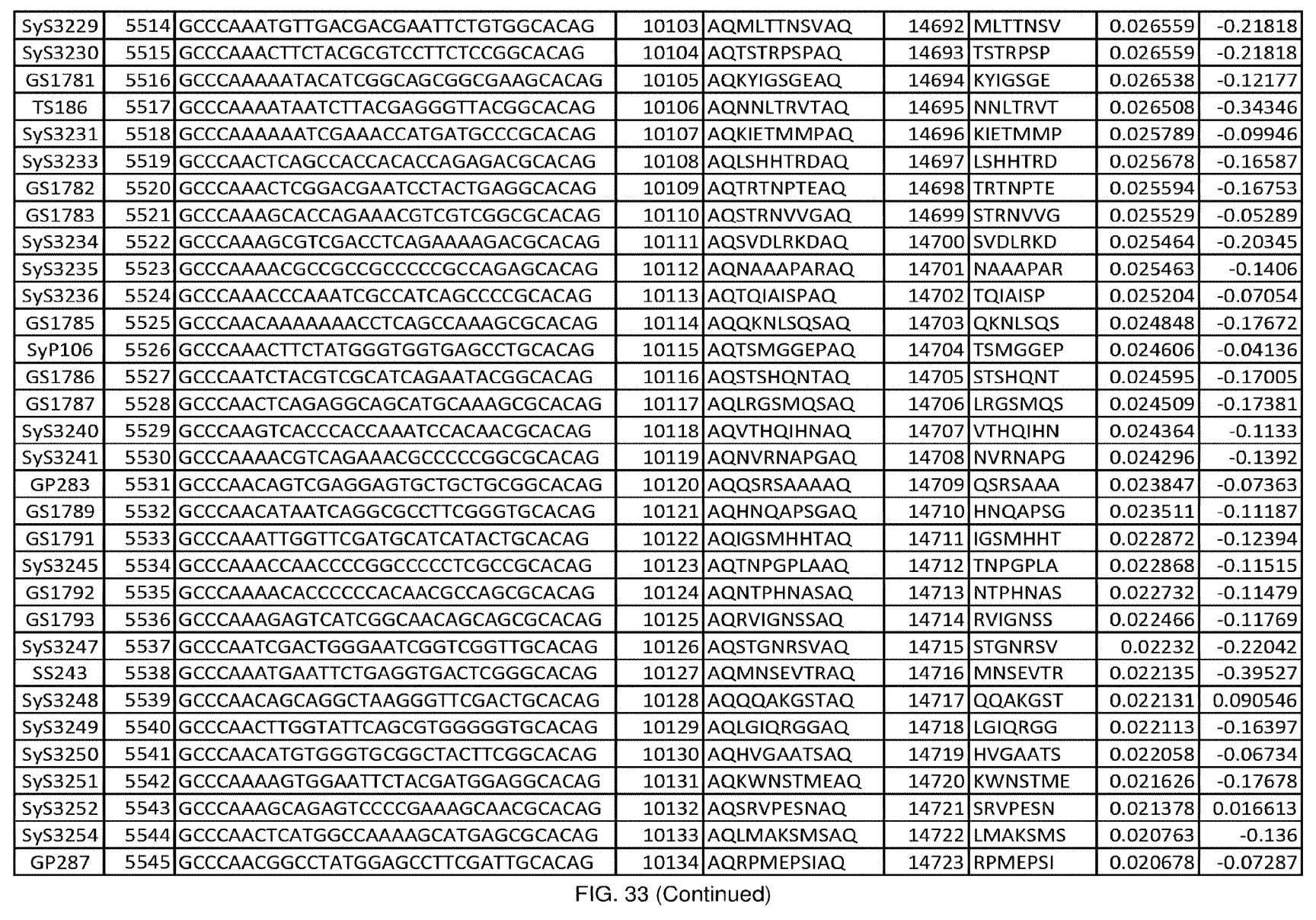

| | | | | | | | |
|---|---|---|---|---|---|---|---|
| SyS3229 | 5514 | GCCCAAATGTTGACGACGAATTCTGTGGCACAG | 10103 | AQMLTTNSVAQ | 14692 | MLTTNSV | 0.026559 | -0.21818 |
| SyS3230 | 5515 | GCCCAAACTTCTACGCGTCCTTCTCCGGCACAG | 10104 | AQTSTRPSPAQ | 14693 | TSTRPSP | 0.026559 | -0.21818 |
| GS1781 | 5516 | GCCCAAAATACATCGGCGGCGAAGCACAG | 10105 | AQKYIGSGEAQ | 14694 | KYIGSGE | 0.026538 | -0.12177 |
| TS186 | 5517 | GCCCAAAATAATCTTACGAGGGTTACGGCACAG | 10106 | AQNNLTRVTAQ | 14695 | NNLTRVT | 0.026508 | -0.34346 |
| SyS3231 | 5518 | GCCCAAAAAATCGAAACCATGATGCCCGCACAG | 10107 | AQKIETMMPAQ | 14696 | KIETMMP | 0.025789 | -0.09946 |
| SyS3233 | 5519 | GCCCAACTCAGCCACCACCAGAGACGCACAG | 10108 | AQLSHHTRDAQ | 14697 | LSHHTRD | 0.025678 | -0.16587 |
| GS1782 | 5520 | GCCCAAACTCGGACGAATCCTACTGAGGCACAG | 10109 | AQTRTNPTEAQ | 14698 | TRTNPTE | 0.025594 | -0.16753 |
| GS1783 | 5521 | GCCCAAAGCACCAGAAACGTCGTCGGCGCACAG | 10110 | AQSTRNVVGAQ | 14699 | STRNVVG | 0.025529 | -0.05289 |
| SyS3234 | 5522 | GCCCAAAGCGTCGACCTCAGAAAAGAGCACAG | 10111 | AQSVDLRKDAQ | 14700 | SVDLRKD | 0.025464 | -0.20345 |
| SyS3235 | 5523 | GCCCAAAACGCCGCGCCCCCGCCAGAGCACAG | 10112 | AQNAAAPARAQ | 14701 | NAAAPAR | 0.025463 | -0.1406 |
| SyS3236 | 5524 | GCCCAAACCCAAATCGCCATCAGCCCGCACAG | 10113 | AQTQIAISPAQ | 14702 | TQIAISP | 0.025204 | -0.07054 |
| GS1785 | 5525 | GCCCAACAAAAAAACCTCAGCCAAAGCGCACAG | 10114 | AQQKNLSQSAQ | 14703 | QKNLSQS | 0.024848 | -0.17672 |
| SyP106 | 5526 | GCCCAAACTTCTATGGGTGGTGAGCCTGCACAG | 10115 | AQTSMGGEPAQ | 14704 | TSMGGEP | 0.024606 | -0.04136 |
| GS1786 | 5527 | GCCCAATCTACGTCGCATCAGAATACGGCACAG | 10116 | AQSTSHQNTAQ | 14705 | STSHQNT | 0.024595 | -0.17005 |
| GS1787 | 5528 | GCCCAACTCAGAGGCAGCATGCAAAGCGCACAG | 10117 | AQLRGSMQSAQ | 14706 | LRGSMQS | 0.024509 | -0.17381 |
| SyS3240 | 5529 | GCCCAAGTCACCCACCAAATCCACAACGCACAG | 10118 | AQVTHQIHNAQ | 14707 | VTHQIHN | 0.024364 | -0.1133 |
| SyS3241 | 5530 | GCCCAAAACGTCAGAAAACGCCCCGGCGCACAG | 10119 | AQNVRNAPGAQ | 14708 | NVRNAPG | 0.024296 | -0.1392 |
| GP283 | 5531 | GCCCAACAGTCGAGGAGTGCTGCTGGGCACAG | 10120 | AQQSRSAAAAQ | 14709 | QSRSAAA | 0.023847 | -0.07363 |
| GS1789 | 5532 | GCCCACAACATAATCAGGCGCGCCTTCGGGGTGCACAG | 10121 | AQHNQAPSGAQ | 14710 | HNQAPSG | 0.023511 | -0.11187 |
| GS1791 | 5533 | GCCCAAATTGGTTCGATGCATCATACTGCACAG | 10122 | AQIGSMHHTAQ | 14711 | IGSMHHT | 0.022872 | -0.12394 |
| SyS3245 | 5534 | GCCCAAACCAACCCCGCCCCCTCGCCACAG | 10123 | AQTNPGPLAAQ | 14712 | TNPGPLA | 0.022868 | -0.11515 |
| GS1792 | 5535 | GCCCAAAACACCCCCACAAGCGCAGCGCACAG | 10124 | AQNTPHNASAQ | 14713 | NTPHNAS | 0.022732 | -0.11479 |
| GS1793 | 5536 | GCCCAAAGAGTCATCGGCAACAGCAGCGCACAG | 10125 | AQRVIGNSSAQ | 14714 | RVIGNSS | 0.022466 | -0.11769 |
| SyS3247 | 5537 | GCCCAATCGACTGGGAATCGGTCGGTTGCACAG | 10126 | AQSTGNRSVAQ | 14715 | STGNRSV | 0.02232 | -0.22042 |
| SS243 | 5538 | GCCCAAATGAATTCTGAGGTGACTCGGGCACAG | 10127 | AQMNSEVTRAQ | 14716 | MNSEVTR | 0.022135 | -0.39527 |
| SyS3248 | 5539 | GCCCAACAGCAGGCTAAGGGTTCGACTGCACAG | 10128 | AQQQAKGSTAQ | 14717 | QQAKGST | 0.022131 | 0.090546 |
| SyS3249 | 5540 | GCCCAACTTGGTATTCAGCGTGGGGGTGCACAG | 10129 | AQLGIQRGGAQ | 14718 | LGIQRGG | 0.022113 | -0.16397 |
| SyS3250 | 5541 | GCCCAACATGTGGGTGCGGCTACTTCGGCACAG | 10130 | AQHVGAATSAQ | 14719 | HVGAATS | 0.022058 | -0.06734 |
| SyS3251 | 5542 | GCCCAAAAGTGGAATTCTACGATGGAGGCACAG | 10131 | AQKWNSTMEAQ | 14720 | KWNSTME | 0.021626 | -0.17678 |
| SyS3252 | 5543 | GCCCAAAGCAGAGTCCCGAAAGCAACGCACAG | 10132 | AQSRVPESNAQ | 14721 | SRVPESN | 0.021378 | 0.016613 |
| SyS3254 | 5544 | GCCCAACTCATGGCCAAAAGCATGAGCGCACAG | 10133 | AQLMAKSMSAQ | 14722 | LMAKSMS | 0.020763 | -0.136 |
| GP287 | 5545 | GCCCAACGGCCTATGGAGCCTTCGATTGCACAG | 10134 | AQRPMEPSIAQ | 14723 | RPMEPSI | 0.020678 | -0.07287 |

FIG. 33 (Continued)

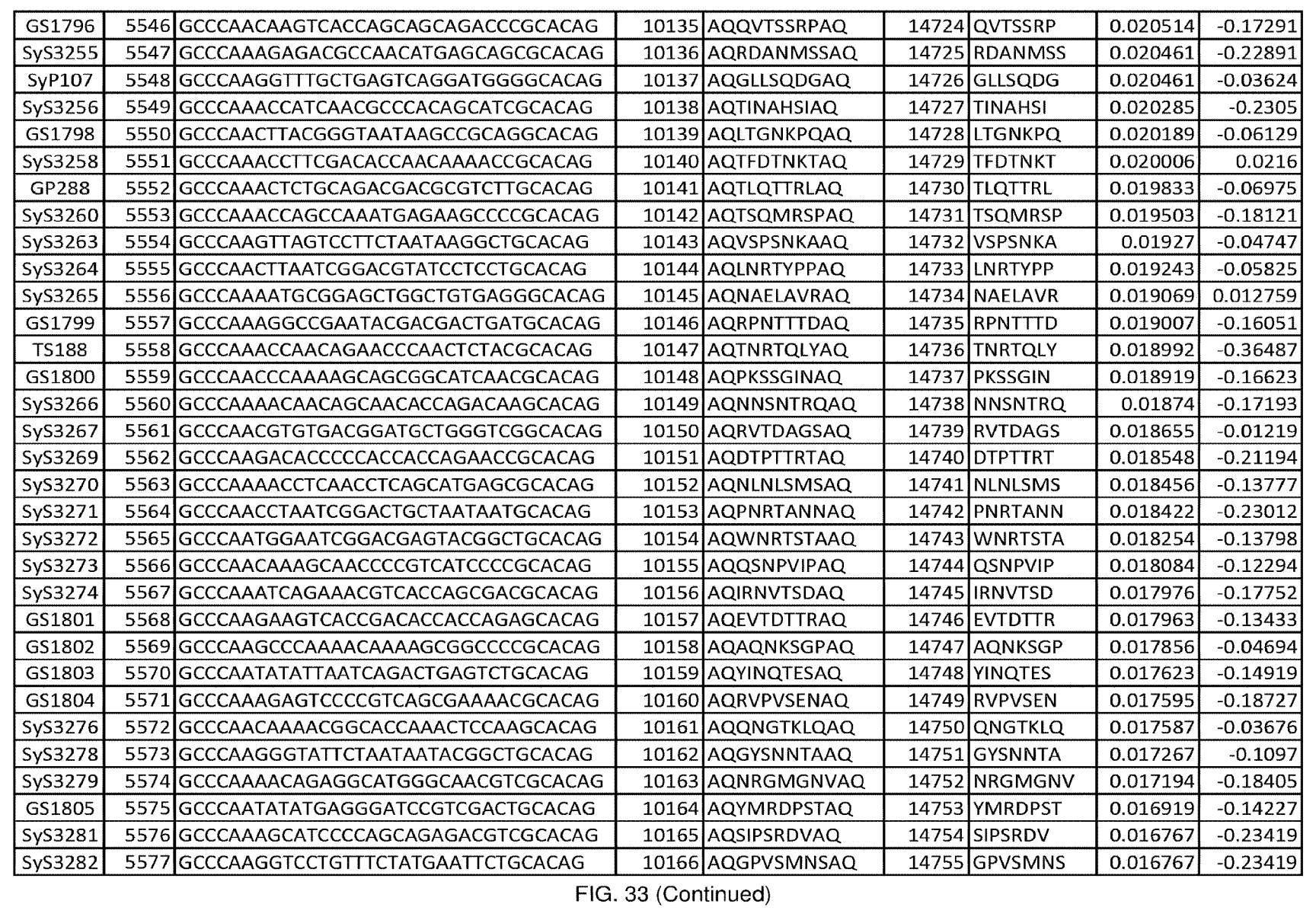

| | | | | | | | |
|---|---|---|---|---|---|---|---|
| GS1796 | 5546 | GCCCAACAAGTCACCAGCAGCAGACCCGCACAG | 10135 | AQQVTSSRPAQ | 14724 | QVTSSRP | 0.020514 | -0.17291 |
| SyS3255 | 5547 | GCCCAAAGAGAGCGCCAACATGAGCAGCGCACAG | 10136 | AQRDANMSSAQ | 14725 | RDANMSS | 0.020461 | -0.22891 |
| SyP107 | 5548 | GCCCAAGGTTTGCTGAGTCAGGATGGGGCACAG | 10137 | AQGLLSQDGAQ | 14726 | GLLSQDG | 0.020461 | -0.03624 |
| SyS3256 | 5549 | GCCCAAACCATCAACGCCCACAGCATCGCACAG | 10138 | AQTINAHSIAQ | 14727 | TINAHSI | 0.020285 | -0.2305 |
| GS1798 | 5550 | GCCCAACTTACGGGTAATAAGCCGCAGGCACAG | 10139 | AQLTGNKPQAQ | 14728 | LTGNKPQ | 0.020189 | -0.06129 |
| SyS3258 | 5551 | GCCCAAACCTTGCACCAACAAAACCGCACAG | 10140 | AQTFDTNKTAQ | 14729 | TFDTNKT | 0.020006 | 0.0216 |
| GP288 | 5552 | GCCCAAACTCTGCAGACGACGCGTCTTGCACAG | 10141 | AQTLQTRLAQ | 14730 | TLQTTRL | 0.019833 | -0.06975 |
| SyS3260 | 5553 | GCCCAAACCAGCCAAATGAGAAGCCCCGCACAG | 10142 | AQTSQMRSPAQ | 14731 | TSQMRSP | 0.019503 | -0.18121 |
| SyS3263 | 5554 | GCCCAAGTTAGTCCTTCTAATAAGGCTGCACAG | 10143 | AQVSPSNKAAQ | 14732 | VSPSNKA | 0.01927 | -0.04747 |
| SyS3264 | 5555 | GCCCAACTTAATCGGACGTATCCTCCTGCACAG | 10144 | AQLNRTYPPAQ | 14733 | LNRTYPP | 0.019243 | -0.05825 |
| SyS3265 | 5556 | GCCCAAAATGCGGAGCTGGCTGTGTGAGGGCACAG | 10145 | AQNAELAVRAQ | 14734 | NAELAVR | 0.019069 | 0.012759 |
| GS1799 | 5557 | GCCCAAAGGCCGAATACGACGACTGATGCACAG | 10146 | AQRPNTTTDAQ | 14735 | RPNTTTD | 0.019007 | -0.16051 |
| TS188 | 5558 | GCCCAAAACCAACAGAACCCAACTCTACGCACAG | 10147 | AQTNRTQLYAQ | 14736 | TNRTQLY | 0.018992 | -0.36487 |
| GS1800 | 5559 | GCCCAACCCAAAAGCAGCGGCATCAACGCACAG | 10148 | AQPKSSGINAQ | 14737 | PKSSGIN | 0.018919 | -0.16623 |
| SyS3266 | 5560 | GCCCAAAACAACAGCAACACCAGACAAGCACAG | 10149 | AQNNSNTRQAQ | 14738 | NNSNTRQ | 0.01874 | -0.17193 |
| SyS3267 | 5561 | GCCCAAGCGTGTGACGGATGCTGGGTCGGCACAG | 10150 | AQRVTDAGSAQ | 14739 | RVTDAGS | 0.018655 | -0.01219 |
| SyS3269 | 5562 | GCCCAAGACACCCCCACCACCAGAACCGCACAG | 10151 | AQDTPTTRTAQ | 14740 | DTPTTRT | 0.018548 | -0.21194 |
| SyS3270 | 5563 | GCCCAAAACCTCAACCTCAGCATGAGCGCACAG | 10152 | AQNLNLSMSAQ | 14741 | NLNLSMS | 0.018456 | -0.13777 |
| SyS3271 | 5564 | GCCCAACCTAATCGGACTGCTAATAATGCACAG | 10153 | AQPNRTANNAQ | 14742 | PNRTANN | 0.018422 | -0.23012 |
| SyS3272 | 5565 | GCCCAATGGAATCGGACGAGTACGGCTGCACAG | 10154 | AQWNRTSTAAQ | 14743 | WNRTSTA | 0.018254 | -0.13798 |
| SyS3273 | 5566 | GCCCAACAAAGCAACCCCGTCATCCCCGCACAG | 10155 | AQQSNPVIPAQ | 14744 | QSNPVIP | 0.018084 | -0.12294 |
| SyS3274 | 5567 | GCCCAAATCAGAAAGTCACCAGCGACGCACAG | 10156 | AQIRNVTSDAQ | 14745 | IRNVTSD | 0.017976 | -0.17752 |
| GS1801 | 5568 | GCCCAAGAAGTCACCGACACCACCAGAGCACAG | 10157 | AQEVTDTTRAQ | 14746 | EVTDTTR | 0.017963 | -0.13433 |
| GS1802 | 5569 | GCCCAAGCCCAAAACAAAGGCGGCCCCGCACAG | 10158 | AQAQNKSGPAQ | 14747 | AQNKSGP | 0.017856 | -0.04694 |
| GS1803 | 5570 | GCCCAATATATTAATCAGACTGAGTCTGCACAG | 10159 | AQYINQTESAQ | 14748 | YINQTES | 0.017623 | -0.14919 |
| GS1804 | 5571 | GCCCAAAGAGTCCCCGTCAGCGAAAACGCACAG | 10160 | AQRVPVSENAQ | 14749 | RVPVSEN | 0.017595 | -0.18727 |
| SyS3276 | 5572 | GCCCAACAACAAAACGGCACCAAACTCCAAGCACAG | 10161 | AQQNGTKLQAQ | 14750 | QNGTKLQ | 0.017587 | -0.03676 |
| SyS3278 | 5573 | GCCCAAGGGTATTCTAATAATACGGCTGCACAG | 10162 | AQGYSNNTAAQ | 14751 | GYSNNTA | 0.017267 | -0.1097 |
| SyS3279 | 5574 | GCCCAAAACAGAGGCATGGGCAACGTCGCACAG | 10163 | AQNRGMGNVAQ | 14752 | NRGMGNV | 0.017194 | -0.18405 |
| GS1805 | 5575 | GCCCAATATATGAGGGATCCGTCGACTGCACAG | 10164 | AQYMRDPSTAQ | 14753 | YMRDPST | 0.016919 | -0.14227 |
| SyS3281 | 5576 | GCCCAAAGCATCCCCAGCAGAGACGTCGCACAG | 10165 | AQSIPSRDVAQ | 14754 | SIPSRDV | 0.016767 | -0.23419 |
| SyS3282 | 5577 | GCCCAAGGTCCTGTTTCTATGAATTCTGCACAG | 10166 | AQGPVSMNSAQ | 14755 | GPVSMNS | 0.016767 | -0.23419 |

FIG. 33 (Continued)

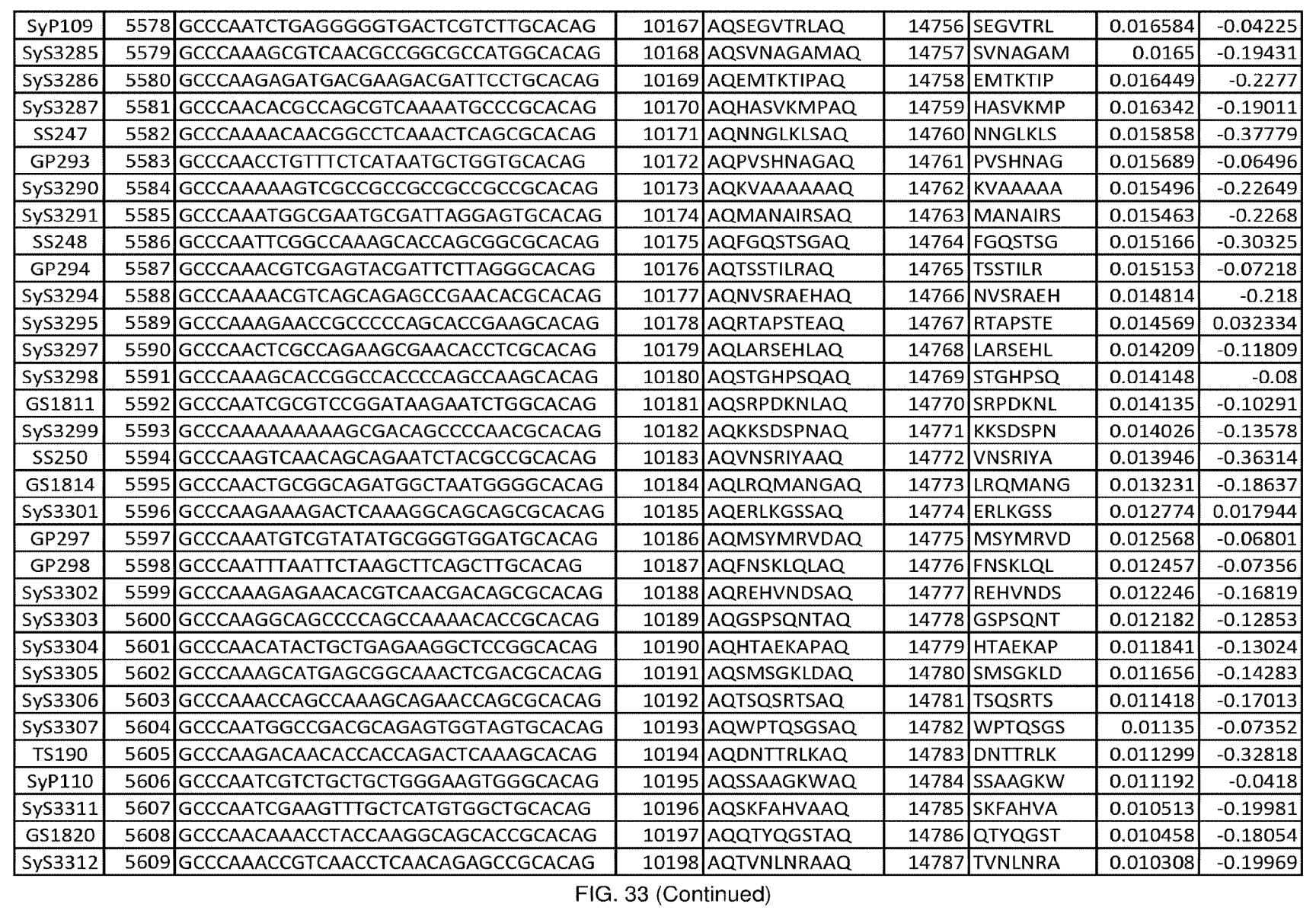

| | | | | | | | | |
|---|---|---|---|---|---|---|---|---|
| SyP109 | 5578 | GCCCAATCTGAGGGGGTGACTCGTCTTGCACAG | 10167 | AQSEGVTRLAQ | 14756 | SEGVTRL | 0.016584 | -0.04225 |
| SyS3285 | 5579 | GCCCAAAGCGTCAACGCCGGCGCCATGGCACAG | 10168 | AQSVNAGAMAQ | 14757 | SVNAGAM | 0.0165 | -0.19431 |
| SyS3286 | 5580 | GCCCAAGAGATGACGAAGACGATTCCTGCACAG | 10169 | AQEMIKTIPAQ | 14758 | EMIKTIP | 0.016449 | -0.2277 |
| SyS3287 | 5581 | GCCCAACACGCCAGCGTCAAAATGCCGCACAG | 10170 | AQHASVKMPAQ | 14759 | HASVKMP | 0.016342 | -0.19011 |
| SS247 | 5582 | GCCCAAAACAACGGCCTCAAACTCAGCGCACAG | 10171 | AQNNGLKLSAQ | 14760 | NNGLKLS | 0.015858 | -0.37779 |
| GP293 | 5583 | GCCCAACCTGTTTCTCATAATGCTGGTGCACAG | 10172 | AQPVSHNAGAQ | 14761 | PVSHNAG | 0.015689 | -0.06496 |
| SyS3290 | 5584 | GCCCAAAAAGTCGCCGCCGCCGCCGCACAG | 10173 | AQKVAAAAAQ | 14762 | KVAAAAA | 0.015496 | -0.22649 |
| SyS3291 | 5585 | GCCCAAATGGCGAATGCGATTAGGAGTGCACAG | 10174 | AQMANAIRSAQ | 14763 | MANAIRS | 0.015463 | -0.2268 |
| SS248 | 5586 | GCCCAATTCGGCCAAAGCACCAGCGGCGCACAG | 10175 | AQFGQSTSGAQ | 14764 | FGQSTSG | 0.015166 | -0.30325 |
| GP294 | 5587 | GCCCAAACGTCGAGTACGATTCTTAGGGCACAG | 10176 | AQTSSTILRAQ | 14765 | TSSTILR | 0.015153 | -0.07218 |
| SyS3294 | 5588 | GCCCAAAAACGTCAGCAGAGCCGAACACGCACAG | 10177 | AQNVSRAEHAQ | 14766 | NVSRAEH | 0.014814 | -0.218 |
| SyS3295 | 5589 | GCCCAAAGAACCGCCCCAGCACCGAAGCACAG | 10178 | AQRTAPSTEAQ | 14767 | RTAPSTE | 0.014569 | 0.032334 |
| SyS3297 | 5590 | GCCCAACTCGCCAGAAGCGAACACCTCGCACAG | 10179 | AQLARSEHLAQ | 14768 | LARSEHL | 0.014209 | -0.11809 |
| SyS3298 | 5591 | GCCCAAAGCACCGGCCACCCAGCCAAGCACAG | 10180 | AQSTGHPSQAQ | 14769 | STGHPSQ | 0.014148 | -0.08 |
| GS1811 | 5592 | GCCCAATCGCGTCCGGATAAGAATCTGGCACAG | 10181 | AQSRPDKNLAQ | 14770 | SRPDKNL | 0.014135 | -0.10291 |
| SyS3299 | 5593 | GCCCAAAAAAAGCGACAGCCCAACGCACAG | 10182 | AQKKSDSPNAQ | 14771 | KKSDSPN | 0.014026 | -0.13578 |
| SS250 | 5594 | GCCCAAGTCAACAGCAGAATCTACGCCGCACAG | 10183 | AQVNSRIYAAQ | 14772 | VNSRIYA | 0.013946 | -0.36314 |
| GS1814 | 5595 | GCCCAACTGCGGCAGAGATGGCTAATGGGGCACAG | 10184 | AQLRQMANGAQ | 14773 | LRQMANG | 0.013231 | -0.18637 |
| SyS3301 | 5596 | GCCCAAGAAAGACTCAAAGGCAGCAGCGCACAG | 10185 | AQERLKGSSAQ | 14774 | ERLKGSS | 0.012774 | 0.017944 |
| GP297 | 5597 | GCCCAAATGTCGTATATGCGGGTGGATGCACAG | 10186 | AQMSYMRVDAQ | 14775 | MSYMRVD | 0.012568 | -0.06801 |
| GP298 | 5598 | GCCCAATTTAATTCTAAGCTTCAGCTTGCACAG | 10187 | AQFNSKLQLAQ | 14776 | FNSKLQL | 0.012457 | -0.07356 |
| SyS3302 | 5599 | GCCCAAAGAGAACAGTCAACGACAGCGGCACAG | 10188 | AQREHVNDSAQ | 14777 | REHVNDS | 0.012246 | -0.16819 |
| SyS3303 | 5600 | GCCCAAGGCAGCCCAGCCAAAACACCGCACAG | 10189 | AQGSPSQNTAQ | 14778 | GSPSQNT | 0.012182 | -0.12853 |
| SyS3304 | 5601 | GCCCAACATACTGCTGAGAAGGCTCCGGCACAG | 10190 | AQHTAEKAPAQ | 14779 | HTAEKAP | 0.011841 | -0.13024 |
| SyS3305 | 5602 | GCCCAAAGCATGAGCGGCAAACTGACGCACAG | 10191 | AQSMSGKLDAQ | 14780 | SMSGKLD | 0.011656 | -0.14283 |
| SyS3306 | 5603 | GCCCAAACCAGCCAAAGCAGAACCAGCGCACAG | 10192 | AQTSQSRTSAQ | 14781 | TSQSRTS | 0.011418 | -0.17013 |
| SyS3307 | 5604 | GCCCAATGGCCGACGCAGAGTGGTAGTGCACAG | 10193 | AQWPTQSGSAQ | 14782 | WPTQSGS | 0.01135 | -0.07352 |
| TS190 | 5605 | GCCCAAGACAACACCACCAGACTCAAAGCACAG | 10194 | AQDNTTRLKAQ | 14783 | DNTTRLK | 0.011299 | -0.32818 |
| SyP110 | 5606 | GCCCAATCGTCTGCTGGGAAGTGGGCACAG | 10195 | AQSSAAGKWAQ | 14784 | SSAAGKW | 0.011192 | -0.0418 |
| SyS3311 | 5607 | GCCCAATCGAAGTTTGCTCATGTGGCTGCACAG | 10196 | AQSKFAHVAAQ | 14785 | SKFAHVA | 0.010513 | -0.19981 |
| GS1820 | 5608 | GCCCAACAACAAACCTACCAAGGCAGCACCGCACAG | 10197 | AQQTYQGSTAQ | 14786 | QTYQGST | 0.010458 | -0.18054 |
| SyS3312 | 5609 | GCCCAAACCGTCAACCTCAACAGAGCGCCGCACAG | 10198 | AQTVNLNRAAQ | 14787 | TVNLNRA | 0.010308 | -0.19969 |

FIG. 33 (Continued)

| | | | | | | | | |
|---|---|---|---|---|---|---|---|---|
| SyS3313 | 5610 | GCCCAAAGATACGGCAGCAGCCTCCCGCACAG | 10199 | AQRYGSSLPAQ | 14788 | RYGSSLP | 0.009869 | -0.21072 |
| GS1822 | 5611 | GCCCAAAGAAGCAACAGCAGCAGCAGCAACCTCGCACAG | 10200 | AQRSNSSNLAQ | 14789 | RSNSSNL | 0.009735 | -0.09744 |
| GS1823 | 5612 | GCCCAACAAGGCCCAGCATCAGAGACGCACAG | 10201 | AQQGPSIRDAQ | 14790 | QGPSIRD | 0.00931 | -0.17112 |
| GS1824 | 5613 | GCCCAATGGAGAGACCTGCCCCCCGTCGCACAG | 10202 | AQWRDLAPVAQ | 14791 | WRDLAPV | 0.009233 | -0.1186 |
| SyS3316 | 5614 | GCCCAACACAGCGACATCCAAAGACCCGCACAG | 10203 | AQHSDIQRPAQ | 14792 | HSDIQRP | 0.009085 | -0.01571 |
| GS1825 | 5615 | GCCCAATTGGGCGGCGATGACGAATGCTGCACAG | 10204 | AQLAAMTNAAQ | 14793 | LAAMTNA | 0.008985 | -0.10156 |
| SyS3317 | 5616 | GCCCAAAGCGCCAACCACACCACCGCACAG | 10205 | AQSANHTHTAQ | 14794 | SANHTHT | 0.008908 | -0.08086 |
| SyS3318 | 5617 | GCCCAAGGGAAGCTGTCGGTGGAGAATGCACAG | 10206 | AQGKLSVENAQ | 14795 | GKLSVEN | 0.008617 | -0.07767 |
| SyS3319 | 5618 | GCCCAAAAAACCGGCGCCAACCCCCCGCACAG | 10207 | AQKPGANPPAQ | 14796 | KPGANPP | 0.008265 | -0.07573 |
| GP301 | 5619 | GCCCAACTTACTGAGGGTCGTCATGATGCACAG | 10208 | AQLTEGRHDAQ | 14797 | LTEGRHD | 0.008187 | -0.07148 |
| SyP112 | 5620 | GCCCAACTTGGGTGAATATTTATCGGCACAG | 10209 | AQLGSNIYPAQ | 14798 | LGSNIYP | 0.00806 | -0.03861 |
| SyS3321 | 5621 | GCCCAAAACGGCGCCCACAGCAGCGAAGCACAG | 10210 | AQNGAHSSEAQ | 14799 | NGAHSSE | 0.007822 | -0.08193 |
| GS1826 | 5622 | GCCCAAAATACGATGGGTGGTGCGGGGCACAG | 10211 | AQNTMGGAAAQ | 14800 | NTMGGAA | 0.007814 | -0.14962 |
| SyS3322 | 5623 | GCCCAAGAGAACCCCATCGGCCAACCCGCACAG | 10212 | AQRTPIGQPAQ | 14801 | RTPIGQP | 0.007542 | -0.18648 |
| SyS3323 | 5624 | GCCCAATATAGTGTGGCTCAGCAGCCGGCACAG | 10213 | AQYSVAQQPAQ | 14802 | YSVAQQP | 0.007381 | -0.22064 |
| GP303 | 5625 | GCCCAACCTCATTCTAAGGGGATGCTTGCACAG | 10214 | AQPHSKGMLAQ | 14803 | PHSKGML | 0.007181 | -0.0685 |
| GS1827 | 5626 | GCCCAAGTTCGGCGCATGGGATGGGTGCACAG | 10215 | AQVPAHGMGMGAQ | 14804 | VPAHGMG | 0.007168 | -0.12619 |
| SyS3324 | 5627 | GCCCAAATTTGGTGGGGTTCCTCAGCGTGCACAG | 10216 | AQIGGVPQRAQ | 14805 | IGGVPQR | 0.007145 | -0.12889 |
| SyS3325 | 5628 | GCCCAAGTGCAGGGGACGGTTTCGAGGGCACAG | 10217 | AQVQGTVSRAQ | 14806 | VQGTVSR | 0.007118 | -0.15153 |
| SyS3326 | 5629 | GCCCAAAGTGGTGGGAGTGGTGCTCCTGCACAG | 10218 | AQSGGSGAPAQ | 14807 | SGGSGAP | 0.006964 | -0.05146 |
| SyS3327 | 5630 | GCCCAAAAAGTCCCACCCAAACGAAGCACAG | 10219 | AQKVPTQTEAQ | 14808 | KVPTQTE | 0.006686 | -0.09626 |
| SyS3328 | 5631 | GCCCAAATTTCGACGATGAAGCCTAGTGCACAG | 10220 | AQISTMKPSAQ | 14809 | ISTMKPS | 0.006591 | -0.15981 |
| SyS3329 | 5632 | GCCCAAAGCAGAGTCGTCGAACAAGCCGCACAG | 10221 | AQSRVVEQAAQ | 14810 | SRVVEQA | 0.006345 | -0.21818 |
| SyS3331 | 5633 | GCCCAAGTCCTCAGCAGACAAAGCACCGCACAG | 10222 | AQVLSRQSTAQ | 14811 | VLSRQST | 0.006155 | -0.23376 |
| SyS3332 | 5634 | GCCCAAGTCGTCACCACCACCAGCAGCATGGCACAG | 10223 | AQVVTTSSMAQ | 14812 | VVTTSSM | 0.006155 | -0.23376 |
| SyP114 | 5635 | GCCCAAAGTACGGGTTCTTCGGGGTTTGGCACAG | 10224 | AQSTGSSGLAQ | 14813 | STGSSGL | 0.006086 | -0.04068 |
| TS192 | 5636 | GCCCAACCCAACAGAGCCGCCAACAACGCACAG | 10225 | AQPNRAANNAQ | 14814 | PNRAANN | 0.005926 | -0.37804 |
| SyS3333 | 5637 | GCCCAATATCCTGTTAATAGTCAGCCTGCACAG | 10226 | AQYPVNSQPAQ | 14815 | YPVNSQP | 0.005608 | -0.22042 |
| SyS3334 | 5638 | GCCCAAAAAGCGCCAGCCCCTACGACGCACAG | 10227 | AQKSASPYDAQ | 14816 | KSASPYD | 0.005437 | -0.08849 |
| GS1830 | 5639 | GCCCAAAGCAAAAGTGGGGCGCCGGCACAG | 10228 | AQSKSWGAAAQ | 14817 | SKSWGAA | 0.005259 | -0.13947 |
| SyS3335 | 5640 | GCCCAATCTGCGATGCTGAAGGTTGATGCACAG | 10229 | AQSAMLKVDAQ | 14818 | SAMLKVD | 0.005199 | -0.20339 |
| SP62 | 5641 | GCCCAACGGAGTCAGACGATTCAGGCTGCACAG | 10230 | AQRSQTIQAAQ | 14819 | RSQTIQA | 0.004569 | -0.05254 |

FIG. 33 (Continued)

| | | | | | | | | |
|---|---|---|---|---|---|---|---|---|
| SyS3336 | 5642 | GCCCAACCCAGCAGCAGACTCGGCGACGCACAG | 10231 | AQPSRLGDAQ | 14820 | PSSRLGD | 0.004505 | 0.004214 |
| GS1831 | 5643 | GCCCAAATCGGCCCCAGAGGCACCCAAGCACAG | 10232 | AQIGPRGTQAQ | 14821 | IGPRGTQ | 0.004293 | -0.15764 |
| SyS3337 | 5644 | GCCCAAGCAGCAGCAAAGGCAATACCTCGCACAG | 10233 | AQASKGQYLAQ | 14822 | ASKGQYL | 0.004037 | -0.23497 |
| GP306 | 5645 | GCCCAAGTTAGGACTCTTACTGTTGATGCACAG | 10234 | AQVRTLTVDAQ | 14823 | VRTLTVD | 0.003991 | -0.06489 |
| SyS3339 | 5646 | GCCCAACGTGGGAATGCTGCGAATGAGGCACAG | 10235 | AQRGNAANEAQ | 14824 | RGNAANE | 0.003862 | -0.12561 |
| SyS3340 | 5647 | GCCCAATTCGGCAGCCACCCCAGCGTCGCACAG | 10236 | AQFGSHPSVAQ | 14825 | FGSHPSV | 0.003469 | -0.2231 |
| GP309 | 5648 | GCCCAAGGTCATCCGACTCCTGTTAATGCACAG | 10237 | AQGHPTPVNAQ | 14826 | GHPTPVN | 0.003421 | -0.06822 |
| GS1833 | 5649 | GCCCAAAGCCTCAACCCGTCAGAATGGCACAG | 10238 | AQSLNPVRMAQ | 14827 | SLNPVRM | 0.002868 | -0.1138 |
| GP312 | 5650 | GCCCAAAGTATTCGGGGTCAGCCTTTGCACAG | 10239 | AQSIRGQPFAQ | 14828 | SIRGQPF | 0.002583 | -0.07405 |
| GS1835 | 5651 | GCCCAAACCGCCAAATTCAACCAAGGCGCACAG | 10240 | AQTAKFNQGAQ | 14829 | TAKFNQG | 0.002515 | -0.11596 |
| SyS3342 | 5652 | GCCCAATTGATTTCGACGCATGATATGGCACAG | 10241 | AQLISTHDMAQ | 14830 | LISTHDM | 0.002485 | -0.14369 |
| SyS3345 | 5653 | GCCCAACAAAGCAGAGACAACATCAGAGCACAG | 10242 | AQQSRDNIRAQ | 14831 | QSRDNIR | 0.002214 | -0.11916 |
| SyS3346 | 5654 | GCCCAAAACAACGGCAACAAAGGCTTCGCACAG | 10243 | AQNNGNKGFAQ | 14832 | NNGNKGF | 0.002093 | -0.21325 |
| GP315 | 5655 | GCCCAAAATGTGAATTATGATGGGCGGGCACAG | 10244 | AQNVNYDGRAQ | 14833 | NVNYDGR | 0.001863 | -0.07225 |
| GS1841 | 5656 | GCCCAATTCATGAAAGGCGCCAGCGCCGCACAG | 10245 | AQFMKGASAAQ | 14834 | FMKGASA | 0.001531 | -0.15945 |
| SyS3349 | 5657 | GCCCAACTCGCCACCAGCACCCAAATGGCACAG | 10246 | AQLATSTQMAQ | 14835 | LATSTQM | 0.001488 | -0.218 |
| SyS3350 | 5658 | GCCCAAGTTCATGGTGGGTATTCGGCTGCACAG | 10247 | AQVHGGYSAAQ | 14836 | VHGGYSA | 0.001485 | -0.22434 |
| SS254 | 5659 | GCCCAAAGAGGCAGCAGCGAACCCATGCAAGCACAG | 10248 | AQRGSEPMQAQ | 14837 | RGSEPMQ | 0.001241 | -0.3679 |
| GP317 | 5660 | GCCCAAGGTCTGCGTACGAGTGGGACGCGGCACAG | 10249 | AQGLRTSGTAQ | 14838 | GLRTSGT | 0.001025 | -0.06413 |
| SyS3351 | 5661 | GCCCAACTCTACAAAGGCGGGCGTCAGCGCACAG | 10250 | AQLYKGGVSAQ | 14839 | LYKGGVS | 0.000806 | -0.23012 |
| SyS3353 | 5662 | GCCCAAATGAAAACCCACCACAGCCCCCGCACAG | 10251 | AQMKTHSPPAQ | 14840 | MKTHSPP | 0.000291 | -0.09473 |

FIG. 33 (Continued)

| Enrich_rank (within libraries) | SEQ ID NO: | Sequence | SEQ ID NO: | 11 mer Amino Acid | SEQ ID NO: | 7 mer Amino acid | Brain-mean-enrichment score (log10) | Brain-mean-standardized-read count (RC) |
|---|---|---|---|---|---|---|---|---|
| TS32 | 14841 | GCCCAAAGCAACAGCATCAGACTCGTCGCACAG | 14881 | AQSNSIRLVAQ | 14921 | SNSIRLV | 0.763114 | 1.058208 |
| TS70 | 14842 | GCCCAACCCAACACCATCAGAAACGTCGCACAG | 14882 | AQPNTIRNVAQ | 14922 | PNTIRNV | 0.660528 | 0.629407 |
| SyS52 | 14843 | GCCCAAACCAGCCTCGGCTACAGCAGCGCACAG | 14883 | AQTSLGYSSAQ | 14923 | TSLGYSS | 0.727167 | 0.736367 |
| SyS140 | 14844 | GCCCAAATGGGCGGCGACCACAGAACCGCACAG | 14884 | AQMGADHRTAQ | 14924 | MGADHRT | 0.548749 | 0.159265 |
| SyS58 | 14845 | GCCCAAGGTGATAATAGTCTGACTAGGGCACAG | 14885 | AQGDNSLTRAQ | 14925 | GDNSLTR | 0.717624 | 0.075033 |
| SyS201 | 14846 | GCCCAAACCCCCAAAGCCAAGAAATGGCACAG | 14886 | AQTPQSQEMAQ | 14926 | TPQSQEM | 0.494147 | 0.127468 |
| SyS61 | 14847 | GCCCAAAGCGGCGTCAGCACCACCGACGCACAG | 14887 | AQSGVSTTDAQ | 14927 | SGVSTTD | 0.711249 | -0.01534 |
| SyS97 | 14848 | GCCCAAGAAGGCCTCGGCAACGCCGCCGCACAG | 14888 | AQEGLGNAAAQ | 14928 | EGLGNAA | 0.59339 | -0.02116 |
| SyS176 | 14849 | GCCCAAAATTGCTGAGAATCTGAGTGCTGCACAG | 14889 | AQIAENLSAAQ | 14929 | IAENLSA | 0.517935 | -0.10864 |
| SyS154 | 14850 | GCCCAACTCGGCGACATCACCGGCTTCGCACAG | 14890 | AQLGDITGFAQ | 14930 | LGDITGF | 0.537047 | -0.10198 |
| SyS101 | 14851 | GCCCAAAGTCAGCTGCATAGGTTGCAGGCACAG | 14891 | AQSQLHRLQAQ | 14931 | SQLHRLQ | 0.588997 | -0.13052 |
| SyS45 | 14852 | GCCCAACCTATTATTACTATGCCTGCTGCACAG | 14892 | AQPITMPAAQ | 14932 | PIITMPA | 0.767318 | -0.10299 |
| SyS205 | 14853 | GCCCAATGGAGCCACAGCGAAAACAGCGCACAG | 14893 | AQWSHSENSAQ | 14933 | WSHSENS | 0.492196 | -0.02126 |
| SyS30 | 14854 | GCCCAATTGACTCAGCGAGACGGATGTTGCACAG | 14894 | AQLTQQTDVAQ | 14934 | LTQQTDV | 0.936974 | 0.055201 |
| SyS136 | 14855 | GCCCAAGGTATGAGTGGGGTTGCTCAGGCACAG | 14895 | AQGMSGVAQAQ | 14935 | GMSGVAQ | 0.552736 | -0.0578 |
| SyS128 | 14856 | GCCCAACCGACTAATATTATGCTTGATGCACAG | 14896 | AQPTNIMLDAQ | 14936 | PTNIMLD | 0.560313 | -0.07894 |
| SyS71 | 14857 | GCCCAAAAACCCACCCTCATCACCCTCGCACAG | 14897 | AQNPTLITLAQ | 14937 | NPTLITL | 0.655924 | 0.146275 |
| SyS100 | 14858 | GCCCAACCGGGTGGGGTTGACTCCGGCACAG | 14898 | AQPGGGLTPAQ | 14938 | PGGGLTP | 0.591748 | -0.07925 |
| SyS134 | 14859 | GCCCAAGATCGTGATTCTGTGCAGAATGCACAG | 14899 | AQDRDSVQNAQ | 14939 | DRDSVQN | 0.55654 | -0.05483 |
| SyS152 | 14860 | GCCCAACTTAATGGGTTGAATGTGTCTGCACAG | 14900 | AQLNGLNVSAQ | 14940 | LNGLNVS | 0.537505 | -0.02999 |
| SyS68 | 14861 | GCCCAAGCCAAACCAGCAACGACCCCGCACAG | 14901 | AQAQTSNDPAQ | 14941 | AQTSNDP | 0.669325 | 0.289379 |
| SyS137 | 14862 | GCCCAATCTGCGCTAATGTGACTATTGCACAG | 14902 | AQSAPNVTIAQ | 14942 | SAPNVTI | 0.551278 | 0.041441 |
| SyS129 | 14863 | GCCCAACCCAACATGAGCGCCATGATCGCACAG | 14903 | AQPNMSAMIAQ | 14943 | PNMSAMI | 0.559451 | 0.270198 |
| GS64 | 14864 | GCCCAATACAGCGCCGACAAAACCACCGCACAG | 14904 | AQYSADKTTAQ | 14944 | YSADKTT | 0.583168 | 0.057165 |

FIG. 34

| | | | | | | | | |
|---|---|---|---|---|---|---|---|---|
| SyS48 | 14865 | GCCCAACGTGTGGATGCGGTTTGAGTGCACAG | 14905 | AQRVDAVLSAQ | 14945 | RVDAVLS | 0.750458 | 0.650222 |
| SyS138 | 14866 | GCCCAAGGCACCGCCGCCGTCTTCACCGCCGCACAG | 14906 | AQGTAVFTAAQ | 14946 | GTAVFTA | 0.549912 | 0.15966 |
| SyS83 | 14867 | GCCCAAACCCTCAGCGCCCTCACCGCACAG | 14907 | AQTLSGALTAQ | 14947 | TLSGALT | 0.628275 | 0.306806 |
| SyS59 | 14868 | GCCCAACACGCCGACAACAGACTCAAAGCACAG | 14908 | AQHADNRLKAQ | 14948 | HADNRLK | 0.714815 | -0.04579 |
| SyS173 | 14869 | GCCCAAACTCAGGGTCCGGGTCCGAAGGCACAG | 14909 | AQTQGPGPKAQ | 14949 | TQGPGPK | 0.522239 | 0.297383 |
| SyS148 | 14870 | GCCCAAGTCGACGCCCTCAGCCACCATGGCACAG | 14910 | AQVDALSHMAQ | 14950 | VDALSHM | 0.539694 | 0.216373 |
| SyS162 | 14871 | GCCCAAACGGAATGATGCGATTCTGAATGCACAG | 14911 | AQRNDAILNAQ | 14951 | RNDAILN | 0.53456 | 0.251531 |
| SP47 | 14872 | GCCCAATTGACGGTGGCGGTTGAGACTGCACAG | 14912 | AQLTVAVETAQ | 14952 | LTVAVET | 0.139972 | -0.05361 |
| SS33 | 14873 | GCCCAAAGCCAAGCCATCGCCCCAAAGCACAG | 14913 | AQSQAIAPKAQ | 14953 | SQAIAPK | 0.51343 | -0.30374 |
| GS29 | 14874 | GCCCAAGTCCTCAGCGTCAACCACCTCGCACAG | 14914 | AQVLSVNHLAQ | 14954 | VLSVNHL | 0.765014 | 0.050802 |
| SyS84 | 14875 | GCCCAAAGCATCTACTACCACACGGAAGCACAG | 14915 | AQSIYYHTEAQ | 14955 | SIYYHTE | 0.618441 | -0.07907 |
| GS45 | 14876 | GCCCAAATGAACATCCTCAGAGAAGTCGCACAG | 14916 | AQMNILREVAQ | 14956 | MNILREV | 0.654097 | -0.09985 |
| GS84 | 14877 | GCCCAAAATATGCTTAAGCAGAGTGAGGCACAG | 14917 | AQNMLKQSEAQ | 14957 | NMLKQSE | 0.537354 | -0.06179 |
| GS113 | 14878 | GCCCAAATTCATGCCCATCAGCGGCGCACAG | 14918 | AQFMPISSAAQ | 14958 | FMPISSA | 0.50124 | -0.12446 |
| GS27 | 14879 | GCCCAAAAAGAATGCTCCGATGCCTGATGCACAG | 14919 | AQKNAPMPDAQ | 14959 | KNAPMPD | 0.772397 | 0.130152 |
| GS117 | 14880 | GCCCAAACCAACTACGACCTCAGAGCCGCACAG | 14920 | AQTNYDLRAAQ | 14960 | TNYDLRA | 0.494623 | -0.03099 |

FIG. 34 (Continued)

| Enrich_rank (within libraries) | SEQ ID NO: | Sequence (for 11 mer AA) | SEQ ID NO: | 11 mer Amino Acid | Liver-mean-enrichment score (log10) |
|---|---|---|---|---|---|
| TS1 | 14961 | GCCCAAAAAGCCTACAGCGGTCCAAGTCGCACAG | 15054 | AQKAYSVQVAQ | 1.15776 |
| TS2 | 14962 | GCCCAAAGAACCGCCAACGCCCTCGGCGCACAG | 15055 | AQRTANALGAQ | 0.802247 |
| TS3 | 14963 | GCCCAAGTGACGGGGGTTCGGATTGGGGCACAG | 15056 | AQVTGVRIGAQ | 0.75699 |
| TS4 | 14964 | GCCCAACCGCGGCCGGTGTGAATGGGGCACAG | 15057 | AQPRPVSNGAQ | 0.7305 |
| TS5 | 14965 | GCCCAATTCAGCGTCACCAGACAAGCCGCACAG | 15058 | AQFSVTRQAAQ | 0.718621 |
| TS6 | 14966 | GCCCAATACCCCACATGACCCACGACGCACAG | 15059 | AQYPHMTHDAQ | 0.655794 |
| TS7 | 14967 | GCCCAAAGCAGCAGACTCAGCGTCGGCGCACAG | 15060 | AQSSRLSVGAQ | 0.637971 |
| TS8 | 14968 | GCCCAACCGTTGAGTGGGGGTGTTCGTGCACAG | 15061 | AQPLSGGVRAQ | 0.598554 |
| TS9 | 14969 | GCCCAAGGGCTGAAGGTGTCTGGGTCTGCACAG | 15062 | AQGLKVSGSAQ | 0.569576 |
| TS10 | 14970 | GCCCAAAGCACCAGAAACGTCGTCGCGCACAG | 15063 | AQSTRNVVGAQ | 0.532567 |
| TS11 | 14971 | GCCCAAAGGCGGCACCAGAGAAGGCGCACAG | 15064 | AQSGGTREGAQ | 0.501512 |
| SyS1 | 14972 | GCCCAAGGGCTGAAGGTGTCTGGGTCTGCACAG | 15065 | AQGLKVSGSAQ | 0.777335 |
| SyS2 | 14973 | GCCCAAAACAACAACCAAAAAGTCTACGCACAG | 15066 | AQNNNQKVYAQ | 0.610002 |
| SyS3 | 14974 | GCCCAAAGGCTTGATAGGACTGGTTTGGCACAG | 15067 | AQRLDRTGLAQ | 0.585542 |
| SyS4 | 14975 | GCCCAAGTGGCGGGGTCTGACTGTTCAGGCACAG | 15068 | AQVAGLTVQAQ | 0.581695 |
| SyS5 | 14976 | GCCCAACATTCTGCGAAGACTATTGCGGCACAG | 15069 | AQHSAKTIAAQ | 0.579949 |
| SyS6 | 14977 | GCCCAAAGCATCAGAGCCCCGTCAGCGCACAG | 15070 | AQSIRAPVSAQ | 0.572426 |
| SyS7 | 14978 | GCCCAACCGTCGGCACCAGAACCAGCGCACAG | 15071 | AQPVGTRTSAQ | 0.560759 |
| SyS8 | 14979 | GCCCAAATCAACACCGCCAGCTACAAAGCACAG | 15072 | AQINTASYKAQ | 0.542125 |
| SyS9 | 14980 | GCCCAAGGGAGGACGGTGCAGGATAGGGCACAG | 15073 | AQGRTVQDRAQ | 0.528631 |
| SyS10 | 14981 | GCCCAAAGACTCACCAACAGCAACCAAGCACAG | 15074 | AQRLTNSNQAQ | 0.516161 |
| SyS11 | 14982 | GCCCAAATGATCAGAGGCACCAGCAGCGCACAG | 15075 | AQMIRGTSSAQ | 0.512891 |

FIG. 35

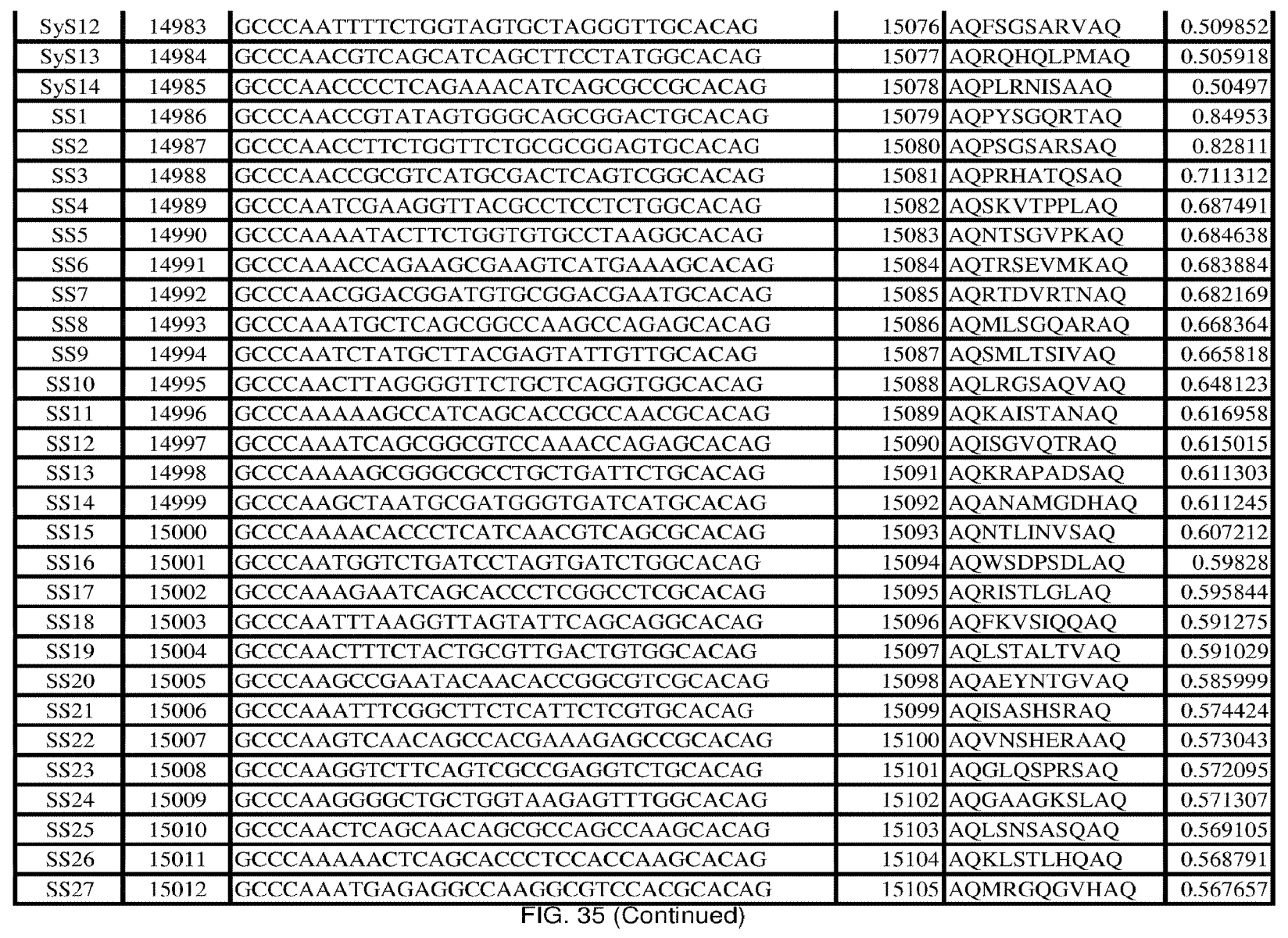

| | | | | | |
|---|---|---|---|---|---|
| SyS12 | 14983 | GCCCAATTTCTGGTAGTGCTAGGGTTGCACAG | 15076 | AQFSGSARVAQ | 0.509852 |
| SyS13 | 14984 | GCCCAACGTCAGCATCAGCTTCCTATGGCACAG | 15077 | AQRQHQLPMAQ | 0.505918 |
| SyS14 | 14985 | GCCCAACCCTCAGAAACATCAGCGCCGCACAG | 15078 | AQPLRNISAAQ | 0.50497 |
| SS1 | 14986 | GCCCAACGTATAGTGGGCAGCGGACTGCACAG | 15079 | AQPYSGQRTAQ | 0.84953 |
| SS2 | 14987 | GCCCAACCTTCTGGTTCTCCGCGGAGTGCACAG | 15080 | AQPSGSARSAQ | 0.82811 |
| SS3 | 14988 | GCCCAACCGCGTCATGCGACTCAGTCGGCACAG | 15081 | AQPRHATQSAQ | 0.711312 |
| SS4 | 14989 | GCCCAATCGAAGGTTACGCCTCCTCTGGCACAG | 15082 | AQSKVTPPLAQ | 0.687491 |
| SS5 | 14990 | GCCCAAAATACTTCTGGTGTGCTAAGGCACAG | 15083 | AQNTSGVPKAQ | 0.684638 |
| SS6 | 14991 | GCCCAAACCAGAAGCGAAGTCATGAAAGCACAG | 15084 | AQTRSEVMKAQ | 0.683884 |
| SS7 | 14992 | GCCCAACGGACGGATGTGCGGACGAATGCACAG | 15085 | AQRTDVRTNAQ | 0.682169 |
| SS8 | 14993 | GCCCAAATGCTCAGCGGCCAAGCCAGAGCACAG | 15086 | AQMLSGQARAQ | 0.668364 |
| SS9 | 14994 | GCCCAATCTATGCTTACGAGTATTGTTGCACAG | 15087 | AQSMLTSIVAQ | 0.665818 |
| SS10 | 14995 | GCCCAACTTAGGGGTTCTGCTCAGGTGGCACAG | 15088 | AQLRGSAQVAQ | 0.648123 |
| SS11 | 14996 | GCCCAAAAAGCCATCAGCACCGCCAACGCACAG | 15089 | AQKAISTANAQ | 0.616958 |
| SS12 | 14997 | GCCCAAATCAGCGGCGTCCAAACCAGAGCACAG | 15090 | AQISGVQTRAQ | 0.615015 |
| SS13 | 14998 | GCCCAAAAGCGGCGGCGCCTGCTGATTCTGCACAG | 15091 | AQKRAPADSAQ | 0.611303 |
| SS14 | 14999 | GCCCAAGCTAATGCGATGGGTGATCATGCACAG | 15092 | AQANAMGDHAQ | 0.611245 |
| SS15 | 15000 | GCCCAAAAACACCCTCATCAACGTCAGCGCACAG | 15093 | AQNTLINVSAQ | 0.607212 |
| SS16 | 15001 | GCCCAATGGTCTGATCTCTAGTGATCTGGCACAG | 15094 | AQWSDPSDLAQ | 0.59828 |
| SS17 | 15002 | GCCCAAAGAATCAGCACCCTCGGCCTCGCACAG | 15095 | AQRISTLGLAQ | 0.595844 |
| SS18 | 15003 | GCCCAATTTAAGGTTAGTATTCAGCAGGCACAG | 15096 | AQFKVSIQQAQ | 0.591275 |
| SS19 | 15004 | GCCCAACTTTCTACTGCGTTGACTGTGGCACAG | 15097 | AQLSTALTVAQ | 0.591029 |
| SS20 | 15005 | GCCCAAGCCGAATACAACACCGGCGTCGCACAG | 15098 | AQAEYNTGVAQ | 0.585999 |
| SS21 | 15006 | GCCCAAATTTCGGCTTCTCATTCTCGTGCACAG | 15099 | AQISASHSRAQ | 0.574424 |
| SS22 | 15007 | GCCCAAGTCAACAGCCACGAAAGAGCCGCACAG | 15100 | AQVNSHERAAQ | 0.573043 |
| SS23 | 15008 | GCCCAAGGTCTTCAGTCGCCGAGGTCTGCACAG | 15101 | AQGLQSPRSAQ | 0.572095 |
| SS24 | 15009 | GCCCAAGGGGCTGCTGGTAAGAGTTTGGCACAG | 15102 | AQGAAGKSLAQ | 0.571307 |
| SS25 | 15010 | GCCCAACTCAGCAACAGCGCCAAGCACACAG | 15103 | AQLSNSASQAQ | 0.569105 |
| SS26 | 15011 | GCCCAAAAACTCAGCACCCTCCACCAAGCACAG | 15104 | AQKLSTLHQAQ | 0.568791 |
| SS27 | 15012 | GCCCAATGAGAGAGGCCAAGGCGTCCACGCACAG | 15105 | AQMRGQGVHAQ | 0.567657 |

FIG. 35 (Continued)

| | | | | | |
|---|---|---|---|---|---|
| SS28 | 15013 | GCCCAACTTCCGGGTGGTGCCGAGGTTGGCACAG | 15106 | AQLPGGARLAQ | 0.564086 |
| SS29 | 15014 | GCCCAACTTGGTTCTGCGCTTACGAGGGCACAG | 15107 | AQLGSALTRAQ | 0.563314 |
| SS30 | 15015 | GCCCAAGGCACCACCAGAAGCCCCACCGCACAG | 15108 | AQGTTRSPTAQ | 0.560705 |
| SS31 | 15016 | GCCCAAGGTCATATTTCGGCGCTTGCGGCACAG | 15109 | AQGHISALAAQ | 0.552655 |
| SS32 | 15017 | GCCCAATCGATTTCCTCCTCGTACGGCACAG | 15110 | AQSISPPRTAQ | 0.550578 |
| SS33 | 15018 | GCCCAATTTCAGCAGGATACTTATCTGGCACAG | 15111 | AQFQQDTYLAQ | 0.548808 |
| SS34 | 15019 | GCCCAACTTCTTGCGACTGGGCTTAAGGCACAG | 15112 | AQLLATGLKAQ | 0.545453 |
| SS35 | 15020 | GCCCAACTTAAGGTTGCGTCTGGTTTGGCACAG | 15113 | AQLKVASGLAQ | 0.540598 |
| SS36 | 15021 | GCCCAATTCGACAACCCAACAACGTCGCACAG | 15114 | AQFDNPNNVAQ | 0.539231 |
| SS37 | 15022 | GCCCAATACCTCACCAGCGGCGGCTACGCACAG | 15115 | AQYLTSGGYAQ | 0.538789 |
| SS38 | 15023 | GCCCAAAGAGACACCGTCAGCAGATACGCACAG | 15116 | AQRDTVSRYAQ | 0.535765 |
| SS39 | 15024 | GCCCAAATCAACAAAGACAACAACCAAGCACAG | 15117 | AQINKDNNQAQ | 0.531458 |
| SS40 | 15025 | GCCCAAATGGCCAACCACCAGAAGCGCCGCACAG | 15118 | AQMANTRSAAQ | 0.525721 |
| SS41 | 15026 | GCCCAAGAAAGCATCCAACAACTCAGCGCACAG | 15119 | AQESIQQLSAQ | 0.525712 |
| SS42 | 15027 | GCCCAACTCACCAGAGTCGGCACCGTCGCACAG | 15120 | AQLTRVGTVAQ | 0.520831 |
| SS43 | 15028 | GCCCAAGTCAAGTCGCGCCATGAGAGCCGCACAG | 15121 | AQVQVAMRAAQ | 0.520831 |
| SS44 | 15029 | GCCCAAACGGCTGCGCATGTTAGTTATGCACAG | 15122 | AQTAAHVSYAQ | 0.520336 |
| SS45 | 15030 | GCCCAACCCAGCAGCGCCAGAGCCAGCGCACAG | 15123 | AQPSHARASAQ | 0.520336 |
| SS46 | 15031 | GCCCAAAAATGTGCCGACTTCGCGGGGCACAG | 15124 | AQNVPTSPRAQ | 0.520245 |
| SS47 | 15032 | GCCCAAAAAACCCAACTCGGCCAAATGGCACAG | 15125 | AQKTQLGQMAQ | 0.519843 |
| SS48 | 15033 | GCCCAAAAAGCCAACAGCCAAATCACCGCACAG | 15126 | AQKANSQITAQ | 0.519425 |
| SS49 | 15034 | GCCCAAAACAACAGCGGCCACATCAGCGCACAG | 15127 | AQNNSGHISAQ | 0.518228 |
| SS50 | 15035 | GCCCAATTTCTTCTTACTTCGGATCCGGCACAG | 15128 | AQFLLTSDPAQ | 0.515975 |
| SS51 | 15036 | GCCCAAGTTAAGACTGATCGGGTTCTGCACAG | 15129 | AQVKTDRVLAQ | 0.51183 |
| SS52 | 15037 | GCCCAAGTCAGCATCAGCGTCATGGGGCACAG | 15130 | AQVSISVMGAQ | 0.510987 |
| SS53 | 15038 | GCCCAAGCCGGCCTCGCCCACGCCACCGCACAG | 15131 | AQAGLAHATAQ | 0.510068 |
| SS54 | 15039 | GCCCAACGGACTACGGCTAATTCGCTTGCACAG | 15132 | AQRTTANSLAQ | 0.509233 |
| SS55 | 15040 | GCCCAATCGGTTCCTCCGAATAGGAATGCACAG | 15133 | AQSVPPNRNAQ | 0.508166 |
| SS56 | 15041 | GCCCAACACAGCGGCCCCACCAGCAGCGCACAG | 15134 | AQHSGPTSSAQ | 0.505295 |
| SS57 | 15042 | GCCCAAAAACCAACAACAACACCGTTCCTCGCACAG | 15135 | AQKTNNTVLAQ | 0.504377 |

FIG. 35 (Continued)

| | | | | |
|---|---|---|---|---|
| SS58 | 15043 | GCCCAACCCGCCAGAATCCCCGGCAGCGCACAG | 15136 | AQPARIPGSAQ | 0.50309 |
| SS59 | 15044 | GCCCAATTGTCTGCTCAGCTTCCGCGGGCACAG | 15137 | AQLSAQLPRAQ | 0.503052 |
| SS60 | 15045 | GCCCAAGTTGGTTCTAGTAATACGTATGCACAG | 15138 | AQVGSSNTYAQ | 0.502229 |
| SS61 | 15046 | GCCCAACTCATCAGCACCACCACAGAGCACAG | 15139 | AQLISTTHRAQ | 0.502083 |
| GS1 | 15047 | GCCCAATATGTTAATAGTGCTCCGAAGGCACAG | 15140 | AQYVNSAPKAQ | 0.551681 |
| GS2 | 15048 | GCCCAAAACAACAACCAAAAGTCTACGCACAG | 15141 | AQNNNQKVYAQ | 0.532399 |
| Gs3 | 15049 | GCCCAAGGCACCAAACCCACAGCCTCGCACAG | 15142 | AQGTKTHSLAQ | 0.518459 |
| GS4 | 15050 | GCCCAACCCATCAGCGCCAACAGACTCGCACAG | 15143 | AQPISANRLAQ | 0.512571 |
| GS5 | 15051 | GCCCAACACCCCAGCCTCAGACAAAGGCACAG | 15144 | AQHPSLRQSAQ | 0.508478 |
| GS6 | 15052 | GCCCAACCCCAACAGAGCGCCAACAACGCACAG | 15145 | AQPNRAANNAQ | 0.508143 |
| GS7 | 15053 | GCCCAACCCAGCCACGCCAGAGCCAGCGCACAG | 15146 | AQPSHARASAQ | 0.504054 |

FIG. 35 (Continued)

Acceptor Vector: rAAV-ΔCap-in-cis-lox2
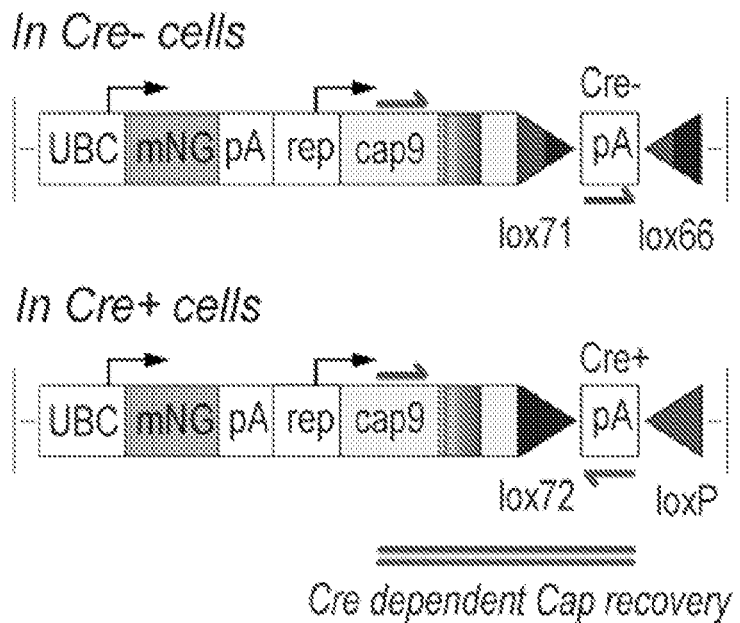
Rep-AAPΔCap Vector: Rep-AAP-ΔCap-in-trans
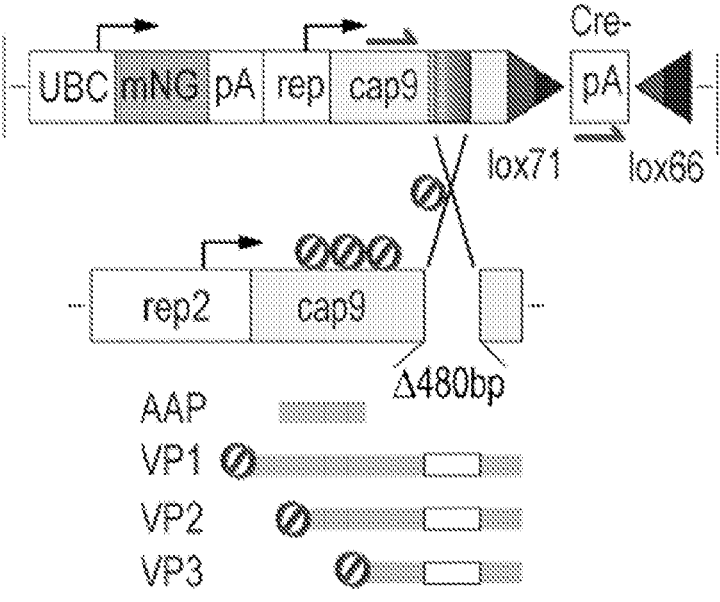
FIG. 36

Selective recovery of AAV genome in Cre+ cells using conventional PCR.

Process the recovered AAV genome for deep sequencing (NGS) by adding Read and Adaptor Sequences along with unique Barcodes (6 bases single barcode or 8 bases dual barcode).

Multiplexed AAV library analysis by deep sequencing all libraries with unique barcodes.

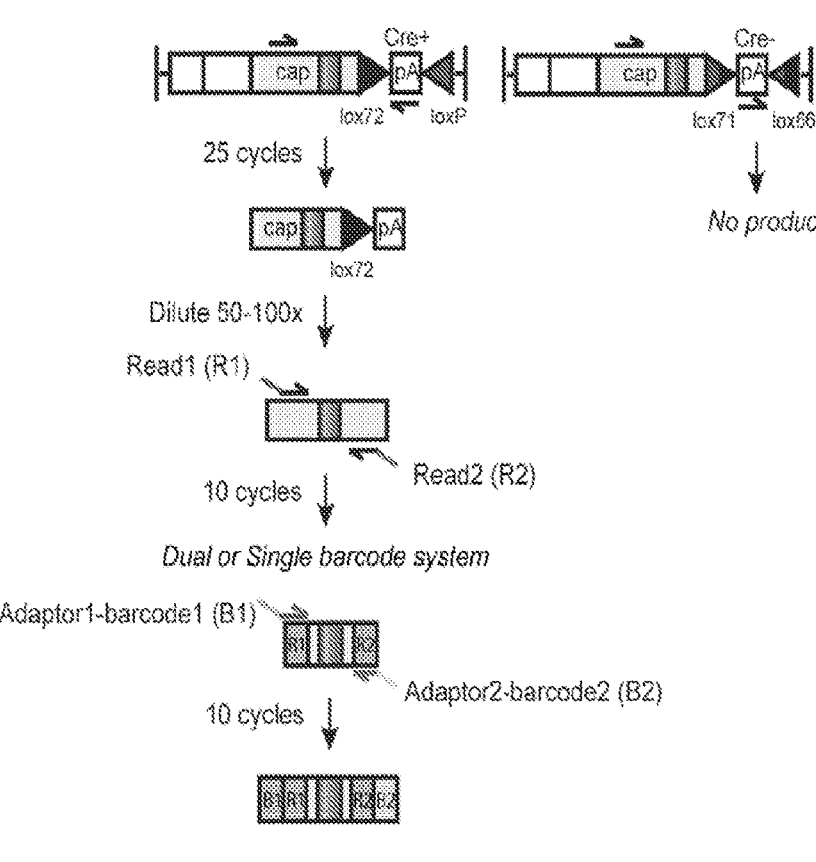

25 cycles

No product

Dilute 50-100x

Read1 (R1)
Read2 (R2)

10 cycles

Dual or Single barcode system

Adaptor1-barcode1 (B1)
Adaptor2-barcode2 (B2)

10 cycles

Deep Sequencing

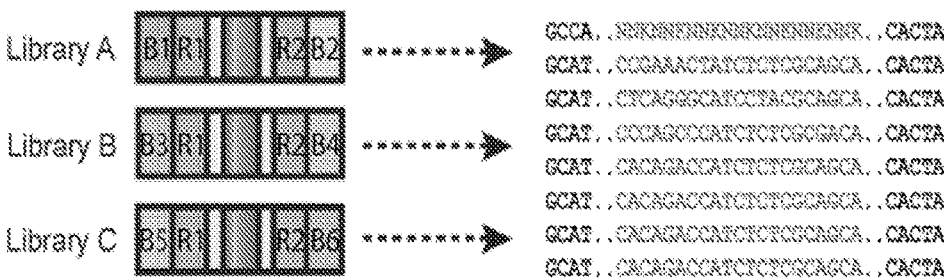

Library A
Library B
Library C

FIG. 37

*Library coverage*

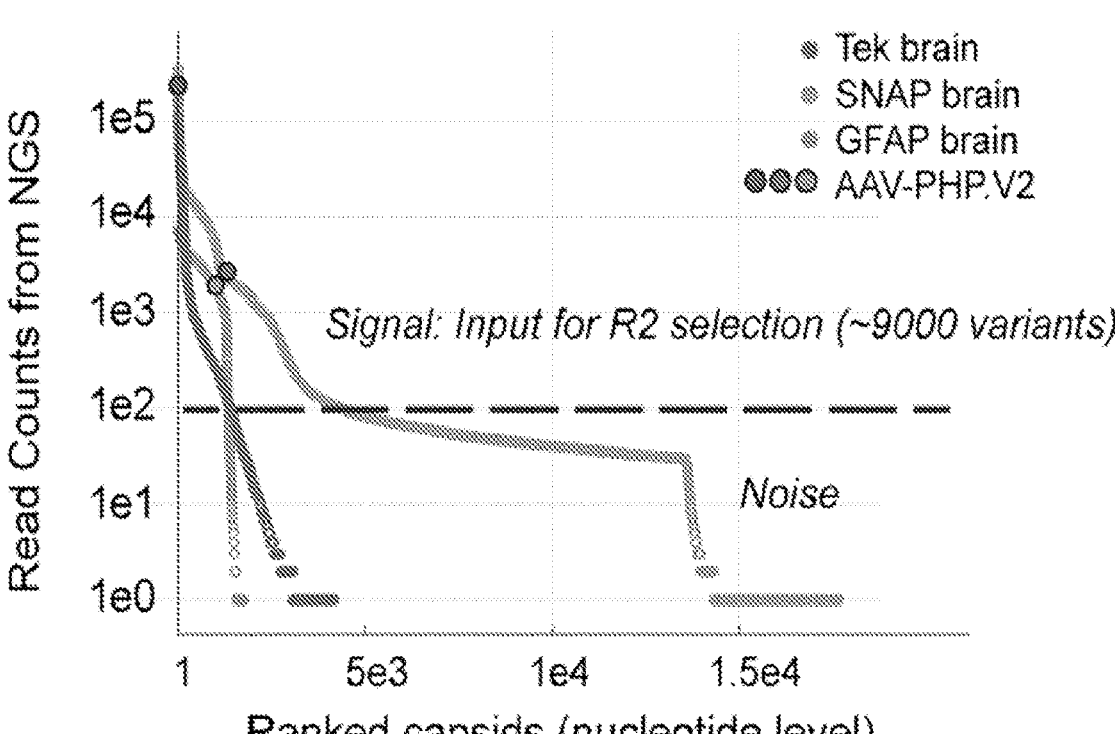
FIG. 40
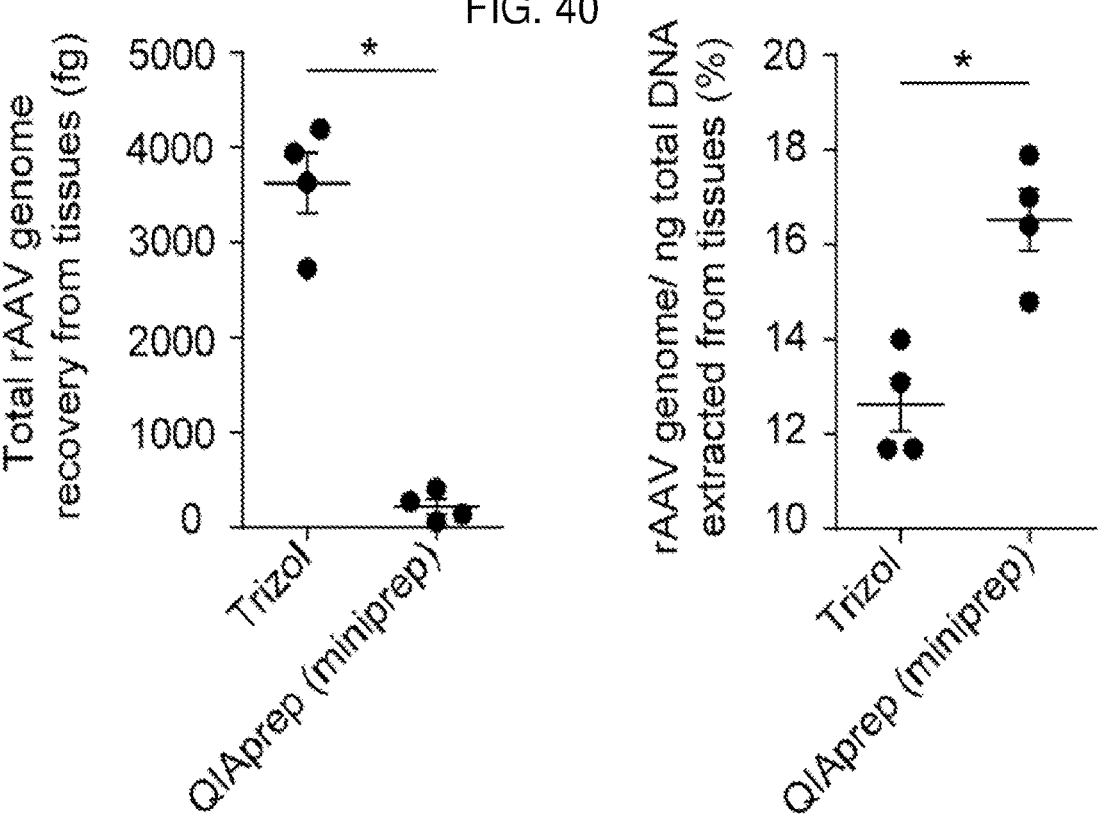
FIG. 41                                             FIG. 42

PCR pool

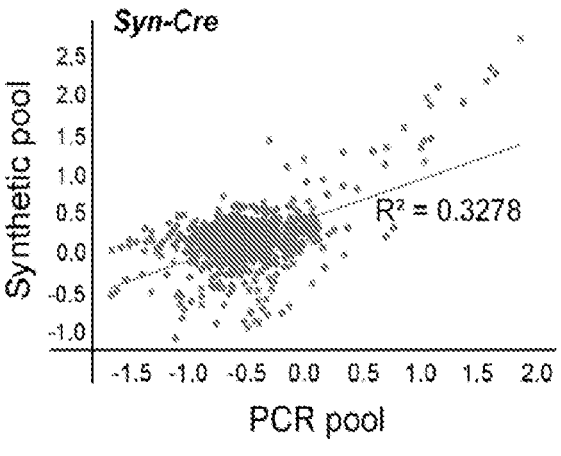
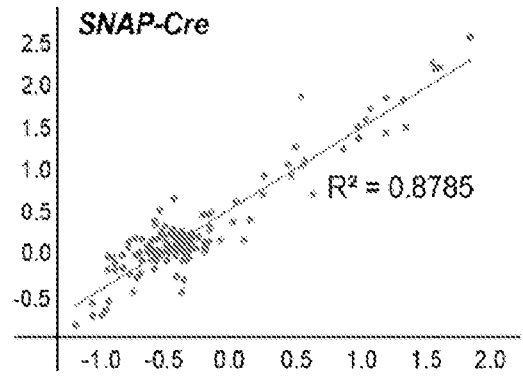
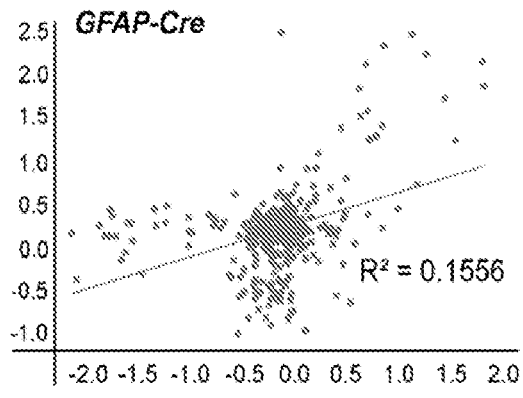
FIG. 49
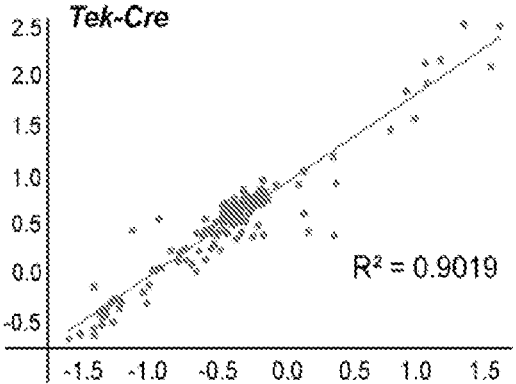

FIG. 53 (Continued)

*ssAAV-PHP.V1: Ple261-iCre*          *scAAV-PHP.V1: CB6/ CAG-EGFP*

Specific vascular cell transduction by ssAAV- and scAAV-PHP.V1

FIG. 58

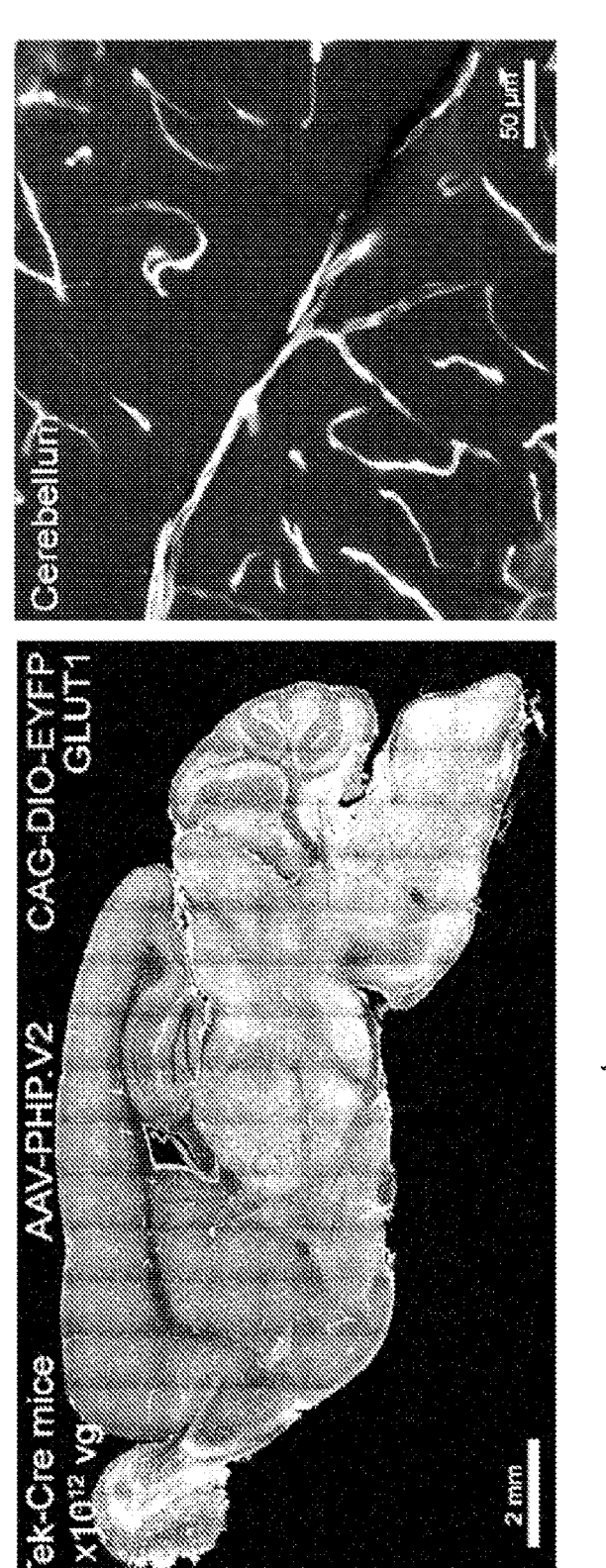
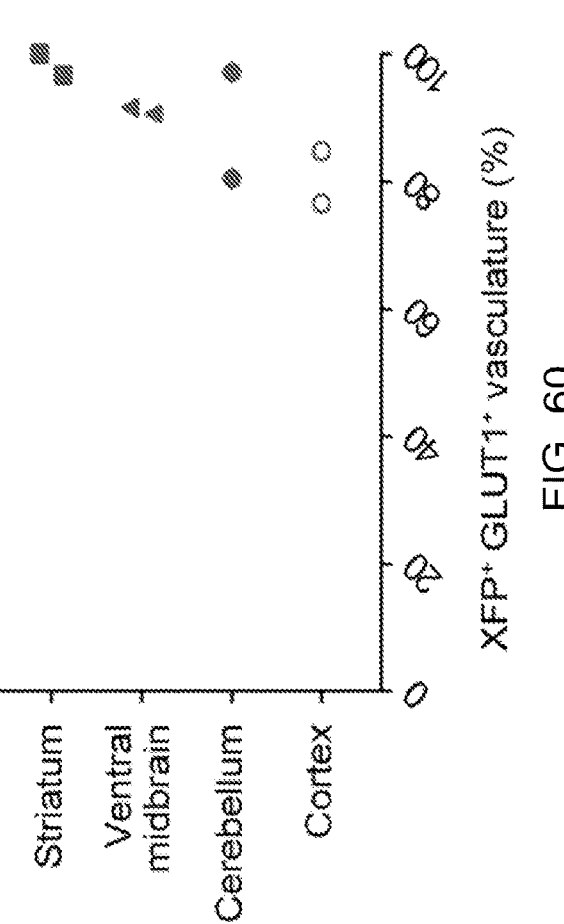
FIG. 60

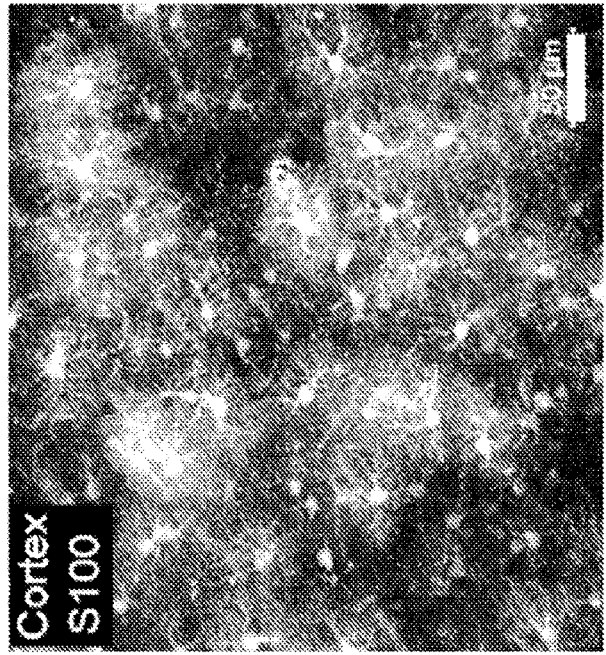
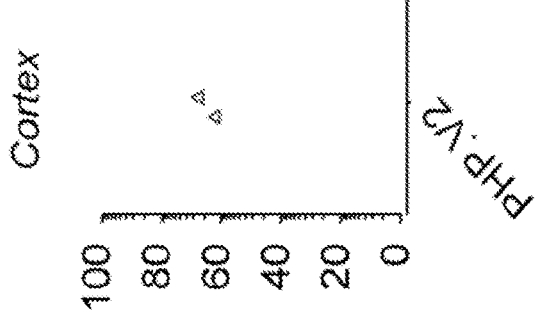
FIG. 61

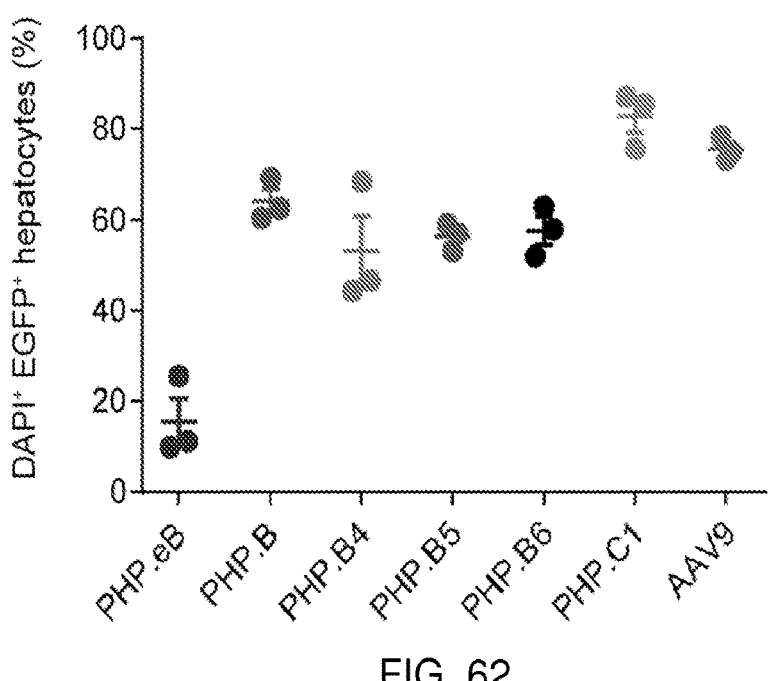
Liver hepatocytes
$1 \times 10^{11}$ vg/adult C57BL/6J
FIG. 62
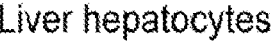
Synthetic pool: Positively enriched variants
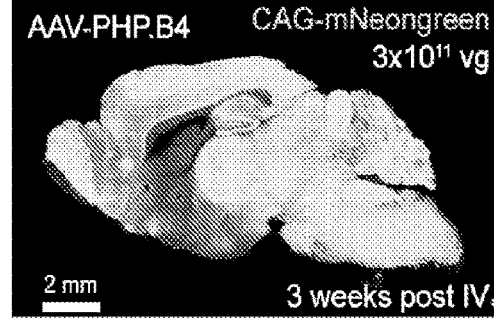
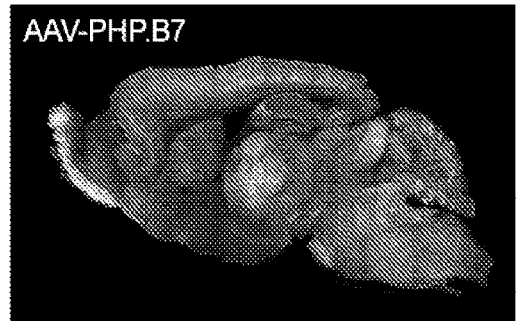
Synthetic pool: Negatively enriched variants
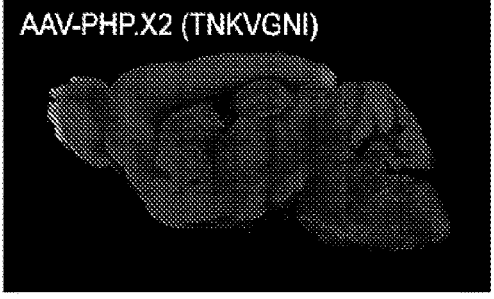
FIG. 63

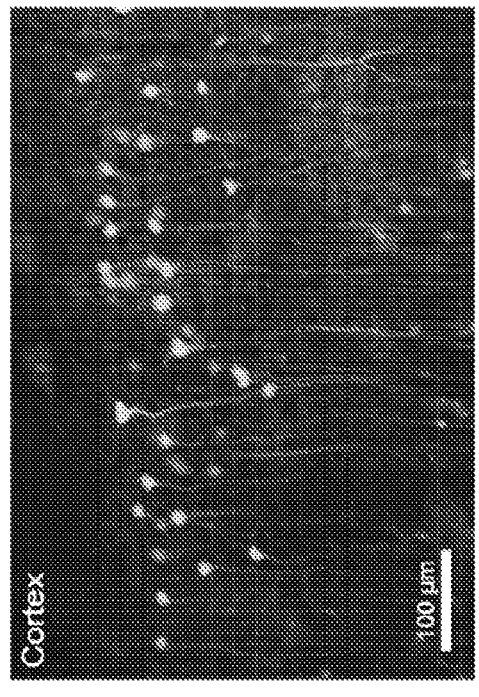
FIG. 64

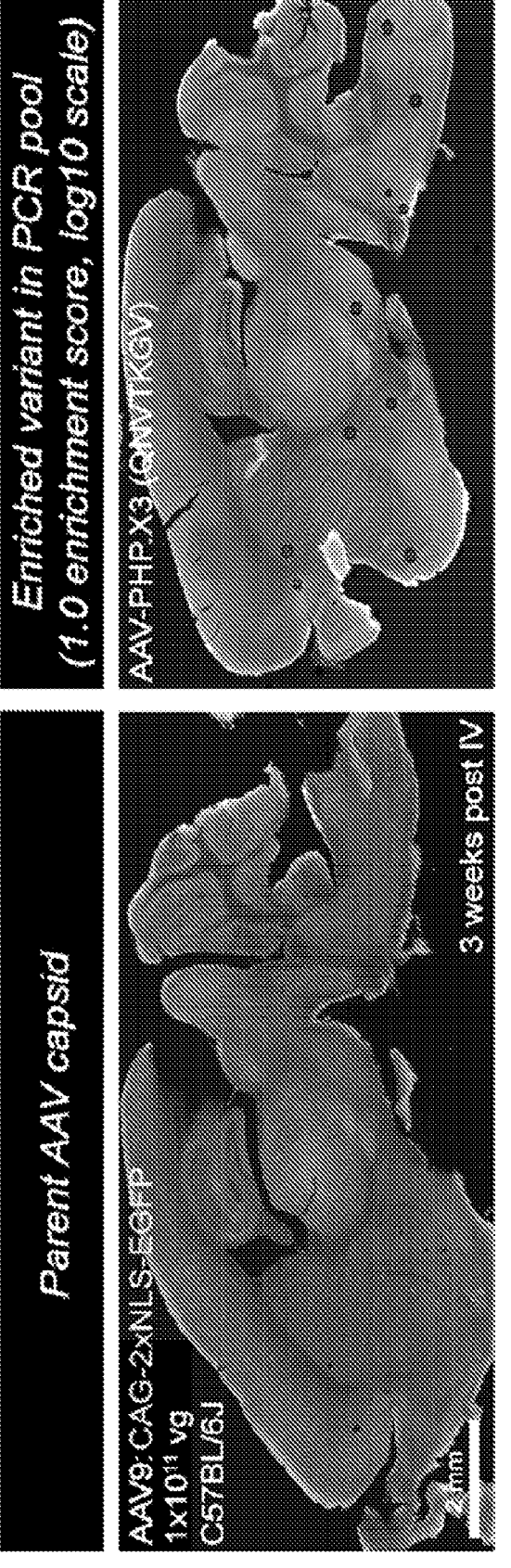
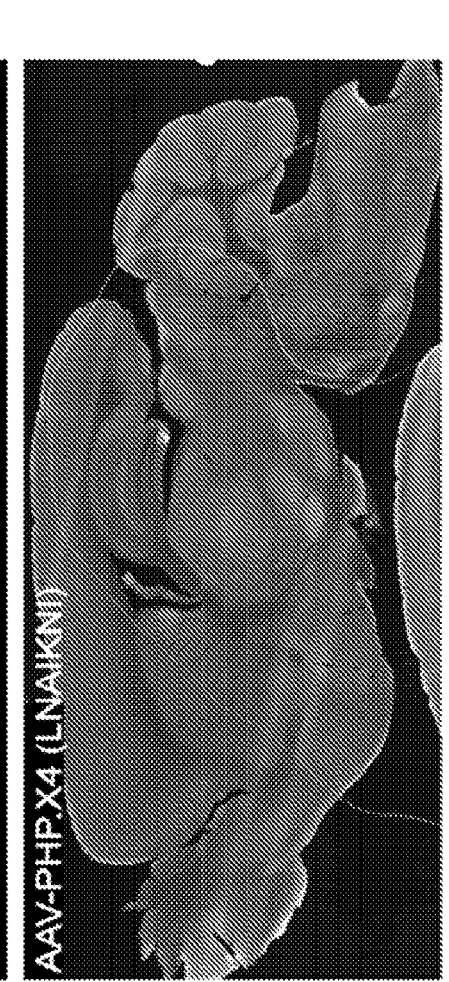
FIG. 65

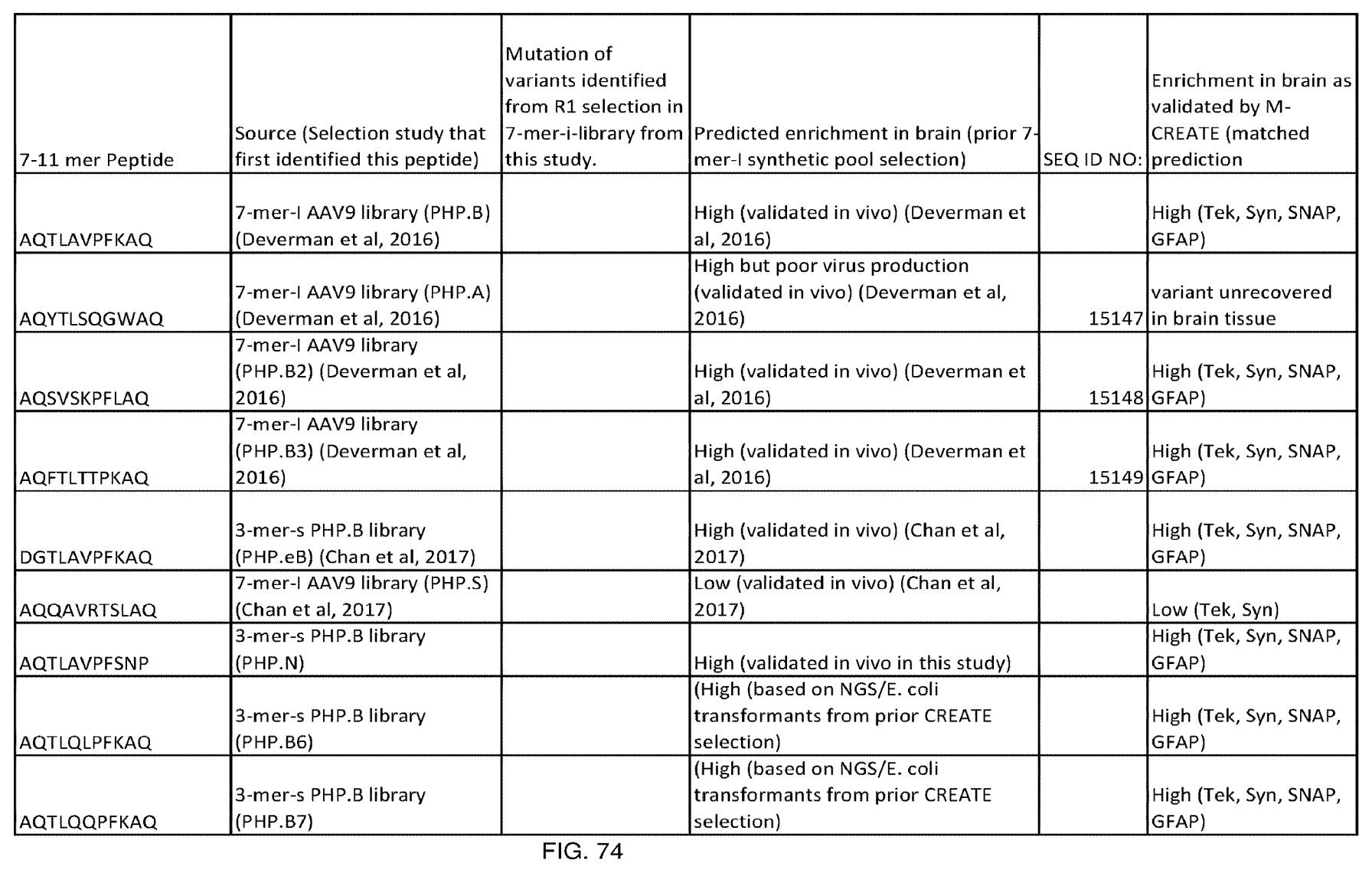

| 7-11 mer Peptide | Source (Selection study that first identified this peptide) | Mutation of variants identified from R1 selection in 7-mer-i-library from this study. | Predicted enrichment in brain (prior 7-mer-i synthetic pool selection) | SEQ ID NO: | Enrichment in brain as validated by M-CREATE (matched prediction) |
|---|---|---|---|---|---|
| AQTLAVPFKAQ | 7-mer-I AAV9 library (PHP.B) (Deverman et al, 2016) | | High (validated in vivo) (Deverman et al, 2016) | | High (Tek, Syn, SNAP, GFAP) |
| AQYTLSQGWAQ | 7-mer-I AAV9 library (PHP.A) (Deverman et al, 2016) | | High but poor virus production (validated in vivo) (Deverman et al, 2016) | 15147 | variant unrecovered in brain tissue |
| AQSVSKPFLAQ | 7-mer-I AAV9 library (PHP.B2) (Deverman et al, 2016) | | High (validated in vivo) (Deverman et al, 2016) | 15148 | High (Tek, Syn, SNAP, GFAP) |
| AQFTLTTPKAQ | 7-mer-I AAV9 library (PHP.B3) (Deverman et al, 2016) | | High (validated in vivo) (Deverman et al, 2016) | 15149 | High (Tek, Syn, SNAP, GFAP) |
| DGTLAVPFKAQ | 3-mer-s PHP.B library (PHP.eB) (Chan et al, 2017) | | High (validated in vivo) (Chan et al, 2017) | | High (Tek, Syn, SNAP, GFAP) |
| AQQAVRTSLAQ | 7-mer-I AAV9 library (PHP.S) (Chan et al, 2017) | | Low (validated in vivo) (Chan et al, 2017) | | Low (Tek, Syn) |
| AQTLAVPFSNP | 3-mer-s PHP.B library (PHP.N) | | High (validated in vivo in this study) | | High (Tek, Syn, SNAP, GFAP) |
| AQTLQLPFKAQ | 3-mer-s PHP.B library (PHP.B6) | | (High (based on NGS/E. coli transformants from prior CREATE selection) | | High (Tek, Syn, SNAP, GFAP) |
| AQTLQQPFKAQ | 3-mer-s PHP.B library (PHP.B7) | | (High (based on NGS/E. coli transformants from prior CREATE selection) | | High (Tek, Syn, SNAP, GFAP) |

FIG. 74

| Sequence | Source | Description | Expression | SEQ ID | Variant recovery in brain tissue |
|---|---|---|---|---|---|
| DGTTLKPFLAQ | Current study | "AQ" on PHP.V2 substituted with "DG" | Unknown | | variant unrecovered in brain tissue |
| DGTALKPFLAQ | Current study | "AQ" on PHP.V1 substituted with "DG" | Unknown | | High (Syn, GFAP) |
| DGTTLKPFSNP | Current study | "AQ" on PHP.V2 substituted with "DG" and "LAQ" substituted with "SNP" | Unknown | | Low (Syn) |
| AQTTLKPFSNP | Current study | "LAQ" on PHP.V2 substituted with "SNP" | Unknown | | High (Tek, Syn, SNAP, GFAP) |
| ESTLAVPFKAQ | 3-mer-s PHP.B library | | (High (based on NGS/E. coli transformants from prior CREATE selection) | 15150 | High (Tek, Syn, SNAP, GFAP) |
| GGTLAVPFKAQ | 3-mer-s PHP.B library | | (High (based on NGS/E. coli transformants from prior CREATE selection) | 15151 | High (Tek, Syn, SNAP, GFAP) |
| AQTLATPFKAQ | 3-mer-s PHP.B library | | (High (based on NGS/E. coli transformants from prior CREATE selection) | 15152 | High (Syn, SNAP, GFAP) |
| ATTLATPFKAQ | 3-mer-s PHP.B library | | (High (based on NGS/E. coli transformants from prior CREATE selection) | 15153 | High (Tek, Syn, SNAP, GFAP) |
| DGTLATPFKAQ | 3-mer-s PHP.B library | | (High (based on NGS/E. coli transformants from prior CREATE selection) | 15154 | High (Tek, Syn, SNAP, GFAP) |
| GGTLATPFKAQ | 3-mer-s PHP.B library | | (High (based on NGS/E. coli transformants from prior CREATE selection) | 15155 | High (Tek, Syn, SNAP, GFAP) |

FIG. 74 (Continued)

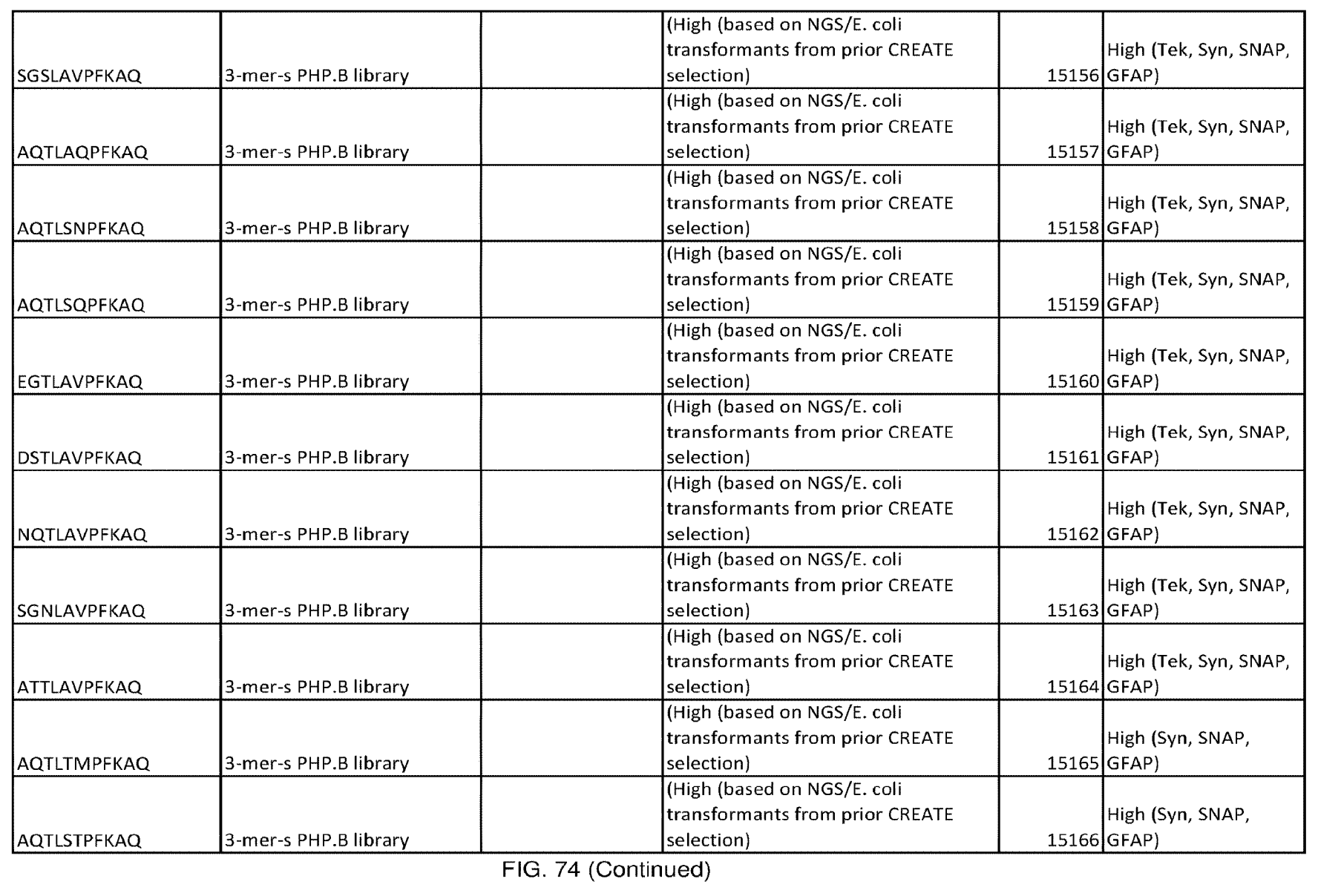

| | | | |
|---|---|---|---|
| SGSLAVPFKAQ | 3-mer-s PHP.B library | (High (based on NGS/E. coli transformants from prior CREATE selection) | High (Tek, Syn, SNAP, GFAP) 15156 |
| AQTLAQPFKAQ | 3-mer-s PHP.B library | (High (based on NGS/E. coli transformants from prior CREATE selection) | High (Tek, Syn, SNAP, GFAP) 15157 |
| AQTLSNPFKAQ | 3-mer-s PHP.B library | (High (based on NGS/E. coli transformants from prior CREATE selection) | High (Tek, Syn, SNAP, GFAP) 15158 |
| AQTLSQPFKAQ | 3-mer-s PHP.B library | (High (based on NGS/E. coli transformants from prior CREATE selection) | High (Tek, Syn, SNAP, GFAP) 15159 |
| EGTLAVPFKAQ | 3-mer-s PHP.B library | (High (based on NGS/E. coli transformants from prior CREATE selection) | High (Tek, Syn, SNAP, GFAP) 15160 |
| DSTLAVPFKAQ | 3-mer-s PHP.B library | (High (based on NGS/E. coli transformants from prior CREATE selection) | High (Tek, Syn, SNAP, GFAP) 15161 |
| NQTLAVPFKAQ | 3-mer-s PHP.B library | (High (based on NGS/E. coli transformants from prior CREATE selection) | High (Tek, Syn, SNAP, GFAP) 15162 |
| SGNLAVPFKAQ | 3-mer-s PHP.B library | (High (based on NGS/E. coli transformants from prior CREATE selection) | High (Tek, Syn, SNAP, GFAP) 15163 |
| ATTLAVPFKAQ | 3-mer-s PHP.B library | (High (based on NGS/E. coli transformants from prior CREATE selection) | High (Tek, Syn, SNAP, GFAP) 15164 |
| AQTLTMPFKAQ | 3-mer-s PHP.B library | (High (based on NGS/E. coli transformants from prior CREATE selection) | High (Syn, SNAP, GFAP) 15165 |
| AQTLSTPFKAQ | 3-mer-s PHP.B library | (High (based on NGS/E. coli transformants from prior CREATE selection) | High (Syn, SNAP, GFAP) 15166 |

FIG. 74 (Continued)

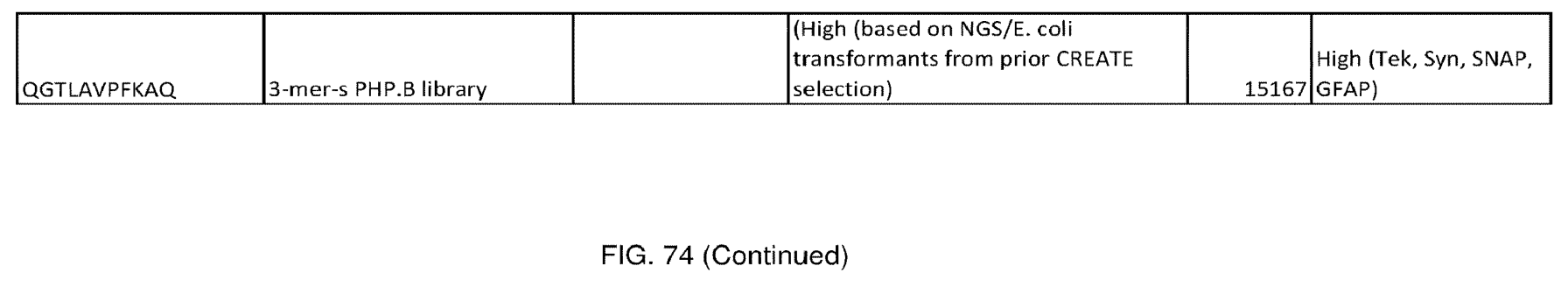

| QGTLAVPFKAQ | 3-mer-s PHP.B library | (High (based on NGS/E. coli transformants from prior CREATE selection) | 15167 | High (Tek, Syn, SNAP, GFAP) |

FIG. 74 (Continued)

| SEQ ID | 7-11 mer Peptide | Source (Selection study that first identified this peptide) | Mutation of variants identified from R1 selection in 7-mer-i library from this study. | Predicted enrichment in brain (prior 7-mer-i synthetic pool selection) | Enrichment in brain as validated by M-CREATE (against prediction) | Enrichment in brain as validated by M-CREATE (matched prediction) |
|---|---|---|---|---|---|---|
| | AQTLAVPFKAQ | 7-mer-i AAV9 library (PHP.B) (Deverman et al, 2016) | | High (validated in vivo) (Deverman et al, 2016) | | High (Tek, Syn, SNAP, GFAP) |
| | AQYTLSQGWAQ | 7-mer-i AAV9 library (PHP.A) (Deverman et al, 2016) | | High but poor virus production (validated in vivo) (Deverman et al, 2016) | | variant unrecovered in brain tissue |
| | AQSVSKPFLAQ | 7-mer-i AAV9 library (PHP.B2) (Deverman et al, 2016) | | High (validated in vivo) (Deverman et al, 2016) | | High (Tek, Syn, SNAP, GFAP) |
| | AQFTLTTPKAQ | 7-mer-i AAV9 library (PHP.B3) (Deverman et al, 2016) | | High (validated in vivo) (Deverman et al, 2016) | | High (Tek, Syn, SNAP, GFAP) |
| | DGTLAVPFKAQ | 3-mer-s PHP.B library (PHP.eB) (Chan et al, 2017) | | High (validated in vivo) (Chan et al, 2017) | | High (Tek, Syn, SNAP, GFAP) |
| | AQQAVRTSLAQ | 7-mer-i AAV9 library (PHP.S) (Chan et al, 2017) | | Low (validated in vivo) (Chan et al, 2017) | | Low (Tek, Syn) |
| | AQTLAVPFSNP | 3-mer-s PHP.B library (PHP.N) | | High (validated in vivo in this study) | | High (Tek, Syn, SNAP, GFAP) |

FIG. 75

| Peptide | Source | Notes | Production | Tropism |
|---|---|---|---|---|
| AQTLQLPFKAQ | 3-mer-s PHP.B library (PHP.B6) | | High (based on NGS/E.coli transformants from prior CREATE selection) | High (Tek, Syn, SNAP, GFAP) |
| AQTLQQPFKAQ | 3-mer-s PHP.B library (PHP.B7) | | High (based on NGS/E.coli transformants from prior CREATE selection) | High (Tek, Syn, SNAP, GFAP) |
| DGTTLKPFLAQ | Current study (New design inspired from previously identified peptides) | "AQ" on PHP.V2 substituted with "DG" | Unknown | variant unrecovered in brain tissue |
| DGTALKPFLAQ | Current study (New design inspired from previously identified peptides) | "AQ" on PHP.V1 substituted with "DG" | Unknown | High (Syn, GFAP) |
| DGTTLKPFSNP | Current study (New design inspired from previously identified peptides) | "AQ" on PHP.V2 substituted with "DG" and "LAQ" substituted with "SNP" | Unknown | |
| AQTTLKPFSNP | design inspired from | PHP.V2 | Unknown | Low (Syn) |
| ESTLAVPFKAQ | 3-mer-s PHP.B library | | High (based on NGS/E.coli transformants from prior CREATE selection) | SNAP, GFAP |
| GGTLAVPFKAQ | 3-mer-s PHP.B library | | High (based on NGS/E.coli transformants from prior CREATE selection) | High (Tek, Syn, SNAP, GFAP) |

FIG. 75 (Continued)

| | | | |
|---|---|---|---|
| AQTLATPFKAQ | 3-mer-s PHP.B library | High (based on NGS/E.coli transformants from prior CREATE selection) | High (Syn, SNAP, GFAP) |
| ATTLATPFKAQ | 3-mer-s PHP.B library | High (based on NGS/E.coli transformants from prior CREATE selection) | High (Tek, Syn, SNAP, GFAP) |
| DGTLATPFKAQ | 3-mer-s PHP.B library | High (based on NGS/E.coli transformants from prior CREATE selection) | High (Tek, Syn, SNAP, GFAP) |
| GGTLATPFKAQ | 3-mer-s PHP.B library | High (based on NGS/E.coli transformants from prior CREATE selection) | High (Tek, Syn, SNAP, GFAP) |
| SGSLAVPFKAQ | 3-mer-s PHP.B library | High (based on NGS/E.coli transformants from prior CREATE selection) | High (Tek, Syn, SNAP, GFAP) |
| AQTLAQPFKAQ | 3-mer-s PHP.B library | High (based on NGS/E.coli transformants from prior CREATE selection) | High (Tek, Syn, SNAP, GFAP) |
| AQTLSNPFKAQ | 3-mer-s PHP.B library | High (based on NGS/E.coli transformants from prior CREATE selection) | High (Tek, Syn, SNAP, GFAP) |
| AQTLSQPFKAQ | 3-mer-s PHP.B library | High (based on NGS/E.coli transformants from prior CREATE selection) | High (Tek, Syn, SNAP, GFAP) |
| EGTLAVPFKAQ | 3-mer-s PHP.B library | High (based on NGS/E.coli transformants from prior CREATE selection) | High (Tek, Syn, SNAP, GFAP) |
| DSTLAVPFKAQ | 3-mer-s PHP.B library | High (based on NGS/E.coli transformants from prior CREATE selection) | High (Tek, Syn, SNAP, GFAP) |

FIG. 75 (Continued)

| | | | | | |
|---|---|---|---|---|---|
| | NQTLAVPFKAQ | 3-mer-s PHP.B library | High (based on NGS/E.coli transformants from prior CREATE selection) | | High (Tek, Syn, SNAP, GFAP) |
| | SGNLAVPFKAQ | 3-mer-s PHP.B library | High (based on NGS/E.coli transformants from prior CREATE selection) | | High (Tek, Syn, SNAP, GFAP) |
| | ATTLAVPFKAQ | 3-mer-s PHP.B library | High (based on NGS/E.coli transformants from prior CREATE selection) | | High (Tek, Syn, SNAP, GFAP) |
| | AQTLTMPFKAQ | 3-mer-s PHP.B library | High (based on NGS/E.coli transformants from prior CREATE selection) | | High (Syn, SNAP, GFAP) |
| | AQTLSTPFKAQ | 3-mer-s PHP.B library | High (based on NGS/E.coli transformants from prior CREATE selection) | | High (Syn, SNAP, GFAP) |
| | QGTLAVPFKAQ | 3-mer-s PHP.B library | High (based on NGS/E.coli transformants from prior CREATE selection) | | High (Tek, Syn, SNAP, GFAP) |
| 15168 | DGTLAVPFSNP | 3-mer-s PHP.B library | High (based on NGS/E.coli transformants from prior CREATE selection) | | High (Tek, Syn, SNAP, GFAP) |
| 15169 | DGTLAVPFRAQ | 3-mer-s PHP.B library | High (based on NGS/E.coli transformants from prior CREATE selection) | variant unrecovered in brain tissue | |
| 15170 | AQNSREVNIAQ | 7-mer-i AAV9 library (prior selection study in GFAP-cre) | High in GFAP (based on NGS/E.coli transformants from prior CREATE selection) | Low (GFAP) | Low (Syn, SNAP) |
| 15171 | AQTREVNVIAQ | 7-mer-i AAV9 library (prior selection study in GFAP-cre) | High in GFAP (based on NGS/E.coli transformants from prior CREATE selection) | | Low (Syn) |

FIG. 75 (Continued)

| | | | | |
|---|---|---|---|---|
| 15172 | AQIGMGHTLAQ | 7-mer-i AAV9 library (prior selection study in GFAP-cre) | High in GFAP (based on NGS/E.coli transformants from prior CREATE selection) | | Low (Syn) |
| 15173 | AQTAETKFLAQ | 7-mer-i AAV9 library (prior selection study in GFAP-cre) | High in GFAP (based on NGS/E.coli transformants from prior CREATE selection) | | Low (Syn) |
| 15174 | AQKATPPTEAQ | 7-mer-i AAV9 library (prior selection study in GFAP-cre) | High in GFAP (based on NGS/E.coli transformants from prior CREATE selection) | Low (GFAP) | |
| 15175 | AQAETSRSVAQ | 7-mer-i AAV9 library (prior selection study in GFAP-cre) | High in GFAP (based on NGS/E.coli transformants from prior CREATE selection) | | Low (Syn) |
| 15176 | AQTNRTIQTAQ | 7-mer-i AAV9 library (prior selection study in GFAP-cre) | High in GFAP (based on NGS/E.coli transformants from prior CREATE selection) | | High (Tek), Low (Syn, SNAP, GFAP) |
| 15177 | AQYALTNDRAQ | 7-mer-i AAV9 library (prior selection study in GFAP-cre) | High in GFAP (based on NGS/E.coli transformants from prior CREATE selection) | variant unrecovered in brain tissue | |
| 15178 | AQSVTNKMLAQ | 7-mer-i AAV9 library (prior selection study in GFAP-cre) | High in GFAP (based on NGS/E.coli transformants from prior CREATE selection) | | Low (Syn, Tek) |
| 15179 | AQSVQIVRGAQ | 7-mer-i AAV9 library (prior selection study in GFAP-cre) | High in GFAP (based on NGS/E.coli transformants from prior CREATE selection) | Low (GFAP) | |

FIG. 75 (Continued)

| 15180 | | | | |
|---|---|---|---|---|
| | AQYPNTSQVAQ | 7-mer-i AAV9 library (prior selection study in GFAP-cre) | High in GFAP (based on NGS/E.coli transformants from prior CREATE selection) | Low (GFAP) | Low (Syn, Tek) |
| 15181 | AQYTLSQGTAQ | 7-mer-i AAV9 library (prior selection study in GFAP-cre) | High in GFAP (based on NGS/E.coli transformants from prior CREATE selection) | | Low (Syn) |
| 15182 | AQWGLNRGTAQ | 7-mer-i AAV9 library (prior selection study in GFAP-cre) | High in GFAP (based on NGS/E.coli transformants from prior CREATE selection) | variant unrecovered in brain tissue | |
| 15183 | AQTPKNVPDAQ | 7-mer-i AAV9 library (prior selection study in GFAP-cre) | High in GFAP (based on NGS/E.coli transformants from prior CREATE selection) | variant unrecovered in brain tissue | |
| 15184 | AQYDPRGTDAQ | 7-mer-i AAV9 library (prior selection study in GFAP-cre) | High in GFAP (based on NGS/E.coli transformants from prior CREATE selection) | variant unrecovered in brain tissue | |
| 15185 | AQVDTRPIQAQ | 7-mer-i AAV9 library (prior selection study in GFAP-cre) | High in GFAP (based on NGS/E.coli transformants from prior CREATE selection) | Low (GFAP) | |
| 15186 | AQTKSSYGVAQ | 7-mer-i AAV9 library (prior selection study in GFAP-cre) | High in GFAP (based on NGS/E.coli transformants from prior CREATE selection) | | Low (Syn, Tek) |
| 15187 | AQMNSTKNVAQ | 7-mer-i AAV9 library (prior selection study in GFAP-cre) | High in GFAP (based on NGS/E.coli transformants from prior CREATE selection) | | High (Tek), Low (Syn, SNAP, GFAP) |

FIG. 75 (Continued)

| | | | | |
|---|---|---|---|---|
| 15188 | AQSLHHGSSAQ | 7-mer-i AAV9 library (prior selection study in GFAP-cre) | High in GFAP (based on NGS/E.coli transformants from prior CREATE selection) | | Low (Syn) |
| 15189 | AQSSPGAMHAQ | 7-mer-i AAV9 library (prior selection study in GFAP-cre) | High in GFAP (based on NGS/E.coli transformants from prior CREATE selection) | variant unrecovered in brain tissue | |
| 15190 | AQSSYNDHPAQ | 7-mer-i AAV9 library (prior selection study in GFAP-cre) | High in GFAP (based on NGS/E.coli transformants from prior CREATE selection) | Low (GFAP) | Low (Syn) |
| 15191 | AQGAPRSSIAQ | 7-mer-i AAV9 library (prior selection study in GFAP-cre) | High in GFAP (based on NGS/E.coli transformants from prior CREATE selection) | | Low (Tek, Syn) |
| 15192 | AQQGSLYTSAQ | 7-mer-i AAV9 library (prior selection study in GFAP-cre) | High in GFAP (based on NGS/E.coli transformants from prior CREATE selection) | | Low (Syn) |
| 15193 | AQHNAPGSLAQ | 7-mer-i AAV9 library (prior selection study in GFAP-cre) | High in GFAP (based on NGS/E.coli transformants from prior CREATE selection) | Low (GFAP) | Low (Syn) |
| 15194 | AQSLSPTINAQ | 7-mer-i AAV9 library (prior selection study in GFAP-cre) | High in GFAP (based on NGS/E.coli transformants from prior CREATE selection) | | Low (Syn) |
| 15195 | AQNNVTLLSAQ | 7-mer-i AAV9 library (prior selection study in GFAP-cre) | High in GFAP (based on NGS/E.coli transformants from prior CREATE selection) | Low (GFAP) | Low(Syn) |

FIG. 75 (Continued)

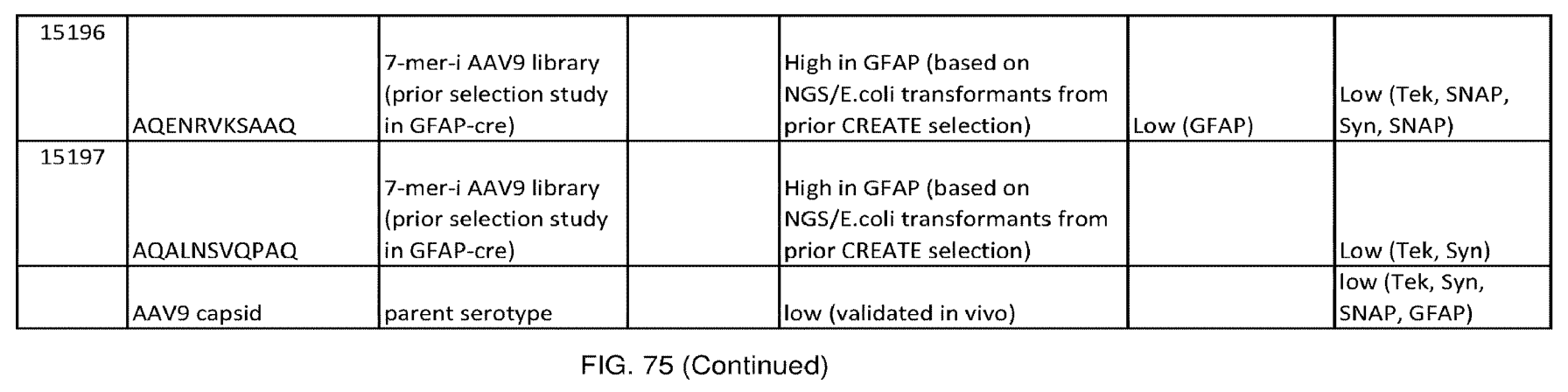

| 15196 | AQENRVKSAAQ | 7-mer-i AAV9 library (prior selection study in GFAP-cre) | High in GFAP (based on NGS/E.coli transformants from prior CREATE selection) | Low (GFAP) | Low (Tek, SNAP, Syn, SNAP) |
| 15197 | AQAINSVQPAQ | 7-mer-i AAV9 library (prior selection study in GFAP-cre) | High in GFAP (based on NGS/E.coli transformants from prior CREATE selection) | | Low (Tek, Syn) |
| | AAV9 capsid | parent serotype | low (validated in vivo) | | low (Tek, Syn, SNAP, GFAP) |

FIG. 75 (Continued)

| 7-11 mer Peptide | SNAP-Cre brain mean enrichment score (log10 scale) |
|---|---|
| AQTLQLPFKAQ | 2.635622315 |
| QGTLAVPFKAQ | 2.560366902 |
| AQTLSNPFKAQ | 2.502118769 |
| EGTLAVPFKAQ | 2.482752751 |
| DGTLAVPFKAQ | 2.463683642 |
| AQTLQQPFKAQ | 2.419778506 |
| AQTLATPFKAQ | 2.413504952 |
| SGSLAVPFKAQ | 2.332201386 |
| AQTLSTPFKAQ | 2.299687253 |
| DGTLATPFKAQ | 2.291973997 |
| GGTLAVPFKAQ | 2.29043988 |
| AQSVSKPFLAQ | 2.284711601 |
| AQTLAVPFKAQ | 2.278601473 |
| AQTLTMPFKAQ | 2.221290966 |
| ESTLAVPFKAQ | 2.117205819 |
| SGNLAVPFKAQ | 2.105494998 |
| AQTLSQPFKAQ | 2.0935429 |
| NQTLAVPFKAQ | 2.016639766 |
| AQTLAQPFKAQ | 1.995025038 |
| ATTLATPFKAQ | 1.92915754 |
| DSTLAVPFKAQ | 1.905246666 |
| AQTLAVPFSNP | 1.738130019 |
| GGTLATPFKAQ | 1.695996385 |
| ATTLAVPFKAQ | 1.647772357 |
| AQFTLTTPKAQ | 1.10964487 |
| DGTLAVPFSNP | 0.989170037 |
| AQTTLKPFSNP | 0.848064508 |
| AQMNSTKNVAQ | 0.133837545 |
| AQTNRTIQTAQ | 0.070636377 |
| AQNSREVNIAQ | 0.010923571 |
| AQENRVKSAAQ | -0.270391873 |
| *AAV9 parent* | *-0.717369399* |

FIG. 76

| 7-11 mer Peptide | GFAP-Cre brain mean enrichment score (log10 scale) |
|---|---|
| AQSVSKPFLAQ | 2.432111357 |
| AQTLQLPFKAQ | 2.426669581 |
| AQTLAVPFKAQ | 2.424167734 |
| SGSLAVPFKAQ | 2.413393158 |
| GGTLAVPFKAQ | 2.397707224 |
| SGNLAVPFKAQ | 2.35782662 |
| AQTLTMPFKAQ | 2.35516667 |
| AQTLQQPFKAQ | 2.327525492 |
| QGTLAVPFKAQ | 2.306177613 |
| DGTLAVPFKAQ | 2.284953655 |
| EGTLAVPFKAQ | 2.254372157 |
| AQTLSNPFKAQ | 2.214426568 |
| AQTLATPFKAQ | 2.189159997 |
| DGTLATPFKAQ | 2.142993798 |
| AQTLSQPFKAQ | 2.114492139 |
| ATTLATPFKAQ | 2.109425827 |
| AQTLSTPFKAQ | 1.960573055 |
| AQTLAQPFKAQ | 1.922063594 |
| ESTLAVPFKAQ | 1.876988733 |
| NQTLAVPFKAQ | 1.793802999 |
| ATTLAVPFKAQ | 1.700418599 |
| AQTLAVPFSNP | 1.613667889 |
| GGTLATPFKAQ | 1.566031662 |
| DSTLAVPFKAQ | 1.378544566 |
| AQTTLKPFSNP | 1.101507461 |
| AQFTLTTPKAQ | 1.066406048 |
| DGTLAVPFSNP | 0.635613469 |
| DGTALKPFLAQ | 0.42534062 |
| AQTNRTIQTAQ | 0.394388797 |
| AQMNSTKNVAQ | 0.358805861 |
| AQSSYNDHPAQ | 0.295857683 |
| AQSVQIVRGAQ | 0.183522142 |
| AQYPNTSQVAQ | 0.180040989 |
| AQVDTRPIQAQ | 0.178271526 |
| AQHNAPGSLAQ | 0.141306671 |
| AQKATPPTEAQ | 0.13263146 |
| AQENRVKSAAQ | -0.025808641 |
| AQQAVRTSLAQ | -0.219734424 |
| AQNSREVNIAQ | -0.272580586 |
| *AAV9 parent* | *-0.463061913* |
| AQNNVTLLSAQ | -0.666668537 |

| 7-11 mer Peptide | SNAP-Cre brain mean enrichment score (log10 scale) | 7-11 mer Peptide | GFAP-Cre brain mean enrichment score (log10 scale) |
|---|---|---|---|
| AQTLQLPFKAQ | 2.635622315 | AQSVSKPFLAQ | 2.432111357 |
| QGTLAVPFKAQ | 2.560366902 | AQTLQLPFKAQ | 2.426669581 |
| AQTLSNPFKAQ | 2.502118769 | AQTLAVPFKAQ | 2.424167734 |
| EGTLAVPFKAQ | 2.482752751 | SGSLAVPFKAQ | 2.413393158 |
| DGTLAVPFKAQ | 2.463683642 | GGTLAVPFKAQ | 2.397707224 |
| AQTLQQPFKAQ | 2.419778506 | SGNLAVPFKAQ | 2.35782662 |
| AQTLATPFKAQ | 2.413504952 | AQTLTMPFKAQ | 2.35516667 |
| SGSLAVPFKAQ | 2.332201386 | AQTLQQPFKAQ | 2.327525492 |
| AQTLSTPFKAQ | 2.299687253 | QGTLAVPFKAQ | 2.306177613 |
| DGTLATPFKAQ | 2.291973997 | DGTLAVPFKAQ | 2.284953655 |
| GGTLAVPFKAQ | 2.29043988 | EGTLAVPFKAQ | 2.254372157 |
| AQSVSKPFLAQ | 2.284711601 | AQTLSNPFKAQ | 2.214426568 |
| AQTLAVPFKAQ | 2.278601473 | AQTLATPFKAQ | 2.189159997 |
| AQTLTMPFKAQ | 2.221290966 | DGTLATPFKAQ | 2.142993798 |
| ESTLAVPFKAQ | 2.117205819 | AQTLSQPFKAQ | 2.114492139 |
| SGNLAVPFKAQ | 2.105494998 | ATTLATPFKAQ | 2.109425827 |
| AQTLSQPFKAQ | 2.0935429 | AQTLSTPFKAQ | 1.960573055 |
| NQTLAVPFKAQ | 2.016639766 | AQTLAQPFKAQ | 1.922063594 |
| AQTLAQPFKAQ | 1.995025038 | ESTLAVPFKAQ | 1.876988733 |
| ATTLATPFKAQ | 1.92915754 | NQTLAVPFKAQ | 1.793802999 |
| DSTLAVPFKAQ | 1.905246666 | ATTLAVPFKAQ | 1.700418599 |
| AQTLAVPFSNP | 1.738130019 | AQTLAVPFSNP | 1.613667889 |
| GGTLATPFKAQ | 1.695996385 | GGTLATPFKAQ | 1.566031662 |
| ATTLAVPFKAQ | 1.647772357 | DSTLAVPFKAQ | 1.378544566 |
| AQFTLTTPKAQ | 1.10964487 | AQTTLKPFSNP | 1.101507461 |
| DGTLAVPFSNP | 0.989170037 | AQFTLTTPKAQ | 1.066406048 |
| AQTTLKPFSNP | 0.848064508 | DGTLAVPFSNP | 0.635613469 |
| AQMNSTKNVAQ | 0.133837545 | DGTALKPFLAQ | 0.42534062 |
| AQTNRTIQTAQ | 0.070636377 | AQTNRTIQTAQ | 0.394388797 |
| AQNSREVNIAQ | 0.010923571 | AQMNSTKNVAQ | 0.358805861 |
| AQENRVKSAAQ | -0.270391873 | AQSSYNDHPAQ | 0.295857683 |
| *AAV9 parent* | *-0.717369399* | AQSVQIVRGAQ | 0.183522142 |
| | | AQYPNTSQVAQ | 0.180040989 |
| | | AQVDTRPIQAQ | 0.178271526 |
| | | AQHNAPGSLAQ | 0.141306671 |
| | | AQKATPPTEAQ | 0.13263146 |
| | | AQENRVKSAAQ | -0.025808641 |
| | | AQQAVRTSLAQ | -0.219734424 |
| | | AQNSREVNIAQ | -0.272580586 |
| | | *AAV9 parent* | *-0.463061913* |
| | | AQNNVTLLSAQ | -0.666668537 |

FIG. 76 (Continued)

VIRUS COMPOSITIONS WITH ENHANCED SPECIFICITY IN THE BRAIN

RELATED APPLICATIONS

This Application claims the benefit of and priority to U.S. Provisional Patent Application Ser. No. 62/832,836, filed Apr. 11, 2019, the content of which is incorporated herein in its entirety.

STATEMENT AS TO FEDERALLY SPONSORED RESEARCH

This invention was made with government support under NS087949, MH117069, and OD025535 awarded by National Institutes of Health. The government has certain rights in the invention.

SUMMARY

Recombinant adeno-associated viruses (rAAVs) are widely used as vectors for gene delivery in basic scientific research and therapeutic applications because of their ability to transduce both dividing and non-dividing cells, their long-term persistence as episomal DNA in infected cells, and their low immunogenicity. These characteristics make them appealing for applications in both basic science and in clinics, such as gene therapy. However, there is a need to significantly improve the performance of existing serotypes to specifically target distinct brain cell-types, upon systemic delivery to a subject. This need is especially acute when the AAV must across the blood brain barrier (BBB) to reach the central nervous system (CNS).

Systemic delivery of existing AAV serotypes show limited transduction of certain cell types and organs, and non-specific, overlapping tropisms in others. This leads to several complications in gene therapy applications, including but not limited to off-target effects due to transduction of unimpacted organs and cell types (in particular, the liver), and the necessity for a larger viral dosage to achieve sufficient therapeutic levels in the tissue or organ of interest.

Disclosed herein are rAAVs with engineered specificity into the capsid structure through iterative rounds of positive and negative selection, yielding variants with tropisms having an increased specificity and transduction efficiency when measured in the CNS, and in some cases, a decreased specificity and transduction efficiency in an off-target environment, like the liver. The rAAVs described herein achieve widespread transduction to target environment (e.g., target cell types or tissues) in a subject upon systemic delivery (e.g., intravenous injection).

Also provided are methods of engineering the rAAVs of the present disclose using a multiplexed Cre recombination-based AAV targeted evolution (M-CREATE) method. The M-CREATE method generates enhanced transduction efficiency and/or specificity by (1) introducing variations in the capsid protein sequence, (2) in vivo unbiased selection and recovery of only those variants that travel to defined cell populations, (3) cross the cell membrane, (4) travel to the nucleus, and (5) unpackage and express their genetic dosage amount. Variant capsids exhibiting the most desirable tropism (e.g., enhanced efficiency and specificity for a particular in vivo environment) are recovered and identified by deep sequencing. Strategies for unbiased selection and analysis include determining variants' enrichment score (by normalizing the target tissue library to starting virus library) and unbiased propagation between rounds of selections through a synthetic library construction (where each variant is represented equally). Also disclosed are detailed characterizations of the resultant libraries from sequencing data which provide useful insights on the selection of variants towards a target.

Disclosed herein are AAV capsid libraries generated using M-CREATE. The first library, a 7-mer peptide insertion in AAV9 (7-mer-i library) was built for parallel in vivo selections across different brain cell types—endothelial cells, neurons, and astrocytes—and yielded a large pool of AAV9 variants with enhanced ability to target as well as cross the blood-brain barrier (BBB) and broadly transduce the central nervous system (CNS). The second library, a 3-mer peptide substitution in AAV-PHP.B (3-mer-s library), was reinvestigated by incorporating deep sequencing to recover capsids. A pool of AAV-PHP.B variants were discovered including a variant that transduce CNS neurons with greater specificity. The rAAVs of the present disclosure can efficiently target the endothelial cells of the blood-brain barrier, variants that can broadly transduce different cell types in the central nervous system, and a variant exhibiting greater specificity towards transducing neuron.

Aspects disclosed herein provide AAV capsids comprising: (a) an AAV capsid protein comprising: (i) a first amino acid sequence that is at least 98% identical to amino acid 217 to amino acid 736 of SEQ ID NO: 1; and (ii) a second amino acid sequence at least 57.1% identical to an amino acid sequence provided in Tables 2-3 or FIG. 33 inserted at an amino acid position 588_589 within SEQ ID NO: 1, wherein the AAV capsid protein is characterized by at least one of an increased specificity and an increased transduction efficiency when measured in a central nervous system (CNS) in a subject when delivered to the subject systemically, relative to a native AAV capsid protein provided in SEQ ID NO: 1. In some embodiments, the second amino acid sequence is at least 71.4% identical to the amino acid sequence provided in Tables 2-3 or FIG. 33. In some embodiments, the second amino acid sequence is at least 86.7% identical to the amino acid sequence provided in Tables 2-3 or FIG. 33. In some embodiments, the second amino acid sequence is selected from the group consisting of TALKPFL, TTLKPFL, TLQIPFK, TMQKPFI, SIERPFK, RYQGDSV, and TTLKPFS. In some embodiments, the AAV capsid protein is present in VP1, VP2, and VP3 of the AAV capsid. In some embodiments, the AAV capsid is chimeric. In some embodiments, 60 copies of the AAV capsid protein are assembled into the AAV capsid. In some embodiments, the CNS comprises a cell-type selected from the group consisting of a neuron, an oligodendrocyte, an astrocyte, and a brain vascular cell. In some embodiments, the CNS comprises a tissue that is selected from the group consisting of a brain, a thalamus, a cortex, a striatum, a ventral midbrain, and a spinal cord. In some embodiments, the AAV capsid protein further comprises an amino acid substitution A587D. In some embodiments, the AAV capsid protein further comprises an amino acid substitution Q588G. In some embodiments, the AAV capsid protein further comprises an amino acid substitution comprising A589N. In some embodiments, the AAV capsid protein further comprises an amino acid substitution comprising Q590P. In some embodiments, the second amino acid sequence at the amino acid position 588_589 within SEQ ID NO: 1 is not TLAVPFK, KFPVALT, SVSKPFL, FTLTTPK, MNATKNV, NGGTSSS, TRTNPEA, or YTLSQGW. In some embodiments, the AAV capsid is isolated and purified. In some embodiments, the AAV capsid is formulated as a pharmaceutical formulation for intravenous administration to treat a disease or a condition of the liver, the pharmaceutical formulation further comprising a pharmaceutically acceptable carrier. In some embodiments, the pharmaceutical formulation further comprises a therapeutic agent.

Aspects disclosed herein provide AAV capsids comprising an AAV capsid protein comprising a seven amino acid insertion (X1-X2-X3-X4-X5-X6-X7) between amino acid 588 and amino acid 589 in an amino acid sequence of the AAV capsid protein provided in SEQ ID NO: 1, wherein X1 is an amino acid selected from the group consisting of E, D, G, R, S and T. In some embodiments, X2 is an amino acid selected from the group consisting of A, G, I, L, M, N, Q, T, and Y. In some embodiments, X3 is an amino acid selected from the group consisting of E, K, L, T, and Q. In some embodiments, X4 is an amino acid selected from the group consisting of G, I, K, L, R, T, and V. In some embodiments, X5 is an amino acid selected from the group consisting of A, D, G, P, L, Q, and V. In some embodiments, X6 is an amino acid selected from the group consisting of F, K, N, P, Q, S, and V. In some embodiments, X7 is an amino acid selected from the group consisting of I, K, L, P, and V. In some embodiments, the seven amino acid insertion is selected from the group consisting of TALKPFL, TTLKPFL, TLQIPFK, TMQKPFI, SIERPFK, RYQGDSV, and TTLKPFS. In some embodiments, the AAV capsid protein is present in VP1, VP2, and VP3 of the AAV capsid. In some embodiments, the AAV capsid is chimeric. In some embodiments, 60 copies of the AAV capsid protein are assembled into the AAV capsid. In some embodiments, the AAV capsid protein is characterized by at least one of an increased specificity and an increased transduction efficiency when measured in a central nervous system (CNS) in a subject when delivered to the subject systemically, relative to a native AAV capsid protein provided in SEQ ID NO: 1. In some embodiments, the CNS comprises a cell-type selected from the group consisting of a neuron, a glial cell, a oligodendrocyte, an ependymal cell, an astrocyte, a Schwann cell, a satellite cell, and an enteric glial cell. In some embodiments, the CNS comprises a tissue that is selected from the group consisting of a brain, a thalamus, a cortex, a striatum, a ventral midbrain, and a spinal cord. In some embodiments, the AAV capsid protein further comprises an amino acid substitution comprising A587D. In some embodiments, the AAV capsid protein further comprises an amino acid substitution comprising Q588G. In some embodiments, the AAV capsid protein further comprises an amino acid substitution comprising A589N. In some embodiments, the AAV capsid protein further comprises an amino acid substitution comprising Q590P. In some embodiments, the seven amino acid insertion is not TLAVPFK, KFPVALT, SVSKPFL, FTLTTPK, MNATKNV, NGGTSSS, TRTNPEA, or YTLSQGW. In some embodiments, the AAV capsid is isolated and purified. In some embodiments, the AAV capsid is formulated as a pharmaceutical formulation for intravenous administration to treat a disease or a condition of the liver, the pharmaceutical formulation further comprising a pharmaceutically acceptable carrier. In some embodiments, the pharmaceutical formulation further comprises a therapeutic agent.

Aspects provided herein provide AAV capsids comprising: (a) an AAV capsid protein comprising: (i) a first amino acid sequence that is at least 98% identical to amino acid 217 to amino acid 736 of SEQ ID NO: 1; and (ii) a second amino acid sequence provided in Table 4 or FIG. 35 at an amino acid position 588_589 within SEQ ID NO: 1, wherein the AAV capsid protein is characterized by at least one of an increased specificity and an increased transduction efficiency when measured in a liver in a subject when delivered to the subject systemically, relative to a native AAV capsid protein provided in SEQ ID NO: 1. In some embodiments, the second amino acid sequence is at least 71.4% identical to the amino acid sequence provided in Table 4 or FIG. 35. In some embodiments, the second amino acid sequence is at least 86.7% identical to the amino acid sequence provided in Table 4 or FIG. 35. In some embodiments, the second amino acid sequence is selected from the group consisting of KAYSVQV, PSGSARS, and RTANALG. In some embodiments, the AAV capsid protein is present in VP1, VP2, and VP3 of the AAV capsid. In some embodiments, the AAV capsid is chimeric. In some embodiments, 60 copies of the AAV capsid protein are assembled into the AAV capsid. In some embodiments, the AAV capsid is isolated and purified. In some embodiments, the AAV capsid is formulated as a pharmaceutical formulation for intravenous administration to treat a disease or a condition of the liver, the pharmaceutical formulation further comprising a pharmaceutically acceptable carrier. In some embodiments, the pharmaceutical formulation further comprises a therapeutic agent.

Aspects disclosed herein provide AAV capsid proteins comprising: (i) a first amino acid sequence that is at least 98% identical to amino acid 217 to amino acid 736 of SEQ ID NO: 1; and (ii) a second amino acid sequence at least 57.1% identical to an amino acid sequence provided in Tables 2-3 or FIG. 33 inserted at an amino acid position 588_589 within SEQ ID NO: 1, wherein the AAV capsid protein is characterized by at least one of an increased specificity and an increased transduction efficiency when measured in a central nervous system (CNS) in a subject when delivered to the subject systemically, relative to a native AAV capsid protein provided in SEQ ID NO: 1. In some embodiments, the second amino acid sequence is at least 71.4% identical to the amino acid sequence provided in Tables 2-3 or FIG. 33. In some embodiments, the second amino acid sequence is at least 86.7% identical to the amino acid sequence provided in Tables 2-3 or FIG. 33. In some embodiments, the second amino acid sequence is selected from the group consisting of TALKPFL, TTLKPFL, TLQIPFK, TMQKPFI, SIERPFK, RYQGDSV, and TTLKPFS. In some embodiments, the AAV capsid protein is present in VP1, VP2, and VP3 of an AAV capsid. In some embodiments, the AAV capsid is chimeric. In some embodiments, 60 copies of the AAV capsid protein are assembled into the AAV capsid. In some embodiments, the CNS comprises a cell-type selected from the group consisting of a neuron, an oligodendrocyte, an astrocyte, and a brain vascular cell. In some embodiments, the CNS comprises a tissue that is selected from the group consisting of a brain, a thalamus, a cortex, a striatum, a ventral midbrain, and a spinal cord. In some embodiments, the AAV capsid protein further comprises an amino acid substitution A587D. In some embodiments, the AAV capsid protein further comprises an amino acid substitution Q588G. In some embodiments, the AAV capsid protein further comprises an amino acid substitution comprising A589N. In some embodiments, the AAV capsid protein further comprises an amino acid substitution comprising Q590P. In some embodiments, the second amino acid sequence at the amino acid position 588_589 within SEQ ID NO: 1 is not TLAVPFK, KFPVALT, SVSKPFL, FTLTTPK, MNATKNV, NGGTSSS, TRTNPEA, or YTLSQGW. In some embodiments, the AAV capsid protein is isolated and purified. In some embodiments, the AAV capsid protein is formulated as a pharmaceutical formulation for intravenous administration to treat a disease or a condition of the liver, the pharmaceutical formulation further comprising a pharmaceutically acceptable carrier. In some embodiments, the pharmaceutical formulation further comprises a therapeutic agent.

Aspects disclosed herein provide AAV capsids proteins comprising a seven amino acid insertion (X1-X2-X3-X4-X5-X6-X7) between amino acid 588 and amino acid 589 in an amino acid sequence of the AAV capsid protein provided in SEQ ID NO: 1, wherein X1 is an amino acid selected from the group consisting of E, D, G, R, S and T. In some embodiments, X2 is an amino acid selected from the group consisting of A, G, I, L, M, N, Q, T, and Y. In some embodiments, X3 is an amino acid selected from the group consisting of E, K, L, T, and Q. In some embodiments, X4 is an amino acid selected from the group consisting of G, I, K, L, R, T, and V. In some embodiments, X5 is an amino acid selected from the group consisting of A, D, G, P, L, Q, and V. In some embodiments, X6 is an amino acid selected from the group consisting of F, K, N, P, Q, S, and V. In some embodiments, X7 is an amino acid selected from the group consisting of I, K, L, P, and V. In some embodiments, the seven amino acid insertion is selected from the group consisting of TALKPFL, TTLKPFL, TLQIPFK, TMQKPFI, SIERPFK, RYQGDSV, and TTLKPFS. In some embodiments, the AAV capsid protein is present in VP1, VP2, and VP3 of a AAV capsid. In some embodiments, the AAV capsid is chimeric. In some embodiments, 60 copies of the AAV capsid protein are assembled into the AAV capsid. In some embodiments, the AAV capsid protein is characterized by at least one of an increased specificity and an increased transduction efficiency when measured in a central nervous system (CNS) in a subject when delivered to the subject systemically, relative to a native AAV capsid protein provided in SEQ ID NO: 1. In some embodiments, the CNS comprises a cell-type selected from the group consisting of a neuron, a glial cell, a oligodendrocyte, an ependymal cell, an astrocyte, a Schwann cell, a satellite cell, and an enteric glial cell. In some embodiments, the CNS comprises a tissue that is selected from the group consisting of a brain, a thalamus, a cortex, a striatum, a ventral midbrain, and a spinal cord. In some embodiments, the AAV capsid protein further comprises an amino acid substitution comprising A587D. In some embodiments, the AAV capsid protein further comprises an amino acid substitution comprising Q588G. In some embodiments, the AAV capsid protein further comprises an amino acid substitution comprising A589N. In some embodiments, the AAV capsid protein further comprises an amino acid substitution comprising Q590P. In some embodiments, the seven amino acid insertion is not TLAVPFK, KFPVALT, SVSKPFL, FTLTTPK, MNATKNV, NGGTSSS, TRTNPEA, or YTLSQGW. In some embodiments, the AAV capsid protein is isolated and purified. In some embodiments, the AAV capsid protein is formulated as a pharmaceutical formulation for intravenous administration to treat a disease or a condition of the liver, the pharmaceutical formulation further comprising a pharmaceutically acceptable carrier. In some embodiments, the pharmaceutical formulation further comprises a therapeutic agent.

Aspects provided herein provide AAV capsids proteins comprising: (i) a first amino acid sequence that is at least 98% identical to amino acid 217 to amino acid 736 of SEQ ID NO: 1; and (ii) a second amino acid sequence at least 57.1% identical to an amino acid sequence provided in Table 4 or FIG. 35 at an amino acid position 588_589 within SEQ ID NO: 1, wherein the AAV capsid protein is characterized by at least one of an increased specificity and an increased transduction efficiency when measured in a liver in a subject when delivered to the subject systemically, relative to a native AAV capsid protein provided in SEQ ID NO: 1. In some embodiments, the second amino acid sequence is at least 71.4% identical to the amino acid sequence provided in Table 4 or FIG. 35. In some embodiments, the second amino acid sequence is at least 86.7% identical to the amino acid sequence provided in Table 4 or FIG. 35. In some embodiments, the second amino acid sequence is selected from the group consisting of KAYSVQV, PSGSARS, and RTANALG. In some embodiments, the AAV capsid protein is present in VP1, VP2, and VP3 of an AAV capsid. In some embodiments, the AAV capsid is chimeric. In some embodiments, 60 copies of the AAV capsid protein are assembled into the AAV capsid. In some embodiments, the AAV capsid protein is isolated and purified. In some embodiments, the AAV capsid protein is formulated as a pharmaceutical formulation for intravenous administration to treat a disease or a condition of the liver, the pharmaceutical formulation further comprising a pharmaceutically acceptable carrier. In some embodiments, the pharmaceutical formulation further comprises a therapeutic agent.

Aspects disclosed herein comprise plasmid vectors comprising a nucleic acid sequence encoding the AAV capsids and AAV capsid proteins described herein. In some instances, the plasmid vector is bacterial. In some instances, the plasmid vector is derived from *Escherichia coli*. In some instances, the nucleic acid sequence comprises, in a 5' to 3' direction: (1) a 5' inverted terminal repeat (ITR) sequence, (2) a Replication (Rep) gene, (3) a Capsid (Cap) gene, and (4) a 3' ITR, wherein the Cap gene encodes the AAV capsid protein described herein. In some instances, the plasmid vector encodes a pseudotyped AAV capsid protein. In some instances, the Cap gene is derived from the deoxyribose nucleic acid (DNA) provided in any one of SEQ ID NOs: 6-10. In some instances, the nucleic acid sequence comprising the Cap gene is at least 90%, 91%, 92%, 93%, 94%, 95%, 96%, 97%, 98%, 99%, or 100% identical to any one of the DNA sequences provided in U.S. application. Ser. No. 16/582,635, incorporated herein by reference. In some instances, the 5' ITR and the 3' ITR are derived from an AAV2 serotype. In some instances, the 5' ITR and the 3' ITR are derived from an AAV5 serotype. In some instances, the 5' ITR and the 3' ITR are derived from an AAV9 serotype.

Aspects disclosed herein provide methods of treating a disease or condition in a subject comprising administering a therapeutically effective amount of a pharmaceutical formulation comprising the AAV capsid protein or the AAV capsid of the present disclosure. In some embodiments, the disease or the condition is a disease or a condition of a central nervous system (CNS) or a liver of the subject. In some embodiments, the disease or condition of the liver is selected from the group consisting of Alagille Syndrome, Alcohol-Related Liver Disease, Alpha-1 Antitrypsin Deficiency, Autoimmune Hepatitis, Benign Liver Tumors, Biliary Atresia, Cirrhosis, Crigler-Najjar Syndrome, Galactosemia, Gilbert Syndrome, Hemochromatosis, Hepatic Encephalopathy, Hepatitis A, Hepatitis B, Hepatitis C, Hepatorenal Syndrome, Intrahepatic Cholestasis of Pregnancy (ICP), Lysosomal Acid Lipase Deficiency (LAL-D), Liver Cysts, Liver Cancer, Newborn Jaundice, Non-Alcoholic Fatty Liver Disease, Primary Biliary Cholangitis (PBC), Primary Sclerosing Cholangitis (PSC), Reye Syndrome, Type I Glycogen Storage Disease, and Wilson Disease. In some embodiments, the disease or condition of the CNS is selected from group consisting of Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Cerebral Autosomal Dominant Arteriopathy with Subcortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavemous Malformation, Cerebral Gigantism, Cerebral Hypoxia, Cerebral Palsy, Cerebro-Oculo-Facio-Skeletal Syndrome (COFS), Charcot-Marie-Tooth Disease, Charcot-Marie-Tooth syndrome, classical rhizomelic chondrodysplasia punctata (RCDP), Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, Deafness, De Morsier's Syndrome, Dejerine-Klumpke Palsy, Dementia, Dementia-Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Duchenne muscular dystrophy, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy (familial infantile), Encephalotrigeminal Angiomatosis, Epilepsy, Epileptic Hemiplegia, Erb's Palsy, Erb-Duchenne and Dejerine-Klumpke Palsies, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses, Gerstmann's Syndrome, Gerstmann-Straussler-Scheinker Disease, Giant Axonal Neuropathy, Giant Cell Arteritis, Giant Cell Inclusion Disease, glioblastoma, Globoid Cell Leukodystrophy, Glossopharyngeal Neuralgia, Glycogen Storage Disease, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydrocephalus—Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kliiver-Bucy Syndrome, Korsakoff s Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus—Neurological Sequelae, Lyme Disease—Neurological Complications, Machado—Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Moebius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy-Congenital, Myopathy—Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy-Hereditary, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain—Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, and X-Linked Spinal and Bulbar Muscular Atrophy. In some embodiments, the pharmaceutical formulation comprises a therapeutic nucleic acid encoding a therapeutic gene expression product. In some instances, the therapeutic gene expression product is effective to modulate an activity or an expression of a target gene or gene expression product selected from the group consisting of Sarcoglycan Alpha (SGCA), glutamic acid decarboxylase 65 (GAD65), glutamic acid decarboxylase 67 (GAD67), CLN2, Nerve Growth Factor (NGF), Survival Of Motor Neuron 1, Telomeric (SMN1), Factor X (FIX), Retinoid Isomerohydrolase (RPE65), sarco/endoplasmic reticulum Ca2+-ATPase (SERCA2a), β-Glucocerebrosidase (GCase), Frataxin (FXN), Huntingtin (HTN), methyl-CpG binding protein 2 (MECP2), a peroxisomal biogenesis factor (PEX), progranulin (GRN), an antitubulin agent, copper-zinc superoxide dismutase (SOD1), Glucosylceramidase Beta (GBA), NPC Intracellular Cholesterol Transporter 1 (NPC1), and a NLRP3 inflammasome. In some instances, the therapeutic gene expression product comprises gene editing components. In some instances, the gene editing components are selected from the group consisting of small interfering RNA (siRNA), short hairpin RNA (shRNA), a microRNA (miRNA), artificial site-specific RNA endonuclease (ASRE), zinc finger endonuclease (ZFN), CRISPR/Cas, and transcription factor like effector nuclease (TALEN).

Aspects disclosed herein provide methods of manufacturing a recombinant AAV particle from the AAV capsid of the present disclosure, the method comprising: (a) introducing into a cell a nucleic acid comprising: (i) a first nucleic acid sequence encoding a therapeutic gene expression product; (ii) a second nucleic acid sequence encoding a recombinant viral genome comprising a capsid (Cap) gene modified to express the AAV capsid of the present disclosure; and (iii) a third nucleic acid sequence encoding an AAV helper virus genome; and (b) assembling the recombinant AAV particle, the recombinant AAV particle comprising the AAV capsid encapsidating the first nucleic acid.

Aspects disclosed herein provide methods of manufacturing comprising: (a) introducing into a cell a nucleic acid comprising: (i) a first nucleic acid sequence encoding a therapeutic gene expression product enclosed by a 5' and a 3' inverted terminal repeat (ITR) sequence; (ii) a second nucleic acid sequence encoding a viral genome comprising a 5' ITR sequence, a Replication (Rep) gene, Capsid (Cap) gene, and a 3' ITR, wherein the Cap gene encodes the AAV capsid protein described herein; and (iii) a third nucleic acid sequence encoding a first helper virus protein selected from the group consisting of E4orf6, E2a, and VA RNA, and optionally, a second helper virus protein comprising Ela or E1b55k; (b) expressing in the cell the AAV capsid protein described herein; (c) assembling an AAV particle comprising the AAV capsid proteins disclosed herein; and (d) packaging the first nucleic acid sequence in the AAV particle. In some instances, the cell is mammalian. In some instances, the cell is immortalized. In some instances, the immortalized cell is an embryonic stem cell. In some instances, the embryonic stem cell is a human embryonic stem cell. In some instances, the human embryonic stem cell is a human embryonic kidney 293 (HEK-293) cell. In some instances, the Cap gene is derived from the deoxyribose nucleic acid (DNA) provided in any one of SEQ ID NOs: 6-10. In some instances, the nucleic acid sequence comprising the Cap gene is at least 90%, 91%, 92%, 93%, 94%, 95%, 96%, 97%, 98%, 99%, or 100% identical to any one of the DNA sequences provided in U.S. application. Ser. No. 16/582,635, incorporated herein by reference. In some instances, the 5' ITR and the 3' ITR are derived from an AAV2 serotype. In some instances, the 5' ITR and the 3' ITR are derived from an AAV5 serotype. In some instances, the 5' ITR and the 3' ITR are derived from an AAV9 serotype. In some instances, the first nucleic acid sequence and the second nucleic acid sequence are in trans. In some instances, the first nucleic acid sequence and the second nucleic acid sequence are in cis. In some instances, the first nucleic acid sequence, the second nucleic acid sequence and the third nucleic acid sequence, are in trans.

Aspects disclosed herein provide methods of manufacturing a recombinant AAV particle, the method comprising: (a) providing a recombinant AAV genome comprising: (i) an AAV capsid gene, and (ii) a recognition sequence for a Cre recombinase, wherein the recognition sequence facilitates a recombinase-dependent change that is detectable, and wherein the recombinase recognition sequence comprises two Cre-recognition sites; (iii) transfecting a population of cells expressing the Cre recombinase with the recombinant AAV genome, whereby the Cre recombinase induces a recombination event to generate the recombinase-dependent change in the recombinant AAV genome, and wherein the recombinase-dependent change comprises an inversion of the sequence that is flanked by the Cre-recognition sites; (iv) detecting an increased rate of the recombinase-dependent change a target cell in the population of cells; (v) detecting a decreased rate of the recombinase-dependent change in an off-target cell in the population of cells; and (vi) identifying a recombinant AAV genome generated by the recombinase-dependent change, wherein said identified rAAV genome comprises the inversion, and wherein said identified recombinant AAV genome encodes an AAV capsid particle characterized having an increased specificity for the target cell and a decreased specificity for the off-target cell. In some embodiments, the off-target cell is a hepatocyte. In some embodiments, the target cell is a cell selected from the group consisting of a neuron, a glial cell, a oligodendrocyte, an ependymal cell, an astrocyte, a Schwann cell, a satellite cell, and an enteric glial cell.

Aspects disclosed herein provide kits comprising: (a) a first vector comprising the recombinant vector of the present disclosure; (b) a second vector encoding a helper virus protein; and (c) a third vector comprising a therapeutic nucleic acid encoding a therapeutic gene expression product.

Aspects disclosed herein provide kits comprising: (a) a first vector comprising a first nucleic acid sequence encoding a viral genome comprising in a 5' to 3' direction: (i) a 5' inverted terminal repeat (ITR) sequence; (ii) a Replication (Rep) gene; (iii) a Capsid (Cap) gene encoding the AAV capsid proteins described herein, and (iv) a 3' ITR; and (b) optionally, a second vector comprising a second nucleic acid sequence encoding a helper virus protein comprising at least one of E4orf6, E2a, VA RNA, Ela and E1b55k. In some instances, the kit further comprises a cell. In some instances, the cell is mammalian. In some instances, the cell is immortalized. In some instances, the immortalized cell is an embryonic stem cell. In some instances, the embryonic stem cell is a human embryonic stem cell. In some instances, the human embryonic stem cell is a human embryonic kidney 293 (HEK-293) cell. In some instances, the kit further comprises an AAV vector comprising a heterologous nucleic acid encoding a therapeutic gene expression product. In some instances, the AAV vector is an episome.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 shows distributions of variants recovered from three R1 libraries from Tek-Cre, SNAP25-Cre, and GFAP-Cre brain tissue (n=2 per Cre line), with capsid libraries sorted by decreasing order of the enrichment score. The enrichment scores of the AAV-PHP.V2 variant are mapped as well.

FIG. 5 is a schematic of R2 synthetic pool (left) and PCR pool (right) library design.

FIG. 13 shows the 7-mer insertion peptide sequences of AAV-PHP variants between AA positions 588-589 of AAV9 capsid.

In FIGS. 31 and 32, the white box on the sagittal brain images represents the location of thalamus and not the precise area that is zoomed-in on the figure to the left. The microscope settings of acquired images were matched across all sagittal sections and across all thalamus regions. The insets in AAV-PHP.V1 are zoom-ins with enhanced brightness. The indicated capsids were used to package ssAAV:CAG-mNeongreen (n=2-3 per group, $1 \times 10^{11}$ vg IV dose per 6-8 weeks old adult mouse, 3 weeks of expression. The data reported in FIGS. 31 and 32 are from one independent trial where all viruses were freshly prepared and titered in the same assay for dosage consistency. AAV-PHP.C2 and AAV-PHP.C3 were further validated in an independent trial for BALB/cJ, n=2 per group).

FIG. 33 provides 7-mer and 11-mer variants that were positively enriched in the brain tissue in all cell lines.

FIG. 34 provides 7-mer and 11-mer variants enriched in one specific library, but negatively enriched in all other brain and liver libraries.

FIG. 35 provides 11-mer variants that were positively enriched in all cre lines in liver tissue.

FIG. 36 is a diagram of the genetic switch used in M-CREATE. The Acceptor Vector shows the position of the forward and reverse primers between the Lox sites that are used for selective recovery of capsids from the Cre+ cells. The Rep-AAPΔCap vector shows a deletion of 480 bp in Cap gene in addition to the stop codons that are designed to prevent synthesis of VP1, VP2, and VP3 proteins. AAP protein translation is unaffected by these modifications.

FIG. 37 is a schematic of the protocol to selectively recover rAAV genomes from the target population using the Cre-Lox flipping strategy and preparation of the sample for deep sequencing.

FIG. 40 shows the distributions of AAV capsid read counts for libraries recovered by NGS from brain tissue across different Cre transgenic mice post R1 selection. The dotted line is illustrative only and roughly separates the signal from noise (see Methods for estimation of signal v.s. noise) where signal in this context represents the input for the R2 selection.

FIG. 41 shows rAAV genome recovery from tissues using different treatments are shown with total rAAV genome recovery from 0.1 g of liver.

FIG. 42 shows the percentage of rAAV genomes recovered per ng of total extracted DNA.

In FIGS. 41-44, n=4 mice; 2 from GFAP-Cre line and 2 from Tek-Cre line, each data point is drawn from the mean of three technical replicates, error bar is mean±S.E.M., Mann-Whitney test, two-tailed (exact P-value of 0.0286 (*P≤0.05), in FIGS. 41, 42, and 44, and 0.1143 (n.s.,P>0.05, CI 95%) in FIG. 43). The data reported FIGS. 41, 42, and 44 are from one independent trial, and FIG. 43, from three independent trials.

FIG. 49 illustrates correlations of enrichment scores of variants from the brain libraries (n=2 per Cre line, mean is plotted) produced by synthetic pool and PCR pool methods is determined by the same method described with respect to FIG. 47.

FIG. 58 shows expression of packaging Ple261 promoter carrying iCre transgene in Ai14-tdTomato reporter adult mouse (n=2-3 per group, $3\times10^{11}$ vg dose per adult mouse, 3 weeks of expression) on the left. In the right column, FIG. 58 shows expression of self-complementary (sc) AAV-PHP.V1 carrying CB6 ubiquitous promoter driving EGFP (above) and CAG promoter driving EGFP (below). Lectin DyLight 594 staining is also shown (n=2-3, $3\times10^{11}$ vg dose per adult C57BL/6J mouse, 2 weeks of expression). Experiments in FIGS. 56, 57, and the left column of FIG. 58 are reported from one independent trial from a fresh batch of viruses, and titered in the same assay for dosage consistency. Experiments in FIG. 58 were validated in two independent trials (n=2 per group).

FIG. 60 shows Transduction of brain vasculature by AAV-PHP.V2 carrying CAG-DIO-EYFP in Tek-Cre adult mice (left, $1\times10^{12}$ vg IV dose per mouse, 4 weeks of expression), and its efficiency (right) is determined by the overlap of αGLUT1 staining with EYFP expression across different brain areas (n=2, mean of 3 images per brain region per mouse).

FIG. 61 shows transduction of astrocytes by AAV-PHP.V2 in GFAP-Cre adult mouse ($1\times10^{12}$ vg IV dose per mouse, 4 weeks of expression). Percentage of cortical S100$^+$ cells that overlapped with EYFP expression is quantified (n=2, mean of 3 images per mouse).

FIG. 62 shows transduction levels of liver hepatocytes quantified as the percentage of DAPI$^+$ cells that are EGFP$^+$ (n=3, vectors packaged with CAG-2xNLS-EGFP, $1\times10^{11}$ vg IV dose/adult C57BL/6J mouse, 3 weeks of expression, mean±S.E.M, 4 images per mouse per group). One-way ANOVA, non-parametric Kruskal-Wallis test gave an approximate P-value of 0.0088).

FIG. 63 shows transduction of brain tissue by AAV-PHP.B4, B7, AAV-PHP.X1 (ARQMDLS), and AAV-PHP.X2 (TNKVGNI) packaging CAG-mNeonGreen genome (n=3, $1\times10^{11}$ vg IV dose/adult C57BL/6J mouse, 3 weeks of expression), were acquired using the same microscope settings to that of AAV9 and AAV-PHP.V1 sagittal brain images in FIG. 14.

FIG. 64 shows transduction of the brain by AAV-PHP.B8 using the CAG-mRuby2 genome (n=3, $3\times10^{11}$ vg IV dose/adult C57BL/6J mouse, 3 weeks of expression).

FIG. 65 shows Transduction of AAV9 (left), AAV-PHP.X3 (QNVTKGV) (middle) and AAV-PHP.X4 (LNAIKNI) (right) vectors packaging CAG-2xNLS-EGFP (n=2, $1\times10^{11}$ vg IV dose/adult C57BL/6J mouse, 3 weeks of expression). Data in FIGS. 62-65 is reported from one independent trial.

FIG. 74 provides details of a spike-in library of AAV9 and ~50 additional variants (and their alternative codon duplicates), identified in prior publications (includes well characterized variants like AAV-PHP.B or AAVPHP.eB as well as many variants identified using the previous methodology but uncharacterized in vivo) act as internal selection controls and standards for the relative performance of the new variants. Deverman, B. E. et al. Cre-dependent selection yields AAV variants for widespread gene transfer to the adult brain. Nat. Biotechnol. 34, 204-209 (2016) and Chan, K. Y. et al. Engineered AAVs for efficient noninvasive gene delivery to the central and peripheral nervous systems. Nat. Neurosci. 20, 1172-1179 (2017); the content of each of which is incorporated herein by reference. The spike-in library was generated as part of the synthetic pool library.

FIG. 75 shows enrichment scores for the spike-in library.

DETAILED DESCRIPTION

Figure 1:
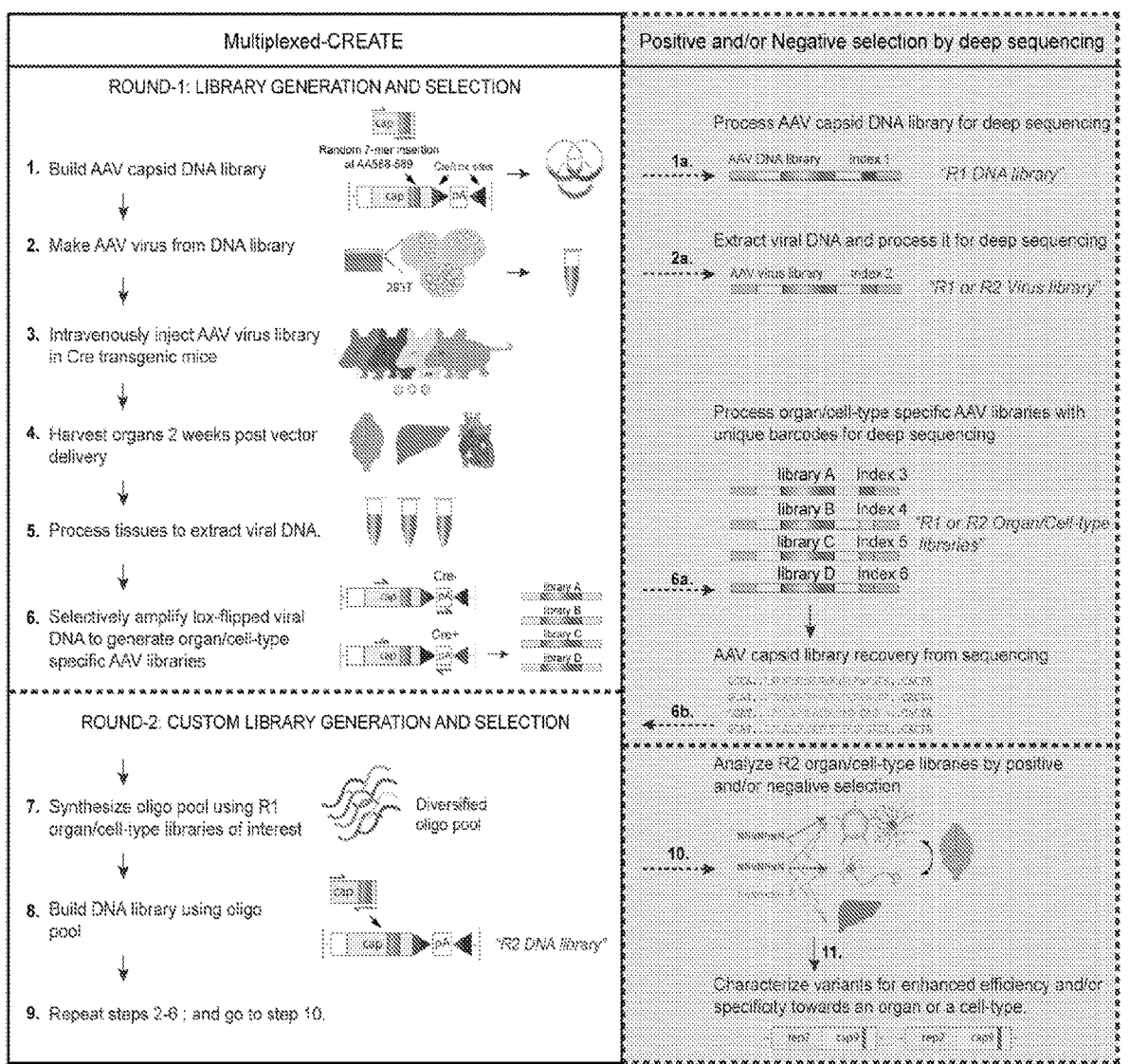
FIG. 1 shows a multiplexed selection approach to identify capsids with specific and broad tropisms. Steps 1-6 describe the workflow in Round-1 (R1) selection, steps 7-9 describe Round-2 (R2) selection using synthetic pool method, steps 1a, 2a, and 6a-b show the incorporation of deep sequencing to recover capsids after R1 and R2 selection, and steps 10-11 describe positive and/or negative selection criteria followed by variant characterization.

While preferred instances of the present disclosure have been shown and described herein, it will be obvious to those skilled in the art that such instances are provided by way of example only. Numerous variations, changes, and substitutions will now occur to those skilled in the art without departing from the disclosure. It should be understood that various alternatives to the instances of the disclosure described herein may be employed in practicing the disclosure. It is intended that the following claims define the scope of the disclosure and that methods and structures within the scope of these claims and their equivalents be covered thereby.

Provided herein are modified adeno-associated (AAV) virus capsid compositions useful for integrating a transgene into a target cell or environment (e.g., a cell-type or tissue) in a subject when they are administered systemically (e.g., intravenous, intranasal) to the subject. The modified AAV capsid proteins of the present disclosure comprise at least one insertion or substitution of an amino acid in a corresponding parental AAV capsid protein that confers a desired tropism such as an increased or decreased specificity as compared to a reference AAV capsid protein, or increased or decreased transgene transduction efficiency as compared to a reference AAV capsid protein.

Disclosed herein are AAV capsids engineered with desired tropisms, such as an increased specificity of viral transduction in a target in vivo environment, such as a tissue or cell. In some embodiments, the AAV capsids of the present disclosure are engineered to specifically target the central nervous system (CNS) of a subject. In some embodiments, the AAV capsids of the present disclosure are engineered to specifically target the liver of a subject. The AAV capsids can encapsidate a viral vector with a heterologous nucleic acid encoding, for example, a therapeutic gene expression product. Highly specific transduction of the heterologous nucleic acid in a target in vivo environment (e.g., brain, liver) can be achieved upon systemic delivery to a subject of the AAV capsid of the present disclosure encapsidating a heterologous nucleic acid. The AAV capsids disclosed herein are advantageous for many applications, such as diagnosing and/or treating monogenetic disorders of the brain (e.g., GLUT1-deficiency syndrome, mucoploysaccharidosis type IIIC), producing adoptive cellular therapies, and biomedical research applications.

The AAV capsids comprise AAV capsid proteins (e.g., VP1, VP2, and VP3), each with an insertion or a substitution of at least one amino acid at an amino acid in the 588 loop of a parental AAV capsid protein structure (AAV9 VP1 numbering). The 588 loop contains the site of heparan sulfate binding of AAV2 and amenable to peptide display. The only known receptors for AAV9 is N-linked terminal galactose and AAV receptor (AAVR), but many indications point toward there being others. Modifications to AAV9 588 loop are shown herein to confer an increased specificity and transgene transduction in target in vivo environments as compared to a reference AAV in rodent models. In some cases, the parental AAV capsid protein has an AAV serotype 9 (alias AAV9).

The most common method of AAV-mediated transgene delivery is by direct injection to the target in vivo environment, which is disadvantageous for many reasons, including risk of injury or death, pain, and higher cost, as compared to less invasive methods. For example, intracranial injection can cause hemorrhaging of the brain. Previous AAV-mediated delivery by intravenous administration avoids a need for a direct injection, but suffers from reduced specificity for the target in vivo environment (e.g., tissue or cell) resulting in off-target transduction events and necessitating a larger viral load to achieve sufficient therapeutic levels in the target in vivo environment. This is especially evident when the AAV must cross the blood brain barrier (BBB).

Methods are disclosed comprising systemically administering an AAV capsid of the present disclosure encapsidating a viral vector comprising a transgene (e.g., therapeutic nucleic acid) with an increased specificity, as compared to a reference AAV capsid protein. The AAV capsids of the present disclosure are capable of crossing the BBB, and transducing a transgene in a particular target cell-type (e.g., neuron, endothelial cell) in a subject. Accordingly, the AAV capsid proteins of the present disclosure are suitable for transgene therapy to treat human disease, particularly disease that effects the target in vivo environment.

The transgenes contained in a recombinant AAV (rAAV) vector and encapsidated by the AAV capsid proteins of the present disclosure are also provided herein. The transgenes disclosed herein are delivered to a subject for a variety of purposes, such as to treat a disease or condition in the subject. The transgene can be gene editing components that modulate the activity or expression of a target gene or gene expression product. Alternatively, the transgene is a gene encoding a therapeutic gene expression product that is effective to modulate the activity or expression of itself, or another target gene or gene expression product.

Provided herein, are methods of identifying the 7-mer or 3-mer peptide insertions comprising multiplexed Cre recombination-based AAV targeted evolution (M-CREATE). The M-CREATE method of the present disclosure supports (1) the calculation of a true enrichment score for each variant by using deep sequencing to correct for biases in viral production prior to selection, (2) reduced propagation of bias in successive rounds of selection through the creation of a post-round 1 synthetic pool library with equal variant representation, (3) the reduction of false positives by including two codon replicates of each selected variant in the pool, and (4) both positive and negative selection criteria by comparing deep sequencing of recovered capsid libraries among multiple targets (cells types or organs). These features allow informed, confident choices on variants worthy of validation and characterization in vivo.

Disclosed herein are methods of producing the AAV capsids comprising the AAV capsid proteins and viral vector encoding a therapeutic nucleic acid. The AAV capsid proteins are produced by introducing into a cell (e.g., immortalized stem cell) a first vector encoding the transgene (e.g., containing the therapeutic nucleic acid), a second vector encoding the AAV genome with a AAV capsid protein, and a third vector encoding helper virus proteins, required for assembly of the AAV capsid structure and packaging of the transgene in the AAV capsid. The assembled AAV capsid can be isolated and purified from the cell using suitable methods known in the art.

The recombinant AAV vectors comprising a nucleic acid sequence encoding the AAV capsid proteins of the present disclosure as also provided herein. For example, the viral vectors of the present disclosure comprise a nucleic acid sequence comprising the AAV viral Cap (Capsid) encoding VP1, VP2, and VP3, at least one of which is modified to produce the AAV capsid proteins of the present disclosure. The recombinant AAV vector provided can be derived from an AAV serotype (e.g., AAV9).

I. Compositions

Recombinant adeno-associated virus (rAAV) mediated gene delivery leverages the AAV mechanism of viral transduction for nuclear expression of an episomal heterologous nucleic acid (e.g., a transgene, therapeutic nucleic acid). Upon delivery to a host in vivo environment, a rAAV will (1) bind or attach to cellular surface receptors on the target cell, (2) endocytose, (3) traffic to the nucleus, (4) uncoat the virus to release the encapsidated heterologous nucleic acid, (5) convert of the heterologous nucleic acid from single-stranded to double-stranded DNA as a template for transcription in the nucleus, and (6) transcribe of the episomal heterologous nucleic acid in the nucleus of the host cell ("transduction"). rAAVs engineered to have an increased specificity (binding to cellular surface receptors on the target cell) and transduction efficiency (transcription of the episomal heterologous nucleic acid in the host cell) are desirable for gene therapy applications.

Figure 2:
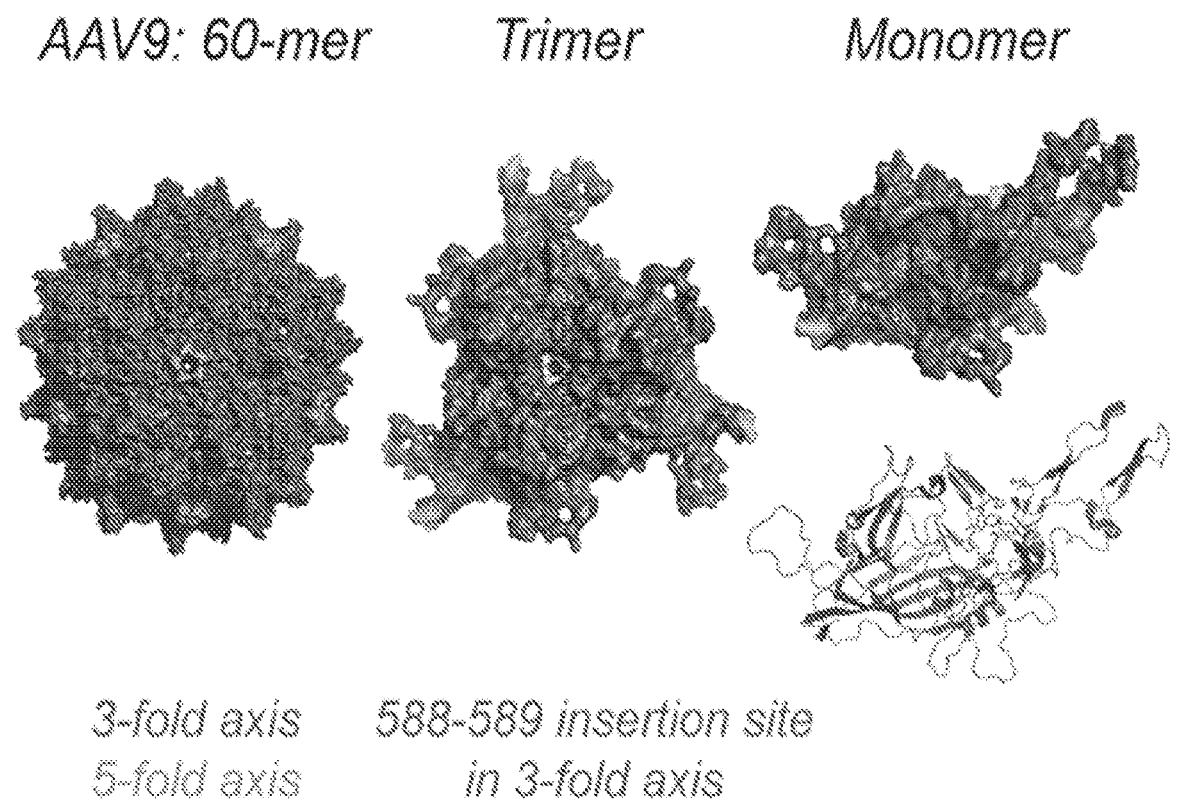
FIG. 2 shows a structural model of the AAV9 capsid (PDB 3UX1) with the insertion site for the 7-mer-i library highlighted in red in the 60-meric (left), trimeric (middle), and monomeric (right) forms.

A rAAV comprises an AAV capsid that can be engineered to encapsidate a heterologous nucleic acid (e.g., therapeutic nucleic acid, gene editing machinery). The AAV capsid is made up of three AAV capsid protein monomers, VP1, VP2, and VP3. Sixty copies of these three VP proteins interact in a 1:1:10 ratio to form the viral capsid (FIG. 2). VP1 covers the whole of VP2 protein in addition to a ~137 amino acid N-terminal region (VP1u), VP2 covers the whole of VP3 in addition to ~65 amino acid N-terminal region (VP1/2 common region). The three capsid proteins share a conserved amino acid sequence of VP3, which in some cases is the region beginning at amino acid position 138 (e.g., AA139-736).

The AAV VP3 structure contains highly conserved regions that are common to all serotypes, a core eight-stranded β-barrel motif (βB-βI) and a small α-helix (αA). The loop regions inserted between the β-strands consist of the distinctive HI loop between β-strands H and I, the DE loop between β-strands D and E, and nine variable regions (VRs), which form the top of the loops. These VRs, such as the AA588 loop, are found on the capsid surface and can be associated with specific functional roles in the AAV life cycle including receptor binding, transduction and antigenic specificity.

Disclosed herein are AAV capsids comprising AAV capsid proteins with a substitution at the 588 loop that confer a desired tropism characterized by a higher specificity for transduction in specific cell-types, including for e.g., brain cell types (e.g., brain endothelial cells, neurons, astrocytes) and liver cell types. In particular, the AAV capsid proteins disclosed herein enable rAAV-mediated transduction of a heterologous nucleic acid (e.g., transgene) in the brain or the liver of a subject. The AAV capsids of the present disclosure, or the AAV capsid proteins, may be formulated as a pharmaceutical composition. In addition, the AAV capsids or the AAV capsid proteins can be isolated and purified to be used for a variety of applications.

A. Adeno-Associated Virus (AAV) Capsid Proteins

Disclosed herein are recombinant AAV (rAAV) capsids comprise AAV capsid proteins that are engineered with a modified capsid protein (e.g., VP1, VP2, VP3). In some embodiments, the rAAV capsid proteins of the present disclosure are generated using the methods disclosed herein (e.g., M-CREATE). In some embodiments, the AAV capsid proteins are used in the methods of delivering a therapeutic nucleic acid (e.g., a transgene) to a subject. In some instances, the rAAV capsid proteins have desired AAV tropisms rendering them particularly suitable for certain therapeutic applications, e.g., the treatment of a disease or disorder in a subject such as those disclosed herein.

The rAAV capsid proteins are engineered for optimized entry into and through the blood brain barrier (BBB) of a subject upon systemic administration of the rAAV to the subject, such as those provided in Tables 2-3, and FIG. 33. Prior methods of AAV-mediated delivery of a therapeutic transgene to the brain required intracranial injection. Intracranial injection is an invasive procedure that causes a subject discomfort, and in some cases, pain. For example, intracranial injection can cause hemorrhaging of the brain. Additionally, intracranial delivery has limited spread and is highly heterogeneous. The rAAV capsid proteins provided in Tables 2-4, and FIG. 33 are engineered to have tropisms that eliminate the need for intracranial injection, while also achieving widespread and efficient transduction of an encapsidated transgene. In particular, the tropisms comprise at least one of an increased specificity and efficiency (e.g., of viral transduction) in the central nervous system (CNS) of a subject, as compared to a reference AAV.

The engineered AAV capsid proteins described herein have, in some cases, an insertion of an amino acid that is heterologous to the parental AAV capsid protein at the amino acid position in the 588 loop. In some embodiments, the amino acid is not endogenous to the parental AAV capsid protein at the amino acid position of the insertion. The amino acid may be a naturally occurring amino acid in the same or equivalent amino acid position as the insertion of the substitution in a different AAV capsid protein.

Aspects provided herein provide amino acid insertions comprising seven amino acid polymer (7-mer) inserted at AA588_589, and may additionally include a substitution of one or two amino acids at amino acid positions flanking the 7-mer sequence (e.g., AA587-588 and/or AA589-590) to produce an eleven amino acid polymer (11-mer) at the 588 loop of a parental AAV capsid protein. The 7-mers described herein were advantageously generated using polymerase chain reaction (PCR) with degenerate primers, where each of the seven amino acids is encoded by a deoxyribose nucleic acid (DNA) sequence N-N-K. "N" is any of the four DNA nucleotides and K is guanine (G) or thymine (T). This method of generating random 7-mer amino acid sequences enables 1.28 billion possible combinations at the protein level. Since the 7-mers developed are random, some amino acids in the 7-mer may be naturally occurring in the AAC capsid protein at that amino acid position, while other amino acids may differ.

Recombinant AAVs (rAAVs) were generated, each with a unique 7-mer or 11-mer at the 588 loop and each encapsidating a reporter gene that, when administered systemically in multiple transgenic animals, enabled the selective amplification and recovery of sequences that effectively transduced the reporter gene in a target in vivo environment of the transgenic animal. 7-mers and 11-mers that were found to be positively enriched in the target in vivo environment (e.g, central nervous system, liver) are provided herein. "Enrichment" is the prevalence of a given 7-mer or an 11-mer in the tissue of the in vivo environment compared to its prevalence in the viral library that was administered to the transgenic animal. An enrichment score above 0 indicates a positive enrichment. An enrichment score below 0 indicates a negative enrichment. A subset of the rAAVs with desired enrichment profiles were tested individually in vivo to determine exact systemic expression (e.g., specificity and transduction efficiency). rAAVs from this subset exhibiting a desired tropism comprising increased specificity of viral transduction, and in some cases, transduction efficiency are considered to be uniquely suited for targeted rAAV-mediated transgene delivery useful for a wide variety of purposes (e.g., therapeutic, diagnostic, scientific discovery).

The rAAV particles with the 7-mers or 11-mers described herein have an increased transduction efficiency in a target in vivo environment (e.g., tissue or cell type). In some instances, the increased transduction efficiency comprises a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 75-fold, or 100-fold increase, or more, relative to a reference AAV. In some instances, the increased transduction efficiency is at least 30-fold. In some instances, the increased transduction efficiency is at least 40-fold. In some instances, the increased transduction efficiency is at least 50-fold. In some instances, the increased transduction efficiency is at least 60-fold. In some instances, the increased transduction efficiency is at least 80-fold. In some instances, the increased transduction efficiency is at least 90-fold. In some instances, the increased transduction efficiency is at least 100-fold.

The rAAV particles with the 7-mers or 11-mers described herein have an increased specificity in a target in vivo environment (e.g., tissue or cell type), as compared to a reference AAV. Detecting whether a rAAV possesses more or less specificity for a target in vivo environment than a reference AAV, includes measuring a level of gene expression product (e.g., RNA or protein) expressed from the heterologous nucleic acid encapsidated by the rAAV in a tissue sample obtained from the target in vivo environment in a subject; and comparing the measured level to a control level (such as, for e.g., the gene expression product expressed from a heterologous nucleic acid encapsidated by a reference AAV (e.g., AAV9)). Suitable methods for measuring expression of a gene expression product luciferase reporter assay and quantitative polymerase chain reaction (qPCR).

The increased specificity is correlated with an increased enrichment in the target in vivo environment, which in some cases is represented with an enrichment score provided herein in FIGS. 33-35. As a non-limiting example, AAV-PHP.V2 (TTLKPFL), which is shown herein to be positively enriched in the brain (enrichment score of ~2.51) also exhibited an increase in reporter gene expression (e.g., measured by fluorescence reporter assay) in the brain (~60% of cortical brain vasculature cells and ~60% cortical astrocytes transduced with the reporter gene) as compared to a reference AAV9 (~0%). Without being bound by a particular theory, the inventors of the present disclosure would expect to see this correlation for all rAAVs disclosed herein, and further, would expect that a more significant the enrichment score (whether negative or positive) would correlate with a more significant specificity to the in vivo environment(s) as indicated by a measured level of the gene expression product in the in vivo environment(s).

Transduction efficiency, as disclosed herein, may be measured by at least one of (1) a number of cells in a target in vivo or off-target in vivo environment expressing the heterologous nucleic acid encapsidated by the modified AAV capsid proteins disclosed herein, and (2) a quantity of expression of the heterologous nucleic acid in a single cell. Specificity for a target in vivo environment may be inferred when a presence, or an increase in a level, of rAAV-mediated transduction in a target in vivo environment is observed, as compared to a reference AAV. A lack of, or reduced, specificity to an off-target in vivo environment may be inferred when an absence, or a decrease in a level, of rAAV-mediated transduction in the off-target in vivo environment is observed, as compared to a reference AAV.

The reference AAV may have a serotype selected from the group consisting of AAV1, AAV2, AAV3, AAV4, AAVS, AAV6, AAV7, AAV8, AAV9, AAV10, AAV11, AAV12, or variant thereof. For example, the reference AAV can have a serotype selected from the group consisting of AAV-PHP.B, AAV-PHP.eB, and AAV-PHP.S.

The rAAV capsid proteins of the present disclosure comprise an insertion of an amino acid in an amino acid sequence of an AAV capsid protein. The AAV capsid, from which an engineered AAV capsid protein of the present disclosure is produced, is referred to as a "parental" AAV capsid. In some cases, the parental AAV has a serotype selected from the group consisting of AAV1, AAV2, AAV3, AAV4, AAV5, AAV6, AAV7, AAV8, AAV9, AAV10, AAV11, and AAV12. The complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); the AAV-11 genome is provided in Virology, 330(2): 375-383 (2004); portions of the AAV-12 genome are provided in Genbank Accession No. DQ813647; portions of the AAV-13 genome are provided in Genbank Accession No. EU285562.

In some cases, the parental AAV is derived from an AAV with a serotype selected from the group consisting of AAV1, AAV2, AAV3, AAV4, AAV5, AAV6, AAV7, AAV8, AAV9, AAV10, AAV11, and AAV12. The AAV capsid protein that is "derived" from another may be a variant AAV capsid protein. A variant may include, for example, a heterologous amino acid in an amino acid sequence of the AAV capsid protein. The heterologous amino acid may be non-naturally occurring in the AAV capsid protein. The heterologous amino acid may be naturally occurring in a different AAV capsid protein. In some instances, the parental AAV capsid is described in U.S. Pat. App. Ser. Nos. 62/736,904; 16/582, 635; 62/832,812; and 62/832,826; the content of each of which is incorporated herein. For example, the parental AAV capsid may be modified at the 455 loop of the AAV capsid protein (e.g., substitutions of 7-mer at AA452-458, AAV9 VP1 numbering).

In some instances, the parental AAV is AAV9. In some instances, the amino acid sequence of the AAV9 capsid protein comprises SEQ ID NO: 1. The amino acid sequence of AAV9 VP1 capsid protein (>trlQ6JC40|Q6JC40_9VIRU Capsid protein VP1 OS=Adeno-associated virus 9 OX= 235455 GN=cap PE=1 SV=1) is provided in SEQ ID NO: 1 (MAADGYLPDWLEDNLSEGIREWWALKPGAPQPKA NQQHQDNARGLVLPGYKYLGPG NGLDKGEPVNAA DAAALEHDKAYDQQLKAGDNPYLKYNHADAEF QERLKEDTSFGG NLGRAVFQAKKRLLEPLGLVEEA AKTAPGKKRPVEQSPQEPDSSAGIGKSGAQPAKKRL NFGQTGDTESVPDPQPIGEPPAAPSGVGSLTMASGG-GAPVADNNEGADGVGSSSGNWH CDSQWLGDRVI TTSTRTWALPTYNNHLYKQISNSTSGGSSNDNAYFG YSTPWGYFDFN RFHCHFSPRDWQRLINNNWGFRP KRLNFKLFNIQVKEVTDNNGVKTIANNLTSTVQVFT DSDYQLPYVLGSAHEGCLPPFPADVFMIPQYGYLTL NDGSQAVGRSSFYCLEYFPSQML RTGNNFQFSYEFE NVPFHSSYAHSQSLDRLMNPLIDQYLYYLSKTINGSG QNQQTLKFSV AGPSNMAVQGRNYIPGPSYRQ QR V STTVTQNNNSEFAWPGASSWALNGRNSLMNPGP AMASHKEGEDRFFPLSGSLIFGKQGTGRDNVDAD-KVMITNEEEIKTTNPVATESYGQVA TNHQSAQAQA QTGWVQNQGILPGMVWQDRDVYLQGPIWAKIPH-TDGNFHPSPLMGGF GMKHPPPQILIKNTPVPADPP TAFNKDKLNSFITQYSTGQVSVEIEWELQKEN SKR WNPE IQYTSNYYKSNNVEFAVNTEGVYSEPRPI GTRYLTRNL). In some instances, the parental AAV capsid protein sequence is 70%, 75%, 80%, 85%, 90%, 91%, 92%, 93%, 94%, 95%, 96%, 97%, 98%, 99%, or 100% homologous to SEQ ID NO: 1.

Disclosed herein are insertions of an amino acid (or amino acid sequence) in an amino acid sequence of an AAV capsid protein at an amino acid position between amino acid 588 and amino acid 589. As used herein, "AA588_589" indicates that the insertion of the amino acid (or amino acid sequence) is immediately after an amino acid (AA) at position 588 and immediately before an AA at position 589 within an amino acid sequence of a parental AAV VP capsid protein (VP1 numbering). Amino acids 587-591 include a motif comprising "AQAQA" as set forth in SEQ ID NO: 1. Exemplary AAV capsid protein sequences are provided in Table 1. For example, QAVRTSL is inserted at AA588_589 in an AAV9 capsid amino acid sequence, and is provided SEQ ID NO: 3. In another example, TLAVPFK is inserted at AA588_589 in an AAV9 capsid amino acid sequence, and is provided in SEQ ID NO: 2. It is envisioned that the 7-mer insertions disclosed herein (FIGS. 33-35, Tables 2-4) may be inserted at AA588_589 in an amino acid sequence of a parental AAV9 capsid protein, a variant thereof, or equivalent amino acid position a parental AAV of a different serotype (e.g., AAV1, AAV2, AAV3, and the like).

The 11-mers described herein may, in some cases, comprise a 7-mer insertion at AA588_589, and substitutions of one or more amino acids at amino acid positions AA587-590. In some cases, the amino acids 587-590 are substituted with an amino acid that is not endogenous to the parental AAV capsid protein at that position. In some cases, AA587 is substituted with D (e.g., A587D). In some cases, AA587 is substituted with an A (e.g., Q587A). In some cases, AA587 is substituted with an S (e.g., Q587S). In some cases, AA587 is substituted with a G (e.g., Q587G). In some cases, AA588 is substituted with a G (e.g., Q588G). In some cases, AA589 is substituted with an N (e.g., A589N). In some cases, AA590 is substituted with a P (e.g., A590). In a non-limiting example SEQ ID NO: 4 (PHP-AAV.eB) comprises an insertion at AA588_AA589 of TLAVPFK, and substitutions A587D and Q588G. In another non-limiting example, SEQ ID NO: 5 (PHP-AAV.N) comprises an insertion at AA588_AA589 of TTLKPFS, and substitutions A587D, Q588G, A589N, and Q590P. It is envisioned that any 7-mer insertion disclosed herein in addition to a substitution with any amino acid at amino acid positions 587-590 may comprise an 11-mer.

TABLE 1

| SEQ ID NO: | Identifier | Sequence |
|---|---|---|
| | | Exemplary AAV Capsid Protein Sequences |
| 2 | AAV-PHP.B | MAADGYLPDWLEDNLSEGIREWWALKPGAPQPKANQQHQDN ARGLVLPGYKYLGPGNGLDKGEPVNAADAAALEHDKAYDQQ LKAGDNPYLKYNHADAEFQERLKEDTSFGGNLGRAVFQAKK RLLEPLGLVEEAAKTAPGKKRPVEQSPQEPDSSAGIGKSGAQP AKKRLNFGQTGDTESVPDPQPIGEPPAAPSGVGSLTMASGGGA PVADNNEGADGVGSSSGNWHCDSQWLGDRVITTSTRTWALPT YNNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYGY LTLNDGSQAVGRSSFYCLEYFPSQMLRTGNNFQFSYEFENVPF HSSYAHSQSLDRLMNPLIDQYLYYLSRTINGSGQNQQTLKFSV AGPSNMAVQGRNYIPGPSYRQQRVSTTVTQNNNSEFAWPGAS SWALNGRNSLMNPGPAMASHKEGEDRFFPLSGSLIFGKQGTG RDNVDADKVMITNEEEIKTTNPVATESYGQVATNHQSAQTLA VPFKAQAQTGWVQNQGILPGMVWQDRDVYLQGPIWAKIPHT DGNFHPSPLMGGFGMKHPPPQILIKNTPVPADPPTAFNKDKLN SFITQYSTGQVSVEIEWELQKENSKRWNPEIQYTSNYYKSNNV EFAVNTEGVYSEPRPIGTRYLTRNL |
| 3 | AAV-PHP.S | MAADGYLPDWLEDNLSEGIREWWALKPGAPQPKANQQHQDN ARGLVLPGYKYLGPGNGLDKGEPVNAADAAALEHDKAYDQQ LKAGDNPYLKYNHADAEFQERLKEDTSFGGNLGRAVFQAKK RLLEPLGLVEEAAKTAPGKKRPVEQSPQEPDSSAGIGKSGAQP AKKRLNFGQTGDTESVPDPQPIGEPPAAPSGVGSLTMASGGGA PVADNNEGADGVGSSSGNWHCDSQWLGDRVITTSTRTWALPT |

TABLE 1-continued

Exemplary AAV Capsid Protein Sequences

| SEQ ID NO: | Identifier | Sequence |
|---|---|---|
| | | YNNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYGY LTLNDGSQAVGRSSFYCLEYFPSQMLRTGNNFQFSYEFENVPF HSSYAHSQSLDRLMNPLIDQYLYYLSRTINGSGQNQQTLKFSV AGPSNMAVQGRNYIPGPSYRQQRVSTTVTQNNNSEFAWPGAS SWALNGRNSLMNPGPAMASHKEGEDRFFPLSGSLIFGKQGTG RDNVDADKVMITNEEEIKTTNPVATESYGQVATNHQSAQQAV RTSLAQAQTGWVQNQGILPGMVWQDRDVYLQGPIWAKIPHT DGNFHPSPLMGGFGMKHPPPQILIKNTPVPADPPTAFNKDKLN SFITQYSTGQVSVEIEWELQKENSKRWNPEIQYTSNYYKSNNV EFAVNTEGVYSEPRPIGTRYLTRNL |
| 4 | AAV-PHP.eB | MAADGYLPDWLEDNLSEGIREWWALKPGAPQPKANQQHQDN ARGLVLPGYKYLGPGNGLDKGEPVNAADAAALEHDKAYDQQ LKAGDNPYLKYNHADAEFQERLKEDTSFGGNLGRAVFQAKK RLLEPLGLVEEAAKTAPGKKRPVEQSPQEPDSSAGIGKSGAQP AKKRLNFGQTGDTESVPDPQPIGEPPAAPSGVGSLTMASGGGA PVADNNEGADGVGSSSGNWHCDSQWLGDRVITTSTRTWALPT YNNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYGY LTLNDGSQAVGRSSFYCLEYFPSQMLRTGNNFQFSYEFENVPF HSSYAHSQSLDRLMNPLIDQYLYYLSRTINGSGQNQQTLKFSV AGPSNMAVQGRNYIPGPSYRQQRVSTTVTQNNNSEFAWPGAS SWALNGRNSLMNPGPAMASHKEGEDRFFPLSGSLIFGKQGTG RDNVDADKVMITNEEEIKTTNPVATESYGQVATNHQSDGTLA VPFKAQAQTGWVQNQGILPGMVWQDRDVYLQGPIWAKIPHT DGNFHPSPLMGGFGMKHPPPQILIKNTPVPADPPTAFNKDKLN SFITQYSTGQVSVEIEWELQKENSKRWNPEIQYTSNYYKSNNV EFAVNTEGVYSEPRPIGTRYLTRNL |
| 5 | AAV-PHP.N | MAADGYLPDWLEDNLSEGIREWWALKPGAPQPKANQQHQDN ARGLVLPGYKYLGPGNGLDKGEPVNAADAAALEHDKAYDQQ LKAGDNPYLKYNHADAEFQERLKEDTSFGGNLGRAVFQAKK RLLEPLGLVEEAAKTAPGKKRPVEQSPQEPDSSAGIGKSGAQP AKKRLNFGQTGDTESVPDPQPIGEPPAAPSGVGSLTMASGGGA PVADNNEGADGVGSSSGNWHCDSQWLGDRVITTSTRTWALPT YNNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYGY LTLNDGSQAVGRSSFYCLEYFPSQMLRTGNNFQFSYEFENVPF HSSYAHSQSLDRLMNPLIDQYLYYLSRTINGSGQNQQTLKFSV AGPSNMAVQGRNYIPGPSYRQQRVSTTVTQNNNSEFAWPGAS SWALNGRNSLMNPGPAMASHKEGEDRFFPLSGSLIFGKQGTG RDNVDADKVMITNEEEIKTTNPVATESYGQVATNHQSAQTLA VPFSNPAQTGWVQNQGILPGMVWQDRDVYLQGPIWAKIPHT DGNFHPSPLMGGFGMKHPPPQILIKNTPVPADPPTAFNKDKLN SFITQYSTGQVSVEIEWELQKENSKRWNPEIQYTSNYYKSNNV EFAVNTEGVYSEPRPIGTRYLTRNL |

The rAAV capsid proteins described herein may be isolated and purified. The AAV may be isolated and purified by methods standard in the art such as by column chromatography or cesium chloride gradients. Methods for purifying AAV from helper virus are known in the art and may include methods disclosed in, for example, Clark et al., Hum. Gene Ther., 10(6): 1031-1039 (1999); Schenpp and Clark, Methods Mol. Med., 69: 427-443 (2002); U.S. Pat. No. 6,566,118 and WO 98/09657.

The rAAV capsid protein can be conjugated to a nanoparticle, a second molecule, or a viral capsid protein. In some cases, the nanoparticle or viral capsid protein would encapsidate the therapeutic nucleic acid described herein. In some instances, the second molecule is a therapeutic agent, e.g., a small molecule, antibody, antigen-binding fragment, peptide, or protein, such as those described herein. In some instances, the second molecule is a detectable moiety. For example, the modified AAV capsid protein conjugated to a detectable moiety may be used for in vitro, ex vivo, or in vivo biomedical research applications, the detectable moiety used to visualize the modified capsid protein. The modified AAV capsid protein conjugated to a detectable moiety may also be used for diagnostic purposes.

AAV Capsid Proteins Targeting the Central Nervous System

Disclosed herein are AAV capsid proteins with a substitution or an insertion of at least one amino acid at an amino acid position described above in a parental AAV capsid protein that confers an increased specificity for a central nervous system (CNS) or peripheral nervous system (PNS) in a subject, even when delivered systemically. One of the many advantages of the AAV capsid proteins described herein is their ability to target the CNS and penetrate the blood brain barrier (BBB).

The in vivo environment can be a cell. The cell can be a cell-type selected from the group consisting of a central nervous system (CNS) cell and a peripheral nervous system (PNS) cell. Non-limiting examples of CNS cells include a neuron and a glial cell. Glial cells can be selected from the group consisting of an oligodendrocyte, an ependymal cell, and an astrocyte. Non-limiting examples of a PNS cell includes a neuron or a glial cell. The glial cell can be selected from the group consisting of a Schwann cell, a satellite cell, and an enteric glial cell.

The in vivo environment can be a tissue. The tissue can be the brain, or the spinal cord. The tissue can be a region of an organ, example, the cerebrum, the cerebellum, the brainstem, the cortex, the striatum, the thalamus, the lateral ventricles, the putamen, the hypothalamus, the medulla, the pons, the hippocampus, the amygdala, the motor cortex, or a combination thereof.

Disclosed herein are AAV capsid proteins with at least one amino acid insertion or substitution in a parental AAV capsid protein. The insertion or substitution can be of at least one, two, three, four, five, six, seven, eight, nine, ten, or eleven amino acids, or more. In some instances, the amino acids are contiguous. In some instances, the amino acids are not contiguous.

Figure 6:
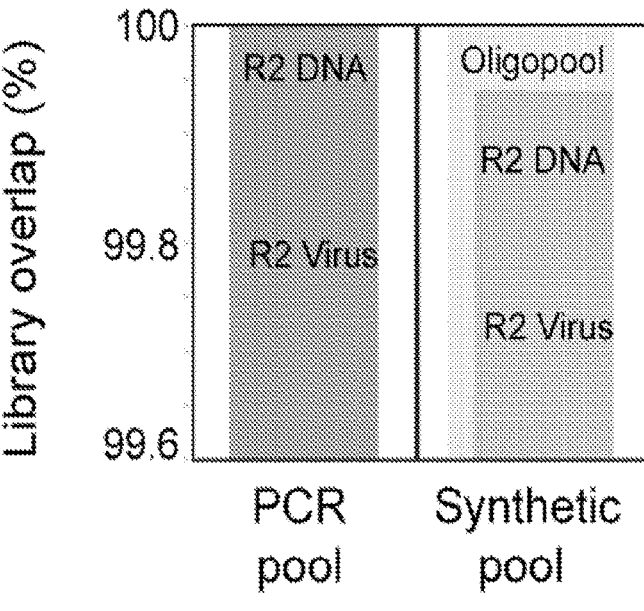
FIG. 6 shows an overlapping bar chart showing the percentage of library overlap between the mentioned libraries and their theoretical composition.

In some instances, the insertion is of at least one amino acid is provided in any one of the sequences provided in any one of Tables 2-3, or FIG. 6. In some instances, the insertion is of at least two amino acids provided in any one of the sequences provided in any one of Tables 2-3, or FIG. 6. In some instances, the insertion is of at least three amino acids provided in any one of the sequences provided in any one of Tables 2-3, or FIG. 6. In some instances, the insertion is of at least four amino acids provided in any one of the sequences provided in any one of Tables 2-3, or FIG. 6. In some instances, the insertion is of at least five amino acids provided in any one of Tables 2-3, or FIG. 6. In some instances, the insertion is of at least six amino acids provided in any one of Tables 2-3, or FIG. 6. In some instances, the insertion is of at least seven amino acids provided in any one of Tables 2-3, or FIG. 6.

Disclosed herein are AAV capsid proteins with an insertion of at least one amino acid X1, wherein X1 is selected from the group consisting of A, E, D, G, R, S and T. In some instances, the insertion further comprises two amino acids, wherein X2 is selected from the group consisting of A, G, I, L, M, N, Q, R, T, and Y. In some instances, the insertion further comprises three amino acids, wherein X3 is selected from the group consisting of E, K, L, T, and Q. In some instances, the insertion further comprises at least four amino acids, wherein X1 is selected from the group consisting of A, E, D, G, R, S and T, X2 is selected from the group consisting of A, G, I, L, M, N, Q, R, T, and Y, X3 is selected from the group consisting of E, K, L, T, and Q, and X4 is selected from the group consisting of G, I, K, L, M, R, T, and V. In some instances, the insertion further comprises five amino acids wherein X5 is selected from the group consisting of A, D, G, P, L, Q, and V. In some instances, the insertion further comprises at least six amino acids, wherein X6 is selected from the group consisting of F, K, L, N, P, Q, S, and V. In some instances, the insertion further comprises at least seven amino acids, wherein X7 is selected from the group consisting of I, K, L, P, S, and V.

In some embodiments, X1, X2, X3, X4, X5, X6, and X7 are contiguous (X1-X2-X3-X4-X5-X6-X7). In some embodiments, any two of X1, X2, X3, X4, X5, X6, and X7 are contiguous. In some embodiments, any three of X1, X2, X3, X4, X5, X6, and X7 are contiguous. In some embodiments, any four of X1, X2, X3, X4, X5, X6, and X7 are contiguous. In some embodiments, any five of X1, X2, X3, X4, X5, X6, and X7 are contiguous. In some embodiments, any six of X1, X2, X3, X4, X5, X6, and X7 are contiguous. In some embodiments, any seven of X1, X2, X3, X4, X5, X6, and X7 are contiguous. In some embodiments, X1, X2, X3, X4, X5, X6, and X7 are not contiguous. In some embodiments, the insertion is not TLAVPFK.

The 7-mers disclosed herein, in some cases share a common motif. A 7-mer (X1-X2-X3-X4-X5-X6-X7) may in some cases advantageously have a T in position X1, an L in position X2, a P in positive X5, an F in position X6, and a K or L in position X7. In some embodiments, the 7-mer comprises T-L-X3-X4-P-F-K, wherein X3 and X4 are any amino acid. In some embodiments, the 7-mer comprises T-L-X3-X4-P-F-L, wherein X3 and X4 are any amino acid. In some cases, X3 is not an A. In some cases, X3 is A, S, Q, or E or L. In some cases, X4 is not a V. In some cases, X4 is R, K, V, or a Q.

In some cases, the 7-mer may be X1-L-A-V-P-F-K, wherein X1 is any amino acid other than T, S, or N; X1-X2-A-V-P-F-K, wherein X1 is any amino acid other than T, S, or N, and X2 is any amino acid other than L or V; or X1-X2-X3-V-P-F-K, wherein X1 is any amino acid other than T, S, or N, X2 is any amino acid other than L or V, and X3 is any amino acid other than A, S, Q, P, or T; or X1-X2-X3-X4-P-F-K, wherein X1 is any amino acid other than T, S, or N, X2 is any amino acid other than L or V, X3 is any amino acid other than A, S, Q, P, or T, and X4 is any amino acid other than V, T, Q, N, L, or M. In some instances, the 7-mer is T-L-A-X4-P-F-K, wherein X is any amino acid other than V. In some instances, the 7-mer is T-L-A-X4-P-F-K, wherein X is any amino acid other than, T, Q, N, L, or M.

In some cases, the 7-mer (X1-X2-X3-X4-X5-X6-X7) comprises TALKPFL. In some instances, the 7-mer comprises TTLKPFL. In some instances, the 7-mer comprises TLQIPFK. In some instances, the 7-mer comprises TMQKPFI. In some instances, the 7-mer comprises SIER-PFK. In some instances, the 7-mer comprises RYQGDSV.

In some instances, the AAV capsid protein comprises an insertion of at least or about three, four, five, six, or seven amino acids of an amino acid sequence T-X2 L K P F L at an amino acid position 588_589 in a parental AAV9 capsid protein (SEQ ID NO: 1), wherein X2 is A or T. In some cases, the AAV capsid protein has an increased specificity for viral transduction in brain vascular cells (GLUT1+), as compared to a reference AAV (e.g., AAV9). In some cases, the AAV capsid protein has increased specificity for viral tranduction in astrocytes, as compared to a reference AAV (e.g., AAV9).

In some instances, the AAV capsid protein comprises an insertion of at least or about three, four, five, six, or seven amino acids of an amino acid sequence T-X2-Q-X4-P-F-X7 at an amino acid position 588_589 in a parental AAV9 capsid protein (SEQ ID NO: 1), wherein X2 is L or M; X4 is I, K, or L; X7 is K or I. In some cases, the AAV capsid protein has increased specificity for viral transduction in neurons and astrocytes, as compared to a reference AAV (e.g., AAV9). In some instances, the amino acid sequence is TLQIPFK. In some instances, the amino acid sequence is TMQKPFI. In some instances, the amino acid sequence is TLQLPFK.

In some instances, the AAV capsid protein comprises an insertion of at least or about three, four, five, six, or seven amino acids of an amino acid sequence S-I E R P F K at an amino acid position 588_589 in a parental AAV9 capsid protein (SEQ ID NO: 1). In some cases, the AAV capsid protein has increased specificity for viral transduction in neurons and astrocytes, as compared to a reference AAV (e.g., AAV9).

In some instances, the AAV capsid protein comprises an insertion of at least or about three, four, five, six, or seven amino acids of an amino acid sequence R-Y-Q-G-D-S-V at an amino acid position 588_589 in a parental AAV9 capsid protein (SEQ ID NO: 1). In some cases, the AAV capsid protein has increased specificity for viral transduction in astrocytes, as compared to a reference AAV (e.g., AAV9).

TABLE 2

List of 7-mer targeting peptides that can target the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 10 | ACGTTGCAGATTCCTTTTAAG | 435 | TLQIPFK | 2.730563 |
| 11 | ACCGCCCTCAAACCCTTCCTC | 436 | TALKPFL | 2.536397 |
| 12 | ACCACCCTCAAACCCTTCCTC | 437 | TTLKPFL | 2.513839 |
| 13 | AGCATCGAAAGACCCTTCAAA | 438 | SIERPFK | 2.357132 |
| 14 | ACCCAAACAGACCCTTCCTC | 439 | TQNRPFL | 2.22812 |
| 15 | ACCATGCAAAAACCCTTCATC | 440 | TMQKPFI | 2.165359 |
| 16 | ACTAGTACGCGGCCGTTTTTG | 441 | TSTRPFL | 2.14357 |
| 17 | GGCACCTTCGTCCCCCCCACC | 442 | GTFVPPT | 2.110151 |
| 18 | TGGTCGACTAATGCGGGTTAT | 443 | WSTNAGY | 1.979177 |
| 19 | ACCCTCGAAAGACCCTTCACC | 444 | TLERPFT | 1.892846 |
| 20 | ACTGCTGCTAAGCCGTTTCTG | 445 | TAAKPFL | 1.863541 |
| 21 | ATTAGGATTGGTTATTCGCAG | 446 | IRIGYSQ | 1.835644 |
| 22 | GAGCGTGTGGGTTTTGCTCAG | 447 | ERVGFAQ | 1.73803 |
| 23 | GCCGACCTCCTCAACTACAGA | 448 | ADLLNYR | 1.599571 |
| 24 | CTCGTCGCCGGCTTCAGCCAA | 449 | LVAGFSQ | 1.591793 |
| 25 | TCGTCTCTGAAGCCTTTTCTG | 450 | SSLKPFL | 1.574365 |
| 26 | ACGCATTCTAGGCCGTTTATT | 451 | THSRPFI | 1.566468 |
| 27 | CCTTTTCCTGGTTATTCTGCG | 452 | PFPGYSA | 1.555967 |
| 28 | ATTATTGTTGGGTATAGTCAG | 453 | IIVGYSQ | 1.515858 |
| 29 | AGGTATCAGGGTGATTCTGTT | 454 | RYQGDSV | 1.486197 |
| 30 | AGGTATGCTGGGGATTCTATT | 455 | RYAGDSI | 1.456352 |
| 31 | AAGACGATTGGGGAGCATTGG | 456 | KTIGEHW | 1.44094 |
| 32 | TGGATGACGCATGGTTCTGCG | 457 | WMTHGSA | 1.432726 |
| 33 | GCTGCTTCGAGGCCGTTTCTT | 458 | AASRPFL | 1.3791 |
| 34 | ACTACTTCTAGGCCGTTTCTT | 459 | TTSRPFL | 1.353519 |
| 35 | GCTCGTGTGGGTTTGGCTCAG | 460 | ARVGLAQ | 1.345499 |
| 36 | GGGACTAGTCCGAATCTTGCG | 461 | GTSPNLA | 1.306429 |
| 37 | GTGCGTACGGGGTATAGTTCT | 462 | VRTGYSS | 1.302979 |
| 38 | ATTCGGGTGGGGTATAGTTCT | 463 | IRVGYSS | 1.286795 |

TABLE 2-continued

List of 7-mer targeting peptides that can target the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 39 | ACTACTTTGCGTCCGTTTATT | 464 | TTLRPFI | 1.284391 |
| 40 | GGTATTACGTCTCTGTTTAAG | 465 | GITSLFK | 1.251837 |
| 41 | ACCACCCAAACCCCCTTCAGA | 466 | TTQTPFR | 1.192121 |
| 42 | ACTGTGTCGAGGCCGTTTTTG | 467 | TVSRPFL | 1.171604 |
| 43 | TATGGGACGAATCCGTTTCGT | 468 | YGTNPFR | 1.13664 |
| 44 | CCCACCATGGTCGACAGCAGC | 469 | PTMVDSS | 1.099202 |
| 45 | AATAAGGCTAGTTCTCAGAAT | 470 | NKASSQN | 1.084711 |
| 46 | ACTTTTCGTAGTTCGAATGAT | 471 | TFRSSND | 1.032118 |
| 47 | CTGCCGGATCGTTATCCTAAT | 472 | LPDRYPN | 1.019382 |
| 48 | CAGAATGTTACGAAGGGTGTT | 473 | QNVTKGV | 1.000865 |
| 49 | GCTCAGTCTCCGATTCTTCGG | 474 | AQSPILR | 0.979922 |
| 50 | GTGGCTACTGGTTATTCTTCG | 475 | VATGYSS | 0.978116 |
| 51 | TTGAATTCGAATCGGCCTAAT | 476 | LNSNRPN | 0.9672 |
| 52 | ACGATTCGTAATAATACGATT | 477 | TIRNNTI | 0.959641 |
| 53 | GATCTTAGTCGTATTTTTAAG | 478 | DLSRIFK | 0.950386 |
| 54 | CTCAGCAACAGCGCCAGCCAA | 479 | LSNSASQ | 0.941212 |
| 55 | CTCGAAAACATGGTCATGAGC | 480 | LENMVMS | 0.937552 |
| 56 | TTGACTCAGCAGACGGATGTT | 481 | LTQQTDV | 0.936974 |
| 57 | GCCGGCCTCGCCCACGCCACC | 482 | AGLAHAT | 0.936046 |
| 58 | AATGCTCATACTGCGCTGGAT | 483 | NAHTALD | 0.933184 |
| 59 | TGGCCGATTCTTCGGGCTGAT | 484 | WPILRAD | 0.931545 |
| 60 | GCGCTGGCTGGTCTGTCTCTG | 485 | ALAGLSL | 0.930454 |
| 61 | CGTATTGATATGCCTTTTAAG | 486 | RIDMPFK | 0.920205 |
| 62 | ACGATGTCGTTGAGTAGTAGT | 487 | TMSLSSS | 0.919718 |
| 63 | CAAAACGTCGCCAAAAACCTC | 488 | QNVAKNL | 0.916602 |
| 64 | TTCGACAACCCCAACAACGTC | 489 | FDNPNNV | 0.915503 |
| 65 | GTCCTCATGAGAGAAAGCCTC | 490 | VLMRESL | 0.914386 |
| 66 | CACCACGACACCGGCAGCGCC | 491 | HHDTGSA | 0.912951 |
| 67 | GATGCGCCGAATAGTGTGGAT | 492 | DAPNSVD | 0.901999 |
| 68 | ACTGCGAGTAGGGATGCTAAG | 493 | TASRDAK | 0.889552 |
| 69 | ACTAATTATACGAAGCAGATT | 494 | TNYTKQI | 0.889024 |
| 70 | CCTCATAATGCTTCTGTGTTG | 495 | PHNASVL | 0.864707 |
| 71 | ACCAACAACACCAGAAACATC | 496 | TNNTRNI | 0.862873 |
| 72 | ATGGTTCCTAATCATTCTGGT | 497 | MVPNHSG | 0.859604 |
| 73 | CCGGTGCCGCAGTCTGAGCAT | 498 | PVPQSEH | 0.852761 |
| 74 | CTCTACCACGGCGGCAGCACC | 499 | LYHGGST | 0.851158 |

TABLE 2-continued

List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 75 | ATGATTCATACTAGGGAGACG | 500 | MIHTRET | 0.850116 |
| 76 | ACTAATAATACGAAGCCTCTT | 501 | TNNTKPL | 0.849557 |
| 77 | CTCAACACCACCAGAAACACC | 502 | LNTTRNT | 0.839304 |
| 78 | GCTTTGCATAATTCTCAGAAT | 503 | ALHNSQN | 0.827469 |
| 79 | GTGAATAGTACGAGGAATGTT | 504 | VNSTRNV | 0.826565 |
| 80 | GGTGTTGGGGTTGTTACGAAG | 505 | GVGVVTK | 0.820556 |
| 81 | GTTTTGTCGAAGCAGTTGGCT | 506 | VLSKQLA | 0.816495 |
| 82 | TCTAAGTCTCTGCAGCCGTTG | 507 | SKSLQPL | 0.815502 |
| 83 | TCGAATTCTACGCGGTTGGTT | 508 | SNSTRLV | 0.815119 |
| 84 | CTCAACCAAACCAAACAAATC | 509 | LNQTKQI | 0.811665 |
| 85 | AACAACAGCGTCAGACAACTC | 510 | NNSVRQL | 0.806765 |
| 86 | ATGTCGGGGTATTCGCATACT | 511 | MSGYSHT | 0.804194 |
| 87 | GTCAAAGTCCCCATCATCACC | 512 | VKVPIIT | 0.799412 |
| 88 | GGGAATAATACTCGGGCGGTG | 513 | GNNTRAV | 0.797634 |
| 89 | CAGAATCAGATTAAGAATATT | 514 | QNQIKNI | 0.797303 |
| 90 | ACCAACATGACCAAACCCCTC | 515 | TNMTKPL | 0.791064 |
| 91 | AACAACAGCACCAGACTCAGC | 516 | NNSTRLS | 0.790429 |
| 92 | AGCATGCTCACCAGCATCGTC | 517 | SMLTSIV | 0.790252 |
| 93 | CTCAACGCCACCGCCAGCAGA | 518 | LNATASR | 0.785269 |
| 94 | AATACTGGGGTGCAGGTTAGG | 519 | NTGVQVR | 0.785026 |
| 95 | ACCAACACCGTCAGACCCATC | 520 | TNTVRPI | 0.780569 |
| 96 | CAGTCTACGCCGGGGGCTACT | 521 | QSTPGAT | 0.779842 |
| 97 | GGTCATTCTGAGAATTCTCGT | 522 | GHSENSR | 0.778724 |
| 98 | CTCCCCACCCAAACCCTCAGA | 523 | LPTQTLR | 0.773756 |
| 99 | AAGAATGCTCCGATGCCTGAT | 524 | KNAPMPD | 0.772397 |
| 100 | AGCAACAGCACCAAACCCACC | 525 | SNSTKPT | 0.768053 |
| 101 | CCTATTATTACTATGCCTGCT | 526 | PIITMPA | 0.767318 |
| 102 | CCCCTCAAAGGCATCGGCAGC | 527 | PLKGIGS | 0.767253 |
| 103 | GTCCTCAGCGTCAACCACCTC | 528 | VLSVNHL | 0.765014 |
| 104 | AGTGTGGCTGCTGTGCATATG | 529 | SVAAVHM | 0.764013 |
| 105 | AGCAACAGCATCAGACTCGTC | 530 | SNSIRLV | 0.763114 |
| 106 | CATAATGATACTCGTCCTCTT | 531 | HNDTRPL | 0.759962 |
| 107 | CCTCCGGTGAGGTCTACGGCT | 532 | PPVRSTA | 0.755777 |
| 108 | ATGAACACCGTCAGAAACCTC | 533 | MNTVRNL | 0.754463 |
| 109 | TTGACGGATGGTCATCGGATT | 534 | LTDGHRI | 0.754429 |
| 110 | ACGAATGCGGTGAAGCTGACT | 535 | TNAVKLT | 0.752766 |

TABLE 2-continued

List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 111 | CGTGTGGATGCGGTTTTGAGT | 536 | RVDAVLS | 0.750458 |
| 112 | ACCAACGCCGTCAAAAGCACC | 537 | TNAVKST | 0.749271 |
| 113 | ATGCTCAACACCACCGCCAGA | 538 | MLNTTAR | 0.747921 |
| 114 | GGCAACAACACCAGACCCACC | 539 | GNNTRPT | 0.747523 |
| 115 | CAGTCTGGGGGTAGTGCGTTG | 540 | QSGGSAL | 0.744332 |
| 116 | GTGATTGCTTTGTCTACTATG | 541 | VIALSTM | 0.743901 |
| 117 | CTGAATACGATTCGGAATGTG | 542 | LNTIRNV | 0.743811 |
| 118 | AGCAACGCCACCAGAAGCGTC | 543 | SNATRSV | 0.740235 |
| 119 | GGCAACGGCACCAAATTCATC | 544 | GNGTKFI | 0.736944 |
| 120 | AGCAACACCATCAGACCCGTC | 545 | SNTIRPV | 0.736197 |
| 121 | AGCAACAGCACCAGAGCCATC | 546 | SNSTRAI | 0.734716 |
| 122 | TTTCATTTGACTGATAGGGGT | 547 | FHLTDRG | 0.733831 |
| 123 | CCGATTAGGTCGGATACTGTG | 548 | PIRSDTV | 0.731286 |
| 124 | GCCAACCAAATCCACAACACC | 549 | ANQIHNT | 0.730071 |
| 125 | TCGAATACGGTTCGGAATACT | 550 | SNTVRNT | 0.727807 |
| 126 | ACCAGCCTCGGCTACAGCAGC | 551 | TSLGYSS | 0.727167 |
| 127 | ATCAGCGGCGTCCAAACCAGA | 552 | ISGVQTR | 0.724309 |
| 128 | TCGAATGCTGTTAGGCAGACT | 553 | SNAVRQT | 0.72361 |
| 129 | TCTCTTTCTGAGCTTAGGATT | 554 | SLSELRI | 0.723061 |
| 130 | AGTACTGAGAAGAGGGATGAG | 555 | STEKRDE | 0.721349 |
| 131 | AACCTCGTCGGCACCCTCATC | 556 | NLVGTLI | 0.72103 |
| 132 | GGCAACAACATCAGACTCACC | 557 | GNNIRLT | 0.719643 |
| 133 | GCCGTCCCCACCGGCCTCAGA | 558 | AVPTGLR | 0.717951 |
| 134 | GGTGATAATAGTCTGACTAGG | 559 | GDNSLTR | 0.717624 |
| 135 | CACGCCGACAACAGACTCAAA | 560 | HADNRLK | 0.714815 |
| 136 | AGCAACGCCACCAGAAACTTC | 561 | SNATRNF | 0.714052 |
| 137 | GGGAATACGACTAGGGGGCTG | 562 | GNTTRGL | 0.713945 |
| 138 | CTCAACCTCACCGCCACCAAC | 563 | LNLTATN | 0.71358 |
| 139 | AGCGGCGTCAGCACCACCGAC | 564 | SGVSTTD | 0.711249 |
| 140 | TATGCTAAGACGTTGGCTATG | 565 | YAKTLAM | 0.710703 |
| 141 | ATGAACCACACCAAACCCACC | 566 | MNHTKPT | 0.710702 |
| 142 | GCTAATGCTACGAGGAATTCT | 567 | ANATRNS | 0.707423 |
| 143 | CAAAACCAAACCAAAATCACC | 568 | QNQTKIT | 0.707235 |
| 144 | TCTAATGCTATTAAGGCTACG | 569 | SNAIKAT | 0.70699 |
| 145 | TATCCTGATAATTATGGTAAG | 570 | YPDNYGK | 0.706343 |
| 146 | GGCAACACCACCATCAGAAGC | 571 | GNTTIRS | 0.705947 |

TABLE 2-continued

List of 7-mer targeting peptides that can target the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 147 | CTGGGTCTTACGGGTGCGGTT | 572 | LGLTGAV | 0.705628 |
| 148 | GCGAATAGTACGCGTATTCTG | 573 | ANSTRIL | 0.704068 |
| 149 | GATAATGCGATTCGTGCGCAG | 574 | DNAIRAQ | 0.703945 |
| 150 | ACGAATTATACTAAGCTTATG | 575 | TNYTKLM | 0.702916 |
| 151 | CATAATAGTCCTAGTAGTTAT | 576 | HNSPSSY | 0.70154 |
| 152 | GAGAATATGGTTCGGTCTGTG | 577 | ENMVRSV | 0.700139 |
| 153 | ACCAACAACATCAAAAGCTAC | 578 | TNNIKSY | 0.698201 |
| 154 | ACTAATTCGACGAGGCCTGTG | 579 | TNSTRPV | 0.696679 |
| 155 | CATACGGCTCCGCCTCATCCT | 580 | HTAPPHP | 0.695156 |
| 156 | GCCCTCAGCCAAAACACCAGC | 581 | ALSQNTS | 0.692869 |
| 157 | CCGAATGTGACTAAGAATGCT | 582 | PNVTKNA | 0.692038 |
| 158 | CTTGATACGCTGACGGGTTAT | 583 | LDTLTGY | 0.690142 |
| 159 | CCTAATAGTGTGCGTTCTGTT | 584 | PNSVRSV | 0.689082 |
| 160 | ACCAGCAGCCACCTCCCCCAC | 585 | TSSHLPH | 0.688469 |
| 161 | GTTCTTCATGGTGGTAATGAT | 586 | VLHGGND | 0.687991 |
| 162 | AGCAACTACGTCAAAAGCGCC | 587 | SNYVKSA | 0.687276 |
| 163 | GACAACAACAGCACCAGATGG | 588 | DNNSTRW | 0.687057 |
| 164 | ACTGTGATGAAGGGTTTTACT | 589 | TVMKGFT | 0.687036 |
| 165 | AGCCACACCCTCAGCACCCTC | 590 | SHTLSTL | 0.686592 |
| 166 | CCTGGTCCTCAGCAGGCGAAG | 591 | PGPQQAK | 0.685365 |
| 167 | ACTTTTGGGACGTCTAAGTTG | 592 | TFGTSKL | 0.684153 |
| 168 | AGCAACGCCGTCACCAACAGA | 593 | SNAVTNR | 0.683838 |
| 169 | TTGTCTATGTCGACGGTGCCT | 594 | LSMSTVP | 0.682136 |
| 170 | AGGCGTTATGATGGTAGGGAG | 595 | RRYDGRE | 0.681722 |
| 171 | ACCAACAGCACCAAAAACATC | 596 | TNSTKNI | 0.678439 |
| 172 | ATTAATGCTCAGTGGTCTGCG | 597 | INAQWSA | 0.672085 |
| 173 | GCCCAAACCAGCAACGACCCC | 598 | AQTSNDP | 0.669325 |
| 174 | ACGAATGAGACTAGGATGGTG | 599 | TNETRMV | 0.669307 |
| 175 | GCCAACGCCACCAGAGGCGTC | 600 | ANATRGV | 0.667153 |
| 176 | GCGGATGTGAATGCTTCGGGT | 601 | ADVNASG | 0.666574 |
| 177 | CTTAGTGAGCGGAATTATGTG | 602 | LSERNYV | 0.665675 |
| 178 | AGTGGTGAGCTTGCGCGGGCG | 603 | SGELARA | 0.663381 |
| 179 | GGGAATACTGCTAAGAATATT | 604 | GNTAKNI | 0.662988 |
| 180 | GACAACGCCGTCAGACCCCTC | 605 | DNAVRPL | 0.662435 |
| 181 | ATGATGCTCAGCGGCCTCAAC | 606 | MMLSGLN | 0.660837 |
| 182 | CCCAACACCATCAGAAACGTC | 607 | PNTIRNV | 0.660528 |

TABLE 2-continued

List of 7-mer targeting peptides that can target the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 183 | GAGAATTTGACGCGTGGGGTG | 608 | ENLTRGV | 0.659884 |
| 184 | TTTAGTGCTCGGAGTACGGGG | 609 | FSARSTG | 0.659095 |
| 185 | GAAAACGCCACCAGAACCTAC | 610 | ENATRTY | 0.657305 |
| 186 | GGCAACAGCACCAGAATGAAC | 611 | GNSTRMN | 0.656999 |
| 187 | GGGAATTCTACTAAGTCTCCT | 612 | GNSTKSP | 0.656908 |
| 188 | ATGCAAACCACCCTCCACCTC | 613 | MQTTLHL | 0.656525 |
| 189 | AACCCCACCCTCATCACCCTC | 614 | NPTLITL | 0.655924 |
| 190 | CTTATTTCTGGTCATGCGCAG | 615 | LISGHAQ | 0.655121 |
| 191 | TTCAACCAAGTCAGAAGCCTC | 616 | FNQVRSL | 0.65493 |
| 192 | ATGAACATCCTCAGAGAAGTC | 617 | MNILREV | 0.654097 |
| 193 | AGTGCTATGATGCGTGGTGTT | 618 | SAMMRGV | 0.653566 |
| 194 | CCCATGCTCAGCAGCCCCAGC | 619 | PMLSSPS | 0.652269 |
| 195 | CAGAATAATACGCTTAGGTCG | 620 | QNNTLRS | 0.651653 |
| 196 | AGGCATTCGGATCCGGTGGAG | 621 | RHSDPVE | 0.65144 |
| 197 | GTGAATACGACGTTTTCTACG | 622 | VNTTFST | 0.65142 |
| 198 | ATCAACAGCACCAGAGGCATC | 623 | INSTRGI | 0.650374 |
| 199 | ACCAACGCCGTCAGAGACCTC | 624 | TNAVRDL | 0.649865 |
| 200 | TCTAATAGTACTAGGCTGTCG | 625 | SNSTRLS | 0.649567 |
| 201 | ACGTCTATTGCTGGGTCGTTT | 626 | TSIAGSF | 0.647793 |
| 202 | CTCGGCAGCACCTACCCCAGA | 627 | LGSTYPR | 0.644533 |
| 203 | GCCAACGTCACCACCCAAAGA | 628 | ANVTTQR | 0.643299 |
| 204 | AGCAACAGCGTCAGACTCAGC | 629 | SNSVRLS | 0.641635 |
| 205 | GCTACGAATGAGCCTGATCGG | 630 | ATNEPDR | 0.641008 |
| 206 | AGAATGAACCCCGAACAAAGC | 631 | RMNPEQS | 0.640866 |
| 207 | TCGGTTAGTGGTTCGGCTAAT | 632 | SVSGSAN | 0.640362 |
| 208 | CCGAGTAATAGTACTACGCGT | 633 | PSNSTTR | 0.639664 |
| 209 | CTTTTTCATGGTACGCATGAG | 634 | LFHGTHE | 0.639176 |
| 210 | CCCCAACTCGGCAGCACCAAA | 635 | PQLGSTK | 0.638022 |
| 211 | CCCATCAGCGCCAACAGACTC | 636 | PISANRL | 0.637814 |
| 212 | AATTCGGGTAATCTTTCTATG | 637 | NSGNLSM | 0.637206 |
| 213 | AAGGTTGAGGCTATTGGGATG | 638 | KVEAIGM | 0.63585 |
| 214 | AAGACTTTGCTTAATAGTGTT | 639 | KTLLNSV | 0.635567 |
| 215 | AATGCTATGGATCTTAAGGTG | 640 | NAMDLKV | 0.633592 |
| 216 | ATGATGGGTAATGGGTCTTCG | 641 | MMGNGSS | 0.632846 |
| 217 | AGCAACAGCACCAAAGCCCTC | 642 | SNSTKAL | 0.630646 |
| 218 | TCTAATAGTACGCGGGGTACG | 643 | SNSTRGT | 0.630359 |

37

38

TABLE 2-continued

TABLE 2-continued

List of 7-mer targeting peptides that can target
the CNS with greater efficiency and specificity List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 219 | AGCCTCAGCAGCCTCCACGTC | 644 | SLSSLHV | 0.629137 |
| 220 | ACCCTCAGCGGCGCCCTCACC | 645 | TLSGALT | 0.628275 |
| 221 | CCGAATACGGTGAGGAATAAT | 646 | PNTVRNN | 0.627943 |
| 222 | AATAATAATGTGAAGATGACT | 647 | NNNVKMT | 0.627302 |
| 223 | TCTGTTGCTAAGCCTTTTATG | 648 | SVAKPFM | 0.627075 |
| 224 | ACGCAGACGACTCGGCTTTCG | 649 | TQTTRLS | 0.625657 |
| 225 | AATAATGCGACTCGGGGTGGG | 650 | NNATRGG | 0.622765 |
| 226 | ACCAACACCACCGCCAGAATC | 651 | TNTTARI | 0.621665 |
| 227 | GAGAATAGTATTCGGACTATT | 652 | ENSIRTI | 0.619021 |
| 228 | ATTAGGGAGACTTCTGGGAAG | 653 | IRETSGK | 0.618732 |
| 229 | AGCATCTACTACCACACCGAA | 654 | SIYYHTE | 0.618441 |
| 230 | GTCCTCGACAACAGCGGCCAA | 655 | VLDNSGQ | 0.618183 |
| 231 | AGCCACAACATGACCATCAGA | 656 | SHNMTIR | 0.614114 |
| 232 | ACCATCCCCAGCGCCGGCAAA | 657 | TIPSAGK | 0.612816 |
| 233 | CCTAGGCATACTTTGAGTCAG | 658 | PRHTLSQ | 0.60799 |
| 234 | TCGCTTAATGTGCAGGATGTG | 659 | SLNVQDV | 0.607203 |
| 235 | TATCAGTCTCTGGCTAATCCG | 660 | YQSLANP | 0.607005 |
| 236 | ATTCTGAATATGTCTACGGAT | 661 | ILNMSTD | 0.606834 |
| 237 | GTCCTCCACCTCGGCCACAGC | 662 | VLHLGHS | 0.605932 |
| 238 | GGTGTTACTCAGACTCCGCGT | 663 | GVTQPR | 0.6059 |
| 239 | ACCAACGACACCAGAAGAATC | 664 | TNDTRRI | 0.604587 |
| 240 | CAAACCGACCACACCAGCAGA | 665 | QTDHTSR | 0.604031 |
| 241 | AAGAATGAGATTAAGAATGTG | 666 | KNEIKNV | 0.603838 |
| 242 | TGGACTGGTAATGAGAGGCTT | 667 | WTGNERL | 0.603412 |
| 243 | GGTAAGAGTGATGCTATGCGG | 668 | GKSDAMR | 0.603322 |
| 244 | GGGAATGCGACTCGTACTTAT | 669 | GNATRTY | 0.602016 |
| 245 | GCCAGCAACCTCGGCCTCCCC | 670 | ASNLGLP | 0.600647 |
| 246 | AGCAGCCTCAGCGGCAGCCCC | 671 | SSLSGSP | 0.599424 |
| 247 | GCCGCCGTCAACCAAGGCGTC | 672 | AAVNQGV | 0.599283 |
| 248 | GACCAAAACCAACCCAGAGAA | 673 | DQNQPRE | 0.59872 |
| 249 | CTCACCCAAGACAAACAAGCC | 674 | LTQDKQA | 0.59843 |
| 250 | TTCGGCAGCAACGAACACAAC | 675 | FGSNEHN | 0.59773 |
| 251 | CTGAATCAGCCGAATGTGCGG | 676 | LNQPNVR | 0.59703 |
| 252 | ATGAATACTACGCGTAATCTG | 677 | MNTTRNL | 0.596819 |
| 253 | ACTAATTCTACTAGGACGAGT | 678 | TNSTRTS | 0.596817 |
| 254 | TTTGAGCTTTCGCATGTGCCT | 679 | FELSHVP | 0.595373 |

| SEQ ID NO | Sequence (7 mer Amino acid) | SEQ ID NO | 7 mer Amino acid | Brain-mean-enrich (log10) |
|---|---|---|---|---|
| 255 | GAAGGCCTCGGCAACGCCGCC | 680 | EGLGNAA | 0.59339 |
| 256 | CTCACCGTCACCCTCAACCAC | 681 | LTVTLNH | 0.593104 |
| 257 | TTTGGGAATGCGATTCAGTCT | 682 | FGNAIQS | 0.593063 |
| 258 | CCGGGTGGGGGTTTGACTCCG | 683 | PGGGLTP | 0.591748 |
| 259 | CCCAACATGACCAGAAGCCTC | 684 | PNMTRSL | 0.591633 |
| 260 | AGTCAGCTGCATAGGTTGCAG | 685 | SQLHRLQ | 0.588997 |
| 261 | AATGATCCTGTGCTGACTGTG | 686 | NDPVLTV | 0.587622 |
| 262 | GAAAACAGCGTCAGAACCACC | 687 | ENSVRTT | 0.586872 |
| 263 | GATCGTGTGACTAATCCGAAG | 688 | DRVTNPK | 0.585898 |
| 264 | CTCAACACCGGCCAAATGAGA | 689 | LNTGQMR | 0.584482 |
| 265 | ATTAGTCCTTCTCAGGTGAAG | 690 | ISPSQVK | 0.583565 |
| 266 | TACAGCGCCGACAAAACCACC | 691 | YSADKTT | 0.583168 |
| 267 | ATTGATAGTGCGGGGATGGCG | 692 | IDSAGMA | 0.582726 |
| 268 | AGCAACAACATCAAACTCAAC | 693 | SNNIKLN | 0.582501 |
| 269 | CTTGAGACGCAGCCTAGGACT | 694 | LETQPRT | 0.582054 |
| 270 | AATTTGCATAGTAATGTGCTG | 695 | NLHSNVL | 0.581653 |
| 271 | ATGGTCAAAGACACCCAACTC | 696 | MVKDTQL | 0.581409 |
| 272 | CTCATGCACCTCACCAACCCC | 697 | LMHLTNP | 0.579725 |
| 273 | GTCGCCAGCCCCGACAAAAGA | 698 | VASPDKR | 0.579259 |
| 274 | GTCGTCGCCGTCCTCACCAGC | 699 | VVAVLTS | 0.578391 |
| 275 | AACATCATGGTCAACGTCCCC | 700 | NIMVNVP | 0.578008 |
| 276 | CCGTATAGTGGGCAGCGGACT | 701 | PYSGQRT | 0.577882 |
| 277 | CCTCTGCTTAAGACGAATACT | 702 | PLLKTNT | 0.575523 |
| 278 | GGGAATACTACGGTGCGTGGG | 703 | GNTTVRG | 0.574402 |
| 279 | ACCAACAAAGTCAGAGACGAC | 704 | TNKVRDD | 0.573889 |
| 280 | CCCAGCACCGCCCTCCTCGTC | 705 | PSTALLV | 0.573034 |
| 281 | ATCCAAAGCATCACCCTCAAA | 706 | IQSITLK | 0.572783 |
| 282 | CCCCTCCACGCCAACATGAGC | 707 | PLHANMS | 0.570881 |
| 283 | ACCGCCCACGCCGAAGCCAGA | 708 | TAHAEAR | 0.570572 |
| 284 | ACGAATACGGATTCGTATCGT | 709 | TNTDSYR | 0.569365 |
| 285 | ACCCACGTCAGCCTCGACAGA | 710 | THVSLDR | 0.569228 |
| 286 | TTTAGTACGAAGGATCATGTT | 711 | FSTKDHV | 0.568654 |
| 287 | GACAACACCCAAACCGCCCCC | 712 | DNTQTAP | 0.568553 |
| 288 | AGCAACAGAATCATCAGCGGC | 713 | SNRIISG | 0.568551 |
| 289 | ACTAATTCTGTTAGGAATAAT | 714 | TNSVRNN | 0.568237 |
| 290 | AGCAACGAAGTCAGAAACATG | 715 | SNEVRNM | 0.567847 |

TABLE 2-continued

List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 291 | GAACTCTACAAACCCAGCAGA | 716 | ELYKPSR | 0.567258 |
| 292 | TGGATTACGGGGGGTGCGAGT | 717 | WITGGAS | 0.567159 |
| 293 | AACAACAGCGTCAGACCCACC | 718 | NNSVRPT | 0.566945 |
| 294 | CACACCGCCGTCCTCAGAACC | 719 | HTAVLRT | 0.565911 |
| 295 | AATACTTTGTCTCTTGCTCCT | 720 | NTLSLAP | 0.564955 |
| 296 | CCCAACGCCAGCGTCAACAGC | 721 | PNASVNS | 0.564885 |
| 297 | GTTACTGGTGGGAATACTTAT | 722 | VTGGNTY | 0.564099 |
| 298 | GTCAACGAAAACCTCATCGAA | 723 | VNENLIE | 0.563902 |
| 299 | GTTTTGACGACTCATTCGAAT | 724 | VLTTHSN | 0.563552 |
| 300 | CACACCCAACTCCCCCTCACC | 725 | HTQLPLT | 0.562802 |
| 301 | CGGCAGTCTCTTGAGGCGTTG | 726 | RQSLEAL | 0.562715 |
| 302 | CCCGACGTCACCGAAGGCAGA | 727 | PDVTEGR | 0.560929 |
| 303 | CCGACTAATATTATGCTTGAT | 728 | PTNIMLD | 0.560313 |
| 304 | CCCAACATGAGCGCCATGATC | 729 | PNMSAMI | 0.559451 |
| 305 | ATTATGAATGGTCAGGCTCTG | 730 | IMNGQAL | 0.558677 |
| 306 | AATAATAATTCGACGCGTTTT | 731 | NNNSTRF | 0.558656 |
| 307 | GCCAACGTCACCAGAAGCACC | 732 | ANVTRST | 0.558653 |
| 308 | CAGAATCTTGGTCTTAATGTG | 733 | QNLGLNV | 0.558202 |
| 309 | CAAGCCCAAATGAGCAGCGCC | 734 | QAQMSSA | 0.557238 |
| 310 | CTCACCATGGCCACCAACGTC | 735 | LTMATNV | 0.556779 |
| 311 | GATCGTGATTCTGTGCAGAAT | 736 | DRDSVQN | 0.55654 |
| 312 | GTCAACCCCACCAACAACCTC | 737 | VNPTNNL | 0.555076 |
| 313 | CCGTCTTTTACGACTATGAGT | 738 | PSFTTMS | 0.554811 |
| 314 | AGGGAGACGCCTATTCCTAAG | 739 | RETPIPK | 0.553803 |
| 315 | AGCCTCAACTTCACCACCGCC | 740 | SLNFTTA | 0.553055 |
| 316 | GGTATGAGTGGGGTTGCTCAG | 741 | GMSGVAQ | 0.552736 |
| 317 | AAGGTTGATGCGGCTCAGAGT | 742 | KVDAAQS | 0.552569 |
| 318 | CATATTACGACTAATGTGTCT | 743 | HITTNVS | 0.552479 |
| 319 | GAGCGGGAGTCGGCTCGTCTT | 744 | ERESARL | 0.551876 |
| 320 | GATAATAGGACTCAGAGGACG | 745 | DNRTQRT | 0.551636 |
| 321 | TCTGCGCCTAATGTGACTATT | 746 | SAPNVTI | 0.551278 |
| 322 | GAAAACGGCACCAGAAACACC | 747 | ENGTRNT | 0.55012 |
| 323 | GGCACCGCCGTCTTCACCGCC | 748 | GTAVFTA | 0.549912 |
| 324 | GCCAACAACATGAGCCAAACC | 749 | ANNMSQT | 0.549519 |
| 325 | GGTAATCATACTTATAATCTG | 750 | GNHTYNL | 0.549264 |
| 326 | CTGAGTCCTTCGAATTCTAAT | 751 | LSPSNSN | 0.549019 |

TABLE 2-continued

List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 327 | ATGGGCGCCGACCACAGAACC | 752 | MGADHRT | 0.548749 |
| 328 | AGTAATTCGACGCGTGGTTCT | 753 | SNSTRGS | 0.548705 |
| 329 | AATACTTCTGGTGTGCCTAAG | 754 | NTSGVPK | 0.548579 |
| 330 | ATCAACACCGCCGTCGTCAGC | 755 | INTAVVS | 0.54846 |
| 331 | ATGGGGGTTCAGGCTTATGTG | 756 | MGVQAYV | 0.54845 |
| 332 | GGGAATTTTGTTAAGCCGAAT | 757 | GNFVKPN | 0.547942 |
| 333 | GTGAATTCGGTGAGGATGATT | 758 | VNSVRMI | 0.547171 |
| 334 | CACGACAGCGCCAACAGCAGA | 759 | HDSANSR | 0.54671 |
| 335 | CTCGGCGTCAGAGACGACAGC | 760 | LGVRDDS | 0.545708 |
| 336 | AGCAACGCCGTCAGAGCCAAC | 761 | SNAVRAN | 0.545674 |
| 337 | CCCGTCCTCGCCGCCACCATG | 762 | PVLAATM | 0.545458 |
| 338 | AATAAGCCTGTGTCTGGTAAT | 763 | NKPVSGN | 0.544076 |
| 339 | GTCGGCCTCGCCAGCCACACC | 764 | VGLASHT | 0.541637 |
| 340 | GGCAGCAACACCAACATGAAA | 765 | GSNTNMK | 0.540634 |
| 341 | GTTGCTACTACTGTGCATAAT | 766 | VATTVHN | 0.540191 |
| 342 | AACACCCTCGACAGCAGAGTC | 767 | NTLDSRV | 0.539923 |
| 343 | AGGGAGGCTAATTTGCAGGCG | 768 | REANLQA | 0.539717 |
| 344 | GTCGACGCCCTCAGCCACATG | 769 | VDALSHM | 0.539694 |
| 345 | CTTCGTCTTGCTGGTCTTGCT | 770 | LRLAGLA | 0.539525 |
| 346 | ATTACGGTGACTAATTATTCG | 771 | ITVTNYS | 0.539447 |
| 347 | TGGGACAGCGGCAGCGGCGAA | 772 | WDSGSGE | 0.539198 |
| 348 | TTCGCCAGCGAAACCGTCGCC | 773 | FASETVA | 0.537906 |
| 349 | CAGAATGTTACGGGGACGAGG | 774 | QNVTGTR | 0.537867 |
| 350 | CTTAATGGGTTGAATGTGTCT | 775 | LNGLNVS | 0.537505 |
| 351 | AATATGCTTAAGCAGAGTGAG | 776 | NMLKQSE | 0.537354 |
| 352 | TTTAATGAGGTTCCGAAGGCG | 777 | FNEVPKA | 0.537144 |
| 353 | CTCGGCGACATCACCGGCTTC | 778 | LGDITGF | 0.537047 |
| 354 | ATTTCGGCTTCTCATTCTCGT | 779 | ISASHSR | 0.536983 |
| 355 | AGTCAGACGCAGATTGCTCTT | 780 | SQTQIAL | 0.53684 |
| 356 | AATATGGCTACTCAGATGAAG | 781 | NMATQMK | 0.536747 |
| 357 | GTCAACCACAACATCAGACTC | 782 | VNHNIRL | 0.53652 |
| 358 | AACGCCCTCCAAGTCCCCGTC | 783 | NALQVPV | 0.536474 |
| 359 | AATTCGACGGGTATTGATACG | 784 | NSTGIDT | 0.53526 |
| 360 | GTTGTTGCTGGGCATCTTAAT | 785 | VVAGHLN | 0.534827 |
| 361 | CGGAATGATGCGATTCTGAAT | 786 | RNDAILN | 0.53456 |
| 362 | AATCGGGTTGATTCGCGGGCT | 787 | NRVDSRA | 0.53408 |

TABLE 2-continued

List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 363 | TCGACGCATTCTACTTATGTG | 788 | STHSTYV | 0.533753 |
| 364 | AGTGGGCATGGGACTCTGCGG | 789 | SGHGTLR | 0.532267 |
| 365 | CCCAACAGCACCACCCTCAGC | 790 | PNSTTLS | 0.531723 |
| 366 | GACACCAAACCCACCAACACC | 791 | DTKPTNT | 0.531589 |
| 367 | AACAGAGACACCATCAACAAC | 792 | NRDTINN | 0.531212 |
| 368 | CCCAGAACCCTCAGCGACGGC | 793 | PRTLSDG | 0.530962 |
| 369 | ACCAAAGACGTCACCACCAGC | 794 | TKDVTTS | 0.53023 |
| 370 | CTGGGTAATCCTACGCCTTCT | 795 | LGNPTPS | 0.529624 |
| 371 | TATCAGGCGATGTATAGGGAT | 796 | YQAMYRD | 0.528592 |
| 372 | AGCGGCGTCCAAGAATTCGAC | 797 | SGVQEFD | 0.528493 |
| 373 | TCTAATCATCTGTCGACGGTT | 798 | SNHLSTV | 0.528046 |
| 374 | CACGACGAAAGAGCCAACATG | 799 | HDERANM | 0.526932 |
| 375 | ACGAATAGTACTCGGTCGCCT | 800 | TNSTRSP | 0.526707 |
| 376 | CCGACGGATAAGTCTTATCCG | 801 | PTDKSYP | 0.525687 |
| 377 | ATGACCGAACAAAGAACCGCC | 802 | MTEQRTA | 0.524729 |
| 378 | ACCAACGCCACCCACAGCAAA | 803 | TNATHSK | 0.523113 |
| 379 | AATCGGGGTACTTTTAGTGCG | 804 | NRGTFSA | 0.522986 |
| 380 | AACACCACCAAATTCAACACC | 805 | NTTKFNT | 0.522899 |
| 381 | GGGATTCCGCCTTTGACTAAG | 806 | GIPPLTK | 0.522659 |
| 382 | ACCGCCAACAGCACCCAAAGA | 807 | TANSTQR | 0.522626 |
| 383 | ACTCAGGGTCCGGGTCCGAAG | 808 | TQGPGPK | 0.522239 |
| 384 | ATGAATACTACGCGGAATTAT | 809 | MNTTRNY | 0.522193 |
| 385 | CTCAGAGAAGGCACCTTCATG | 810 | LREGTFM | 0.521554 |
| 386 | AACATCAGCAGCACCGACAGA | 811 | NISSTDR | 0.521154 |
| 387 | TCGGTTAGTCGGCCGTTTCAG | 812 | SVSRPFQ | 0.520365 |
| 388 | CCTATGTCTGCTAATGGGAAG | 813 | PMSANGK | 0.518792 |
| 389 | GAAGTCAGAGGCAACACCTTC | 814 | EVRGNTF | 0.518514 |
| 390 | TCGCAGAAGGGTCTGTCTGTG | 815 | SQKGLSV | 0.518477 |
| 391 | ATTGCTGAGAATCTGAGTGCT | 816 | IAENLSA | 0.517935 |
| 392 | TTCAGCAACATGAACCTCAAA | 817 | FSNMNLK | 0.517734 |
| 393 | CCTCGTGAGCGGACTTATACT | 818 | PRERTYT | 0.516835 |
| 394 | TGGTCGCATAATCCGGATTCT | 819 | WSHNPDS | 0.516248 |
| 395 | GGTCTTCAGACTCTGATTACG | 820 | GLQTLIT | 0.516123 |
| 396 | AGCAACAGAACCAAAGACATC | 821 | SNRTKDI | 0.515515 |
| 397 | GTGACTGAGACGATTCTTAAG | 822 | VTETILK | 0.515459 |
| 398 | TATGTTACGCGTAGTGGTCTG | 823 | YVTRSGL | 0.515319 |

TABLE 2-continued

List of 7-mer targeting peptides that can target
the CNS with greater efficiency and specificity

| SEQ ID NO | Sequence (7 mer Amino acid) | SEQ ID NO | 7 mer Amino acid | Brain-mean-enrich (log10) |
|---|---|---|---|---|
| 399 | ATGAACGCCAACATCCTCGTC | 824 | MNANILV | 0.514679 |
| 400 | ACTACGAATCGGGTGGGTACG | 825 | TTNRVGT | 0.51427 |
| 401 | GTCCTCAAAAGCCACCTCCAA | 826 | VLKSHLQ | 0.51406 |
| 402 | AGCGACGGCCTCAGAACCCAA | 827 | SDGLRTQ | 0.514048 |
| 403 | CTCAACAGCGTCAAACCCAAC | 828 | LNSVKPN | 0.513525 |
| 404 | AGCCAAGCCATCGCCCCCAAA | 829 | SQAIAPK | 0.51343 |
| 405 | TCTAATAATGTTCGTGCTCCG | 830 | SNNVRAP | 0.513257 |
| 406 | ATCAGCCACCTCAGCGAAAGC | 831 | ISHLSES | 0.511503 |
| 407 | CTCCTCCCCGGCATGAGATTC | 832 | LLPGMRF | 0.5114 |
| 408 | CTTCTTGCGTCGGCTACGAAG | 833 | LLASATK | 0.510718 |
| 409 | AACCACAACGGCATGGTCAGC | 834 | NHNGMVS | 0.510709 |
| 410 | CACAGCGGCGAACTCAACAAC | 835 | HSGELNN | 0.510488 |
| 411 | CTTTCTGCGCCTAAGGATACT | 836 | LSAPKDT | 0.509967 |
| 412 | ATTGGGACTCATGTGGGGACG | 837 | IGTHVGT | 0.509748 |
| 413 | GCCGTCGCCCTCGCCAGCGCC | 838 | AVALASA | 0.509614 |
| 414 | ATTACTCTTCAGTCTAATGCT | 839 | ITLQSNA | 0.509556 |
| 415 | GTCGACCACAGCCTCACCAGC | 840 | VDHSLTS | 0.509193 |
| 416 | GGCAACGAAGCCACCAGCCTC | 841 | GNEATSL | 0.508729 |
| 417 | CCCGTCAGCAGCACCACCCTC | 842 | PVSSTTL | 0.507682 |
| 418 | CCCTACCAAACCAGCAGCGCC | 843 | PYQTSSA | 0.507351 |
| 419 | ACCAGCGTCGTCAGCGCCTTC | 844 | TSVVSAF | 0.507058 |
| 420 | AACGGCGTCCCCGACAACAAC | 845 | NGVPDNN | 0.50693 |
| 421 | AGCACCCAAACCATCGGCTTC | 846 | STQTIGF | 0.505905 |
| 422 | ATTCGGAGTTCTGATCTTGCG | 847 | IRSSDLA | 0.505273 |
| 423 | AACACCCAAAGCGCCAAATAC | 848 | NTQSAKY | 0.504002 |
| 424 | AGTCTTGAGTCGTCTAGGCAG | 849 | SLESSRQ | 0.503575 |
| 425 | CTCAACCTCGCCAGCGGCAGA | 850 | LNLASGR | 0.503463 |
| 426 | ATGCAGGAGCGTCGGGAGTAT | 851 | MQERREY | 0.503055 |
| 427 | TGGCTCCTCAAAGACGGCTAC | 852 | WLLKDGY | 0.502893 |
| 428 | GGCAGATACCAAACCACCAGC | 853 | GRYQTTS | 0.502776 |
| 429 | AATACGACGAAGTTTCCGTTT | 854 | NTTKFPF | 0.502408 |
| 430 | ATGAGCAACGGCATCAGCAGA | 855 | MSNGISR | 0.501897 |
| 431 | CCGATTCGGGATCCGGAGAAG | 856 | PIRDPEK | 0.501479 |
| 432 | AGTACGCTGAGTCCGCATGTT | 857 | STLSPHV | 0.501315 |
| 433 | TTCATGCCCATCAGCAGCGCC | 858 | FMPISSA | 0.50124 |
| 434 | AGAAGCGACACCCAAAGCAGC | 859 | RSDTQSS | 0.500462 |

TABLE 3

| | | | Mean |
|---|---|---|---|
| SEQ ID NO | 11-mer DNA Sequence | SEQ ID NO | 11-mer Amino Acid Sequence | enrichment score (log 10 scale) |

11-mer targeting peptides that can target the CNS

| SEQ ID NO | 11-mer DNA Sequence | SEQ ID NO | 11-mer Amino Acid Sequence | Mean enrichment score (log 10 scale) |
|---|---|---|---|---|
| 860 | GCCCAAACCACCCTCAAACCCTTCAGCAACCCC | 864 | AQTTLKPFSNP | 1.101507461 |
| 861 | GACGGCACCACCCTCAAACCCTTCAGCAACCCC | 865 | DGTTLKPFSNP | 0.172425316 |
| 862 | GACGGCACCGCCCTCAAACCCTTCCTCGCCCAA | 866 | DGTALKPFLAQ | 0.647416071 |
| 863 | GATGGGACGACTCTTAAGCCGTTTCTGGCACAG | 867 | DGTTLKPFLAQ | sequence predicted based on PHP.eB sequence |

AAV Capsid Proteins Targeting the Liver

Disclosed herein are AAV capsid proteins with a substitution or an insertion of at least one amino acid at an amino acid position described above in a parental AAV capsid protein that confers an increased specificity for the liver. In some instances, the insertion comprises at least one amino acid provided in any one of the sequences provided in Table 4 and/or FIG. 35. In some instances, the insertion comprises at least two amino acids provided in any one of the sequences provided in Table 4 and/or FIG. 35. In some instances, the insertion comprises at least three amino acids provided in any one of the sequences provided in Table 4 and/or FIG. 35. In some instances, the insertion comprises at least four amino acids provided in any one of the sequences provided in Table 4 and/or FIG. 35. In some instances, the insertion comprises at least five amino acids provided in Table 4 and/or FIG. 35. In some instances, the insertion comprises at least six amino acids provided in Table 4 and/or FIG. 35. In some instances, the insertion comprises at least seven amino acids provided in Table 4 and/or FIG. 35. In some instances, the amino acids are contiguous. In some instances, the amino acids are not contiguous. In some instances, the insertion is at an amino acid position 588_589 in a parental AAV capsid protein. In some instances, the parental capsid protein is AAV9 capsid protein, provided in SEQ ID NO: 1.

TABLE 4

List of 7-mer targeting peptides that target the liver

| SEQ ID NO | DNA sequence for 7 mer amino acid | SEQ ID NO | 7 mer amino acid | liver-mean-enrich (log10) |
|---|---|---|---|---|
| 868 | GCCGAATACAACACCGGCGTC | 950 | AEYNTGV | 0.585999 |
| 869 | GCTAATGCGATGGGTGATCAT | 951 | ANAMGDH | 0.611245 |
| 870 | GAAAGCATCCAACAACTCAGC | 952 | ESIQQLS | 0.525712 |
| 871 | TTTAAGGTTAGTATTCAGCAG | 953 | FKVSIQQ | 0.591275 |
| 872 | TTTCTTCTTACTTCGGATCCG | 954 | FLLTSDP | 0.515975 |
| 873 | TTTCAGCAGGATACTTATCTG | 955 | FQQDTYL | 0.548808 |
| 874 | TTTTCTGGTAGTGCTAGGGTT | 956 | FSGSARV | 0.509852 |
| 875 | TTCAGCGTCACCAGACAAGCC | 957 | FSVTRQA | 0.718621 |
| 876 | GGGGCTGCTGGTAAGAGTTTG | 958 | GAAGKSL | 0.571307 |
| 877 | GGTCATATTTCGGCGCTTGCG | 959 | GHISALA | 0.552655 |
| 878 | GGGCTGAAGGTGTCTGGGTCT | 960 | GLKVSGS | 0.777335 |
| 879 | GGTCTTCAGTCGCCGAGGTCT | 961 | GLQSPRS | 0.572095 |
| 880 | GGGAGGACGGTGCAGGATAGG | 962 | GRTVQDR | 0.528631 |
| 881 | GGCACCAAAACCCACAGCCTC | 963 | GTKTHSL | 0.518459 |
| 882 | GGCACCACCAGAAGCCCCACC | 964 | GTTRSPT | 0.560705 |
| 883 | CACCCCAGCCTCAGACAAAGC | 965 | HPSLRQS | 0.508478 |
| 884 | CATTCTGCGAAGACTATTGCG | 966 | HSAKTIA | 0.579949 |

TABLE 4-continued

List of 7-mer targeting peptides that target the liver

| SEQ ID NO | DNA sequence for 7 mer amino acid | SEQ ID NO | 7 mer amino acid | liver-mean-enrich (log10) |
|---|---|---|---|---|
| 885 | CACAGCGGCCCCACCAGCAGC | 967 | HSGPTSS | 0.505295 |
| 886 | ATCAACAAAGACAACAACCAA | 968 | INKDNNQ | 0.531458 |
| 887 | ATCAACACCGCCAGCTACAAA | 969 | INTASYK | 0.542125 |
| 888 | AAAGCCATCAGCACCGCCAAC | 970 | KAISTAN | 0.616958 |
| 889 | AAAGCCAACAGCCAAATCACC | 971 | KANSQIT | 0.519425 |
| 890 | AAAGCCTACAGCGTCCAAGTC | 972 | KAYSVQV | 1.15776 |
| 891 | AAACTCAGCACCCTCCACCAA | 973 | KLSTLHQ | 0.568791 |
| 892 | AAGCGGGCGCCTGCTGATTCT | 974 | KRAPADS | 0.611303 |
| 893 | AAAACCAACAACACCGTCCTC | 975 | KTNNTVL | 0.504377 |
| 894 | AAAACCCAACTCGGCCAAATG | 976 | KTQLGQM | 0.519843 |
| 895 | CTTGGTTCTGCGCTTACGAGG | 977 | LGSALTR | 0.563314 |
| 896 | CTCATCAGCACCACCCACAGA | 978 | LISTTHR | 0.502083 |
| 897 | CTTAAGGTTGCGTCTGGTTTG | 979 | LKVASGL | 0.540598 |
| 898 | CTTCTTGCGACTGGGCTTAAG | 980 | LLATGLK | 0.545453 |
| 899 | CTTCCGGGTGGTGCGAGGTTG | 981 | LPGGARL | 0.564086 |
| 900 | CTTAGGGGTTCTGCTCAGGTG | 982 | LRGSAQV | 0.648123 |
| 901 | TTGTCTGCTCAGCTTCCGCGG | 983 | LSAQLPR | 0.503052 |
| 902 | CTTTCTACTGCGTTGACTGTG | 984 | LSTALTV | 0.591029 |
| 903 | CTCACCAGAGTCGGCACCGTC | 985 | LTRVGTV | 0.520831 |
| 904 | ATGGCCAACACCAGAAGCGCC | 986 | MANTRSA | 0.525721 |
| 905 | ATGATCAGAGGCACCAGCAGC | 987 | MIRGTSS | 0.512891 |
| 906 | ATGCTCAGCGGCCAAGCCAGA | 988 | MLSGQAR | 0.668364 |
| 907 | ATGAGAGGCCAAGGCGTCCAC | 989 | MRGQGVH | 0.567657 |
| 908 | AACAACAACCAAAAAGTCTAC | 990 | NNNQKVY | 0.610002 |
| 909 | AACAACAGCGGCCACATCAGC | 991 | NNSGHIS | 0.518228 |
| 910 | AACACCCTCATCAACGTCAGC | 992 | NTLINVS | 0.607212 |
| 911 | AATACTTCTGGTGTGCCTAAG | 993 | NTSGVPK | 0.684638 |
| 912 | AATGTGCCGACTTCGCCGCGG | 994 | NVPTSPR | 0.520245 |
| 913 | CCCGCCAGAATCCCCGGCAGC | 995 | PARIPGS | 0.50309 |
| 914 | CCCCTCAGAAACATCAGCGCC | 996 | PLRNISA | 0.50497 |
| 915 | CCGTTGAGTGGGGGTGTTCGT | 997 | PLSGGVR | 0.598554 |
| 916 | CCCAACAGAGCCGCCAACAAC | 998 | PNRAANN | 0.508143 |
| 917 | CCGCGTCATGCGACTCAGTCG | 999 | PRHATQS | 0.711312 |
| 918 | CCGCGGCCGGTGTCGAATGGG | 1000 | PRPVSNG | 0.7305 |
| 919 | CCTTCTGGTTCTGCGCGGAGT | 1001 | PSGSARS | 0.82811 |
| 920 | CCCAGCCACGCCAGAGCCAGC | 1002 | PSHARAS | 0.520336 |
| 921 | CCCGTCGGCACCAGAACCAGC | 1003 | PVGTRTS | 0.560759 |

TABLE 4-continued

List of 7-mer targeting peptides that target the liver

| SEQ ID NO | DNA sequence for 7 mer amino acid | SEQ ID NO | 7 mer amino acid | liver-mean-enrich (log10) |
|---|---|---|---|---|
| 922 | AGAGACACCGTCAGCAGATAC | 1004 | RDTVSRY | 0.535765 |
| 923 | AGAATCAGCACCCTCGGCCTC | 1005 | RISTLGL | 0.595844 |
| 924 | AGGCTTGATAGGACTGGTTTG | 1006 | RLDRTGL | 0.588542 |
| 925 | AGACTCACCAACAGCAACCAA | 1007 | RLTNSNQ | 0.516161 |
| 926 | CGTCAGCATCAGCTTCCTATG | 1008 | RQHQLPM | 0.505918 |
| 927 | AGAACCGCCAACGCCCTCGGC | 1009 | RTANALG | 0.802247 |
| 928 | CGGACGGATGTGCGGACGAAT | 1010 | RTDVRTN | 0.682169 |
| 929 | CGGACTACGGCTAATTCGCTT | 1011 | RTTANSL | 0.509233 |
| 930 | AGCGGCGGCACCAGAGAAGGC | 1012 | SGGTREG | 0.501512 |
| 931 | AGCATCAGAGCCCCCGTCAGC | 1013 | SIRAPVS | 0.572426 |
| 932 | TCGATTTCTCCTCCTCGTACG | 1014 | SISPPRT | 0.550578 |
| 933 | TCGAAGGTTACGCCTCCTCTG | 1015 | SKVTPPL | 0.687491 |
| 934 | AGCAGCAGACTCAGCGTCGGC | 1016 | SSRLSVG | 0.637971 |
| 935 | AGCACCAGAAACGTCGTCGGC | 1017 | STRNVVG | 0.532567 |
| 936 | TCGGTTCCTCCGAATAGGAAT | 1018 | SVPPNRN | 0.508166 |
| 937 | ACGGCTGCGCATGTTAGTTAT | 1019 | TAAHVSY | 0.520336 |
| 938 | ACCAGAAGCGAAGTCATGAAA | 1020 | TRSEVMK | 0.683884 |
| 939 | GTGGCGGGTCTGACTGTTCAG | 1021 | VAGLTVQ | 0.581695 |
| 940 | GTTGGTTCTAGTAATACGTAT | 1022 | VGSSNTY | 0.502229 |
| 941 | GTTAAGACTGATCGGGTTCTG | 1023 | VKTDRVL | 0.51183 |
| 942 | GTCAACAGCCACGAAAGAGCC | 1024 | VNSHERA | 0.573043 |
| 943 | GTCCAAGTCGCCATGAGAGCC | 1025 | VQVAMRA | 0.520831 |
| 944 | GTCAGCATCAGCGTCATGGGC | 1026 | VSISVMG | 0.510987 |
| 945 | GTGACGGGGGTTCGGATTGGG | 1027 | VTGVRIG | 0.75699 |
| 946 | TGGTCTGATCCTAGTGATCTG | 1028 | WSDPSDL | 0.59828 |
| 947 | TACCTCACCAGCGGCGGCTAC | 1029 | YLTSGGY | 0.538789 |
| 948 | TACCCCCACATGACCCACGAC | 1030 | YPHMTHD | 0.655794 |
| 949 | TATGTTAATAGTGCTCCGAAG | 1031 | YVNSAPK | 0.551681 |

The AAV capsids and AAV capsid proteins disclosed herein, in some embodiments, are isolated. In some instances, the AAV capsids and AAV capsid proteins disclosed herein are isolated and purified. In addition, the AAV capsids and AAV capsid proteins disclosed herein, either isolated and purified, or not, may be formulated into a pharmaceutical formulation, which in some cases, further comprises a pharmaceutically acceptable carrier.

B. Heterologous Nucleic Acids

Disclosed herein are therapeutic nucleic acids useful for the treatment or prevention of a disease or condition, or symptom of the disease or condition, disclosed herein. In some embodiments, the therapeutic nucleic acids encode a therapeutic gene expression product. Non-limiting examples of gene expression products include proteins, polypeptides, peptides, enzymes, antibodies, antigen binding fragments, nucleic acid (RNA, DNA, antisense oligonucleotide, siRNA, and the like), and gene editing components, for use in the treatment, prophylaxis, and/or amelioration of the disease or disorder, or symptoms of the disease or disorder. In some instances, the therapeutic nucleic acids are placed in an organism, cell, tissue or organ of a subject by way of a rAAV, such as those disclosed herein.

Disclosed herein are rAAVs, each comprising a viral vector (e.g., a single stranded DNA molecule (ssDNA)). In some instances, the viral vector comprises two inverted terminal repeat (ITR) sequences that are about 145 bases each, flanking a transgene. In some embodiments, the transgene comprises a therapeutic nucleic acid, and in some cases, a promoter in cis with the therapeutic nucleic acid in an open reading frame (ORF). The promoter is capable of initiating transcription of therapeutic nucleic acid in the nucleus of the target cell. The ITR sequences can be from any AAV serotype. Non-limiting examples of AAV serotypes include AV1, AAV2, AAV3, AAV4, AAV5, AAV6, AAV7, AAV8, AAV9, AAV10, AAV11, and AAV12. In some cases, an ITR is from AAV2. In some cases, an ITR is from AAV9.

Disclosed herein are transgenes that can comprise any number of nucleotides. In some cases, a transgene can comprise less than about 100 nucleotides. In some cases, a transgene can comprise at least about 100 nucleotides. In some cases, a transgene can comprise at least about 200 nucleotides. In some cases, a transgene can comprise at least about 300 nucleotides. In some cases, a transgene can comprise at least about 400 nucleotides. In some cases, a transgene can comprise at least about 500 nucleotides. In some cases, a transgene can comprise at least about 1000 nucleotides. In some cases, a transgene can comprise at least about 5000 nucleotides. In some cases, a transgene can comprise at least about 10,000 nucleotides. In some cases, a transgene can comprise at least about 20,000 nucleotides. In some cases, a transgene can comprise at least about 30,000 nucleotides. In some cases, a transgene can comprise at least about 40,000 nucleotides. In some cases, a transgene can comprise at least about 50,000 nucleotides. In some cases, a transgene can comprise between about 500 and about 5000 nucleotides. In some cases, a transgene can comprise between about 5000 and about 10,000 nucleotides. In any of the cases disclosed herein, the transgene can comprise DNA, RNA, or a hybrid of DNA and RNA. In some cases, the transgene can be single stranded. In some cases, the transgene can be double stranded.

Disclosed herein are transgenes useful for modulating the expression or activity of a target gene or gene expression product thereof. In some instances, the transgene is encapsidated by an rAAV capsid protein of an rAAV particle described herein. In some instances, the rAAV particle is delivered to a subject to treat a disease or condition disclosed herein in the subject. In some instances, the delivery is systemic (e.g., intravenous, intranasal).

The transgenes disclosed herein are useful for expressing an endogenous gene at a level similar to that of a healthy or normal individual. This is particularly useful in the treatment of a disease or condition related to the underexpression, or lack of expression, of a gene expression product. In some embodiments, the transgenes disclosed herein are useful for overexpressing an endogenous gene, such that an expression level of the endogenous gene is above the expression level of a healthy or normal individual. Additionally, transgenes can be used to express exogenous genes (e.g., active agent such as an antibody, peptide, nucleic acid, or gene editing components). In some embodiments, the therapeutic gene expression product is capable of altering, enhancing, increasing, or inducing the activity of one or more endogenous biological processes in the cell. In some embodiments, the transgenes disclosed herein are useful for reducing expressing an endogenous gene, example, a dominant negative gene. In some embodiments, the therapeutic gene expression product is capable of altering, inhibiting, reducing, preventing, eliminating, or impairing the activity of one or more endogenous biological processes in the cell. In some aspects, the increase of gene expression refers to an increase by at least about 20%, 30%, 40%, 50%, 60%, 70%, 80%, 85%, 90%, 95% and 100%. In one aspect, the protein product of the targeted gene may be increased by at least about 20%, 30%, 40%, 50%, 60%, 70%, 80%, 85%, 90%, 95% and 100%. In some aspects, the decrease of gene expression refers to an increase by at least about 20%, 30%, 40%, 50%, 60%, 70%, 80%, 85%, 90%, 95% and 100%. In one aspect, the protein product of the targeted gene may be decreased by at least about 20%, 30%, 40%, 50%, 60%, 70%, 80%, 85%, 90%, 95% and 100%.

When endogenous sequences (endogenous or part of a transgene) are expressed with a transgene, the endogenous sequences can be full-length sequences (wild-type or mutant) or partial sequences. The endogenous sequences can be functional. Non-limiting examples of the function of these full length or partial sequences include increasing the serum half-life of the polypeptide expressed by a transgene (e.g., therapeutic gene) and/or acting as a carrier.

A transgene can be inserted into an endogenous gene such that all, some or none of the endogenous gene is expressed. For example, a transgene as described herein can be inserted into an endogenous locus such that some (N-terminal and/or C-terminal to a transgene) or none of the endogenous sequences are expressed, for example as a fusion with a transgene. In other cases, a transgene (e.g., with or without additional coding sequences of the endogenous gene) is integrated into any endogenous locus, for example a safe-harbor locus. For example, a Frataxin (FXN) transgene can be inserted into an endogenous FXN gene. A transgene can be inserted into any gene, e.g., the genes as described herein.

At least one advantage of the present disclosure is that virtually any therapeutic nucleic acid may be used to express any therapeutic gene expression product. In some instances, the therapeutic gene expression product is a therapeutic protein or a peptide (e.g., antibody, antigen-binding fragment, peptide, or protein). In one embodiment the protein encoded by the therapeutic nucleic acid is between 50-5000 amino acids in length. In some embodiments the protein encoded is between 50-2000 amino acids in length. In some embodiments the protein encoded is between 50-1000 amino acids in length. In some embodiments the protein encoded is between 50-1500 amino acids in length. In some embodiments the protein encoded is between 50-800 amino acids in length. In some embodiments the protein encoded is between 50-600 amino acids in length. In some embodiments the protein encoded is between 50-400 amino acids in length. In some embodiments the protein encoded is between 50-200 amino acids in length. In some embodiments the protein encoded is between 50-100 amino acids in length. In some embodiments the peptide encoded is between 4-50 amino acids in length. In some embodiments, the protein encoded is a tetrapeptide, a pentapeptide, a hexapeptide, a heptapeptide, an octapeptide, a nonapeptide, or a decapeptide. In some embodiments, the protein encoded comprises a peptide of 2-30 amino acids, such as for example 5-30, 10-30, 2-25, 5-25, 10-25, or 10-20 amino acids. In some embodiments, the protein encoded comprises a peptide of at least 11, 12, 13, 14, 15, 17, 20, 25 or 30 amino acids, or a peptide that is no longer than 50 amino acids, e.g. no longer than 35, 30, 25, 20, 17, 15, 14, 13, 12, 11 or 10 amino acids.

Non-limiting examples of therapeutic protein or peptides include an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphoring, a semaphorin receptor, a serotonin transport protein, a serotonin uptake inhibitor, a serotonin receptor, a serpin, a serpin receptor, and a tumor suppressor. In certain embodiments, the therapeutic protein or peptide is selected from the group consisting of brain-derived neurotrophic factor (BDNF), ciliary neurotrophic factor (CNTF), macrophage colony-stimulating factor (CSF), epidermal growth factor (EGF), fibroblast growth factor (FGF), gonadotropin, interferon-gamma (IFN), insulin-like growth factor 1 (IFG-1), nerve growth factor (NGF), platelet-derived growth factor (PDGF), pigment epithelium-derived factor (PEDF), transforming growth factor (TGF), transforming growth factor-beta (TGF-B), tumor necrosis factor (TNF), vascular endothelial growth factor (VEGF), prolactin, somatotropin, X-linked inhibitor of apoptosis protein 1 (XIAP1), interleukin 1 (IL-1), IL-2, IL-3, IL-4, IL-5, IL-6, IL-7, IL-8, IL-9, IL-10, IL-10, viral IL-10, IL-11, IL-12, IL-13, IL-14, IL-15, IL-16, IL-17, and IL-18.

A therapeutic gene expression product can comprise gene editing components. Non-limiting examples of gene editing components include those required for CRISPR/Cas, artificial site-specific RNA endonuclease (ASRE), zinc finger endonuclease (ZFN), and transcription factor like effector nuclease (TALEN). In a non-limiting example, a subject having Huntington's disease is identified. The subject is then systemically administered a first amount of a rAAV encapsidating a viral vector encoding ZFN engineered to represses the transcription of the Huntingtin (HTT) gene. In some instances, the route of administration is intravenous. The rAAV will include a modified AAV capsid protein that includes an amino acid sequence provided in any one of Tables 2-3, or FIG. 33, so as to allow proper targeting of the ZFN to the nervous system, while retargeting off-target organs, such as the liver. If needed, the subject is administered a second or third dose of the rAAV, until a therapeutically effective amount of the ZFN is expressed in the subject's nervous system. In another non-limiting example, a subject with cystic fibrosis is identified. The subject is then systemically administered a first amount of a rAAV encapsidating a viral vector encoding ZFN engineered to represses the transcription of the cystic fibrosis transmembrane conductance regulator (CFTR) gene. In some instances, the route of administration is intranasal (e.g., intranasal spray). The rAAV will include a modified AAV capsid protein that includes an amino acid sequence provided in FIG. 33 or Tables 2-3, so as to allow proper targeting of the ZFN to the lung. If needed, the subject is administered a second or third dose of the rAAV, until a therapeutically effective amount of the ZFN is expressed in the subject's lung.

A therapeutic nucleic acid can comprise a non-protein coding gene e.g., sequences encoding antisense RNAs, RNAi, shRNAs and micro RNAs (miRNAs), miRNA sponges or decoys, recombinase delivery for conditional gene deletion, conditional (recombinase-dependent) expression, includes those required for the gene editing components described herein. The non-protein coding gene may also encode a tRNA, rRNA, tmRNA, piRNA, double stranded RNA, snRNA, snoRNA, and/or long non-coding RNA (lncRNA). In some cases, the non-protein coding gene can modulate the expression or the activity of a target gene or gene expression product. For example, the RNAs described herein may be used to inhibit gene expression in a target cell, for example, a cell in the central nervous system (CNS) or peripheral organ (e.g., lung). In some cases, inhibition of gene expression refers to an inhibition by at least about 20%, 30%, 40%, 50%, 60%, 70%, 80%, 85%, 90%, 95% and 100%. In some cases, the protein product of the targeted gene may be inhibited by at least about 20%, 30%, 40%, 50%, 60%, 70%, 80%, 85%, 90%, 95% and 100%. The gene can be either a wild type gene or a gene with at least one mutation. The targeted protein may be either a wild type protein or a protein with at least one mutation.

A therapeutic nucleic acid can modulate the expression or activity of a gene or gene expression product expressed from the gene that is implicated in disease or disorder of the brain. For example, the therapeutic nucleic acid, in some cases is a gene or a modified version of the gene described herein. In another example, the therapeutic nucleic acid comprises an effector gene expression product such as a gene editing component specific to target a gene therein. Non-limited examples of genes include Sarcoglycan Alpha (SGCA), glutamic acid decarboxylase 65 (GAD65), glutamic acid decarboxylase 67 (GAD67), CLN2 gene, Nerve Growth Factor (NGF), glial cell derived neurotrophic factor (GDNF), Neurturin, Survival Of Motor Neuron 1, Telomeric (SMN1), β-Glucocerebrosidase (GCase), Frataxin (FXN), Huntingtin (HTN), methyl-CpG binding protein 2 (MECP2), peroxisomal biogenesis factor (PEX), progranulin (GRN), an antitubulin agent, copper-zinc superoxide dismutase (SOD1), Glucosylceramidase Beta (GBA), NPC Intracellular Cholesterol Transporter 1 (NPC1), and NPS3. In some embodiments, the peroxisomal biogenesis factor (PEX) is selected from the group consisting of PEX1, PEX2, PEX3, PEX4, PEX5, PEX6, PEX7, PEX10, PEX11(3, PEX12, PEX13, PEX14, PEX16, PEX19, and PEX26. In some instances, the gene or gene expression product is inhibited. In some instances, the gene or gene expression product is enhanced.

A therapeutic nucleic acid modulates expression or activity of a gene or gene expression product expressed from the gene that is implicated in disease or disorder of a particular organ (e.g., lung, heart, liver, muscle, eye). Non-limited examples of genes include Cystic Fibrosis Transmembrane Conductance Regulator (CFTR), Factor X (FIX), RPE65, Retinoid Isomerohydrolase (RPE65), Sarcoglycan Alpha (SGCA), and sarco/endoplasmic reticulum Ca2+-ATPase (SERCA2a). In some embodiments, the therapeutic gene expression product is of human, murine, avian, porcine, bovine, ovine, feline, canine, equine, epine, caprine, lupine or primate origin. In some instances, the gene or gene expression product is inhibited. In some instances, the gene or gene expression product is enhanced.

C. AAV Vectors

Disclosed herein are adeno-associated virus (AAV) vectors comprising genetic information. AAV vectors described herein are useful for the assembly of a rAAV and viral packaging of a heterologous nucleic acid. In addition, an AAV vector may encode a transgene comprising the heterologous nucleic acid. In some instances, the AAV vector is from an AAV serotypes selected from the group consisting of AV1, AAV2, AAV3, AAV4, AAV5, AAV6, AAV7, AAV8, AAV9, AAV10, AAV11, and AAV12. In some instances, the AAV vector is selected from a modified AAV serotype selected from the group consisting of AAV-PHP.B, AAV-PHP.eB, and AAV-PHP.S.

An AAV vector can comprise a transgene, which in some cases encodes a heterologous gene expression product (e.g., therapeutic gene expression product, recombinant capsid protein, and the like). The transgene is in cis with two inverted terminal repeats (ITRs) flanking the transgene. The transgene may comprise a therapeutic nucleic acid encoding a therapeutic gene expression product. Due to the limited packaging capacity of the rAAV (~2.5 kB), in some cases, a longer transgene may be split between two AAV vectors, the first with 3' splice donor and the second with a 5' splice acceptor. Upon co-infection of a cell, concatemers form, which are spliced together to express a full-length transgene.

A transgene is generally inserted so that its expression is driven by the endogenous promoter at the integration site, namely the promoter that drives expression of the endogenous gene into which a transgene is inserted. In some instances, a transgene comprises a promoter and/or enhancer, for example a constitutive promoter or an inducible or tissue/cell specific promoter. As a non-limiting example, the promoter may be CMV promoter, a CMV-β-Actin-intron-β-Globin hybrid promoter (CAG), CBA promoter, FRDA or FXN promoter, UBC promoter, GUSB promoter, NSE promoter, Synapsin promoter, MeCP2 promoter, GFAP promoter, H1 promoter, U6 promoter, NFL promoter, NFH promoter, SCN8A promoter, or PGK promoter. As a non-limiting example, promoters can be tissue-specific expression elements include, but are not limited to, human elongation factor 1α-subunit (EF1α), immediate-early cytomegalovirus (CMV), chicken β-actin (CBA) and its derivative CAG, the β glucuronidase (GUSB), and ubiquitin C (UBC). The transgene may include a tissue-specific expression elements for neurons such as, but not limited to, neuron-specific enolase (NSE), platelet-derived growth factor (PDGF), platelet-derived growth factor B-chain (PDGF-β), the synapsin (Syn), the methyl-CpG binding protein 2 (MeCP2), Ca2+/calmodulin-dependent protein kinase II (CaMKII), metabotropic glutamate receptor 2 (mGluR2), NFL, NFH, np32, PPE, Enk and EAAT2 promoters. The transgene may comprise a tissue-specific expression element for astrocytes such as, but not limited to, the glial fibrillary acidic protein (GFAP) and EAAT2 promoters. The transgene may comprise tissue-specific expression elements for oligo-dendrocytes such as, but not limited to, the myelin basic protein (MBP) promoter.

In some embodiments, the promoter is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. The promoter may provide expression of the therapeutic gene expression product for a period of time in targeted tissues such as, but not limited to, the central nervous system and peripheral organs (e.g., lung). Expression of the therapeutic gene expression product may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years. Expression of the payload may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years or 10-15 years, or 15-20 years, or 20-25 years, or 25-30 years, or 30-35 years, or 35-40 years, or 40-45 years, or 45-50 years, or 50-55 years, or 55-60 years, or 60-65 years.

An AAV vector can comprise a genome of a helper virus. Helper virus proteins are required for the assembly of a recombinant AAV (rAAV), and packaging of a transgene containing a heterologous nucleic acid into the rAAV. The helper virus genes are adenovirus genes E4, E2a and VA, that when expressed in the cell, assist with AAV replication. In some embodiments, an AAV vector comprises E2. In some embodiments, an AAV vector comprises E4. In some embodiments, an AAV vector comprises VA. In some instances, the AAV vector comprises one of helper virus proteins, or any combination.

An AAV vector can comprise a viral genome comprising a nucleic acid encoding the recombinant AAV (rAAV) capsid protein described herein. The viral genome can comprise a Replication (Rep) gene encoding a Rep protein, and Capsid (Cap) gene encoding an AAP protein in the first open reading frame (ORF1) or a Cap protein in the second open reading frame (ORF2). The Rep protein is selected from the group consisting of Rep78, Rep68, Rep52, and Rep40. In some instances, the Cap gene is modified encoding a modified AAV capsid protein described herein. A wild-type Cap gene encodes three proteins, VP1, VP2, and VP3. In some cases, VP1 is modified. In some cases, VP2 is modified. In some cases, VP3 is modified. In some cases, all three VP1-VP3 are modified. The AAV vector can comprise nucleic acids encoding wild-type Rep78, Rep68, Rep52, Rep40 and AAP proteins.

Disclosed herein are AAV vectors comprising any one of SEQ ID NOS: 10-434, 860-863, 868-949, 1068-5661, 14841-14880, and 14961-15053 which are the DNA sequences encoding modified portions of AAV capsid proteins of the present disclosure. In some instances, the AAV vector comprises a nucleic acid sequences provided in any one of SEQ ID NOS: 10-434 and 868-949, encoding 7-mer modified AAV capsid protein portions. The AAV vector of the present disclosure can comprise the VP1 Cap gene comprises any one of SEQ ID NOS: 6-9 provided in Table 5. An AAV vector can comprise 70%, 75%, 80%, 85%, 90%, 91%, 92%, 93%, 94%, 95%, 96%, 97%, 98%, 99%, or 100% of any one of SEQ ID NOS: 6-9.

In some instances, the AAV9 VP1 gene provided in SEQ ID NO: 6, which is provided in Table 5, is modified to include any one of SEQ ID NOS: 10-434, 860-863, 868-949, 1068-5661, 14841-14880, and 14961-15053. In some instances, the AAV-PHP.eB VP1 (SEQ ID NO: 9), which is also provided in Table 5 is modified to include any one of SEQ ID NOS: 10-434, 860-863, 868-949, 1068-5661, 14841-14880, and 14961-15053. The AAV vector described herein may be used to produce a variant AAV capsid by the methods described herein.

TABLE 5

| VP1 Capsid Protein Nucleic Acid Sequences | | |
|---|---|---|
| SEQ ID NO: | Identifier | Sequence |
| 6 | AAV9 >AY530579.1 Adeno- associated virus 9 isolate hu.14 capsid protein VP1 (cap) gene, complete cds | ATGGCTGCCGATGGTTATCTTCCAGATTGGCTCGAGGACAA CCTTAGTGAAGGAATTCGCGAGTGGTGGGCTTTGAAACCTG GAGCCCCTCAACCCAAGGCAAATCAACAACATCAAGACAA CGCTCGAGGTCTTGTGCTTCCGGGTTACAAATACCTTGGACC CGGCAACGGACTCGACAAGGGGGAGCCGGTCAACGCAGCA GACGCGGCGGCCCTCGAGCACGACAAGGCCTACGACCAGC AGCTCAAGGCCGGAGACAACCCGTACCTCAAGTACAACCAC GCCGACGCCGAGTTCCAGGAGCGGCTCAAAGAAGATACGTC TTTTGGGGGCAACCTCGGGCGAGCAGTCTTCCAGGCCAAAA AGAGGCTTCTTGAACCTCTTGGTCTGGTTGAGGAAGCGGCT AAGACGGCTCCTGGAAAGAAGAGGCCTGTAGAGCAGTCTCC TCAGGAACCGGACTCCTCCGCGGGTATTGGCAAATCGGGTG CACAGCCCGCTAAAAAGAGACTCAATTTCGGTCAGACTGGC GACACAGAGTCAGTCCCAGACCCTCAACCAATCGGAGAACC TCCCGCAGCCCCTCAGGTGTGGGATCTCTTACAATGGCTTC AGGTGGTGGCGCACCAGTGGCAGACAATAACGAAGGTGCC GATGGAGTGGGTAGTTCCTCGGGAAATTGGCATTGCGATTC CCAATGGCTGGGGGACAGAGTCATCACCACCAGCACCCGAA CCTGGGCCCTGCCCACCTACAACAATCACCTCTACAAGCAA ATCTCCAACAGCACATCTGGAGGATCTTCAAATGACAACGC CTACTTCGGCTACAGCACCCCCTGGGGGTATTTTGACTTCAA CAGATTCCACTGCCACTTCTCACCACGTGACTGGCAGCGAC TCATCAACAACAACTGGGGATTCCGGCCTAAGCGACTCAAC TTCAAGCTCTTCAACATTCAGGTCAAAGAGGTTACGGACAA CAATGGAGTCAAGACCATCGCCAATAACCTTACCAGCACGG TCCAGGTCTTCACGGACTCAGACTATCAGCTCCCGTACGTGC TCGGGTCGGCTCACGAGGGCTGCCTCCCGCCGTTCCCAGCG GACGTTTTCATGATTCCTCAGTACGGGTATCTGACGCTTAAT GATGGAAGCCAGGCCGTGGGTCGTTCGTCCTTTTACTGCCT GGAATATTTCCCGTCGCAAATGCTAAGAACGGGTAACAACT TCCAGTTCAGCTACGAGTTTGAGAACGTACCTTTCCATAGCA GCTACGCTCACAGCCAAAGCCTGGACCGACTAATGAATCCA CTCATCGACCAATACTTGTACTATCTCTCAAAGACTATTAAC GGTTCTGGACAGAATCAACAAACGCTAAAATTCAGTGTGGC CGGACCCAGCAACATGGCTGTCCAGGGAAGAAACTACATAC CTGGACCCAGCTACCGACAACAACGTGTCTCAACCACTGTG ACTCAAAACAACAACAGCGAATTTGCTTGGCCTGGAGCTTC TTCTTGGGCTCTCAATGGACGTAATAGCTTGATGAATCCTGG ACCTGCTATGGCCAGCCACAAAGAAGGAGAGGACCGTTTCT TTCCTTTGTCTGGATCTTTAATTTTTGGCAAACAAGGAACTG GAAGAGACAACGTGGATGCGGACAAAGTCATGATAACCAA CGAAGAAGAAATTAAAACTACTAACCCGGTAGCAACGGAG TCCTATGGACAAGTGGCCACAAACCACCAGAGTGCCCAAGC ACAGGCGCAGACCGGCTGGGTTCAAAACCAAGGAATACTTC CGGGTATGGTTTGGCAGGACAGAGATGTGTACCTGCAAGGA CCCATTTGGGCCAAAATTCCTCACACGGACGGCAACTTTCA CCCTTCTCCGCTGATGGGAGGGTTTGGAATGAAGCACCCGC CTCCTCAGATCCTCATCAAAAACACACCTGTACCTGCGGAT CCTCCAACGGCCTTCAACAAGGACAAGCTGAACTCTTTCAT CACCCAGTATTCTACTGGCCAAGTCAGCGTGGAGATCGAGT GGGGAGCTGCAGAAGGAAAACAGCAAGCGCTGGAACCCGGA GATCCAGTACACTTCCAACTATTACAAGTCTAATAATGTTGA ATTTGCTGTTAATACTGAAGGTGTATATAGTGAACCCCGCCC CATTGGCACCAGATACCTGACTCGTAATCTGTAA |
| 7 | AAV- PHP.B | ATGGCTGCCG ATGGTTATCT TCCAGATTGG CTCGAGGACA ACCTTAGTGAAGGAATTCGC GAGTGGTGGG CTTTGAAACC TGGAGCCCCT CAACCCAAGGCAAATCAACA ACATCAAGAC AACGCTCGAG GTCTTGTGCT TCCGGGTTACAAATACCTTG GACCCGGCAA CGGACTCGAC AAGGGGGAGC GGTCAACGC AGCAGACGCG GCGGCCCTCG AGCACGACAA GCCTACGAC CAGCAGCTCAAGGCCGGAGA CAACCCGTAC CTCAAGTACA ACCACGCCGA CGCCGAGTTCCAGGAGCGGC TCAAAGAAGA TACGTCTTTT GGGGGCAACC TCGGGCGAGCAGTCTTCCAG GCCAAAAAGA GGCTTCTTGA ACCTCTTGGT CTGGTTGAGG AAGCGGCTAA GACGGCTCCT GGAAAGAAGA GGCCTGTAGA GCAGTCTCCTCAGGAACCGG ACTCCTCCGC GGGTATTGGC AAATCGGGTG CACAGCCCGCTAAAAAGAGA CTCAATTTCG GTCAGACTGG CGACACAGAG TCAGTCCCAGACCCTCAACC AATCGGAGAA CCTCCCGCAG CCCCCTCAGG TGTGGGATCT CTTACAATGG CTTCAGGTGG TGGCGCACCA GTGGCAGACA ATAACGAAGGTGCCGATGGA GTGGGTAGTT CCTCGGGAAA TTGGCATTGC GATTCCCAATGGCTGGGGGA CAGAGTCATC ACCACCAGCA CCCGAACCTG GCCCTGCCCACCTACAACA ATCACCTCTA |

TABLE 5-continued

| SEQ ID NO: | Identifier | Sequence |
|---|---|---|
| | | CAAGCAAATC TCCAACAGCA CATCTGGAGG |
| | | ATCTTCAAAT GACAACGCCT ACTTCGGCTA CAGCACCCCC |
| | | TGGGGGTATTTTGACTTCAA CAGATTCCAC TGCCACTTCT |
| | | CACCACGTGA CTGGCAGCGACTCATCAACA ACAACTGGGG |
| | | ATTCCGGCCT AAGCGACTCA ACTTCAAGCTCTTCAACATT |
| | | CAGGTCAAAG AGGTTACGGA CAACAATGGA |
| | | GTCAAGACCA TCGCCAATAA CCTTACCAGC ACGGTCCAGG |
| | | TCTTCACGGA CTCAGACTATCAGCTCCCGT ACGTGCTCGG |
| | | GTCGGCTCAC GAGGGCTGCC TCCCGCCGTTCCCAGCGGAC |
| | | GTTTTCATGA TTCCTCAGTA CGGGTATCTG |
| | | ACGCTTAATGATGGAAGCCA GGCCGTGGGT CGTTCGTCCT |
| | | TTTACTGCCT GGAATATTTC CCGTCGCAAA TGCTAAGAAC |
| | | GGGTAACAAC TTCCAGTTCA GCTACGAGTTTGAGAACGTA |
| | | CCTTTCCATA GCAGCTACGC TCACAGCCAA |
| | | AGCCTGGACCGACTAATGAA TCCACTCATC GACCAATACT |
| | | TGTACTATCT CTCTAGAACT ATTAACGGTT CTGGACAGAA |
| | | TCAACAAACG CTAAAATTCA GTGTGGCCGG |
| | | ACCCAGCAAC ATGGCTGTCC AGGGAAGAAA CTACATACCT |
| | | GGACCCAGCTACCGACAACA ACGTGTCTCA ACCACTGTGA |
| | | CTCAAAACAA CAACAGCGAATTTGCTTGGC CTGGAGCTTC |
| | | TTCTTGGGCT CTCAATGGAC GTAATAGCTT GATGAATCCT |
| | | GGACCTGCTA TGGCCAGCCA CAAAGAAGGA |
| | | GAGGACCGTTTCTTTCCTTT GTCTGGATCT TTAATTTTTG |
| | | GCAAACAAGG TACCGGCAGAGACAACGTGG |
| | | ATGCGGACAA AGTCATGATA ACCAACGAAG |
| | | AAGAAATTAAAACTACTAAC CCGGTAGCAA CGGAGTCCTA |
| | | TGGACAAGTG GCCACAAACCACCAGAGTGC CCAAACTTTG |
| | | GCGGTGCCTT TTAAGGCACA GGCGCAGACCGGTTGGGTTC |
| | | AAAACCAAGG AATACTTCCG GGTATGGTTT |
| | | GGCAGGACAGAGATGTGTAC CTGCAAGGAC CCATTTGGGC |
| | | CAAAATTCCT CACACGGACG GCAACTTTCA CCCTTCTCCG |
| | | CTGATGGGAG GGTTTGGAAT GAAGCACCCGCCTCCTCAGA |
| | | TCCTCATCAA AAACACACCT GTACCTGCGG |
| | | ATCCTCCAACGGCCTTCAAC AAGGACAAGC TGAACTCTTT |
| | | CATCACCCAG TATTCTACTGGCCAAGTCAG CGTGGAGATC |
| | | GAGTGGGAGC TGCAGAAGGA AAACAGCAAG |
| | | CGCTGGAACC CGGAGATCCA GTACACTTCC AACTATTACA |
| | | AGTCTAATAATGTTGAATTT GCTGTTAATA CTGAAGGTGT |
| | | ATATAGTGAA CCCCGCCCCATTGGCACCAG ATACCTGACT |
| | | CGTAATCTGT AA |
| 8 | AAV-PHP.S | ATGGCTGCCGATGGTTATCTTCCAGATTGGCTCGAGGACAA |
| | | CCTTAGTGAAGGAATTCGCGAGTGGTGGGCTTTGAAACCTG |
| | | GAGCCCCTCAACCCAAGGCAAATCAACAACATCAAGACAA |
| | | CGCTCGAGGTCTTGTGCTTCCGGGTTACAAATACCTTGGACC |
| | | CGGCAACGGACTCGACAAGGGGGAGCCGGTCAACGCAGCA |
| | | GACGCGGCGGCCCTCGAGCACGACAAGGCCTACGACCAGC |
| | | AGCTCAAGGCCGGAGACAACCCGTACCTCAAGTACAACCAC |
| | | GCCGACGCCGAGTTCCAGGAGCGGCTCAAAGAAGATACGTC |
| | | TTTTGGGGGCAACCTCGGGCGAGCAGTCTTCCAGGCCAAAA |
| | | AGAGGCTTCTTGAACCTCTTGGTCTGGTTGAGGAAGCGGCT |
| | | AAGACGGCTCCTGGAAAGAAGAGGCCTGTAGAGCAGTCTCC |
| | | TCAGGAACCGGACTCCTCCGCGGGTATTGGCAAATCGGGTG |
| | | CACGCCCGCTAAAAAGAGACTCAATTTCGGTCAGACTGGC |
| | | GACACAGAGTCAGTCCCAGACCCTCAACCAATCGGAGAACC |
| | | TCCCGCAGCCCCCTCAGGTGTGGGATCTCTTACAATGGCTTC |
| | | AGGTGGTGGCGCACCAGTGGCAGACAATAACGAAGGTGCC |
| | | GATGGAGTGGGTAGTTCCTCGGGAAATTGGCATTGCGATTC |
| | | CCAATGGCTGGGGGACAGAGTCATCACCACCAGCACCCGAA |
| | | CCTGGGCCCTGCCCACCTACAACAATCACCTCTACAAGCAA |
| | | ATCTCCAACAGCACATCTGGAGGATCTTCAAATGACAACGC |
| | | CTACTTCGGCTACAGCACCCCCTGGGGGTATTTTGACTTCAA |
| | | CAGATTCCACTGCCACTTCTCACCACGTGACTGGCAGCGAC |
| | | TCATCAACAACAACTGGGGATTCCGGCCTAAGCGACTCAAC |
| | | TTCAAGCTCTTCAACATTCAGGTCAAAGAGGTTACGGACAA |
| | | CAATGGAGTCAAGACCATCGCCAATAACCTTACCAGCACGG |
| | | TCCAGGTCTTCACGGACTCAGACTATCAGCTCCCGTACGTGC |
| | | TCGGGTCGGCTCACGAGGGCTGCCTCCCGCCGTTCCCAGCG |
| | | GACGTTTTCATGATTCCTCAGTACGGGTATCTGACGCTTAAT |
| | | GATGGAAGCCAGGCCGTGGGTCGTTCGTCCTTTTACTGCCTG |
| | | GAATATTTCCCGTCGCAAATGCTAAGAACGGGTAACAACTT |
| | | CCAGTTCAGCTACGAGTTTGAGAACGTACCTTTCCATAGCA |
| | | GCTACGCTCACAGCCAAAGCCTGGACCGACTAATGAATCCA |
| | | CTCATCGACCAATACTTGTACTATCTCTCAAAGACTATTAAC |
| | | GGTTCTGGACAGAATCAACAAACGCTAAAATTCAGTGTGGC |

TABLE 5-continued

| | VP1 Capsid Protein Nucleic Acid Sequences | |
|---|---|---|

| SEQ ID NO: | Identifier | Sequence |
|---|---|---|
| | | CGGACCCAGCAACATGGCTGTCCAGGGAAGAAACTACATAC CTGGACCCAGCTACCGACAACAACGTGTCTCAACCACTGTG ACTCAAAACAACAACAGCGAATTTGCTTGGCCTGGAGCTTC TTCTTGGGCTCTCAATGGACGTAATAGCTTGATGAATCCTGG ACCTGCTATGGCCAGCCACAAAGAAGGAGAGGACCGTTTCT TTCCTTTGTCTGGATCTTTAATTTTTGGCAAACAAGGAACTG GAAGAGACAACGTGGATGCGGACAAAGTCATGATAACCAA CGAAGAAGAAATTAAAACTACTAACCCGGTAGCAACGGAG TCCTATGGACAAGTGGCCACAAACCACCAGAGTGCCCAACA GGCGGTTAGGACGTCTTTGGCACAGGCGCAGACCGGCTGGG TTCAAAACCAAGGAATACTTCCGGGTATGGTTTGGCAGGAC AGAGATGTGTACCTGCAAGGACCCATTTGGGCCAAAATTCC TCACACGGACGGCAACTTTCACCCTTCTCCGCTGATGGGAG GGTTTGGAATGAAGCACCCGCCTCCTCAGATCCTCATCAAA AACACACCTGTACCTGCGGATCCTCCAACGGCCTTCAACAA GGACAAGCTGAACTCTTTCATCACCCAGTATTCTACTGGCCA AGTCAGCGTGGAGATCGAGTGGGAGCTGCAGAAGGAAAAC AGCAAGCGCTGGAACCCGGAGATCCAGTACACTTCCAACTA TTACAAGTCTAATAATGTTGAATTTGCTGTTAATACTGAAGG TGTATATAGTGAACCCCGCCCCATTGGCACCAGATACCTGA CTCGTAATCTGTAA |
| 9 | AAV-PHP.eB | ATGGCTGCCGATGGTTATCTTCCAGATTGGCTCGAGGACAA CCTTAGTGAAGGAATTCGCGAGTGGTGGGCTTTGAAACCTG GAGCCCCTCAACCCAAGGCAAATCAACAACATCAAGACAA CGCTCGAGGTCTTGTGCTTCCGGGTTACAAATACCTTGGACC CGGCAACGGACTCGACAAGGGGGAGCCGGTCAACGCAGCA GACGCGGCGGCCCTCGAGCACGACAAGGCCTACGACCAGC AGCTCAAGGCCGGAGACAACCCGTACCTCAAGTACAACCAC GCCGACGCCGAGTTCCAGGAGCGGCTCAAAGAAGATACGTC TTTTGGGGGCAACCTCGGGCGAGCAGTCTTCCAGGCCAAAA AGAGGCTTCTTGAACCTCTTGGTCTGGTTGAGGAAGCGGCT AAGACGGCTCCTGGAAAGAAGAGGCCTGTAGAGCAGTCTCC TCAGGAACCGGACTCCTCCGCGGGTATTGGCAAATCGGGTG CACAGCCCGCTAAAAAGAGACTCAATTTCGGTCAGACTGGC GACACAGAGTCAGTCCCAGACCCTCAACCAATCGGAGAACC TCCCGCAGCCCCCTCAGGTGTGGGATCTCTTACAATGGCTTC AGGTGGTGGCGCACCAGTGGCAGACAATAACGAAGGTGCC GATGGAGTGGGTAGTTCCTCGGGAAATTGGCATTGCGATTC CCAATGGCTGGGGGACAGAGTCATCACCACCAGCACCCGAA CCTGGGCCCTGCCCACCTACAACAATCACCTCTACAAGCAA ATCTCCAACAGCACATCTGGAGGATCTTCAAATGACAACGC CTACTTCGGCTACAGCACCCCCTGGGGGTATTTTGACTTCAA CAGATTCCACTGCCACTTCTCACCACGTGACTGGCAGCGAC TCATCAACAACAACTGGGGATTCCGGCCTAAGCGACTCAAC TTCAAGCTCTTCAACATTCAGGTCAAAGAGGTTACGGACAA CAATGGAGTCAAGACCATCGCCAATAACCTTACCAGCACGG TCCAGGTCTTCACGGACTCAGACTATCAGCTCCCGTACGTGC TCGGGTCGGCTCACGAGGGCTGCCTCCCGCCGTTCCCAGCG GACGTTTTCATGATTCCTCAGTACGGGTATCTGACGCTTAAT GATGGAAGCCAGGCCGTGGGTCGTTCGTCCTTTTACTGCCTG GAATATTTCCCGTCGCAAATGCTAAGAACGGGTAACAACTT CCAGTTCAGCTACGAGTTTGAGAACGTACCTTTCCATAGCA GCTACGCTCACAGCCAAAGCCTGGACCGACTAATGAATCCA CTCATCGACCAATACTTGTACTATCTCTCTAGAACTATTAAC GGTTCTGGACAGAATCAACAAACGCTAAAATTCAGTGTGGC CGGACCCAGCAACATGGCTGTCCAGGGAAGAAACTACATAC CTGGACCCAGCTACCGACAACAACGTGTCTCAACCACTGTG ACTCAAAACAACAACAGCGAATTTGCTTGGCCTGGAGCTTC TTCTTGGGCTCTCAATGGACGTAATAGCTTGATGAATCCTGG ACCTGCTATGGCCAGCCACAAAGAAGGAGAGGACCGTTTCT TTCCTTTGTCTGGATCTTTAATTTTTGGCAAACAAGGTACCG GCAGAGACAACGTGGATGCGGACAAAGTCATGATAACCAA CGAAGAAGAAATTAAAACTACTAACCCGGTAGCAACGGAG TCCTATGGACAAGTGGCCACAAACCACCAGAGTGATGGGAC TTTGGCGGTGCCTTTTAAGGCACAGGCGCAGACCGGTTGG TTCAAAACCAAGGAATACTTCCGGGTATGGTTTGGCAGGAC AGAGATGTGTACCTGCAAGGACCCATTTGGGCCAAAATTCC TCACACGGACGGCAACTTTCACCCTTCTCCGCTGATGGGAG GGTTTGGAATGAAGCACCCGCCTCCTCAGATCCTCATCAAA AACACACCTGTACCTGCGGATCCTCCAACGGCCTTCAACAA GGACAAGCTGAACTCTTTCATCACCCAGTATTCTACTGGCCA AGTCAGCGTGGAGATCGAGTGGGAGCTGCAGAAGGAAAAC AGCAAGCGCTGGAACCCGGAGATCCAGTACACTTCCAACTA TTACAAGTCTAATAATGTTGAATTTGCTGTTAATACTGAAGG |

TABLE 5-continued

| VP1 Capsid Protein Nucleic Acid Sequences |
| --- |

```
SEQ
ID NO:  Identifier  Sequence

TGTATATAGTGAACCCCGCCCCATTGGCACCAGATACCTGA
                    CTCGTAATCTGTAA
```

II. Methods

A. Methods of Producing AAVs

Disclosed herein are methods of identifying a recombinant AAV (rAAV), such as those disclosed herein. The AAV peptide specific to target in vivo environments are identified using multiplexed Cre recombination-based AAV targeted evolution (M-CREATE). FIG. 1 provides a workflow using M-CREATE. M-CREATE uses an rAAV capsid genome (rAAV-Cap-in-cis-lox or rAAV-ΔCap-in-cis-lox2 as described in Example 2 below) that couples a full-length AAV Cap gene, controlled by regulatory elements from the AAV Rep gene, with a Cre-invertible switch. The rAAV-ΔCap-in-cis-lox2 backbone has a bi-directional polyA flanked by two Lox sites (lox71 and lox66). The ΔCap backbone is nonfunctional as it is missing a portion of the capsid gene. Upon insertion of a library fragment with mutagenesis at a specific site into the capsid, it then becomes a fully functional vector. In a cell expressing the Cre recombinase, the Cre-Lox recombination facilitates inversion of the polyA in addition to flipping the Lox sites to Lox72 and LoxP. (See FIGS. 1 and 36) The randomized 7-mer and 11-mers disclosed herein are generated using PCR, which are then inserted into the rAAV-ΔCap-in-cis-lox to generate virus libraries with randomized insertions or substitutions in the capsid protein sequence (e.g., at the AA588_589). (FIG. 1). In a first round of in vivo selection, the virus libraries are injected into the blood stream (e.g., intravenously) of transgenic animals expressing Cre recombinase. Tissues obtained from the transgenic animals following injection in in vivo environment (e.g., brain/liver). The inverted reporter expression cassette is detected using selective amplification expression of the reporter gene expression product. The rAAVs in the tissues are isolated and the viral genome around the insertion site is sequenced and aligned with an AAV9 template DNA fragment. The 7-mers and 11-mers that were recovered were enriched in the target in vivo environment, and were cloned into another rAAV-ΔCap-in-cis-lox2 backbone, and another round of in vivo selection is performed. The 7-mers and 11-mers enriched in the target in vivo environment, and negatively enriched in an off-target in vivo environment are sequenced using suitable methods, such as next generation sequencing. FIGS. 33-35 provide DNA sequences identified using the methods provided herein.

Methods comprise providing a rAAV genome comprising an AAV capsid gene, and a recognition sequence for a Cre recombinase. In some cases, the rAAV genome has two recognition sequences for Cre recombinase that flank a reporter expression cassette. The recognition sequences for Cre recombinase (e.g., LoxP) are oriented such that an inversion of the reporter cassette is facilitated in the presence of Cre recombinase in a cell. Methods comprise transfecting a population of cells expressing the Cre recombinase with the rAAV genome. The Cre recombinase induces an inversion (e.g., "flip" of the reporter gene into a genome of the transgenic animal). In some cases, the rate of inversion (e.g., a level of expression of the reporter gene in a target cell) may be measured using any suitable method, such as quantitative polymerase chain reaction, or immunohistochemistry. The level of expression of the reporter gene is compared to a reference value, which in some cases is the rate of inversion by a reference AAV (e.g., AAV9). Methods disclosed herein provide that an increase in the rate of inversion is detected in a target in vivo environment, as compared to the rate of inversion of a reference AAV. In some cases, a decrease in a rate of inversion is detected in an off-target cell, as compared to the rate of inversion of a reference AAV. The rAAV genome recovered using the methods described herein encodes for an AAV capsid particle (e.g., capsid protein, capsid) with an increased specificity for the target cell, and a decreased specificity for the off-target cell.

Disclosed herein are methods of producing a rAAV disclosed herein. In some instances, all elements that are required for AAV production in target cell (e.g., HEK293cells) are transiently transfected into the target cell using suitable methods known in the art. For example, the rAAV of the present disclosure can be product by co-transfecting three plasmid vectors, a first vector with ITR-containing plasmid carrying the transgene (e.g., therapeutic nucleic acid), a second vector that carries the AAV Rep and Cap genes; and (3), a third vector that provides the helper genes isolated from adenovirus. The methods described herein generate high-titer AAV vectors that are free of adenovirus. The Cap gene disclosed here comprises any one of SEQ ID NOS: 10-434, 860-863, 868-949, 1068-5661, 14841-14880, and 14961-15053 which are DNA sequences encoding the modified AAV capsid protein portions of the present disclosure. In some cases, rAAVs of the present disclosure are generated using the methods described in Challis, R. C. et al. Systemic AAV vectors for widespread and targeted gene delivery in rodents. Nat. Protoc. 14, 379 (2019), which is hereby incorporated by reference in its entirety. Briefly, triple transfection of HEK293T cells (ATCC) using polyethylenimine (PEI) is performed, viruses are collected after 120 hours from both cell lysates and media, and purified over iodixanol.

Disclosed herein, are methods comprising: (a) introducing into a cell a nucleic acid comprising: (1) a first nucleic acid sequence encoding a therapeutic gene expression product; (2) a second nucleic acid sequence encoding viral genome components comprising: (i) a Replication (Rep) gene encoding a Rep protein; and (ii) a modified capsid (Cap) gene encoding a modified AAV capsid protein described herein, and (3) a third nucleic acid sequence encoding a genome of an AAV helper virus; and (b) assembling a recombinant AAV (rAAV) capsid encapsidating the first nucleic acid, the rAAV capsid comprising a tropism with an increased specificity for a target in vivo environment in a subject and a decreased specificity for an off-target in vivo environment, relative to a tropism of a corresponding parental AAV capsid protein. In some instances, the methods further comprise packing the first nucleic acid sequence encoding the therapeutic gene expression product such that it becomes encapsidated by the modified AAV capsid protein. In some embodiments, the rAAV particles are isolated, concentrated, and purified using suitable viral purification methods, such as those described herein.

In a non-limiting example, the rAAVs are generated by triple transfection of precursor cells (e.g., HEK293T) cells using a standard transfection protocol (e.g., PEI). Viral particles are harvested from the media after a period of time (e.g., 72 h post transfection) and from the cells and media at a later point in time (e.g., 120 h post transfection). Virus present in the media is concentrated by precipitation with 8% poly(ethylene glycol) and 500 mM sodium chloride and the precipitated virus is added to the lysates prepared from the collected cells. The viruses are purified over iodixanol (Optiprep, Sigma) step gradients (15%, 25%, 40% and 60%). Viruses are concentrated and formulated in PBS. Virus titers are determined by measuring the number of DNaseI-resistant vector genome copies (VGs) using qPCR and the linearized genome plasmid as a control.

The Rep protein can be selected from the group consisting of Rep78, Rep68, Rep52, and Rep40. The genome of the AAV helper virus comprises an AAV helper gene selected from the group consisting of E2, E4, and VA. The second nucleic acid and the first nucleic acid can be in trans. The second nucleic acid and the first nucleic acid can be in cis.

The cell can be selected from a group consisting of a human, a primate, a murine, a feline, a canine, a porcine, an ovine, a bovine, an equine, an epine, a caprine and a lupine host cell. In some instances, the cell is a progenitor or precursor cell, such as a stem cell. In some instances, the stem cell is a mesenchymal cell, embryonic stem cell, induced pluripotent stem cell (iPSC), fibroblast or other tissue specific stem cell. The cell can be immortalized. In some cases, the immortalized cell is a HEK293cell. In some instances, the cell is a differentiated cell. Based on the disclosure provided, it is expected that this system can be used in conjunction with any transgenic line expressing a recombinase in the target cell type of interest to develop AAV capsids that more efficiently transduce that target cell population.

B. Methods of rAAV-Mediated Delivery of a Heterologous Nucleic Acid

Disclosed herein are methods of delivering a heterologous nucleic acid (e.g., therapeutic nucleic acid or transgene disclosed herein) to subject in need thereof. The transgene may be encapsidated by a recombinant AAV (rAAV) capsid protein or rAAV particle such as those described herein.

Methods may be ex vivo, e.g., scientific research purposes or for producing adoptive cellular therapies. The subject may be a human primary cell or a mature cell, or cell line. The subject may be a cell from a monkey, hamster, or mouse. In either case, delivery may include contacting the composition with the cell or cell line.

Methods may be in vivo, e.g., treating a disease or a condition in a subject in need thereof. In some instances, the subject may be mammal, such as a human or non-human primate, in which case delivery of the composition may comprise administering the composition to the subject. In some embodiments, delivery of the heterologous nucleic acid comprises administering to the subject the composition using any one of the routes of administration described herein.

In some embodiments, methods of increasing transduction of a heterologous nucleic acid in a target in vivo environment comprise delivering a rAAV particle described herein, the rAAV engineered to have an increased transduction efficiency in a target in vivo environment (e.g., tissue or cell type). In some instances, the increased transduction efficiency comprises a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 75-fold, or 100-fold increase, or more, relative to a reference AAV. In some instances, the increased transduction efficiency is at least 30-fold. In some instances, the increased transduction efficiency is at least 40-fold. In some instances, the increased transduction efficiency is at least 50-fold. In some instances, the increased transduction efficiency is at least 60-fold. In some instances, the increased transduction efficiency is at least 80-fold. In some instances, the increased transduction efficiency is at least 90-fold. In some instances, the increased transduction efficiency is at least 100-fold.

Methods of delivering a heterologous nucleic acid to a target in vivo environment are also provided comprising delivering the rAAV particle described herein that has been engineered to have an increased specificity in a target in vivo environment (e.g., tissue or cell type), as compared to a reference AAV. Methods, in some cases, comprise detecting whether a rAAV possesses more specificity for a target in vivo environment than a reference AAV, includes measuring a level of gene expression product (e.g., RNA or protein) expressed from the heterologous nucleic acid encapsidated by the rAAV in a tissue sample obtained from the target in vivo environment in a subject; and comparing the measured level to a control level (such as, for e.g., the gene expression product expressed from a heterologous nucleic acid encapsidated by a reference AAV (e.g., AAV9)). Suitable methods for measuring expression of a gene expression product luciferase reporter assay and quantitative polymerase chain reaction (qPCR).

In some instances, the reference AAV has a serotype selected from the group consisting of AAV1, AAV2, AAV3, AAV4, AAVS, AAV6, AAV7, AAV8, AAV9, AAV10, AAV11, AAV12, or variant thereof. For example, the reference AAV can have a serotype selected from the group consisting of AAV-PHP.B, AAV-PHP.eB, and AAV-PHP.S.

Delivery to the CNS

Provided herein are methods of delivering a heterologous nucleic acid to a target in vivo environment comprising delivering a composition to the target in vivo environment selected from the group consisting of a central nervous system (CNS) in a subject, the composition comprising a rAAV particle with a rAAV capsid protein, the rAAV capsid protein encapsidating a viral vector encoding a heterologous nucleic acid (e.g., therapeutic nucleic acid). In some embodiments, the rAAV particle encapsidating the heterologous nucleic acid comprises a rAAV capsid protein engineered with an increased specificity and, in some cases, transduction efficiency when measured in the CNS or the PNS of the subject, even when administered to the subject systemically, as compared to a reference AAV.

Methods comprise delivering a rAAV particle comprising an rAAV capsid protein with increased specificity and/or transduction efficiency when measured in the CNS in the subject, as compared to a reference AAV (e.g., AAV9). In some embodiments, delivery is systemic. Alternatively, delivery is direct (e.g., into the affected area of the CNS).

The rAAV capsid protein may comprise a substitution of at least one, two, three, four, five, six, seven, eight, nine, ten, or eleven amino acids provided in an amino acid sequence provided in any one of Tables 2-3, in an amino acid sequence of a parental AAV. In some instances, X1 is selected from the group consisting of A, E, D, G, R, S and T. In some instances, the insertion further comprises two amino acids, wherein X2 is selected from the group consisting of A, G, I, L, M, N, Q, R, T, and Y. In some instances, the insertion further comprises three amino acids, wherein X3 is selected from the group consisting of E, K, L, T, and Q. In some instances, the insertion further comprises at least four amino acids, wherein X1 is selected from the group consisting of A, E, D, G, R, S and T, X2 is selected from the group consisting of A, G, I, L, M, N, Q, R, T, and Y, X3 is selected from the group consisting of E, K, L, T, and Q, and X4 is selected from the group consisting of G, I, K, L, M, R, T, and V. In some instances, the insertion further comprises five amino acids wherein X5 is selected from the group consisting of A, D, G, P, L, Q, and V. In some instances, the insertion further comprises at least six amino acids, wherein X6 is selected from the group consisting of F, K, L, N, P, Q, S, and V. In some instances, the insertion further comprises at least seven amino acids, wherein X7 is selected from the group consisting of I, K, L, P, S, and V.

Disclosed herein are methods comprising delivering a rAAV particle encapsidating a heterologous nucleic acid to a CNS in a subject, the rAAV particle comprising (i) an increased specificity and/or transduction efficiency of the heterologous nucleic acid for the CNS, wherein the rAAV particle has an rAAV capsid protein comprising an insertion of at least or about three, four, five, six, or seven amino acids of an amino acid sequence TALKPFL, TTLKPFL, TLQIPFK, TMQKPFI, or RYQGDSV, or any amino acid sequence provided in Tables 2-3 or FIG. 33, at an amino acid position 588_589 in a parental AAV capsid protein. In some embodiments, the delivering is systemic. In some embodiments, the delivery is direct (e.g., injected into the in vivo environment). In some embodiments, the parental AAV capsid protein is AAV9 capsid protein (for e.g., provided in SEQ ID NO: 1). In some embodiments, delivery is more specific than a delivery of the heterologous nucleic acid by a reference AAV, e.g., AAV9. In some embodiments, the delivery is systemic (e.g., intravenous). In some embodiments, the subject is a mammal. In some embodiments, the subject is a human.

Delivery to the Liver

In some cases, the methods of delivering a heterologous nucleic acid comprise delivering to a target in vivo environment in a subject a composition, the composition comprising a rAAV particle with a rAAV capsid protein, the rAAV capsid protein encapsidating a viral vector encoding a heterologous nucleic acid (e.g., therapeutic nucleic acid). In some cases, the target in vivo environment is the liver. In some embodiments, the rAAV particle encapsidating the heterologous nucleic acid comprises a rAAV capsid protein engineered with an increased specificity and, in some cases, transduction efficiency when measured in the target in vivo environment of the subject, even when administered to the subject systemically.

In some embodiments, methods comprise delivering a rAAV particle comprising an rAAV capsid protein with increased specificity and/or transduction efficiency of the heterologous nucleic acid for the liver in the subject, as compared to a reference AAV (e.g., AAV9). In some embodiments, rAAVs optimized for targeting the liver have amino acid sequences that comprise an amino acid sequence provided in SEQ ID NOS: 950-1031 and 15054-15146 (FIG. 35).

The rAAV capsid protein suitable for delivery of the heterologous nucleic acid to the liver can comprise an insertion of at least one amino acid in a parental AAV capsid protein. In some instances, the insertion comprises at least one, two, three, four, five, six, seven, eight, nine, ten, or eleven amino acids provided in an amino acid sequence provided in Table 4, or FIG. 35.

Disclosed herein are methods comprising delivering a rAAV particle encapsidating a heterologous nucleic acid to the target in vivo environment selected from the group consisting of the liver in a subject, the rAAV particle comprising an increased specificity and/or transduction efficiency of the heterologous nucleic acid for the target in vivo environment, wherein the rAAV particle has an rAAV capsid protein comprising an insertion of at least or about three, four, five, six, seven, eight, nine, ten, or eleven amino acids of an amino acid sequence provided in Table 4, or FIG. 35. In some embodiments, delivery is more specific than a delivery of the heterologous nucleic acid by a reference AAV, e.g., AAV9. In some embodiments, methods further comprise reducing or ablating delivery of the heterologous nucleic acid in an off-target in vivo environment, such as the liver, compared to a reference AAV. In some embodiments, delivery is characterized by an increase in efficiency of transduction (e.g., of the heterologous nucleic acid) in the target in vivo environment than a transduction efficiency in the target in vivo environment of the reference AAV. In some embodiments, the delivery is systemic (e.g., intravenous). In some embodiments, the subject is a mammal. In some cases, the mammal is a human.

C. Methods of Treatment

Disclosed herein are methods of treating a disease or condition, or a symptom of the disease or condition, in a subject, comprising administrating of therapeutically effective amount of one or more compositions (e.g., rAAV particle, AAV vector, pharmaceutical composition) disclosed herein to the subject. In some embodiments, the composition is a rAAV capsid protein described herein. In some embodiments, the composition is an isolated and purified rAAV capsid protein described herein. In some embodiments, the rAAV particle encapsidates an AAV vector comprising a transgene (e.g., therapeutic nucleic acid). In some embodiments, the composition is a rAAV capsid protein described herein conjugated with a therapeutic agent disclosed herein. In some embodiments, the composition is a pharmaceutical composition comprising the rAAV particle and a pharmaceutically acceptable carrier. In some embodiments, the one or more compositions are administered to the subject alone (e.g., standalone therapy). In some embodiments, the one or more compositions are administered in combination with an additional agent. In some embodiments, the composition is a first-line therapy for the disease or condition. In some embodiments, the composition is a second-line, third-line, or fourth-line therapy, for the disease or condition.

Provided herein are methods of treating a disease or a condition, or a symptom of the disease or condition, in a subject, comprising: (a) diagnosing a subject with a disease or a condition affecting a target in vivo environment; and (b) treating the disease or the condition by administering to the subject a therapeutically effective amount of a composition disclosed herein (e.g., rAAV particle, AAV vector, pharmaceutical composition), wherein the composition is engineered with an increased specificity for the target in vivo environment.

Disclosed herein are methods of treating a disease or a condition, or a symptom of the disease or the condition, afflicting a target in vivo environment in a subject comprising: (a) administering to the subject a composition (e.g., rAAV particle, AAV vector, pharmaceutical composition); and (b) expressing the therapeutic nucleic acid into a target in vivo environment in the subject with an increased specificity and/or transduction efficiency, as compared to a reference AAV. In some cases, the reference AAV is AAV9, or a variant thereof.

Methods of treating a disease or condition affecting the central nervous system (CNS) comprise administering a rAAV particle to a CNS in a subject, the rAAV particle comprising an rAAV capsid protein comprising an insertion of at least or about three, four, five, six, seven, eight, nine, ten, or eleven amino acids of an amino acid sequence TALKPFL, TTLKPFL, TLQIPFK, TMQKPFI, RYQGDSV, or TTLKPFS, or any amino acid sequence provided in Tables 2-3, or FIG. 33, at an amino acid position 588_589 in a parental AAV capsid protein. In some cases, the insertion is not TLAVPFK, KFPVALT, SVSKPFL, FTLTTPK, MNATKNV, NGGTSSS, TRTNPEA, or YTLSQGW. In some embodiments, the parental AAV capsid protein is AAV9 capsid protein (for e.g., provided in SEQ ID NO: 1. In some instances, the parental AAV capsid protein comprises an amino acid sequence that is at least 95%, 96%, 96.1, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.7%, 98.8%, 98.9%, 99.0%, 99.1%, 99.2%, 99.3%, 99.4%, 99.5%, 99.6%, 99.7%, 99.8%, 99.9%, or 100.0% identical to SEQ ID NO: 1. In some embodiments, delivery is more specific than a delivery of the heterologous nucleic acid by a reference AAV, e.g., AAV9. In some embodiments, delivery is systemic (e.g., intravenous). In some embodiments, the subject is a human or a non-human primate.

Methods of treating a disease or a condition afflicting a target in vivo environment comprising a liver comprise administering a rAAV particle to the target in vivo environment in a subject, the rAAV particle comprising an rAAV capsid protein comprising a substitution of at least or about three, four, five, six, seven, eight, nine, ten, or eleven, amino acids of an amino acid sequence provided in any one of SEQ ID NOS: 950-1031 and 15054-15146 (FIG. 35). In some embodiments, methods comprise delivering a rAAV particle comprising an rAAV capsid protein with increased specificity for the liver in the subject, as compared to a reference AAV (e.g., AAV9). In some embodiments, rAAVs optimized for targeting the liver have amino acid sequences comprising an amino acid sequence KAYSVQV, PSGSARS, and RTANALG at an amino acid position 588_589 in a parental AAV capsid protein. In some embodiments, the parental AAV capsid protein is AAV9 capsid protein (for e.g., provided in SEQ ID NO: 1). In some instances, the parental AAV capsid protein comprises an amino acid sequence that is at least 95%, 96%, 96.1, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.7%, 98.8%, 98.9%, 99.0%, 99.1%, 99.2%, 99.3%, 99.4%, 99.5%, 99.6%, 99.7%, 99.8%, 99.9%, or 100.0% identical to SEQ ID NO: 1. In some embodiments, delivery is more specific than a delivery of the heterologous nucleic acid by a reference AAV, e.g., AAV9. In some embodiments, the delivery is systemic (e.g., intravenous or intranasal). In some embodiments, the subject is a human or a non-human primate.

Also provided are methods of modulating a target gene expression product, the methods comprising administering to a subject in need thereof a composition (e.g., rAAV particle, AAV vector, pharmaceutical composition) disclosed herein. For example, methods provided herein comprise administering to a subject a rAAV with a rAAV capsid protein encapsidating a viral vector comprising a heterologous nucleic acid that modulates the expression or the activity of the target gene expression product. In some embodiments, the disease or the condition is characterized by an increased or enhanced expression or activity of a gene or gene expression product thereof, as compared to a normal individual. In some cases, administering the therapeutically effective amount of the composition restores the expression or the activity of the gene or gene expression product thereof to a level that is typical in a normal individual. The term "normal individual" refers to an individual that is not afflicted with the disease or the condition characterized by the variation in expression or activity of the gene or gene expression product thereof.

Non-limiting examples of genes involved in central nervous system (CNS) diseases or disorders include Sarcoglycan Alpha (SGCA), glutamic acid decarboxylase 65 (GAD65), glutamic acid decarboxylase 67 (GAD67), CLN2 gene, Nerve Growth Factor (NGF), glial cell derived neurotrophic factor (GDNF), Neurturin, Survival Of Motor Neuron 1, Telomeric (SMN1), β-Glucocerebrosidase (GCase), Frataxin (FXN), Huntingtin (HTN), methyl-CpG binding protein 2 (MECP2), peroxisomal biogenesis factor (PEX), progranulin (GRN), an antitubulin agent, copper-zinc superoxide dismutase (SOD1), Glucosylceramidase Beta (GBA), NPC Intracellular Cholesterol Transporter 1 (NPC1), and NPS3. In some embodiments, the peroxisomal biogenesis factor (PEX) is selected from the group consisting of PEX1, PEX2, PEX3, PEX4, PEX5, PEX6, PEX7, PEX10, PEX11(3, PEX12, PEX13, PEX14, PEX16, PEX19, and PEX26. Non-limiting examples of genes implicated in disease or disorder of a particular organ (e.g., lung, heart, liver, muscle, eye) include Cystic Fibrosis Transmembrane Conductance Regulator (CFTR), Factor X (FIX), RPE65, Retinoid Isomerohydrolase (RPE65), Sarcoglycan Alpha (SGCA), and sarco/endoplasmic reticulum Ca2+-ATPase (SERCA2a). In some instances, the expression of a gene or expression or activity of a gene expression product is inhibited by the administration of the composition to the subject. In some instances, the expression of a gene or the expression or the activity of a gene expression product is enhanced by the administration of the composition to the subject.

In some cases, the composition is administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some cases, the viral genome (vg) concentration of the composition that is administered is between $1.0 \times 10^{11}$ vg per kilogram (kg) and $1.0 \times 10^{16}$ vg/kg. In some cases, the concentration of infectious particles of at least or about $10^7$, $10^8$, $10^9$, $10^{10}$, $10^{11}$, $10^{12}$, $10^{13}$, $10^{14}$, $10^{15}$, $10^{16}$, or $10^{17}$. In some cases, the concentration of infectious particles is $2 \times 10^7$, $2 \times 10^8$, $2 \times 10^9$, $2 \times 10^{10}$, $2 \times 10^{11}$, $2 \times 10^{12}$, $2 \times 10^{13}$, $2 \times 10^{14}$, $2 \times 10^{15}$, $2 \times 10^{16}$, or $2 \times 10^{17}$. In some cases, the concentration of the infectious particles $3 \times 10^7$, $3 \times 10^8$, $3 \times 10^9$, $3 \times 10^{10}$, $3 \times 10^{11}$, $3 \times 10^{12}$, $3 \times 10^{13}$, $3 \times 10^{14}$, $3 \times 10^{15}$, $3 \times 10^{16}$, or $3 \times 10^{17}$. In some cases, the concentration of the infectious particles $4 \times 10^7$, $4 \times 10^8$, $4 \times 10^9$, $4 \times 10^{10}$, $4 \times 10^{11}$, $4 \times 10^{12}$, $4 \times 10^{13}$, $4 \times 10^{14}$, $4 \times 10^{15}$, $4 \times 10^{16}$, or $4 \times 10^{17}$. In some cases, the concentration of the infectious particles $5 \times 10^7$, $5 \times 10^8$, $5 \times 10^9$, $5 \times 10^{10}$, $5 \times 10^{11}$, $5 \times 10^{12}$, $5 \times 10^{13}$, $5 \times 10^{14}$, $5 \times 10^{15}$, $5 \times 10^{16}$, or $5 \times 10^{17}$. In some cases, the concentration of the infectious particles $6 \times 10^7$, $6 \times 10^8$, $6 \times 10^9$, $6 \times 10^{10}$, $6 \times 10^{11}$, $6 \times 10^{12}$, $6 \times 10^{13}$, $6 \times 10^{14}$, $6 \times 10^{15}$, $6 \times 10^{16}$, or $6 \times 10^{17}$. In some cases, the concentration of the infectious particles $7 \times 10^7$, $7 \times 10^8$, $7 \times 10^9$, $7 \times 10^{10}$, $7 \times 10^{11}$, $7 \times 10^{12}$, $7 \times 10^{13}$, $7 \times 10^{14}$, $7 \times 10^{15}$, $7 \times 10^{16}$, or $7 \times 10^{17}$. In some cases, the concentration of the infectious particles $8 \times 10^7$, $8 \times 10^8$, $8 \times 10^9$, $8 \times 10^{10}$, $8 \times 10^{11}$, $8 \times 10^{12}$, $8 \times 10^{13}$, $8 \times 10^{14}$, $8 \times 10^{15}$, $8 \times 10^{16}$, or $8 \times 10^{17}$. In some cases, the concentration of the infectious particles $9 \times 10^7$, $9 \times 10^8$, $9 \times 10^9$, $9 \times 10^{10}$, $9 \times 10^{11}$, $9 \times 10^{12}$, $9 \times 10^{13}$, $9 \times 10^{14}$, $9 \times 10^{15}$, $9 \times 10^{16}$, or $9 \times 10^{17}$.

In some embodiments, the administering of step is performed once. Alternatively, the administering of step is repeated at least twice. The administering of step may be performed once daily. In some cases, the administering of step comprises intravenous administration. In some cases, the administering comprises pulmonary administration. In some cases, the administering comprises intranasal administration (such as a spray). In some cases, the administering of step comprises injecting the composition into a target in vivo environment. In some cases, the administering of step does not comprise injecting the composition into the target in vivo environment.

Subject

Disclosed herein methods of delivering at least one of an AAV particle and viral vector to a subject, for example—to treat or prevent a disease or condition in a subject. The subject, in some cases, is a mammal. Non-limiting examples of a mammal include a mouse, rat, guinea pig, rabbit, chimpanzee, or farm animal. In some instances, the mammal is a non-human primate. In some instances, the subject is human. The subject of the present disclosure may not be diagnosed with a disease or condition. Alternatively, the subject may be a patient that is diagnosed with a disease or disorder, or suspected of having the disease or the disorder.

Disease or Condition

Disclosed herein are methods of treating a disease or condition in a subject by administering a composition comprising a rAAV such as those disclosed herein. At least one advantage of the rAAVs disclosed herein, is that the rAAV may be used to treat virtually any disease or condition that would benefit from a transgene therapy, including but not limited to spinal muscular atrophy (SMA), amyotrophic lateral sclerosis (ALS), Parkinson's disease, Pompe disease, Huntington's disease, Alzheimer's disease, Battens disease, lysosomal storage disorders, glioblastoma multiforme, Rett syndrome, Leber's congenital amaurosis, Late infantile neuronal ceroid lipofuscinosis (LINCL), chronic pain, stroke, spinal cord injury, traumatic brain injury and lysosomal storage disorders.

The disease or the condition may, in some embodiments, be characterized by a reduced or ablated expression or activity of a gene or gene expression product thereof, as compared to a normal individual. In some embodiments, be characterized by an increased or enhanced expression or activity of a gene or gene expression product thereof, as compared to a normal individual.

In some cases, the disease or condition is localized to a particular in vivo environment in the subject, e.g., the brain or the liver. The compositions of the present disclosure are particularly useful for the treatment of the diseases or conditions described herein because they specifically target the in vivo environment and deliver a therapeutic nucleic acid engineered to modulate the activity or the expression of a target gene expression product involved with the pathogenesis or pathology of the disease or condition.

In some instances, the disease or condition comprises a disease or condition of the central nervous system (CNS). Non-limiting examples of disease of the CNS include Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Cerebral Autosomal Dominant Arteriopathy with Subcortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavemous Malformation, Cerebral Gigantism, Cerebral Hypoxia, Cerebral Palsy, Cerebro-Oculo-Facio-Skeletal Syndrome (COFS), Charcot-Marie-Tooth Disease, Charcot-Marie-Tooth syndrome, classical rhizomelic chondrodysplasia punctata (RCDP), Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, Deafness, De Morsier's Syndrome, Dejerine-Klumpke Palsy, Dementia, Dementia-Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Duchenne muscular dystrophy, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy (familial infantile), Encephalotrigeminal Angiomatosis, Epilepsy, Epileptic Hemiplegia, Erb's Palsy, Erb-Duchenne and Dejerine-Klumpke Palsies, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses, Gerstmann's Syndrome, Gerstmann-Straussler-Scheinker Disease, Giant Axonal Neuropathy, Giant Cell Arteritis, Giant Cell Inclusion Disease, glioblastoma, Globoid Cell Leukodystrophy, Glossopharyngeal Neuralgia, Glycogen Storage Disease, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydrocephalus—Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kliiver-Bucy Syndrome, Korsakoff s Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Moebius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myoclonic Encephalopathy of Infants, Myoclonus, Myopathy, Myopathy-Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy-Hereditary, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain—Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, and X-Linked Spinal and Bulbar Muscular Atrophy.

In some instances, the disease or condition comprises a liver disease or disorder, or is associated with a liver disease or disorder. Non-limiting examples include disorders of bile acid synthesis (e.g., Wilson disease, Progressive familial intrahepatic cholestasis type 3), disorders of carbohydrate metabolism (e.g., Hereditary fructose intolerance, Glycogen storage disease type IV), disorders of amino acids metabolism (e.g., tyrosinemia type I), Urea cycle disorders (e.g., argininosuccinate lyase deficiency, citrin deficiency (CTLN2, NICCD)), disorders of lipid metabolism (e.g., cholesteryl ester storage disease), and others including but not limited to Alpha-1 antitrypsin deficiency, cystic fibrosis, hereditary hemochromatosis, Alström syndrome, and congenital hepatic fibrosis.

In some instances, the disease or condition is a disease or condition is of the liver Non-limiting examples of liver diseases or disorders include Alagille Syndrome, Alcohol-Related Liver Disease, Alpha-1 Antitrypsin Deficiency, Autoimmune Hepatitis, Benign Liver Tumors, Biliary Atresia, Cirrhosis, Crigler-Najjar Syndrome, Galactosemia, Gilbert Syndrome, Hemochromatosis, Hepatic Encephalopathy, Hepatitis A, Hepatitis B, Hepatitis C, Hepatorenal Syndrome, Intrahepatic Cholestasis of Pregnancy (ICP), Lysosomal Acid Lipase Deficiency (LAL-D), Liver Cysts, Liver Cancer, Newborn Jaundice, Non-Alcoholic Fatty Liver Disease, Primary Biliary Cholangitis (PBC), Primary Sclerosing Cholangitis (PSC), Reye Syndrome, Type I Glycogen Storage Disease, and Wilson Disease.

Provided here, are methods of treating a disease or a condition associated with an aberrant expression or activity of a target gene or gene expression product thereof, the method comprising modulating the expression or the activity of a target gene or gene expression product in a subject by administering a rAAV encapsidating a heterologous nucleic acid of the present disclosure. In some instances, administration is systemic administration. In some instances, the expression or the activity of the target gene or gene expression product is decreased, relative to that in a normal (non-diseased) individual; and administering the rAAV to the subject is sufficient to increase the expression of the activity of the target gene or gene expression product to that of a normal individual. In some instances, the expression or the activity of the gene or gene expression product is increased, relative to that in a normal individual; and administering the rAAV to the subject is sufficient to decrease the expression or the activity of the target gene or gene expression product. In a non-limiting example, a subject diagnosed with Alzheimer's disease, which is caused, in some cases, by a gain-of-function of a Presenilin 1 and/or Presenilin 2 (encoded by the gene PSEN1 and PSEN2, respectively) is administered a rAAV disclosed herein encapsidating a therapeutic nucleic acid that is a silencing RNA (siRNA), or other RNAi with a loss-of-function effect on PSEN1 mRNA.

Also provided are methods of treating or preventing a disease or condition disclosed herein in a subject comprising administering to the subject a therapeutically effective amount of an AAV vector comprising a nucleic acid sequence encoding a therapeutic gene expression product described herein. The AAV vector may be encapsidated in the modified capsid protein or AAV viral particle described herein. In some instances, the therapeutic gene expression product is effective to modulate the activity or expression of a target gene or gene expression product.

Formulations, Dosages, and Routes of Administration

In general, methods disclosed herein comprise administering a therapeutic rAAV composition by systemic administration. In some instances, methods comprise administering a therapeutic rAAV composition by oral administration. In some instances, methods comprise administering a therapeutic rAAV composition by intraperitoneal injection. In some instances, methods comprise administering a therapeutic rAAV composition in the form of an anal suppository. In some instances, methods comprise administering a therapeutic rAAV composition by intravenous ("i.v.") administration. It is conceivable that one may also administer therapeutic rAAV compositions disclosed herein by other routes, such as subcutaneous injection, intramuscular injection, intradermal injection, transdermal injection percutaneous administration, intranasal administration, intralymphatic injection, rectal administration intragastric administration, intraocular administration, intracerebro-ventricularl administration, intrathecally, or any other suitable parenteral administration. In some instances, methods comprise administering a therapeutic rAAV composition by topical administration, example, by brushing or otherwise contacting the rAAV composition to a region of the subject (e.g., eardrum, bladder). In some embodiments, routes for local delivery closer to site of injury or inflammation are preferred over systemic routes. Routes, dosage, time points, and duration of administrating therapeutics may be adjusted. In some embodiments, administration of therapeutics is prior to, or after, onset of either, or both, acute and chronic symptoms of the disease or condition.

An effective dose and dosage of pharmaceutical compositions to prevent or treat the disease or condition disclosed herein is defined by an observed beneficial response related to the disease or condition, or symptom of the disease or condition. Beneficial response comprises preventing, alleviating, arresting, or curing the disease or condition, or symptom of the disease or condition. In some embodiments, the beneficial response may be measured by detecting a measurable improvement in the presence, level, or activity, of biomarkers, transcriptomic risk profile, or intestinal microbiome in the subject. An "improvement," as used herein refers to shift in the presence, level, or activity towards a presence, level, or activity, observed in normal individuals (e.g. individuals who do not suffer from the disease or condition). In instances wherein the therapeutic rAAV composition is not therapeutically effective or is not providing a sufficient alleviation of the disease or condition, or symptom of the disease or condition, then the dosage amount and/or route of administration may be changed, or an additional agent may be administered to the subject, along with the therapeutic rAAV composition. In some embodiments, as a patient is started on a regimen of a therapeutic rAAV composition, the patient is also weaned off (e.g., step-wise decrease in dose) a second treatment regimen.

In some embodiments, pharmaceutical compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect. It will be understood that the above dosing concentrations may be converted to vg or viral genomes per kg or into total viral genomes administered by one of skill in the art.

In some cases, a dose of the pharmaceutical composition may comprise a concentration of infectious particles of at least or about $10^7$, $10^8$, $10^9$, $10^{10}$, $10^{11}$, $10^{12}$, $10^{13}$, $10^{14}$, $10^{15}$, $10^{16}$, or $10^{17}$. In some cases, the concentration of infectious particles is $2\times10^7$, $2\times10^8$, $2\times10^9$, $2\times10^{10}$, $2\times10^{11}$, $2\times10^{12}$, $2\times10^{13}$, $2\times10^{14}$, $2\times10^{15}$, $2\times10^{16}$, or $2\times10^{17}$. In some cases, the concentration of the infectious particles is $3\times10^7$, $3\times10^8$, $3\times10^9$, $3\times10^{10}$, $3\times10^{11}$, $3\times10^{12}$, $3\times10^{13}$, $3\times10^{14}$, $3\times10^{15}$, $3\times10^{16}$, or $3\times10^{17}$. In some cases, the concentration of the infectious particles is $4\times10^7$, $4\times10^8$, $4\times10^9$, $4\times10^{10}$, $4\times10^{11}$, $4\times10^{12}$, $4\times10^{13}$, $4\times10^{14}$, $4\times10^{15}$, $4\times10^{16}$, or $4\times10^{17}$. In some cases, the concentration of the infectious particles is $5\times10^7$, $5\times10^8$, $5\times10^9$, $5\times10^{10}$, $5\times10^{11}$, $5\times10^{12}$, $5\times10^{13}$, $5\times10^{14}$, $5\times10^{15}$, $5\times10^{16}$, or $5\times10^{17}$. In some cases, the concentration of the infectious particles is $6\times10^7$, $6\times10^8$, $6\times10^9$, $6\times10^{10}$, $6\times10^{11}$, $6\times10^{12}$, $6\times10^{13}$, $6\times10^{14}$, $6\times10^{15}$, $6\times10^{16}$, or $6\times10^{17}$. In some cases, the concentration of the infectious particles is $7\times10^7$, $7\times10^8$, $7\times10^9$, $7\times10^{10}$, $7\times10^{11}$, $7\times10^{12}$, $7\times10^{13}$, $7\times10^{14}$, $7\times10^{15}$, $7\times10^{16}$, or $7\times10^{17}$. In some cases, the concentration of the infectious particles is $8\times10^7$, $8\times10^8$, $8\times10^9$, $8\times10^{10}$, $8\times10^{11}$, $8\times10^{12}$, $8\times10^{13}$, $8\times10^{14}$, $8\times10^{15}$, $8\times10^{16}$, or $8\times10^{17}$. In some cases, the concentration of the infectious particles is $9\times10^7$, $9\times10^8$, $9\times10^9$, $9\times10^{10}$, $9\times10^{11}$, $9\times10^{12}$, $9\times10^{13}$, $9\times10^{14}$, $9\times10^{15}$, $9\times10^{16}$, or $9\times10^{17}$.

Disclosed herein, in some embodiments are formulations of pharmaceutically-acceptable excipients and carrier solutions suitable for delivery of the rAAV compositions described herein, as well as suitable dosing and treatment regimens for using the particular compositions described herein in a variety of treatment regimens. In some embodiments, the amount of therapeutic gene expression product in each therapeutically-useful composition may be prepared is such a way that a suitable dosage will be obtained in any given unit dose of the compound. Factors such as solubility, bioavailability, biological half life, route of administration, product shelf life, as well as other pharmacological considerations will be contemplated by one skilled in the art of preparing such pharmaceutical formulations, and as such, a variety of dosages and treatment regimens may be desirable. In some instances, the rAAV compositions are suitably formulated pharmaceutical compositions disclosed herein, to be delivered either intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

In some embodiments, the pharmaceutical forms of the AAV-based viral compositions suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some cases, for administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Disclosed herein are sterile injectable solutions comprising the rAAV compositions disclosed herein, which are prepared by incorporating the rAAV compositions disclosed herein in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Injectable solutions may be advantageous for systemic administration, for example by intravenous administration.

Also provided herein are formulations in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

Pulmonary administration may be advantageously achieved via the buccal administration. In some embodiments, formulations may comprise dry particles comprising active ingredients. In such embodiments, dry particles may have a diameter in the range from about 0.5 nm to about 7 nm or from about 1 nm to about 6 nm. In some embodiments, formulations may be in the form of dry powders for administration using devices comprising dry powder reservoirs to which streams of propellant may be directed to disperse such powder. In some embodiments, self-propelling solvent/powder dispensing containers may be used. In such embodiments, active ingredients may be dissolved and/or suspended in low-boiling propellant in sealed containers. Such powders may comprise particles wherein at least 98% of the particles by weight have diameters greater than 0.5 nm and at least 95% of the particles by number have diameters less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form. Low boiling propellants generally include liquid propellants having a boiling point of below 65° F. at atmospheric pressure. Generally, propellants may constitute 50% to 99.9% (w/w) of the composition, and active ingredient may constitute 0.1% to 20% (w/w) of the composition. Propellants may further comprise additional ingredients such as liquid non-ionic and/or solid anionic surfactant and/or solid diluent (which may have particle sizes of the same order as particles comprising active ingredients).

Pharmaceutical compositions formulated for pulmonary delivery may provide active ingredients in the form of droplets of solution and/or suspension. Such formulations may be prepared, packaged, and/or sold as aqueous and/or dilute alcoholic solutions and/or suspensions, optionally sterile, comprising active ingredients, and may conveniently be administered using any nebulization and/or atomization device. Such formulations may further comprise one or more additional ingredients including, but not limited to, a flavoring agent such as saccharin sodium, a volatile oil, a buffering agent, a surface-active agent, and/or a preservative such as methylhydroxybenzoate. Droplets provided by this route of administration may have an average diameter in the range from about 0.1 nm to about 200 nm. Formulations described herein useful for pulmonary delivery may also be useful for intranasal delivery. In some embodiments, formulations for intranasal administration comprise a coarse powder comprising the active ingredient and having an average particle size from about 0.2 μm to 500 μm. Such formulations are administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, comprise 0.1% to 20% (w/w) active ingredient, the balance comprising an orally dissolvable and/or degradable composition and, optionally, one or more of the additional ingredients described herein. Alternately, formulations suitable for buccal administration may comprise powders and/or an aerosolized and/or atomized solutions and/or suspensions comprising active ingredients. Such powdered, aerosolized, and/or aerosolized formulations, when dispersed, may comprise average particle and/or droplet sizes in the range of from about 0.1 nm to about 200 nm, and may further comprise one or more of any additional ingredients described herein.

Suitable dose and dosage administrated to a subject is determined by factors including, but not limited to, the particular therapeutic rAAV composition, disease condition and its severity, the identity (e.g., weight, sex, age) of the subject in need of treatment, and can be determined according to the particular circumstances surrounding the case, including, e.g., the specific agent being administered, the route of administration, the condition being treated, and the subject or host being treated.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, example, a single injection of sufficient numbers of infectious particles to provide therapeutic benefit to the patient undergoing such treatment. This is made possible, at least in part, by the fact that certain target cells (e.g., neurons) do not divide, obviating the need for multiple or chronic dosing.

Alternatively, in some circumstances, it may be desirable to provide multiple, or successive administrations of the AAV vector compositions, either over a relatively short, or a relatively prolonged period of time, as may be determined by the medical practitioner overseeing the administration of such compositions. For example, the number of infectious particles administered to a mammal may be on the order of about $10^7$, $10^8$, $10^9$, $10^{10}$, $10^{11}$, $10^{12}$, $10^{13}$, or even higher, infectious particles/ml given either as a single dose, or divided into two or more administrations as may be required to achieve therapy of the particular disease or disorder being treated. In fact, in certain embodiments, it may be desirable to administer two or more different AAV vector compositions, either alone, or in combination with one or more other therapeutic drugs to achieve the desired effects of a particular therapy regimen. In various embodiments, the daily and unit dosages are altered depending on a number of variables including, but not limited to, the activity of the therapeutic rAAV composition used, the disease or condition to be treated, the mode of administration, the requirements of the individual subject, the severity of the disease or condition being treated, and the judgment of the practitioner.

In some embodiments, the administration of the therapeutic rAAV composition is hourly, once every 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours 22 hours, 23 hours, 1 day, 2 days, 3 days, 4 days, 5 days, 6 days, 7 days, 8 days, 9 days, 10 days, 11 days, 12 days, 13 days, 14 days, 15 days, 1 month, 2 months, 3 months, 4 months, 5 months, 6 months, 7 months, 8 months, 9 months, 10 months, 11 months, 1 year, 2 years, 3 years, 4 years, or 5 years, or 10 years. The effective dosage ranges may be adjusted based on subject's response to the treatment. Some routes of administration will require higher concentrations of effective amount of therapeutics than other routes.

Although not anticipated given the advantages of the present disclosure, in certain embodiments wherein the patient's condition does not improve, upon the doctor's discretion the administration of therapeutic rAAV composition is administered chronically, that is, for an extended period of time, including throughout the duration of the patient's life in order to ameliorate or otherwise control or limit the symptoms of the patient's disease or condition. In certain embodiments wherein a patient's status does improve, the dose of therapeutic rAAV composition being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In certain embodiments, the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the dosage amount of the therapeutic rAAV composition described herein lies within a range of circulating concentrations that include the ED50 with minimal toxicity. In certain embodiments, the daily dosage range and/or the unit dosage amount varies within this range depending upon the dosage form employed and the route of administration utilized.

Additional Therapeutic

A therapeutic nucleic acid may be used alone or in combination with an additional therapeutic agent (together, "therapeutic agents"). In some cases, an "additional therapeutic agent" as used herein is administered alone. The therapeutic agent may be administered together or sequentially in a combination therapy. The combination therapy may be administered within the same day, or may be administered one or more days, weeks, months, or years apart. In some cases, a therapeutic nucleic acid provided herein is administered if the subject is determined to be non-responsive to a first line of therapy.

The additional therapeutic agent can comprise a small molecule. The additional therapeutic agent can comprise an antibody, or antigen-binding fragment. The additional therapeutic agent can comprise a cell-based therapy. Exemplary cell-based therapies include without limitation immune effector cell therapy, chimeric antigen receptor T-cell (CAR-T) therapy, natural killer cell therapy and chimeric antigen receptor natural killer (NK) cell therapy. Either NK cells, or CAR-NK cells, or a combination of both NK cells and CAR-NK cells can be used in combination with the methods disclosed herein. In some embodiments, the NK cells and CAR-NK cells are derived from human induced pluripotent stem cells (iPSC), umbilical cord blood, or a cell line. The NK cells and CAR-NK cells can comprise a cytokine receptor and a suicide gene. The cell-based therapy can comprises a stem cell therapy. The stem cell therapy may be embryonic or somatic stem cells. The stem cells may be isolated from a donor (allogeneic) or isolated from the subject (autologous). The stem cells may be expanded adipose-derived stem cells (eASCs), hematopoietic stem cells (HSCs), mesenchymal stem (stromal) cells (MSCs), or induced pluripotent stem cells (iPSCs) derived from the cells of the subject.

III. Kits

Disclosed herein are kits comprising compositions disclosed herein. Also disclosed herein are kits for the treatment or prevention of a disease or conditions of the central nervous system (CNS), or target organ or environment (e.g., liver). In some instances, the disease or condition is cancer, a pathogen infection, pulmonary disease or condition, neurological disease, muscular disease, or an immune disorder, such as those described herein. In one embodiment, a kit can include a therapeutic or prophylactic composition containing an effective amount of a composition of a rAAV particle encapsidating a recombinant AAV vector encoding a therapeutic nucleic acid (e.g., therapeutic nucleic acid) and a recombinant AAV (rAAV) capsid protein of the present disclosure. In another embodiment, a kit can include a therapeutic or prophylactic composition containing an effective amount of cells modified by the rAAV described herein ("modified cell"), in unit dosage form that express therapeutic nucleic acid. In some embodiments, a kit comprises a sterile container which can contain a therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In some cases, rAAV are provided together with instructions for administering the rAAV to a subject having or at risk of developing the disease or condition (e.g., disease of the CNS, PNS, liver, and the like). Instructions can generally include information about the use of the composition for the treatment or prevention of the disease or condition.

In some cases, a kit can include allogenic cells. In some cases, a kit can include cells that can comprise a genomic modification. In some cases, a kit can comprise "off-the-shelf" cells. In some cases, a kit can include cells that can be expanded for clinical use. In some cases, a kit can contain contents for a research purpose.

In some cases, the instructions include at least one of the following: description of the therapeutic rAAV composition; dosage schedule and administration for treatment or prevention of the disease or condition disclosed herein; precautions; warnings; indications; counter-indications; overdosage information; adverse reactions; animal pharmacology; clinical studies; and/or references. The instructions can be printed directly on the container (when present), or as a label applied to the container, or as a separate sheet, pamphlet, card, or folder supplied in or with the container. In some cases, instructions provide procedures for administering the rAAV to the subject alone. In some cases, instructions provide procedures for administering the rAAV to the subject at least about 1 hour (hr), 2 hr, 3 hr, 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 25 hr, 26 hr, 27 hr, 28 hr, 29 hr, 30 hr, or up to 2 days, 3 days, 4 days, 5 days, 6 days, or 7 days after or before administering an additional therapeutic agent disclosed herein. In some instances, the instructions provide that the rAAV is formulated for intravenous injection.

IV. Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

As used herein "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure, such as compositions for treating skin disorders like acne, eczema, psoriasis, and rosacea.

The terms "homologous," "homology," or "percent homology" are used herein to generally mean an amino acid sequence or a nucleic acid sequence having the same, or similar sequence to a reference sequence. Percent homology of sequences can be determined using the most recent version of BLAST, as of the filing date of this application.

The terms "increased," or "increase" are used herein to generally mean an increase by a statically significant amount. In some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased" or "decrease" are used herein generally to mean a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The terms "subject" is any organism. In some instances, the organism is a mammal. Non-limiting examples of mammal include, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In some instances, the subject is a patient, which as used herein, may refer to a subject diagnosed with a particular disease or disorder.

The term "gene," as used herein, refers to a segment of nucleic acid that encodes an individual protein or RNA (also referred to as a "coding sequence" or "coding region"), optionally together with associated regulatory region such as promoter, operator, terminator and the like, which may be located upstream or downstream of the coding sequence.

The term "adeno-associated virus," or "AAV" as used herein refers to the adeno-associated virus or derivatives thereof. Non-limited examples of AAV's include AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), AAV type 12 (AAV12), avian AAV, bovine AAV, canine AAV, equine AAV, primate AAV, non-primate AAV, and ovine AAV. In some instances, the AAV is described as a "Primate AAV," which refers to AAV that infect primates. Likewise an AAV may infect bovine animals (e.g., "bovine AAV", and the like). In some instances, the AAV is wildtype, or naturally occurring. In some instances, the AAV is recombinant.

The term "AAV capsid" as used herein refers to a capsid protein or peptide of an adeno-associated virus. In some instances, the AAV capsid protein is configured to encapsidate genetic information (e.g., a transgene, therapeutic nucleic acid, viral genome). In some instances, the AAV capsid of the instant disclosure is a modified AAV capsid, relative to a corresponding parental AAV capsid protein.

The term "tropism" as used herein refers to a quality or characteristic of the AAV capsid that may include specificity for, and/or an increase or a decrease in efficiency of, expressing the encapsidated genetic information into one in in vivo environment, relative to a second in vivo environment. An in vivo environment, in some instances, is a cell-type. An in vivo environment, in some instances, is an organ or organ system.

The term "AAV vector" as used herein refers to nucleic acid polymer encoding genetic information related to the virus. The AAV vector may be a recombinant AAV vector (rAAV), which refers to an AAV vector generated using recombinatorial genetics methods. In some instances, the rAAV vector comprises at least one heterologous polynucleotide (e.g. a polynucleotide other than a wild-type or naturally occurring AAV genome such as a transgene).

The term "AAV particle" as used herein refers to an AAV virus, virion, AAV capsid protein or component thereof. In some cases, the AAV particle is modified relative to a parental AAV particle.

The term "gene product" of "gene expression product" refers to an expression product of a polynucleotide sequence such as, for e.g., a polypeptide, peptide, protein or RNA, including interfering RNA (e.g., siRNA, miRNA, shRNA) and messenger RNA (mRNA).

The terms "operatively linked" or "operably linked" refers to a location of two or more elements being close together, and in some cases, next to one other (e.g., genetic elements such as a promoter, enhancer, termination signal sequence, polyadenylation sequence, and the like) that enables a functional relationship between the two or more elements. In one non-limiting example, a promoter that is operatively linked to a coding region enables the initiation of transcription of the coding sequence.

The term "heterologous" as used herein refers to a genetic element (e.g., coding region) or gene expression product (e.g., RNA, protein) that is derived from a genotypically distinct entity from that of the rest of the entity to which it is being compared.

The term "endogenous" as used herein refers to a genetic element (e.g., coding region) or gene expression product (e.g., RNA, protein) that is naturally occurring in or associated with an organism or a particular cell within the organism.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radio-labeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

The terms "treat," "treating," and "treatment" as used herein refers to alleviating or abrogating a disorder, disease, or condition; or one or more of the symptoms associated with the disorder, disease, or condition; or alleviating or eradicating a cause of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" refers to the amount of a compound or therapy that, when administered, is sufficient to prevent development of, or alleviate to some extent, one or more of the symptoms of a disorder, disease, or condition of the disease; or the amount of a compound that is sufficient to elicit biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition; Lippincott Williams & Wilkins: Philadelphia, PA, 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, FL, 2004).

The term "pharmaceutical composition" refers to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration.

Non-limiting examples of "sample" include any material from which nucleic acids and/or proteins can be obtained. As non-limiting examples, this includes whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. In various embodiments, the sample comprises tissue from the large and/or small intestine. In various embodiments, the large intestine sample comprises the cecum, colon (the ascending colon, the transverse colon, the descending colon, and the sigmoid colon), rectum and/or the anal canal. In some embodiments, the small intestine sample comprises the duodenum, jejunum, and/or the ileum. Alternatively, a sample can be obtained through primary patient derived cell lines, or archived patient samples in the form of preserved samples, or fresh frozen samples.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

The section headings used herein are for organizational purposes only and are not to be construed as limiting the subject matter described.

V. Examples

Example 1. Method of Producing an rAAV

A recombinant AAV (rAAV) is produced. Three plasmid vectors are triple-transfected into an immortalized HEK293 using a standard transfection protocol (e.g., with PEI). The first vector contains a transgene cassette flanked by inverted terminal repeat (ITR) sequences from a parental AAV virus.

The transgene cassette has a promoter sequence and that drives transcription of a heterologous nucleic acid in the nucleus of the target cell. The second vector contains nucleic acids encoding the AAV Rep gene, as well as a modified Cap gene e.g., AAV2/9 REP-AAP-ΔCap). Modified Cap gene comprises any one of the DNA sequences provided in FIGS. 33-35, which are the DNA sequences encoding the modified AAV capsid proteins of the present disclosure. The third vector contains nucleic acids encoding helper virus proteins needed for viral assembly, and packaging of the heterologous nucleic acid into the modified capsid structure.

Viral particles are harvested from the media after 72 h post transfection and from the cells and media at 120 h post transfection. Virus present in the media is concentrated by precipitation with 8% poly(ethylene glycol) and 500 mM sodium chloride and the precipitated virus is added to the lysates prepared from the collected cells. The viruses are purified over iodixanol (Optiprep, Sigma) step gradients (15%, 25%, 40% and 60%). Viruses are concentrated and formulated in PBS. Virus titers are determined by measuring the number of DNaseI-resistant vector genome copies (VGs) using qPCR and the linearized genome plasmid as a control.

Example 2. Methods of Identifying Variant AAV Capsid Proteins

Plasmid

Library generation. The rAAV-ΔCap-in-cis-Lox2 plasmid (FIG. 36) is a modification of the rAAV-ΔCap-in-cis-Lox plasmid. For 7-mer-i library fragment generation, the pCRII-9Cap-XE plasmid was used as a template. The AAV2/9 REP-AAP-ΔCap plasmid (FIG. 36) was modified from the AAV2/9 REP-AAP plasmid.

The rAAV-ΔCap-in-cis-Lox2 plasmid consists of three major elements that are flanked by AAV2 ITRs. (i) UBC ubiquitous promoter driving the expression of fluorescent protein, mNeongreen, followed by a synthetic polyadenylation sequence. The mCherry expression cassette of the previous version of the plasmid was replaced by mNeon-Green cassette. (ii) A portion of AAV2 rep gene that has the splicing sequences and AAV5 p41 promoter (1680-1974 residues of GenBank AF085716.1) followed by AAV9 cap gene. The prior version of this plasmid, rAAV-ΔCap-in-cis-Lox, has a short 12 bp sequence between restriction sites XbaI and AgeI at AA 450 and 592 of the AAV9 Cap gene. This was replaced by a 723 bp sequence of mRuby2 gene in-frame (acts as filler DNA) in the newer version of the plasmid. (iii) SV40 polyadenylation sequence that is flanked by lox71 and lox66 sites. The minor changes were introduced to the prior version of the plasmid to facilitate ease of cloning and to visualize mammalian cell transfection. The Lox sites in these rAAV plasmids show modest levels of Cre-independent flipping. This was minimized during PCR-based capsid recovery by lowering the number of amplification cycles to a point where we cannot recover any rAAV capsids from the control DNA extracted from wild-type mice (i.e., lacking Cre expression) that were injected with the library. The pCRII-9Cap-XE plasmid contains the AAV9 capsid gene sequence from AAs 450-592 and is flanked by XbaI and AgeI restriction sites.

The AAV2/9 REP-AAP-ΔCap plasmid has the five previously existing stop codons of AAV2/9 REP-AAP in addition to the deletion of AAs 450-592 of the AAV9 capsid sequence. These modifications did not affect vector production. The deletion of the overlapping fragment between REP-AAP and rAAV-ΔCap-in-cis-Lox2 plasmids minimizes recombination between plasmids that could potentially generate AAV9 wild-type capsids during co-transfection in vector production.

Capsid Characterization

AAV capsids. The AAV capsid variants with 7-mer insertions or 11-mer substitutions were made between positions 587-597 of AAV-PHP.B capsid using the pUCmini-iCAP-PHP.B backbone (Addgene ID: 103002).

ssAAV genomes. To characterize the AAV capsid variants, the single stranded (ss) rAAV genomes were used. Genomes such as pAAV:CAG-mNeonGreen27 (equivalent plasmid, pAAV: CAG-eYFP35; Addgene ID: 104055), pAAV:CAG-NLS-EGFP26 (equivalent version with one NLS is on Addgene ID 104061), pAAV:CAG-DIO-EYFP35 (Addgene ID: 104052), pAAV: GfABC1D-2xNLS-mTurquoise235 (Addgene ID: 104053), and pAAV-Ple261-iCre30 (Addgene ID 49113) were used.

pAAV:CAG-mNeonGreen2 genome consists of a ubiquitous CMV-β-Actin-intron-β-Globin (CAG) hybrid promoter driving the expression of a fluorescent protein, mNeonGreen (equivalent plasmid, pAAV: CAG-eYFP3; Addgene ID: 104055). pAAV:CAG-NLS-EGFP1 consists of NLS sequences at the N- and C-termini of EGFP and is driven by the CAG promoter. An equivalent version with one NLS is on Addgene (ID 104061). pAAV:CAG-DIO-EYFP3 (Addgene ID: 104052) consists of a EYFP gene built in the reverse direction of the CAG promoter, and it is flanked by a pair of Cre-Lox sites (Lox P and Lox 2272) on either ends.

In cells expressing Cre, the Cre-lox pair inverts EYFP enabling transcription and translation, followed by excision in the lox site to prevent re-inversion. pAAV: GfABC1D-2xNLS-mTurquoise23, referred to elsewhere as pAAV: GFAP-2xNLS-mTurquoise2 (Addgene ID: 104053), consists of NLS sequences at the N- and C-termini of mTurquoise2 and is driven by the astrocyte-specific promoter GfABC1D4. pAAV:Ple261-iCre5 (Addgene ID 49113) contains an endothelial-cell-specific promoter driving the expression of iCre.

pAAV:CAG-XFP (mNeongreen) was packaged for characterizing AAV variants. However, when performing quantification of cell-types: neurons, astrocytes and oligodendrocytes, CAG-NLS-EGFP was used to restrict the expression to nucleus for easier quantification using microscope images. GFAP-NLS-mTurq2 is used to quantify astrocytes. CAG-DIO-EYFP is used for Cre driver lines, due to the presence of lox sites in this plasmid.

The self-complementary genome from Dr. Guangping Gao, scAAV:CB6-EGFP genome has a hybrid ubiquitous CB6 promoter (975 bp) comprising a CMV enhancer (cytomegalovirus immediate early enhancer), a chicken-f3-actin promoter and hybrid intron, that drives the expression of EGFP. The genome has a rabbit globin poly A (127 bp) following the EGFP gene. The scAAV:CAG-EGFP (Addgene ID:83279), vector uses a ubiquitous CMV-β-Actin-intron-β-Globin (CAG) hybrid promoter to drive the expression of EGFP.

Round-I AAV Capsid Library Generation

Mutagenesis strategy. The 7-mer randomized insertion was designed using the NNK saturation mutagenesis strategy, involving degenerate primers (from Integrated DNA Technologies, Inc.) containing mixed bases. N can be A, C, G, or T bases and K can be G, or T. Using this strategy, combinations of all 20 AAs at each position of the 7-mer peptide using 33 codons were obtained, resulting in a library size of 1.28 billion at the level of AA combinations. The mutagenesis strategy for the 3-mer-s PHP.B library is described in Chan, K. Y. et al. Engineered AAVs for efficient noninvasive gene delivery to the central and peripheral nervous systems. *Nat. Neurosci.* 20, 1172-1179 (2017).

Library cloning. The 480 bp AAV capsid fragment (450-592 AAs) with the 7-mer random insertion between AAs 588 and 589 was generated by conventional PCR methods with a mixed base degenerate primer. The library fragment was amplified from the pCRII-9Cap-XE template by Q5 Hot Start High-Fidelity 2× Master Mix (NEB; M0494S) with forward primer, XF: 5'-ACTCATCGACCAATACTTGTAC-TATCTCTCTAGAAC-3' and reverse primer, 7×MNN-588i: 5'-GTATTCCTTGGTTTTGAACCCAACCGGTCTGCG-CCT- GTGCMNNMNNMNNMNNMNN MNNMNNTTG-GGCACTCTGGTGGTTTGTG-3'. To avoid PCR-induced biases resulting from point mutations, recombination, and template switching, PCR amplification was limited to 15-20 cycles and the reactions were scaled up to get the required yield. The resulting PCR products were run on a 1% agarose gel and extracted with a Zymoclean Gel DNA Recovery kit (Zymo Research; D4007). It is critical to avoid AAV contamination during this step by taking precautionary measures like using a clean gel-running box and freshly prepared 1×TAE buffer.

rAAV-ΔCap-in-cis-Lox2 plasmid (6960 bp) was linearized with the restriction enzymes AgeI and XbaI by following the NEB recommended protocol for double digestion. The digested plasmid was run on a 0.8%-1% agarose gel to extract the linearized backbone (6237 bp) with a Zymoclean Gel DNA Recovery kit.

The amplified library fragment was assembled into the linearized vector with the NEBuilder HiFi DNA Assembly Master Mix (NEB; E2621S) and a 1:2 molar ratio of vector to insert, to assemble at 50° C. for 60 min.

Library purification. The assembled library was then subjected to Plasmid Safe (PS) DNase (Epicentre; E3105K) treatment to purify the assembled product by degrading the un-assembled DNA fragments from the mixture. For the R1 library, around 3U of PS DNase per 1 μg of input DNA was used in a 30 min reaction at 37° C. Alternatively, Exonuclease V (RecBCD) was used following the NEB recommended protocol (NEB; M0345S). Both procedures yielded comparable results. The resulting mixture was further purified with a DNA Clean and Concentrator kit (Zymo Research; D4013).

Library yield. With an assembly efficiency of 15%-20% post-PS treatment, a yield of about 15-20 ng per 100 ng of input DNA per 20 μL reaction was obtained. For building the 7-mer-i DNA library, approximately 5-6 μg of input DNA was used to obtain around 800 ng of assembled library.

Quality control. To validate successful assembly of the library, 1 ng of the final assembled library was transformed into *E. coli* SURE 2 Supercompetent Cells (Integrated Sciences; 200152). Colonies on an LB/Agar plate containing carbenicillin antibiotic after overnight incubation at 37° C. were identified. The DNA library was sequenced around the insertion site (Laragen; Sanger Sequencing). A non-biased library shows multiple nucleotide peaks of equal diversity (25% each of A, T, G, C) across every base position of the diversified region. To verify that the ITRs were intact, SmaI digestion was carried out as per the NEB recommended protocol (NEB; R0141S). To validate successful transfection and assess the vector-production yield per 150 mm dish, 10 ng of 7-mer-i library was used to transfect HEK293 producer cells. Uniform expression of mNeonGreen protein across HEK cells was observed, and an average yield of 0.1-1×10^{11} vg was obtained per 150 mm dish. Using the average yield per dish, the vector production for in vivo selection was scaled up (See FIG. 45).

Round-2 AAV Capsid DNA Library

PCR pool design. To maintain proportionate pooling, the fraction of each sample/library that needs to be pooled based on an individual library's diversity was mathematically determined. This process involved estimation of the diversity precluding noise and consideration of amplification of this diversity across samples by determining the area under the curve for the interval of high-confidence variants that falls in the higher RC range. The area under the curve (AUC) was estimated using the composite Simpson's rule by plotting all the recovered variants in a library (X-coordinate) to their read counts (RCs or copy number from deep sequencing data, Y-coordinate) (see FIG. 40). To determine the definite intervals for AUC, the data was sorted based on the decreasing order of the RCs. Noticeably, the distribution has two phases, with a steadier slope of variants in the higher RC range, followed by a steep drop in the slope of the curve (~50-1000 fold lower RCs). By observation, this steeper side of the curve is predominant in sequencing errors/PCR mutations, hence this error dominant slope otherwise called noise from was precluded from the AUC estimation. When comparing composite Simpson's rule with another function, such as composite trapezoidal rule, the difference was miniscule.

This area is then used to determine the fraction of an individual library that needs to be pooled into PCR pool library using the formula: [Area under the curve/total number of libraries pooled].

The pooled sample was used as a template for further amplification with 12 cycles of 98° C. for 10 s, 60° C. for 20 s, and 72° C. for 30 s by Q5 polymerase, using the primers 588-R2lib-F: 5'-CACTCATCGACCAATACTTGTACTAT-CTCTCT-3' and 588-R2lib-R: 5'-GTATTCCTTGGTTTT-GAACCCAACCG-3'. Similar to R1 library generation, the PCR product was assembled into the rAAV-ΔCap-in-cis-Lox2 plasmid and the virus was produced.

The R1 libraries used to build R2 were the Cre-Lox flipped rAAV DNA from half of the mouse brains (~0.3 g) and portion of spinal cords (0.1-0.2 g) from all Cre lines. The amount of tissue processed here was sufficient for complete capsid library recovery. The differentially pooled and amplified libraries (by PCR pool or synthetic pool) were assembled using gibson assembly with a follow-up PS or Exonuclease V treatment (as described in R1 library generation). Successful library generation was validated by transformation, Sanger sequencing, and an ITR SmaI digest.

For vector production, about 10 ng of the purified and assembled library was used to transfect each 150 mm dish of 293T cells, and a yield of about 6×10^{11} vg per 150 mm dish was obtained (i.e. the R2 yield was six times that of R1, unsurprisingly given these sequences have already produced well enough to survive R1 selection).

Synthetic pool design. As described in the PCR pool strategy, high-confidence variants were chosen with RCs above the error-dominant noise slope from the plot of library distribution (see FIG. 40). This came to about 9000 sequences from all brain and spinal cord samples of all Cre lines. A similar primer design as mentioned in the description of the R1 library generation was used. Primers XF: 5'-ACTCATCGACCAATACTTGTACTATCTCTCTAG-AAC-3' and 11-mer-588i: 5'-GTATTCCTTGGTTTTGAA-CCCAACCGGTCTGCGCXXXXXXMNNMNNM- NNM-NNMNN MNNMNNXXXXXXACTCTGGTGGTTTGTG-3', where "XXXXXXMNNMNNMNNMNNMNNMNN-MNNXXXXXX" was replaced with unique nucleotide sequence of a 7-mer tissue recovered variant (7×MNN) along with modification of two adjacent codons flanking on either end of the 7-mer insertion site (6×X), which are residues 587-588 "AQ" and residues 589-590 "AQ" on AAV9 capsid. To select sequences for synthesis, the R1 brain and spinal cord libraries were chosen and used the same threshold limit for RC as described in the PCR pool strategy. This came to about 9000 sequences from all brain and spinal cord samples of all Cre lines. Since spike-in library has 11-mer mutated variants, the same primer design where "XXXXXXMNNMNNMNNMNNMNNMNNM-NNXXXXXX" was replaced with a specific nucleotide sequence of a 11-mer variant. A duplicate of each sequence in this library was designed with different codons optimized for mammals. The primers were designed using a custom built python based script (code will be made available in Github). The custom-designed oligopool was synthesized in an equimolar ratio by Twist Biosciences. The oligopool was used to amplify the pCRII-XE Cap9 template over 13 cycles of 98° C. for 10 s, 60° C. for 20 s, and 72° C. for 30 s. To obtain a higher yield for large-scale library preparation, the product of the first PCR was used as a template for the second PCR using the primers XF and 588-R2lib-R (described above) and amplified for 13 cycles. As described in the description of the R1 library generation, the PCR product was assembled into an rAAV backbone and processed and purified for virus production. About 10 ng per 150 mm dish of HEK293 cells produced about $6 \times 10^{11}$ vg of virus library.

AAV Viral Library Production and Purification

To prevent capsid mosaic formation of the 7-mer-i library in HEK293 producer cells, only 10 ng of assembled library per 150 mm dish were transfected along with other required reagents for AAV vector production. In addition to the 10 ng of library transfection per 150 mm dish of 293T producer cells, three plasmids were transfected: AAV2/9 REP-AAP-ΔCap, pUC18 and pHelper (genes encoding adenoviral proteins for AAV replication) at a ratio of 1:1:2. The plasmid pUC18 acts as a filler DNA to compensate for the low amount of library DNA in order to maintain the N:P ratio required for optimal transfection using polyethylenimine (PEI, Polysciences; 24765-1) transfection). The cells and culture media were harvested at 60 h post-transfection to collect the viral particles. rAAV harvest and purification were performed as per the protocol. The small amount of library DNA per plate and early cell harvest time are critical for reducing the possibility of mosaic capsid assemblies during vector production (similar considerations seen in prior reports).

For 7-mer-i library, the production was scaled up to 60 dishes (~$1.8 \times 10^7$ cells/dish) and with ~10% transfected with the library, resulted in ~$1 \times 10^8$ total transformants. For an NNK 7mer library with ~$1 \times 10^8$ total transformants, the number of unique variants is $9.99 \times 10^7$.

For the rAAV DNA extraction from purified rAAV viral library, ~10% of the purified viral library was used to extract the viral genome by proteinase K treatment. In order to degrade any contaminating DNA from the purified library, it was treated with DNase I enzyme (5 μl of 10 U/μl) (Sigma-Aldrich; 4716728001) in 100 μl of DNase I buffer and incubated for 1 h at 37° C. The enzyme was inactivated by adding 5 μl of 0.5 M EDTA at 70° C. for 10 min. Following DNase I treatment, the capsid protein shell was digested by adding 120 μl of proteinase solution containing 5 μl of 20 μg/μl of proteinase K and incubated at 50° C. overnight. To inactivate the proteinase K, the mixture was boiled at 95° C. The extracted rAAV library DNA was then concentrated and purified using phenol chloroform and ethanol. An equal volume of Phenol:Chloroform:Isoamyl Alcohol 25:24:1, pH8.0 (~250 μl; ThermoFisher Scientific; 15593031) was added and vortexed for 30 s. The mixture is incubated for 5 min at room temperature (RT) before centrifugation at 15,000 rpm for 10 min at 4° C. The upper aqueous phase was separated and mixed with an equal volume of chloroform and vortexed for 30 s. Following 5 min incubation at RT, centrifuge at 15,000 rpm for 10 min at 4° C. The upper aqueous phase was separated and one-tenth volume of 3M sodium acetate (pH 5.2) along with 2 μl Co-Precipitant Pink (Bioline; BIO-37075) and 2.5 volumes of ice cold 100% ethanol was added before vortexing for 30 s. The mixture was incubated for at least 1 hr at –20° C. before centrifugation at 15,000 rpm for 15 min at 4° C. The pellet was air dried and resuspended in TE buffer. The DNA concentration was determined using the Qubit ssDNA assay.

Animals

All animal procedures performed in this study were approved by the California Institute of Technology Institutional Animal Care and Use Committee (IACUC). C57BL/6J (000664), Tek-Cre (8863), SNAP25-Cre (23525), GFAP-Cre (012886), Syn1-Cre (3966), and Ai14 (007908) mice lines used in this study were purchased from the Jackson Laboratory (JAX). For in vivo library selection, 6- to 8-week-old adult male and female mice were intravenously injected with the viral libraries. Both genders were used for capsid selection to recover capsid variants with minimal gender bias. The IV injection of rAAVs was into the retro-orbital sinus of adult mice. For testing the transduction phenotypes of rAAVs, 6- to 8-week-old C57BL/6J or Tek-Cre or Ai14 adult male mice were randomly assigned. The experimenter was not blinded for any of the experiments performed in this study.

In Vivo Selection

Figures 43, 44, 45:
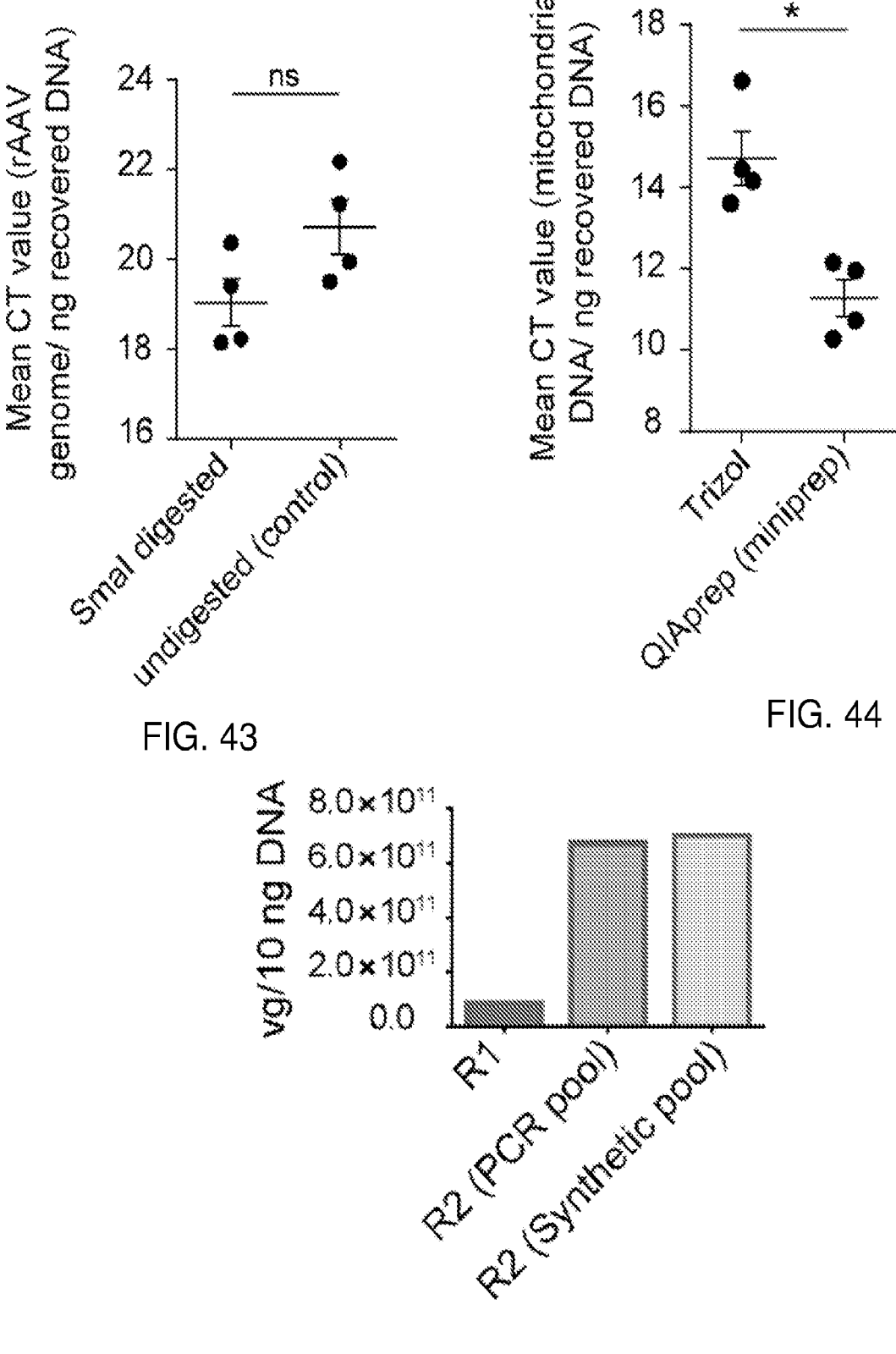
FIG. 43 shows the CT value (cycle threshold from qPCR) of rAAV genome extracted by trizol that were treated with SmaI restriction enzyme or untreated.
FIG. 44 shows CT value of mitochondrial DNA (internal control for smaller genome recovery, fold change=10.79 (2ΔCT)) recovered from 1 ng of total DNA from liver tissue.
FIG. 45 shows the vector yields obtained per 10 ng of capsid DNA library across R1 and R2 vector productions.

The 7-mer-i viral library selections were carried out in different lines of Cre transgenic adult mice: Tek-Cre, SNAP25-Cre, and GFAP-Cre for the R1 selections, and those three plus Syn1-Cre for the R2 selections. Male and female adult mice were intravenously administered with a viral vector dose of $2 \times 10^{11}$ vg/mouse for the R1 selection, and a dose of $1 \times 10^{12}$ vg/mouse for the R2 selection. The dose was determined based on the virus yield which was different across selection rounds (FIG. 45). Both genders were used to recover capsid variants with minimal gender bias. Two weeks post-injection, mice were euthanized and all organs including brain were collected, snap frozen on dry ice, and stored at –80° C.

rAAV Genome Extraction from Tissue

Optimization. For rAAV genome extraction from tissues, both the Trizol method (Life Technologies; 15596) and the QlAprep Spin Miniprep kit (Qiagen, Inc; 27104) were used according to the manufacturers' recommended protocols, and found the Trizol method to be more efficient. The total rAAV genome recovery from 0.1 g of mouse liver was quantified by quantitative PCR using the primers mNeon-Green-F: 5'-CGACACATGAGTTACACATCTTTGGCTC-3' and mNeonGreen-R: 5'-GGAGGTCACCCTT-GGTGGACTTC-3', which binds to the mNeonGreen gene of the ssAAV-ΔCap-in-cis-Lox2 genome. As an internal control, the amount of mitochondrial DNA (a measure of the recovery of smaller genomes) was quantified using primers Mito-F: 5'-CCCAGCTACTACCATCATTCAAGT-3' and Mito-R: 5'-GATGGTTTGGGAGATTGGTTGATGT-3'. Although the percentage of viral DNA per 1 ng total extracted DNA was about 1.5 fold higher with the QlAprep kit than with the Trizol method, the overall recovery was lower with the QlAprep kit.

The extracted viral genome was digested with a restriction enzyme, such as SmaI (found within the ITRs), to improve rAAV genome recovery by PCR. This was analyzed by quantitative PCR with Cre+ primers, CapF-56: 5'-AT-TGGCACCAGATACCTG ACTCGTAA-3', Cre+R-58: 5'-CAAGTAAAACCTCTACAAATGTGGTAAAATCG-3' and Cre-primers, CapF-56 (see above) and Cre-R-57: 5'-GTCCAAACTCATCAATGTATCTTATCATGTCTG-3'.

rAAV genome extraction with the Trizol method. Half of a frozen brain hemisphere (0.3 g approx.) was homogenized with a 2 ml glass homogenizer (Sigma Aldrich; D8938) or a motorized plastic pestle (Fisher Scientific; 12-141-361, 12-141-363) (for smaller tissues) and processed as described in prior work. The extracted DNA was then treated with 3-6

µl of 10 µg/µl RNase Cocktail Enzyme Mix (ThermoFisher Scientific; AM2286) to remove RNA and digested with SmaI restriction enzyme. The treated mixture was then purified with a Zymo DNA Clean and Concentrator kit (D4033). From deep sequencing data analysis, it was observed that the amount of tissue processed for rAAV genome recovery is sufficient.

rAAV genome recovery by Cre-dependent PCR. rAAV genomes with Lox sites flipped by Cre recombination were selectively recovered and amplified using PCR with primers that yield a PCR product only if the Lox sites are flipped (See FIG. 37). The primers 71F: 5'-CTTCCAGTTCAGC-TACGAGTTTGAGAAC-3' and CDF/R: 5'-CAAGT-AAAACCTCTACAAATGTGGTAAAATCG-3' were used and amplified the Cre-recombined genomes over 25 cycles of 98° C. for 10 s, 58° C. for 30 s, and 72° C. for 1 min, using Q5 DNA polymerase Total rAAV genome recovery by PCR (Cre-independent). To recover all rAAV genomes from a tissue, the primers XF (5'-ACTCATCGACCAATACTTGTACTATCTCTCT-AGAAC-3') and 588-R2lib-R (5'-GTATTCCTTGGTTTT-GAACCCAACCG-3') were used to amplify the genomes over 25 cycles of 98° C. for 10 s, 60° C. for 30 s, and 72° C. for 30 min, using Q5 DNA polymerase.

Sample Preparation for NGS

To analyze selections using deep sequencing, the DNA library was processed, the virus library, and the tissue libraries post-in vivo selection to add flow cell adaptors around the diversified 7-mer insertion region (See FIG. 37).

Preparation of rAAV DNA and Viral DNA library. The Gibson-assembled rAAV DNA library and the DNA extracted from the viral library were amplified by Q5 DNA polymerase using the primers 588i-lib-PCR1-6bpUID-F: 5'-CACGACGCTCTTCCGATCTAANNNNNNAGTCC-TATGGACAAGTGGCCACA-3' and 588i-lib-PCR1-R: 5'-GTGACTGGAGTTCAGACGTGTGCTCTTCC-GATCTTCCTTGGTTTTGAACCCAACCG-3' that are positioned around 50 bases from the randomized 7-mer insertion on the capsid, and that contain the Read1 and Read2 flow cell sequences on the 5' end.

The primer, 588i-lib-PCR1-6bpUID-F: 5' CACGACGCTCTTCCGATCTAANNNNNNAGTCC-TATGGACAAGTGGCCACA-3' used to minimally amplify DNA and virus libraries for NGS has 6 nucleotides long UID (unique identifier) "NNNNNN" that sits after 19 nucleotides of Read-1 sequence used in NGS "5'-CACGACG-CTCTTCCGATCT" and linker "AA". The sequence after UID "AGTCCTATGGACAAGTGGCCACA" is the region that anneals to the AAV9 capsid. UID is an optional feature for NGS data analysis to identify potential PCR amplification errors. However, this feature wasn't utilized in the NGS data analysis in this study to maintain consistency with the primers used in rAAV genome recovery from tissues which lacks this UID feature (primers 71F: 5'-CTTC-CAGTTCAGCTACGAGTTIG.AGAAC-3 and CDF/R: 5' CAAGTAAAACCTCT ACA A ATGTGGTAA AATCG-3). The UID or any kind of overhangs seemed to affect the PCR based recovery from tissue. Presumably, the primer thermo-stability has a key role to play in very low amount of extracted rAAV genomes from tissues.

Using 5-10 ng of template DNA in a 50 µl reaction, the DNA was minimally amplified for 4 cycles of 98° C. for 10 s, 60° C. for 30 s, and 72° C. for 10 s. The mixture was then purified with a PCR purification kit. The eluted DNA was then used as a template in a second PCR to add the unique indices (single or dual) via the recommended primers (NEB; E7335S, E7500S, E7600S) in a 12-cycle reaction using the same temperature cycle as described above. The samples were then sent for deep sequencing following additional processing and validation.

The PCR products post indices addition were run on a freshly prepared 2% low-melting-point agarose gel (ThermoFisher Scientific; 16520050) for better separation and recovery of the approx. 120 bp DNA band on the gel. Before sending the sample for NGS, the nucleotide diversity at the randomized 7-mer position was verified by Sanger sequencing. If needed, an optional PCR was carried out to send sufficient sample for Sanger sequencing using 15-20 cycles of 98° C. for 10 s, 60° C. for 30 s, and 72° C. for 10 s with the primers NGS-QC-F: 5'-AATGATACGGCGACCA-CCGAG-3' and NGS-QC-R: 5'-CAAGCAGAAGACGG-CATACGA-3'. Upon validation, the libraries were sent for deep sequencing using the Illumina HiSeq 2500 System (Millard and Muriel Jacobs Genetics and Genomics Laboratory, Caltech; Integrative Genomics Core, City of Hope).

Preparation of rAAV tissue DNA library. The PCR-amplified rAAV DNA library from tissue (see section: In vivo selection (i) (c)) was further amplified with a 1:100 dilution of this DNA as a template to the primers 1527: 5'-ACACTCTTTCCCTACACGACGCTCTTCCGATCTG-ACAAGTGGCCACAAACCACCAG-3' and 1532: 5'-GT-GACTGGAGTTCAGACGTGTGCTCTTCCGATCT-CCTTGGTTTTGAACCCAACCG-3' that are positioned around 50 bases from the randomized 7-mer insertion on the capsid, and that contain the Read1 and Read2 sequences on the 5' end. The DNA was amplified by Q5 Hot Start High-Fidelity 2× Master Mix or NEBNext Ultra II Q5 Master Mix (NEB; M0544) for 10 cycles of 98° C. for 10 s, 59° C. for 30 s, and 72° C. for 10 s. The mixture was purified with a PCR purification kit. The eluted DNA was then used as a template in a second PCR to add the unique indices (single or dual) using the recommended primers (NEB; E7335S, E7500S, E7600S) in a 10-cycle reaction with the same temperature cycle as described above (for DNA and virus library preparation). The extracted DNA was validated by Sanger sequencing and sent for deep sequencing as described in the previous section.

In Vivo Characterization of AAV Vectors

Cloning AAV capsid variants. The AAV capsid variants were cloned into a pUCmini-iCAP-PHP.B backbone (Addgene ID: 103002) using overlapping forward and reverse primers with 11-mer substitution (in case of 7-mer-i variants, the flanking amino acids from AAV9 capsid AA587-588 "AQ" and AA589-590 "AQ" were subjected to codon modification) that spans from the MscI site (at position 581 AA) to the AgeI site (at position 600 AA) on the pUCmini plasmid. The primers were designed for all capsid variants using a custom python script (Code will be made available on github), and since they cover the entire fragment insertion, these primers are self-annealed and amplified using PCR to create a dsDNA fragment without the use of a template DNA. They are amplified by Q5 Hot Start High-Fidelity 2× Master Mix for 20 cycles of 98° C. for 10 s, 60° C. for 30 s, and 72° C. for 10 s. This fragment was then assembled into the MscI/AgeI digested pUCmini-iCAP-PHP.B backbone by the Gibson assembly method. There is a second MscI site on the backbone; however, this was blocked by methylation. The assembled plasmids were then transformed into NEB Stable Competent E. coli (New England Biolabs, Inc; C3040H), and colonies were selected on carbenicillin/ampicillin-LB agar plates.

List of primers used to clone AAV-PHP variants: The variants from 7-mer-i and 3-mer-s libraries were cloned as 11-mer substitution.

TABLE 6

Primers For AAV-PHP Variants

| Variant Name | Amino acid | Nucleotide sequence | Forward primer (5'-3') | Reverse primer (5'-3') |
|---|---|---|---|---|
| AAV-PHP.V1 | AQTALKP FLAQ | GCCCAAA CCGCCCTC AAACCCTT CCTCGCAC AG | GGAGTCCTATGGAC AAGTGGCCACAAA CCACCAGAGTGCCC AAACCGCCCTCAAA CCC (SEQ ID NO: 1032) | TTCCTTGGTTTTGAAC CCAACCGGTCTGCGC CTGTGCGAGGAAGGG TTTGAGGGCGGTTTGG GC (SEQ ID NO: 1047) |
| AAV-PHP.V2 | AQTTLKP FLAQ | GCCCAAA CCACCCTC AAACCCTT CCTCGCAC AG | GGAGTCCTATGGAC AAGTGGCCACAAA CCACCAGAGTGCCC AAACCACCCTCAAA CCC (SEQ ID NO: 1033) | TTCCTTGGTTTTGAAC CCAACCGGTCTGCGC CTGTGCGAGGAAGGG TTTGAGGGTGGTTTGG GC (SEQ ID NO: 1048) |
| AAV-PHP.B4 | AQTLQIPF KAQ | GCCCAAA CGTTGCAG ATTCCTTT TAAGGCA CAG | GGAGTCCTATGGAC AAGTGGCCACAAA CCACCAGAGTGCCC AAACGTTGCAGATT CCT (SEQ ID NO: 1034) | TTCCTTGGTTTTGAAC CCAACCGGTCTGCGC CTGTGCCTTAAAAGG AATCTGCAACGTTTGG GC (SEQ ID NO: 1049) |
| AAV-PHP.B5 | AQTLQLP FKAQ (SEQ ID NO: 1062) | GCCCAAA CCCTCCAA CTCCCCTT CAAAGCC CAA (SEQ ID NO: 1068) | GGAGTCCTATGGAC AAGTGGCCACAAA CCACCAGAGTGCCC AAACCCTCCAACTC CCC (SEQ ID NO: 1035) | TTCCTTGGTTTTGAAC CCAACCGGTCTGCGCT TGGGCTTTGAAGGGG AGTTGGAGGGTTTGG GC (SEQ ID NO: 1050) |
| AAV-PHP.B6 | AQTLQQP FKAQ (SEQ ID NO: 1063) | GCCCAAA CTTTGCAG CAGCCGTT TAAGGCA CAG (SEQ ID NO: 1069) | GGAGTCCTATGGAC AAGTGGCCACAAA CCACCAGAGTGCCC AAACTTTGCAGCAG CCG (SEQ ID NO: 1036) | TTCCTTGGTTTTGAAC CCAACCGGTCTGCGC CTGTGCCTTAAACGGC TGCTGCAAAGTTTGG GC (SEQ ID NO: 1051) |
| AAV-PHP.B7 | AQSIERPF KAQ | GCCCAAA GCATCGA AAGACCCT TCAAAGC ACAG | GGAGTCCTATGGAC AAGTGGCCACAAA CCACCAGAGTGCCC AAAGCATCGAAAG ACCC (SEQ ID NO: 1037) | TTCCTTGGTTTTGAAC CCAACCGGTCTGCGC CTGTGCTTTGAAGGGT CTTTCGATGCTTTGGG C (SEQ ID NO: 1052) |
| AAV-PHP.B8 | AQTMQKP FIAQ | GCCCAAA CCATGCAA AAACCCTT CATCGCAC AG | GGAGTCCTATGGAC AAGTGGCCACAAA CCACCAGAGTGCCC AAACCATGCAAAA ACCC (SEQ ID NO: 1038) | TTCCTTGGTTTTGAAC CCAACCGGTCTGCGC CTGTGCGATGAAGGG TTTTTGCATGGTTTGG GC (SEQ ID NO: 1053) |
| AAV-PHP.C1 | AQRYQGD SVAQ | GCCCAAA GGTATCAG GGTGATTC TGTTGCAC AG | GGAGTCCTATGGAC AAGTGGCCACAAA CCACCAGAGTGCCC AAAGGTATCAGGG TGAT (SEQ ID NO: 1039) | TTCCTTGGTTTTGAAC CCAACCGGTCTGCGC CTGTGCAACAGAATC ACCCTGATACCTTTGG GC (SEQ ID NO: 1054) |
| AAV-PHP.C2 | AQWSTNA GYAQ | GCCCAAT GGTCGAC AAACGCT GGTTACG CACAG | GGAGTCCTATGGA CAAGTGGCCACAA ACCACCAGAGTGC CCAATGGTCGACA AACGCT (SEQ ID NO: 1040) | TTCCTTGGTTTTGAA CCCAACCGGTCTGCG CCTGTGCGTAACCAG CGTTTGTCGACCATT GGGC (SEQ ID NO: 1055) |
| AAV-PHP.C3 | AQERVGF AQAQ | GCCCAAG AGCGTGT AGGTTTC GCACAGG CACAG | GGAGTCCTATGGA CAAGTGGCCACAA ACCACCAGAGTGC CCAAGAGCGTGTA GGTTTC (SEQ ID NO: 1041) | TTCCTTGGTTTTGAA CCCAACCGGTCTGCG CCTGTGCCTGTGCGA AACCTACACGCTCTT GGGC (SEQ ID NO: 1056) |
| AAV-PHP.N | AQTLAVP FSNP (SEQ ID NO: | GCGCAGA CCCTAGCT GTCCCTTT | GGAGTCCTATGGAC AAGTGGCCACAAA CCACCAGAGTGCGC | TTCCTTGGTTTTGAAC CCAACCGGTCTGCGC AGGGTTCGAAAAAGG |

TABLE 6-continued

| | | | Primers For AAV-PHP Variants | |
| --- | --- | --- | --- | --- |
| Variant Name | Amino acid | Nucleotide sequence | Forward primer (5'-3') | Reverse primer (5'-3') |
| | 1064) | TTCGAACC CT (SEQ ID NO: 1070) | AGACCCTAGCTGTC CCT (SEQ ID NO: 1042) | GACAGCTAGGGTCTG CGC (SEQ ID NO: 1057) |
| AAV-PHP.X1 | AQARQM DLSAQ (SEQ ID NO: 1065) | GCCCAAG CCAGACA AATGGAC CTCAGCGC ACAG (SEQ ID NO: 1071) | GGAGTCCTATGGAC AAGTGGCCACAAA CCACCAGAGTGCCC AAGCCAGACAAAT GGAC (SEQ ID NO: 1043) | TTCCTTGGTTTTGAAC CCAACCGGTCTGCGC CTGTGCGCTGAGGTCC ATTTGTCTGGCTTGGG C (SEQ ID NO: 1058) |
| AAV-PHP.X2 | AQTNKVG NIAQ (SEQ ID NO: 1066) | GCCCAAA CCAACAA AGTCGGC AACATCGC ACAG (SEQ ID NO: 1072) | GGAGTCCTATGGAC AAGTGGCCACAAA CCACCAGAGTGCCC AAACCAACAAAGT CGGC (SEQ ID NO: 1044) | TTCCTTGGTTTTGAAC CCAACCGGTCTGCGC CTGTGCGATGTTGCCG ACTTTGTTGGTTTGGG C (SEQ ID NO: 1059) |
| AAV-PHP.X3 | AQQNVTK GVAQ | GCCCAAC AGAACGT AACGAAG GGTGTGG CACAG | GGAGTCCTATGGA CAAGTGGCCACAA ACCACCAGAGTGC CCAACAGAACGTA ACGAAG (SEQ ID NO: 1045) | TTCCTTGGTTTTGAA CCCAACCGGTCTGCG CCTGTGCCACACCCT TCGTTACGTTCTGTT GGGC (SEQ ID NO: 1060) |
| AAV-PHP.X4 | AQLNAIK NIAQ (SEQ ID NO: 1067) | GCCCAAC TCAACGC TATCAAG AACATCG CACAG (SEQ ID NO: 1073) | GGAGTCCTATGGA CAAGTGGCCACAA ACCACCAGAGTGC CCAACTCAACGCT ATCAAG (SEQ ID NO: 1046) | TTCCTTGGTTTTGAA CCCAACCGGTCTGCG CCTGTGCGATGTTCT TGATAGCGTTGAGTT GGGC (SEQ ID NO: 1061) |

AAV vector production. Using an optimized protocol, AAV vectors were produced from 5-10 150 mm plates, which yielded sufficient amounts for administration to adult mice.

AAV vector administration. AAV vectors were administered intravenously to adult male mice (6-8 weeks of age) via retro-orbital injection at doses of 1-10×10$^{11}$ vg. The AAV doses are determined by the experimental needs. CAG-NLS-GFP related experiments for quantification were done at medium dose of 1×10$^{11}$ vg given this was the dose previously determined for AAV-PHP.eB characterization. Otherwise, the non-NLS genome related experiments were done at 3×10$^{11}$ vg, with the exception of Cre-driver lines (GFAP-Cre or Tek-Cre), or a lower strength promoter containing genome (GFAP-NLS-mTurq) where the dose was 1×10$^{12}$ vg. The high dose was chosen to understand the full potential of the new vectors in these systems.

All experiments with vectors carrying CAG, a strong ubiquitous promoter, were incubated for 3 weeks. The 4 week incubations are those that involved expression from Cre driver lines or cell-type specific promoter where it is generally recommended for a longer wait time. The 2 week incubations are those where the vectors carried self-complementary genomes with strong ubiquitous promoters.

Tissue processing. After 3 weeks of expression (unless noted otherwise), the mice were anesthetized with Euthasol (pentobarbital sodium and phenytoin sodium solution, Virbac AH) and transcardially perfused with 30-50 mL of 0.1 M phosphate buffered saline (PBS) (pH 7.4), followed by 30-50 ml of 4% paraformaldehyde (PFA) in 0.1 M PBS. After this procedure, all organs were harvested and post-fixed in 4% PFA at 4° C. overnight. The tissues were then washed and stored at 4° C. in 0.1 M PBS and 0.05% sodium azide. All solutions used for this procedure were freshly prepared. For the brain and liver, 100-μm thick sections were cut on a Leica VT1200 vibratome.

For vascular labeling, the mice were anesthetized and transcardially perfused with 20 mL of ice-cold PBS, followed by 10 mL of ice-cold PBS containing Texas Red-labeled Lycopersicon Esculentum (Tomato) Lectin (1:100, Vector laboratories, TL-1176), and then placed in 30 mL of ice-cold 4% PFA for fixation.

Immunohistochemistry. Tissue sections—typically 100-μm thick—were first incubated in blocking buffer (10% normal donkey serum, 0.1% Triton X-100, and 0.01% sodium azide in 0.1 M PBS, pH 7.4) with primary antibodies at appropriate dilutions for 24 h at room temperature on a rocker. The primary antibodies used in this study were rabbit S100 (1:400, Abcam, ab868), rabbit Olig2 (1:400; Abcam, ab109186), rabbit NeuN (1:400, Abcam, ab177487), and rabbit GLUT-1 (1:400; Millipore Sigma, 07-1401). After primary antibody incubation, the tissues were washed 1-3 times with wash buffer 1 (0.1% Triton X-100 in 0.1 M PBS buffer, pH 7.4) over a period of 5-6 h in total. The tissues were then incubated in blocking buffer with the secondary antibodies at appropriate dilutions for 12-24 h at room temperature and then washed in three times in 0.1 M PBS, pH 7.4 over a total duration of 5-6 h. The secondary antibody used in this study was Alexa Fluor 647 AffiniPure donkey anti-rabbit IgG (H+L) (Jackson ImmunoResearch Lab, 711-605-152). When performing nuclear staining, 4',6-Diamidine-2'-phenylindole dihydrochloride (DAPI, Sigma Aldrich, 10236276001) is used at a 1:1000 dilution in 0.1 M PBS, pH 7.4 and incubated with tissues for 15 minutes followed by a single wash for 10 minutes in 0.1 M PBS, pH 7.4. The DAPI and/or antibody-stained tissue sections were mounted with ProLong Diamond Antifade Mountant (ThermoFisher Scientific, P36970).

Hybridization chain reaction (HCR) based RNA labeling in tissues. Fluorescence in situ hybridization chain reaction (FITC-HCR) was used to label excitatory neurons with VGLUT1 and inhibitory neurons with GAD1 to characterize the AAV capsid variant AAV-PHP.N in brain tissue using an adapted third-generation HCR protocol. To characterize the AAV capsid variant AAV-PHP.N in brain tissue, HCR method was sought to label excitatory and inhibitory neurons. Fluorescence in situ hybridization chain reaction (FITC-HCR) was used to label excitatory neurons with VGLUT1 and inhibitory neurons with GAD1. Adapting the third-generation HCR, 13 probe sets were designed for each target by using custom-made software (https://github.com/GradinaruLab/HCRprobe). After 3 weeks of expression, the mice were transcardially perfused and fixed as described earlier (Section D. Tissue processing). To minimize RNase enzyme exposure in fixed tissues, following overnight fixation in 4% PFA, the tissues were washed and stored at 4° C. in 0.1 M RNase-free PBS and 0.05% sodium azide. The harvested brains were henceforth handled with care to avoid exposure to RNase using reagents such as RNAlater stabilization solution/RNase-free PBS/RNaseZap (ThermoFisher Scientific, AM7021, AM9624, AM9780). Once the harvested brains were sagittally sliced to 100-µm thick sections, FITC-HCR was performed to detect both genes. Tissue slices were permeabilized with 0.1% Triton X-100 in 0.1 M RNase-free PBS for 1 h at RT and pre-hybridized in hybridization solution (10% dextran sulfate and 10% ethylene carbonate in 2×SSC buffer (saline-sodium citrate)) for >30 min at 37° C. The designed probes were diluted in hybridization solution to get a final concentration of 2 nM. The tissue sections were then subjected to hybridization with the probes overnight at 37° C. Following this, the sections were washed with pre-warmed wash buffer (10% ethylene carbonate in 2×SSC) at 37° C. for 30 min twice, followed by 2×SSC at RT for 30 min twice. Amplification with hairpin pairs (Molecular Technologies, CA) were performed in amplification buffer (10× dextran sulfate in 2×SSC); hairpins were snap-cooled at 95° C. for 90 s, followed by RT for 30 min, and diluted with amplification buffer (60 nM). Tissues were then incubated in this amplification buffer with hairpins overnight at RT with gentle agitation. Once the amplification was done, samples were briefly washed with 2×SSC and mounted in Prolong Diamond for imaging.

Imaging and image processing. All images in this study were acquired either with a Zeiss LSM 880 confocal microscope using the objectives Fluar 5×0.25 M27, Plan-Apochromat 10×0.45 M27 (working distance 2.0 mm), and Plan-Apochromat 25×0.8 Imm Con DIC M27 multi-immersion; or with a Keyence BZ-X700 microscope. The acquired images were processed in Zen Black 2.3 SP1 (Zeiss), BZ-X Analyzer (Keyence), Illustrator CC 2018 (Adobe), Photoshop CC 2018 (Adobe), and Imaris (Bitplane). To prevent any imaging artifacts resulting from multiple fluorescence spectral overlap, the fluorescence excitation and emission spectra were kept distinct following the recommended linear unmixed acquisition of individual colors. A far-red fluorescent dye was chosen for any additional marker staining to keep the imaging parameters distinct from in vivo fluorescent expression thereby preventing any spectral overlap across detector channels. The tissues were routinely monitored for auto fluorescence or imaging artifacts before acquisition, and imaging parameters were adjusted if needed. The imaging parameters were cross-checked with tissues lacking in vivo transduction to avoid any imaging artifacts. The regions used for the images were closely matched across experimental groups to minimize bias during comparisons.

Tissue clearing and imaging of thick tissues. To demonstrate the ability of PHP.V1 to transduce the vasculature across thick tissues, such as half of a mouse-brain hemisphere or a femur bone, tissue from Tek-Cre mice was assessed after 4 weeks' of expression.

The brain hemisphere was stained with the primary antibody, Anti-GFP (Ayes Labs, GFP-1020), and the secondary antibody, goat anti-Chicken IgY, Alexa Fluor 633 (ThermoFisher Scientific, A-21103), and cleared via the iDISCO protocol[38]. For imaging, a commercial light-sheet microscope (Lavision BioTec) with a custom objective lens (4×) was used. The resulting image files were reorganized by a custom MATLAB script to allow stitching with TeraStitcher. For 3-D visualization, Imaris (Bitplane) was used.

To image the mouse femur bone, the bones were sectioned to 300 µm thickness for antibody penetration and stained with the primary antibody, Anti-GFP, and the secondary antibody, Alexa Fluor 488 donkey anti-chicken IgY (Jackson ImmunoResearch Lab, 703-545-155), and then cleared via the TDE (2-2'-thiodiethanol) clearing method[41]. The images were acquired with a confocal microscope (Zeiss LSM 880) and visualized in Imaris software.

Tissue processing and imaging for quantification of rAAV transduction in vivo. For quantification of rAAV transduction, 6- to 8-week-old male mice were intravenously injected with the virus, which was allowed to express for 3 weeks (unless specified otherwise). The mice were randomly assigned to groups and the experimenter was not blinded. The mice were perfused and the organs were fixed in PFA. The brains and livers were cut into 100-µm thick sections and immunostained with different cell-type-specific antibodies, as described above. The images were acquired either with a 25× objective on a Zeiss LSM 880 confocal microscope or with a Keyence BZ-X700 microscope; images that are compared directly across groups were acquired and processed with the same microscope and settings.

For quantification of PHP.B-family variant transduction in tissues, the images were acquired using 25× objective with 1× digital zoom on a Zeiss LSM 880 confocal microscope. With n=3 mice per variant, images were acquired across 4 brain regions—cortex, striatum, ventral midbrain and thalamus, and tissues were stained with 3 cell type markers (NeuN, Olig2, and S100). For each mouse, 2 images per brain region per cell type marker were acquired, and the mean were plotted.

For PHP.N transduction analysis, the images were acquired using 20× objective on Keyence BZ-X700 microscope. With n=3 mice, images across 4 brain regions—cortex, striatum, ventral midbrain and thalamus were acquired to cover the entire brain regions for 3 cell type markers (NeuN, Olig2, and S100). This involved 6-8 images to cover cortex, thalamus and striatum, and 2 images to cover ventral midbrain per mouse per cell-type marker. For each mouse, across each region, the mean from the images were plotted.

For PHP.V GLUT1⁺ transduction analysis, the images were acquired using 25× objective with 1× digital zoom on a Zeiss LSM 880 confocal microscope. Each distinct blood vessel in the image with GLUT1⁺ staining and XFP expression was determined as positive for transduction. Quantification of expression from the CAG-mNeonGreen vector was performed across the cortex (n=3 per group). Each data point is drawn from the mean of 3-2 images per mouse. Different brain regions were quantified for Tek-Cre and Ai14 mouse experiments with n=2 per group. For cortex, cerebellum, striatum and ventral midbrain, the mean was plotted from 3-4 images per mouse per region.

In Vitro Characterization of AAV Vectors

Human Brain Microvascular Endothelial Cells (HBMEC) (ScienCell Research Laboratories, Cat. 1000) were cultured as per the instructions provided by the vendor. HBMEC were cultured from a frozen stock vial in fibronectin-coated T-75 flask (7000-9000 cells/cm$^2$ seeding density) using the Endothelial Cell Medium (Cat. 1001). The cells were sub-cultured in fibronectin-coated 48-well plates (0.95 cm$^2$ growth area) at the recommended seeding density and incubated at 37° C. for ~24-48 h till the cells were completely adherent with ~70-80% confluence. The viral vectors packaging pAAV-CAG-mNeongreen were added to the cell culture at a dose of either 1×10$^8$ or 1×10$^{10}$ vg per well (3 wells per dose per vector). The media was changed 24 hours later and the culture was assessed for fluorescence expression at 3 days' post infection. Per vendor recommendation, the culture media was changed every other day to maintain the cell culture.

Data Analysis

Quantification of rAAV vector transduction in mouse tissue. Manual counting was performed with the Adobe Photoshop CC 2018 Count Tool for cell types in which expression and/or antibody staining covered the whole cell morphology. The Keyence Hybrid Cell Count software (BZ-H3C) was used where the software could reliably detect distinct cells in an entire dataset. To maintain consistency in counting across different markers and groups, one person was assigned to quantify across all groups in all brain areas.

Manual counting was performed for GLUT-1-stained blood vessels and expression of the ssAAV:CAG-mNeon-Green and ssAAV:CAG-DIO-EYFP, where the efficiency was calculated as the percentage of XFP+ vessels relative to the GLUT-1 staining. Manual counting was also performed to quantify nuclear or soma stained cells, including NeuN−, Olig2−, and S100-stained cells. The efficiency was calculated as the percentage of XFP+ cells relative to cell-marker+ cells.

Keyence Hybrid Cell Count software (BZ-H3C) was used to quantify expression of nuclear localized AAV genomes in liver hepatocytes that co-localized with the DNA stain, DAPI; and also for the study involving ssAAV:GFAP-2xNLS-mTurquoise2 genomes with S100 cell marker.

The mean fluorescence intensity across microscopic images were quantified using ImageJ software. The images were processed for background subtraction and using the Threshold operation, the mean fluorescence intensity was measured.

NGS data alignment and processing. The raw fastq files from NGS runs were processed with custom built scripts (codes will be made available on Github) that align the data to AAV9 template DNA fragment containing the diversified region 7×NNK (for R1) or 11×NNN (for R2 since it was synthesized as 11×NNN). The pipeline to process these datasets involved filtering the dataset to remove the low-quality reads by using the deep sequencing quality score for each sequence. The variant sequences were then recovered from the sequencing reads by searching for the flanking template sequences, and extracting the nucleotides of the diversified region (perfect string match algorithm). The quality of the aligned data was further investigated to remove any erroneous sequences (such as ones with stop codons). The raw data was plotted (as shown in Supplementary FIG. 1e) to study the quality of recovery across every library. Based on the RC distribution, we adapted a thresholding method to remove plausible erroneous mutants that may have resulted from PCR or NGS based errors. The assumption is that if there is a PCR mutation or NGS error on the recovered parent sequence, the parent must have existed at least one round earlier than the erroneous sequence, and thus a difference in RCs should exist.

For R1 tissue libraries, a steep drop was observed in the slope of the distribution curve following a long tail of low count sequences, and were found to be rich in sequences that are variations of the parents in the higher counts range. A threshold for RCs was manually set to remove such erroneous mutants. The thresholded data were then processed differently based on the experimental needs as described elsewhere using custom Python based scripts.

For R2 tissue libraries from PCR pool and synthetic pool, given the smaller library size compared to R1, the data was thresholded in two steps. Only the tissue recovered sequences that were present in the respective input DNA and virus library were considered (after removing lower count variants from input libraries following the same principle as R1 tissue libraries). This step partially removed the long tail of low count reads. As a second step, the thresholding that was described for R1 tissue libraries was applied.

While it is plausible that true variants may be lost during thresholding, this method minimized false positives as the low count mutants in tissue and virus libraries often seemed to have very high enrichment score (as RCs are normalized to input library). In other words, thresholding allowed selective investigation on positively and negatively enriched variants that had a higher-confidence in their NGS RCs.

As an alternative to the manual thresholding method, an optional error correction method called "Collapsing" was built to further validate the outcome from filtered datasets. This method starts at the lowest count variants (variants of count 1) and searches for potential parent variants that are off by one nucleotide but have at least 2-fold higher counts (fold change=$2^{ACT}$) where CT is PCR cycle threshold). This error correction method then transfers the counts of these potential erroneous sequences to their originating sequences and repeats recursively until all sequences have been considered. On applying this error correction to the thresholded data, an additional ~0.002-0.03% of sequences were captured (compared to >19% captured by thresholding), confirming that the thresholding strategy was largely successful.

NGS data analysis. The aligned data were then further processed via a custom data-processing pipeline, with scripts written in Python (available on Github). The enrichment scores of variants (Total=N) across different libraries were calculated from the read counts (RCs) according to the following formula: Enrichment score=log 10 [(Variant 1 RC in tissue library1/Sum of variants N RC in library1)/(Variant 1 RC in virus library/Sum of variants N RC in virus library)]

To consistently represent library recovery between R1 and R2 selected variants, the enrichment score of the variants in R1 selection was estimated. The standard score of variants in a specific library was calculated using this formula: Standard score=(read count_i−mean)/standard deviation. Where read count_i is raw copy number of a variant i, Mean is the mean of read counts of all variants across a specific library, Standard deviation is the standard deviation of read counts of all variants across a specific library.

Since the DNA and virus libraries were not completely sampled unlike the tissue libraries, we assigned an estimated RC for variants that were not present in the input library but were present in the output library. For instance, R1 virus library is the input library to the R1 tissue libraries. The estimated RC is defined as a number that is lower than the lowest RC in the library with the assumption that these variants were found at a relatively lower abundance than the variants recovered from the deep sequencing. In virus libraries, since RC of 1.0 was the lowest, we assigned all missing variants an estimated RC of 0.9. We use this method to calculate the enrichment score of the R1 tissue libraries which is normalized to R1 virus library (FIG. 1d). This was done to represent libraries across two selection rounds consistently. Although, the individual enrichment score among R1 variants didn't add a significant value to the variants selected for R2 selection as described in the criteria to separate signal vs noise in R1 using the RCs.

Heatmap generation. The relative AA distributions of the diversified regions are plotted as heatmaps. The plots were generated using the Python Plotly plotting library. The heatmap values were generated from custom scripts written in Python, using functions in the custom "pepars" Python package. Each heatmap uses both an expected (input) distribution of amino acid sequences and an output distribution. The output distribution must be a list of sequences and their count, and the input distribution can be either a list of sequences and their count, or an expected amino acid frequency from a template, such as NNK. For both input and output, the total count of amino acids in each position is tallied in accordance to each sequence's count and then divided by the total sum of counts, giving a frequency of each amino acid at each position. Then, the log 2 fold change is calculated between the output and the input. For amino acids with a count of 0 in either the input or output, no calculation is performed. In order to distinguish between statistically significant amino acid biases, a statistical test was performed using the statsmodels Python library. For the case where there are two amino acid counts, a two-sided, two-proportion z-test was performed; for comparing the output amino acid count to an expected input frequency from a template, a one-proportion z-test was performed. All p-values were then corrected for multiple comparisons using Bonferroni correction. Only bias differences below a significance threshold of 1e-4 are then outlined on the heatmap; all other (insignificant) squares are left empty.

Clustering analysis. Using custom scripts written in MAT-LAB (version R2017b; MathWorks) the reverse Hamming distances representing the number of shared AAs between two peptides was determined. Cytoscape (version 3.7.1[53]) software was then used to cluster the variants. The AA frequency plot representing the highlighted cluster was created using Weblogo (Version 2.8.2). The reverse Hamming distances (representing the number of shared AAs between two peptides) was determined for all unique capsid variants with greater than 10 count and greater than 2.5-fold enrichment after R2 selection. This process iteratively compares each variant with all other variants within the group. Capsid variants were then clustered by their reverse Hamming distances using Cytoscape. The minimum reverse Hamming distance for visualization was chosen manually based on sequence similarity.

For the amino acid frequency plots, the number on the bottom represents the position of the diversified motif starting from 1. The size of the amino acid in the stack reflects the proportion of unique clones in which the AA appears at that specific position in the motif. The color code is based on the AA properties. The positively charged residues K, R, and H are in blue. The negatively charged residues D and E are in red. The amide containing polar residues Q, and N are in magenta. The polar residues T, and S, are in green. The hydrophobic residues A, L, V, I, P, F, M, and W are in black.

Example 3. Multiplexed-CREATE Allows Detailed Characterization of the Capsid Libraries During Round-1 Selection To identify variants that enrich in specific cell types or organs parallel selections across multiple targets were performed, and the enrichment or depletion of each capsid variant across those targets was mapped.

Figure 3:
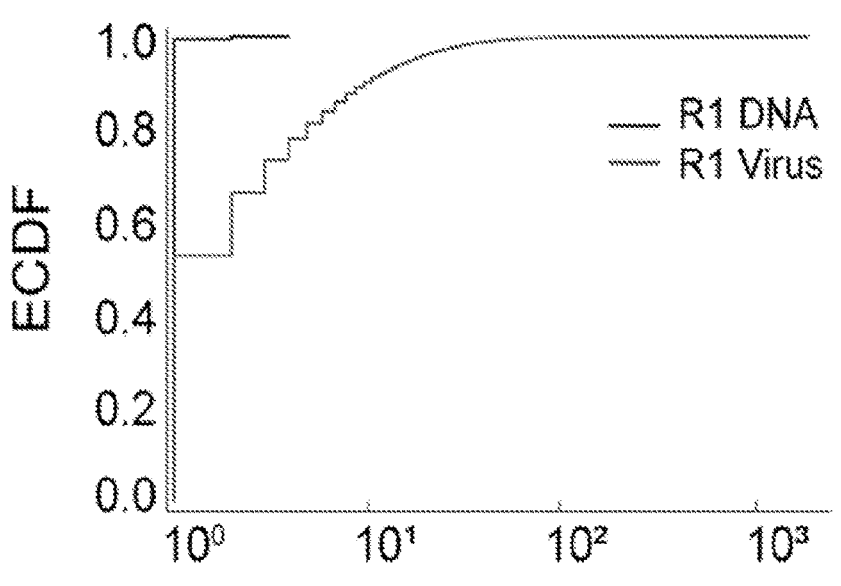
FIG. 3 shows Empirical Cumulative Distribution Frequency (ECDF) of R1 DNA and virus libraries that were recovered by deep sequencing post Gibson assembly and virus production, respectively.
Figure 38:
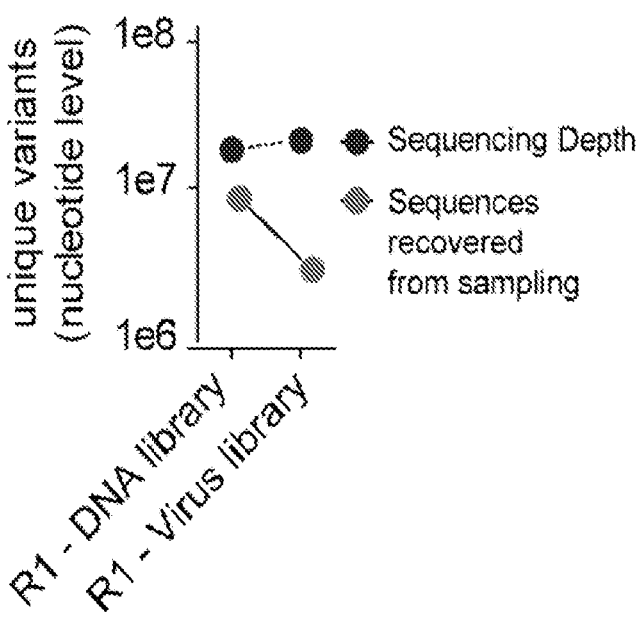
FIG. 38 illustrates the library coverage for R1 DNA and virus libraries obtained from specific sequencing depths.
Figure 39:
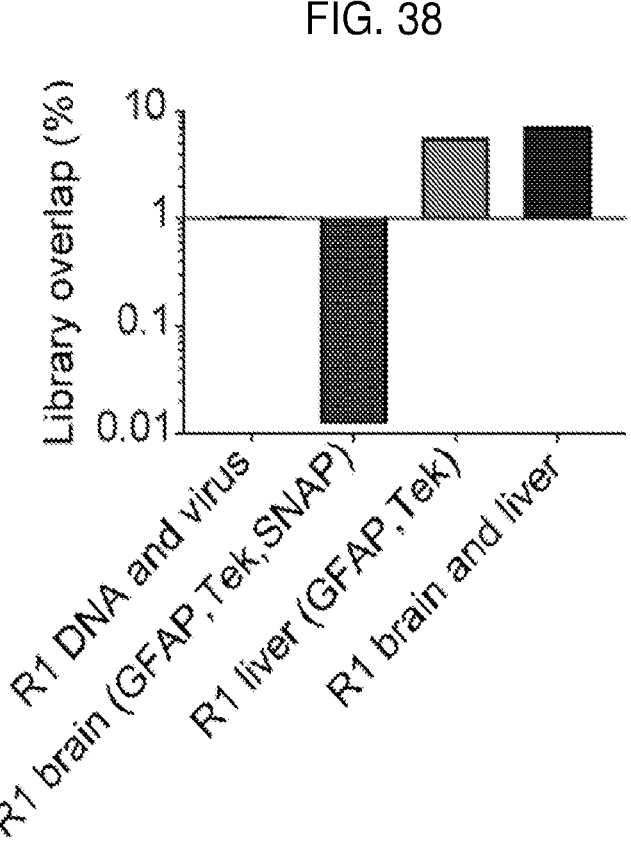
FIG. 39 shows the percentage of variant overlap within the sampled DNA and virus, or across different Cre lines within tissues, or across tissues from R1 selection.

During DNA and virus library generation there is potential for accumulation of biases that over-represent certain capsid variants, obscuring their true enrichment during in vivo selection. These biases may result from PCR amplification bias in the DNA library or sequence bias in the efficiency of virus production across various steps: capsid assembly, genome packaging and stability during purification. This was investigated with the 7-mer-i library, a randomized 7-mer library inserted between positions 588-589 of AAV9 (FIGS. 1 and 2) in rAAV-ΔCap9-in-cis-Lox2 plasmid (FIG. 36). Sequencing libraries after DNA assembly and virus purification to a depth of 10-20 million (M) reads was adequate to capture the bias among variants during virus production (FIG. 3; despite ~1% variant overlap among these libraries; FIGS. 38 and 39), demonstrating that even permissive sites like 588-589 will impose biological constraints on sampled sequence space. The DNA library had a uniform distribution of 9.6 M unique variants within ~10 M total reads (read count (RC) mean=1.0, S.D.=0.074), indicating minimal bias. In contrast, the virus library had 3.6 M unique variants within ~20 M depth (RC mean=4.59, S.D.=11.15) indicating enrichment of a subset of variants during viral production.

For in vivo selection, the 7-mer-i viral library was intravenously injected at a dose of $2 \times 10^{11}$ vg per adult transgenic mouse expressing Cre in different brain cell types: GFAP-Cre mice for astrocytes, SNAP25-Cre mice for neurons, and Tek-Cre mice for endothelial cells (n=2 mice per Cre transgenic line, see Methods). Two weeks after intravenous (IV) injection, the brain and liver tissues were harvested, with the latter serving as a control organ since AAV9 transduces it with high efficiency. The rAAV genomes were extracted from tissues and the capsids that transduced Cre-expressing cells were selectively amplified (FIGS. 40-44). Upon deep sequencing, $\sim 8 \times 10^4$ unique nucleotide variants recovered from brain tissues and <50 variants in spinal cords (~48% of which were identified in virus library) were observed across the transgenic lines, and each variant was represented with an enrichment score reflecting the

| Design Parameters | Synthetic pool design | PCR pool design |
| --- | --- | --- | change in relative abundance between the brain and the starting virus library (FIG. 4).

Two features of this dataset stand out. First, the recovered variants in brain tissue were disproportionately represented among the fraction of the transformed capsid library observed by sequencing after viral production demonstrating how production biases skew selection results. Second, the distribution of capsid read counts (RCs) revealed that more than half of the unique recovered variants after selection appear at remarkably low read counts. These variants may either be unintended mutants from experimental manipulation or AAV9-like variants with low basal level of CNS transduction (FIG. 40).

Example 4. A Novel Round-2 Library Design Improves the Selection Outcome

Concerned that the sequence bias during viral production and recovery would propagate across selection rounds despite post-hoc enrichment scoring, an unbiased library was designed based on the round-1 (R1) output (synthetic pool library) via oligo pools (Twist Bioscience). This library was compared to a library PCR amplified directly from the recovered R1 DNA (PCR pool library) (FIG. 5, Table 7).

Table 7: Comparison between the two methods for R2 selection. The table summarizes the pros and cons of selection design parameters by the synthetic pool and PCR pool R2 selection methods.

| Carryover of R1 selection bias among variants | No, likelihood of false positives is low | Yes, potential to minimize by normalization |
|---|---|---|
| Carryover of R1 selection induced mutants | No | Yes |
| Confidence in library performance | High, using alternate codon replicates | Low |
| Customize library or add internal controls | Yes, in an unbiased manner | Yes, with greater risk of bias |
| Control library size | Yes, without reducing libraries or pooling | Yes, with libraries reduced for pooling |
| Cost for R2 library generation | High | Low |

The synthetic pool library design comprised: (1) equimolar amounts of ~8950 capsid variants present at high read counts in at least one of the R1 selections from brain and spinal cord (FIG. 40); (2) alternative codon replicates of those ~8950 variants (optimized for mammalian codons) to reduce false positives; and (3) a "spike-in" library of controls (FIGS. 74 and 75), resulting in a total library size of 18,000 nucleotide variants.

Figure 7:
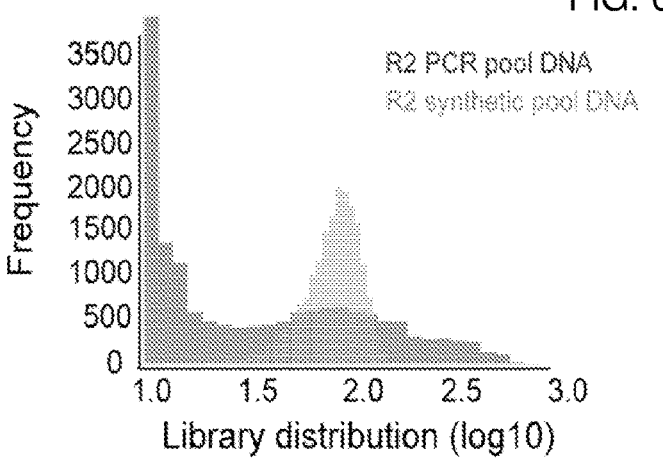
FIG. 7 shows histograms of DNA and virus libraries from the two methods, where the variants in a library are binned by their read counts (in log 10 scale) and the height of the histogram is proportional to their frequency.
Figure 46:
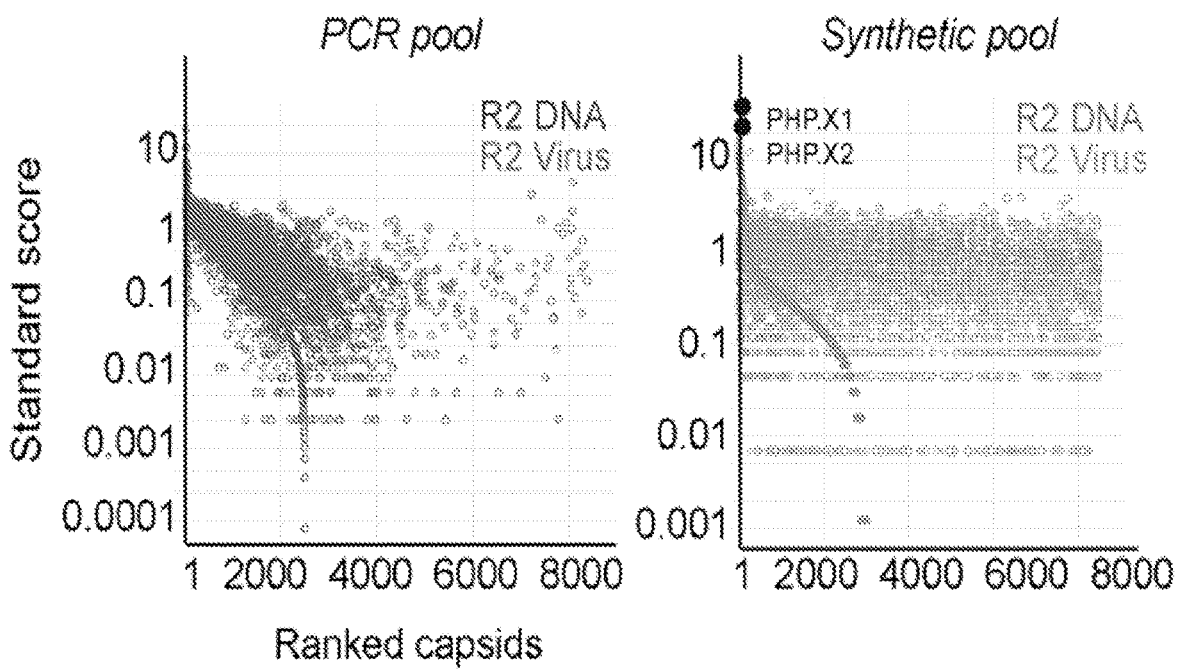
FIG. 46 shows distributions of the DNA and virus libraries produced by the synthetic pool and PCR pool methods by the standard score of NGS read counts. The variants in virus libraries are sorted by the decreasing order of standard score and their scores from respective DNA libraries are mapped onto them.
Figure 47:
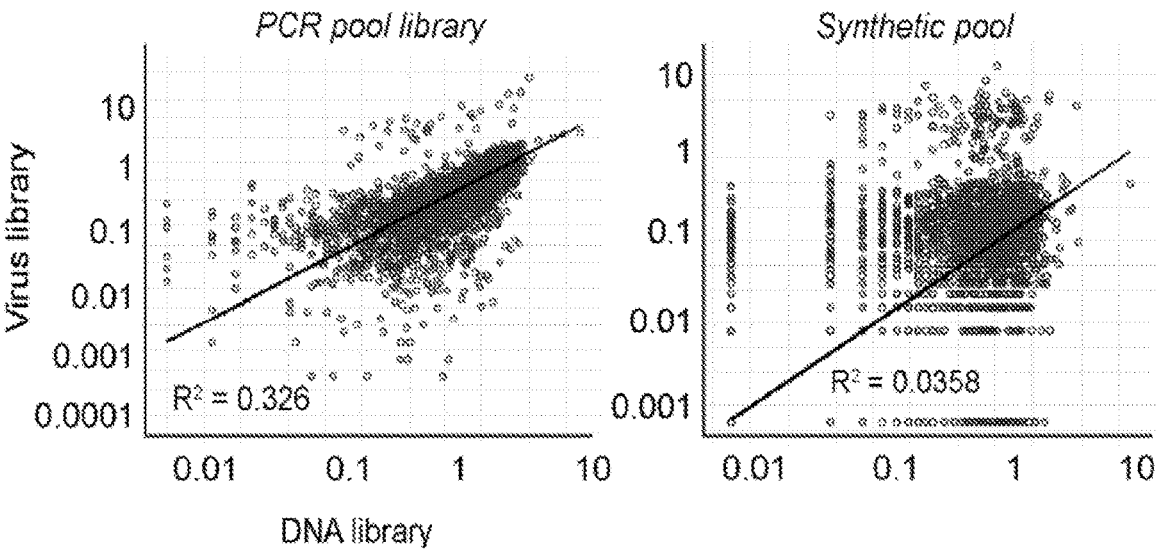
FIG. 47 shows correlations between the standard scores of read counts for the DNA and virus libraries (n=1 per library) produced by the synthetic pool and PCR pool methods is determined by linear least-squares regression, and the regression line (best fit) and R2 representing the coefficient of determination.

As anticipated, both round-2 (R2) virus libraries produced a high titer (~6×10$^{11}$ vg per 10 ng of R2 DNA library per 150 mm dish; FIG. 45), and ~99% of variants from the R2 DNA were found after viral production (FIG. 6). However, the distribution of the DNA and virus libraries from both designs differed significantly. The PCR pool library carries forward the R1 selection biases (FIGS. 7, 46, and 47) where the abundance reflects prior enrichment across tissues in R1 as well as bias from viral production and sample mixing. Comparatively, the synthetic pool DNA library is more evenly distributed, minimizing bias amplification across selection rounds.

Figure 8:
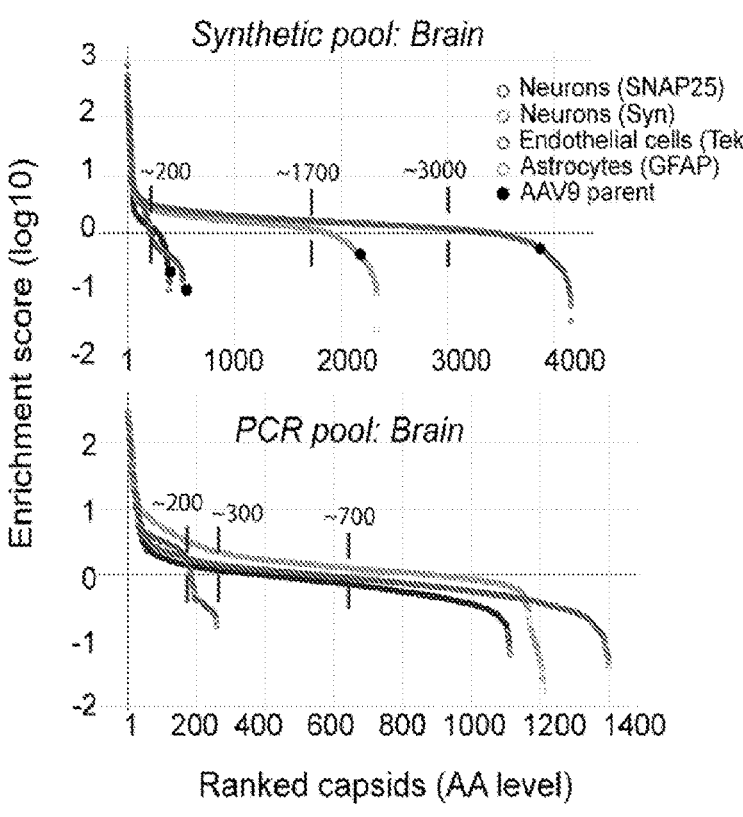
FIG. 8 shows distributions of R2 brain libraries from all Cre transgenic lines (n=2 mice per Cre Line, mean is plotted) and both methods, where the libraries are sorted in decreasing order of enrichment score (log 10 scale). The total number of positively enriched variants from these libraries are highlighted by dotted straight lines and AAV9's relative enrichment is mapped on the synthetic pool plot.
Figure 48:
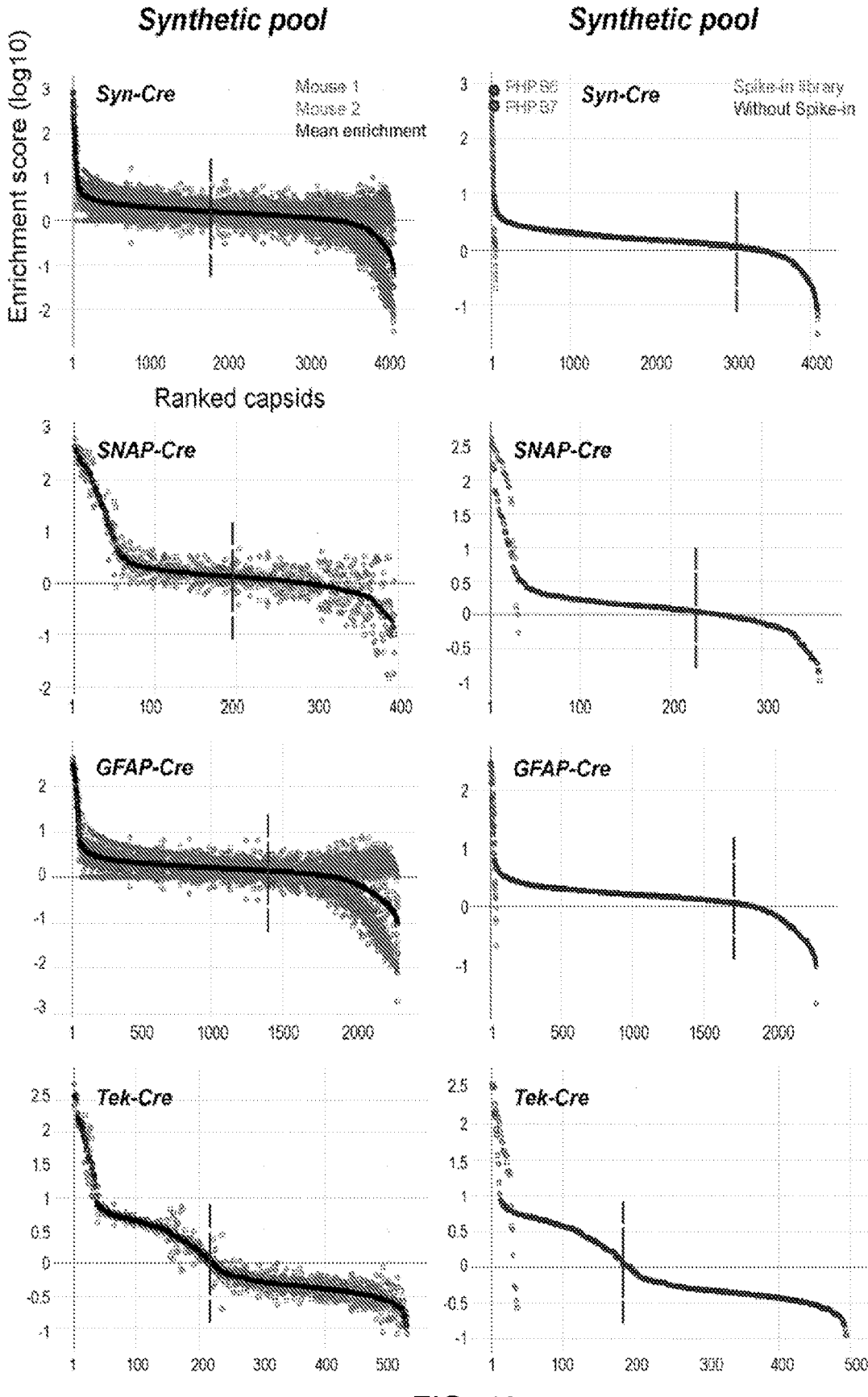
FIG. 48 shows distributions of capsid libraries from brain tissue of two mice used in each Cre line selection, as produced by the synthetic pool (left) and PCR pool (right) designs. The distribution of spike-in library introduced in the synthetic pool library design is shown at center.
Figure 48:
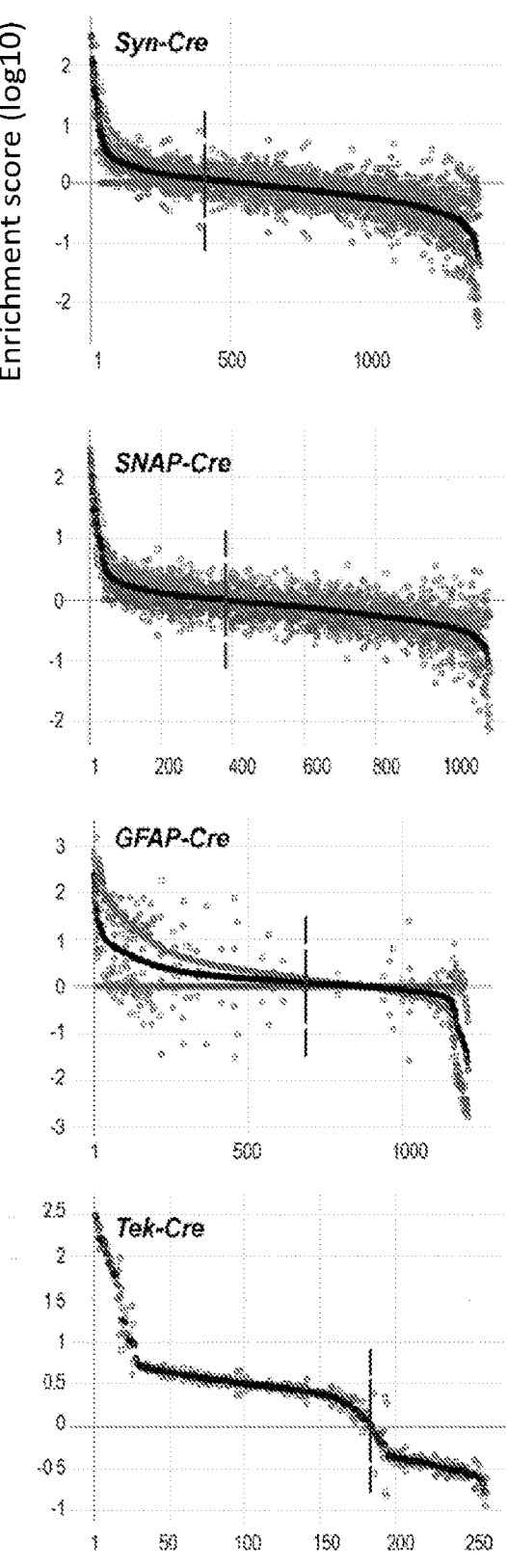

For in vivo selection, a dose of 1×10$^{12}$ vg per adult transgenic mouse was administered into three of the previously used lines (n=2 mice per Cre transgenic line—GFAP, SNAP25, Tek), as well as the Syn-Cre line (for neurons). Two weeks after IV injection, rAAV genomes from brain samples were extracted, selectively amplified, and deep sequenced (as in R1). The synthetic pool library produced a greater number of positively enriched capsid variants than the PCR pool brain library (e.g. ~1700 versus ~700 variants/tissue library at amino acid (AA) level in GFAP-Cre) (FIGS. 8 and 48). In the synthetic pool, ~90% of the variants from the spike-in library were positively enriched as expected (FIG. 48, middle panel; FIG. 74).

Figure 9:
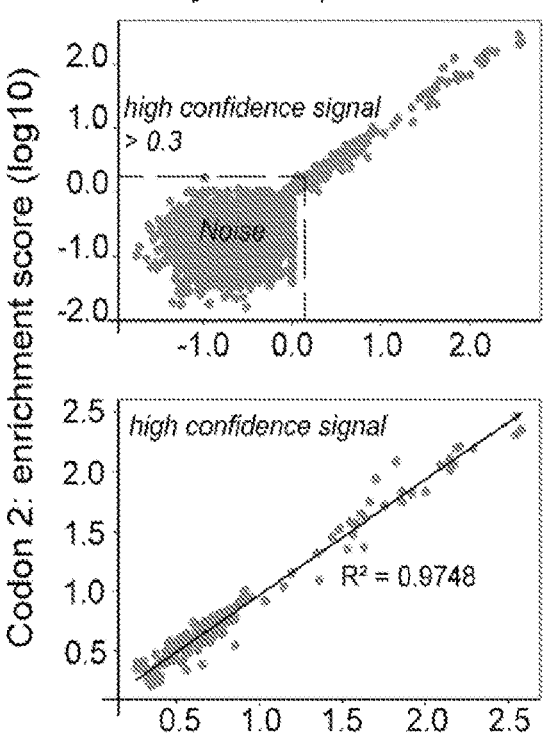
FIG. 9 shows a comparison of the enrichment scores (log 10 scale) of two alternate codon replicates for 8462 variants from the Tek-Cre brain library (n=2 mice, mean is plotted). The broken line separates the high-confidence signal (>0.3) from noise. For the high-confidence signal (below), a linear least-squares regression is determined between the 2 codons and the regression line (best fit). The coefficient of determination R2 is shown.
Figure 50:
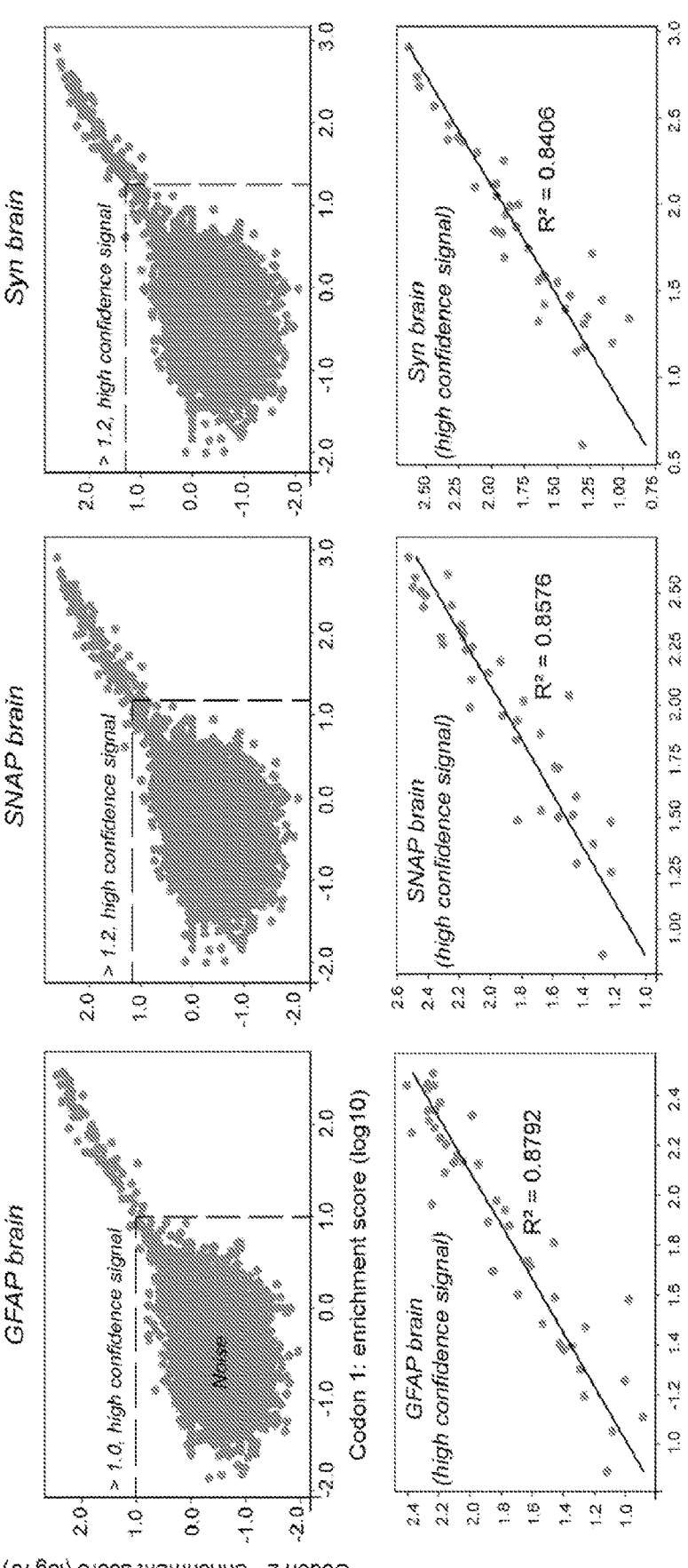
FIG. 50 shows correlation analysis between the enrichment score (log 10) of two alternate codon replicates of variants from the GFAP-Cre (left), SNAP-Cre (center), and Syn-Cre (right) brain libraries by linear least-squares regression (n=2 per Cre line, mean is plotted). The dotted line separates the high-confidence signal from noise. High confidence signal (below) is assessed by a linear regression line (best fit) and R2 represents the coefficient of determination.
Figure 51:
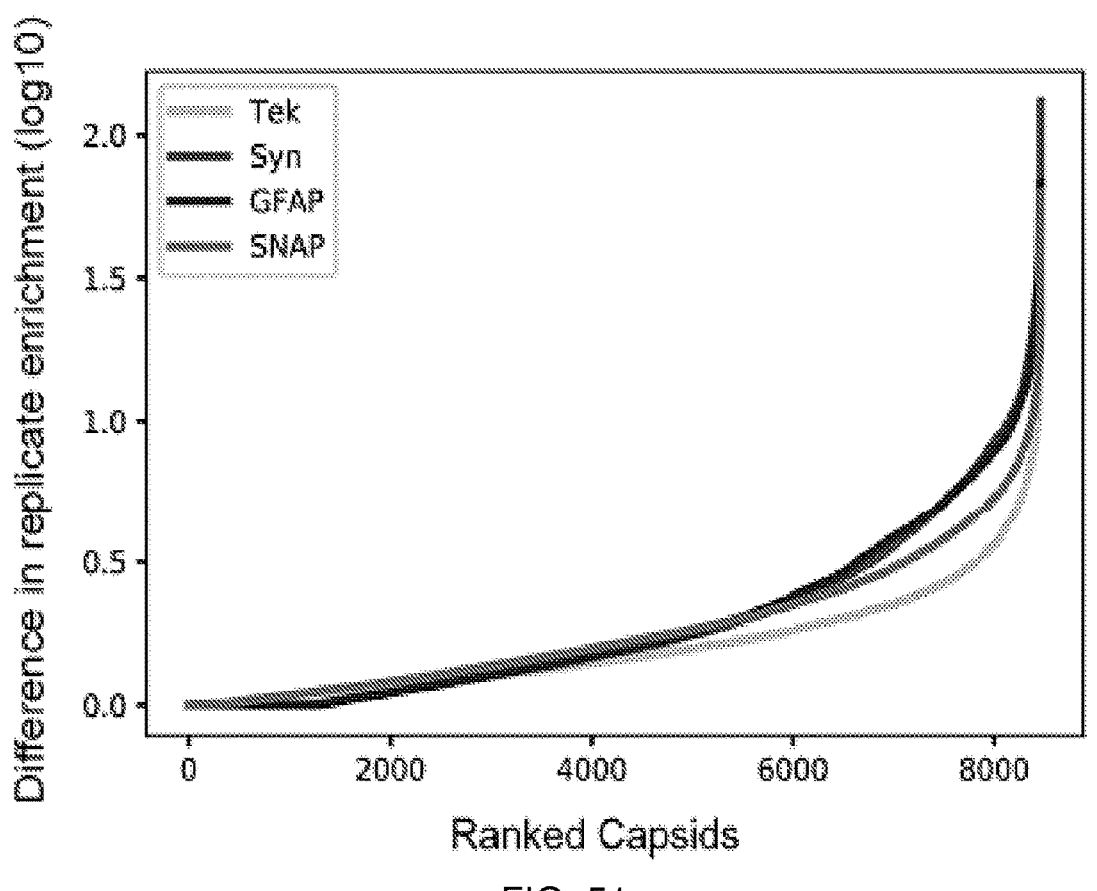
FIG. 51 shows the difference in enrichment score between the two codon replicates of a variant, across different brain libraries, with over 8000 variants recovered in replicates.

The degree of correlation for enrichment scores of variants recovered from both PCR and synthetic pool libraries varies in each Cre transgenic line, demonstrating the presence of noise within experiments (FIG. 49). The synthetic pool's codon replicate feature addresses this predicament by pinpointing the level of enrichment needed within each selection to rise above noise (FIGS. 9, 50, and 51). This is a significant advantage over the PCR pool design, allowing researchers to confidently interpret enrichment scores in a given selection.

The degree of enrichment at which correlation breaks down appears to vary with Cre-line. A downside of PCR pool is that there is no way to tell whether it or synthetic pool is the more 'true' enrichment score or even that there may be cause for concern regarding certain enrichment values. The correlation among positively enriched variants between the two methods was found to improve with the magnitude of positive enrichment. For each experiment there is a level of enrichment below which the scores become irreproducible, or noisy. FIG. 50 demonstrates that neither PCR pool nor Synthetic pool is inherently more 'true' at lower enrichment scores. This is because Synthetic pool methodology with its codon replicates has a self-contained control to determine an enrichment level below which enrichment value has no further predictive power. The term 'noise' has been used herein to refer to regions of enrichment in a particular experiment below which values lose their reproducibility and predictive power. Being able to experimentally determine enrichment signal above noise allows researchers to focus their attention and data analyses on enrichment levels that are internally reproducible and thereby avoid selecting false positive variants or drawing invalid conclusions.

Thus, if one is interested in only the highest enriched variants for a particular tissue, PCR pool design coupled with enrichment normalization to virus library may not drastically differ from synthetic pool design over one additional round of selection for a subset of in vivo selections (such as Tek-Cre or SNAP-Cre). Without additional validation, however, it is difficult to predict whether a given in vivo system will perform akin to Tek-Cre. This becomes critical in a multiplexed selection study where target-specific variants may not garner the highest enrichments in one particular in vivo selection.

Example 5. Analysis of AAV Capsid Libraries After Round-2 Selections

Figure 10:
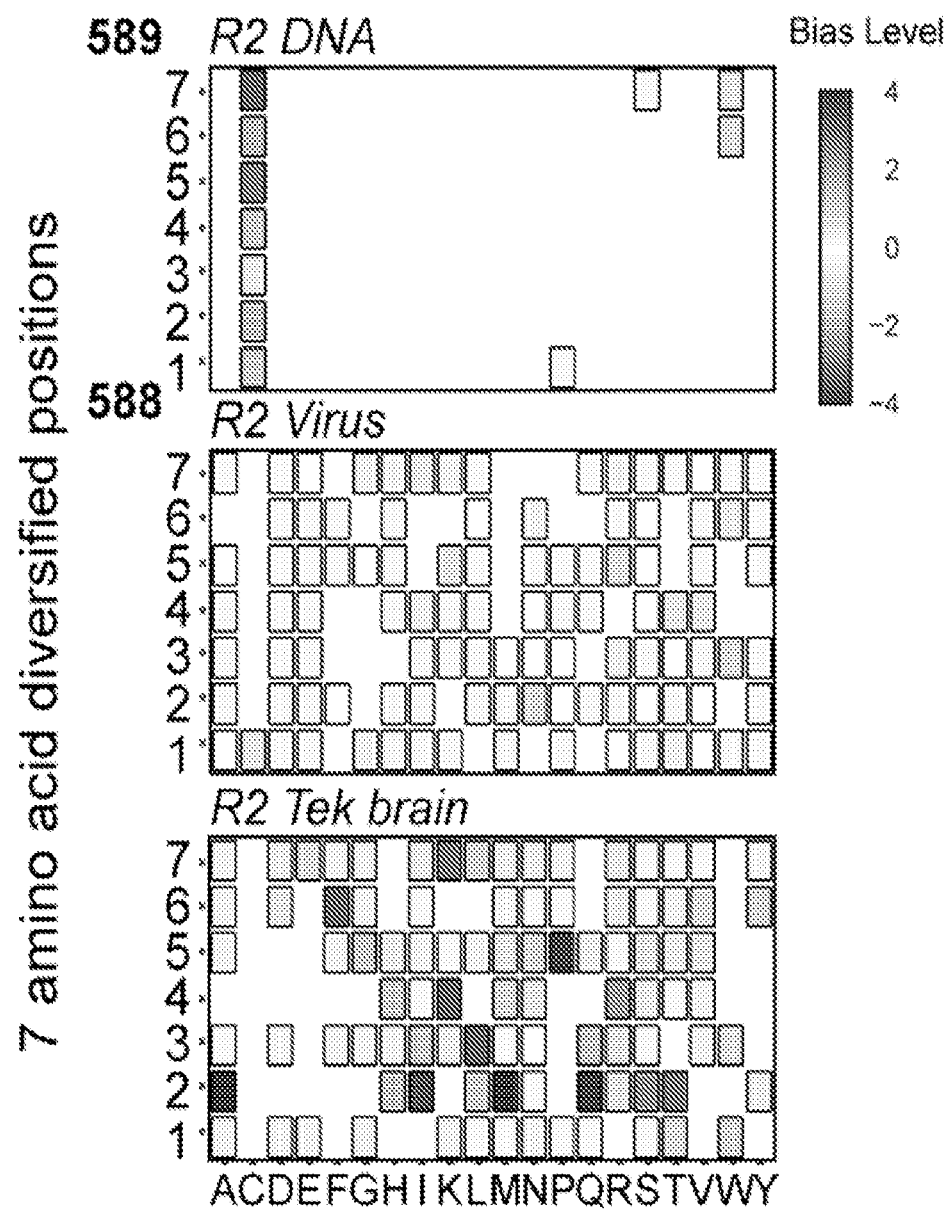
FIG. 10 shows heatmaps representing the magnitude (log 2 fold change) of a given AA's relative enrichment or depletion at each position given statistical significance is reached (boxed if P-value≤0.0001, two-sided, two-proportion z-test, p-values corrected for multiple comparisons using Bonferroni correction). R2 DNA normalized to oligopool (top, ~9000 AA sequences), R2 virus normalized to R2 DNA (middle, n=~9000 sequences), R2 Tek brain library with enrichment over 0.3 (high-confidence signal) from synthetic pool method normalized to R2 virus (bottom, 154 sequences) (n=2 for brain library, one per mouse. All other libraries, n=1).
Figure 52:
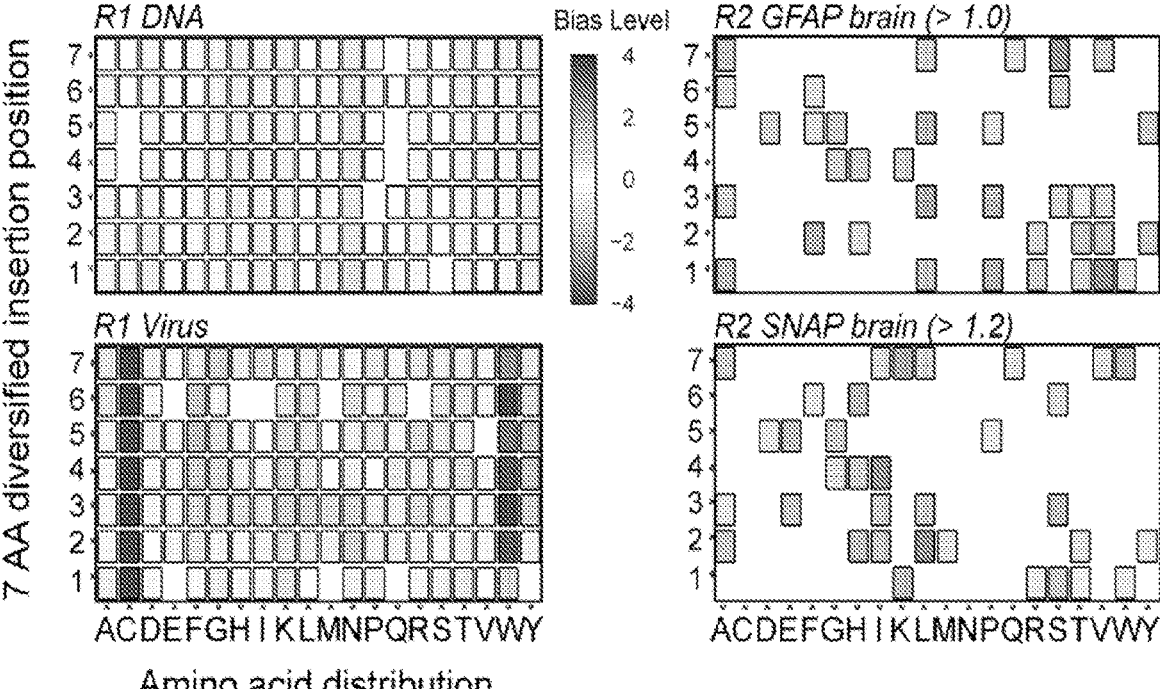
FIG. 52 shows heatmaps represent the magnitude (log 2 fold change) of AA bias in "output" library 1 normalized to "input" library 2 that reach statistical significance (boxed if P-value≤0.0001, two-sided, two-proportion z-test, except in R1 DNA normalized to known NNK template where one-proportion z-test was performed, and P-values corrected for multiple comparisons using Bonferroni correction). R1 DNA library normalized to NNK template (top left, ~9 million sequences), R1 virus normalized to R1 DNA libraries (bottom left, ~10 million sequences), R2 GFAP library with enrichment score above 1.0 in brain normalized to R2 virus (top right, 20 sequences,) and R2 SNAP library with enrichment score above 1.2 normalized to R2 virus (bottom right, 17 sequences) are shown (n=1 for DNA, virus, and n=2 for brain libraries).

Whereas the AA distribution of the DNA library closely matched the Oligopool design, virus production selected for a motif with Asn (N) at position 2, β-branched AAs (I, T, V) at position 4, and positively charged AAs (K, R) at position 5 (FIGS. 10, 52). Fitness for BBB crossing resulted in a very different pattern. In comparison to the R2 virus library, highly enriched variants share preferences, for example, proline (P) in position 5, and phenylalanine (F) in position 6.

Figure 11:
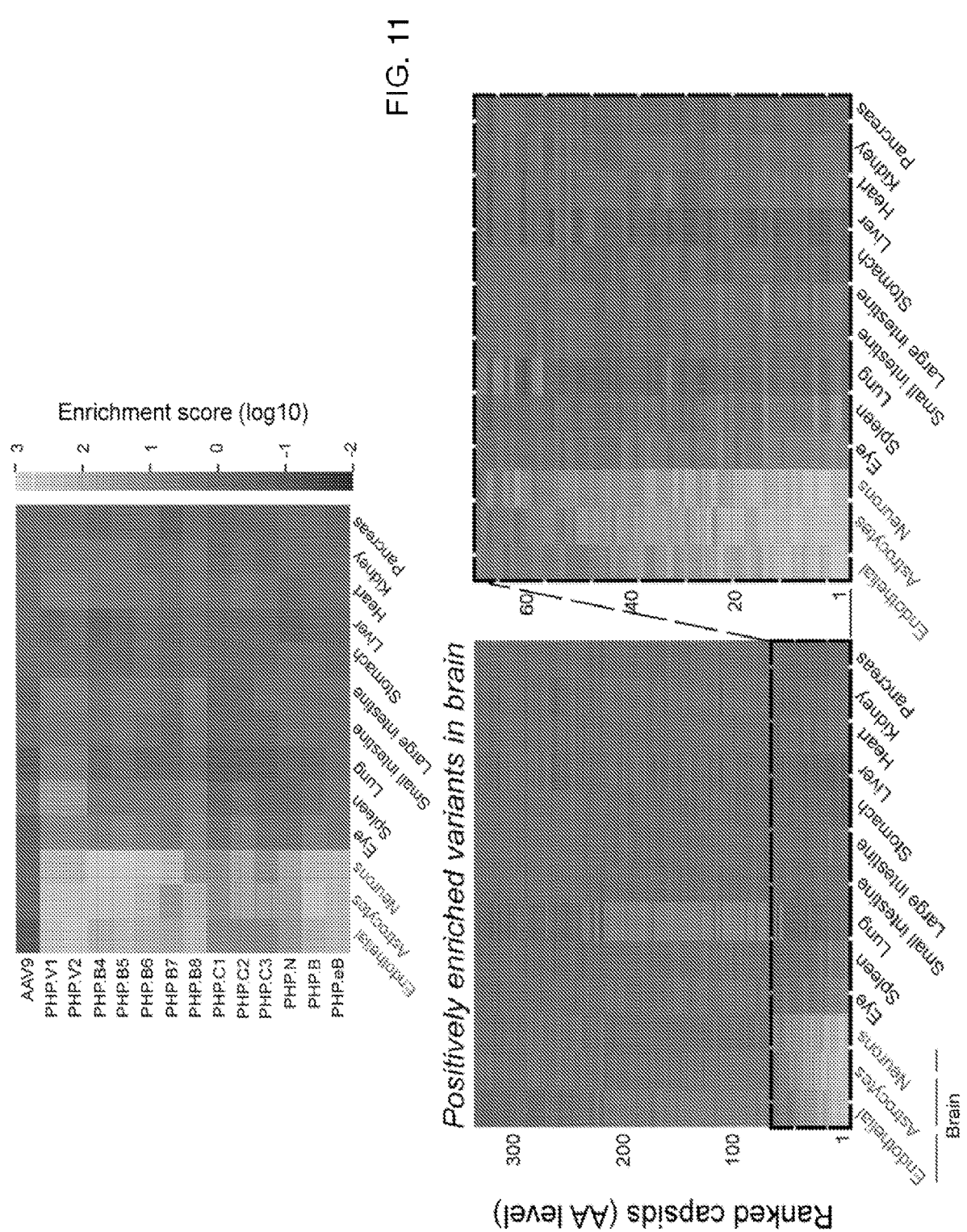
FIG. 11 shows heatmaps of Cre-independent relative enrichment across organs (n=2 mice per Cre line, mean across 6 samples from 3 Cre lines is plotted) for variants enriched in the brain tissue of at least one Cre-dependent synthetic pool selection (lighter text, n=2 mice per cell-type, mean is plotted) (left). Zoom-in of the most CNS-enriched variants (middle), and of the variants that are characterized in the current study along with spike-in library controls (right) are shown.

The distribution of the positively enriched variants from brain across all peripheral organs was then determined (FIG. 11, left). About 60 variants that are highly enriched in brain are comparatively depleted across all other organs (FIG. 11, middle). Encouraged by the expected behavior of spike-in control variants (AAV9, PHP.B, PHP.eB), eleven novel variants were chosen for further validation (FIG. 11, right), including several that would have been overlooked if the choice had been based on PCR pool or CREATE (Table 8).

TABLE 8

Ranking of AAV-PHP capsids across methods.Ranks of selected variants
among all capsids recovered from R2 Tek-Cre selection by synthetic pool enrichment score
(representing M-CREATE), PCR pool enrichment score (representing closer to M-CREATE), or
PCR pool read counts (representing CREATE), the highest ranks of which starts from 1, and
"Not recovered" represent absence of the variant from R2 sequencing data.

| AAV Variants | Synthetic pool enrichment rank | PCR pool enrichment rank | PCR pool read count rank |
|---|---|---|---|
| PHP.V1 | 1 | 4 | 3 |
| PHP.V2 | 2 | 1 | 1 |
| PHP.B4 | 4 | 10 | 56 |
| PHP.B7 | 6 | 13 | 36 |
| PHP.B8 | 3 | 7 | 23 |
| PHP.C1 | 13 | 34 | 74 |
| PHP.C2 | 12 | 20 | 293 |
| PHP.C3 | 16 | Not recovered | Not recovered |

Figure 12:
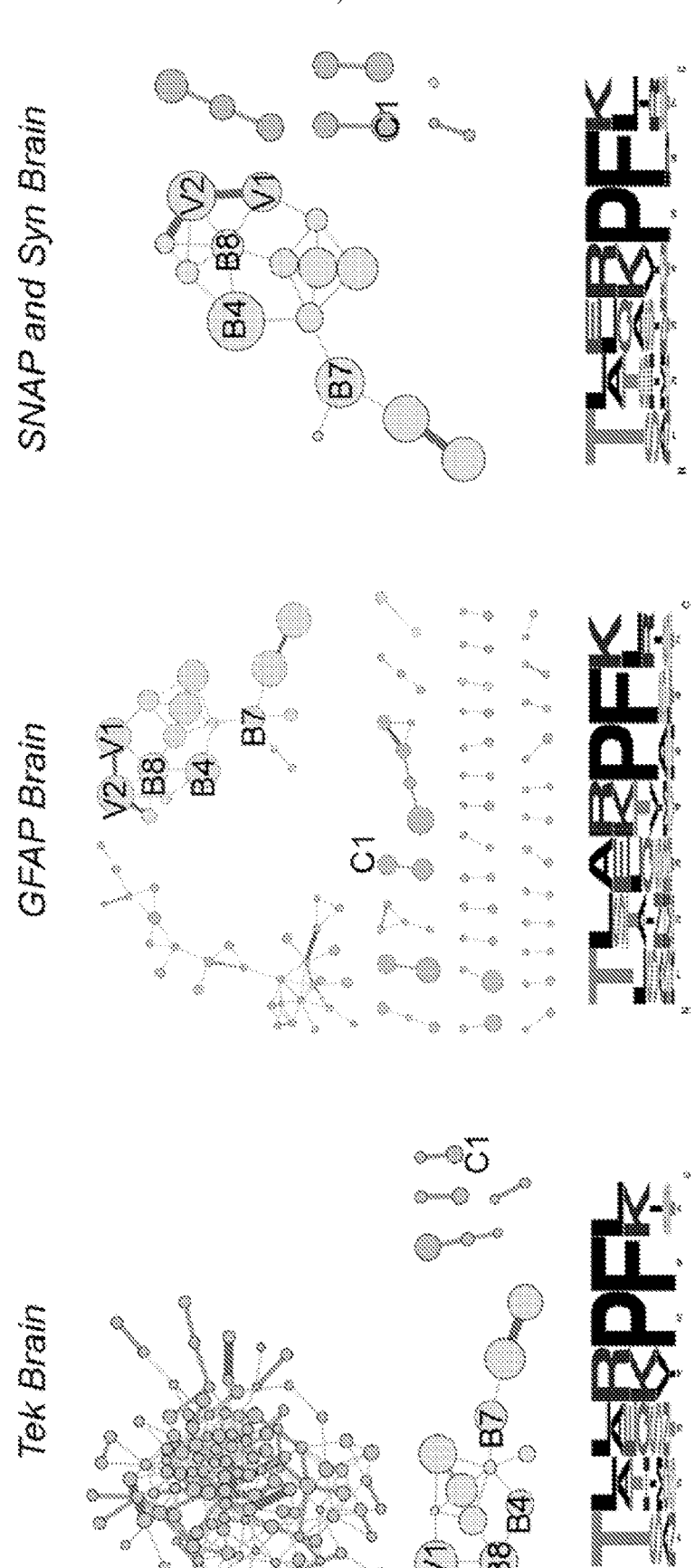
FIG. 12 shows clustering analysis of variants from synthetic pool brain libraries after enrichment in Tek-Cre (left), GFAP-Cre (middle), and combined SNAP-Cre and Syn-Cre (right) selections. Size of nodes represents relative enrichment in brain. Thickness of edges (connecting lines) representing degree of relatedness. Distinct families (yellow) with the corresponding AA frequency logos (AA size represents prevalence and color encodes AA properties).
Figure 53:
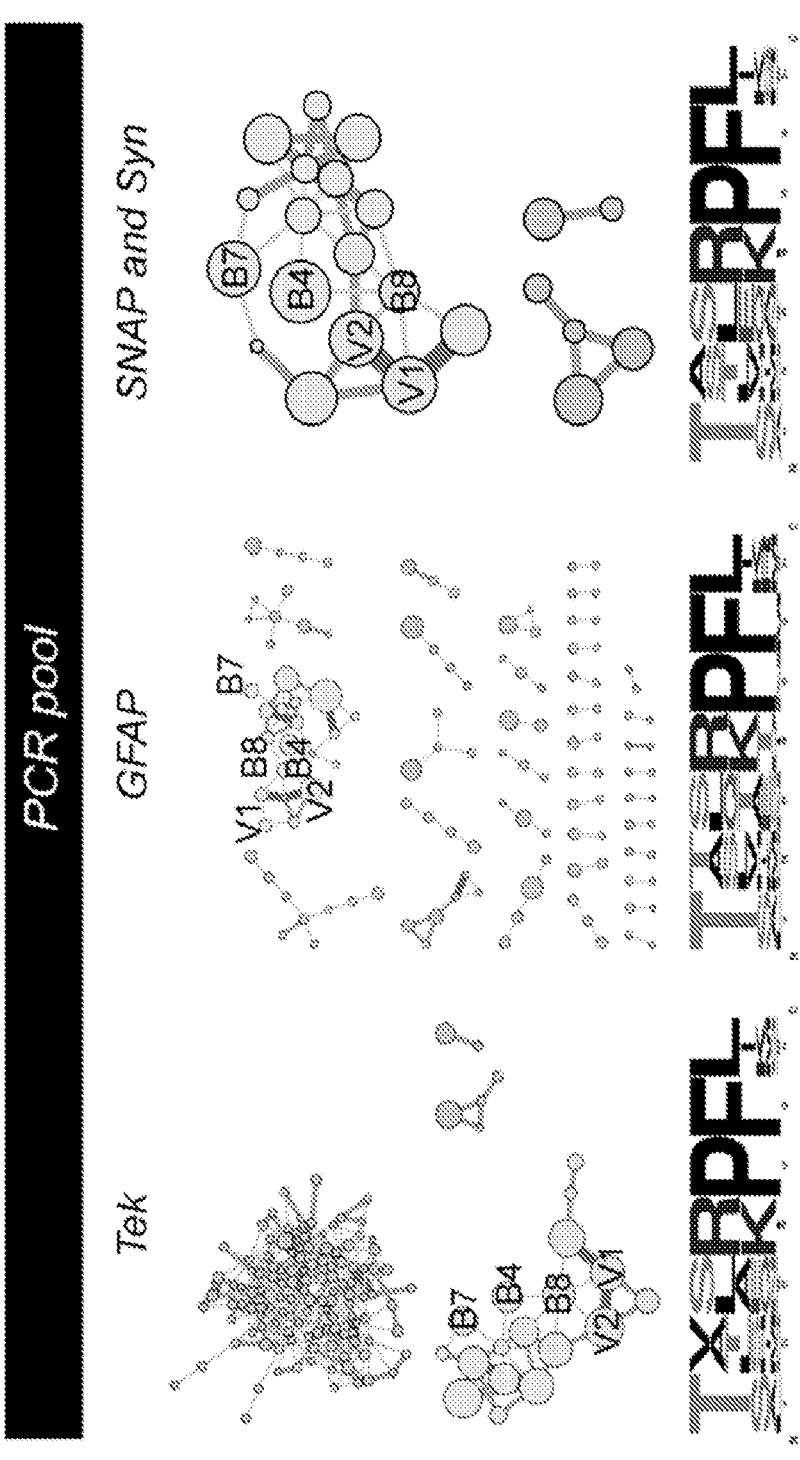
FIG. 53 shows clustering analysis of positively enriched variants from Tek, GFAP, and combined neuron brain libraries (SNAP and Syn) by PCR pool design, and by synthetic pool design with spike-in library are shown with size of nodes representing their relative enrichment in brain, and the thickness of edges (connecting lines) representing the extent of shared AA identity between nodes. A distinct family is highlighted in yellow with the corresponding AA frequency logo below (AA size reflects prevalence and color coded based on AA properties).

These variants were chosen due to their enrichments and where they fall in sequence space. The positively enriched variants were found to cluster into distinct families based on sequence similarity. In agreement with the heatmaps discussed above, the most enriched variants form a distinct family across selections that share a common motif: T in position 1, L in position 2, P in positive 5, F in position 6, and K or L in position 7 (FIGS. 12, 53). This AA pattern closely resembles the previously identified variant, AAV-PHP.B—TLAVPFK. Given the sequence similarity among members, we predicted that they may similarly cross the BBB and target the central nervous system.

The ability to twice recover the AAV-PHP.B sequence family from completely independently constructed and selected libraries confirms that the viral library's sequence space coverage was broad enough to recover a family of variants sharing a common motif. Unlike CREATE which identified only one variant, AAV-PHP.B, M-CREATE yielded a diverse PHP.B-like family that hints toward important chemical features of this motif. The sequence diversity within this family suggests that isolating AAV-PHP.B was not simply good fortune in previous experiments (considering a theoretical starting library size of ~1.3 billion), and that this is a dominant family for this particular experiment.

Figure 14:
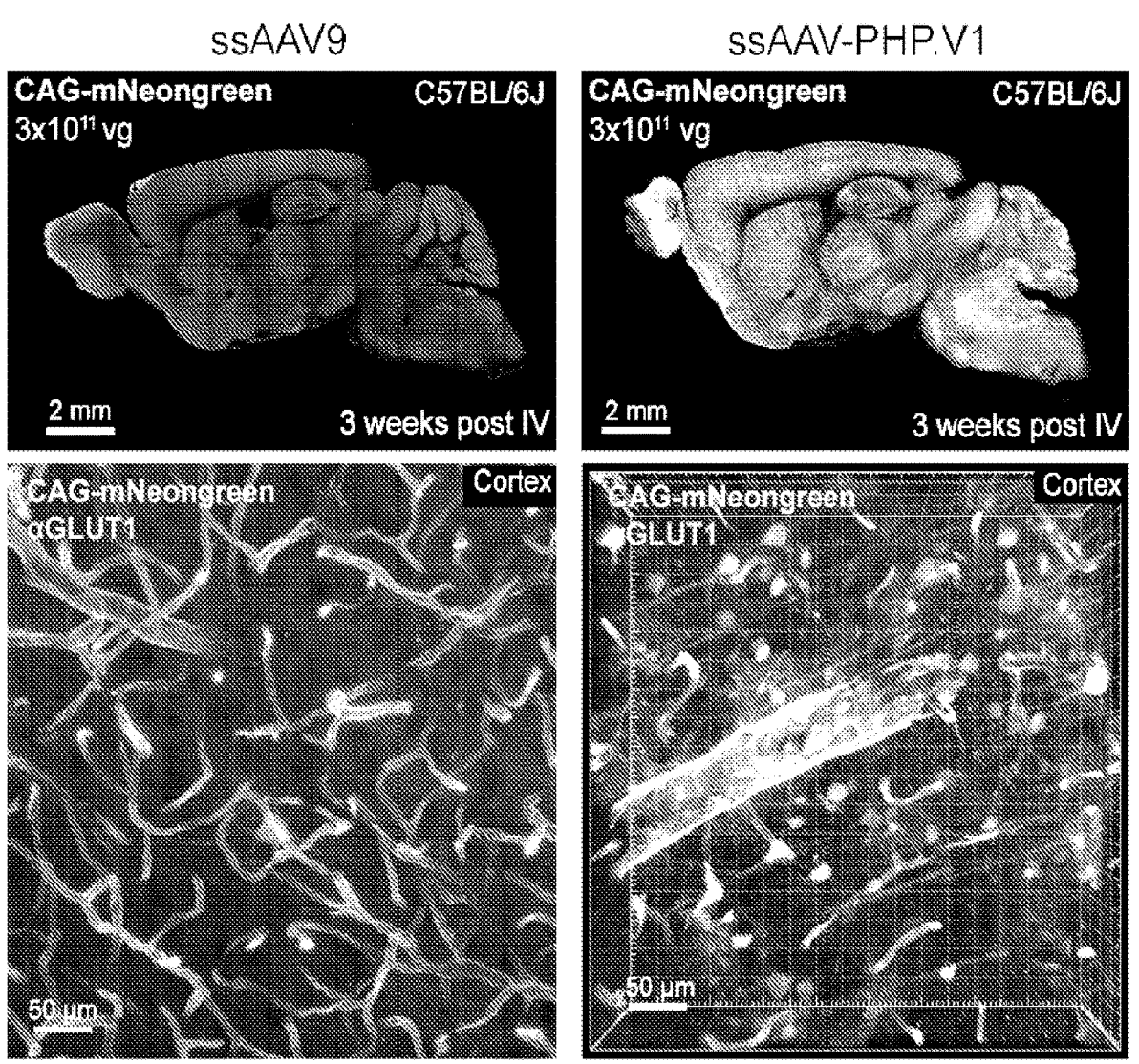
FIG. 14 shows AAV9 (left) and AAV-PHP.V1 (right) mediated expression using ssAAV:CAG-mNeongreen genome (n=3, 3 weeks of expression in C57BL/6J adult mice with $3×10^{11}$ vg IV dose/mouse). The images were acquired under same microscope settings as that of the sagittal sections of brain (top) with higher magnification image from cortex (bottom). αGLUT1 antibody staining was used in the image to show vasculature.
Figures 16, 17:
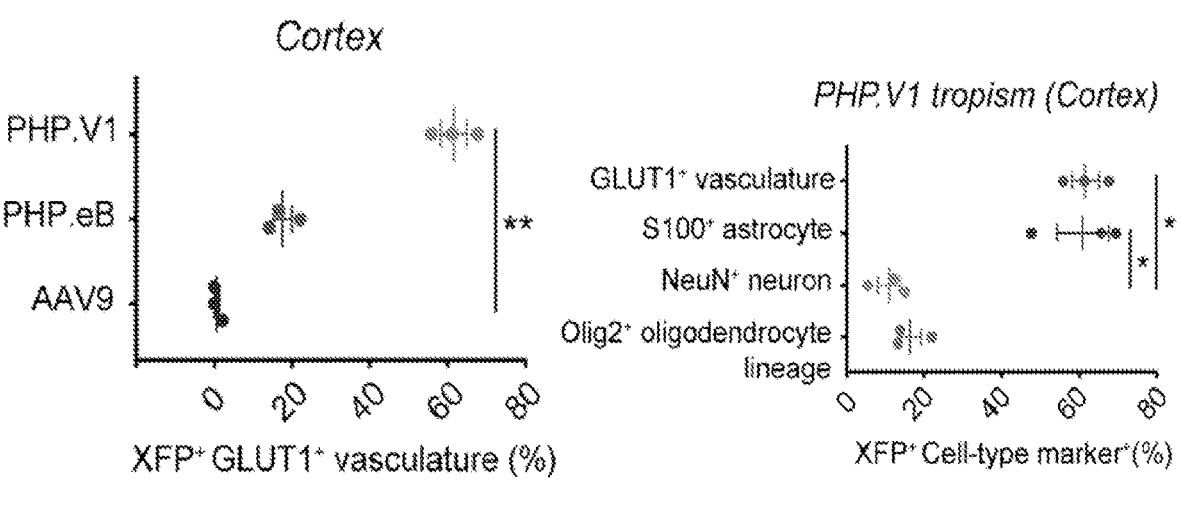
FIG. 16 shows percentage of vasculature stained with αGLUT1 that overlaps with mNeongreen (XFP) expression in cortex. One-way ANOVA non-parametric Kruskal-Wallis test (P-value 0.0036), and follow-up multiple comparisons using uncorrected Dunn's test (P-value of 0.0070 for AAV9 vs PHP.V1) are reported. **$P≤0.01$ is shown, P>0.05 is not shown; data is mean±S.E.M, n=3 mice per AAV variant, cells quantified from 2-4 images per mouse per cell-type.
FIG. 17 shows percentage of cells stained with each cell-type specific marker (αGLUT1, αS100 for astrocytes, αNeuN for neurons, αOlig2 for oligodendrocyte lineage cells) that overlaps with mNeongreen (XFP) expression in cortex. Kruskal-Wallis test (P-value of 0.0078), and uncorrected Dunn's test (P-value of 0.0235 for neuron vs vascular cells, and 0.0174 for neuron vs astrocyte, respectively) are reported. *P 0.05 is shown, and P>0.05 is not shown; data is mean±S.E.M, n=3 mice, cells quantified from 2-4 images per mouse per cell-type.
Figure 54:
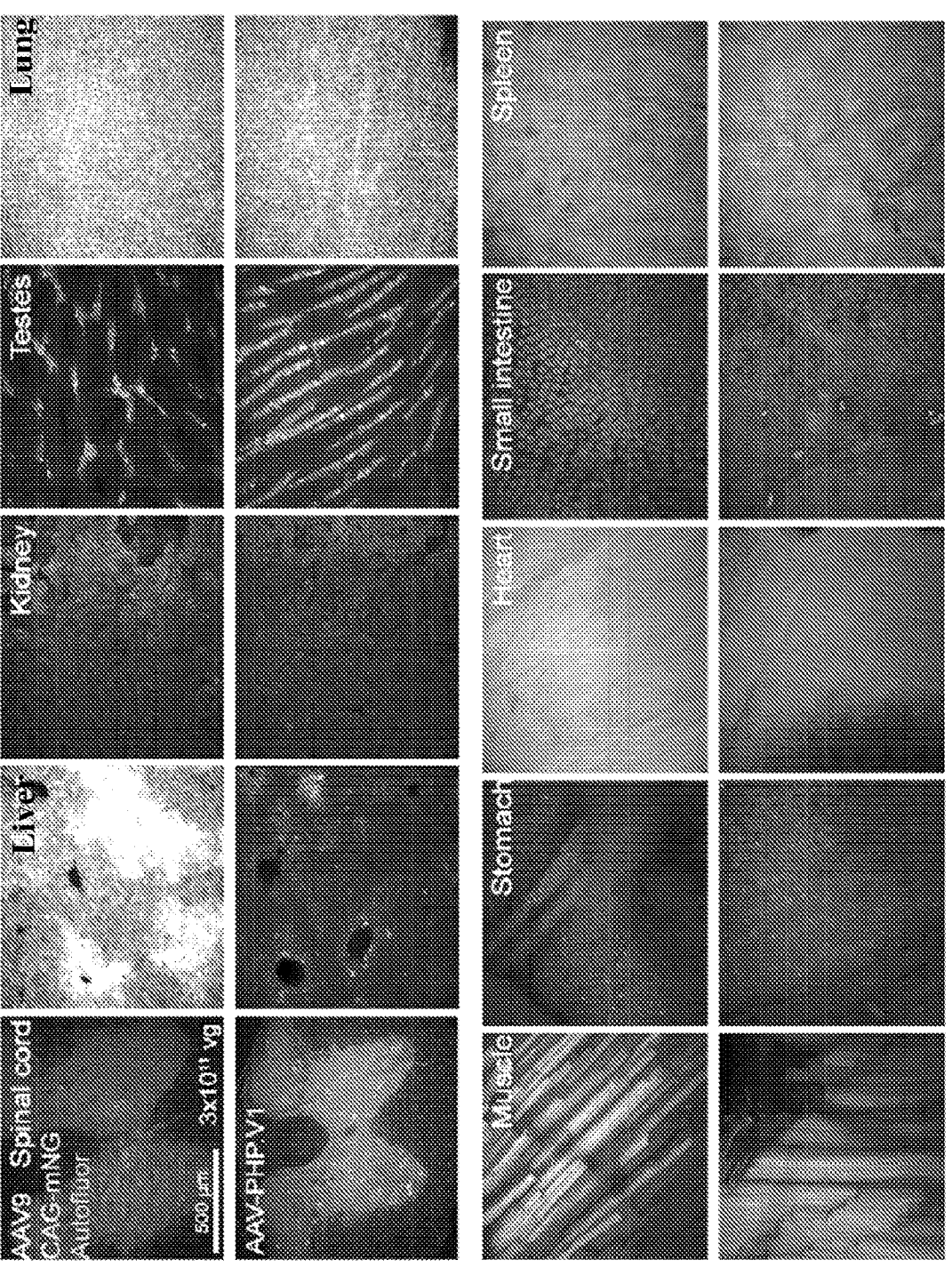
FIG. 54 shows expression of AAV9 (top row) and AAV-PHP.V1 (bottom row) packaging CAG promoter driving mNeonGreen across all organs (n=3, $3\times10^{11}$ vg dose per adult C57BL/6J mouse, 3 weeks of expression).
Figure 55:
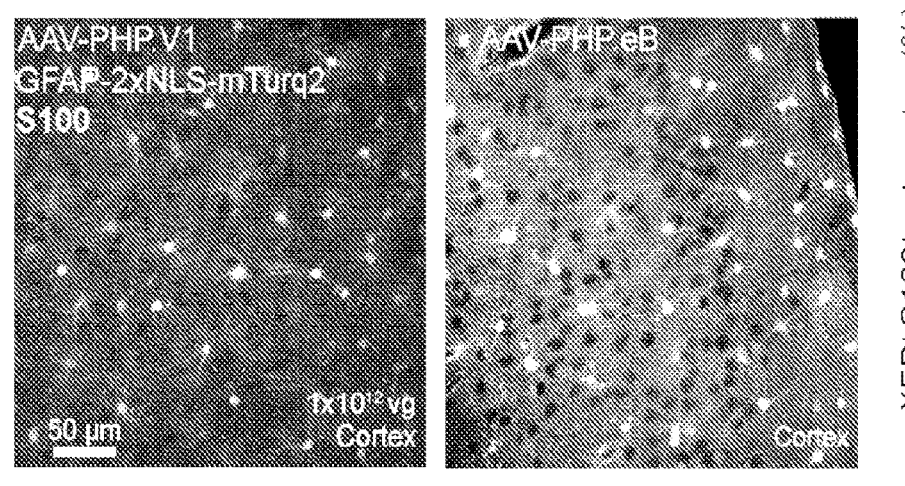
FIG. 55 shows expression in cortical astrocytes (S100+) after IV delivery of AAV-PHP.V1 (left) and AAV-PHP.eB (right) capsids carrying the GfABC1D promoter driving expression of nuclear-localized mTurquoise2 reporter ($1\times10^{12}$ vg dose per adult mouse, 4 weeks of expression). Percentage of cortical S100+ cells that overlapped with mTurquoise2 expression is quantified (n=2, each data point is mean from 3 images per mouse).

Example 6. Capsid Recovery from Round-2 Selection Yields a Pool of AAV9 Variants with Enhanced BBB Entry and CNS Ttransduction Given the dominance of the PHP.B-family in this particular selection, the most enriched member was tested: TALKPFL (FIGS. 12 and 13) henceforth referred to as AAV-PHP.V1. Somewhat surprisingly given its sequence similarity to AAV.PHP.B, the tropism of AAV-PHP.V1 is biased toward transducing brain vascular cells (FIGS. 14, 54). When delivered intravenously, AAV-PHP.V1 carrying a fluorescent reporter under the control of the ubiquitous CAG promoter transduces ~60% of GLUT1+ cortical brain vasculature compared to ~20% with AAV-PHP.eB and almost no transduction with AAV9 (FIGS. 14 and 16). In addition to the vasculature, AAV-PHP.V1 also transduced ~60% of cortical S100+ astrocytes (FIG. 17). However, AAV-PHP.V1 is not as efficient for astrocyte transduction as the previously reported AAV-PHP.eB (when packaged with an astrocyte specific GfABC1D promoter, FIG. 55).

Figure 15:
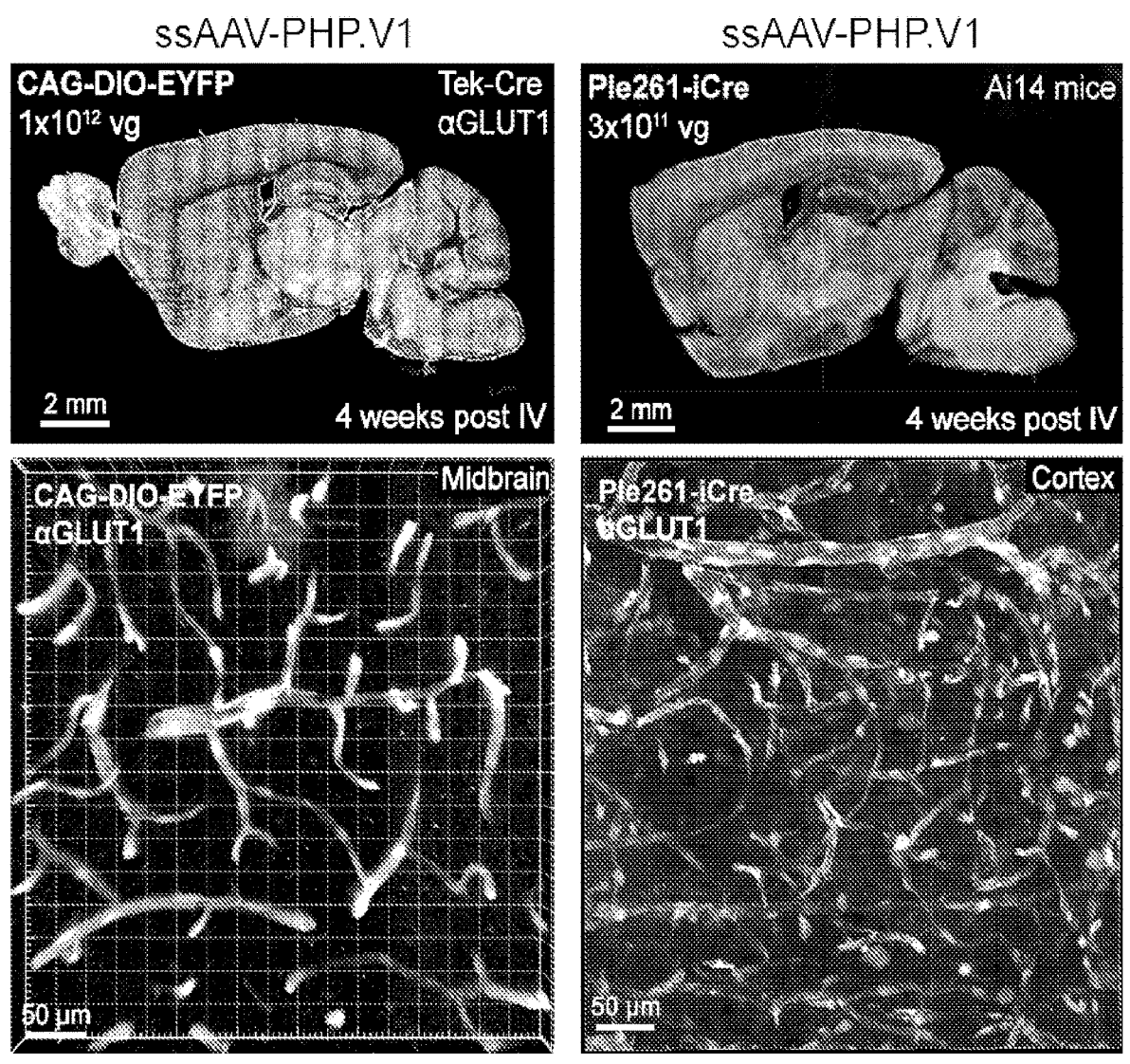
FIG. 15 shows vascular transduction by ssAAV-PHP.V1: CAG-DIO-EYFP in Tek-Cre adult mice (left) (n=2, 4 weeks of expression, $1×10^{12}$ vg IV dose/mouse), and by ssAAV-PHP.V1:Ple261-iCre in Ai14 reporter mice (right) (n=2, 3 weeks of expression, $3×10^{11}$ vg IV dose/mouse). Tissues are stained with αGLUT1.
Figures 18, 19:
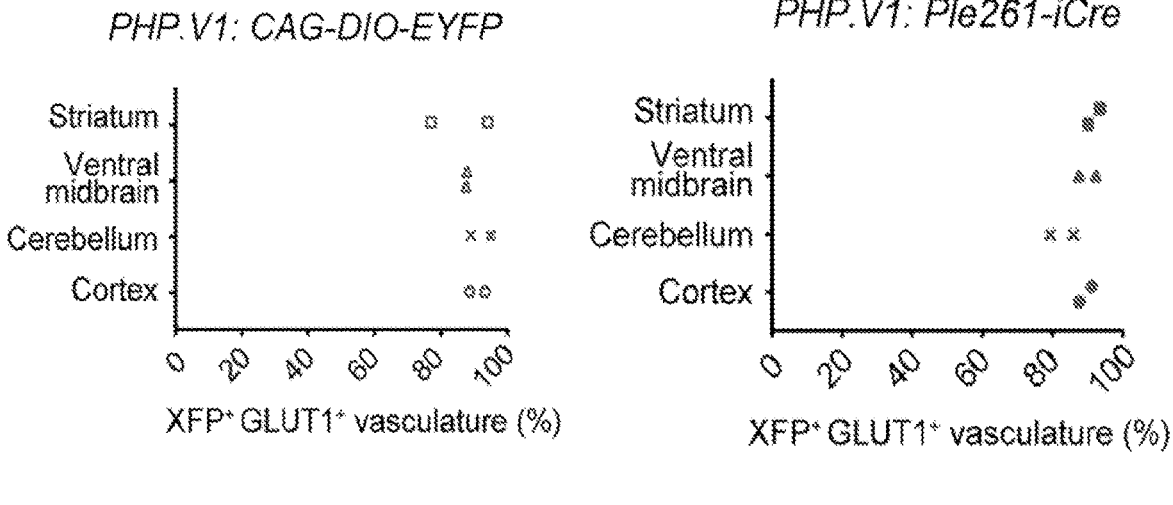
FIG. 18 shows efficiency of vascular transduction (as described in FIG. 16) in Tek-Cre mice (n=2, mean from 3 images per mouse per brain region).
FIG. 19 shows efficiency of vascular transduction in Ai14 mice (n=2, a mean from 4 images per mouse per brain region).
Figure 56:
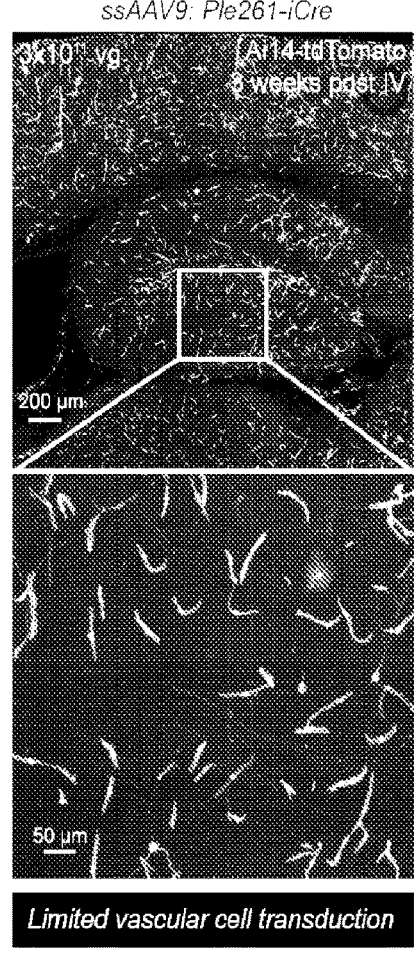
FIG. 56. shows expression of single-stranded (ss) AAV9, PHP.eB in Ai14-tdTomato reporter adult mouse (n=2-3 per group, $3\times10^{11}$ vg dose per adult mouse, 3 weeks of expression)
Figure 57:
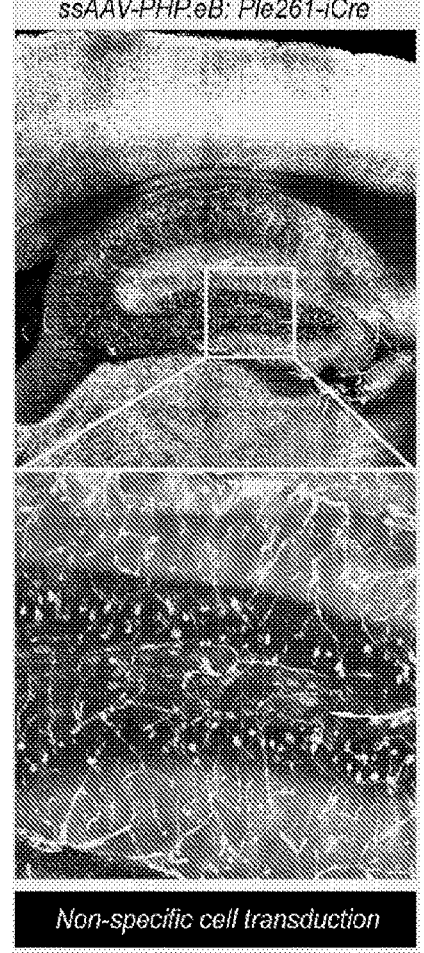
FIG. 57 shows expression of PHP.V1 in Ai14-tdTomato reporter adult mouse (n=2-3 per group, $3\times10^{11}$ vg dose per adult mouse, 3 weeks of expression)
Figure 58:
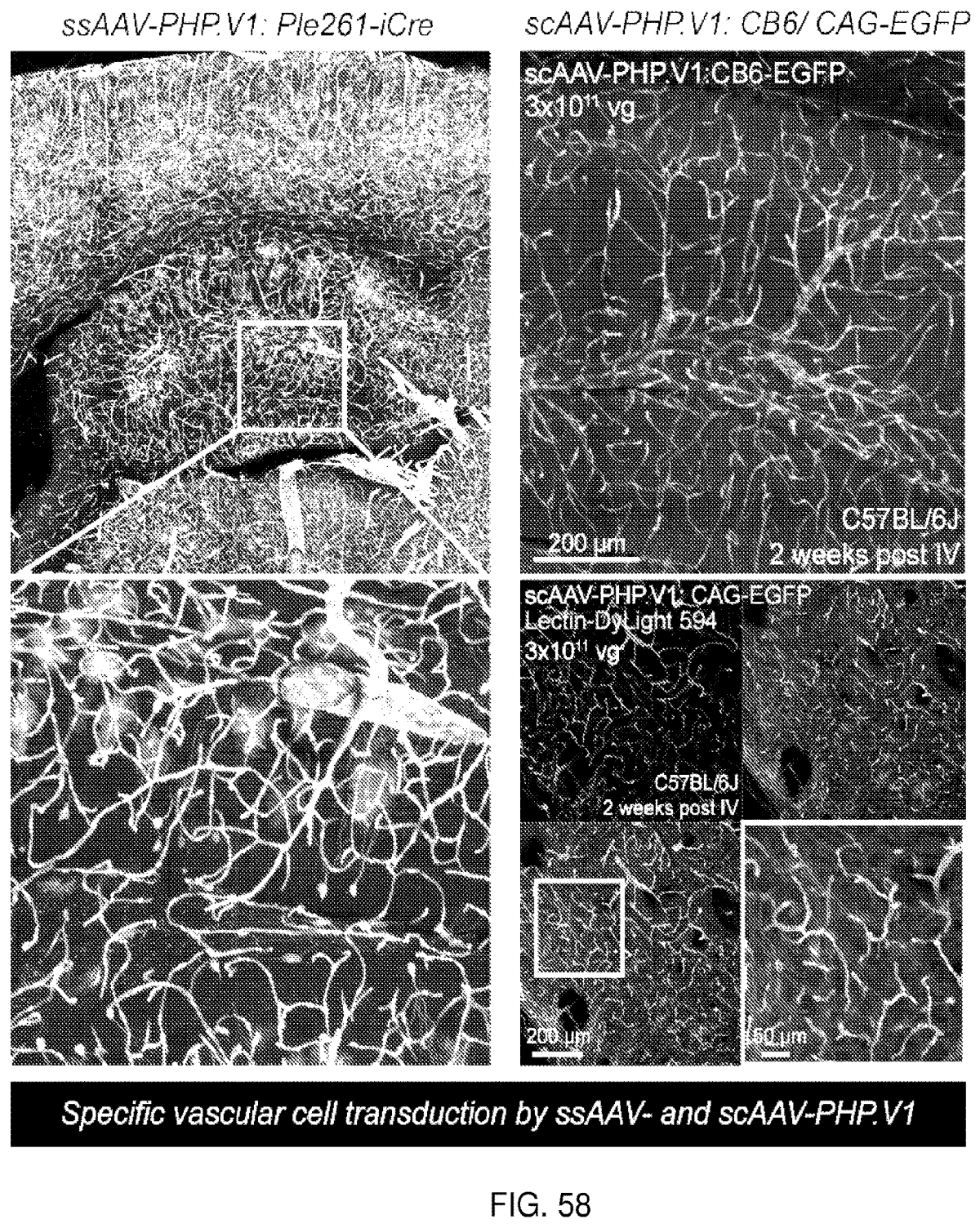

For applications requiring endothelial cell-restricted transduction via intravenous delivery, AAV-PHP.V1 vectors can be used in three different systems: (1) in endothelial cell-type specific Tek-Cre mice with a Cre-dependent expression vector (FIG. 15 (left) and FIG. 18), (2) in fluorescent reporter mice where Cre is delivered with an endothelial cell-type specific MiniPromoter (Ple261) (FIG. 15 (right) and FIGS. 19 and 56 through the left column of FIG. 58), and (3) in wild-type mice by packaging a self-complementary genome (scAAV) containing a ubiquitous promoter (Right column of FIG. 58). The mechanism of endothelial cell-specific transduction by AAV-PHP.V1 using scAAV genomes is unclear, but shifts in vector tropism when packaging scAAV genomes have been reported for another capsid.

Figure 59:
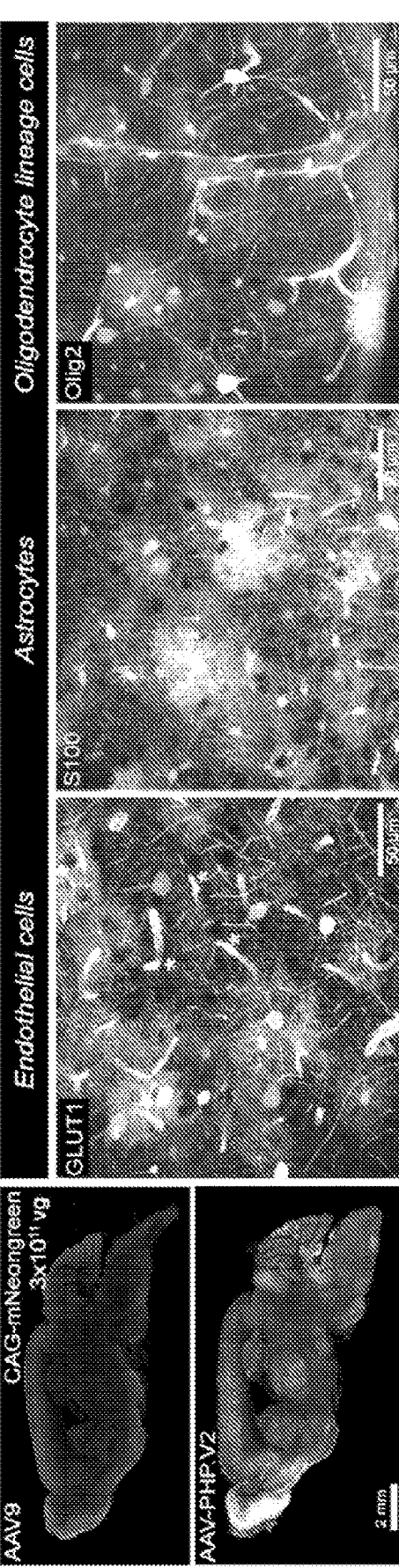
FIG. 59 shows transduction of mouse brain by the AAV-PHP.V2 variant and control AAV9, carrying the CAG promoter that drives the expression of mNeonGreen (n=3, $3\times10^{11}$ vg IV dose per C57BL/6J adult mouse, 3 weeks of expression). The sagittal brain images (left) were acquired using the same microscope settings to that of the sagittal brain images in FIG. 14. Higher magnification images of AAV-PHP.V2 transduced brain sections stained with αGLUT or αS100 or αOlig2 are shown.

Given the dramatic difference in tropism between AAV-PHP.V1 and AAV-PHP.B/eB, we tested several additional variants within the PHP.B-like family. One variant, AAV-PHP.V2—TTLKPFL, differed by only one AA from AAV-PHP.V1, has a similar tropism (FIGS. 59-61). AAV-PHP.V2 was found at high abundance in R1 selection across all brain libraries and was highly enriched in R2 (FIGS. 4, 11 (right panel), 12, 13, and 40). Given its sequence similarity, similar tropism was expected to that of AAV-PHP.V1. This was validated in vivo in C57BL/6J adult mice (ssAAV-PHP.V2: CAG-mNeongreen genome, $3\times10^{11}$ vg dose per adult mice, n=3, FIG. 59), in Tek-Cre mice (ssAAV-PHP.V2:CAG-DIO-EYFP genome, $1\times10^{12}$ vg dose per adult mouse, n=2, FIG. 60), and in GFAP-Cre mice (ssAAV-PHP.V2:CAG-DIO-EYFP, $1\times10^{12}$ vg dose per adult mouse, n=2, FIG. 61).

Three other variants with sequences of roughly equal deviation from both AAV.PHP.V1 and AAV.PHP.B, AAV-PHP.B4—TLQIPFK, AAV-PHP.B7—SIERPFK, and AAV-PHP.B8—TMQKPFI (FIGS. 12, 13, 20, and 21), have PHP.B-like tropism with biased transduction toward neurons and astrocytes (FIGS. 21 and 62-64). Similar variants among the spike-in library, AAV-PHP.B5—TLQLPFK and AAV-PHP.B6—TLQQPFK, also shared this tropism (FIGS. 13, 20, 21, and 62).

Figure 20:
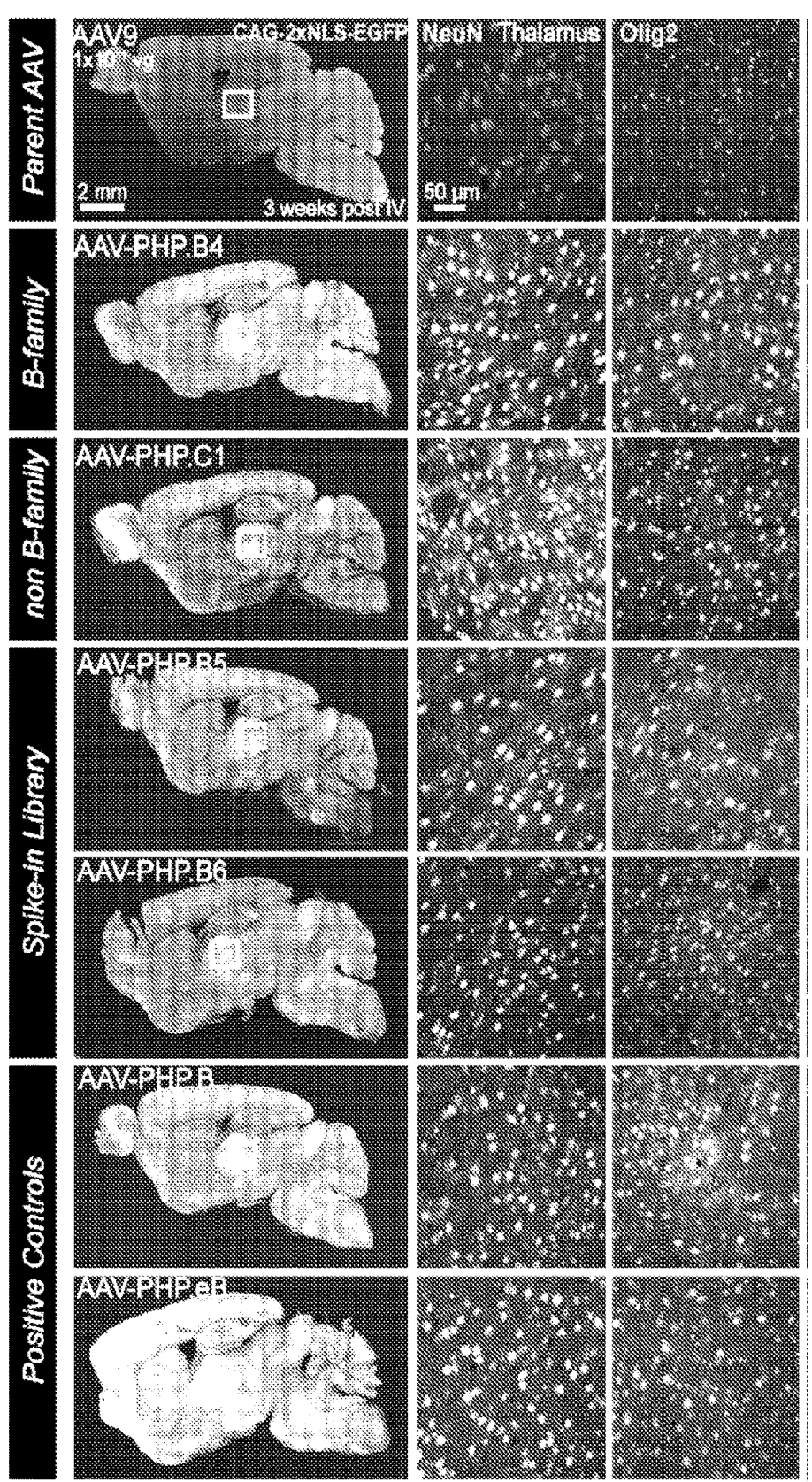
FIG. 20 shows transduction by AAV-PHP.B4-B6 and C1 variants, as well as B, eB, and AAV9 controls in sagittal brain and liver sections. Across each set of images (column-wise) acquired, microscope settings were matched with AAV-PHP.eB. The white box on the sagittal brain images marks the thalamus and not the precise region of the figures to the right. Vectors are packaged with ssAAV:CAG-2xNLS-EGFP genome (n=3 per group, $1×10^{11}$ vg IV dose/adult C57BL/6J mouse, 3 weeks of expression). Tissues are stained with cell-type specific markers: αNeuN for neurons, αS100 for astrocytes and αOlig2 for oligodendrocyte lineage cells. Liver tissues are stained with a DNA stain, DAPI.
Figure 20:
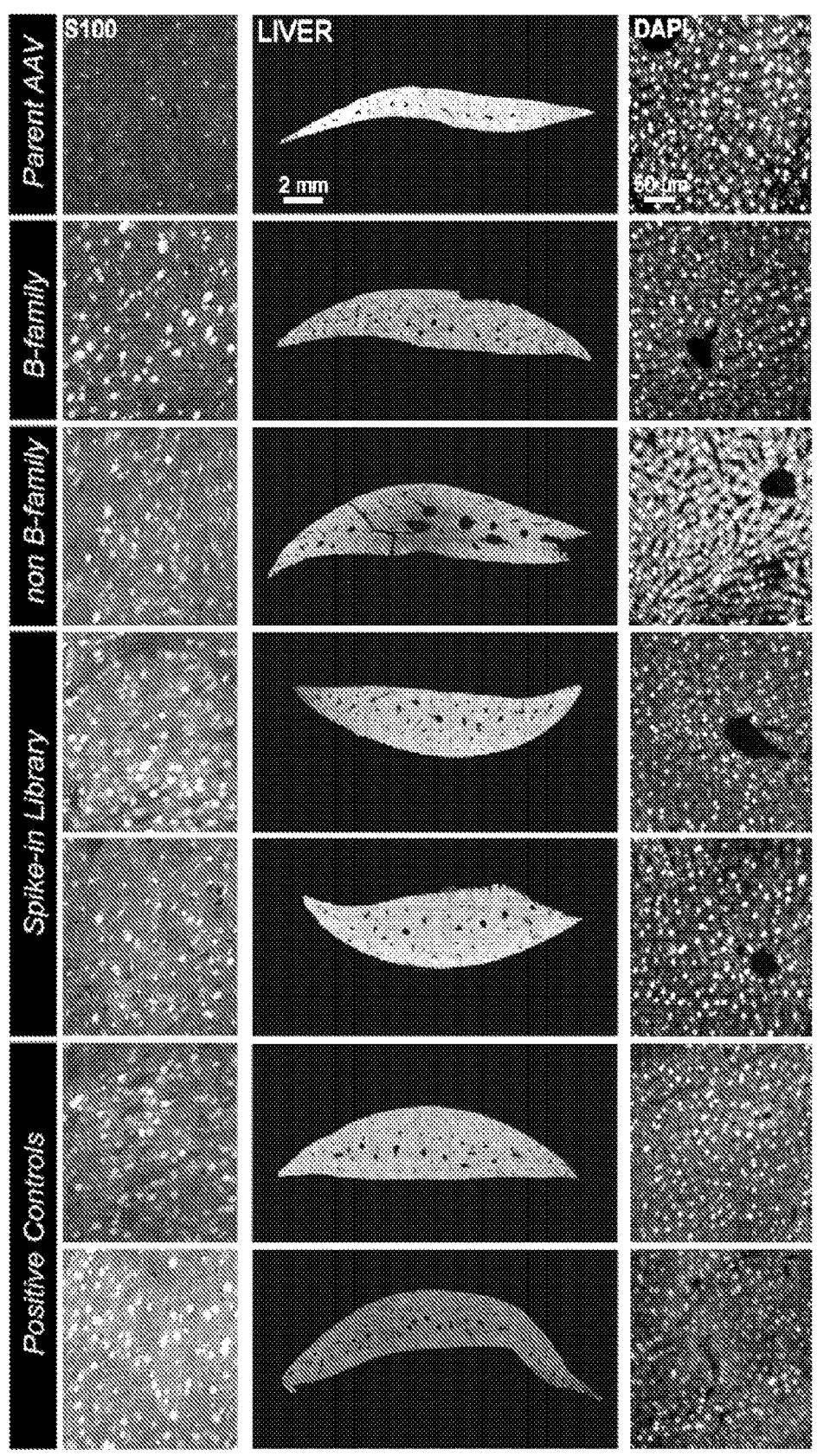
Figure 21:
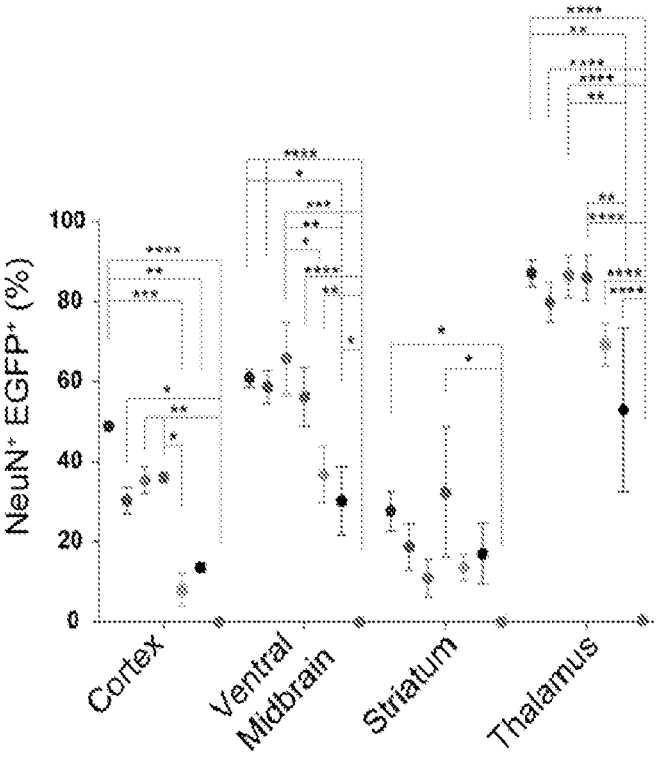
FIGS. 21-23 show the percentage of αNeuN+ (FIG. 21), αS100+ (FIG. 22), and αOlig2+(FIG. 23) cells with detectable nuclear-localized EGFP in the indicated brain regions (n=3 per group, $1×10^{11}$ vg dose). A two-way ANOVA with correction for multiple comparisons using Tukey's test is reported with adjusted P-values (**$P≤0.0001$, *$P≤0.001$, **$P≤0.01$, *$P≤0.05$, is shown, and P>0.05 is not shown on the plot; 95% CI, data is mean±S.E.M. The dataset comprises a mean of 2 images per region per cell-type marker per mouse).
Figure 22:
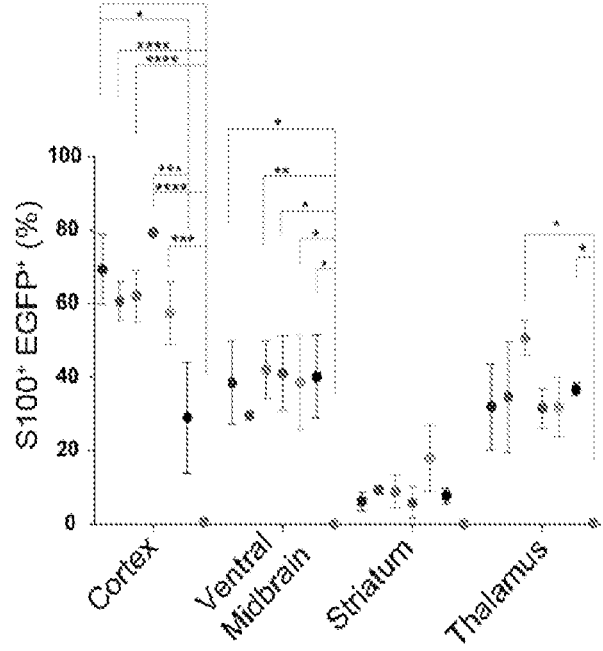

To evaluate the performance of the spike-in library, two highly enriched variants similarly placed in sequence space were chosen: AAV-PHP.B6—TLQLPFK and AAV-PHP.B7—TLQQPFK (FIG. 48 (middle panel), and 53) that were previously identified in the 3-mer-s PHP.B library but never validated in vivo. At a modest dose of $1\times10^{11}$ vg in C57BL/6J adult mice, these variants also display PHP.B-like tropism (FIGS. 20-21 and 62).

A series of variants selected to verify M-CREATE's predictive power outside this family were then investigated: (1) A highly enriched variant with a completely unrelated sequence, AAV-PHP.C1—RYQGDSV (FIGS. 12, 13, 20, and 21), transduced astrocytes at a similar efficiency and neurons at lower efficiency compared to other tested variants from B-family (FIG. 21). (2) Two variants found in high abundance in the R2 synthetic pool virus library and negatively enriched in brain (with both codon replicates in agreement), AAV-PHP.X1—ARQMDLS and AAV-PHP.X2—TNKVGNI (FIG. 46, right), poorly transduced the CNS (FIG. 63). (3) Two variants that were found in higher abundance in brain libraries from the PCR pool R2, AAV-PHP.X3—QNVTKGV and AAV-PHP.X4—LNAIKNI also failed to outperform AAV9 in the brain (FIG. 65).

Collectively, the characterization of these AAV variants demonstrates several key points. First, within a diverse sequence family, there is room for both functional redundancy and the emergence of novel tropisms. Second, highly enriched sequences outside the dominant family are also likely to possess enhanced function. Third, buoyed by codon replicate agreement in the synthetic pool, a variant's enrichment across tissues may be predictive. Fourth, while the synthetic pool R2 library contains a subset of the sequences that are in the PCR pool R2 and may thereby lack some enhanced variants, the excluded PCR pool population is enriched in false positives.

The ability to confidently predict in vivo transduction from a pool of 18,000 variants across mice is a significant advance in the selection process and demonstrates the power of M-CREATE for the evolution of individual vectors.

Figures 23, 24:
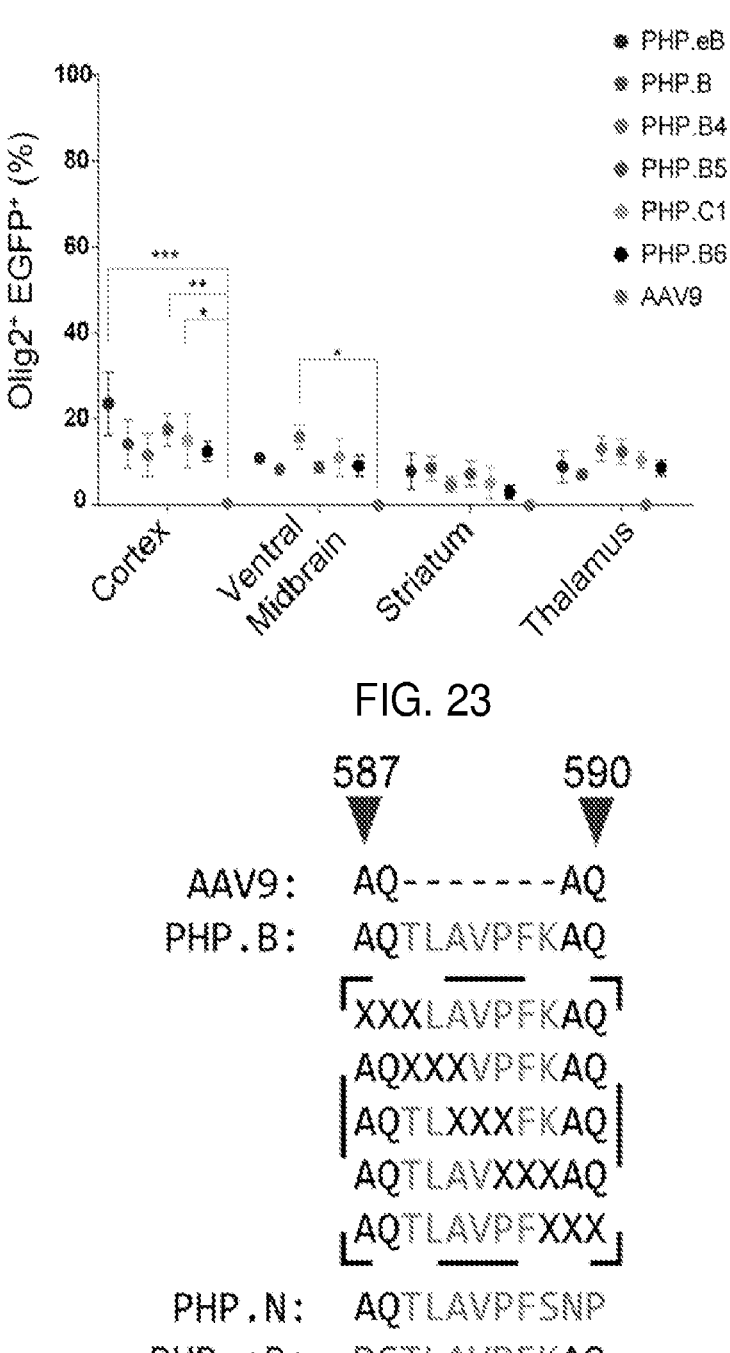
FIG. 24 shows the design of the 3-mer-s PHP.B library with combinations of three AA diversification between AA 587-597 of AAV-PHP.B (or corresponding AA 587-590 of AAV9). Shared AA identity with the parent AAV-PHP.B is shown along with unique motifs for AAV-PHP.N and AAV-PHP.eB.
Figure 25:
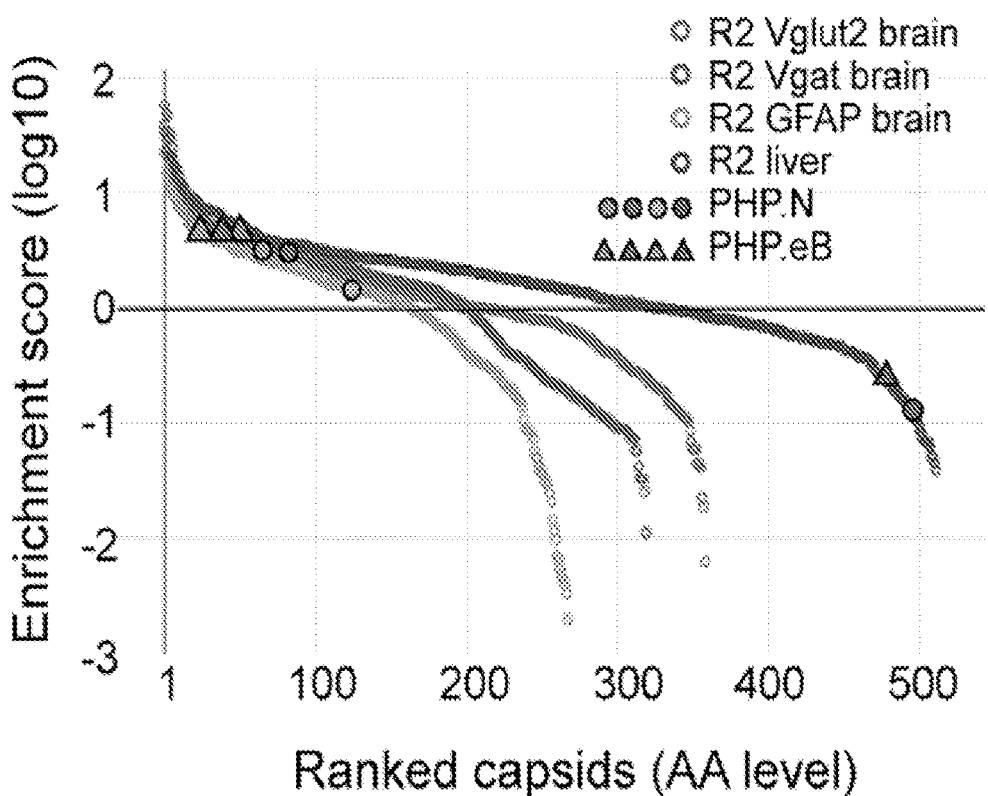
FIG. 25 shows distributions of R2 brain and liver libraries (at AA level) by enrichment score (normalized to R2 virus library, with variants sorted in decreasing order of enrichment score). The enrichment of AAV-PHP.eB and AAV-PHP.N across all libraries are mapped on the plot.
Figure 66:
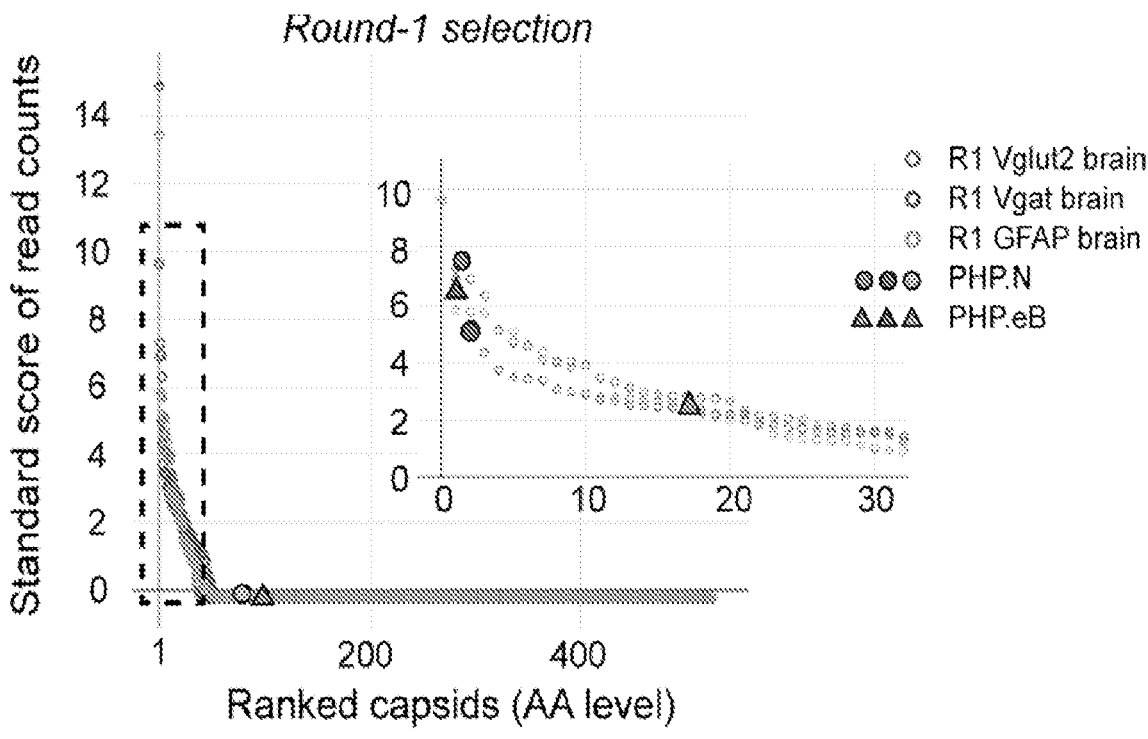
FIGS. 66-67 show distributions of R1 (FIG. 66) and R2 (FIG. 67) brain libraries (at AA level, standard score (SS) of RCs sorted in decreasing order of scores). The SS for AAV-PHP.N and AAV-PHP.eB across libraries are mapped on the zoomed-in view of this plot (dotted line box).
Figure 67:
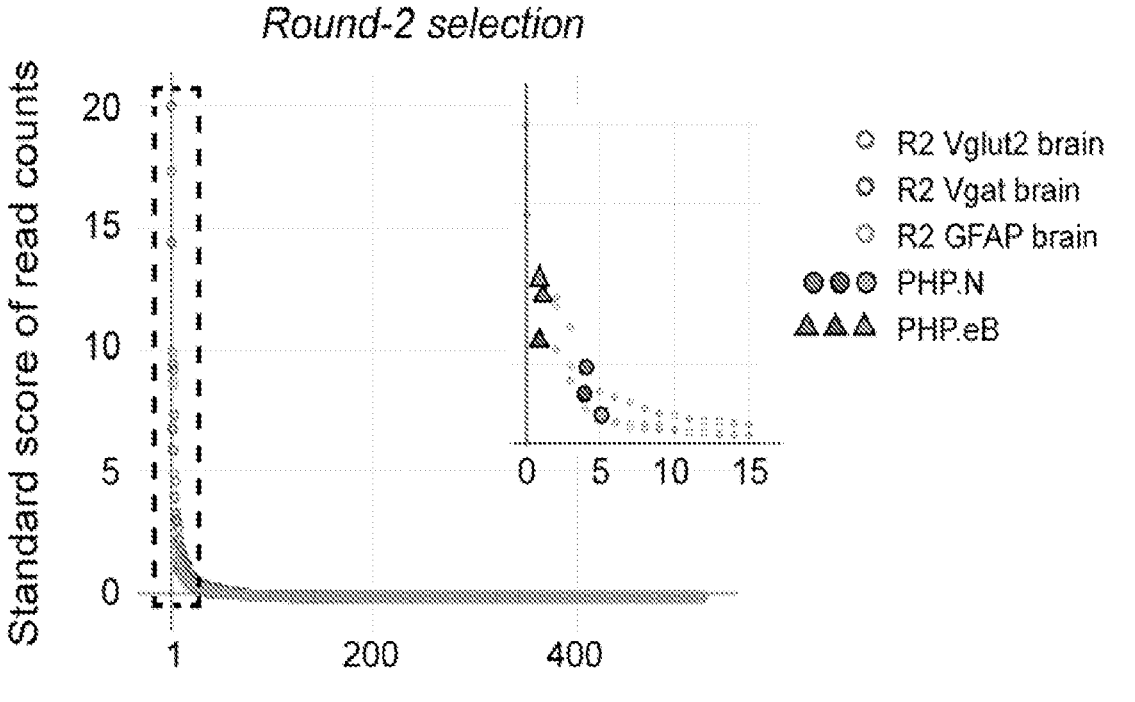

Example 7. Re-Investigation of Capsid Selection that Yielded AAV.PHP.eB Reveals Variant that Specifically Transduces Neurons Using NGS, a 3-mer-s (s-substitution) PHP.B library generated by the prior CREATE methodology that yielded AAV-PHP.eB[27] was reinvestigated (FIG. 24). The brain libraries were deep sequenced using Cre-dependent PCR and a R2 liver library from wild-type mice (processed via PCR for all capsid sequences regardless of Cre-mediated inversion) and identified 150-200 positively enriched capsids in brain tissue (FIGS. 25, 66, and 67). Briefly, the re-investigated 3-mer-s PHP.B library diversified positions 587-597 of the AAV-PHP.B capsid (equivalent of 587-590 AA on AAV9) in portions of three consecutive AAs, (40,000 total variants) (FIG. 24). Selections were performed in three Cre-transgenic lines: Vglut2-IRES-Cre for glutamatergic neurons, Vgat-IRES-Cre for GABAergic neurons, and GFAP-Cre for astrocytes.

Figure 26:
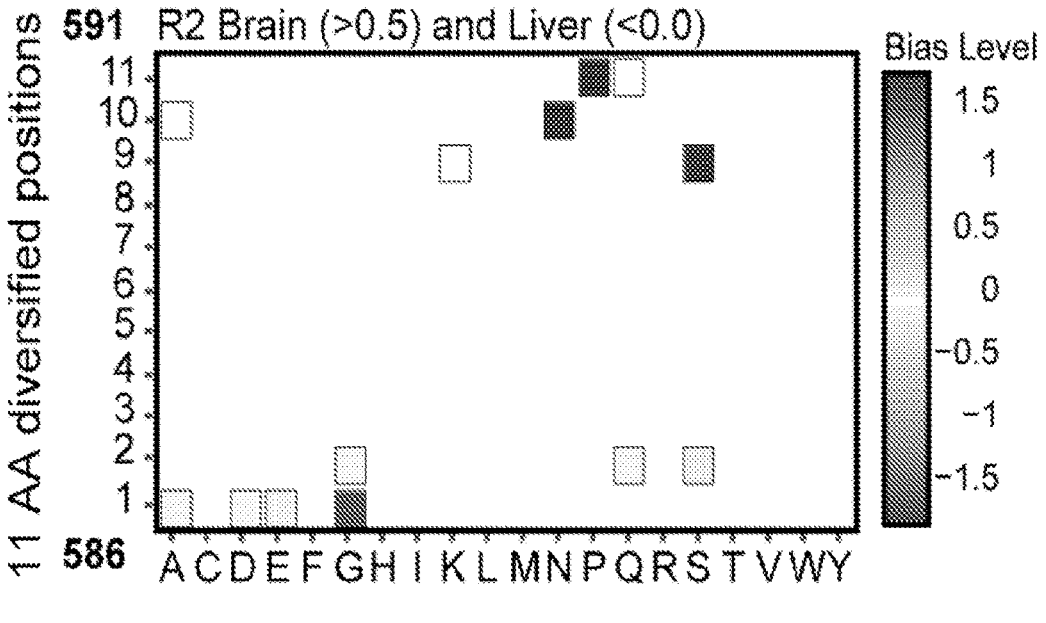
FIG. 26 shows heatmap represents the magnitude (log 2 fold change) of a given AA's relative enrichment or depletion at each position across the diversified region, only if statistical significance is reached on fold change (boxed if p-value≤0.0001, two-sided, two-proportion z-test, p-values corrected for multiple comparisons using Bonferroni correction). Plot includes variants that were highly enriched in brain (>0.5 mean enrichment score, where mean is drawn across Vglut2, Vgat and GFAP, n=1 library per mouse line (sample pooled from 2 mice per line)) and underrepresented in liver (<0.0) (32 AA sequences).
Figure 27:
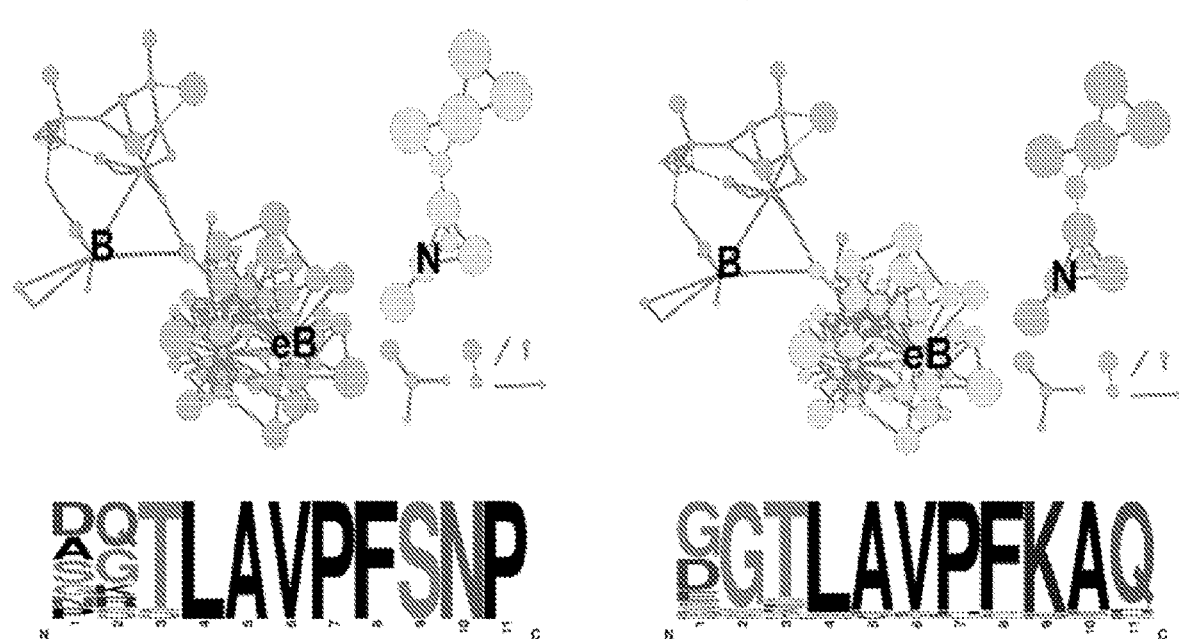
FIG. 27 shows clustering analysis of enriched variants from Vgat brain library with node size representing the degree of negative enrichment in liver and the thickness of edges (connecting lines) representing degree of relatedness between nodes. Two distinct families are highlighted in yellow and their corresponding AA frequency logos are shown below (AA size represents prevalence and color encodes AA properties).
Figure 28:
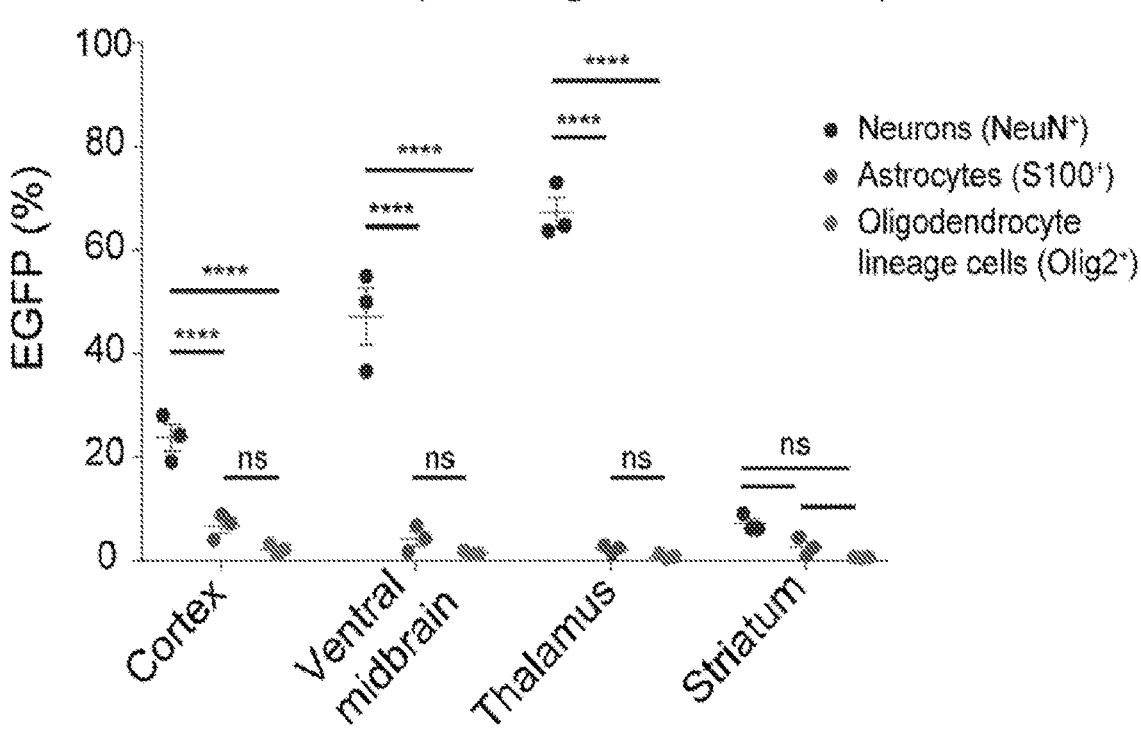
FIG. 28 shows the percentage of neurons, astrocytes and oligodendrocyte lineage cells with ssAAV-PHP.N:CAG-2xNLS-EGFP in the indicated brain regions (n=3, $1×10^{11}$ vg IV dose per adult C57BL/6J mouse, 3 weeks of expression, data is mean±S.E.M, 6-8 images for cortex, thalamus and striatum, and 2 images for ventral midbrain, per mouse per cell-type marker using 20×objective covering the entire regions). A two-way ANOVA with correction for multiple comparisons using Tukey's test gave adjusted P-values reported as ****$P≤0.0001$, ns for P>0.05, 95% CI.
Figure 29:
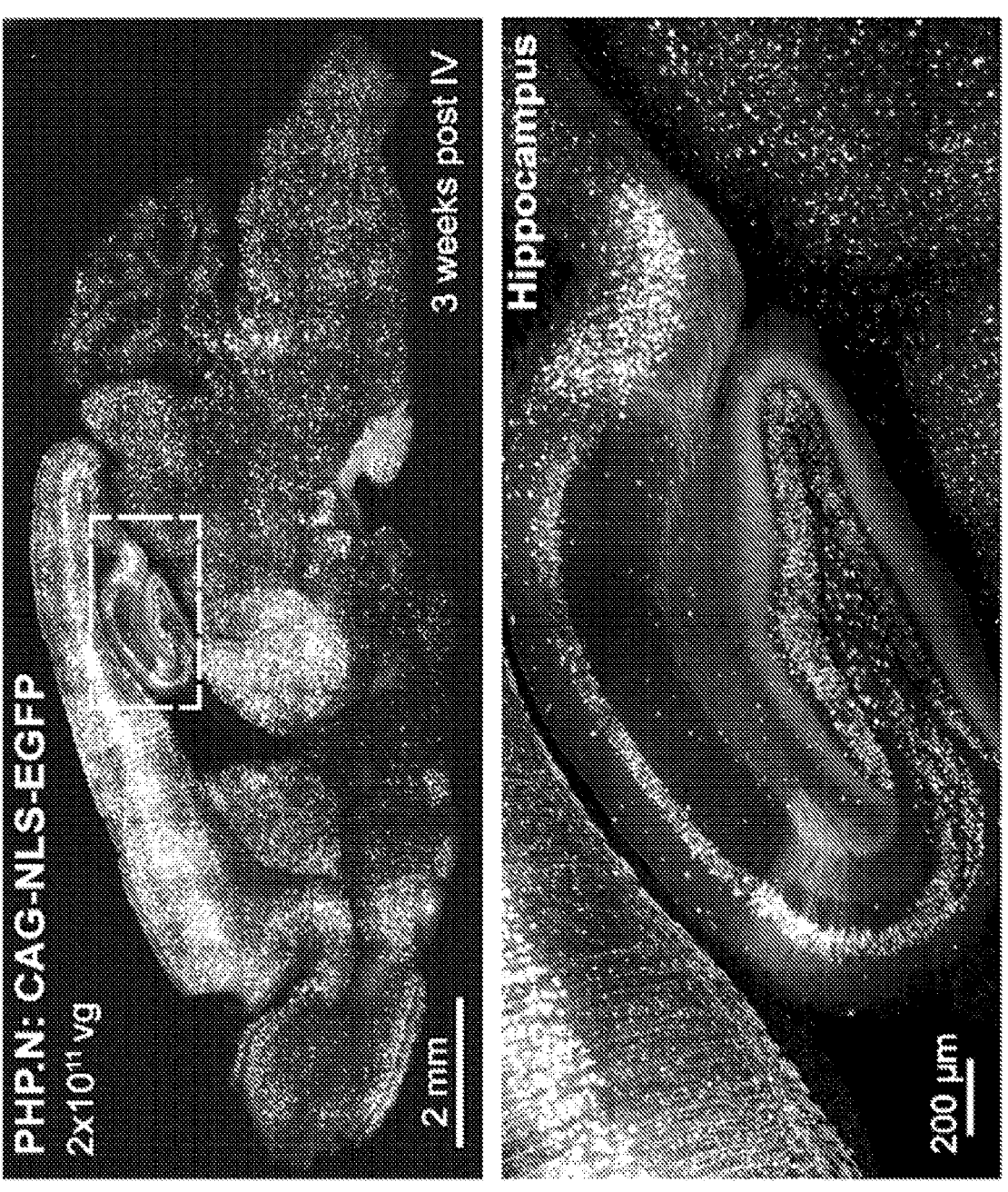
FIG. 29 shows transduction by ssAAV-PHP.N:CAG-NLS-EGFP (n=2, $2×10^{11}$ vg IV dose per adult C57BL/6J mouse, 3 weeks of expression) with NeuN staining (magenta) across three brain areas (cortex, SNc (substantia nigra pars compacta) and thalamus).
Figure 29:
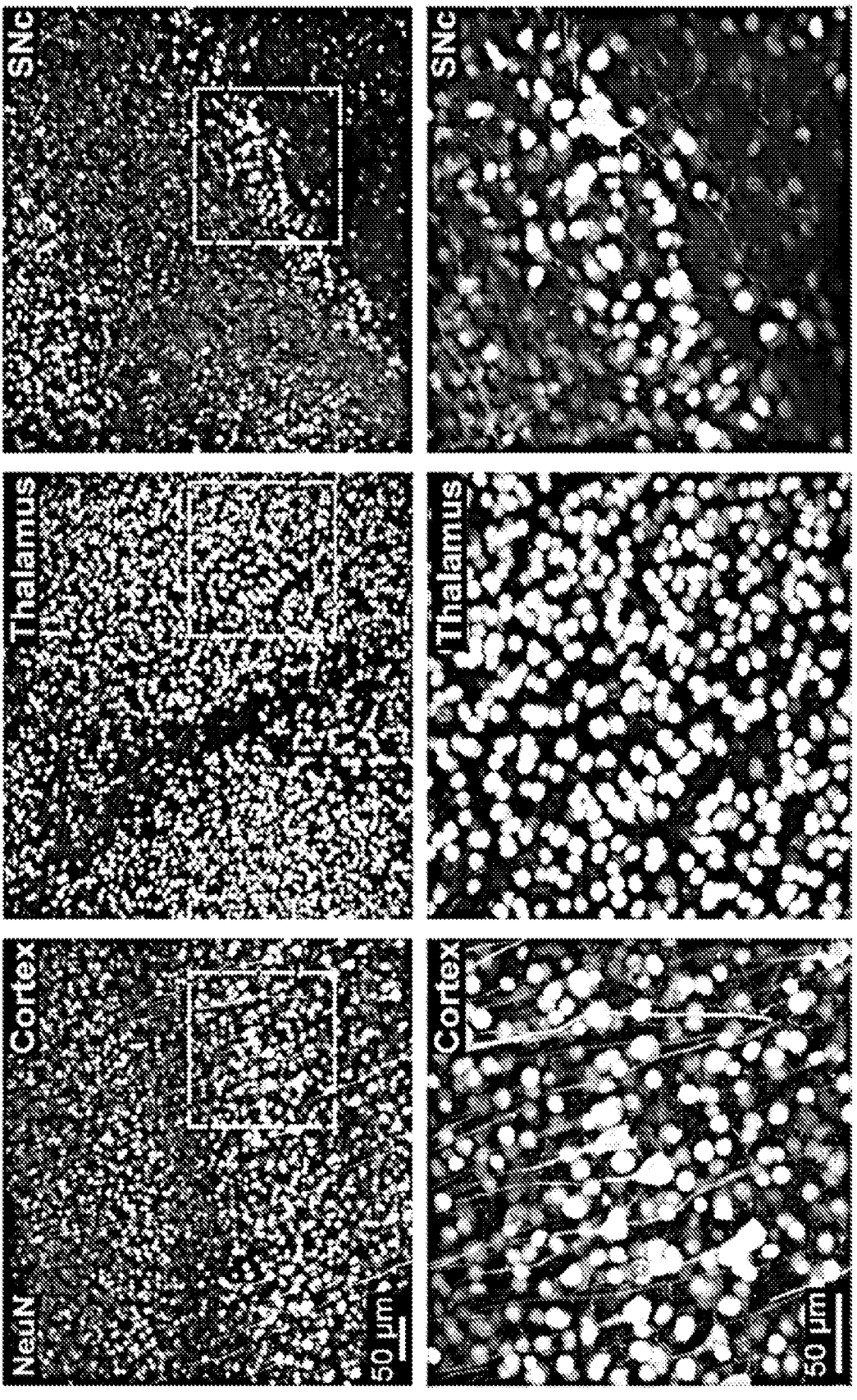
Figure 68:
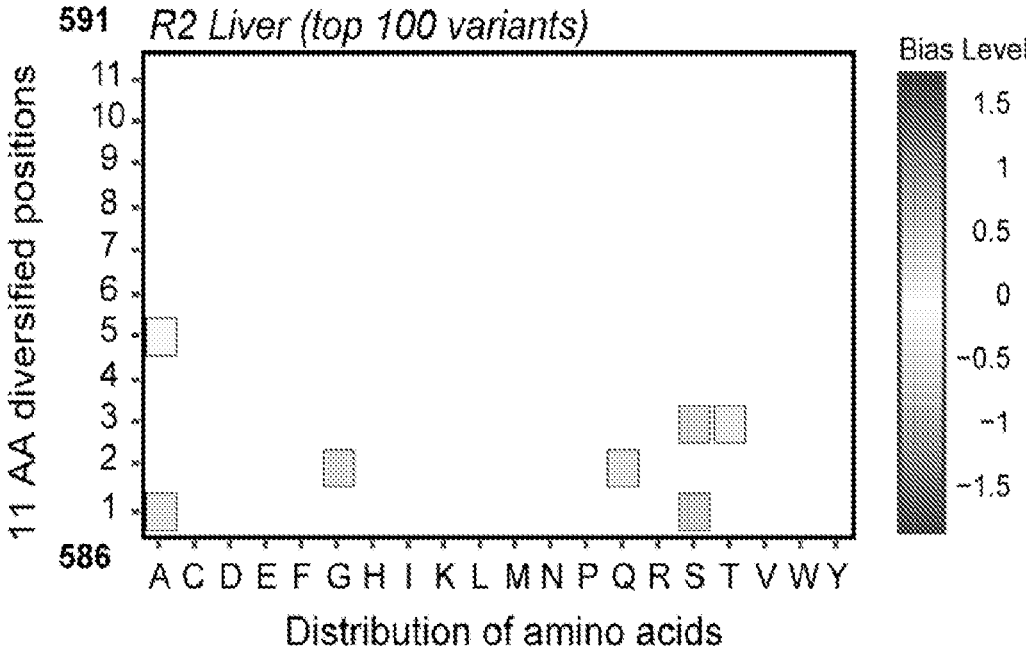
FIG. 68 shows a heatmap of AA distributions across the diversified region of the positively enriched variants from R2 liver library (top 100 sequences) normalized to the R2 virus (input library).
Figure 69:
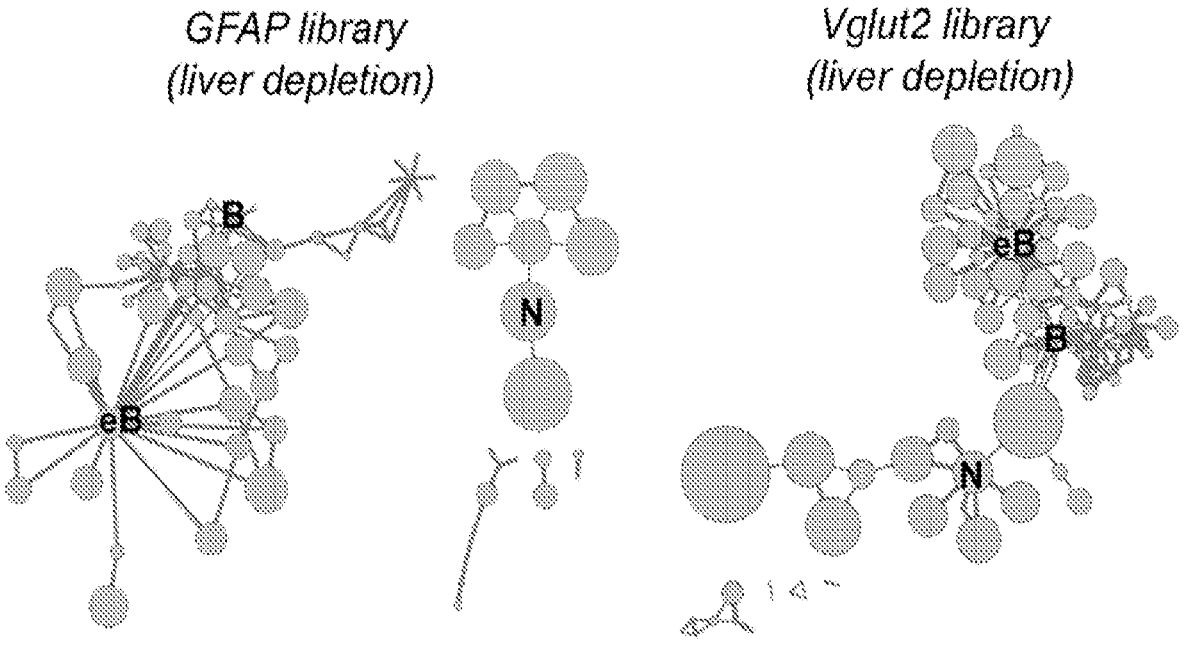
FIG. 69 shows clustering analysis of positively enriched variants from GFAP and Vglut2 brain libraries are shown with size of nodes representing their relative negative enrichment in liver, and the thickness of edges (connecting lines) representing their relative identity between nodes.
Figure 70:
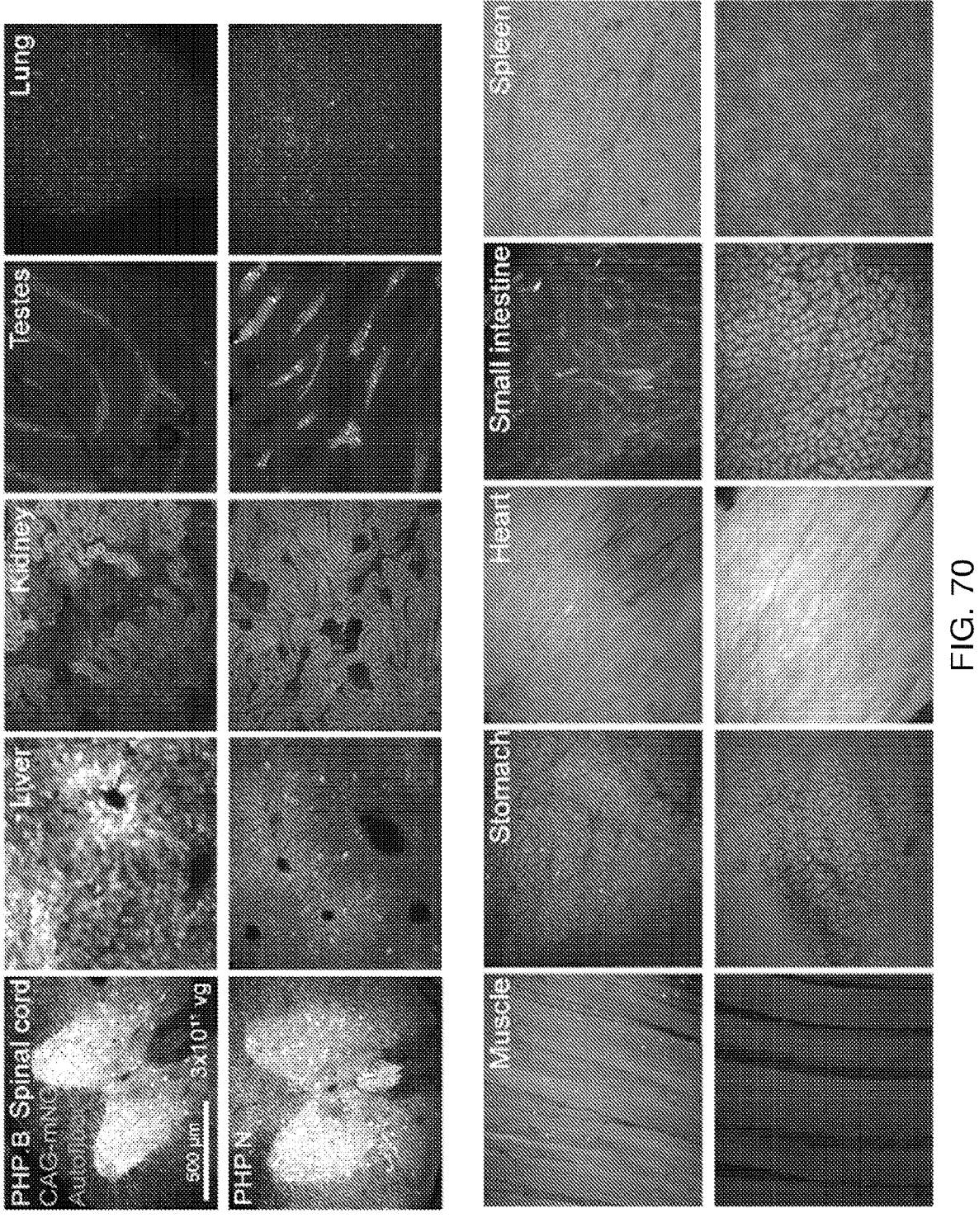
FIG. 70 shows expression of AAV-PHP.B (top row) and AAV-PHP.N (bottom row) packaged with ssAAV:CAG-mNeonGreen across all organs (n=3, $3\times10^{11}$ vg IV dose per adult C57BL/6J mouse, 3 weeks of expression).
Figure 71:
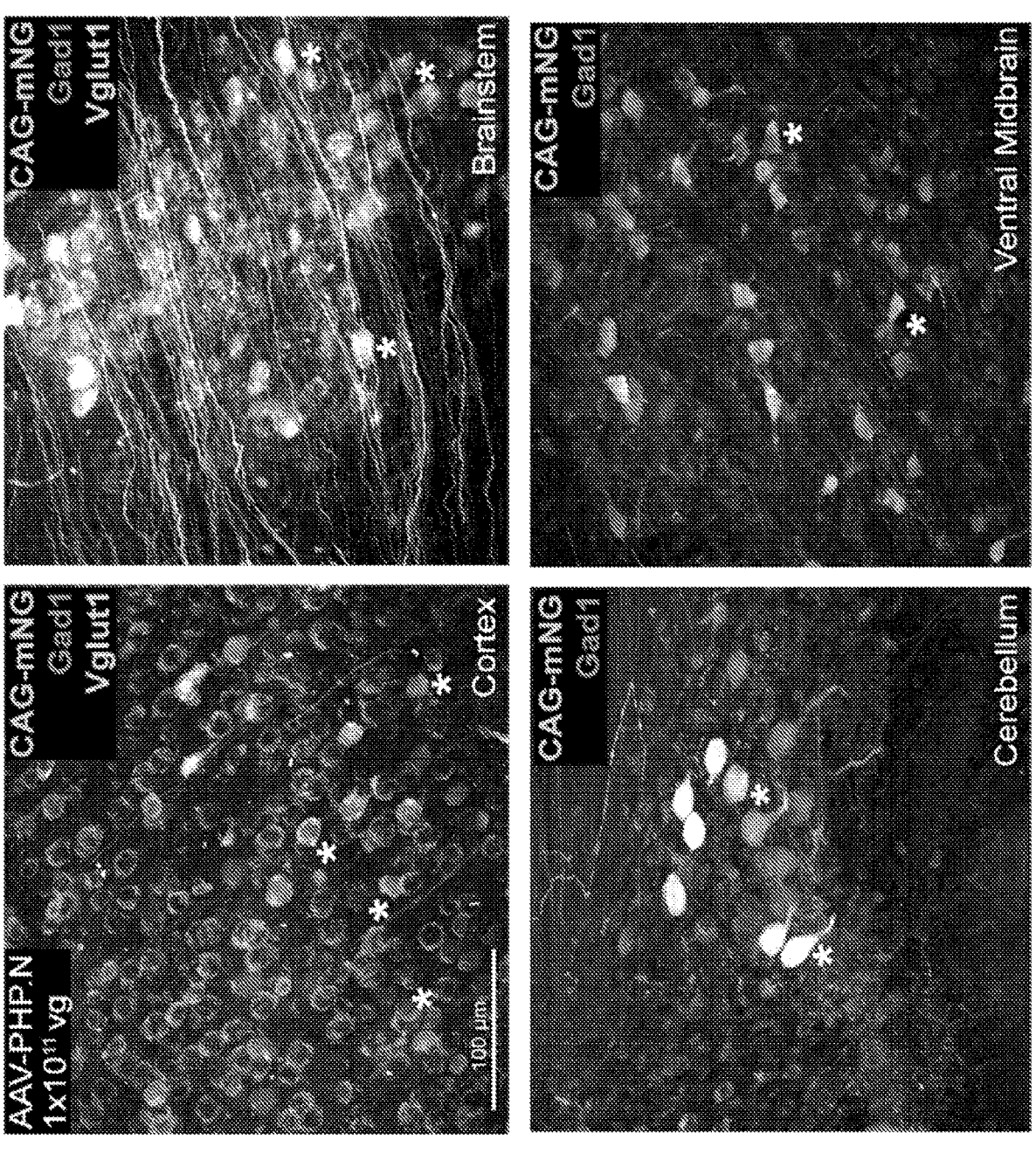
FIG. 71 shows transduction of mouse brain by the AAV-PHP.N variant, carrying the CAG promoter that drives the expression of mNeonGreen (n=3, $1\times10^{11}$ vg IV dose per C57BL/6J adult mouse, 3 weeks of expression). Fluorescence in situ hybridization chain reaction (FITC-HCR) was used to label excitatory neurons with Vglut1 and inhibitory neurons with Gad1. Few cells where EGFP expression co-localized with specific cell markers are highlighted by asterisks symbol.

Variants that were positively enriched in brain and negatively enriched in liver show a significant bias towards certain AAs: G, D, E at position 1; G, S at position 2 (which includes the AAV-PHP.eB motif, DG); and S, N, P at position 9, 10, 11 (FIGS. 26 and 68). Variants that were positively enriched in the brain were clustered according to their sequence similarities and ranked by their negative enrichment in liver (represented by node size in clusters). A distinct family referred to as N emerged with a common motif "SNP" at positions 9-11 on PHP.B backbone (FIGS. 27 and 69).

The core variant of the N-family cluster: AQTLAVPFSNP was found in high abundance in R1 and R2 selections, had higher enrichment score in Vglut2 and Vgat brain tissues compared to GFAP, and had negative enrichment in liver tissue (FIGS. 25 and 66-69). Unlike AAV-PHP.eB, this variant (AAV-PHP.N) specifically transduced NeuN[+] neurons even when packaged with a ubiquitous CAG promoter, although the transduction efficiency varied across brain regions (from ~10-70% in NeuN[+] neurons, including both VGLUT1[+] excitatory and GAD1[+] inhibitory neurons, FIGS. 28, 29, 70, and 71).

Thus, by re-examining the 3-mer-s library several novel variants were identified, including one with notable cell-type-specific tropism. While Vglut2-Cre and Vgat-Cre mice were used for in vivo selection, no variants stood out for neuronal subtype-specific transduction of excitatory and inhibitory populations from initial investigations on the NGS dataset. It is possible that a biological solution to this (stringent) selection was not present in the library.

Example 8. Investigation of Capsid Families Beyond C57BL/6J Mouse Strain

Figure 30:
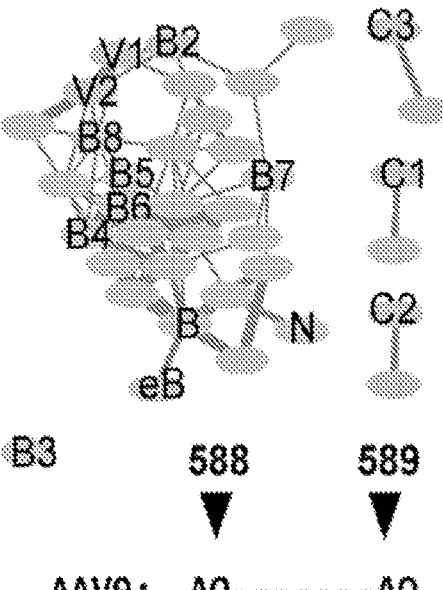
FIG. 30 shows clustering analysis showing the brain-enriched sequence families of all variants described herein, either identified in prior studies (PHP.B-B3, PHP.eB) or in the current study (PHP.B4-B8, PHP.V1-2, PHP.C1-3). The thickness of edges (connecting lines) representing degree of relatedness between nodes. The AA sequences inserted between 588-589 (of AAV9 capsid) for all the variants discussed are shown below.
Figure 31:
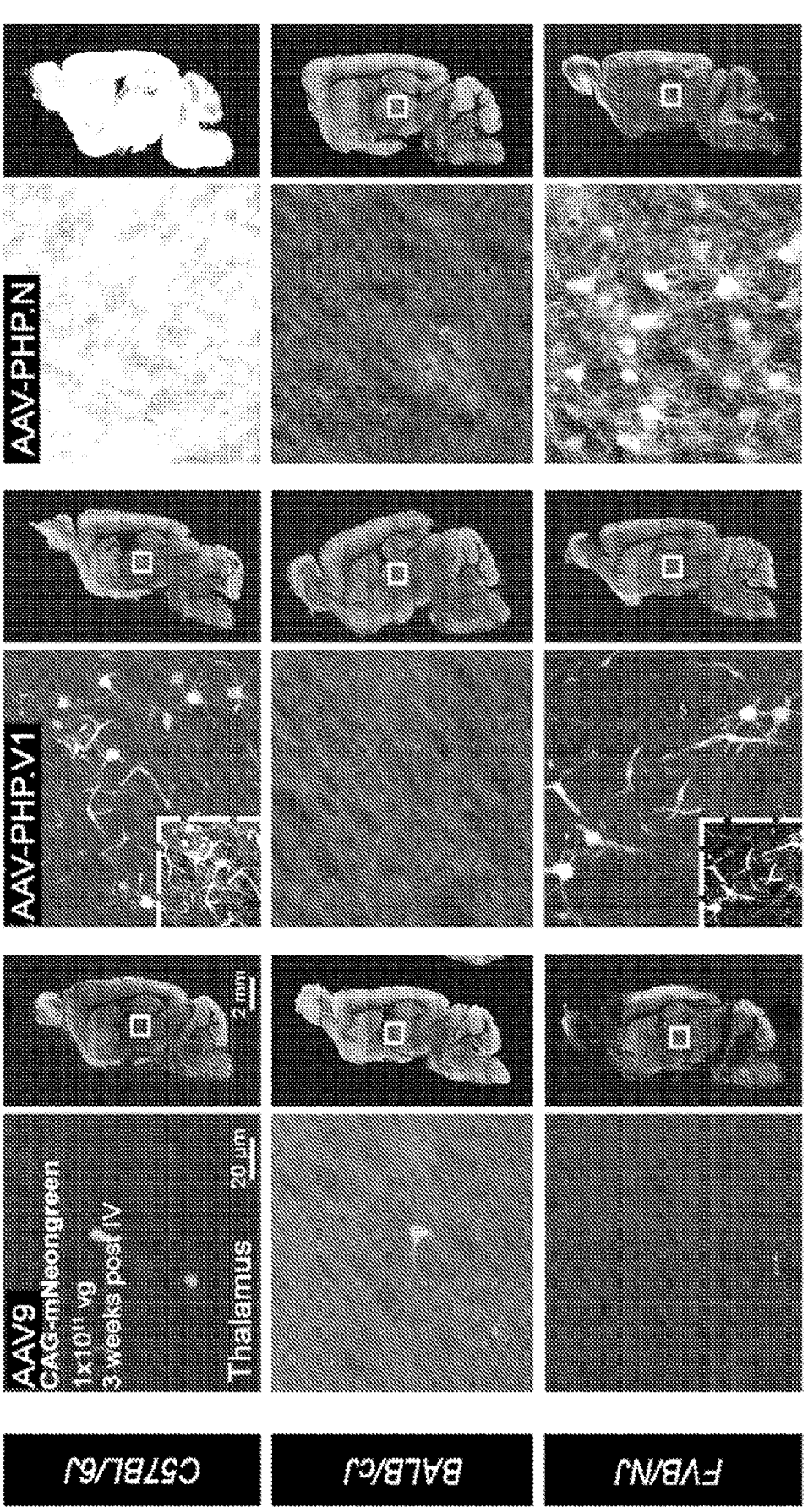
FIG. 31 shows transduction of AAV9, AAV-PHP.V1 and AAV-PHP.N across three different mouse strains: C57BL/6J, BALB/cJ and FVB/NJ in sagittal brain sections (right), along with a higher magnification image of the thalamus brain region (left).
Figure 72:
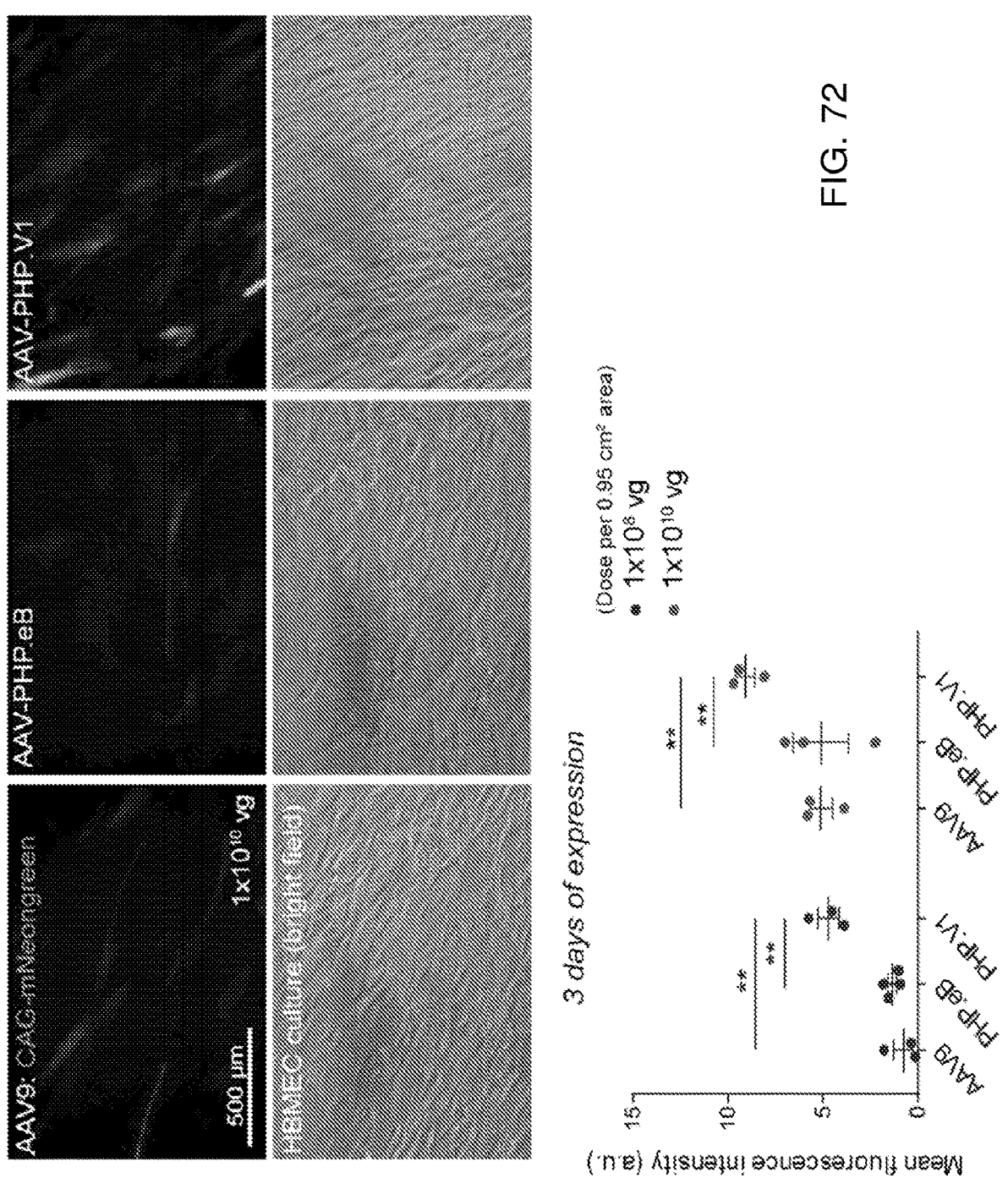
FIG. 72 shows transduction of AAV9, AAV-PHP.eB and AAV-PHP.V1 in human brain microvascular endothelial cell culture (HBMEC). The vectors were packaged with ssAAV:CAG-mNeongreen. The mean fluorescence intensity across the groups were quantified (n=3 tissue culture wells of 0.95 cm$^2$ surface area per group, 3 images per well per group per dose was imaged after three days of expression, doses $1\times10^8$ vg and $1\times10^{10}$ vg per 0.95 cm$^2$ surface area). A two-way ANOVA with correction for multiple comparisons using Tukey's test gave adjusted P-value of 0.0051 for AAV9 vs PHP.V1, 0.0096 for PHP.eB vs PHP.V1, 0.8222 for AAV9 vs PHP.eB for $1\times10^8$ vg, and 0.0052 for AAV9 vs PHP.V1, 0.0049 for PHP.eB vs PHP.V1, 0.9996 for AAV9 vs PHP.eB for $1\times10^{10}$ vg (**P≤0.01, is shown and P>0.05 is not shown on the plot; mean±S.E.M., 95% CI).

The enhanced CNS tropism of AAV-PHP.eB is absent in a subset of mouse strains. It is highly efficient in C57BL/6J, FVB/NCrl, DBA/2, and SJL/J, with intermediate enhancement in 129S1/SvimJ, and no enhancement in BALB/cJ and several additional strains. This pattern holds for the two newly identified variants from the PHP.B family, AAV-PHP.V1 and AAV-PHP.N (FIG. 30, Table 9), which did not transduce the CNS in BALB/cJ, yet transduced the FVB/NJ strain (FIG. 31). AAV-PHP.V1 transduced Human Brain Microvascular Endothelial Cell (HBMEC) culture, resulting in increased mean fluorescent intensity compared to AAV9 and AAV-PHP.eB (FIG. 72) however, suggesting the potential for mechanistic complexity.

TABLE 9

AAV-PHP vectors identified by CREATE and M-CREATE. The table provides a summary of the variants that have been identified so far using CREATE and M-CREATE, along with their tropism and the evolutionary steps from the parent capsid that was involved in their discovery.

| AAV Variants | Reference/ Selection method | Tropism | Production | Rounds of evolution from parent capsid |
|---|---|---|---|---|
| PHP.B, B2, B3 | Deverman et al, 2016/CREATE | Broad CNS transduction | Good | 1 round from AAV9 |
| PHP.A | Deverman et al, 2016/CREATE | Astrocyte transduction | Poor; prone to precipitate upon storage at 4° C. | 1 round from AAV9 |
| PHP.eB | Chan et al, 2017/CREATE | Enhanced Broad CNS transduction | Good | 2 rounds from AAV9 or 1 round from PHP.B |
| PHP.S | Chan et al, 2017/CREATE | Sensory neuron transduction | Good | 1 round from AAV9 |

TABLE 9-continued

AAV-PHP vectors identified by CREATE and M-CREATE. The table provides
a summary of the variants that have been identified so far using CREATE
and M-CREATE, along with their tropism and the evolutionary steps
from the parent capsid that was involved in their discovery.

| AAV Variants | Reference/ Selection method | Tropism | Production | Rounds of evolution from parent capsid |
|---|---|---|---|---|
| PHP.V1, V2 | Current study/ M-CREATE | BBB Vascular cells and astrocytes transduction | Good | 1 round from AAV9 |
| PHP.B4, B7, B8, | Current study/ M-CREATE | Broad CNS transduction | Good | 1 round from AAV9 |
| PHP.B5, B6 | Current study/ M-CREATE and CREATE | Broad CNS transduction | Good | 2 rounds from AAV9 or 1 round from PHP.B |
| PHP.C1, C2, C3 | Current study/ M-CREATE | Broad CNS transduction across mouse strains | Good; PHP.C1 prone to precipitate upon storage at 4° C. | 1 round from AAV9 |
| PHP.N | Current study/ M-CREATE and CREATE | Neuron transduction | Average | 2 rounds from AAV9 or 1 round from PHP.B |

Figure 32:
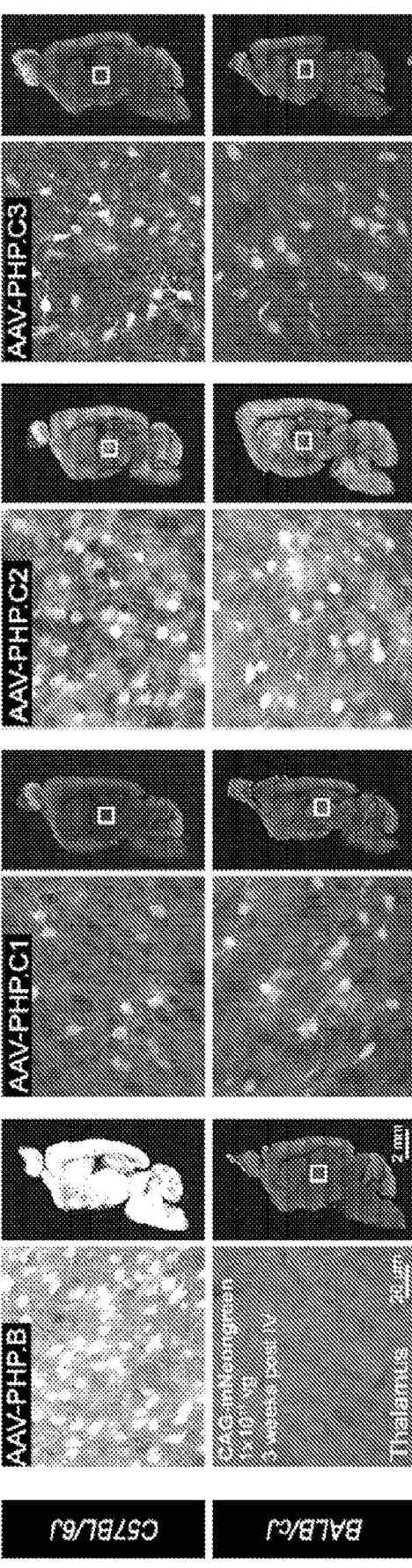
FIG. 32 shows transduction by AAV-PHP.B, AAV-PHP.C1-C3 in C57BL/6J and BALB/cJ mice in sagittal brain sections (right), along with a higher magnification image of the thalamus brain region (left).
Figure 73:
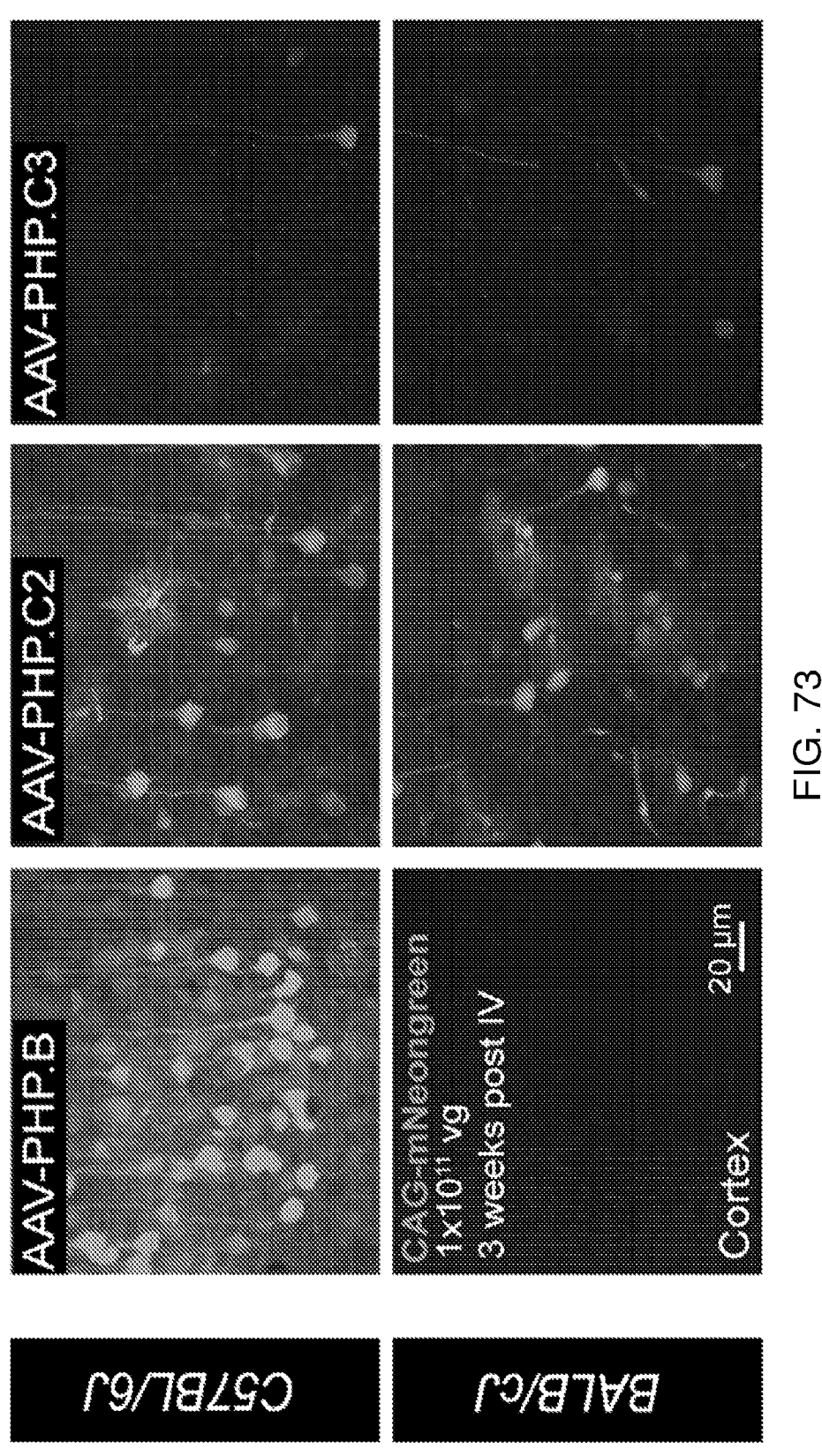
FIG. 73 shows the transduction of cortex brain region by AAV-PHP.B, AAV-PHP.C2 and AAV-PHP.C3 across two different mouse strains: C57BL/6J and BALB/cJ. The vectors were packaged with ssAAV:CAG-mNeongreen (n=2-3 per group, $1\times10^{11}$ vg IV dose/adult mouse, 3 weeks of expression). All images were acquired using the same microscope settings. The data reported in FIGS. 72 and 73 are from one independent trial where all viruses were freshly prepared and tittered in the same assay for dosage consistency, with additional validation for AAV-PHP.C2 and AAV-PHP.C3 in an independent trial for BALB/cJ.

Importantly, M-CREATE revealed many non-PHP.B-like sequence families that enriched through selection for transduction of cells in the CNS. We tested the previously mentioned AAV-PHP.C1: RYQGDSV, as well as AAV-PHP.C2: WSTNAGY, and AAV-PHP.C3: ERVGFAQ (FIG. 30). These showed enhanced BBB crossing irrespective of mouse strain, with roughly equal CNS transduction in BALB/cJ and C57BL/6J (FIGS. 32 and 73). Collectively, these preliminary studies suggest that M-CREATE is capable of finding capsid variants with diverse mechanisms of BBB entry that lack strain-specificity.

Example 8. Exemplary Insertion of Variant AAV Capsid Protein Sequence

Demonstration of 7 amino acid peptide insertion in AAV capsid: Peptide sequence "TLQIPFK" (SEQ ID: 435) is positioned between AA 588-589 of AAV capsid. The insertion sequence is underlined and bold.

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSRT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSAQTLQIPFKAQAQT

GWVQNQGILPGMVWQDRDVYLQGPIWAKIPHTDGNFHPSPLMGGFGMKHP

PPQILIKNTPVPADPPTAFNKDKLNSFITQYSTGQVSVEIEWELQKENSK

RWNPEIQYTSNYYKSNNVEFAVNTEGVYSEPRPIGTRYLTRNL

Demonstration of 11 amino acid peptide insertion in AAV capsid:

Peptide sequence "DGTTLKPFLAQ" (SEQ ID: 867) is positioned by replacing AA 587-590 of AAV capsid. The inserted sequence is underlined and highlighted.

MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSRT

INGSGQNQQTLKFSVAGPSNMAVQGRNYIPGPSYRQQRVSTTVTQNNNSE

FAWPGASSWALNGRNSLMNPGPAMASHKEGEDRFFPLSGSLIFGKQGTGR

DNVDADKVMITNEEEIKTTNPVATESYGQVATNHQSDGTTLKPFLAQAQT

GWVQNQGILPGMVWQDRDVYLQGPIWAKIPHTDGNFHPSPLMGGFGMKHP

PPQILIKNTPVPADPPTAFNKDKLNSFITQYSTGQVSVEIEWELQKENSK

RWNPEIQYTSNYYKSNNVEFAVNTEGVYSEPRPIGTRYLTRNL.

Example 9. Treating Huntington's Disease (HD)

A subject having Huntington's disease is identified. The subject is then systemically administered a first amount of a viral vector that includes a polynucleotide that encodes for a Zinc finger protein (ZFP) engineered to represses the transcription of the Huntingtin (HTT) gene. The vector will be encapsidated by a modified AAV capsid protein with an amino acid sequence provided in FIG. 33 or provided in Tables 2-4, so as to allow proper targeting of the ZFP to the nervous system, among other organs. If needed, the subject is administered a second or third dose of the vector, until a therapeutically effective amount of the ZFP is expressed in the subject in the nervous system.

Example 10. Phase 1A Clinical Trial

A phase 1A clinical trial is performed to evaluate the safety, tolerability, pharmacokinetics, and pharmacodynamics of an one-time intravenous injection of test composition comprising viral vector encapsidated by a modified capsid protein with any of the amino acid sequences provided in FIG. 33 or Tables 2-4, in subjects with late Huntington's Disease (HD). Eligible subjects are men and women between 21 and 65 years of age.

Inclusion Criteria: Eligible subjects are men and women between 21 and 65 years of age. Subjects that (i) sign and date Sign and date International Classification of Functioning, Disability and Health (ICF); (2) male or female participant aged ≥21 and ≤65; (3) participants who submit medical report (PCR) attesting Huntington's disease with a number of CAG repeats on chromosome 4, greater than or equal to 40 and less than or equal to 50 (if the participant has not performed the examination and/or if he does not have the report available, a new exam should be done); (4) Score 5 points or more in motor assessment UHDRS scale (Unified Huntington's Disease Rating Scale) at the time of enrollment; (5) Score between 8 and 11 points in the functional capacity of the UHDRS scale at the time of enrollment.

Exclusion Criteria: (1) Any medical observation data (clinical and physical) that medical research judge as a risk for subject if enrollment at the study; (2) any laboratory exam data that medical research judge as a risk for subject if enrollment at the study; (4) history of epilepsy; (5) diagnostic of major cognitive impairment; (6) active decompensated psychiatric disease; (7) current or prior history of neoplasia; (8) current history of gastrointestinal, hepatic, renal, endocrine, pulmonary, hematologic, immune, metabolic pathology or severe and uncontrolled cardiovascular disease; (8) diagnostic of any active infection, be it viral, bacterial, fungal, or caused by another pathogen; (9) participants who have contraindication to undergo any of the tests performed in this study, for example, have pacemakers or surgical clip; (10) history of alcohol or illegal drugs abusers; (11) history of 1 or more episodes of suicide in the two years before Visit V-4; (12) active smoker or have stopped smoking less than six months prior to enrollment; (13) test positive in at least one of the serological tests: HIV 1 and 2 (Anti-HIV-1,2), HTLV I and II, HBV (HBsAg, anti-HBc), HCV (anti-HCV-Ab) and VDRL (Treponema pallidum); (14) history of drug allergy, including contrasts for imaging, or bovine products; (15) in use or expected use of immunosuppressive drugs or prohibited medicines for the first three months after the first administration of the investigational product; (16) any clinical changes that is interpreted by the medical researcher as a risk to participant's enrollment.

Experimental:

Placebo. One-time injection of placebo at Week 0.

Test High Dose. One-time injection of test composition $2\times10^{10}$ vg at Week 0.

Test Middle Dose. One-time injection of test composition $6\times10^{9}$ vg at Week 0.

Test Low Dose. One-time injection of test composition $2\times10^{9}$ vg at Week 0.

Test Lowest Dose. One-time injection of test composition $2\times10^{8}$ vg at Week 0.

Primary Outcome Measures: Safety of the test composition by periodic monitoring changes at adverse events, vital signs, laboratory tests, ECG and incidence of benign and malignant neoplasms [Time Frame: five years]. The safety of the investigational product will be evaluated in detail from periodic evaluations contemplating monitoring changes of: (1) adverse events including type, frequency, intensity, seriousness, severity, and action taken related to the investigational product study; (2) vital signs (BP, HR, axillary temperature), physical and medical examination (BMI, weight, height, medical condition—cardiovascular, pulmonary, digestive, musculoskeletal and peripheral, with emphasis on the neurological assessment and others); (2) laboratory tests included hematologic, biochemical, urologic and serological analysis; (3) electrocardiogram (ECG) of 12 derivations; (4) and incidence and classification of benign and malignant neoplasms in the following organs/systems: CNS, lung, liver, spleen, pancreas, prostate, testicle, urinary, hematological and skeletal system through the laboratory tests, magnetic resonance imaging, computerized tomography and ultrasonography.

Secondary Outcome Measures: Preliminary efficacy of Cellavita HD by global clinical response (CIBIS) and UHDRS improvement [Time Frame: five years] will be evaluated by statistical comparison of the results of each UHDRS scale component: motor, cognitive and behavior. The global clinical response will be assessed by statistical comparison between baseline score observed by the Investigator before and after Cellavita HD treatment. Preliminary efficacy of Cellavita HD by comparison of the inflammatory markers [Time Frame: one year] will be evaluated by statistical comparison of the inflammatory markers included IL-4, IL-6, IL-10 (interleukin IL) and TNF-alpha (tumoral necrosis factor alpha). Immunological Response of Cellavita HD [Time Frame: one year]. The immunological response induced by Cellavita HD will be evaluated by statistical comparison between baseline results of CD4+ and CD8+ proliferation and the other evaluated times. Preliminary efficacy of Cellavita HD by comparison of the CNS assessment [Time Frame: one year]. Will be evaluated by statistical comparison of the CNS assessment through magnetic resonance image at cortical thickness measurements, volumes of different brain structures, especially the basal ganglia, with special attention to caudate and metabolic changes identified in proton spectroscopy. Risk of suicidal ideation by Hamilton Depression Rating Scale (HDRS) [Time Frame: five years] will be evaluated by suicidal domain. The classificatory pontuation may correspond to mild depression (score: 8 to 13), moderate depression (score: 19-22) and severe depression (score: >23).

While preferred instances of the present examples have been shown and described herein, it will be obvious to those skilled in the art that such instances are provided by way of example only. Numerous variations, changes, and substitutions will now occur to those skilled in the art without departing from the disclosure. It should be understood that various alternatives to the instances of the disclosure described herein may be employed in practicing the disclosure. It is intended that the following claims define the scope of the disclosure and that methods and structures within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

SEQUENCE LISTING

The patent contains a lengthy sequence listing. A copy of the sequence listing is available in electronic form from the USPTO web site (https://seqdata.uspto.gov/docdetail?docId=US12644131B2). An electronic copy of the sequence listing will also be available from the USPTO upon request and payment of the fee set forth in 37 CFR 1.19(b)(3).

---

The invention claimed is:

1. An AAV capsid comprising:
   a) an AAV capsid protein comprising:
      i. a first amino acid sequence that is at least 98% identical to amino acid 217 to amino acid 736 of SEQ ID NO: 1; and
      ii. a second amino acid sequence identical to an amino acid sequence provided in Tables 2-3 or FIG. 33—inserted at an amino acid position 588_589 within SEQ ID NO: 1, wherein the AAV capsid protein comprises at least one of an increased specificity and an increased transduction efficiency when measured in a central nervous system (CNS) in a subject when delivered to the subject systemically, relative to a native AAV capsid protein provided in SEQ ID NO: 1.

2. The AAV capsid of claim 1, wherein the second amino acid sequence is selected from the group consisting of TALKPFL (SEQ ID NO: 436), TTLKPFL (SEQ ID NO: 437), TLQIPFK (SEQ ID NO: 435), TMQKPFI (SEQ ID NO: 440), SIERPFK (SEQ ID NO: 438), RYQGDSV (SEQ ID NO: 454), and TTLKPFS (SEQ ID NO: 5).

3. The AAV capsid of claim 1, wherein the AAV capsid protein is present in VP1, VP2, and VP3 of the AAV capsid.

4. The AAV capsid of claim 1, wherein the AAV capsid is chimeric.

5. The AAV capsid of claim 1, wherein 60 copies of the AAV capsid protein are assembled into the AAV capsid.

6. The AAV capsid protein of claim 1, wherein the CNS comprises a cell-type selected from the group consisting of a neuron, an oligodendrocyte, an astrocyte, and a brain vascular cell.

7. The AAV capsid of claim 1, wherein the CNS comprises a tissue that is selected from the group consisting of a brain, a thalamus, a cortex, a striatum, a ventral midbrain, and a spinal cord.

8. The AAV capsid of claim 1, wherein the AAV capsid protein further comprises an amino acid substitution A587D or Q588G.

9. The AAV capsid protein of claim 1, wherein the AAV capsid protein further comprises an amino acid substitution A589N or Q590P.

10. The AAV capsid of claim 1 that is isolated and purified.

11. The AAV capsid of claim 1 formulated as a pharmaceutical formulation for intravenous administration to treat a disease or a condition of the CNS, the pharmaceutical formulation further comprising a pharmaceutically acceptable carrier.

12. The AAV capsid of claim 11, wherein the pharmaceutical formulation further comprises a therapeutic agent.

* * * * *